US010918284B2

(12) United States Patent
Ando et al.

(10) Patent No.: US 10,918,284 B2
(45) Date of Patent: *Feb. 16, 2021

(54) LIGHT-SOURCE UNIT, MEASUREMENT APPARATUS, NEAR-INFRARED MICROSCOPIC APPARATUS, OPTICAL DETECTION METHOD, IMAGING METHOD, CALCULATION METHOD, FUNCTIONAL BIO-RELATED SUBSTANCE, STATE MANAGEMENT METHOD, AND MANUFACTURING METHOD

(71) Applicant: Hideo Ando, Hino (JP)

(72) Inventors: Hideo Ando, Tokyo (JP); Juichiro Ukon, Kyoto (JP); Toshiaki Iwai, Tokyo (JP); Izumi Nishidate, Tokyo (JP)

(73) Assignee: HIDEO ANDO, Hino (JP)

(*) Notice: Subject to any disclaimer, the term of this patent is extended or adjusted under 35 U.S.C. 154(b) by 0 days.

This patent is subject to a terminal disclaimer.

(21) Appl. No.: 16/852,902

(22) Filed: Apr. 20, 2020

(65) Prior Publication Data

US 2020/0237227 A1 Jul. 30, 2020

Related U.S. Application Data

(62) Division of application No. 15/843,115, filed on Dec. 15, 2017, now Pat. No. 10,660,523.

(30) Foreign Application Priority Data

Jul. 7, 2017 (JP) .............................. JP2017-133512
Dec. 8, 2017 (JP) .............................. JP2017-235820

(51) Int. Cl.
*A61B 5/00* (2006.01)
*G02B 21/08* (2006.01)
(Continued)

(52) U.S. Cl.
CPC .......... *A61B 5/0062* (2013.01); *A61B 5/0066* (2013.01); *A61B 5/0075* (2013.01);
(Continued)

(58) Field of Classification Search
CPC ... A61B 5/0062; A61B 5/0066; A61B 5/0075; A61B 5/7203; G02B 21/08; G02B 27/48; G02B 27/283; G02B 27/30
See application file for complete search history.

(56) References Cited

U.S. PATENT DOCUMENTS

| 5,804,451 A | 9/1998 | Wang |
| 2003/0117618 A1 | 6/2003 | Itoh |
| 2010/0062422 A1 | 3/2010 | Ausserre |

FOREIGN PATENT DOCUMENTS

| JP | H02-240545 | 9/1990 |
| JP | H06-167640 | 6/1994 |

(Continued)

*Primary Examiner* — Christine S. Kim
(74) *Attorney, Agent, or Firm* — Rankin, Hill & Clark LLP

(57) ABSTRACT

Provided is a reliable or accurate optical detection method or such an optical imaging method. Also provided is an application technique using such a method. At least a part of an optical path starting from a light-emitting source or reaching a photodetector includes a plurality of optical paths. At a predetermined position of the optical path, beams of light after passing through the plurality of optical paths are mixed. This mixed light is used for optical detection or optical imaging. An optical-length difference among beams of light passing through the plurality of optical paths may be longer than the coherence length. Means for feed-backing predetermined characteristics of a target to the optical characteristics to be used for optical detection or optical imaging may be included. Such means may be used separately from the above. Such means may be applied to another technique, an application material or an application program.

20 Claims, 94 Drawing Sheets

(51) Int. Cl.
  *G01J 3/00* (2006.01)
  *G02B 21/16* (2006.01)
  *G02B 27/48* (2006.01)
  *G02B 27/30* (2006.01)
  *G02B 27/28* (2006.01)

(52) U.S. Cl.
  CPC .............. *A61B 5/7203* (2013.01); *G01J 3/00* (2013.01); *G02B 21/08* (2013.01); *G02B 21/082* (2013.01); *G02B 21/16* (2013.01); *G02B 27/48* (2013.01); *G02B 27/283* (2013.01); *G02B 27/30* (2013.01)

(56) References Cited

FOREIGN PATENT DOCUMENTS

| | | |
|---|---|---|
| JP | 2003-500255 | 1/2003 |
| JP | 5098028 | 10/2012 |
| JP | 2013-122443 | 6/2013 |
| WO | 2007/069666 | 6/2007 |

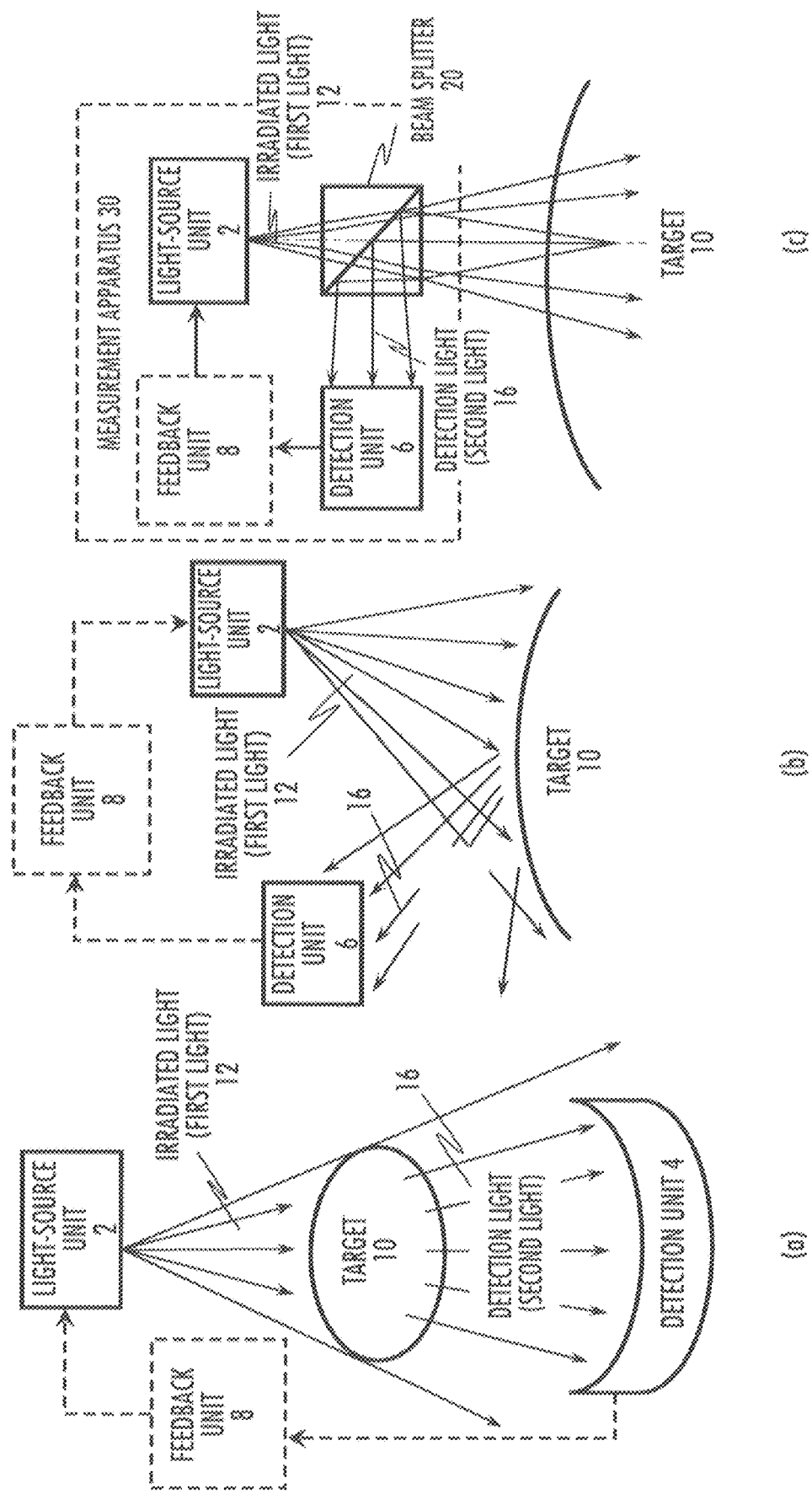

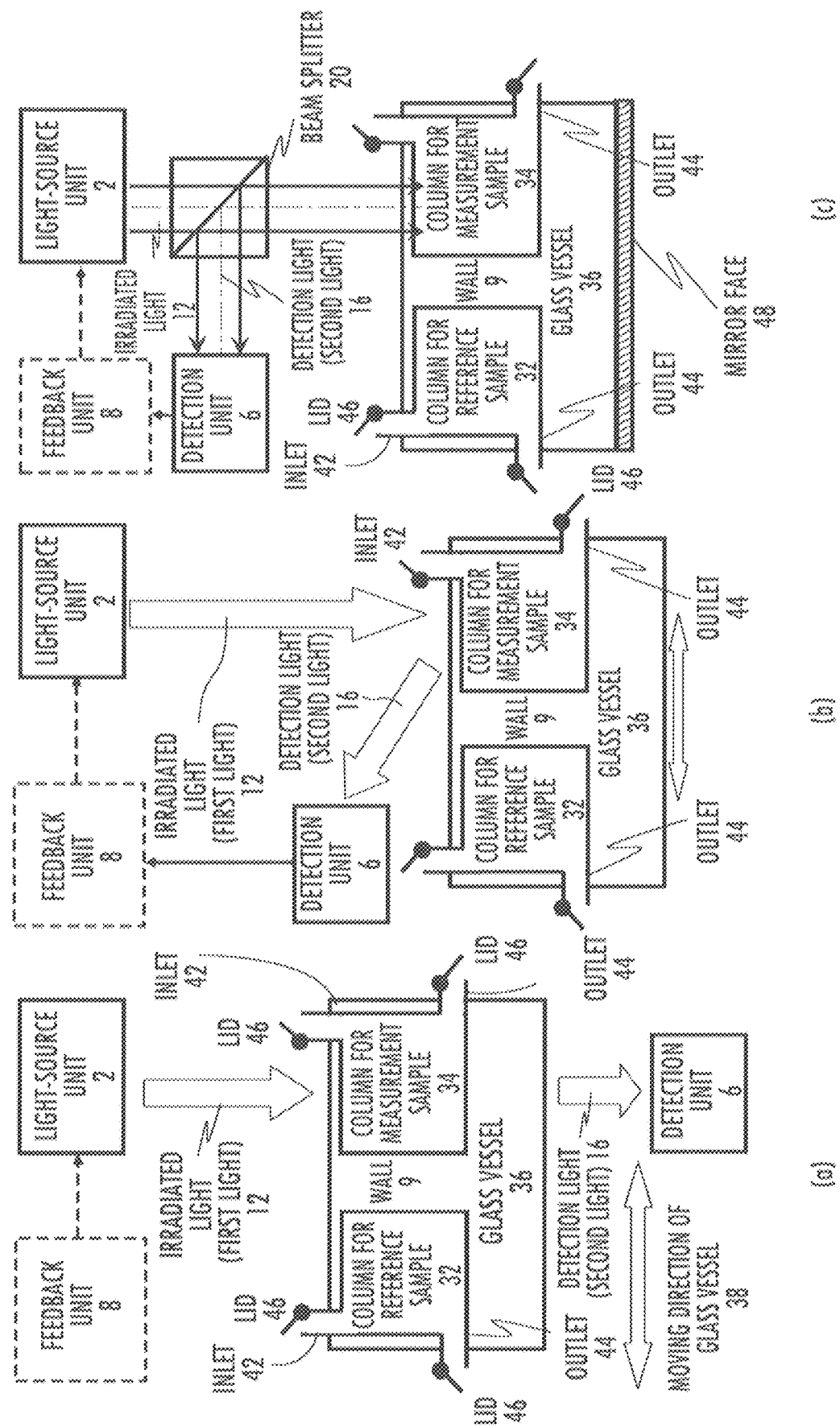

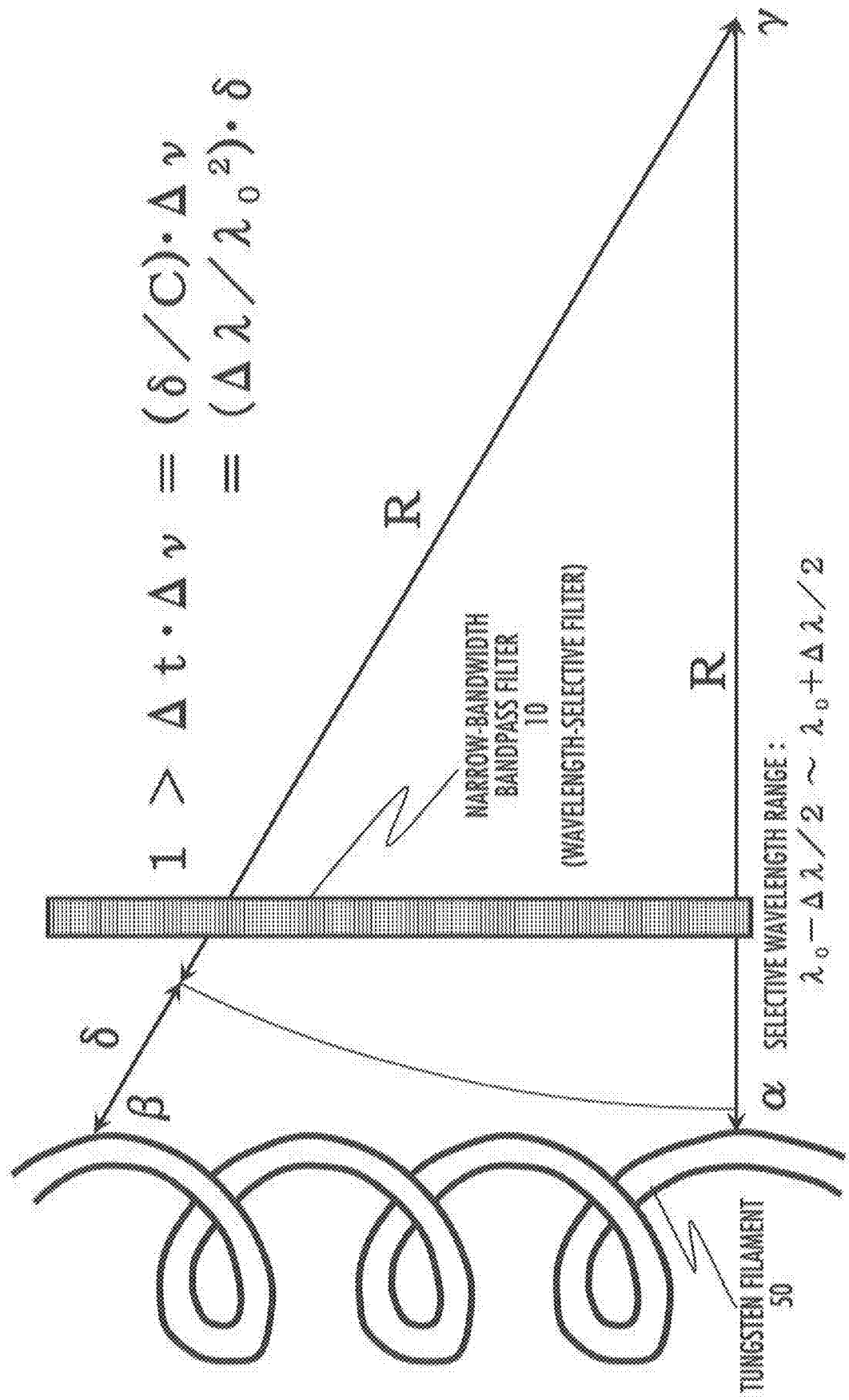

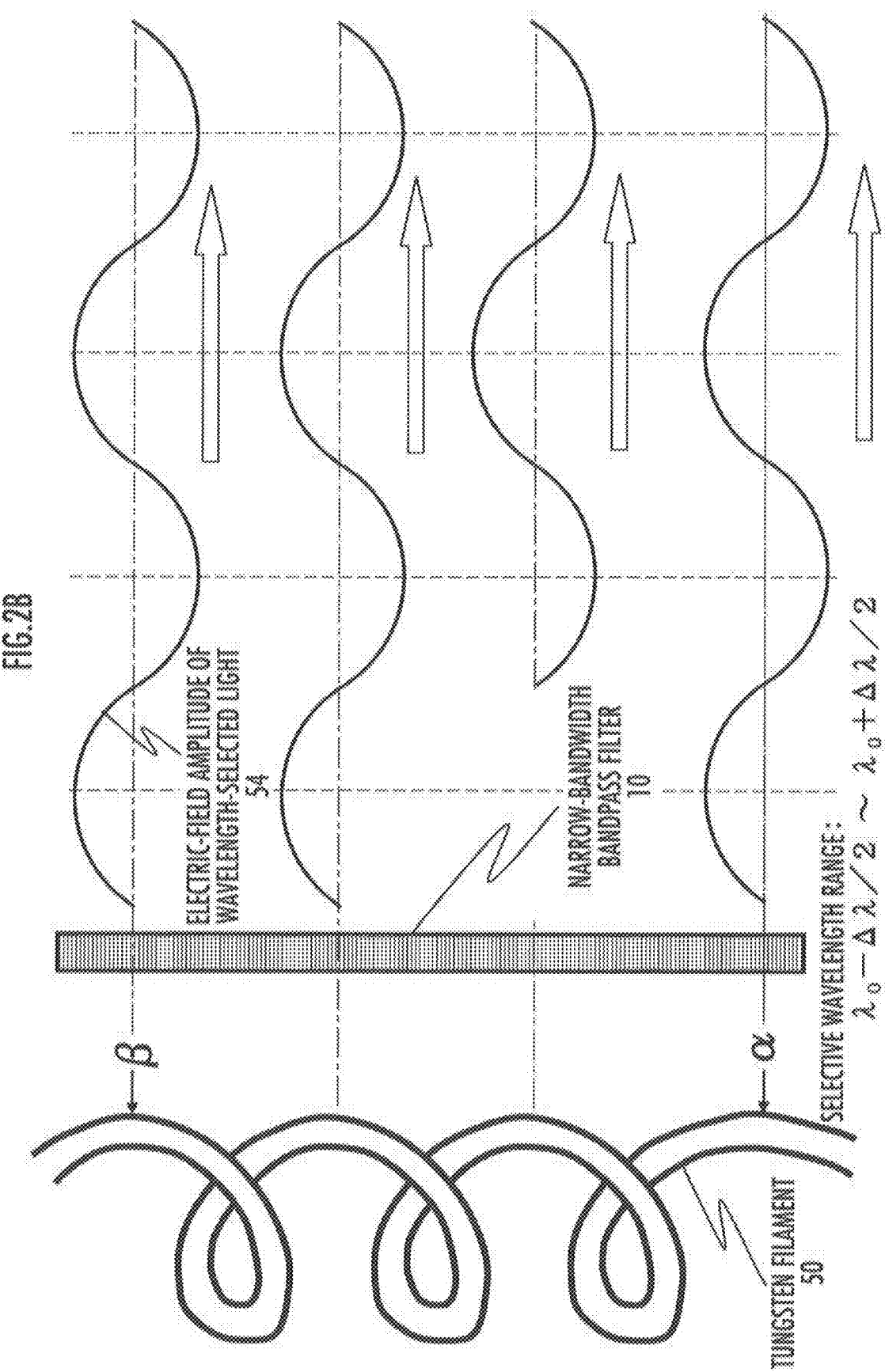

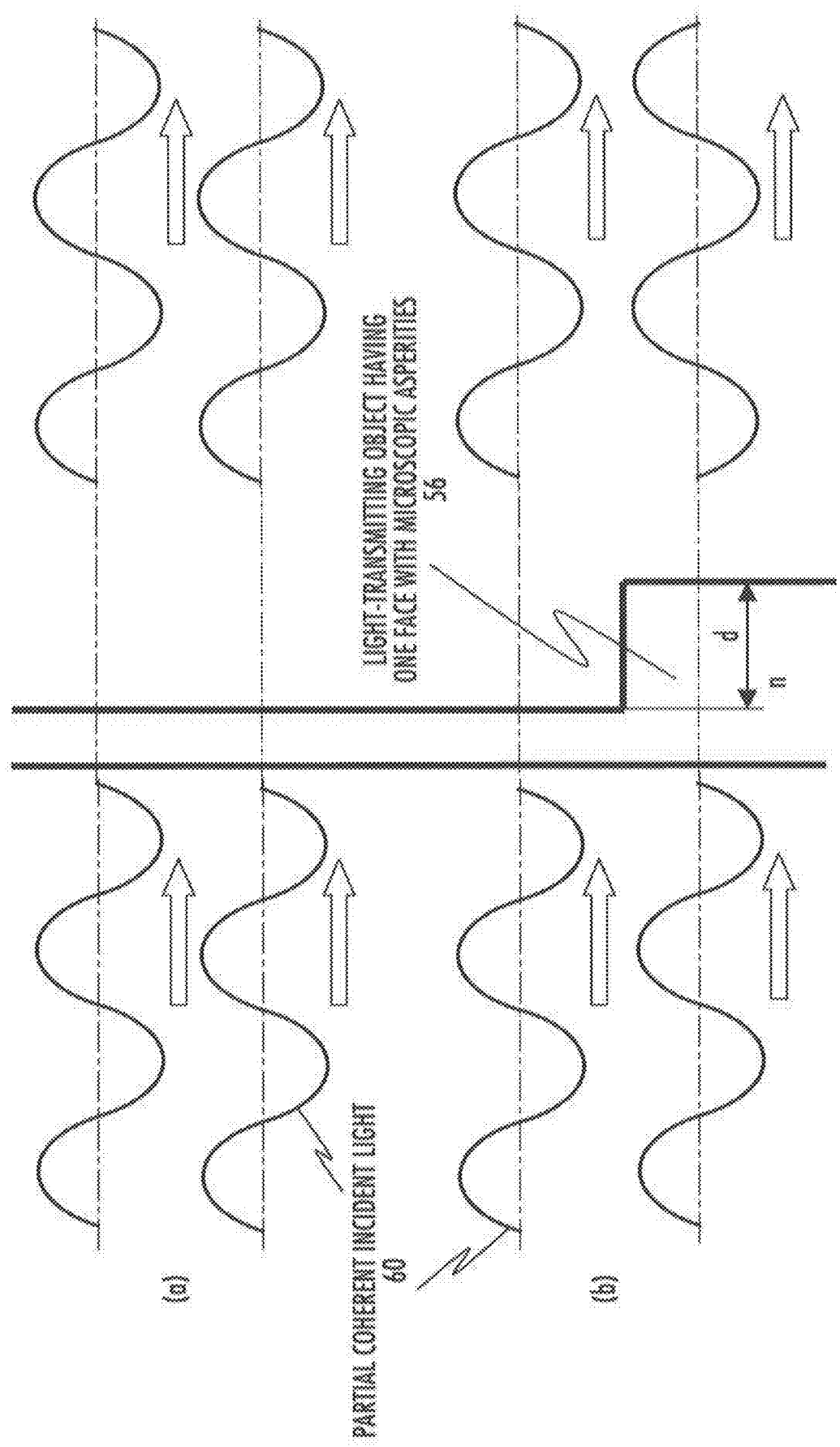

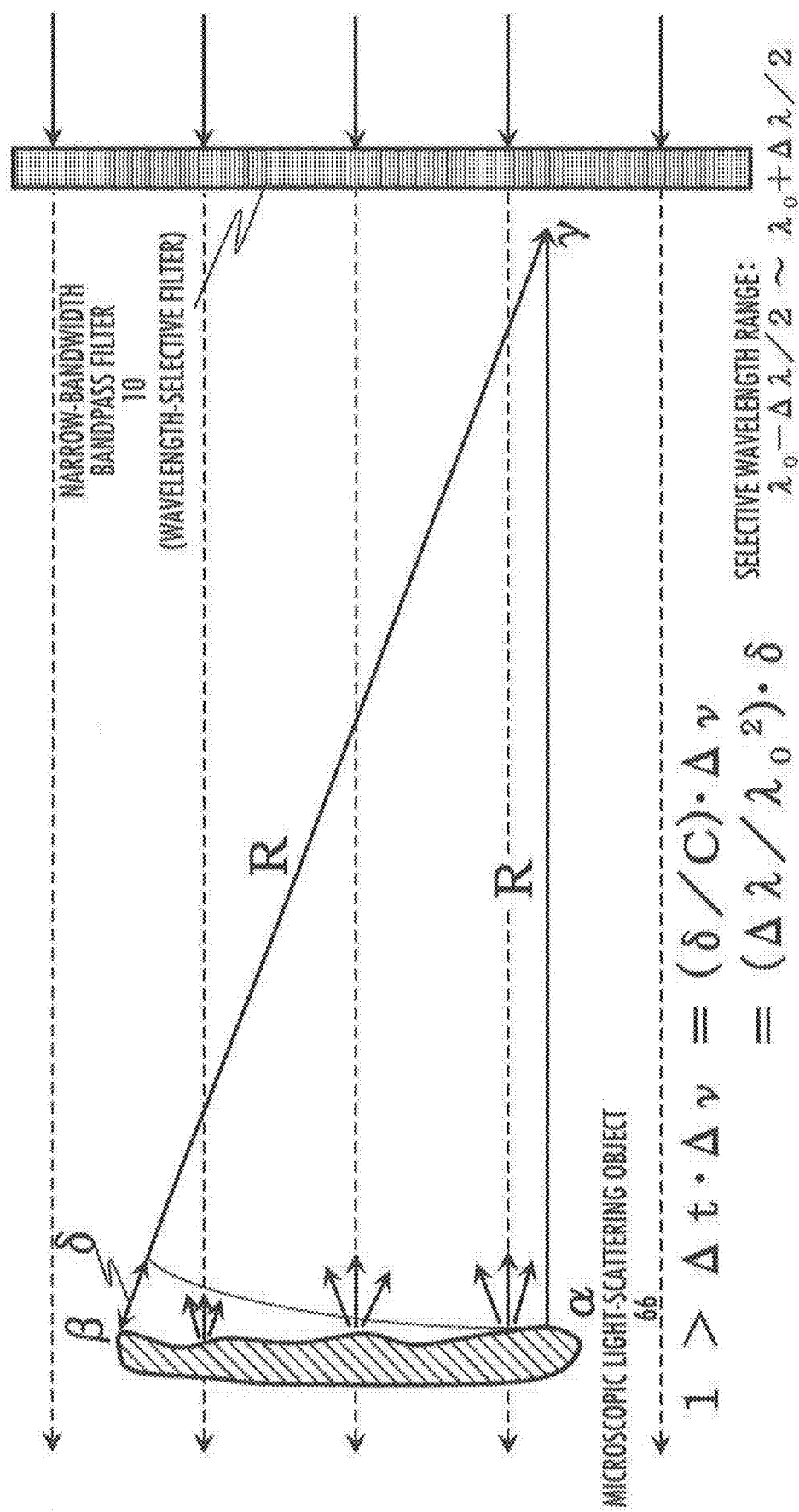

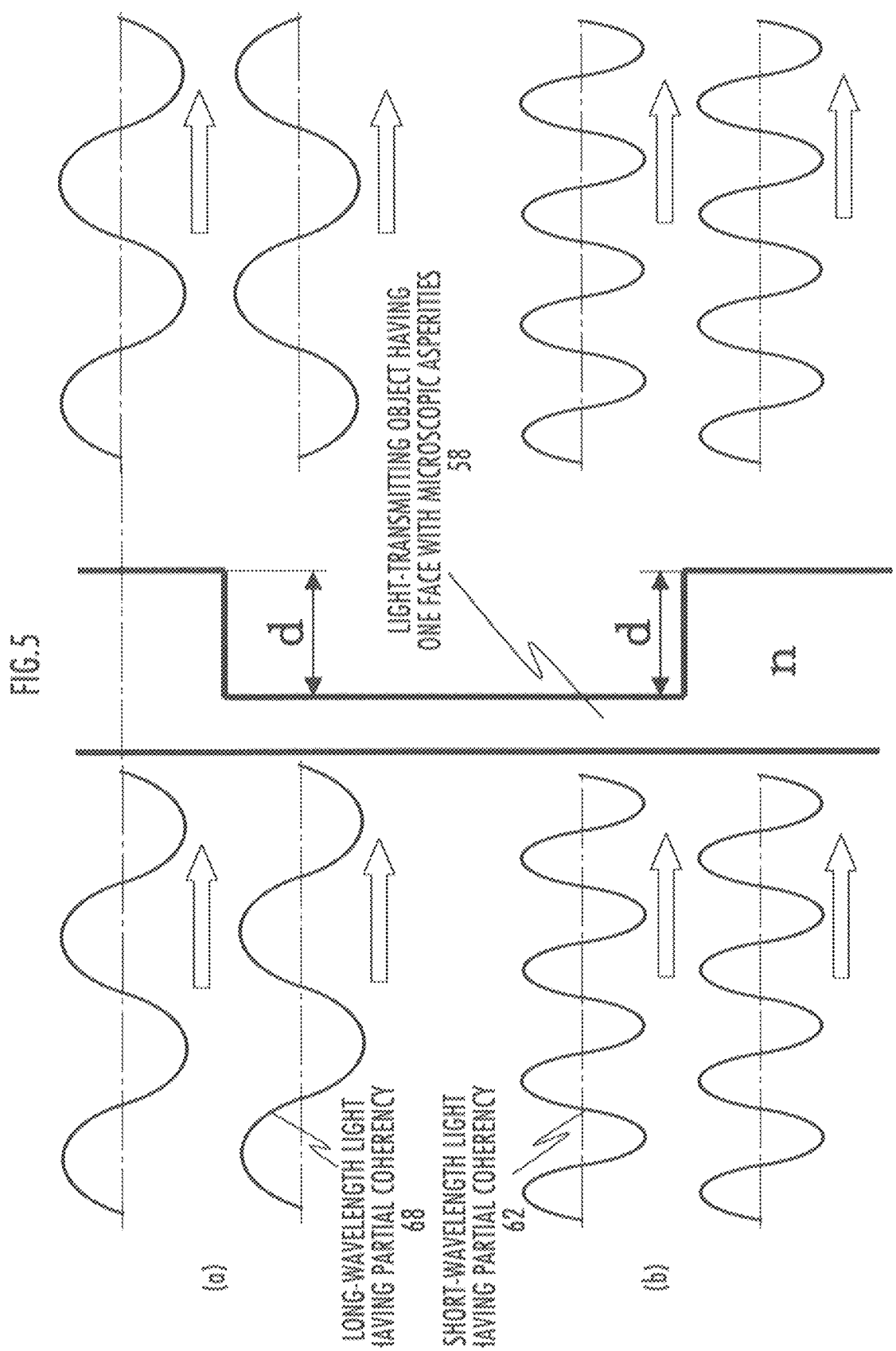

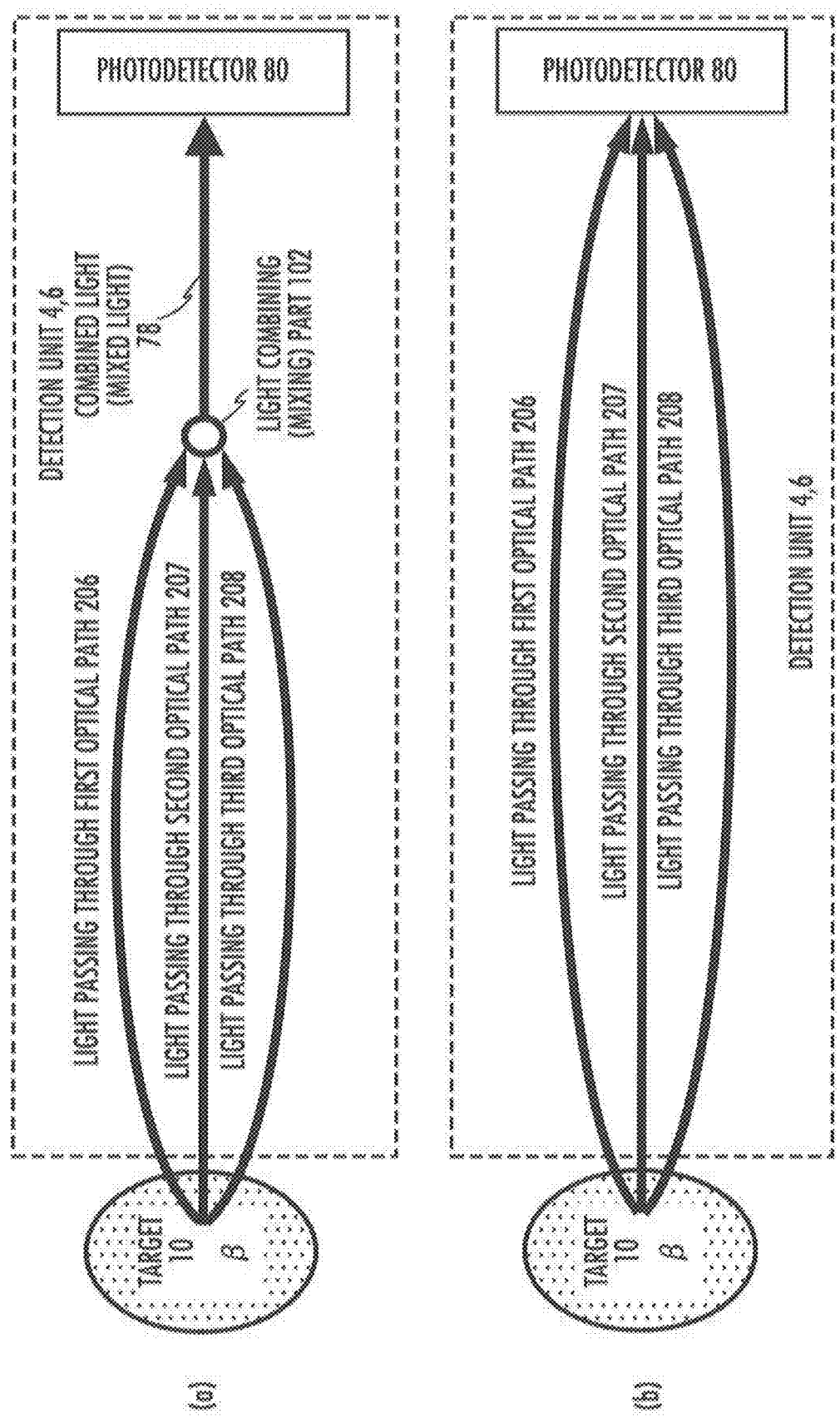

FIG. 9

LIST OF OPTIONS OF LIGHT COMBINING/MIXING METHOD IN THE PRESENT EMBODIMENT

| OPTICAL-PATH STATE BEFORE COMBINING/MIXING | | METHOD OF COMBINING/MIXING LIGHT | LIGHT COMBINING/MIXING POSITION |
|---|---|---|---|
| OPTICAL PATH STATE/OPERATIONS | DETAILS | [CHANGING/CONTROLLING THE COURSE OF EACH OPTICAL PATH] | [PASSING THROUGH SPATIALLY IDENTICAL REGION [NOTE 1]] |
| DIVERSITY OF THE LIGHT-EMITTING STATE | DIFFERENT LIGHT-EMITTING REGIONS | PRISM, SPECIAL LENS [NOTE 2] | SOME PART ALONG THE OPTICAL PATH OF IRRADIATED LIGHT 12 OR DETECTION LIGHT 16, OPTICAL FIBER 100 (CORE AREA 142), CERTAIN REGION 200 IN TARGET 10 INCLUDING IMAGE-FORMING ON DETECTOR PLANE 86, DETECTOR PLANE 86 IN PHOTODETECTOR 80, PINHOLE OR SLIT 130 |
| | DIFFERENT LIGHT-EMITTING METHODS | REFRACTIVE ELEMENT [NOTE 3] SUCH AS LENS, EXTRACT COMBINED/MIXED LIGHT WITH DETECTION UNIT 6, ELEMENT RELATING TO DIFFRACTION [NOTE 4], LIGHT-REFLECTING ELEMENT, OPTICAL-PHASE CONVERSION ELEMENT [NOTE 5], WAVEGUIDE DEVICE (OPTICAL FIBER/OPTICAL WAVEGUIDE) | |
| OPTICAL PATH DIVIDING OPERATION | WAVE FRONT DIVIDING | | |
| | AMPLITUDE DIVIDING | REFLECTING/TRANSMITTING ELEMENT OF A POLARIZED NATURE, ANALYZER, PHASE PLATE | |

[NOTE 1] AT THE SPATIALLY IDENTICAL REGION (LIGHT COMBINING/MIXING POSITION), BEAMS OF THE LIGHT TO BE COMBINED/MIXED MAY HAVE THE SAME TRAVELING DIRECTION. THE BEAMS OF LIGHT TO BE COMBINED/MIXED MAY HAVE THE SAME VIBRATING-PLANE DIRECTION OF THE ELECTRIC FIELD. AT THE SPATIALLY IDENTICAL REGION, THE BEAMS OF LIGHT TO BE COMBINED/MIXED MAY HAVE THE SAME TRAVELING DIRECTION AS WELL AS THE SAME VIBRATING-PLANE DIRECTION OF THE ELECTRIC FIELD.

[NOTE 2] SPECIAL LENS INCLUDES A LENS IN AN ASPHERICAL STATE, AND SPECIFICALLY INCLUDES A LENTICULAR LENS, A CYLINDRICAL LENS, OR A FRESNEL LENS.

[NOTE 3] REFRACTIVE ELEMENT INCLUDES A SPHERICAL LENS, AN ASPHERICAL LENS, A FRESNEL LENS, A PRISM OR A PARALLEL FLAT PLATE.

[NOTE 4] ELEMENT RELATING TO DIFFRACTION INCLUDES A DIFFRACTING GRATING AND A HOLOGRAM ELEMENT, AND MAY BE BLAZED TO HAVE AN INCLINED MICROSCOPIC PLANE.

[NOTE 5] OPTICAL-PHASE CONVERSION ELEMENT INTERNALLY HAS A MICROSCOPIC DISTRIBUTION OF REFRACTIVE INDEX OR HAS MICROSCOPIC ASPERITIES AT THE SURFACE TO CHANGE THE PHASE OF TRANSMITTED LIGHT OR REFLECTED LIGHT LOCALLY. OPTICAL-PHASE CONVERSION ELEMENT INCLUDES A RANDOM PHASE SHIFTER, A DIFFUSER, OR A SAND TREATMENT PLATE.

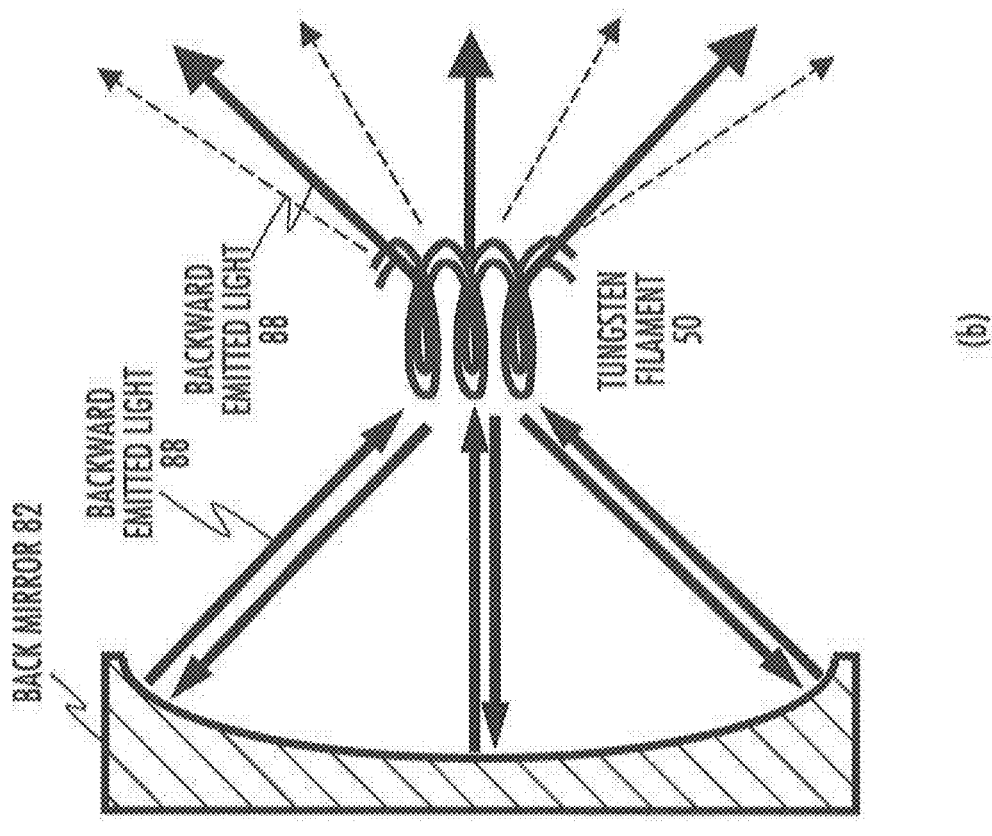
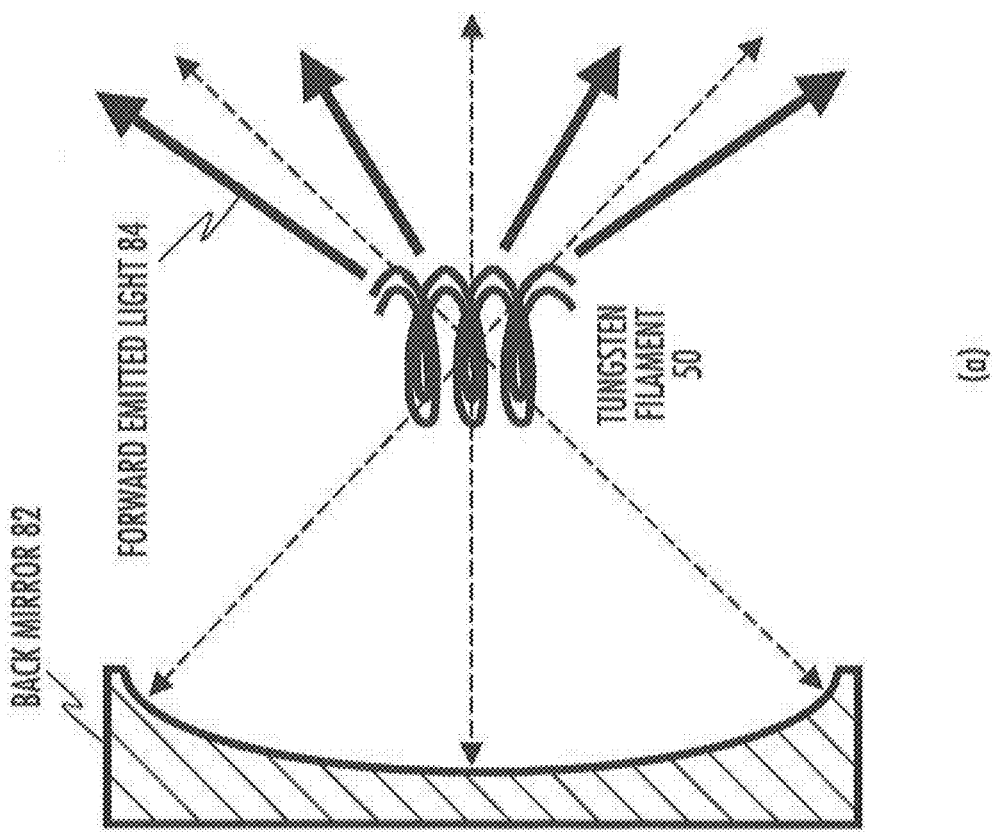
FIG. 11

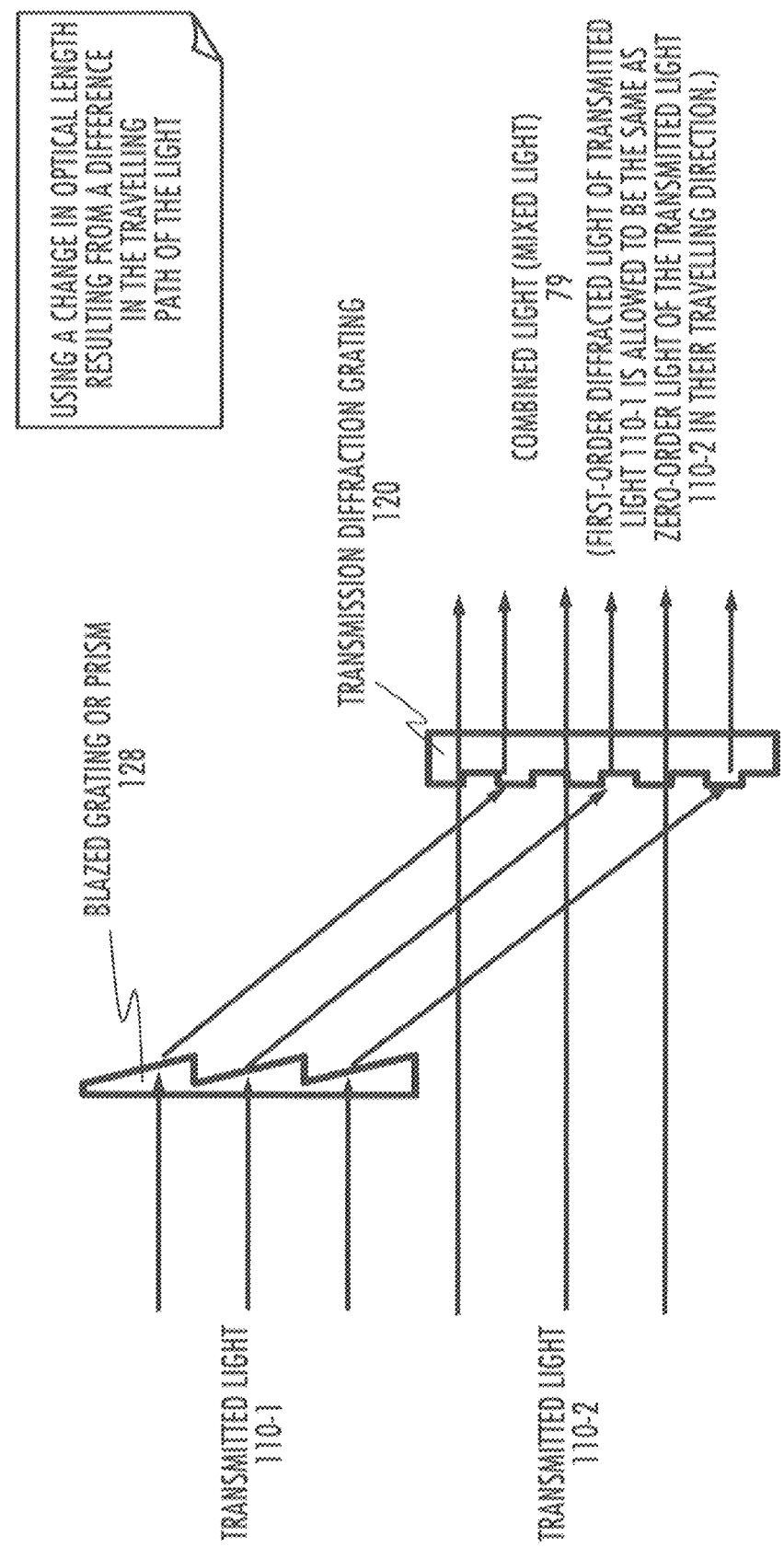

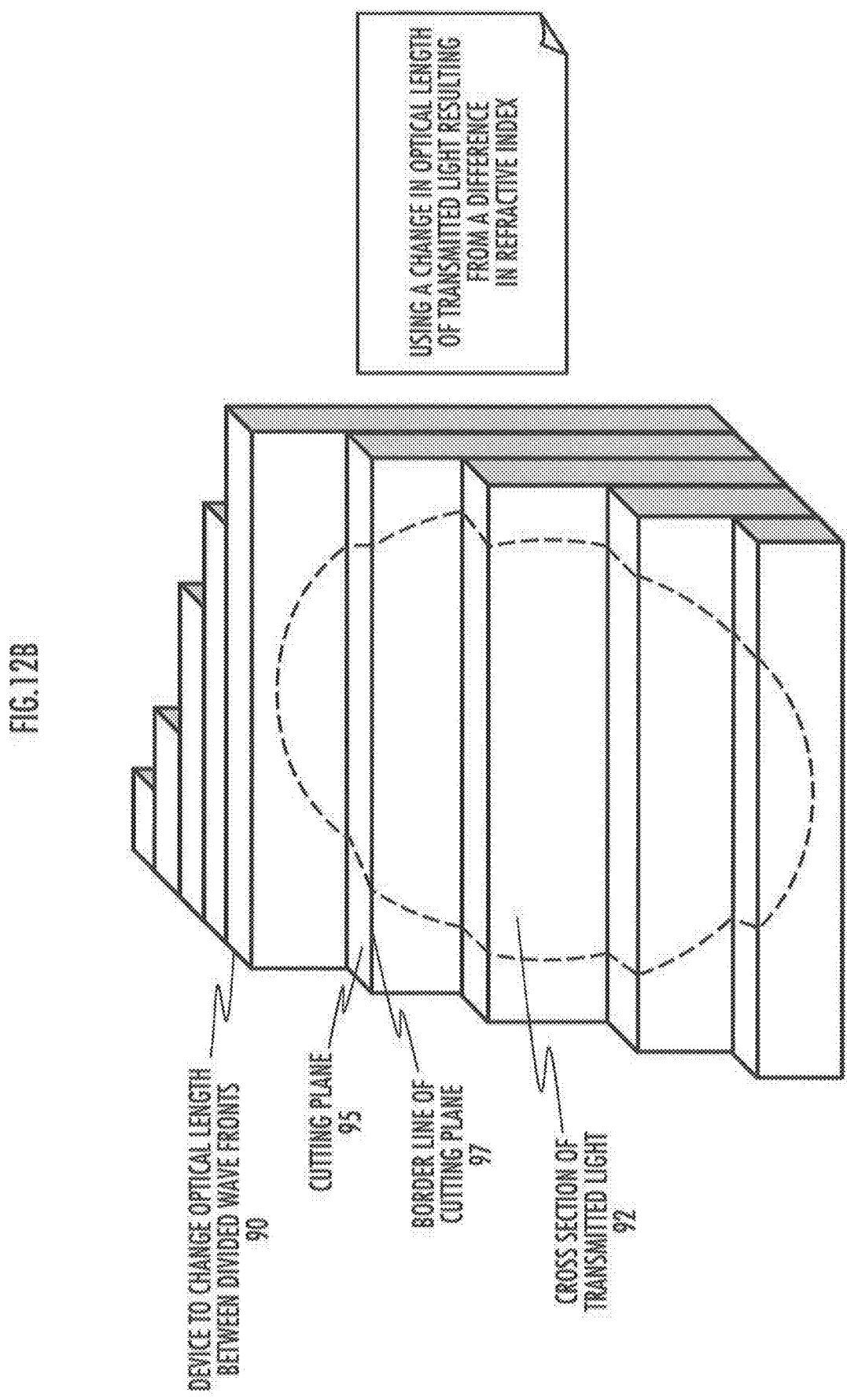

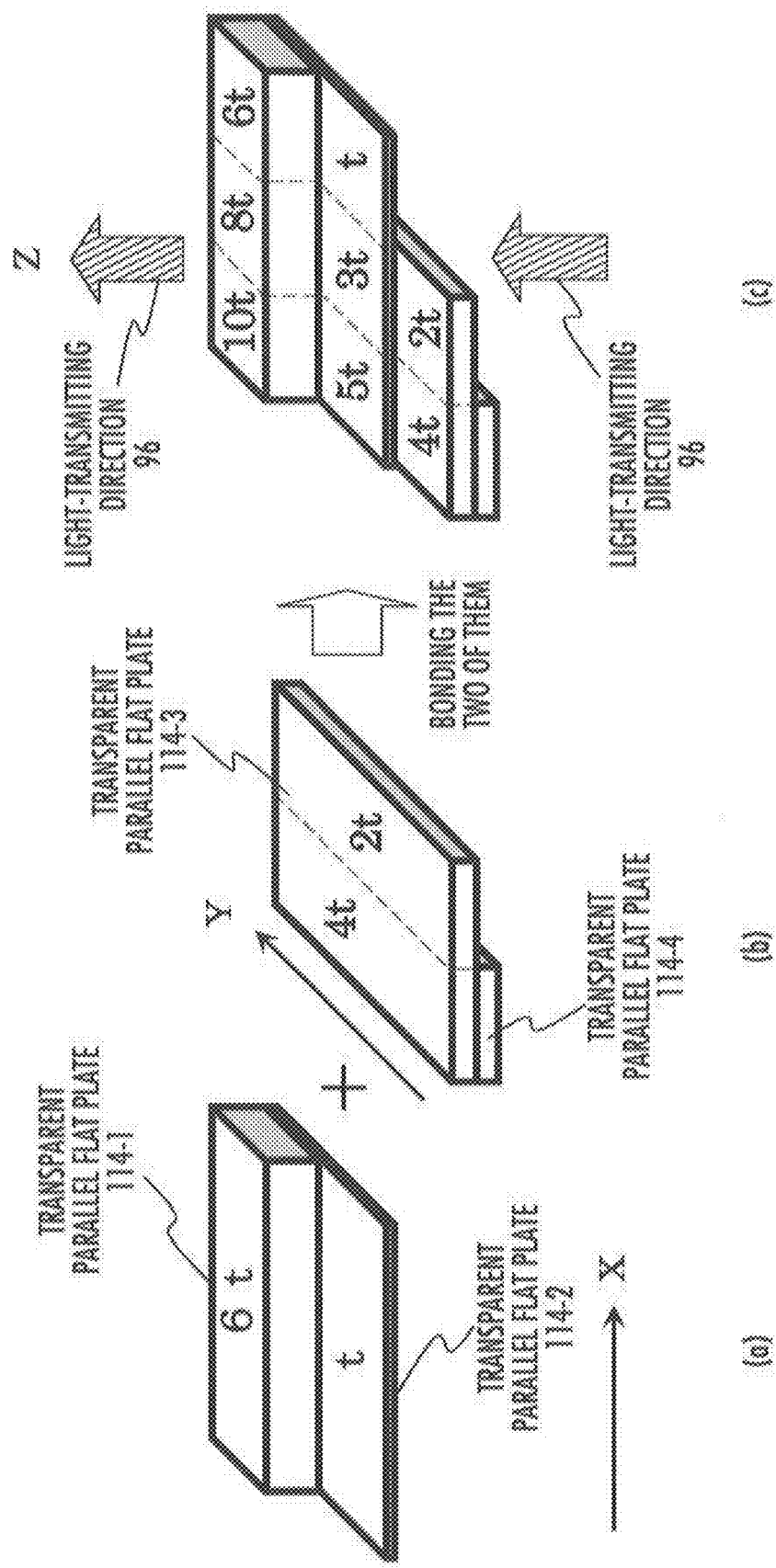

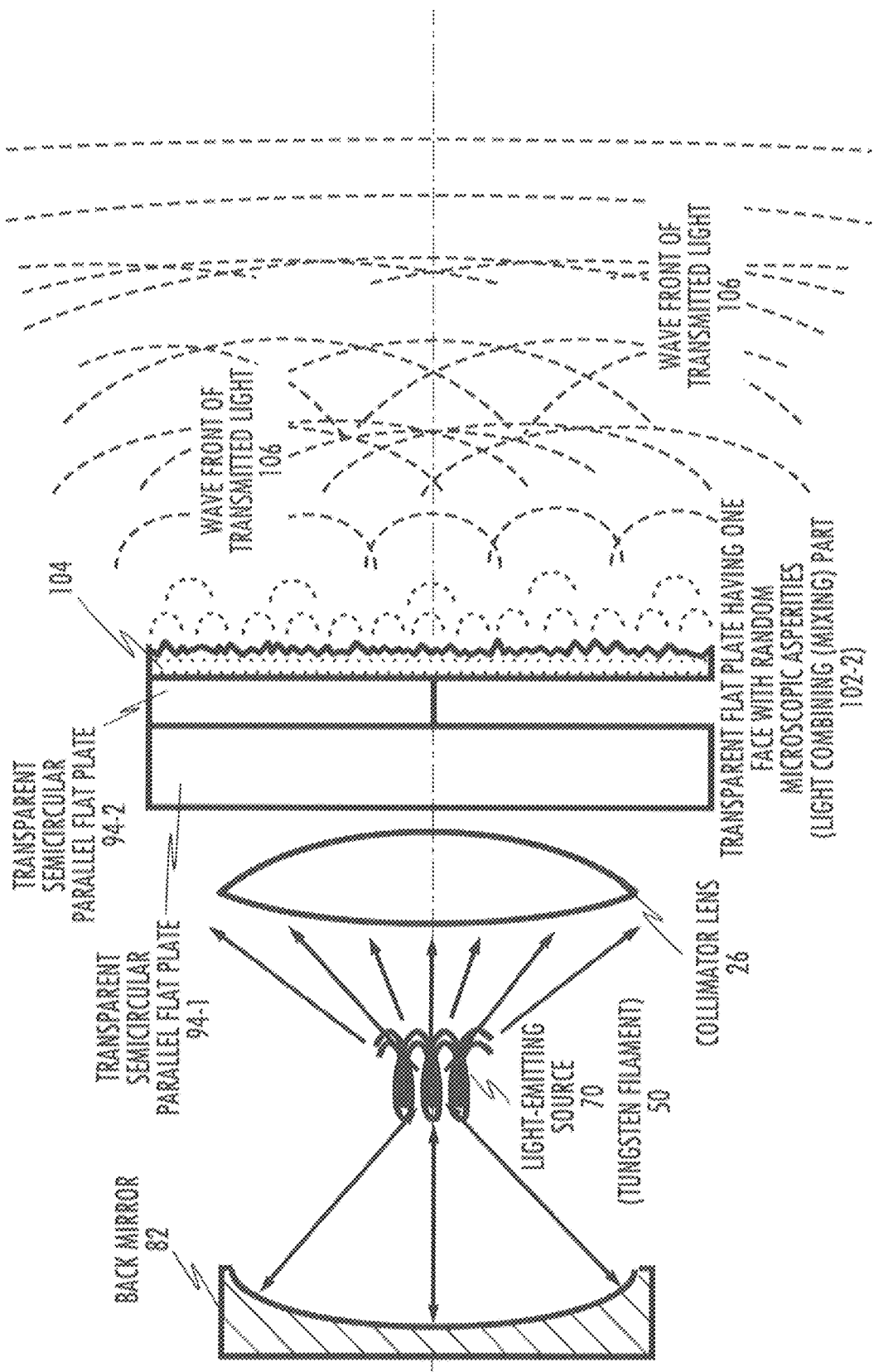

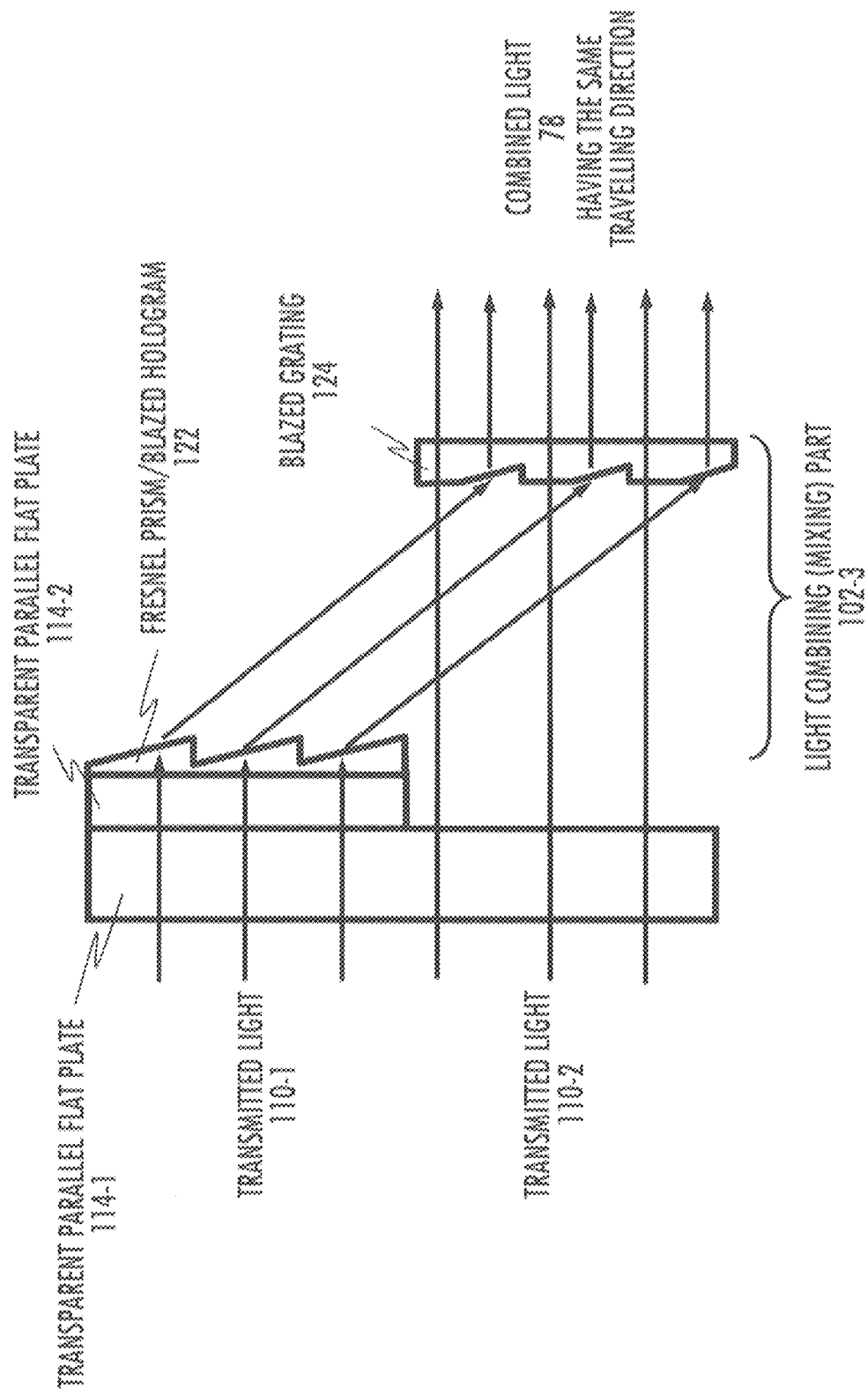

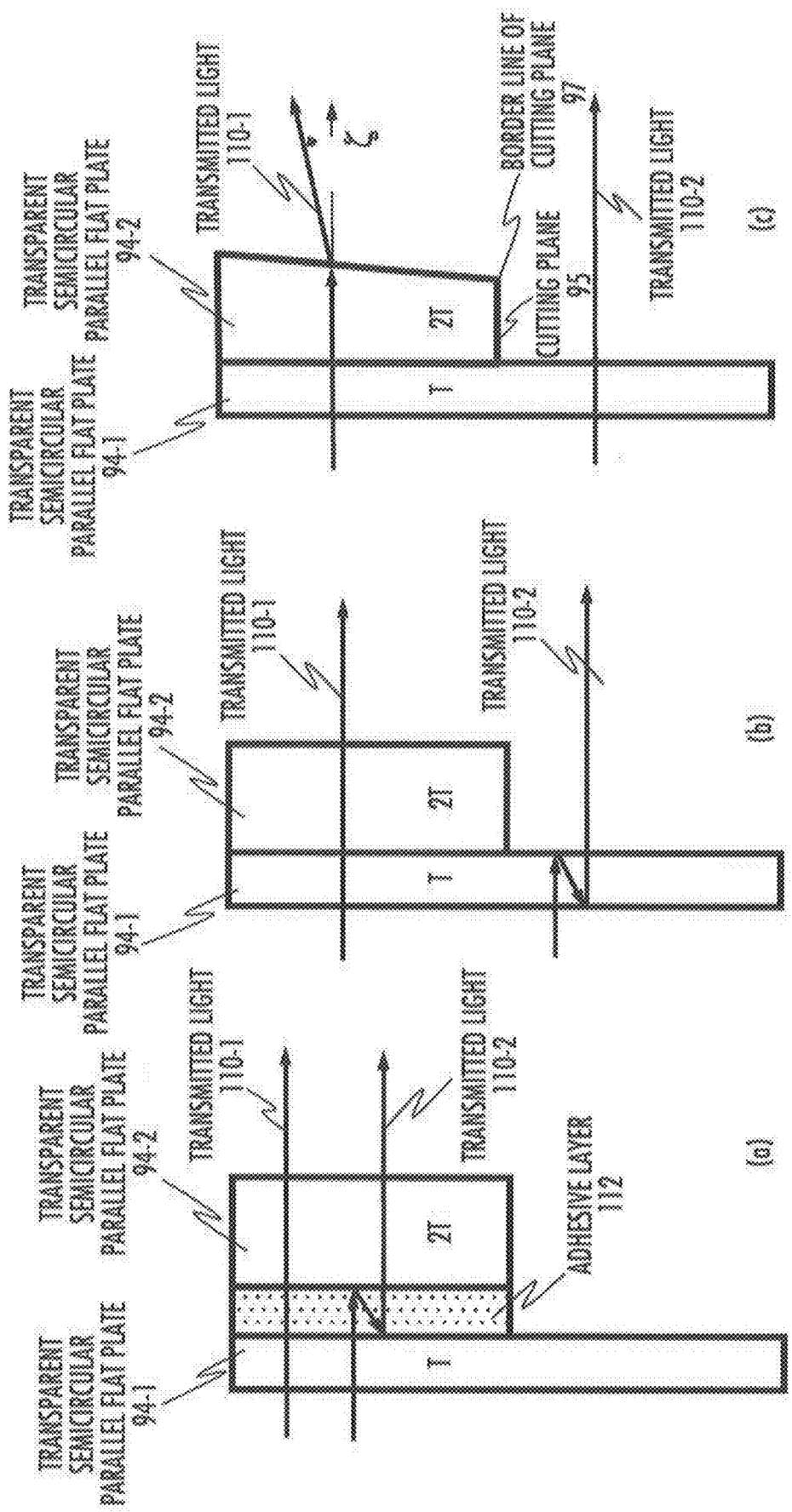

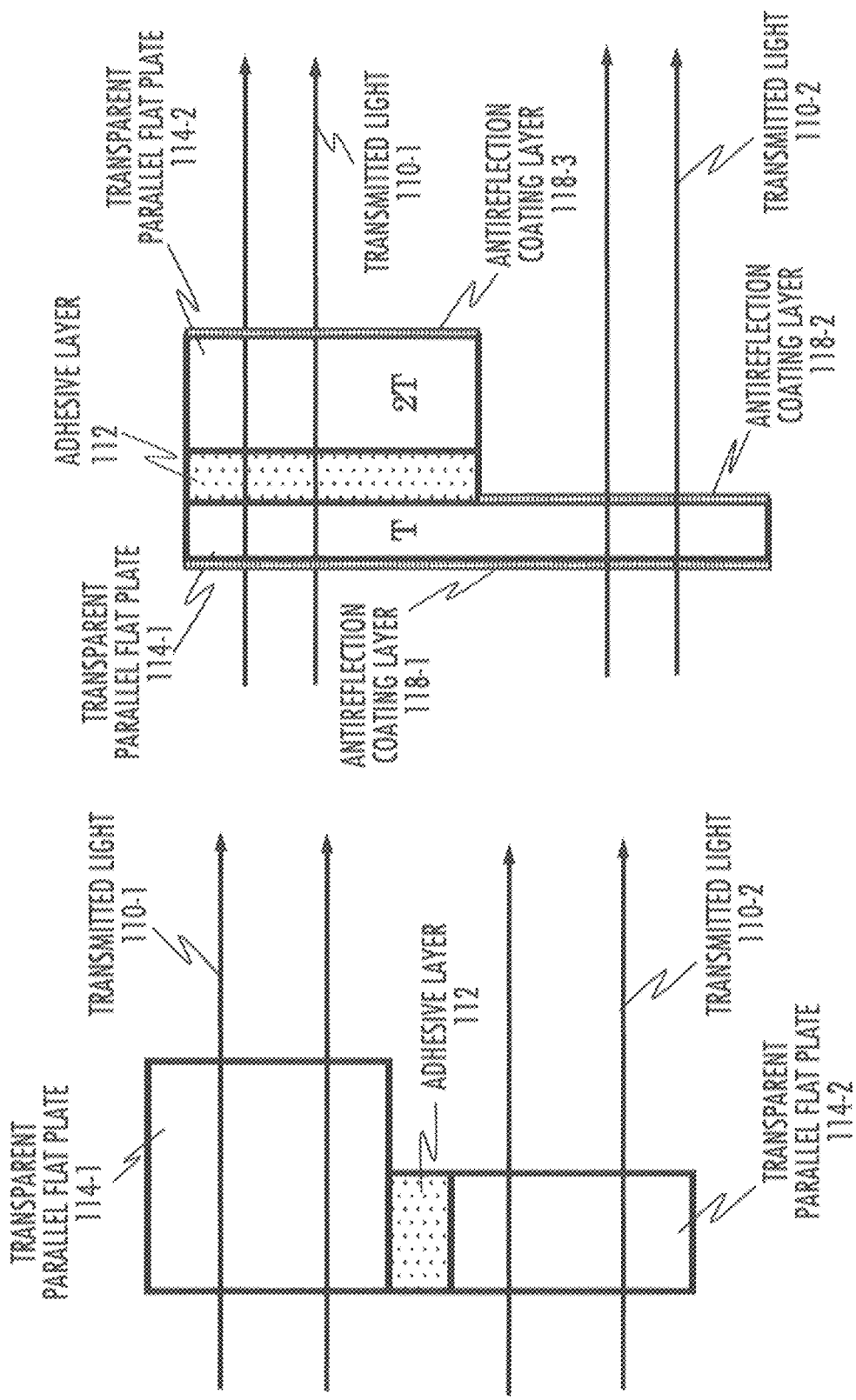

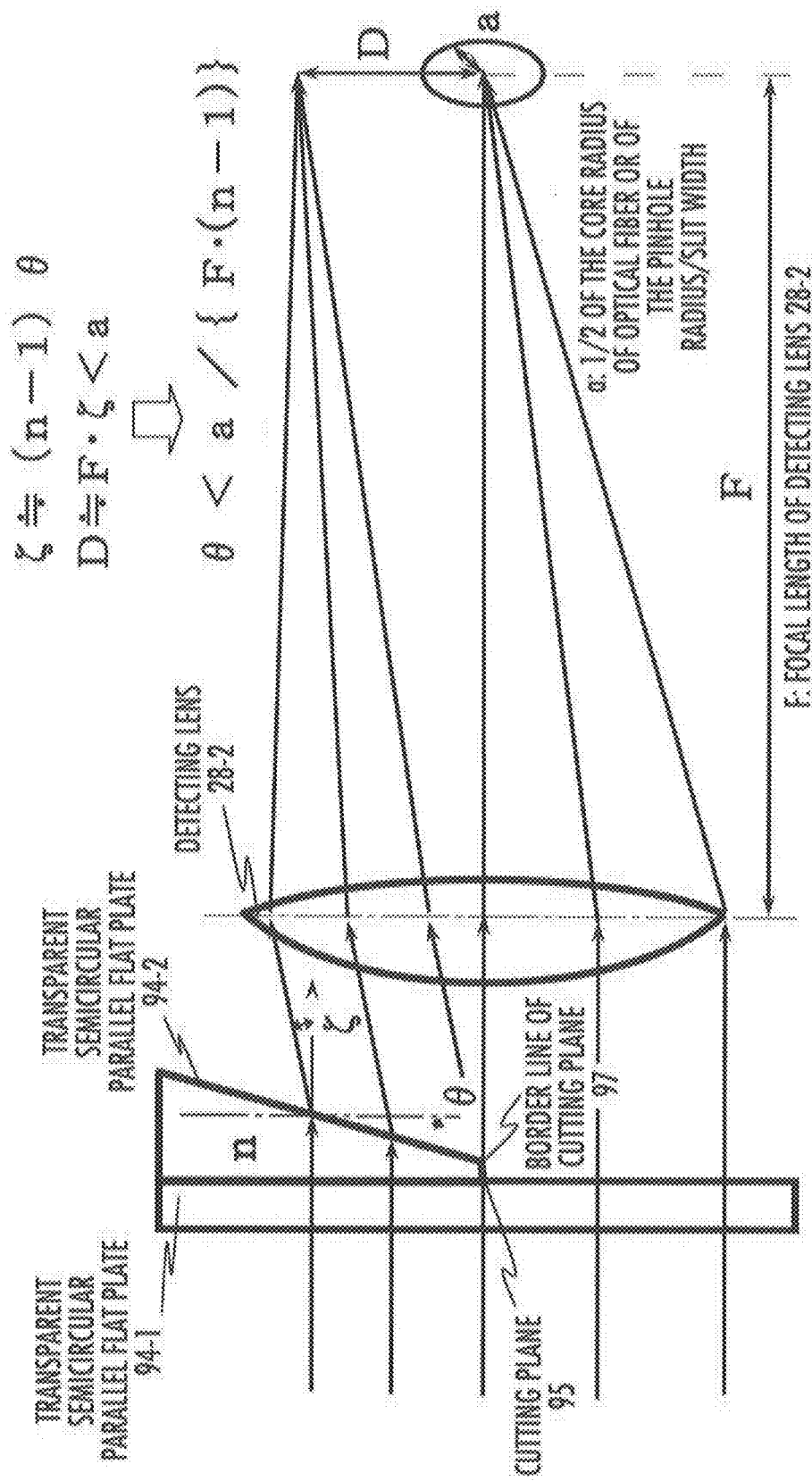

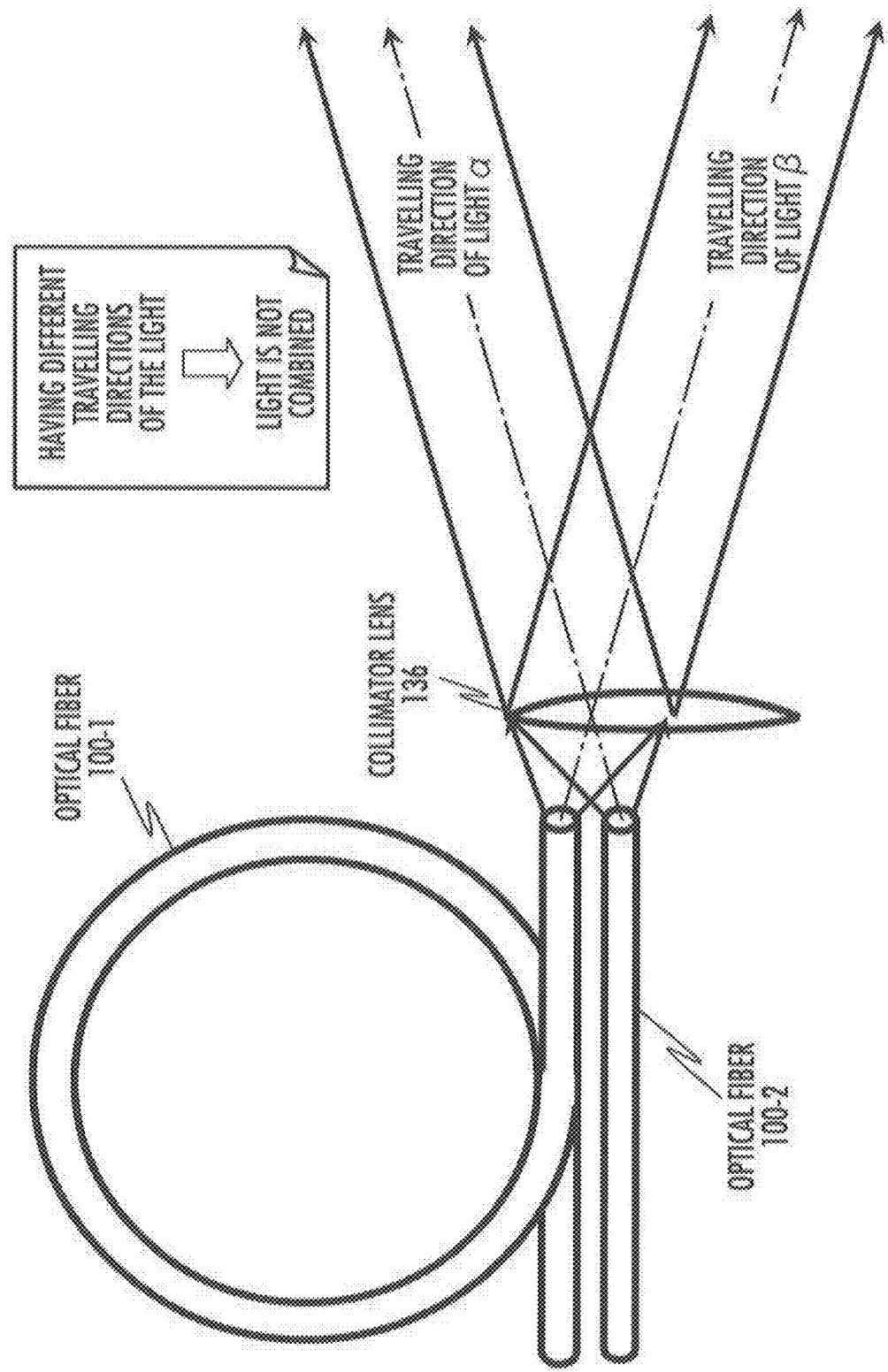

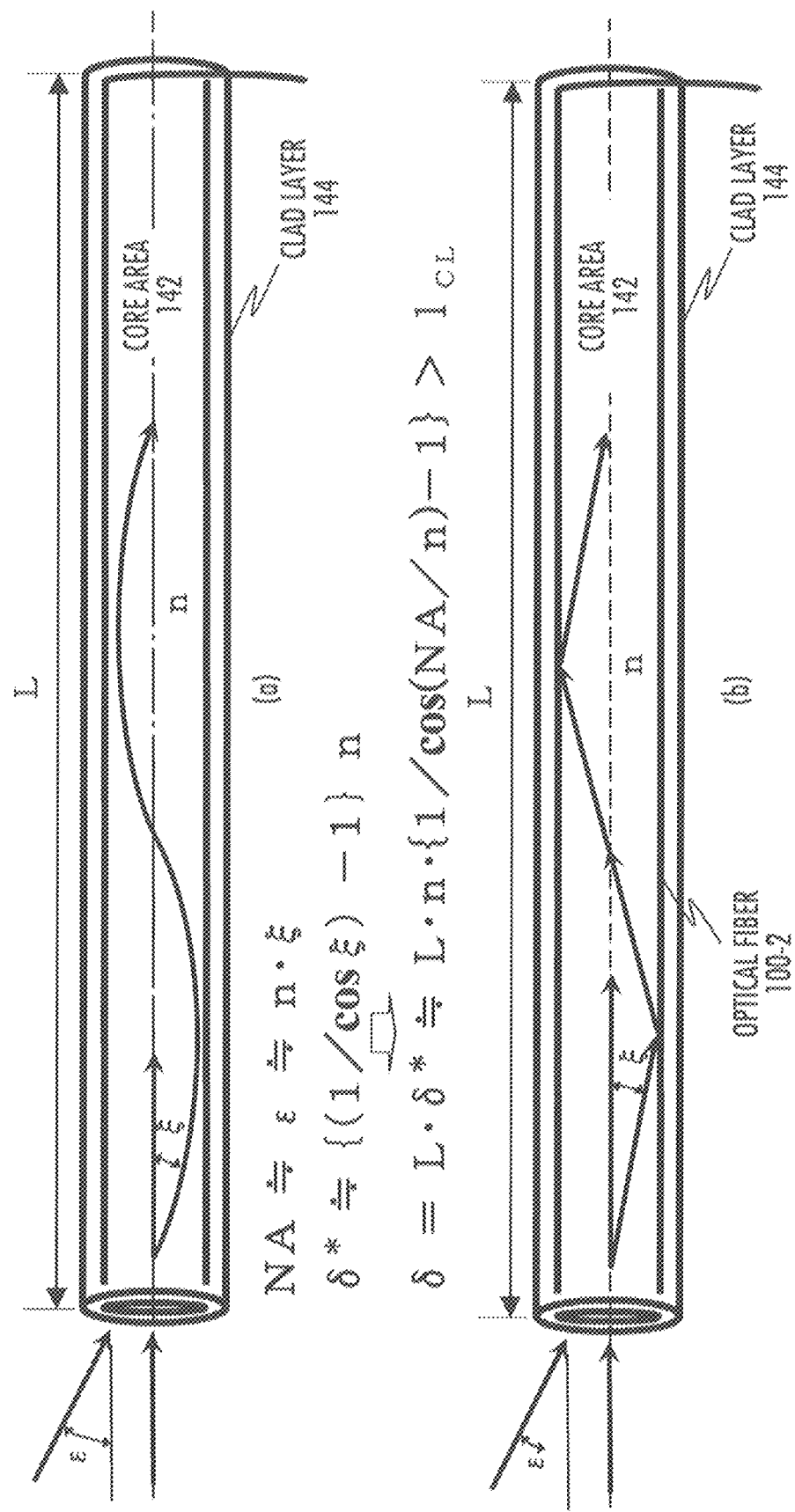

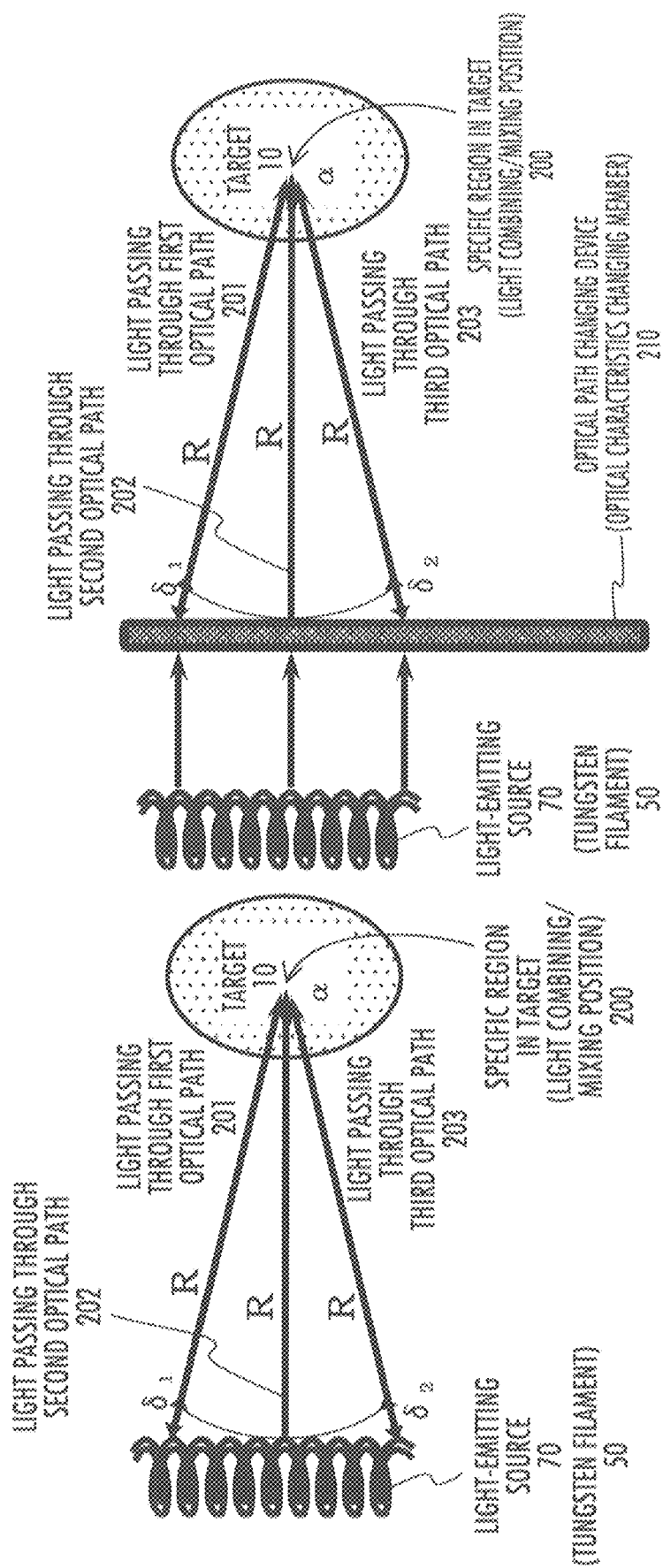

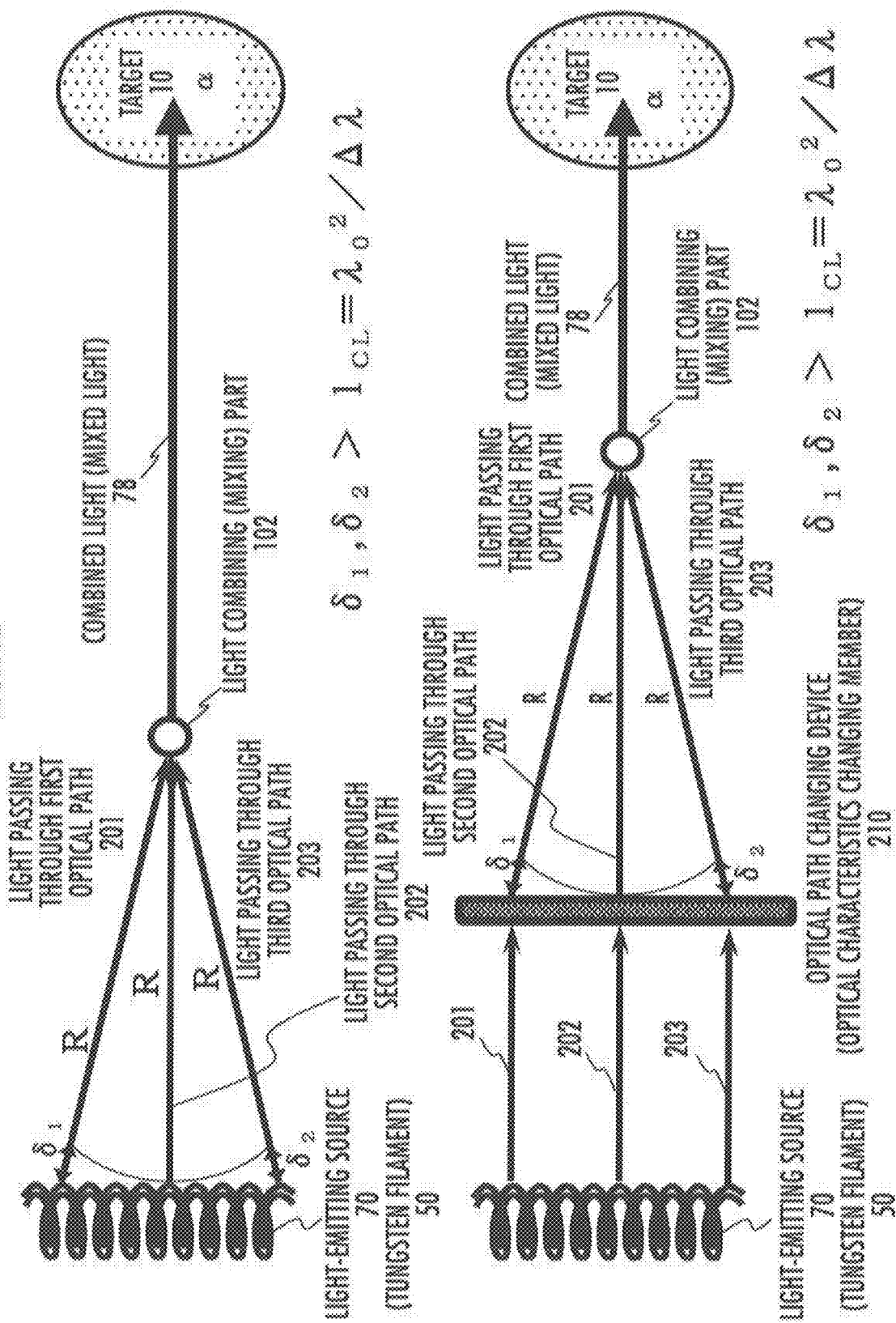

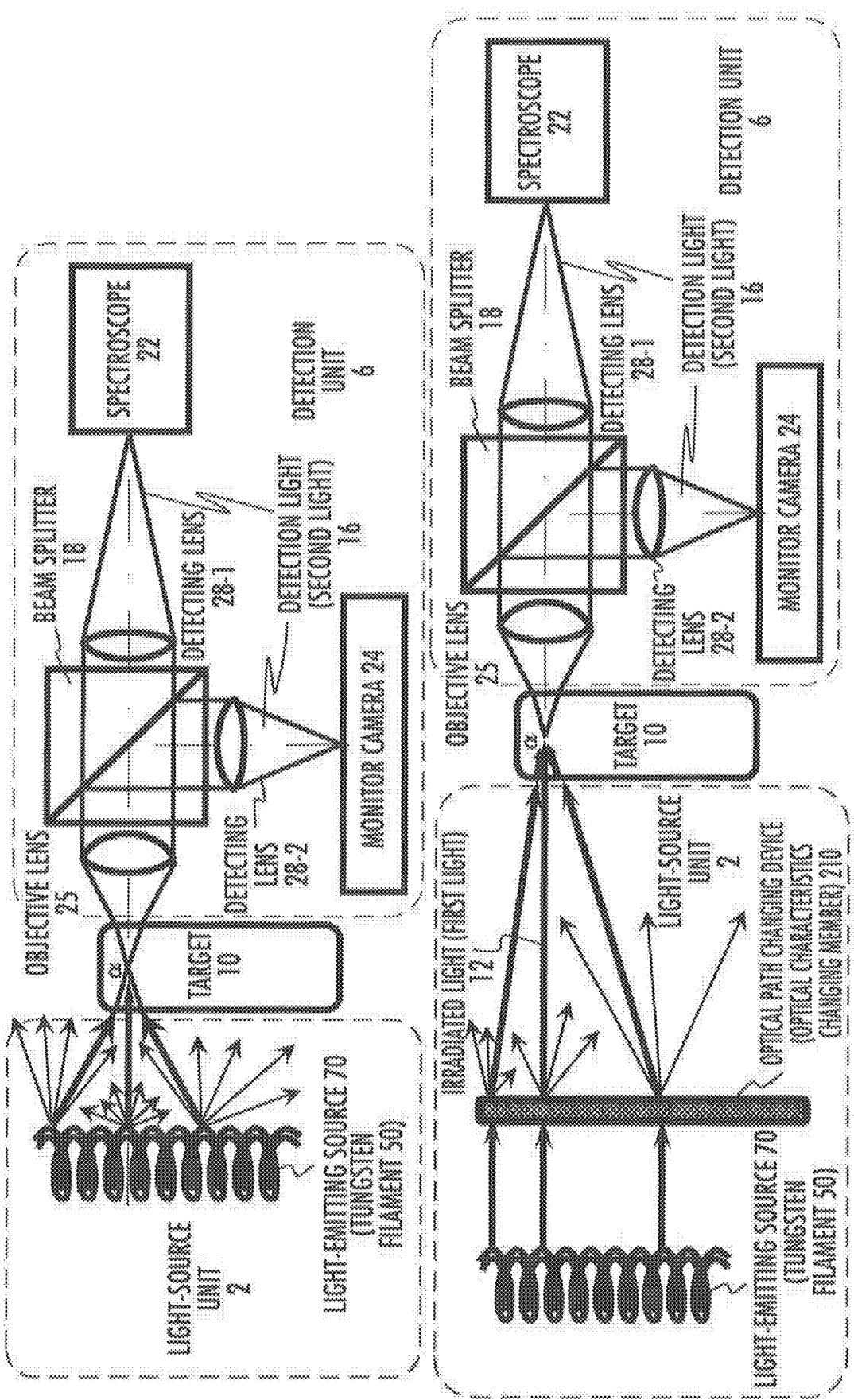

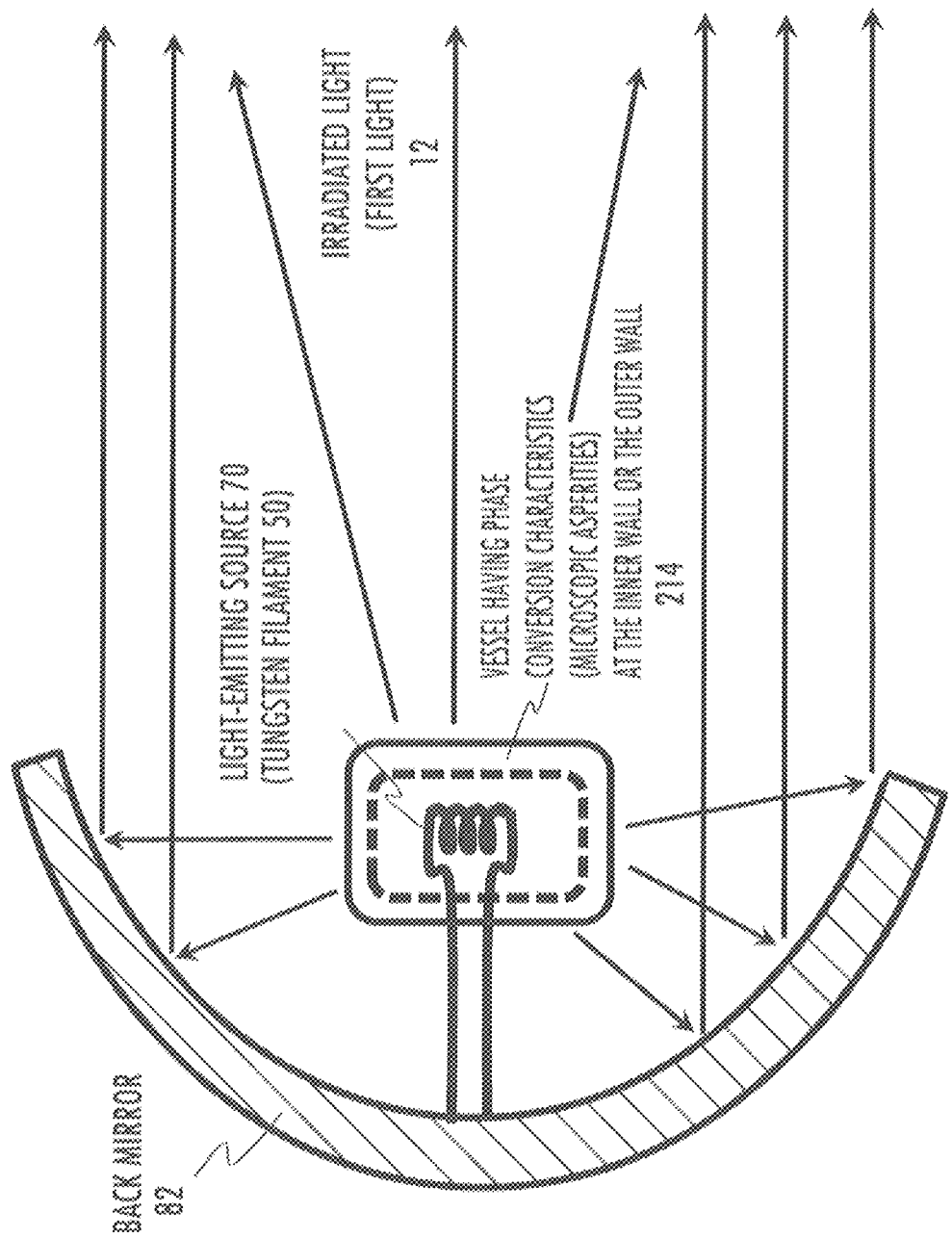

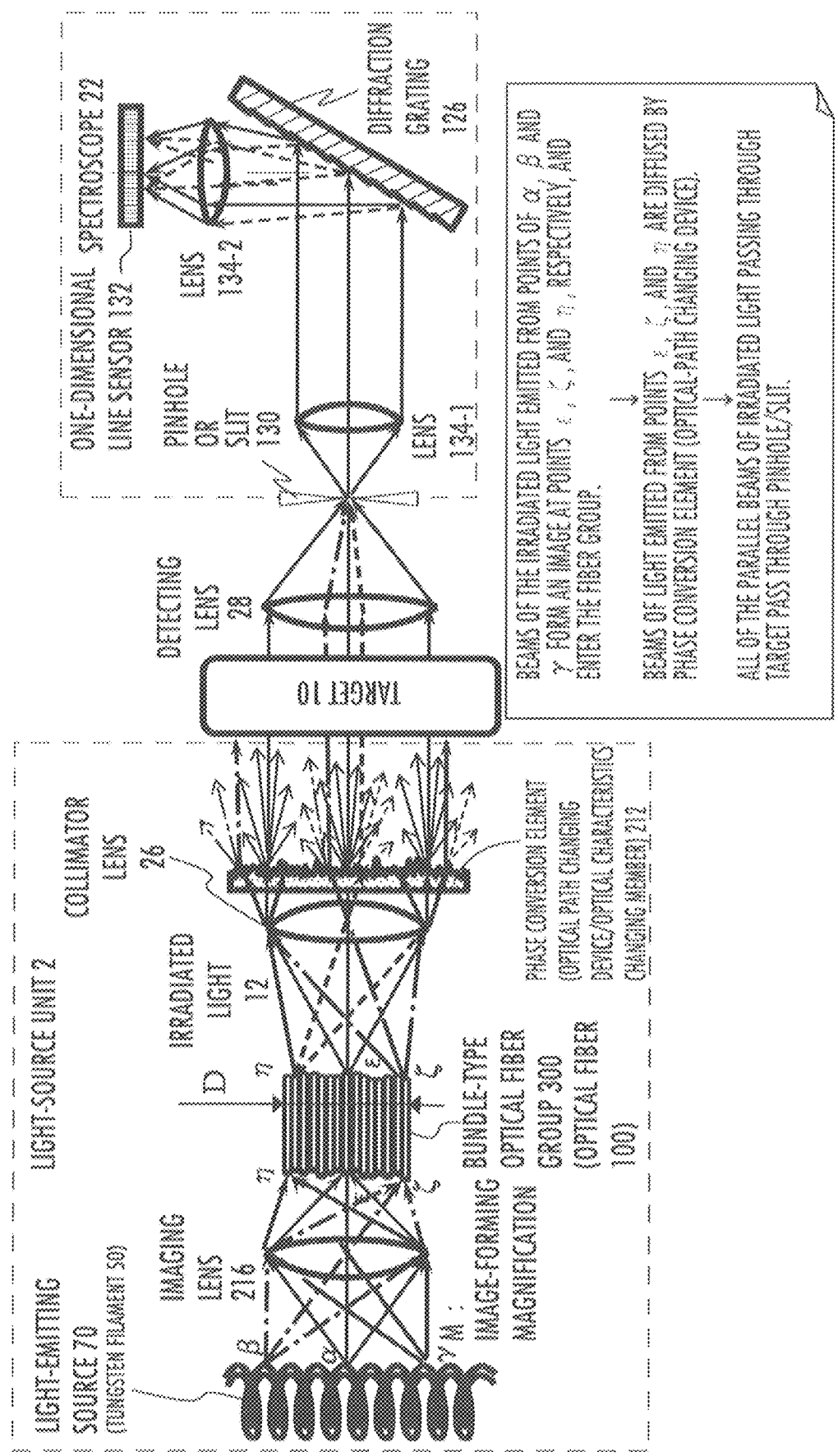

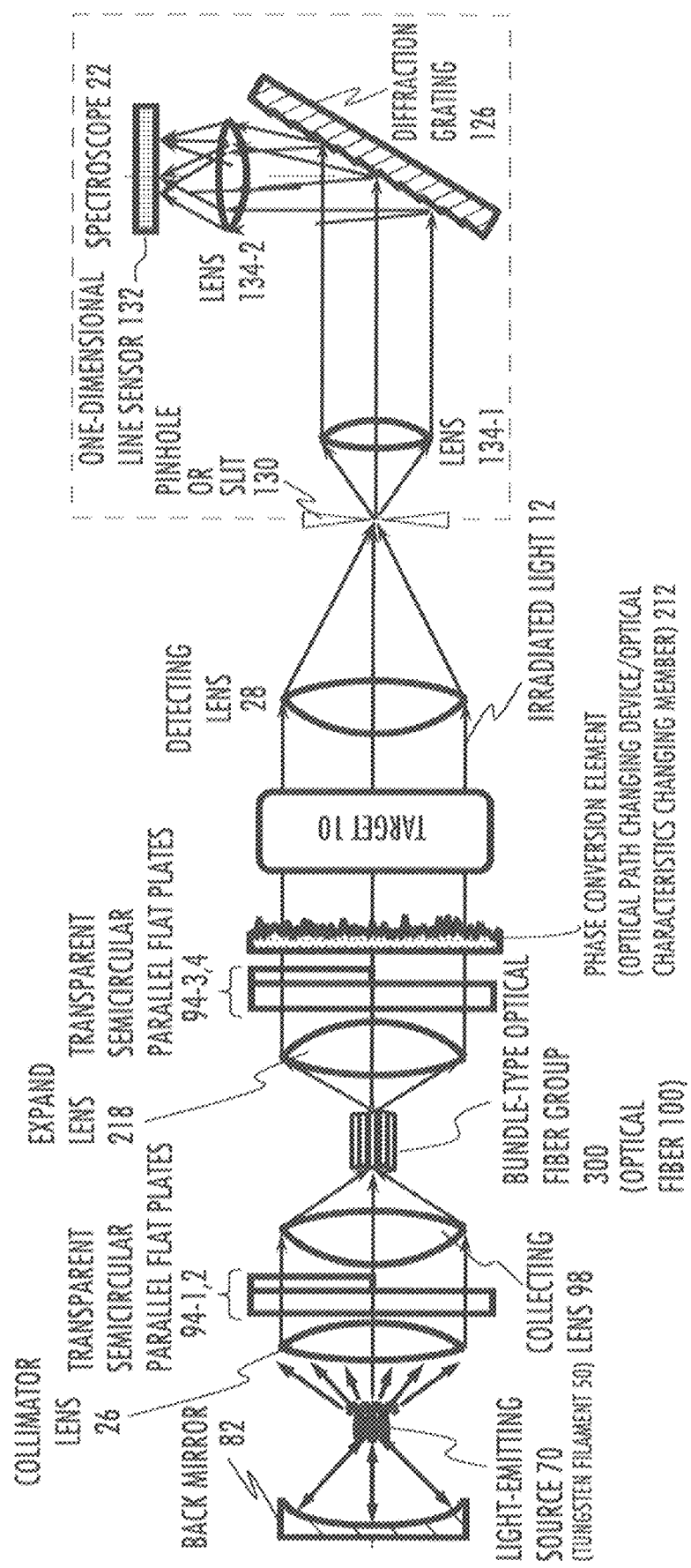

FIG. 23A
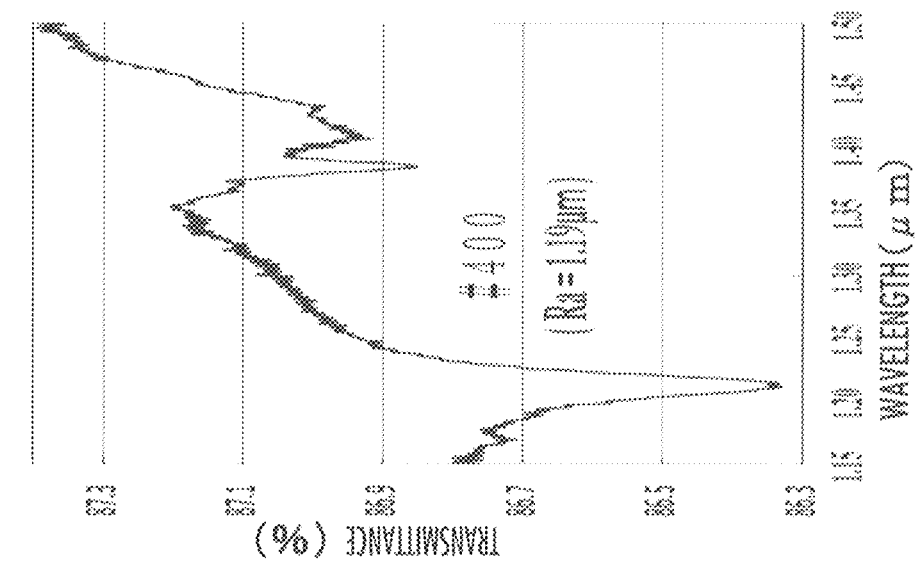
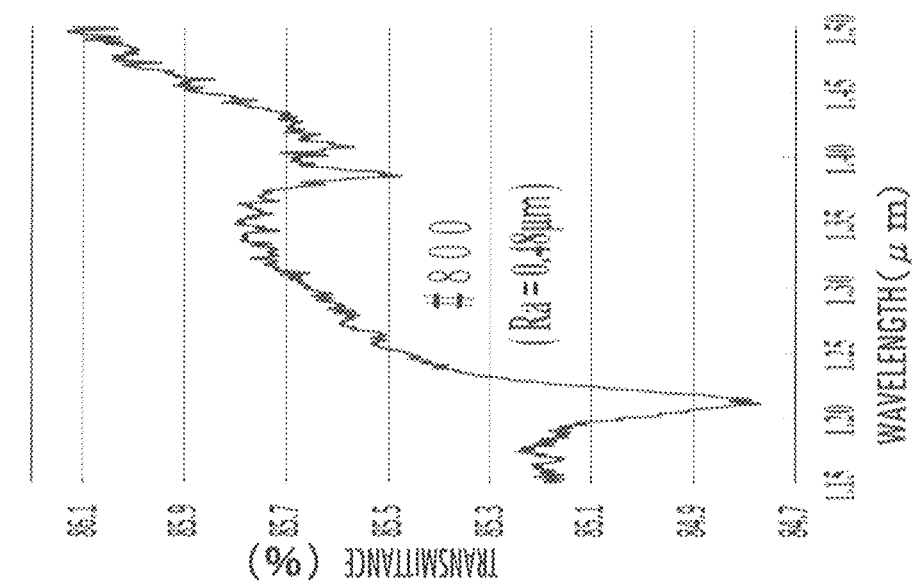
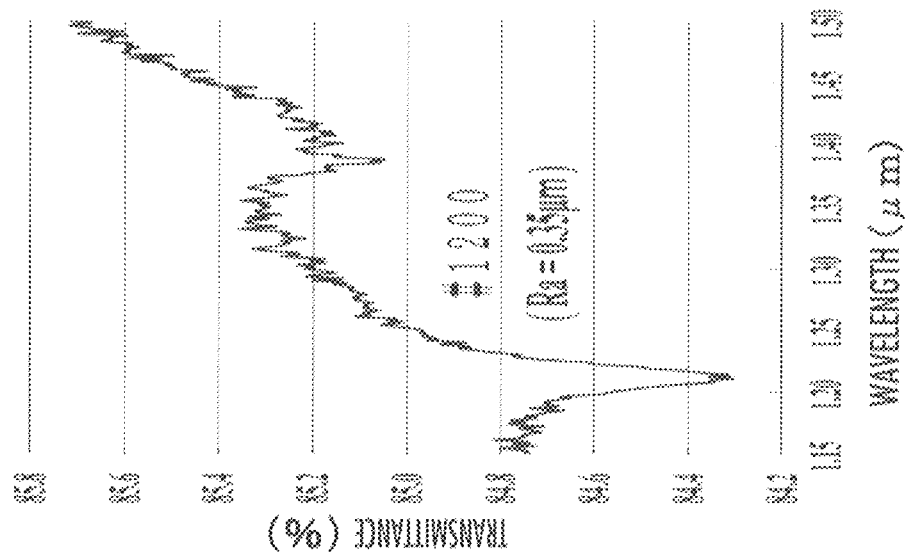

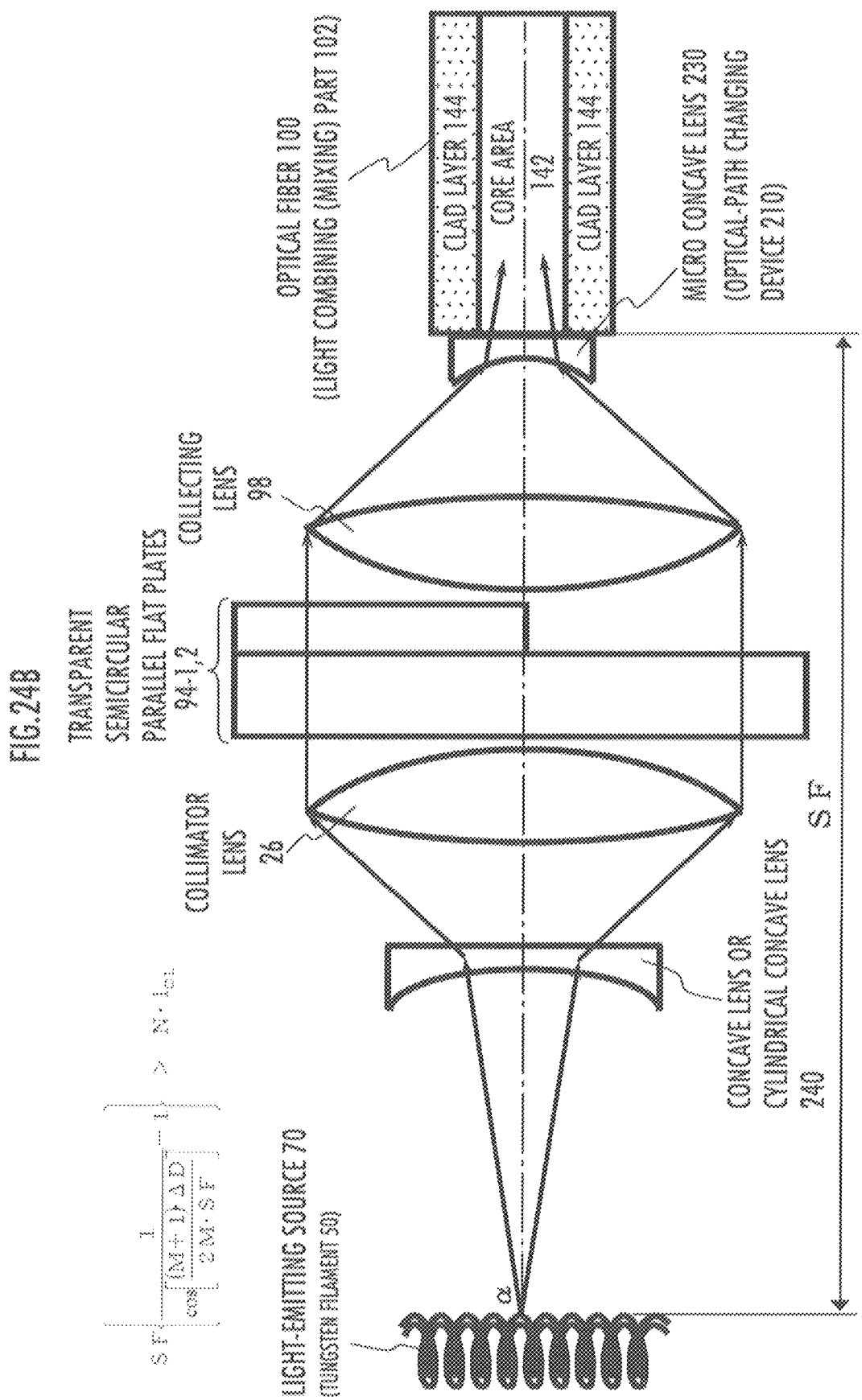

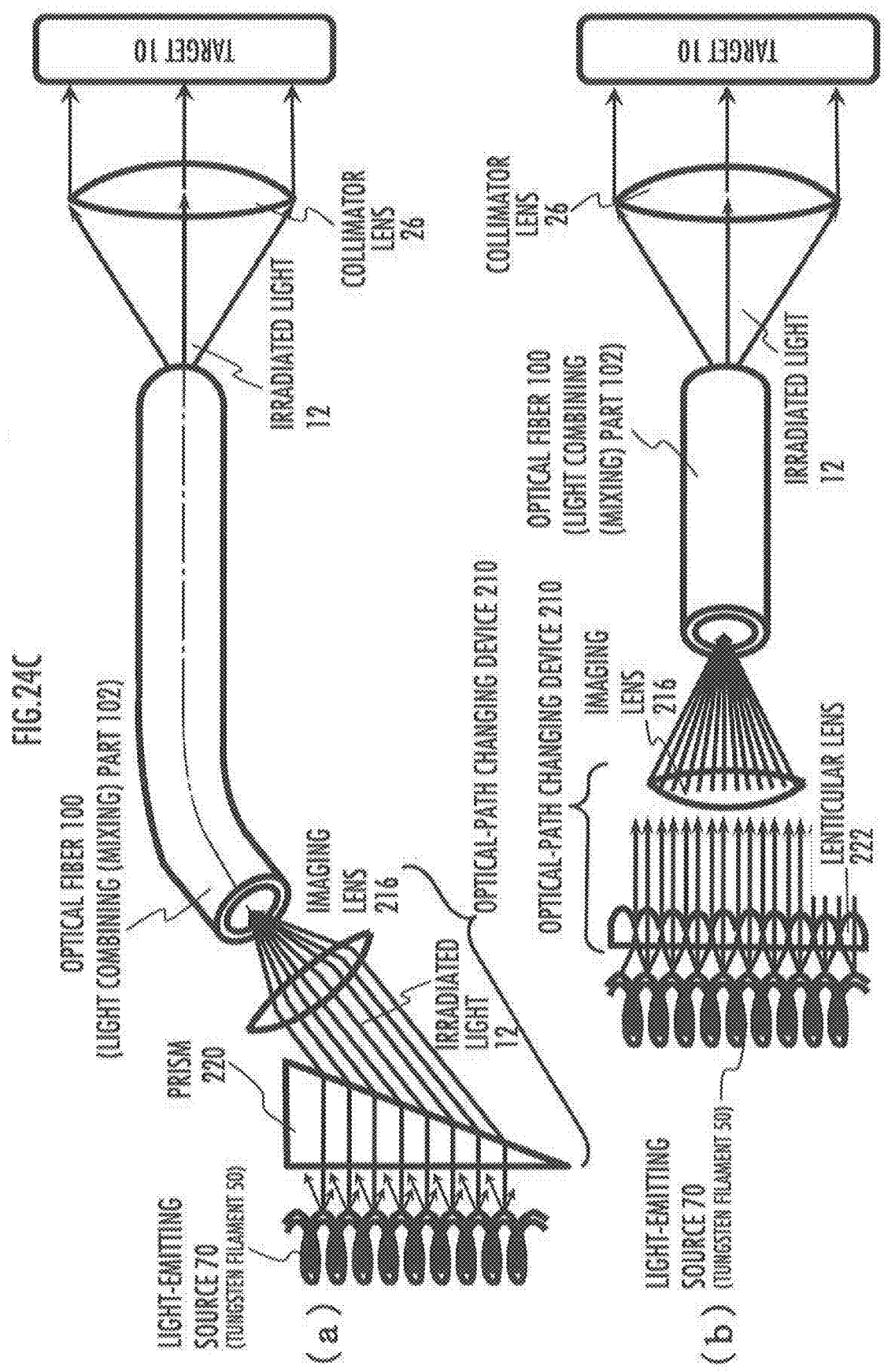

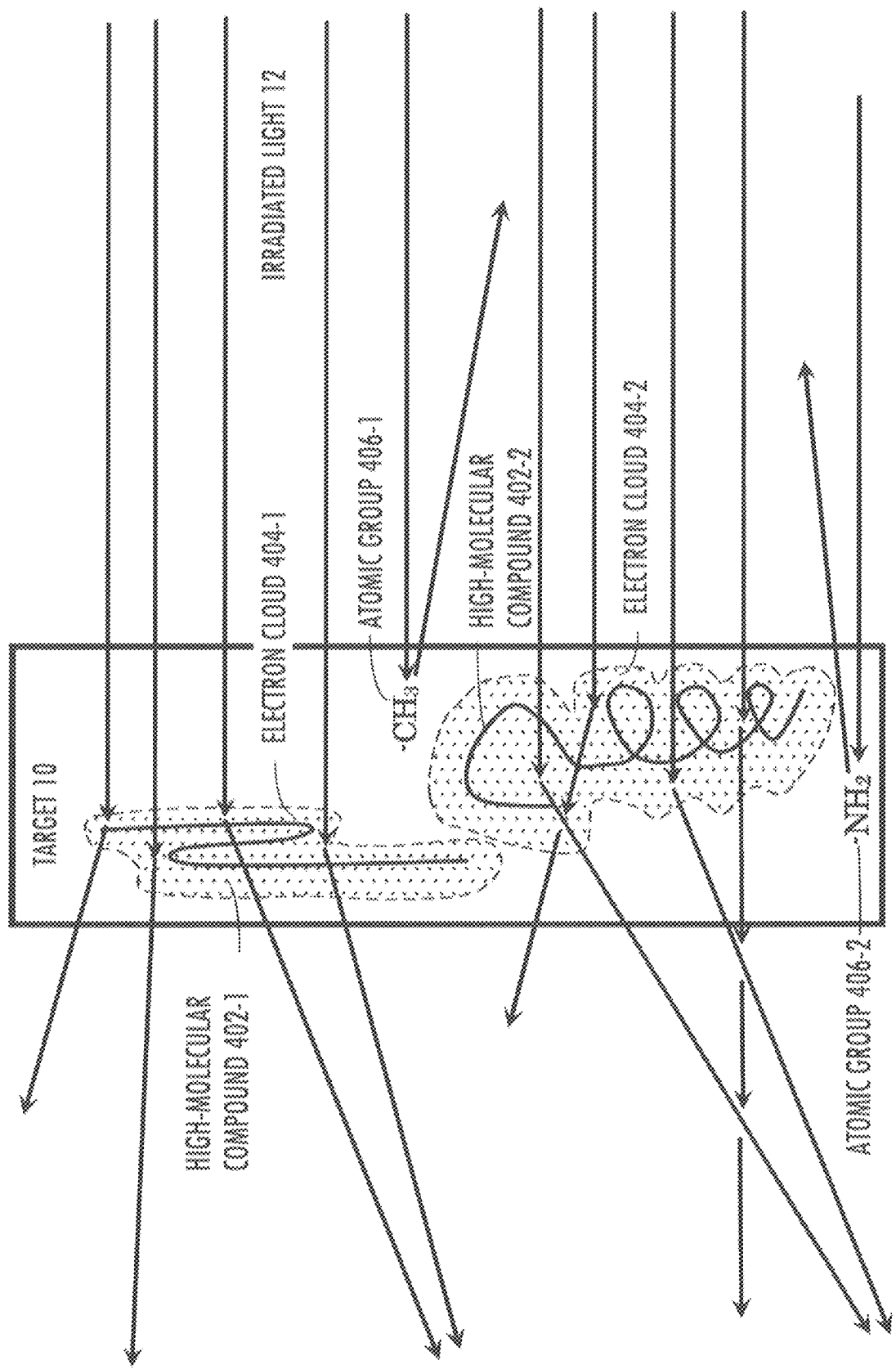

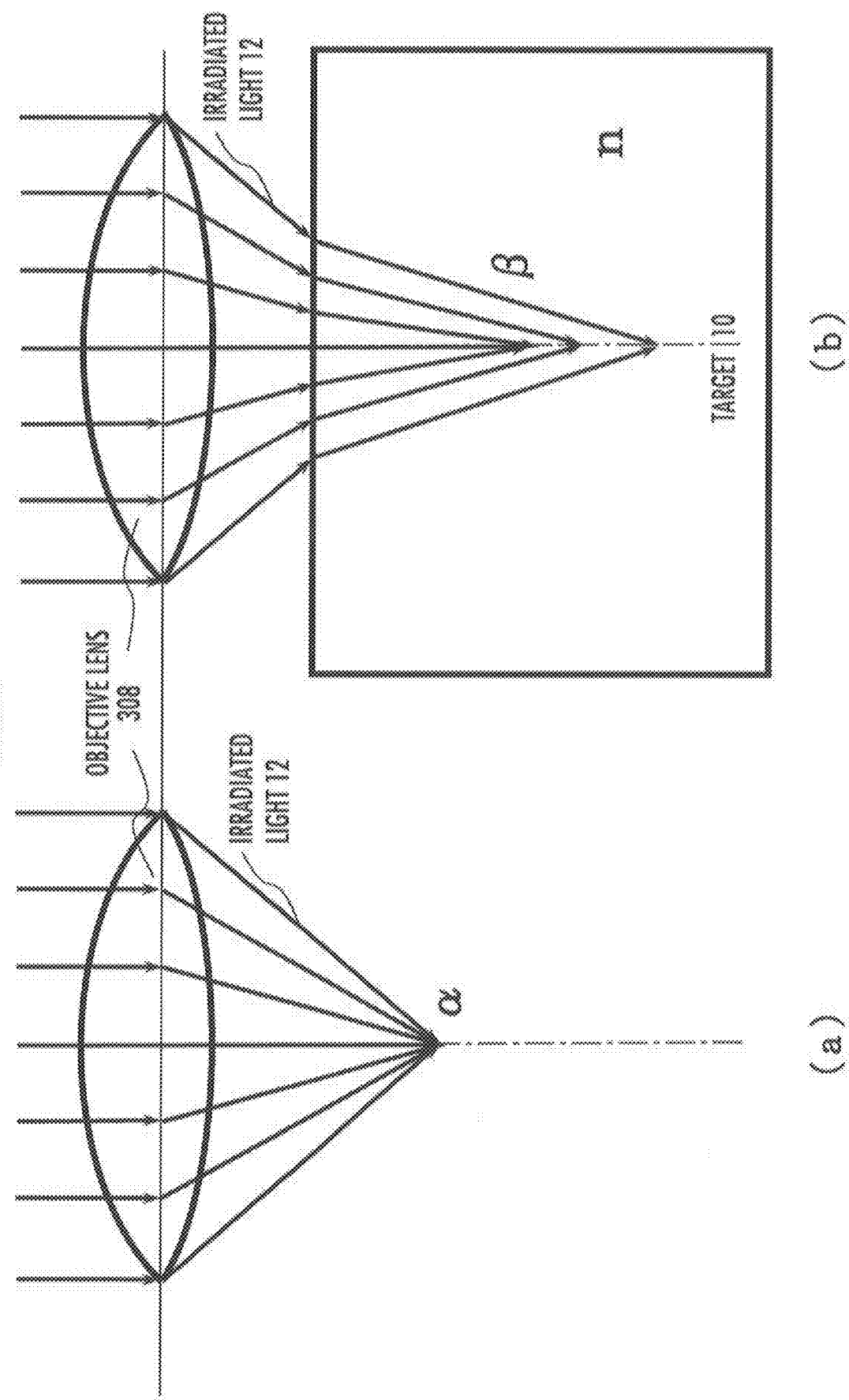

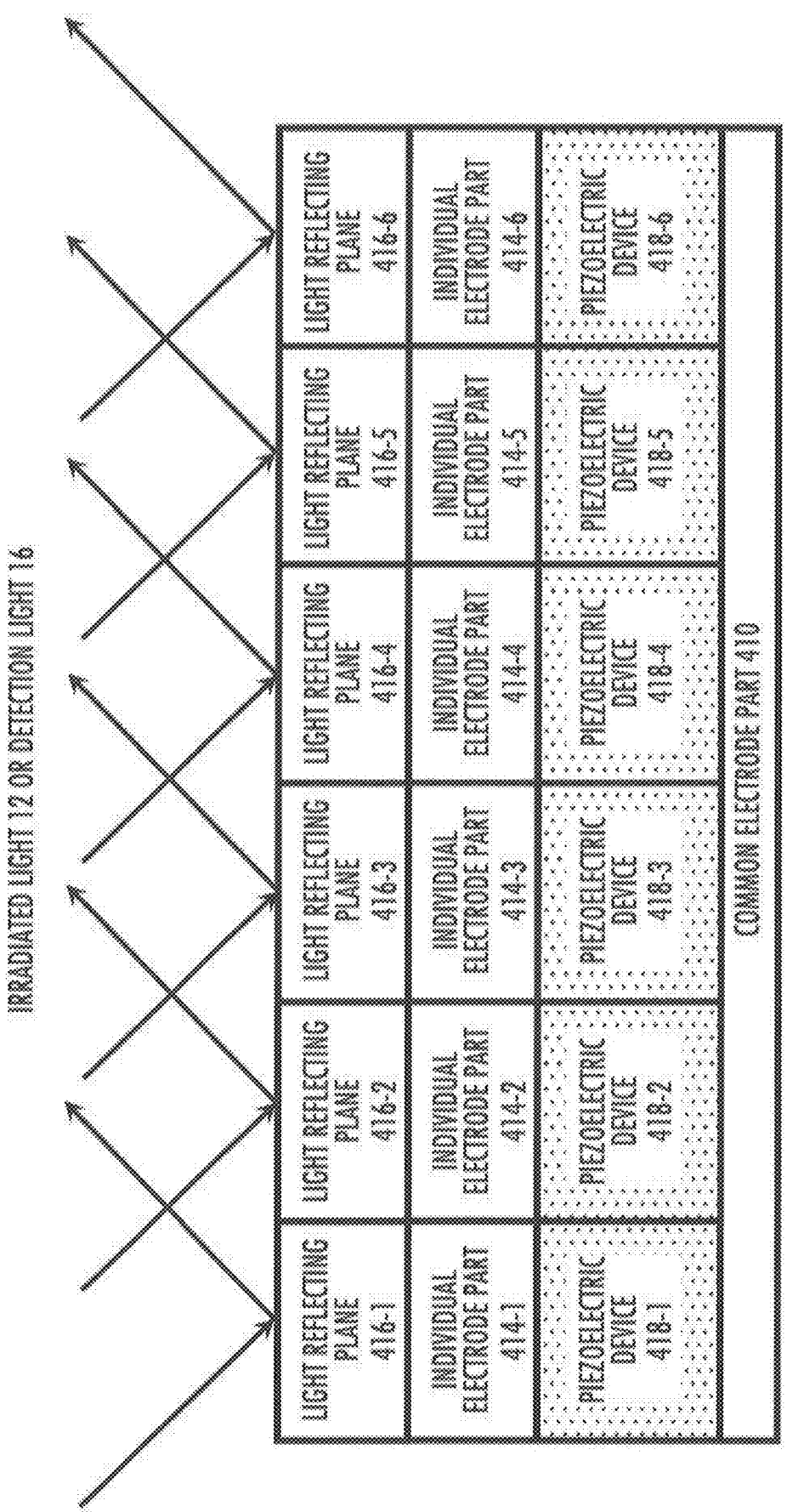

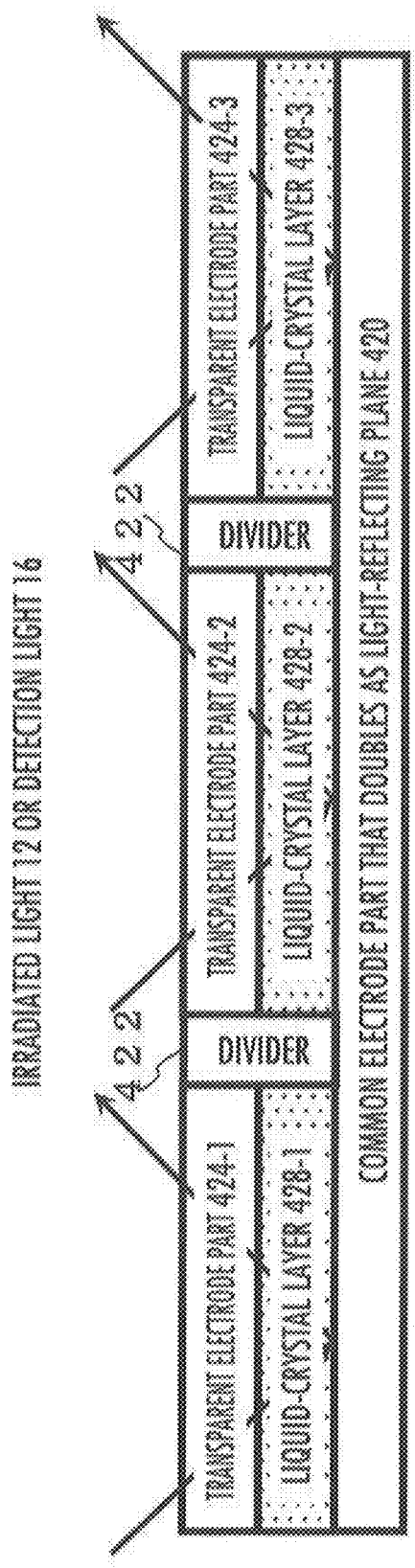

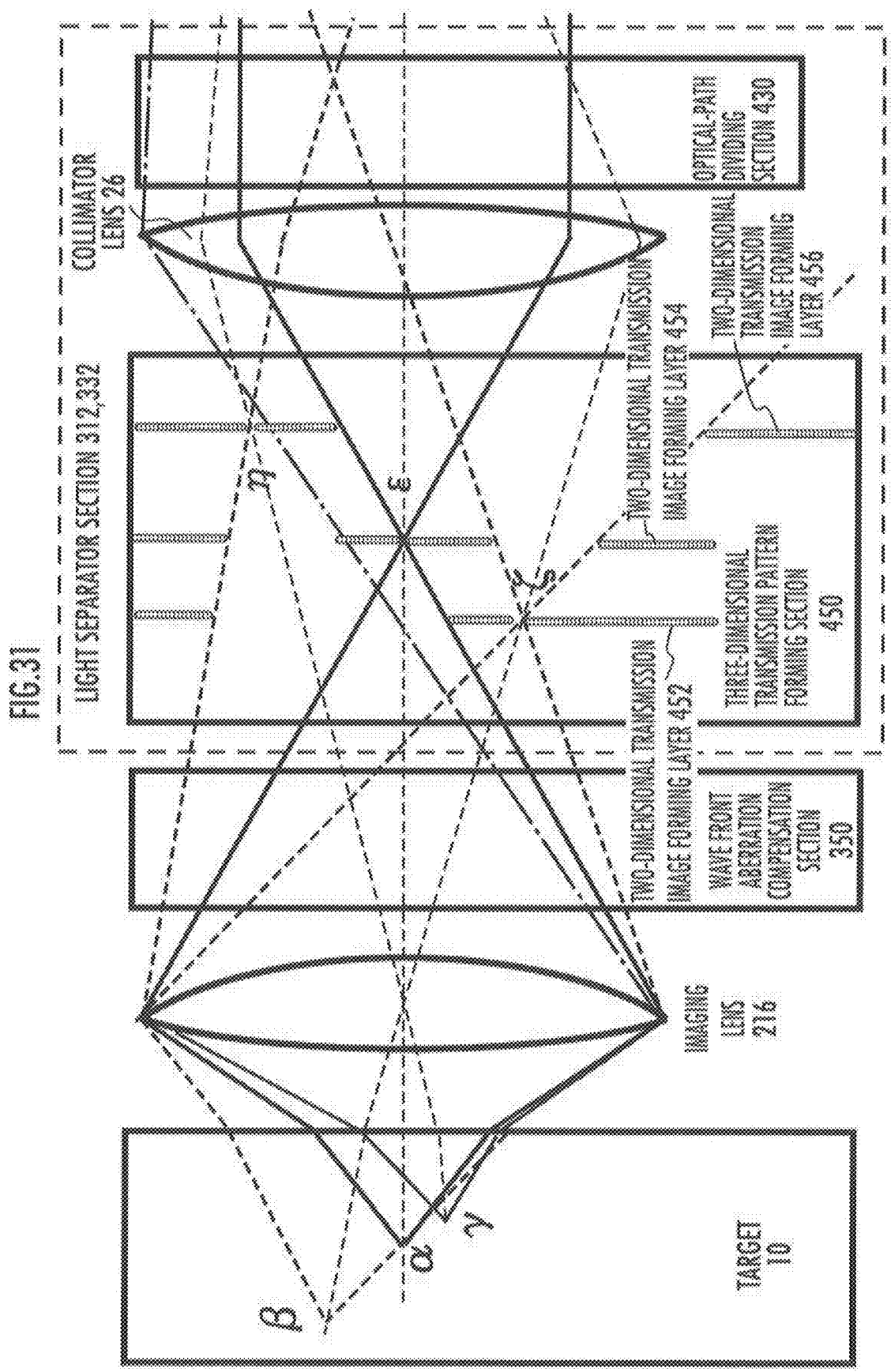

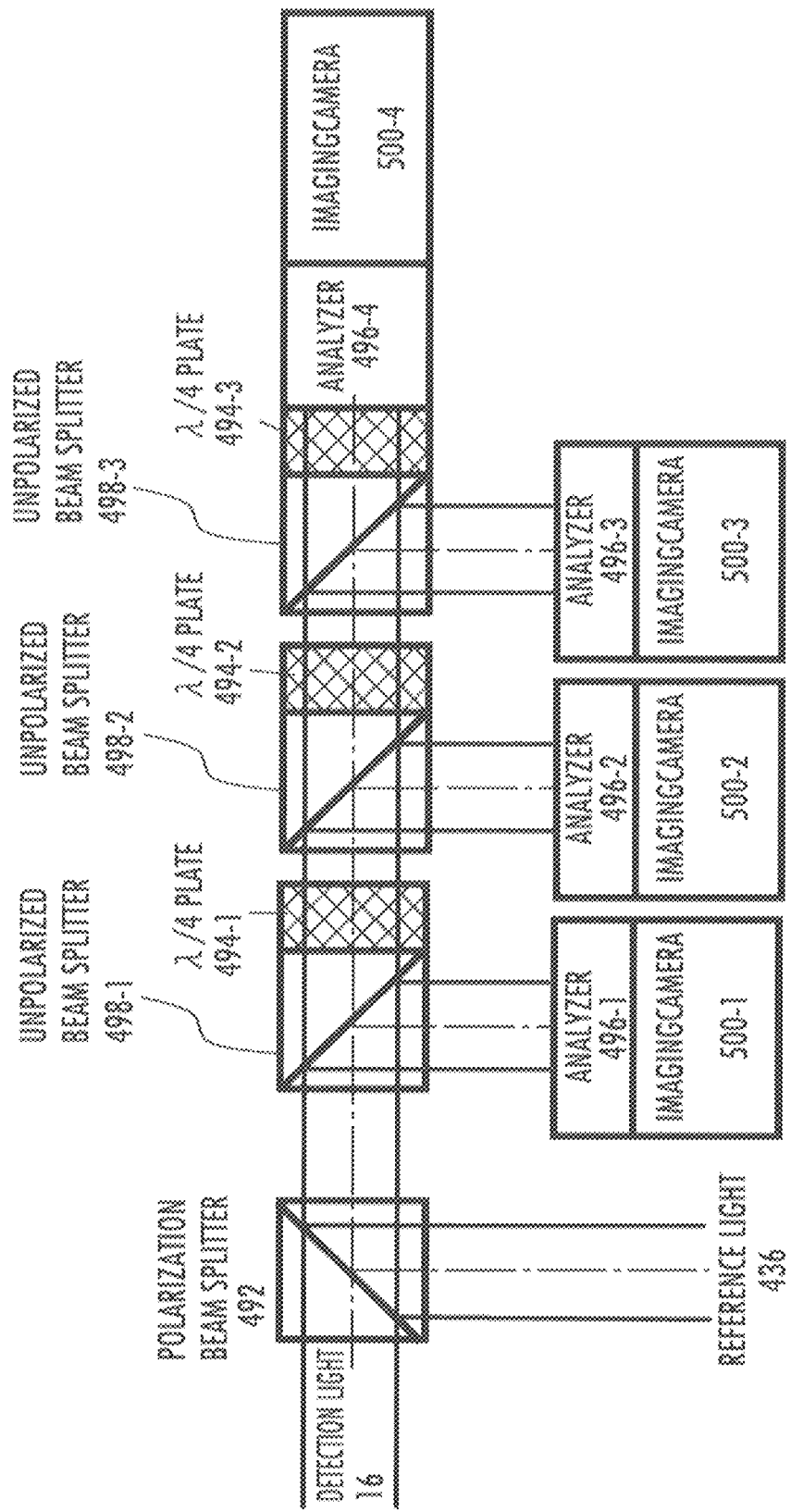

FIG. 37

| WAYS TO HAVE FUNCTIONS | SPECIFIC EXAMPLES | SUPPLEMENTAL EXPLANATION | OPTICAL DETECTION TARGETS |
|---|---|---|---|
| DIFFERENT CONFORMATIONS (INCLUDING SEQUENCE CHANGE) | MECHANICAL CHANGE IN CONFORMATION | PRESSURE/VIBRATION SENSOR: STRUCTURE CHANGE BY PRESSURE/VIBRATIONS | α HELIX/β SHEET RATIO |
| | THERMAL CHANGE IN CONFORMATION | THERMOSENSITIVE SENSOR: CONFORMATION CHANGE WITH TEMPERATURE CHANGE | α HELIX/β SHEET RATIO |
| | FIBROIN TRANSFORMATION | PLEASANT-TOUCH SOFT MATERIAL: REDUCING β-SHEET CRYSTALLINITY | ABSORPTION AMOUNT AT β SHEET ABSORPTION BAND |
| | FIBROIN TRANSFORMATION | RIGID MATERIAL, REINFORCEMENT MATERIAL: INCREASING β-SHEET CRYSTALLINITY | ABSORPTION AMOUNT AT β SHEET ABSORPTION BAND |
| AMINO ACID SEQUENCES | CONTAINING ACID RESIDUE | MOISTURE WATER ABSORBING MATERIAL: BENDING ACID-RESIDUE BASED AMINO ACID IN FIBROIN NON-CRYSTALLINE AREA | n-H OVERTONE ABSORPTION BAND AT ACID RESIDUE-CATION BONDING PART |
| | OLIGOPEPTIDE BONDING | FORMING ADP BONDING AT OLIGOPEPTIDE END | BASIC RESIDUE-PHOSPHATE GROUP ABSORPTION BAND |
| | INCLUDING CHARGED-POLAR RESIDUE | VOLTAGE SENSOR: CONFORMATION CHANGE WITH CHARGED-POLAR RESIDUE | ABSORPTION BAND RESULTING FROM BASIC RESIDUE |
| INTERNAL STRUCTURE OF ACTIVE AREA | FET SWITCHING | USING CONFORMATION CHANGE OF CONDUCTIVE LINE WITH VOLTAGE SENSOR | HYDROGEN BONDING PART/ABSORBING CONFUSION COLORS |
| | UNDERWATER CONDUCTIVE LINES | FORMING α ORBITAL INSIDE OF PEPTIDE DOUBLE-HELICAL SKELETON | FLUOROPHORE FLUORESCENCE WAVELENGTH (WAVELENGTHS) |
| | NIRFP | NEAR INFRARED FLUORESCENCE: INCREASING FLUOROPHORE AREA OF NIRFP | CREATE ACTIVE AREA/CHANGE ABSORPTION BAND |
| NEW ENZYME FUNCTION, SPEEDING UP CURRENT ENZYME | GENERATING NEW ACTIVE AREA | ENZYME FUNCTION TO COAT CONDUCTIVE LINE OR NIRFP ACTIVE AREA (HYDROLYSIS/DEHYDRATION COMPENSATION/OXIDATION/REDUCTION/ETC) | WAVELENGTH/INTENSITY DURING DEGRADATION |
| | NEW HIGH-SPEED DEGRADATIVE ENZYME | COLLECTING STARCH FROM PLANTS WITH HIGH-SPEED/PERFORMANCE CELLULASE | ABSORPTION BAND TO ACTIVATE TRIAD |
| | ARTIFICIAL EDIBLE MEAT | CONTROLLING TEXTURE OF MEAT: REPLACING REINFORCEMENT MATERIAL FOR ACTIN | ABSORPTION BAND OF ADP BONDING PART |
| | STORING SEQUENCE INFORMATION | EDITING AND RECORDING IN GENOME STORAGE OF AMINO ACID SEQUENCE INFORMATION ON ARTIFICIAL PROTEIN IN A CELL | HYDROGEN BONDING PART BETWEEN BASES IN DNA |
| GENOME EDITING | VECTOR CARRIER | DOUBLE PACKING CARRIER OF GENOME-EDITING MODULE | NIRFP, ENZYME ACTIVE AREA |
| GENE REGULATING | GENE REGULATING CARRIER | DOUBLE PACKING CARRIER OF GENE REGULATOR | REGULATOR+DNA ⇌ ABSORPTION BAND |
| SYNTHESIZING ARTIFICIAL PROTEINS | CREATE/RELEASE IN CELL | SIMILAR METHOD TO CREATE HAIR BY ARTIFICIAL CULTURE OF HAIR FOLLICLE | CHANGE IN ABSORPTION BAND DURING PROTEIN SYNTHESIS |

NOTE: IMPROVEMENT OF A FIBROIN STRUCTURE HAVING A FIBER-LIKE SHAPE IS SHOWN AS A SPECIFIC EXAMPLE. ALTERNATIVELY ANY EXISTING PROTEINS MAY BE MODIFIED. ALTERNATIVELY ANY POLYSACCHARIDE MAY BE MODIFIED.

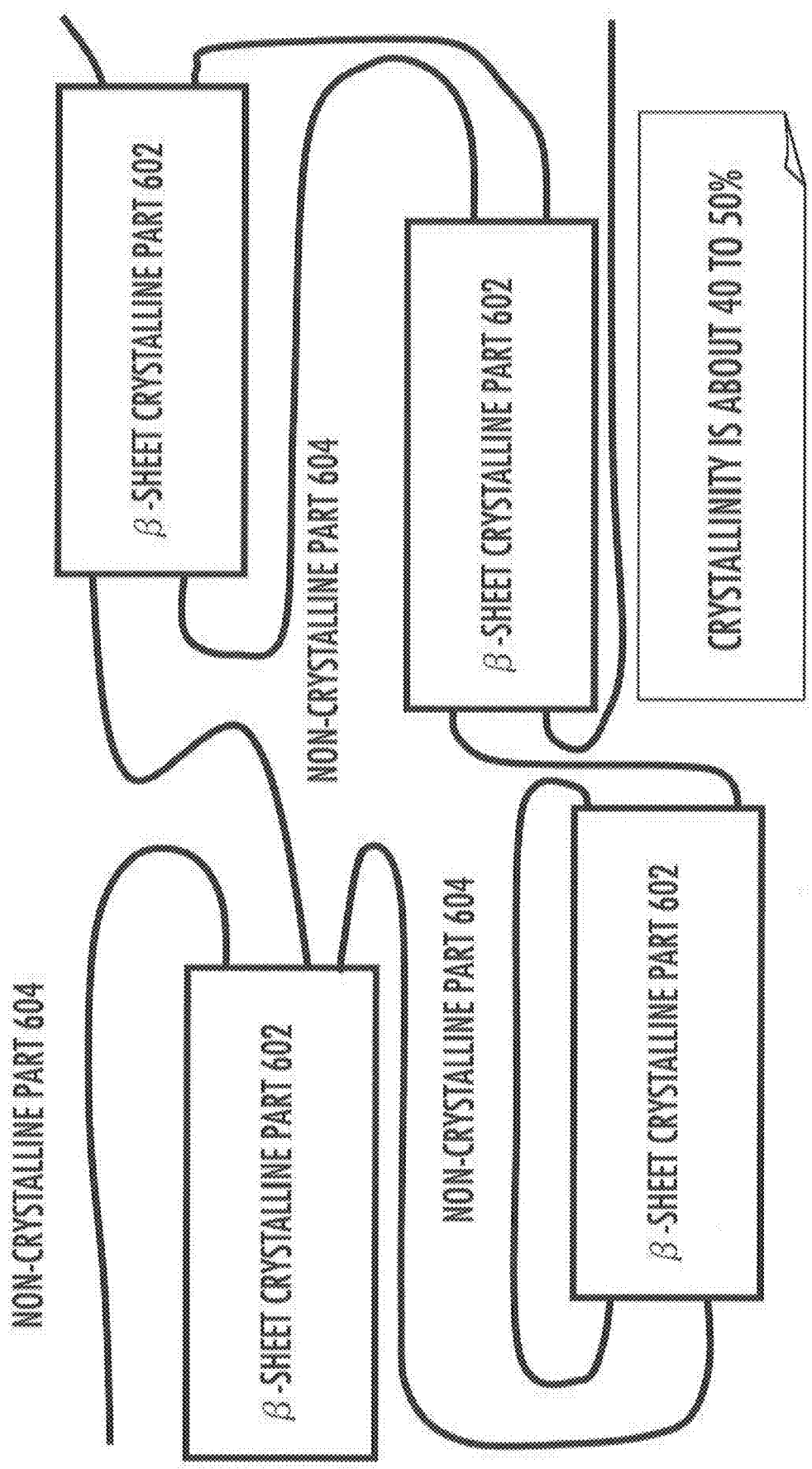

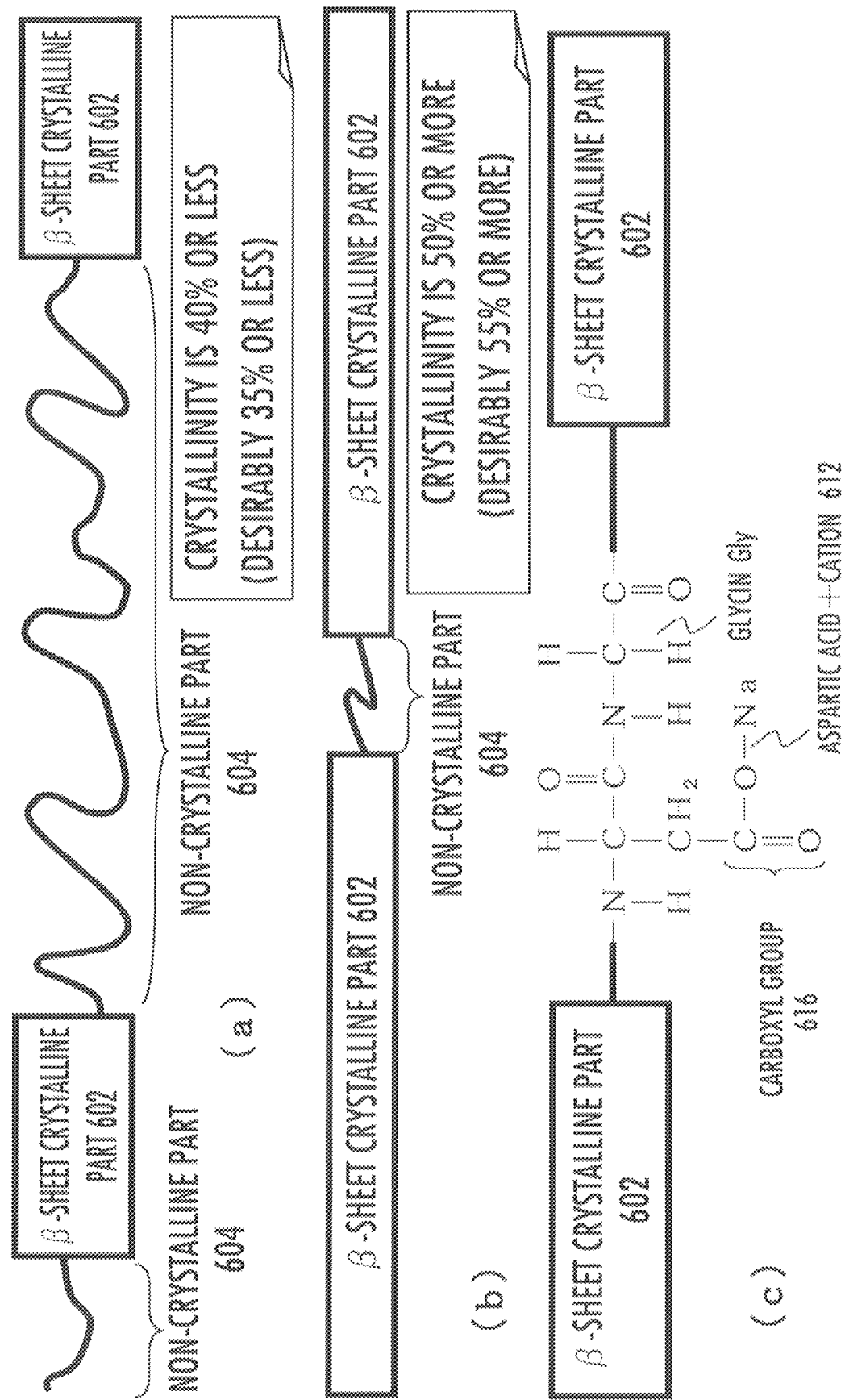

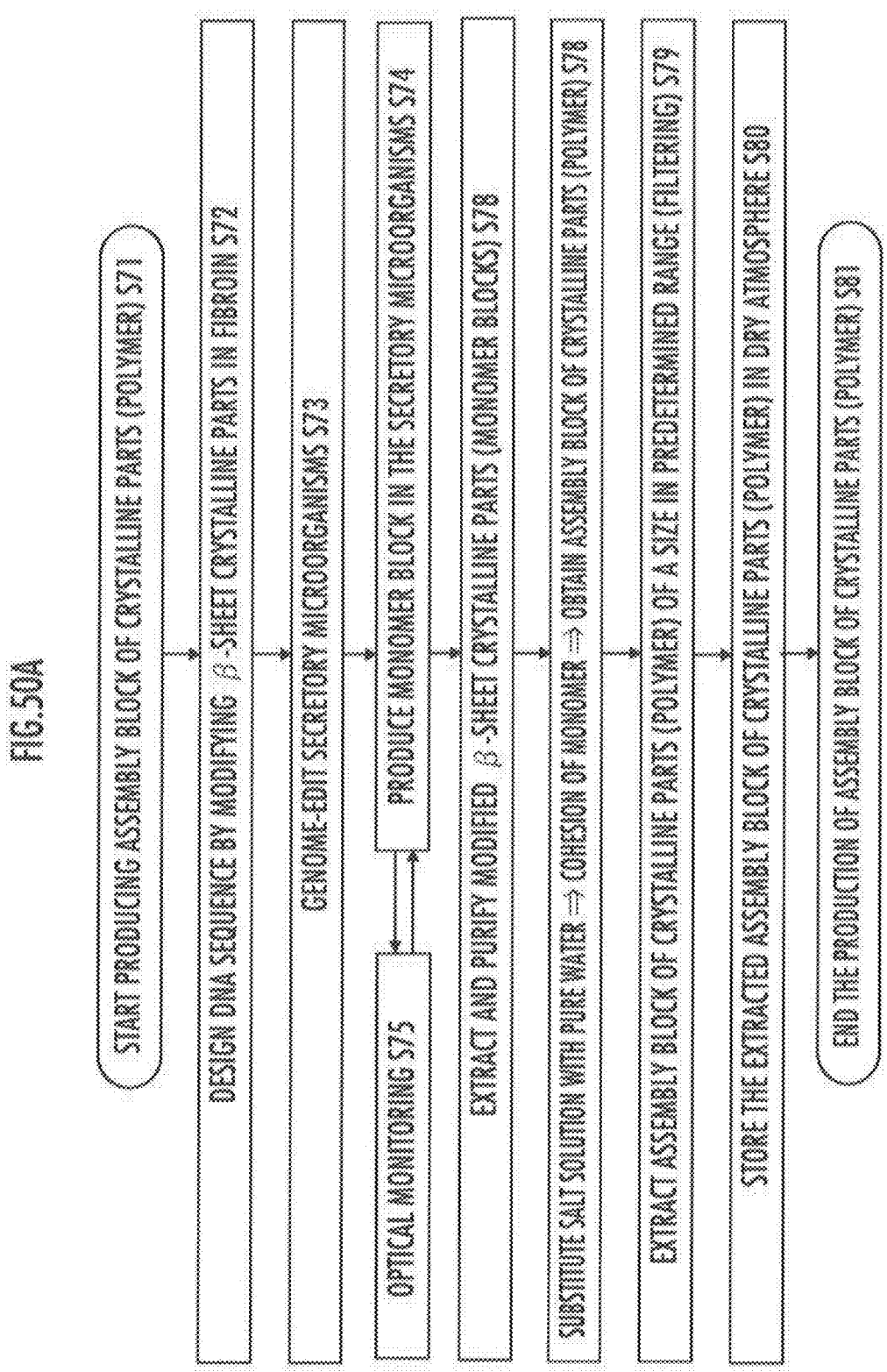

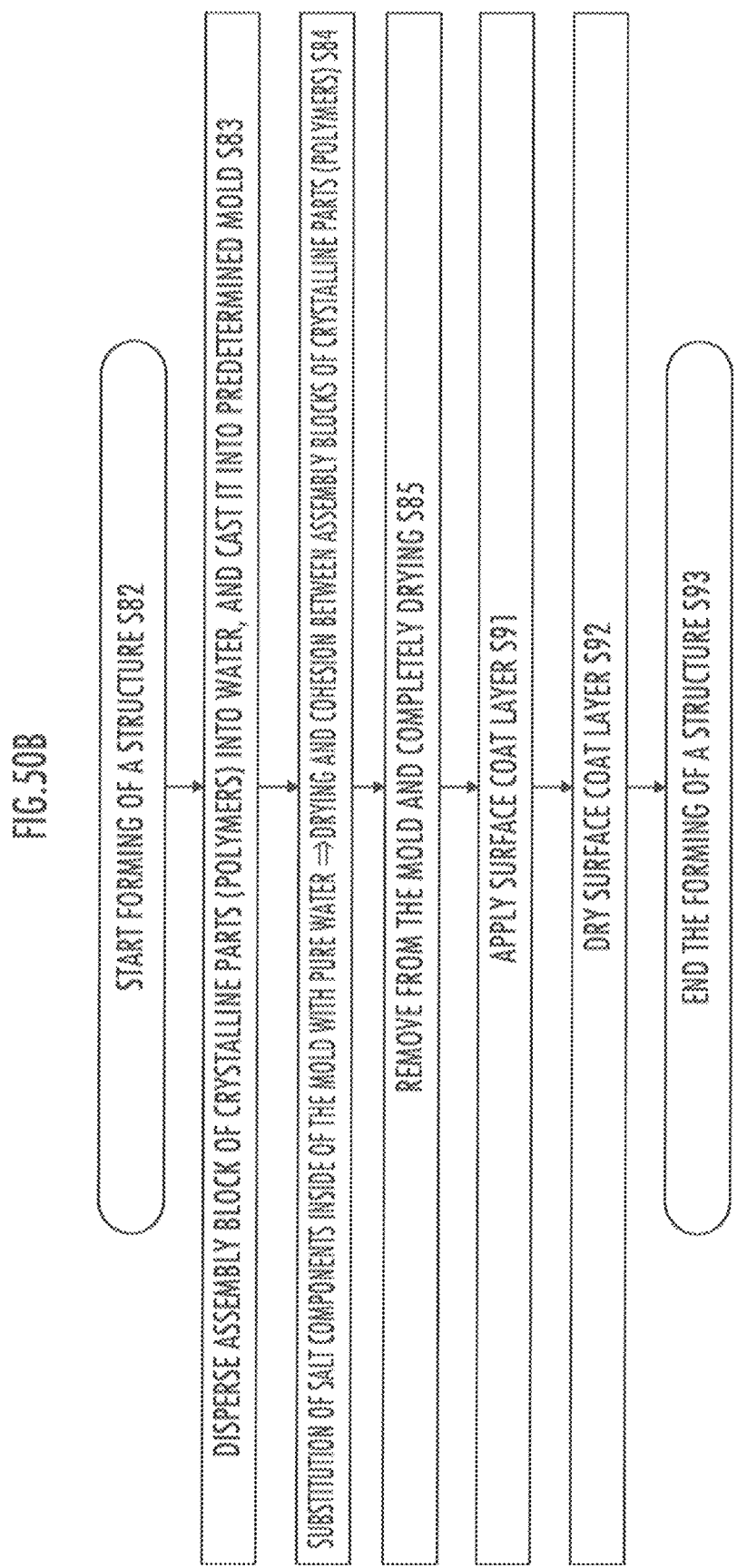

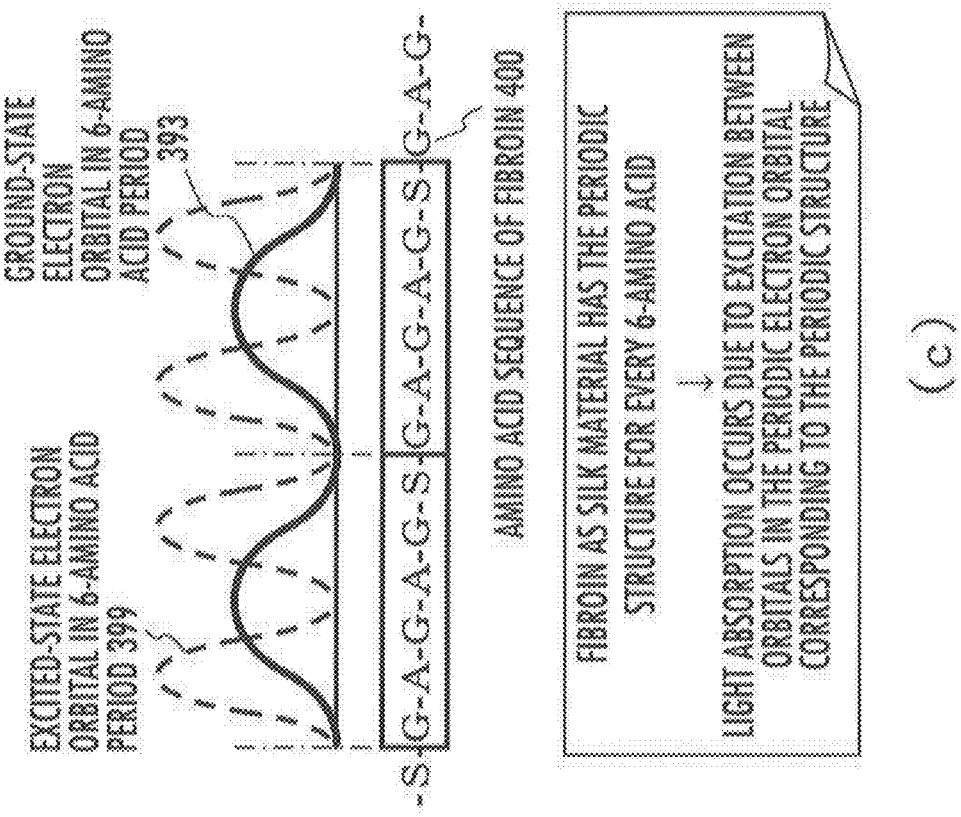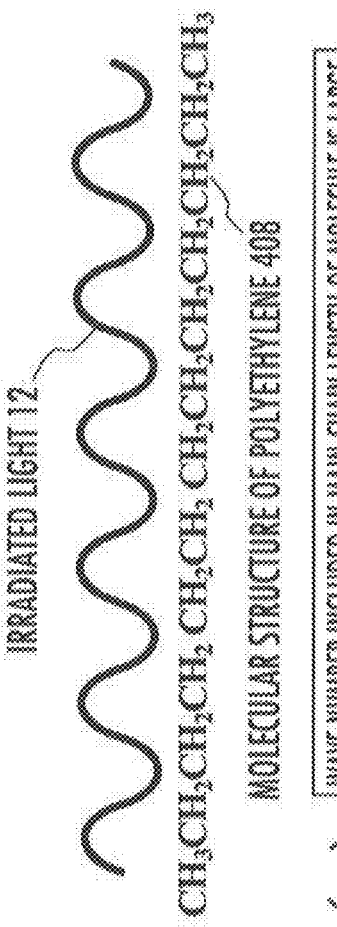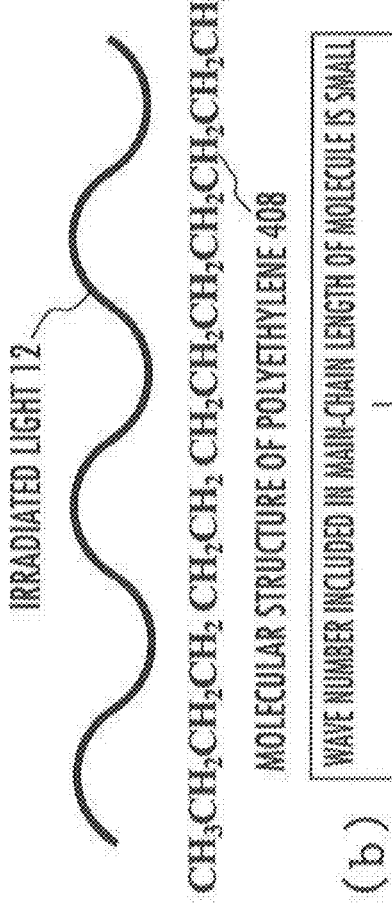
FIG. 64

FIG.65

CENTER-WAVELENGTH RANGE OF ABSORPTION BAND OBSERVED WITH NON-COHERENT NEAR INFRARED LIGHT FOR EACH GROUP OF FOOD/MATERIAL AS FUNCTIONAL-3RD MATERIAL (μm)

| FOOD/MATERIAL GROUP | ATOMIC GROUP INCLUDED | FIRST OVERTONE | SECOND OVERTONE | THIRD OVERTONE |
|---|---|---|---|---|
| PROTEIN GROUP | -NHn | 1.67~1.46 (1.57/1.54/1.50) | 1.11~0.97 | |
| GLUCIDE GROUP | -OH | 1.46~1.38 | 0.99~0.94 | |
| LIPID GROUP | -CH/-CH$_2$ | 1.81~1.70 (1.70μm OR MORE) | 1.23~1.15 (1.210/1.189) | 0.94~0.86 (0.925μm) |
| | -CH$_3$ | 1.80~1.67 (1.683μm) | 1.23~1.12 (1.177μm) | 0.94~0.84 |

NOTE) NUMERAL IN PARENTHESIS INDICATES THE VALUE DIRECTLY READ FROM FIGS. 62 OR 63

FIG. 66

| CENTER ATOM AT THE FORWARD END OF AMINO ACID RESIDUE | α-HELIX | | β-SHEET | |
|---|---|---|---|---|
| | AMINO ACID INCLUDED | CHEMICAL STRUCTURE OF RESIDUE | AMINO ACID INCLUDED | CHEMICAL STRUCTURE OF RESIDUE |
| CARBONS | Methionine | $-(CH_2)_2-S-CH_3$ | | |
| | Alanine | $-CH_3$ | | |
| | Leucine | $-CH_2-CH-(CH_3)_2$ | Isoleucine | $-CH-CH_2-CH_3$<br>$\phantom{-}CH_3$ |
| | | | Valine | $-CH-(CH_3)_2$ |
| OXYGENS | Glutamic Acid | $-(CH_2)_2-COOH$ | Tyrosine | $-CH_2-Hex-OH$ |
| NITROGENS | Lysine | $-(CH_2)_4-NH_3^+$ | | |

NOTE) "Hex" MEANS 6-ATMOS CYCLIC COMPOUND PART

LIGHT-SOURCE UNIT, MEASUREMENT APPARATUS, NEAR-INFRARED MICROSCOPIC APPARATUS, OPTICAL DETECTION METHOD, IMAGING METHOD, CALCULATION METHOD, FUNCTIONAL BIO-RELATED SUBSTANCE, STATE MANAGEMENT METHOD, AND MANUFACTURING METHOD

BACKGROUND OF THE INVENTION

Field of the Invention

The present invention relates to a detection method to obtain a signal from a detection target by light (or to detect predetermined optical characteristics of the target) or an imaging method relating to a detection target.

The present invention is applicable to the application field based on such optical detection or imaging as well. Such an application range includes a substance that can be detected about the internal structure or the internal active state by light (creation of such a substance) or a method for managing a predetermined state or a manufacturing method by light as well.

Additionally the present invention may also include a calculation method to expect the optical characteristics of the detection target.

Description of the Related Art

An optical detection method or an optical imaging method is a noncontact and noninvasive method, and so such a method can greatly reduce the burden on a detection target during the detection. As a result, such a detection method or an imaging method by light is suitable for natural state observation or measurement of a very small change of the detection target. The method therefore can be used in a relatively wide range of fields.

Correspondingly the application range (usage) of these optical detection techniques and optical imaging techniques also has been broadened. A part of such an application range includes a substance that can be detected about the internal structure or the internal active state by light (creation of such a substance) or a method for managing a predetermined state or a manufacturing method by light as well.

In this way, these techniques have been used in a wider range, and so higher accuracy and higher reliability have been needed for the detection result or the measurement result by light. To confirm the reliability and trustworthiness of the detection/measurement result by light, they have to be checked against the theoretical support about accurate matching.

SUMMARY OF THE INVENTION

One of the means to improve the detection accuracy or increase the reliability of the optical detection techniques and the imaging techniques includes lowering of optical noise (a noise component generated due to optical factor) mixed in the detection signal or the optical image.

JP 6-167640 A (hereinafter called Patent Literature 1) discloses one of the specific means. According to this document, the detection accuracy is improved by reducing coherence of light and lowering the amount of optical noise in the detection/measurement system. Such means disclosed by Patent Literature 1 has a limit about speckle noise reduction, and so still needs a higher level of accuracy and reliability.

For these reasons, there is a demand for a reliable or accurate optical detection method and optical imaging method and the application (usage) techniques based on such a method, including a substance that can be detected/measured/evaluated about the internal structure and the internal active state by light, the generation of such a substance, a manufacturing method enabling improved efficiency and control accuracy, and such a method for managing a predetermined state. There is another demand for a measurement apparatus and a light-source unit to implement these methods.

Meanwhile, as another means to support the reliability and trustworthiness of the result of the optical detection and the imaging as stated above, a computer simulation method by various types of software for quantum-chemical calculations is available. Existing software for quantum-chemical calculations, however, needs a great deal of time to calculate vibrations of the n-th overtone of a polymer. Therefore a method is requested, which is capable of easily calculating the characteristics of the n-th overtone or the combination limited to a specific atomic group in a polymer in a short time.

Light beams having different optical lengths are combined or mixed, and such combined or mixed light is used for the optical detection and the optical imaging. Such a difference in optical length may be longer than the coherence length. The beams of such combined or mixed light may be the same or similar in the travelling direction or in the vibrating direction of electric field.

Such a means may be used in the application techniques based on the optical detection method and the optical imaging method. That is, state management may be conducted using such light. Such light may be used to manufacture a predetermined substance or evaluate a predetermined product during the manufacturing process if the chemical state or a change in the state, the physicochemical (or physical) state or a change in the state, the structure or a change in the structure, or the shape or a change in the shape can be detected, measured and managed by the light. Additionally the light may be used for a functional substance that is manufactured or evaluated by such a method.

The following method may be performed separately from the above means, or the following method may be performed in combination with the above means. The method includes:

1) measuring a predetermined characteristic of a target for optical detection or optical imaging; and 2) performing feedback of the optical characteristic used for the optical detection or optical imaging based on a result of the measurement.

The predetermined characteristic relates to the influences on the wavefront characteristics of light used for the optical detection or optical imaging or on the travelling direction of a part of the light. The "optical characteristic" refers to the characteristic causing a change in the wavefront characteristics or a change in the travelling direction of a part of the light.

Additionally, the following calculation method may be conducted to theoretically predict the phenomenon implemented by the optical characteristics of the target obtained from the result of optical detection or optical imaging:

α] calculating potential characteristics relating to group vibration in a predetermined region of the target; and β] predicting the absorption wavelength or absorption wavenumber (frequency of vibrations).

BRIEF DESCRIPTION OF THE DRAWINGS

FIG. 1A describes a basic configuration of a measurement apparatus of the present embodiment (irradiated with scattered light).

FIG. 1B describes a basic configuration of a measurement apparatus of the present embodiment (irradiated with parallel light).

FIG. 2A describes an uncertainty relationship between time and frequency of vibrations of light emitted from a light source.

FIG. 2B describes partial coherency of light with a limited detection wavelength range.

FIG. 3 shows influences on optical imaging from partial coherent light.

FIG. 4 describes optical noise generated in scattered light from a micro light-scattering object.

FIG. 5 describes influences from partially coherent light on spectroscopic measurement.

FIG. 8B describes the basic principle (B) of the method to reduce optical noise in the present embodiment.

FIG. 9 describes the options of a light combining/mixing method in the present embodiment.

FIG. 11 describes an example of the method of combining/mixing beams of light emitted in different directions.

FIG. 12A describes an example of the method of changing optical length using wave-front divided light.

FIG. 12B describes an example of an optical characteristics changing member using wave-front divided light.

FIG. 12C describes an example of an optical characteristics changing member using wave-front divided light in details.

FIG. 14B describes another method of combining/mixing beams of wave-front divided light.

FIG. 14C describes an application example of the method of combining/mixing beams of wave-front divided light.

FIG. 15 describes points to note for the method of changing the optical length among the wave-front divided light beams.

FIG. 16A describes an example of the method for changing the optical length among the wave-front divided light beams.

FIG. 16B describes another example of the method for changing the optical length among the wave-front divided light beams.

FIG. 17 describes conventionally known techniques for comparison.

FIG. 18 describes a method to reduce optical noise using the length of an optical guiding fiber.

FIG. 19A describes a basic method (A) of combining/mixing beams of light emitted from different light-emitting areas.

FIG. 19B describes a basic method (B) of combining/mixing beams of light emitted from different light-emitting areas.

FIG. 20 describes a method of combining/mixing beams of light emitted from different light-emitting areas in a specific area of the target.

FIG. 21B describes an exemplary method (B) to combine/mix beams of light generated at different light-emitting areas with a phase conversion element.

FIG. 21C describes an exemplary method (C) to combine/mix beams of light generated at different light-emitting areas with a phase conversion element.

FIG. 22 describes an optical system that is used for the experiment to verify the effect of a phase conversion element about light combining/mixing.

FIG. 23A describes the effect (A) of combining/mixing light with a phase conversion element.

FIG. 24B describes an exemplary method (B) to combine/mix beams of light generated at different light-emitting areas with a waveguide device.

FIG. 24C describes an exemplary method (C) to combine/mix beams of light generated at different light-emitting areas with a waveguide device.

FIG. 27 shows an image of a light-scattering object in the target.

FIG. 28 describes the principle of generating wave front aberration inside of a target (transparent parallel flat plate).

FIG. 29A shows the internal structure of a wave front aberration coarse compensation section.

FIG. 29B shows the internal structure of a wave front aberration fine compensation section.

FIG. 31 describes the principle of removing unnecessary scattered light generated in the target (partially changed for illustrated purposes).

FIG. 33 describes a method for detecting wave front aberration using coherent light.

FIG. 37 shows the classification of functional-bio materials of the present embodiment by their ways to exert the unique functions.

FIG. 38 schematically describes a molecular structure in fibroin.

FIG. 39A shows an example (A) of a functional-bio material prepared by modifying fibroin.

FIG. 50A describes an exemplary production procedure of an assembly block of crystalline parts (polymer).

FIG. 50B describes an example of the present embodiment, showing the procedure to form a structure of FIG. 49.

FIG. 64 shows a relationship between the baseline characteristics in the absorbance curve and the molecular structure to be measured.

FIG. 65 describes a method for identifying a functional-bio material with non-coherent near-infrared light of the present embodiment.

FIG. 66 describes the relationship between the secondary structure in a functional-bio material and amino acids composing the material in the present embodiment.

DESCRIPTION OF THE PREFERRED EMBODIMENTS

Figure 1C:
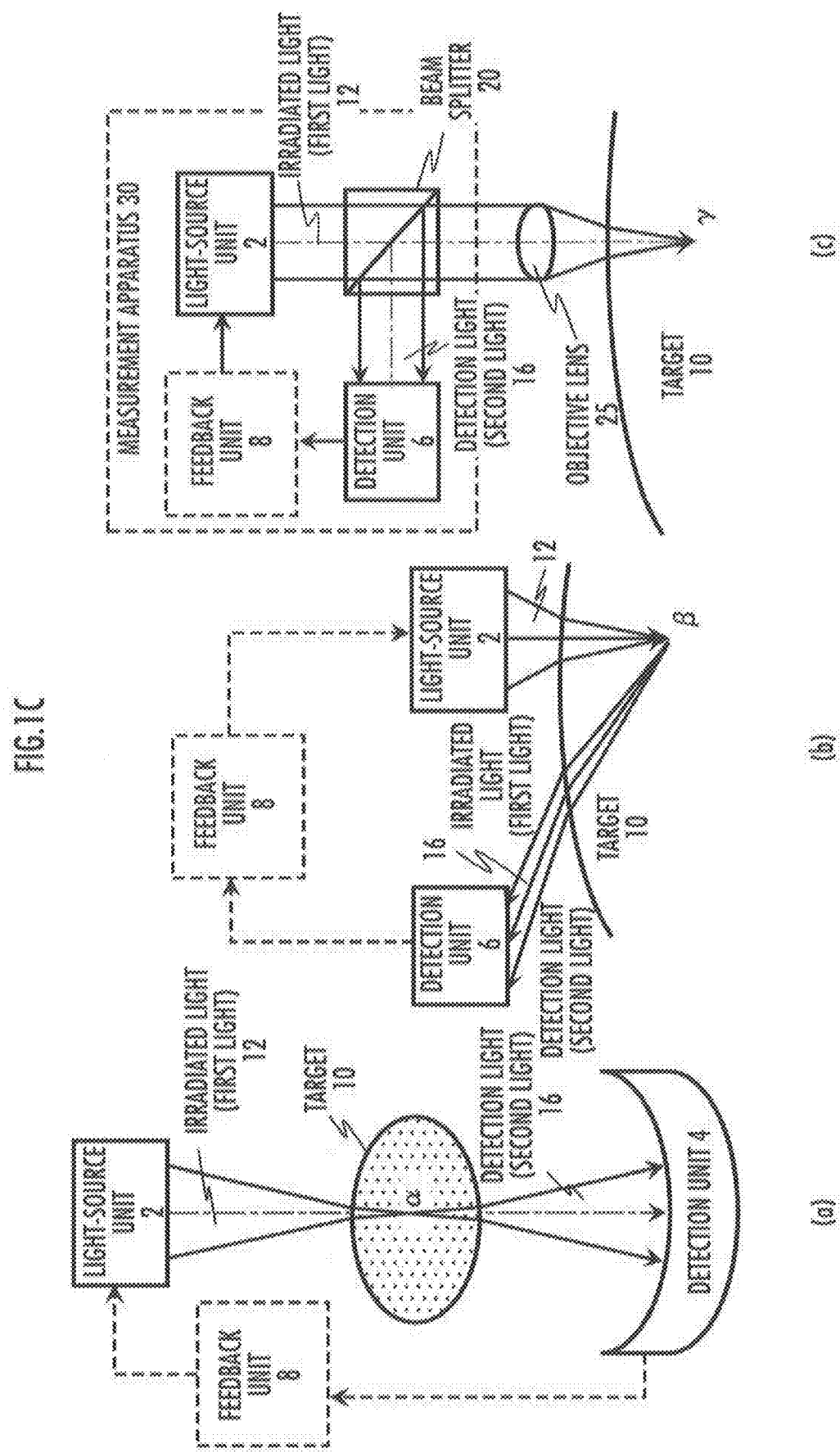
FIG. 1C describes a basic configuration of a measurement apparatus of the present embodiment (irradiated with converging light).

The following describes a light-source unit, a measurement apparatus, a near-infrared microscopic apparatus, an optical detection method, an imaging method, a calculation method, a state management method, and a manufacturing method, with reference to the drawings. A table of contents which provides an outline of the embodiments described below is listed before the embodiment descriptions.

Chapter 1 Basic Configuration of Measurement Apparatus of the Present Embodiment Chapter 2 Influences on Optical Noise from Partial Coherence Section 2.1 Brief Summary of the Procedure of the Present Embodiment to Reduce Optical Noise Section 2.2 Occasion of Partially Coherent White Light and Definition of Technical Terms Section 2.3 Influences on Optical Imaging from Partial Coherent Light Section 2.4 Influences on Measurement of Spectroscopic Characteristics from Partial Coherent light Section 2.5 Mathematical Presentation of an Example of Influences from Partial Coherent Light on Spectroscopic Characteristics Section 2.6 Influences on Detection/Imaging using Near-Infrared Light and its Wavelength Range Chapter 3 Method for Reducing Optical Noise of the Present Embodiment relating to Partial Coherency Section 3.1 Basic Principle to Reduce Optical Noise Section 3.2 Applications of Emitted Light into Different Directions Section 3.3 Optical Characteristics Changing Member having the Function of Wave Front Dividing Section 3.4 Combination (Mixing) of Divided Wave fronts Section 3.5 Light Intensity Formula of Partially Incoherent Light indicating Optical Noise Reduction Effect Section 3.6 Devised Structure of Optical Characteristics Changing Member Section 3.7 Comparison with Conventional Technique based on Wave Front Dividing Section 3.8 Optical Characteristics Changing Member having the Function of Optical Waveguide Section 3.9 Method for Combining/Mixing Light Emitted from Different Regions Section 3.10 Application Examples of Combining (Mixing) of Beams of Light Emitted from Different Areas Section 3.11 Method for Reducing Partial Coherency of Electromagnetic Waves having Wavelength Longer than Near-infrared Light and Application Examples Section 3.12 Simple Description on Method for Controlling Partial Coherency of Light Chapter 4 Method for Mixing/Separating Coherent Light and Partial Incoherent Light Section 4.1 Exemplary Structure in Measurement Apparatus based on both of Coherent Light and Partial Incoherent Light Section 4.2 Method for Mixing and Separating Coherent Light and Partial Incoherent Light Chapter 5 Interaction with Light inside of Measurement Target Section 5.1 Light Scattering and Light Absorption Generated inside of Target and Influences from Multi-scattering Section 5.2 Factors of Scattering/Absorption and Relationship with Cross-sectional Area of Scattering Section 5.3 Features of Scattering Cross-section and Light Scattering Section 5.4 Detection Characteristics using Back Scattered Light (Reflected Light)

Section 5.5 Formulation on Interaction with Electromagnetic Waves inside of Measurement Target Section 5.6 Effects on Measurement Result from Difference in Partial Coherency of Irradiated Light and the Considerations Chapter 6 Method for Feed-backing of Wave Front Aberration Generated along Optical Path Section 6.1 Principle of Generating Wave Front Aberration inside of Target (Transparent Parallel Flat Plate)

Section 6.2 Method for Compensating Wave Front Aberration

Section 6.3 Common Part of Method of Detecting Wave Front Aberration

Section 6.4 Method for Detecting Wave Front Aberration using Partial Incoherent Light Section 6.5 Method for Detecting Wave Front Aberration using Coherent Light Chapter 7 Method for Calculating Characteristics of n-th Overtone Limited to Specific Atomic Group in Polymer Section 7.1 Method for Reducing Optical Noise and Prediction of Wavelength of Absorption Band Belonging to Group Vibrations at Specific Atomic Group Section 7.2 Mathematical Presentation of Group Vibrations in Atomic Group Section 7.3 Signification of Analyzing Group Vibration in Atomic Group Section 7.4 Method for Simulating Absorption-band Wavelength belonging to Group Vibration Chapter 8 Functional-bio Material Section 8.1 Functional-bio Material Section 8.2 Classification of Functional-bio Materials by Their Ways to Exert Unique Functions Section 8.3 Examples of Functional-bio Materials having Functions corresponding to their Amino Acid Sequence or Conformation Section 8.4 Examples of Functional-bio Materials having Functions as Internal Structure of Active Area or Enzyme Section 8.5 Examples of Functional-bio Materials having Function relating to the Generation Procedure Chapter 9 Genome-editing using Functional-bio Materials Section 9.1 Example of Treatment for Affected Area relating to DNA Damages and Current Problems Section 9.2 Structure of Nuclear Delivery Carrier and its Operation Principle Section 9.3 Method for Manufacturing Nuclear Delivery Carrier (for Mass Production)

Chapter 10 Method for Manufacturing Functional-bio Materials and Process Management Section 10.1 Basic Procedure of Manufacturing Method and Process Management Section 10.2 Geographically Distributed Mass-production Procedure Section 10.3 Estimation of Functional-bio Material using Non-coherent Near-infrared Light Section 10.4 Optical Characteristics of Functional-bio material in Present Embodiment Section 10.5 Method for Manufacturing Functional-bio Materials outside of Cell Chapter 1 Basic Configuration of Measurement Apparatus of the Present Embodiment Referring to FIGS. 1A to 1C, the following describes the basic configuration of a measurement apparatus based on an optical detection method and an imaging method according to the present embodiment. The basic configuration of this measurement apparatus includes a light-source unit 2 and a detection unit 4, 6. The light-source unit 2 emits irradiation light 12 as first light so that a target 10 (detection target) as a target of the measurement or detection is irradiated with the light 12.

The target 10 includes a living body, such as animals, plants, and microorganisms (including bacteria and virus) as well as a single substance making up a living body, such as nucleotides, amino acid/proteins, lipids (including phospholipids) and carbohydrates. The target may be organic substances, such as plastic, or inorganic substances that transmit at least a part of light. The detection target 10 may be in the form of solid as well as in the form of liquid or gas. The detection target 10 as a single unit may be of any selected size from a maximum size on the order of meters (the size of human beings or elephants) to a minimum size of atoms and molecules.

Second light (that is, light obtained after the irradiated light 12 is reflected/transmitted/absorbed/scattered inside of or at the surface of the target 10) obtained from the target 10 is projected on the detection unit 4, 6 as detection light 16. As a result, the optical characteristics of the target 10 (detection target) are detected or measured.

The optical characteristics of the target 10 obtained here is not limited to the characteristics of amount of light after reflection/transmission/absorption/scattering at the target 10 and their temporal change, the optical phase characteristics, spectroscopic characteristics (wavelength spectrum), imaging (video/image extracted), and the result of image analysis (including the result of analysis on spatial frequency characteristics), and every optical characteristics may be detected or measured.

Based on the result obtained at the detection units 4, 6, the light-emission characteristics of the irradiated light 12 from the light-source unit 2 may be controlled via a feedback unit 8. Specifically not only the amount of emission of the irradiated light 12 is continuously controlled and a temporal change of such an amount is controlled, but also the distribution of phase or amount of the irradiated light 12 immediately before the irradiation of the target 10 may be controlled, for example. Any control other than the above may be performed.

FIGS. 1A, 1B and 1C show the features of the measurement apparatus during scattering, being parallel, and being converged, respectively, of the irradiated light (first light) 12 to be applied to the target 10. In all of FIGS. 1A, 1B and 1C, (a) shows the detection of transmitted light (including detection of forward scattered light), (b) shows the detection of reflected light/scattered light, and (c) shows the structure including the light-source unit 2 and the detection unit 6 that are stored integrally in the measurement apparatus 30.

In FIGS. 1A(c), 1B(c), and 1C(c), the irradiated light (first light) 12 and the detection light (second light) 16 partially share the optical path via a beam splitter 20. This can easily decrease the measurement apparatus 30 in size.

When the structure of FIGS. 1A(b), 1B(b), and 1C(b) does not include the beam splitter 20, the relative position between the light-source unit 2 and the detection unit 6 can be set freely in the measurement apparatus 30. This can lead to an increase in flexibility of the measurement environment.

A light-emitting source 70 (specific example thereof is described later referring to FIG. 10A) that emits the irradiated light 12 in the light-source unit 2 typically emits diverging light. The configuration of FIG. 1B and FIG. 1C to apply parallel light and converging light to the target 10 therefore needs a collimator lens 26 and a collecting lens 98 in the light-source unit 2. On the contrary, the configuration as in FIG. 1A to directly apply diverging light to the target does not need such lenses, and so the cost and the size of the measurement apparatus 30 as a whole can be reduced.

When the parallel irradiated light 12 is applied as in FIG. 1B, the degree of freedom to place the target 10 relative to the travelling direction of the irradiated light 12 can be increased. This configuration therefore is suitable for the measurement of optical characteristics of the target 10 in a gas state or when the target is dispersed in liquid-state solvent. For the present embodiment relating to the manufacturing method or the state management method, parallel irradiated light 12 may be used as in FIG. 1B.

In this case, the target 10 in a gas state or dispersed in a liquid medium is contained in a column for measurement sample 34 in a transparent glass vessel 36. The column for measurement sample 34 comes with an inlet 42 with a lid 46 and an outlet 44 with a lid 46 for easy replacement of the target 10.

The transparent glass vessel 36 internally includes a column for reference sample 32 that is separated with a wall 9. This column for reference sample 32 also comes with an inlet 42 with a lid 46 and an outlet 44 with a lid 46 similarly, which can generate a vacuum in the column for reference sample 32. Alternatively, the column for reference sample 32 may be filled with liquid solvent alone before dispersing the target 10 in the solvent.

The transparent glass vessel 36 is movable relative to the measurement apparatus 30. Especially the moving direction 38 of this glass vessel has a non-parallel relationship with (may be orthogonal to) the travelling direction of the irradiated light 12. In that case, the optical characteristics in the column for reference sample 32 may be measured first, followed by measurement of the optical characteristics in the column for measurement sample 34, and the result of the measurement may be compared therebetween. Such a comparison can increase the detection accuracy of the optical characteristics obtained as a result of the measurement/detection. For the comparison of these results, a difference between the measurement data after arithmetic processing (this may include normalization) may be obtained. Alternatively division (logarithmic subtraction) may be performed between the measurement results. The measurement apparatus 30 has optical transmission characteristics (function) specific to the device, and the optical characteristics obtained from the column for measurement sample 34 include such optical transmission characteristics. The division (logarithmic subtraction) between the optical characteristics of the column for measurement sample 34 and of the column for reference sample 32 can remove the optical transmission characteristics in the measurement apparatus 30, so that the optical characteristics of the target 10 alone can be obtained.

The detection target 10 that is vaporized (or dispersed in liquid solvent) to be in a molecular state scatters/absorbs the irradiated light (first light) 12. In FIG. 1B(b), the laterally scattered light is detected as detection light (second light) 16. In FIG. 1B(a), loss in the amount of transmitted light due to forward scattering and absorption can be detected. When a mirror face 48 is formed at the bottom of the transparent glass vessel 36 as in FIG. 1B(c), loss in the amount of transmitted light can be detected similarly to FIG. 1B(a). When the vessel does not include a mirror face 48, backward scattered light can be detected as detection light (second light) 16. In this way, when parallel irradiated light 12 is used, various types of scattered light, including forward/backward/laterally scattered light, can be detected, which can improve the detection accuracy.

When the converging irradiated light 12 is applied to the target 10 as in FIG. 1C, the light is collected at the points of α, β, and γ in the target 10 (the method for collecting light is described later in Chapter 7). This can lead to the effect of measuring/detecting optical characteristics limited to a specific position in the target 10. In FIG. 1C(a), forward scattered light can be measured/detected, inn FIG. 1C(b), laterally scattered light can be measured/detected, and in FIG. 1C(c), backward scattered light can be measured/detected.

Chapter 2 Influences on Optical Noise from Partial Coherency

Chapter 2 explains that white light also has partial coherency and so can generate optical noise.

Section 2.1 Brief Summary of the Procedure of the Present Embodiment to Reduce Optical Noise For improved detection accuracy or reliability of the optical detection or optical imaging, optical noise mixed in the measurement apparatus 30 of FIG. 1A to FIG. 1C is lowered. As such a method to lower the optical noise, the optical characteristics of at least any one of the irradiated light (first light) 12 and the detection light (second light) 16 is changed in the present embodiment. Such optical characteristics to be changed include:

(1) lowering optical noise relating to partial coherency (by means of an optical characteristics changing member); and (2) performing feedback of the wavefront aberration or the partial change in travelling direction due to the target 10.

Any one of them or both of them may be performed.

For the above (2), influences on the irradiated light 12 or on the detection light 16 are measured at least at a part in the detection unit 4 or 6, and the optical characteristics of the irradiated light 12 are changed based on the measurement via the feedback unit 8. Similarly, the detection unit 4, 6 may be controlled so as to change the optical characteristics of the detection light 16 (the details are described later in Chapter 6).

Prior to the description of a specific example of the embodiment of the above (1) in Chapter 3, Chapter 2 describes the principle that partially coherent light generates optical noise.

In order to verify the reliability and trustworthiness of the findings obtained from optical detection or optical imaging, computer simulation by software for quantum-chemical calculations may be performed together. Then Chapter 7 describes a method of the present embodiment to theoretically calculate the characteristics of the n-th overtone or the combination limited to a specific atomic group in a polymer.

Section 2.2 Occasion of Partially Coherent White Light and Definition of Technical Terms It is known that single-colored laser light emitted from a laser diode chip has coherency. Correspondingly white light emitted from a small light-emitting source 70, such as a tungsten halogen lamp, also has partial coherency.

For instance, as shown in FIG. 2A, light (white light) emitted from point α and light (white light) emitted from point β on the surface of the tungsten filament 50 are observed simultaneously at point γ. When amplitude correlation between them is very large or when a phase shift value between them is constant over time, the beams of light from both points are called coherent light beams. In this case, interference occurs between the light beams at point γ.

On the contrary, when the light beams have no amplitude correlation or when a phase shift value changes irrelevantly between them, the light beams are called incoherent light. In this case, interference does not occur between the light beams at point γ. Then the light intensity observed at point γ can be obtained by simple addition of the light intensity obtained from point α alone and the light intensity obtained from point β alone.

Light other than laser light that is emitted regularly often has a middle state between the coherence state and the incoherence state as stated above. Such a state other than complete coherence and complete incoherence is typically called partial coherence. Light in such a state is called partial coherent light.

When such partial coherent light is scattered, reflected or transmitted at the detection target, partial "interference" occurs in the following optical path, which becomes a factor of speckle noise. When a signal is obtained from the detection target by light (predetermined optical characteristics are detected at a specific portion of this detection target) or image information is obtained from the detection target, the quality and characteristics of the detected signal or image may deteriorate because of the speckle noise resulting from the "interference of light".

The present embodiment proposes a unique method of (A) achieving incoherency among different light-emitting directions, different light-emitting regions, different separated wavefronts, and different separated amplitudes, and of (B) combining (mixing) the plurality of light beams having incoherency. Therefore in the following description of the present embodiment, the term "partial incoherence" is particularly used to refer to achieving partial incoherency (including an incoherent state to some extent that is not in a complete incoherent state) of the light used for signal detection or imaging. In this way, a difference between the present embodiment and conventional techniques is clarified.

An optical operation for the above (B) includes combining mutually partial incoherent light beams, and the following description refers to this operation as "mixing". The light obtained by mixing is called "mixed light".

Meanwhile, an operation to put light beams together, each passed through a different optical path irrespective of the coherent state, is referred to as "combining" in the description of the present embodiment. That is, the light beams to be combined may have coherency (including partial coherency) or may be in an incoherent state (including partial incoherency).

In some optical operating methods to put light beams in a broad wavelength range together, each passed through a different optical path, the light may show mixed characteristics such that the light of a short wavelength component has partial incoherency and the light of a long wavelength component has partial coherency. In this case also, an operation to put the light beams together is referred to as "combining" and the light obtained by combining is referred to as "combined light" in the description of the present embodiment.

The combined (or mixed) light may be uniform or similar in the travelling direction or in the electric-field vibration direction. As a result, when light beams passed through mutually different optical paths before combining (or mixing) are combined (or mixed), at least at a part of the combined (mixed) light beams pass through a same optical path.

Firstly, the basic principle for "optical coherency" described above is explained below. For the purpose of illustration, the idea of "inconstancy of light-emission time of the light in the frequency width Δν (that cannot be specified uniquely in the time width Δt)" can be used in the following. The latter half of this section (Section 2.2) mainly explains a general method to describe optical coherency.

Consider the case where white light emitted from point α on the surface of the tungsten filament 50 in FIG. 2A passes through an optical narrow-bandwidth bandpass filter (wavelength selective filter) 52 transmitting only the light from $\lambda_0 - \Delta\lambda/2$ to $\lambda_0 + \Delta\lambda/2$ in the wavelength range, and then arrives at point γ at a distance R. The light that can pass through this narrow-bandwidth bandpass filter (wavelength selective filter) 52 can have the range of optical frequency (frequency of vibrations) from $\nu_0 + \Delta\nu/2$ to $\nu_0 - \Delta\nu/2$.

The distance from point γ to point β on the surface of the tungsten filament 50 is R+δ. Apparently the light beam arriving at point γ simultaneously with the light beam leaving point α leaves point β at a time earlier by the following Δt, $$\Delta t = \delta/C \qquad (B\text{·}1),$$

where C denotes the propagation velocity of light in vacuum.

The following uncertainty principle applies to light as well, $$1 \geq \Delta t \cdot \Delta \nu \qquad (B\text{·}2).$$

That is, it is considered difficult for a plurality of optical phenomena generated within the time range Δt specified by the above (B·2) to distinguish their detailed chronological order. That is, light beams emitted from a plurality of different positions within the above time range Δt can be considered as "emitted substantially simultaneously".

Meanwhile, the center wavelength $\lambda_0$, the wavelength range $\Delta\lambda$, the center frequency (frequency of vibrations) $v_0$, and its range $\Delta v$ of the light that can pass through the optical narrow-bandwidth bandpass filter (wavelength selective filter) 52 have the following relationship, $$(\lambda_0-\Delta\lambda/2)\times(v_0+\Delta v/2)=\lambda_0\times v_0=C \quad (B\bullet 3).$$

Therefore considering $\Delta\lambda\times\Delta v/4\approx 0$ in (B•3), the following relationship can be derived, $$\Delta v\approx\Delta\lambda\times C/\lambda_0^2 \quad (B\bullet 4).$$

Then substitution of (B•1) and (B•4) into (B•2), the following relationship can be obtained, $$\delta\leq\lambda_0^2/\Delta\lambda \quad (B\bullet 5).$$

That is, it is considered that, in the range of a difference $\delta$ in optical length in FIG. 2A satisfying (B•5), all of the light beams from different positions (point $\alpha$ and point $\beta$) on the surface of the tungsten filament 50 are emitted "substantially simultaneously". Especially the length satisfying the right side of (B•5) is called a coherence length. That is, the coherence length $l_{CL}$ can be represented by the following expression, $$l_{CL}=\lambda_0^2/\Delta\lambda \quad (B\bullet 6).$$

Therefore light beams in the range satisfying the above (B•5) have a mutually partially coherent relationship. The relationship between light beams that does not satisfy (B•5) but is close to (B•5) is called low coherence. Especially in the description of the present embodiment, a light beam that is controlled to be in a situation different from the above (B•5) is called the partially incoherent light as stated above. Although this term is not used in general, it is used here to emphasize the uniqueness of the present embodiment.

In the example of FIG. 2A, the wavelength range $\Delta\lambda$ satisfying (B•6) is set using the optical narrow-bandwidth bandpass filter (wavelength selective filter) 52. Alternatively, the wavelength range $\Delta\lambda$ (wavelength resolution) that the detection unit 6 (FIGS. 1A to 1C) of the present embodiment can separate and detect can be applied in the above (B•6).

Figure 14A:
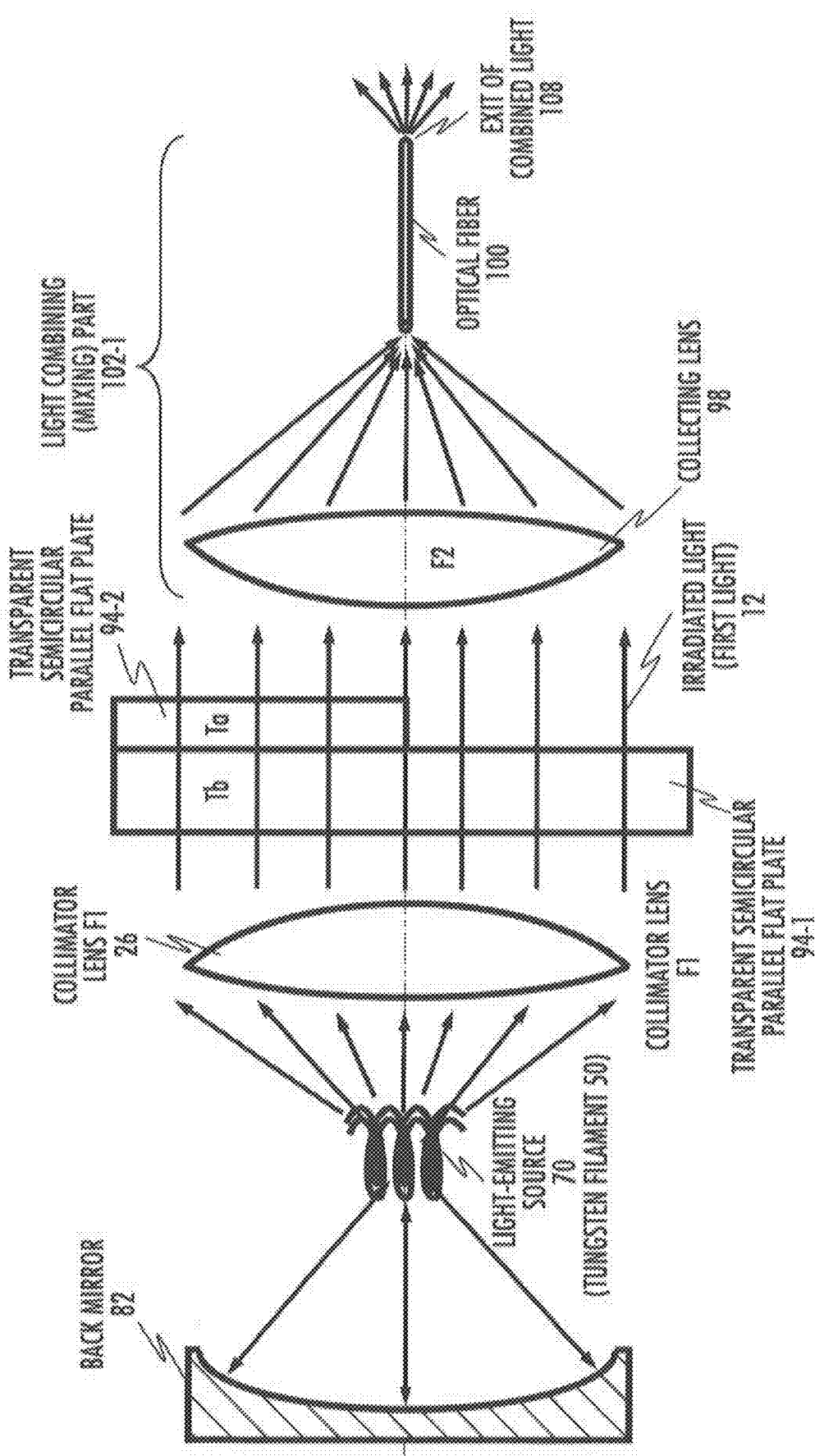
FIG. 14A describes an application example of the structure of a light-source unit using the method to reduce optical noise in the present embodiment.
Figure 14D:
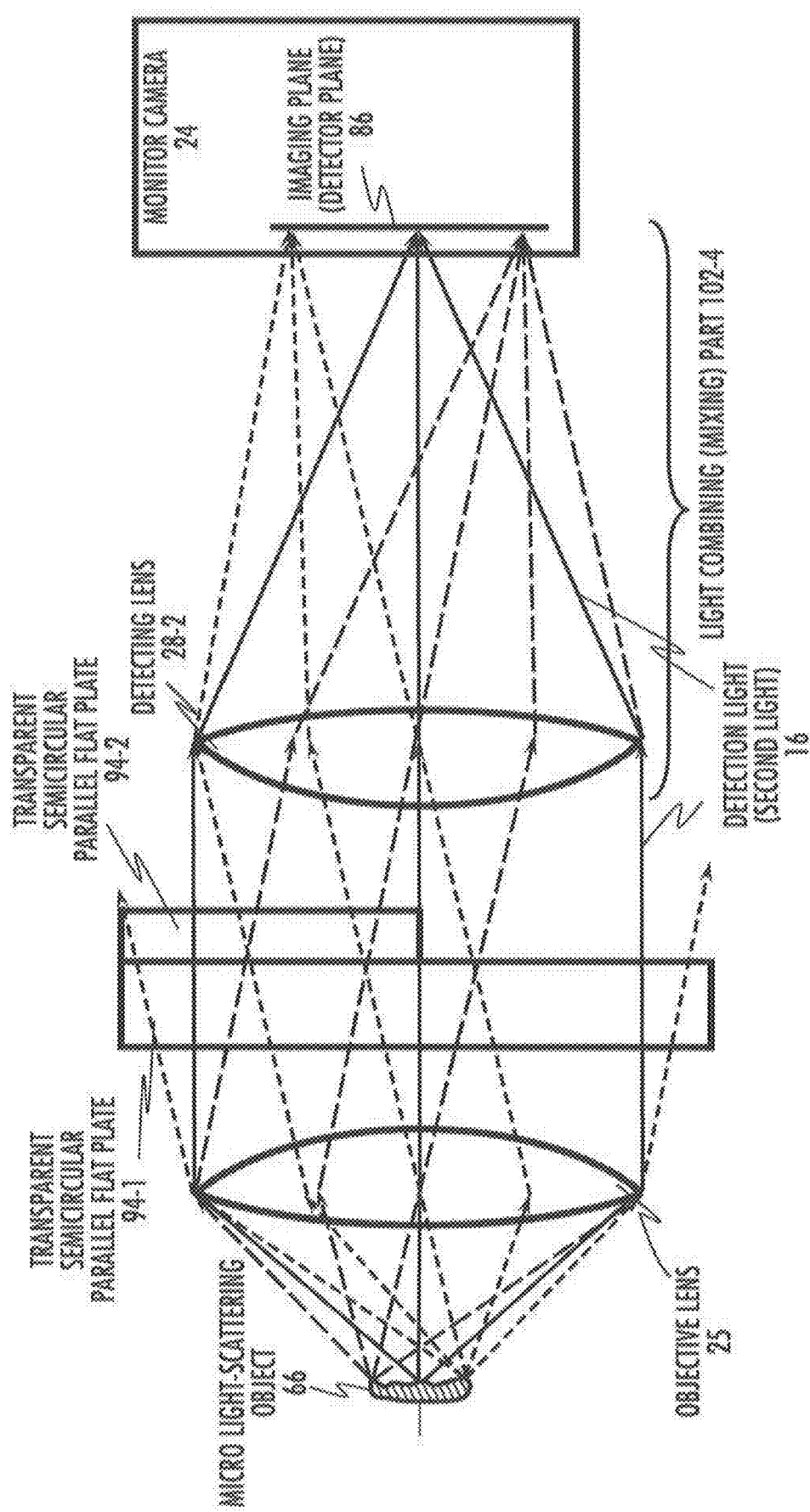
FIG. 14D describes a method of combining/mixing beams of wave-front divided light using imaging characteristics.
Figure 14E:
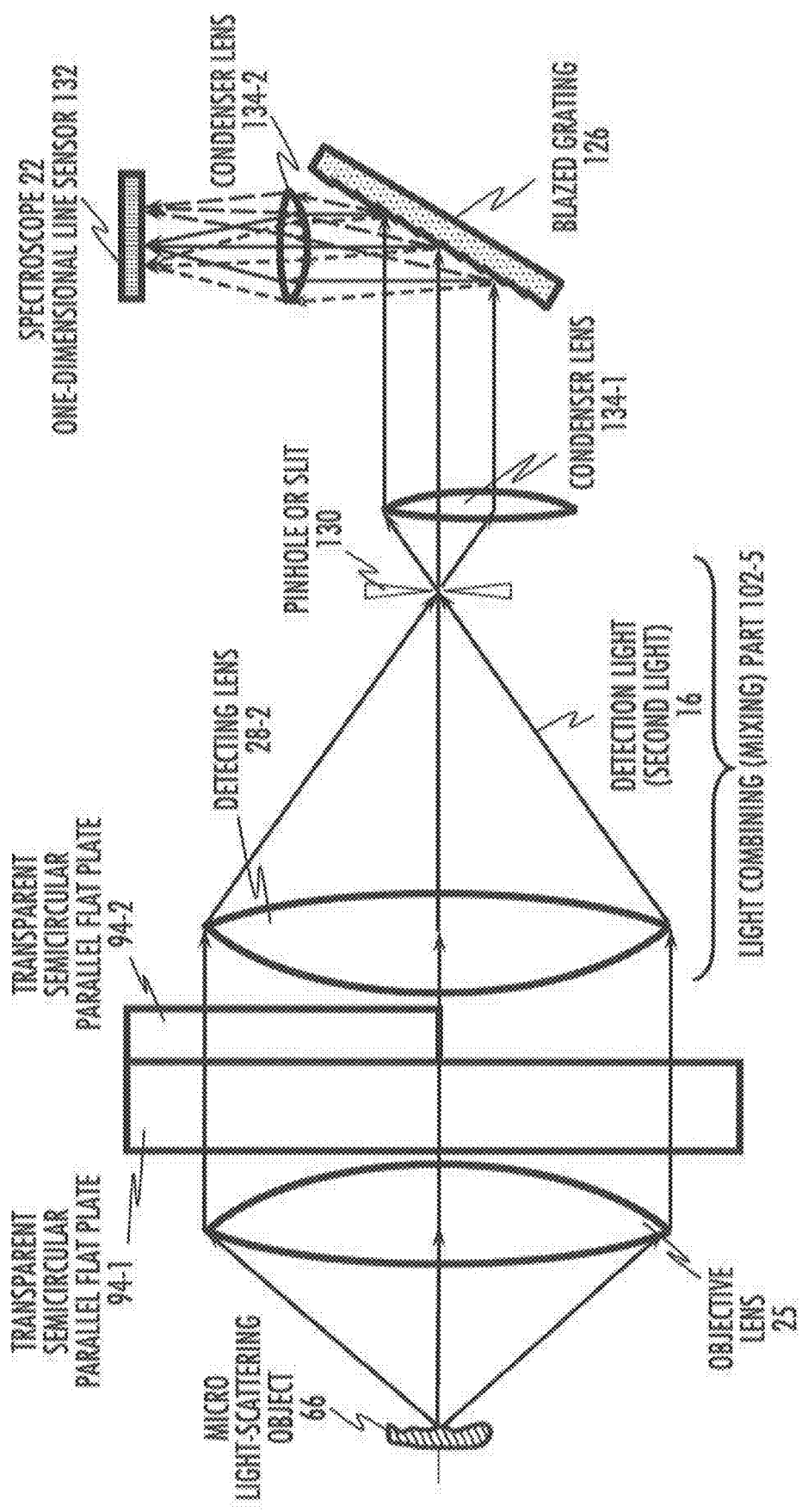
FIG. 14E describes a method of combining/mixing beams of wave-front divided light using optical processing of an imaging/light-collected position.

For instance, the wavelength range that one detection cell in a one-dimensional line sensor 132 disposed in a spectroscope 22 of FIG. 14E can detect can be used as $\Delta\lambda$ in the above (B•6).

Alternatively the value of the wavelength resolution (half width) of the spectroscope 22 in FIG. 14E can be used as $\Delta\lambda$ in the above (B•6). Note here that the wavelength resolution (half width) of the spectroscope 22 in FIG. 14E as one example is greatly influenced from the width W of a slit 130 (or the width of a pinhole).

When a light beam having the wavelength $\lambda$ close to the center wavelength $\lambda_0$ is incident on a blazed diffraction grating 126, the diffraction angle $\theta$ of the light beam is approximated as follows, $$\theta\approx\chi\cdot\lambda \quad (B\bullet 7).$$

Herein $\chi$ denotes a diffraction-angle coefficient relative to the incident wavelength of the diffraction grating. In this (B•7), substitution of $\lambda$ with $\Delta\lambda$, the following expression can be obtained, $$\Delta\theta\approx\chi\cdot\Delta\lambda \quad (B\bullet 8).$$

Let that SL denotes the distance between a condenser lens 134-2 and the one-dimensional line sensor 132, the amount of offset $\Delta Y$ on the one-dimensional line sensor 132 corresponding to $\Delta\theta$ can be represented as follows, $$\Delta Y=SL\cdot\Delta\theta\approx SL\cdot\chi\cdot\Delta\lambda \quad (B\bullet 9).$$

Let that M denotes the image-forming magnification (lateral magnification) of the condenser lens 134-2, M and the width W of the slit 130 (or the pinhole width) have the following relationship, $$\Delta Y=M\cdot W/2 \quad (B\bullet 10).$$

Based on this relationship, the following relationship holds from (B•9) and (B•10), $$\Delta\lambda\approx M\cdot W/(2SL\cdot\chi) \quad (B\bullet 11).$$

Substitution of (B•11) into the above (B•6) leads to the following characteristic formula, $$l_{CL}=2SL\cdot\chi\cdot\lambda_0^2/(M\cdot W) \quad (B\bullet 12).$$

Therefore the configuration of the optical system in the light-source unit 2 or the detection unit 6 of the present embodiment may be devised so as to reduce the optical noise component, such as speckle noise, of the irradiated light (first light) 12 or the detection light (second light) 16 (to be $\delta>l_{CL}$) so as to correspond to the characteristics of various light detection devices (or the optical devices, such as the optical narrow-bandwidth bandpass filter (wavelength selective filter) 10 in FIG. 2A, FIG. 2B or FIG. 4) that depend on the width W of the slit 130 of the measurement apparatus or the near-infrared microscopic apparatus or other parameters M, SL, and X.

The above describes a specific embodiment configured to devise the optical system in the light-source unit 2 or in the detection unit 6 to correspond to the characteristics (optical characteristics of the optical devices in FIG. 2A, FIG. 2B or FIG. 4) receiving influences from the width W of the slit 130 (or pinhole width) in the spectroscope 22 so as to reduce the optical noise component, such as speckle noise (to be $\delta>l_{CL}$). Alternatively the present embodiment may be devised to reduce the optical noise component, such as speckle noise, ($\delta>l_{CL}$) so as to correspond to the characteristics, such as wavelength separation ability and resolution, of a monitor camera 24 shown in FIG. 7, the detection characteristics, such as wavelength separation ability and resolution, of various light detectors not illustrated or the optical characteristics of the optical devices.

That is a description by way of a relatively narrow wavelength range $\Delta\lambda$. (B•5), (B•6), and (B•12) can be applied to a very wide wavelength range $\Delta\lambda$ as in "white light" as well.

For instance, it is roughly estimated that the wavelength range $\Delta\lambda$ of white light emitted from a tungsten halogen lamp is about 2 μm (0.5 μm to 2.5 μm) and its center wavelength $\lambda_0$ is about 1.2 μm. Then, the coherence length $l_{CL}$ in this case will be 0.72 μm in this case from (B•6). This means that beams of white light emitted from a plurality of different points and have a difference $\delta$ in optical length to the measurement point (point γ) that is 0.72 μm or less generate interference therebetween (having a partial coherent state).

The light-emitting source is not limited to the tungsten filament 50 as stated above, and white light emitted from any light-emitting source generates such a phenomenon in a similar manner. For instance, beams of white light from a light-emitting source that emits beams simultaneously from positions in a wide range (that is, the light-emitting region of the light-emitting source is very wide) also generate the same phenomenon (interference) as long as the beams are emitted from a minute light-emitting region satisfying (B•5).

The above describes the coherence length based on the idea of "uncertainty principle about the generation (light-emitting) time within the time range Δt". Instead, this length is often described as a distance enabling interference between different wave trains as follows.

For instance, the following considers the case where white-light beams emitted from light-emitting points propagate in the same direction (e.g., z-axis direction) in the space. Let that light beams of all wavelengths included in the white light have the same phase at t=0, z=0 (the position in the z-axis direction where the value of electric-field amplitude becomes maximum). The distribution range of electric-field amplitudes of all of the wavelengths that are close to the position and are localized in the range of coherence length is defined as "wave trains".

Based on an example of the calculation of coherence length as stated above, when the range of wavelength included in the white light is from 0.5 μm to 2.5 μm, the range of defining one wave train will be −0.36 μm≤z≤0.36 μm (=0.72 μm±2). Since 0.36 μm is shorter than the shortest wavelength of 0.5 μm, the phase of all of the wavelengths is substantially uniform in the same wave train.

Therefore when two wave trains neighboring in the z-axis direction overlap partially, interference of all-wavelength light occurs in the overlapping region.

Section 2.3 Influences on Optical Imaging from Partial Coherent Light

It is considered that, in the range of satisfying (B•5), all of the light beams from different positions (point α and point β) on the surface of the tungsten filament 50 of FIG. 2A are emitted "substantially simultaneously". Therefore it is considered that light beams after passing through the optical narrow-bandwidth bandpass filter 10 have the same phase of the electric-field amplitude 54 (the positions of peaks and troughs in the travelling direction of light) as in FIG. 2B.

FIG. 3 shows an example of the interference that occurs when the partial coherent light having such characteristics passes through a light-transmitting object 56 having one face with microscopic asperities. In FIG. 3(a), the surface of the light-transmitting object 56 does not have asperities, and so the canceling effect between neighboring partial coherent light beams 60 (based on coherence due to phase shifting) is not obtained.

On the contrary, in FIG. 3(B), the surface of the light-transmitting object 56 has asperities having a step height d. Let that n denotes the refractive index of the light-transmitting object 56, the optical length when the light beam passes through this mechanical distance d equals "nd". The optical length when the light beam passes through distance d in vacuum equals d. Therefore a difference in optical length between the light beam passing through the upper path (in vacuum having thickness d) of FIG. 3(b) and the light beam passing through the lower path (light-transmitting object 56 having thickness d) is as follows, $$\delta = (n-1)d \tag{B•13}$$

When $\delta = \lambda_0/2$, interference (cancellation) occurs between the partial coherent light beams passing through the upper path and the lower path of FIG. 3(b), so that the intensity of the light travelling straight equals "0". When the detection unit 6 detects the amount of transmitted light, a difference (influences from interference) between FIGS. 3(a) and (b) appears as optical noise.

FIG. 3 shows an example of the influences on optical imaging from microscopic asperities through which light passes along its optical path. This is not a limiting example, and a similar phenomenon (interference between reflected light beams and scattered light beams) occurs with light reflection or light scattering along the optical path.

Referring to FIG. 2A, the coherence length is described above as a range to generate interference between beams of irradiated light 12 emitted from a light source (FIGS. 1A to 1C). This is not a limiting example, and similar interference occurs between "beams of light (partial coherent light) reflected or scattered (including transmitted) in a microscopic region in the target 10 (FIGS. 1A to 1C)" as a target of observation, measurement or detection.

FIG. 4 shows an example where the irradiated light 12 travels from right to left, and the backward scattered light scattered at a part of a microscopic light-scattering object 66 in the target 10 is used as detection light 16 (see FIGS. 1A to 1C). Consider the case where beams of the backward scattered light at point α and point β in the microscopic light-scattering object 66 are detected (measured) at point γ. When a difference δ between the optical length from point β to point γ and the optical length from point α to point γ satisfies the relationship of (B•5), optical interference occurs at point γ between the light beams from point α and point β.

Further, when the target 10 has microscopic asperities on the surface, interference occurs similarly to FIG. 3 and so non-uniformity of the amount of detected light occurs in the detection direction. This considerably adversely affects the optical imaging. Additionally also when the target 10 has a non-uniform distribution of refractive index, interference occurs similarly (unnecessary non-uniformity of the amount of detected light in the detection direction), and this considerably adversely affects the optical imaging.

Section 2.4 Influences on Measurement of Spectroscopic Characteristics from Partial Coherent Light Section 2.3 describes the reason why optical imaging is degraded due to interference (speckle noise) when the irradiated light 12 or the detection light 16 (FIGS. 1A to 1C) is partial coherent light. The following describes another adverse effect from the partial coherent light on a detected signal obtained after photoelectric conversion or on the measurement result of spectroscopic characteristics (light-absorption characteristics) of the target 10.

FIG. 5 shows a light-transmitting object 58 as an example of the configuration of the target 10 of FIG. 1A/B/C(a), and the configuration has one face with microscopic asperities (step height d). Consider the case where partial coherent light passes through the object, and in FIG. 5(a), long-wavelength light 68 is incident, and in FIG. 5(b), short-wavelength light 62 is incident.

A difference δ in optical length corresponding to (B•13) occurs between the light passing through an upper part and the light passing through a lower part of the step height d. FIG. 5(b) shows the state where this difference δ in optical length and the wavelength λ of the incident light in vacuum satisfy the relationship "δ≈λ", and so the light passing through the upper part and the light passing through the lower part of the step height d have the same phase. This means that a decrease in the amount of transmitted light is small in this state.

On the contrary, when the relationship "δ≈λ/2" holds in the state of FIG. 5(a), cancellation of the amount of light travelling straight due to interference occurs between the light passing through the upper part and the light passing through the lower part of the step height d. This results in a decrease in the amount of light travelling straight.

Such a "change in the amount of light travelling straight due to the wavelength of incident light" may cause a significant error of the measurement result of spectroscopic characteristics (including light-absorbing characteristics) of the target 10 to be measured.

The above describes the light-transmitting object 58 of FIG. 5 as one example, having microscopic asperities on one of the surfaces only. This is not a limiting example, and an optical interference may occur inside of the light-transmitting object 58 as well. That is, light-scattering occurs at every microscopic region in an inorganic dielectric, an organic substance (highly-polymerized substance) or a living matter having a predetermined thickness and capable of transmitting light. Then, when the light beams emitted from the substance are the same in the travelling direction among multi-scattered light beams, then interference of light occurs similarly to FIG. 5.

FIG. 23A shows an experimental result of the measurement of a change in transmittance relative to wavelength about a polyethylene sheet of 30 μm in thickness and having flat surfaces (the detailed conditions of the experiment are described later). FIG. 23A(a) shows the measurement with near-infrared light having high partial coherency, and the degree of partial incoherency of the near-infrared light increases in the order of FIG. 23A(a), FIG. 23A(b) and FIG. 23A(c). In the order of FIG. 23A(a), FIG. 23A(b) and FIG. 23A(c), the transmittance at the wavelength of 1.360 μm increases successively as in 85.3%, 85.80% and 87.2%. Presumably such a change at the same wavelength of the same sample (target 10) results from a difference in partial incoherency of the near-infrared light used for the measurement.

That is, when light passes through a polyethylene sheet, multi-scattered light generated inside of the sheet also passes through the sheet backward. When the detection light 16 after passing through this polyethylene sheet has high partial coherency, interference occurs between beams of the detection light 16 travelling in the same direction, and so the intensity of light travelling straight is lowered. When this detection light 16 has high partial incoherency, the intensity of light travelling straight is not lowered so much due to interference between beams of the detection light 16 travelling in the same direction.

For the purpose of illustration, the above describes the influences on the measurement result of spectroscopic characteristics by way of the example of FIG. 5, where parallel light passes through the target 10. This is not a limiting example, and for all of the configurations of FIGS. 1A to 1C as the measurement apparatuses of the present embodiment, the phenomenon described in Section 2.4 or Section 2.3 occurs.

As described in Section 2.3 referring to FIG. 4, the above phenomenon occurs also when spectroscopic characteristics or light-absorbing characteristics are measured using light reflected from a microscopic light-scattering object 66. Therefore as shown in FIG. 7, a near-infrared microscopic apparatus of the present embodiment to measure a microscopic light-scattering object 66 also may include an optical noise reduction device or a partial coherent reduction device 64 to reduce the optical noise.

Figure 7:
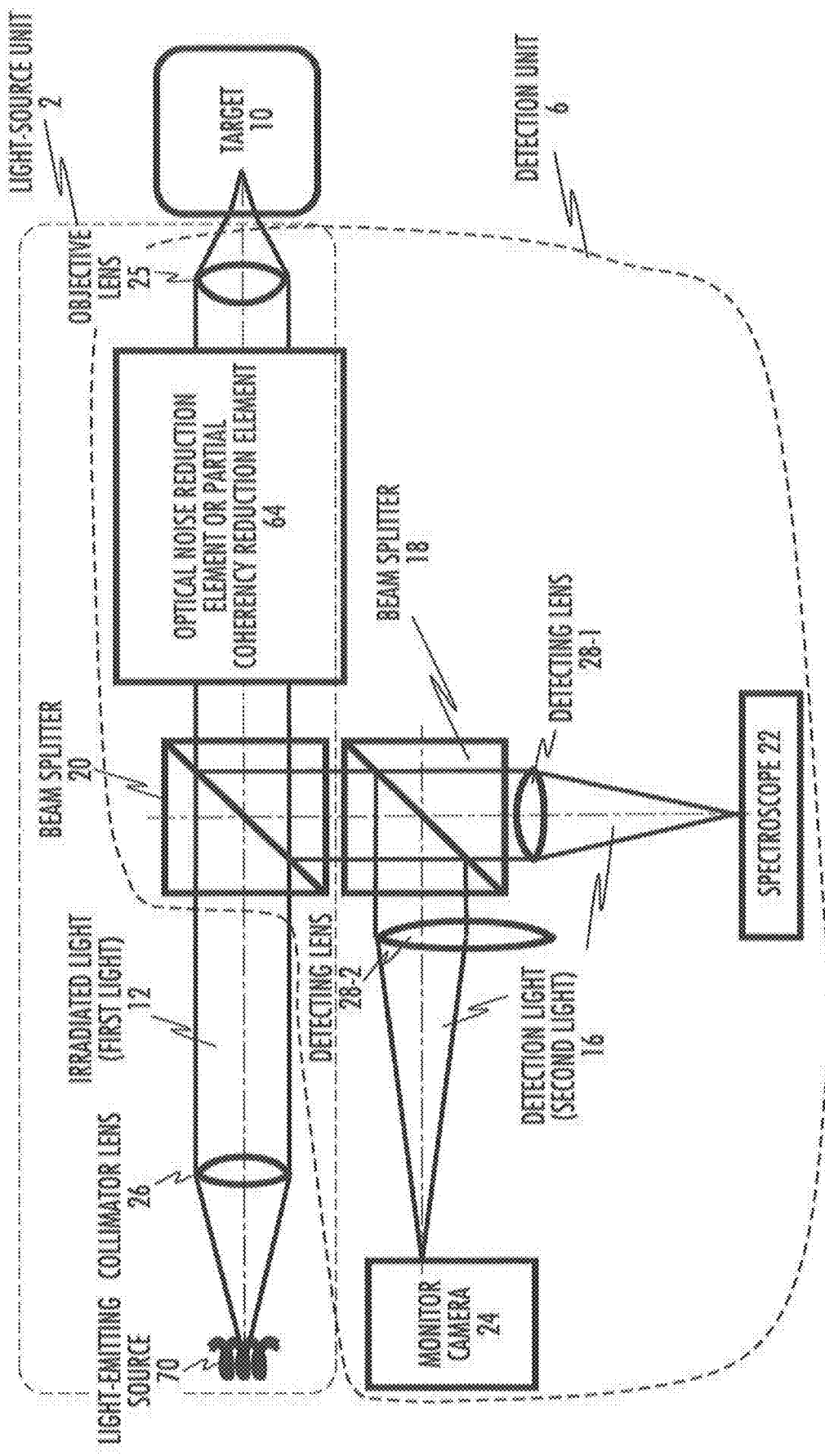
FIG. 7 describes one example of a near-infrared microscopic apparatus including an optical noise reduction element.

In the microscopic apparatus of the present embodiment of FIG. 7, irradiated light (first light) 12 from a light-emitting source 70 is converted into parallel light by a collimator lens 26, and then is collected by an objective lens 25 at a certain position in the target 10. The light reflected from this certain position is the detection light (second light) 16 and forms an image on the spectroscope 22 and on the monitor camera 24.

A specific optical path includes the objective lens 25 at which the detection light (second light) 16 obtained from the inside of the target 10 becomes parallel light, and the beam splitter 20 at which the light is separated from the optical path of the irradiated light (first light) 12. The detection unit 6 includes a beam splitter 18, and the light is separated into different travelling directions at this beam splitter. Separated beams of the detection light (second light) 16 are collected by detecting lenses 28-1 and 2 on the monitor camera 24 and the spectroscope 22 (specifically, the pinhole or the slit 130 of FIG. 14E). An image-forming optical system is defined with the combination of the objective lens 25 and the detecting lenses 28—½ between a certain position inside of the target 10 to be detected or measured by this microscopic apparatus and the detection position (imaging plane or the pinhole or slit 130) of the spectroscope 22 and the monitor camera 24. This enables extraction of only a characteristic signal at a predetermined position in the depth direction inside of the target 10.

The microscopic apparatus of the present embodiment may include an optical noise reduction device or a partial coherent reduction device 64 (the detailed configuration and functions are described later in Chapter 3) at some part along the optical path. This can improve the partial incoherency of the irradiated light (first light) and the detection light (second light) 16, and so optical noise due to optical interference can be reduced.

For the light used for the above microscopic apparatus, near-infrared light included in the wavelength range specified in Section 2.5 may be used. Such a microscopic apparatus based on the near-infrared light is particularly called a "near-infrared microscopic apparatus" in the present embodiment.

Section 2.5 Mathematical Presentation of an Example of Influences from Partial Coherent Light on Spectroscopic Characteristics Section 2.4 gives a quantitative description on the degradation of detection-signal characteristics due to speckle noise resulting from light interference when partial coherent light is used to measure the spectroscopic characteristics (including light-absorbing characteristics) of a measurement target. Section 2.5 gives a qualitative (mathematical) description by way of a certain example of the model.

Examples of known light sources that emit light of a lot of different wavelengths in a panchromatic wide wavelength range including a visible range and a near-infrared range includes a tungsten halogen lamp and a xenon lamp. Such a lamp encloses halogen gas (iodine or bromine compound) or xenon gas around a tungsten filament. From an optical aspect (for the accuracy on the order of optical wavelengths), the vessel made of quartz glass enclosing such gas has non-uniform thickness, that is, the vessel is irregular in thickness from one position to another. Therefore as panchromatic light generated inside of the vessel passes through the vessel, optical interference occurs due to such irregularity in thickness of the vessel.

Figure 6:
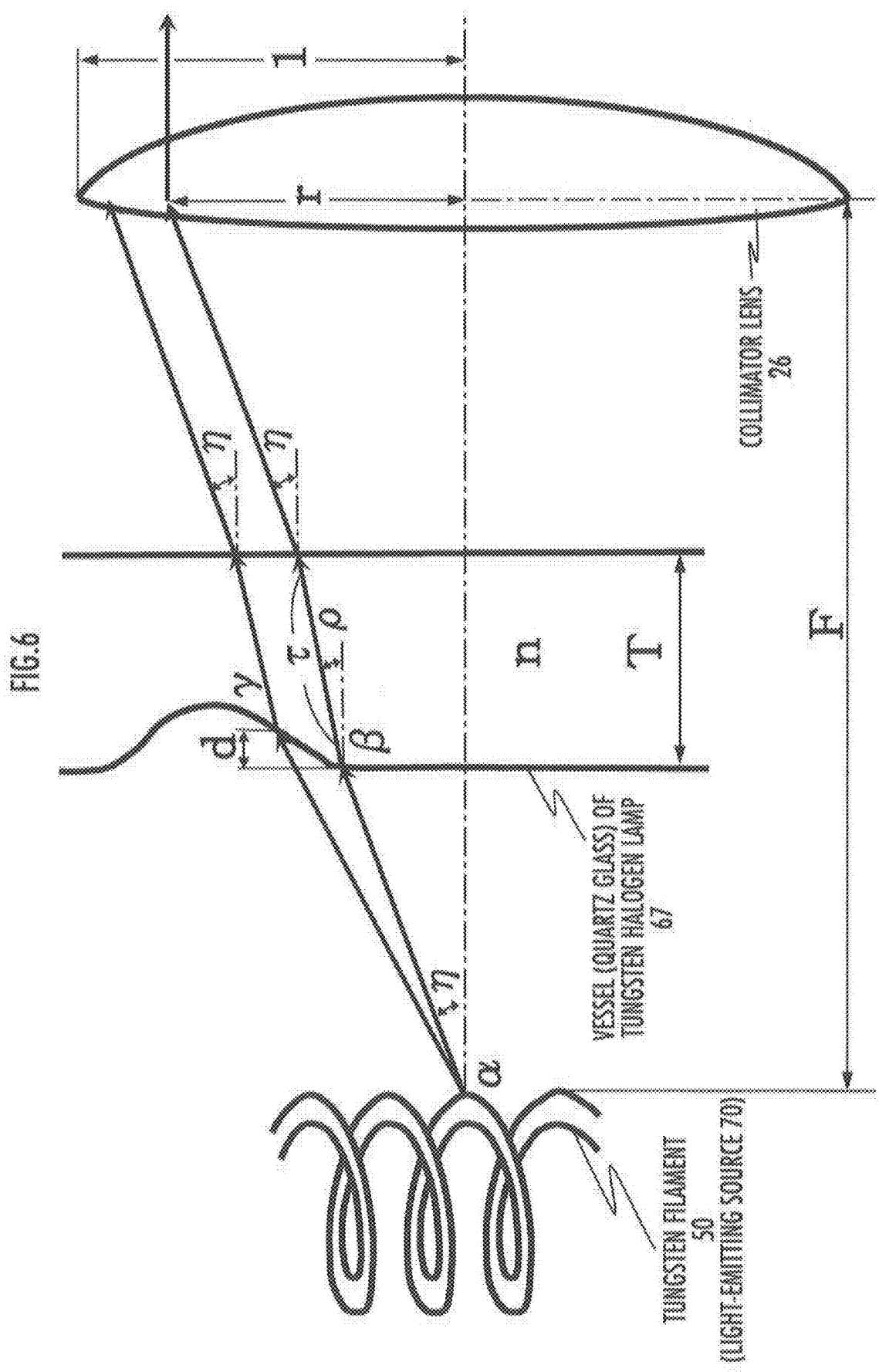
FIG. 6 describes influences from uneven thickness of the tungsten halogen lamp vessel.

FIG. 6 shows the model of this situation. This model assumes the case where scattered light generated from a position close to the tungsten filament 50 as the light-emitting source 70 passes through the vessel 67 and then is converted into parallel light at the collimator lens 26 at a focal distance F. The pupil area of the collimator lens 26 has a radius that is normalized as "1". Then η denotes the angle of the travelling direction of light generated from point α close to the tungsten filament 50 and passing through point β of the surface of the vessel relative to the optical axis of the collimator lens 26, and r denotes the radius of the position of the pupil area of the collimator lens 26 through which the light passes through. Further n denotes the refractive index inside of the vessel (quartz glass) 67 of the tungsten halogen lamp and T denotes the thickness of the vessel.

When the angle η is small enough, it has the following relationship with the angle ρ of the light-travelling direction inside of the vessel (quartz glass) 67 of the tungsten halogen lamp, which is approximated by Snell's law, $$\rho \approx \eta/n \quad (B\cdot 14).$$

Therefore when the angle η is small enough, the mechanical distance τ along which the light passes through the vessel (quartz glass) 67 of the tungsten halogen lamp can be approximated conveniently as follows, $$\tau = T/\cos\rho \approx T \quad (B\cdot 15).$$

Consider the case where the thickness of the vessel (quartz glass) 67 of the tungsten halogen lamp at point γ of the surface of the vessel is smaller by d than the surrounding. Further assume that the light generated at point α, passing through point γ and leaving the vessel 67 toward the collimator lens 26 forms angle η at the vessel. Since the light beams passing through point β and point γ travel in the same direction, interference occurs between them due to their partial coherent characteristics.

Approximation of (B•15) leads to a difference δ in optical length between the light beams passing through points β and γ that is equal to the case of (B•13). Then the combined wave ψ after passing through the vessel (quartz glass) 67 of the tungsten halogen lamp via point β or γ can be represented as follows, $$\psi(r) = e^{ikz} + Ae^{ik[z+(n-1)d]} = \quad (B\cdot 16)$$

$$e^{ik[z+(n-1)d/2]}\{(1-A)e^{-ik(n-1)d/2} + 2A\cos[k(n-1)d/2]\} =$$

$$e^{ik[z+(n-1)d/2]} \times$$

$$\{(1+A)\cos[k(n-1)d/2] - i(1-A)\sin[k(n-1)d/2]\},$$

where k denotes the wave number and z denotes the travelling direction of the light. Herein the amplitude of the light passing through point γ is "1" and the amplitude of the light passing through point β is "A".

Although the vessel (quartz glass) 67 of the tungsten halogen lamp has non-uniform thickness deviation, the following calculation considers that "the thickness deviation d of the vessel is uniform" for a simplified calculation model. Since the pupil area of the collimator lens 26 has radius r and width dr and so the area thereof is 2πrdr, the entire combined wave Ψ passing through the pupil area of the collimator lens 26 is represented by the following expression.

$$\Psi = 2\pi\int_0^1 r\phi(r)dr = \pi\phi \quad \text{[Math. 1]}$$

k=2π/λ, is obtained from the normalization with the maximum value, and so the light intensity $I_C$ of this combined wave Ψ can be obtained as follows.

[Math. 2]

$$I_C = |\Psi|^2 = \frac{1+A^2}{(1+A^2)^2} + \frac{2A}{(1+A^2)^2}\cos\{2\pi(n-1)d/\lambda\} \quad (B\cdot 18)$$

The second term in (B•18) shows that when optical interference occurs during the measurement of spectroscopic characteristics using partial coherent light, the amount of detection light depends on the measurement wavelength and changes like a cosine wave.

When interference occurs between partial coherent light beams due to any reason, which is not limited to such non-uniform thickness deviation of the vessel (quartz glass) 67 of the tungsten halogen lamp, a phenomenon similar to the above occurs. The combined wave ψ of different coherent light beams having a difference δ in optical length due to some reasons in the light-source unit 2 or the detection unit 6 (FIGS. 1A to 1C) and travelling in the same direction (having the same vibrating direction as well) can be represented similarly to (B•16) as follows, $$\psi = e^{ikz} + Ae^{ik(z+\delta)}$$

$$= e^{ik[z+\delta/2]}\{(1+A)\cos(k\delta/2) - i(1-A)\sin(k\delta/2)\} \quad (B\cdot 19).$$

Herein, $$|\psi|^2 = \{(1+A)^2\cos^2(k\delta/2) + (1-A)^2\sin^2(k\delta/2)\}^{1/2} \quad (B\cdot 20).$$

[Math. 3]

$$\tan\sigma \equiv -\frac{(1-A)\sin\left(\frac{k\delta}{2}\right)}{(1+A)\cos\left(\frac{k\delta}{2}\right)} \quad (B\cdot 21)$$

Considering the above, (B•19) can be modified as follows, $$\psi = |\psi|e^{ik(z+\delta/2+\sigma)} \quad (B\cdot 22).$$

(B•22) means that the combined wave ψ as a result of the combination of two plane waves having different phases will be one plane wave having the phase of δ/2+σ. For a similar reason, when three or more plane waves having partial coherency are combined, one plane wave can be obtained.

Let that the combined wave of all beams of light passing through the collimator lens 26 without any factor for light interference (for example, the vessel 67 is not present) is Ψ0, and a new combined wave generated from a factor causing light interference is Ψ1. When these combined waves Ψ0 and Ψ1 have partial coherency, the combination of these Ψ0+Ψ1 generates a "change in the amount of detection light in the direction of detection wavelength" similar to (B•18).

Next the following considers the case where the wall face of the vessel 67 of a tungsten halogen lamp is considered as a flat and parallel plate, and diverging light passes through this wall face toward the collimator lens 26 as another calculation model different from the above as well as the characteristics thereof. For simplified calculation, it is considered that the light passing through the collimator lens 26 has a uniform amplitude distribution everywhere.

Let that NA denotes the value of numerical aperture of the collimator lens 26, then the following expression can be obtained based on FIG. 6, $$r = \eta/NA \quad (B\cdot 23).$$

Although expression (B•14) obtained by approximation of Snell's law is used here, the following approximate expression having higher accuracy is used for (B•15).

[Math. 4]

$$\tau = \frac{T}{\cos\rho} \approx T\left(1 + \frac{\rho^2}{2}\right) = T + \frac{T \cdot NA^2}{2n^2}r^2 \quad (B\cdot 24)$$

The second term on the right side of this (B•24) corresponds to "d" in (B•13) (or (B•16)).

Since the pupil area of the collimator lens 26 has radius r and width dr and so the area thereof is $2\pi r dr$ similarly to the above calculation model, the entire combined wave $\Psi$ passing through the pupil area of the collimator lens 26 is given by the following expression,

[Math. 5]

$$\Psi \approx 2\pi \int_0^1 r \cdot \exp\left\{ik\left[z - \frac{(n-1)T \cdot NA^2}{2n^2}r^2\right]\right\}dr \quad (B\cdot 25)$$

Let that $v = r^2$, the integration of (B•25) results in the following expression because $rdr = (\frac{1}{2})dv$.

[Math. 6]

$$\Psi \approx i\frac{2\pi n^2}{k(n-1)T \cdot NA^2} e^{ikz}\left\{1 - \exp\left[-ik\frac{(n-1)T \cdot NA^2}{2n^2}\right]\right\} \quad (B\cdot 26)$$

Herein, $\Psi$ in (B•16) is replaced with $\Psi$, and let that "A=−1". Then, when the following replacement is performed, the result is proportional to (B•26), $$d = -T \cdot NA^2/(2n^2) \quad (B\cdot 27).$$

Therefore when the above replacement is performed for (B•18), the light intensity Ic after normalization for the combined wave $\Psi$ can be obtained as follows,

[Math. 7]

$$I_C = |\Psi|^2 \approx \frac{1}{2} - \frac{1}{2}\cos\left\{\frac{\pi(n-1)T \cdot NA^2}{\lambda n^2}\right\} \quad (B\cdot 28)$$

The second term on the right side of (B•28) shows that the detection intensity changes periodically with a change of the measurement wavelength $\lambda$. The period of such a change in detection intensity in accordance with the measurement wavelength $\lambda$ changes with the thickness of the parallel flat plate (vessel) 67 or the NA value of the collimator lens 26.

Parallel light after passing through the collimator lens 26 of FIG. 6 passes through the target 10 and then enters the detection unit 6 as in FIG. 1B(a), for example. In the detection unit 6, the light is collected by a detection lens 28-2 and then the spectroscope 22 detects or measures a signal having the characteristics of (B•28) as shown in FIG. 14E, for example. Any one of the optical systems of FIGS. 1A to 1C can detect or measure such a signal having the characteristics of (B•28). That is, (B•28) shows that a transparent parallel flat plate (such as the wall of a vessel) disposed at some part along the optical path from the light-emitting source 70 to the photodetector 80 (FIG. 8B) and in the diverging optical path or the converging optical path of partial coherent light generates optical noise due to the influences from interference of the light, and the intensity of the optical noise changes periodically with a change in wavelength $\lambda$.

In (B•28), the amount of change of optical noise generated periodically as stated above is very large. When (B•27) is substituted into (B•13), the maximum $\delta$max of the difference in optical length can be given as follows, $$\delta\text{max} = -(n-1)T \cdot NA^2/(2n^2) \quad (B\cdot 29).$$

In (B•29), when the thickness T of the parallel flat plate (such as the wall of the vessel) increases, then $\delta\text{max} > l_{CL}$. The actual calculation value of the coherence length $l_{CL}$ is described later in Section 2.7. In this state, beams of the light passing through the center and the periphery of the pupil area of the collimator lens 26 do not interfere in the spectroscope 22.

Approximation of (B•24) holds only for a sufficient small range of the value of $\rho$. Further, the thickness of the vessel 67 of a tungsten halogen lamp made of quartz glass is not uniform so much, and significant unevenness of the thickness is expected. The pupil area of the collimator lens 26 also has an amplitude distribution that is not uniform. As a result, a very small amount of optical noise will be actually observed as compared with (B•28).

For a panchromatic light source, such as a tungsten halogen lamp or a xenon lamp, a difference in optical path can be generated in the vessel disposed around the tungsten filament. As a result, panchromatic light emitted from the light-emitting source (including such a vessel) often contains the optical noise component as in (B•28).

When the amount of the optical noise component in the light emitted from such a panchromatic light source is measured actually, the amount is not so large as given by (B•28). It can be considered that the amount of the optical noise component decreases from that of (B•28) for the above various factors.

When the light emitted from a plurality of types of and a plurality of tungsten halogen lamps (including the vessel) was actually examined, their optical noise component (the coefficient of the second term on the right side of (B•28)) was about 0.1 to 1.0% while setting the DC component (the coefficient of the first term on the right side of (B•28)) at "1".

The following describes the amount of optical noise component that can be permitted for a panchromatic light source. When parallel light travelling straight passes through a polyethylene film of 30 μm in thickness, the amount of light absorption at the absorption band belonging to the second overtone of methylene ($-CH_2$) group stretching changes by about 0.5% (the details are described later in Chapter 5, for example) as shown in FIG. 23A.

That is, the amount of optical noise component that can be permitted for a panchromatic light source is requested to be 0.5% or less in average at worst (desirably 0.1% or less in average). Not limited to the experimental condition of FIG. 23A, there is another demand for measurement with a sample (film) thinner than 30 μm. Therefore the amount of optical noise component needs to be 0.05% or less in average or to be 0.02% or less. The amount of optical noise component is defined as a ratio of the optical noise component (corresponding to the coefficient of the second term on the right side of (B•28)) when the DC component (the coefficient of the first term on the right side of (B•28)) is set at "1".

Panchromatic (not monochromatic) light emitted from a light source (due to the vessel or the like) originally has an optical noise component of about 0.1 to 1.0%. The present embodiment described in Chapter 3 can reduce this optical noise component to be 0.5% or less in average (or 0.1% or less in average, desirably 0.05% or less or 0.02% or less in average). As described above in SUMMARY OF THE INVENTION, the conventional techniques such as Patent Literature 1 has a limit to reduce the optical noise, and it has been difficult conventionally to reduce the optical noise to be 0.5% or less in average (or 0.1% or less in average, desirably 0.05% or less or 0.02% or less in average). Then as shown in FIG. 9, the present embodiment described later in Chapter 3 exhaustively provides every method to effectively reduce the optical noise due to light interference.

Therefore when some processing to reduce the optical noise for the irradiated light 12 (or detection light 16) obtained from a non-monochromatic light source including a vessel in the light source results in the amount of optical noise component in the irradiated light 12 (detection light 16) that can be reduced to be 0.5% or less in average (or 0.1% or less in average, desirably 0.05% or less or 0.02% or less in average), such a case can be considered that any one of the methods of the present embodiment (described in Chapter 3) or the combination thereof is performed to the light.

Section 2.6 Influences on Detection/Imaging Using Near-Infrared Light and its Wavelength Range Spectroscopic characteristics (light-absorbing characteristics) or light-scattering characteristics appear as a relatively large change at the visible range or the infrared range (mainly the wavelength range of mid-wavelength infrared or far-infrared). Therefore a signal obtained at the visible range or the far-infrared range is not so affected from optical noise. Few substances in the natural world are transparent to visible light, and the types of a target that can be measured with visible light to the inside deeper than the surface are limited. Since water molecules absorb mid-wavelength infrared light or far-infrared light well, it is difficult to use such mid-wavelength infrared light or far-infrared light to measure the internal characteristics of a target when the target is moist even only slightly or the surface of the target is wet.

On the contrary, near-infrared light having the wavelength range of 0.7 to 2.5 has excellent transmission characteristics for dielectrics, organic substances or living matters. Therefore near-infrared light is suitable for the measurement of internal characteristics of the target 10 of these substances. Especially since near-infrared light has excellent light transmission characteristics in living bodies, the light is called a "window of life".

The active state in a living body is often visualized (imaging) by f-MRI (Functional Magnetic Resonance Imaging). Especially for imaging, pulse Fourier transform spectroscopy is often used for a higher processing speed. This method, however, has a pulse width of magnetic excitation on the order of microseconds, and so the method cannot detect a change at a higher speed than that.

The activity (biological reaction, biochemical reaction or catalytic reaction) in the living body often ends at a higher speed of microseconds or less. Therefore the above f-MRI (or NRI) cannot detect the activity in the living body that occurs at a high speed. On the contrary a high-speed photodetector (or an imaging device) can detect a high-speed change inside of the living body using near-infrared light. That is, near-infrared light is suitable for the detection of a high-speed (microseconds or less) change (activity) in the living body.

Such near-infrared light, which has good transmission characteristics for dielectrics, organic substances or living matters, generates less absorption or scattering in these substances. Therefore the amount of a signal change obtained by near-infrared light from a specific region inside of the measurement target 10 is very small.

In a specific example thereof, as shown by experimental data of FIG. 23A, a difference in light transmittance between the actually-measured minimum value at the wavelength of 1.213 µm and an interpolated value (at the same wavelength position) estimated from an envelope curve connecting the surroundings is very small of about "0.5%".

In this way, since a variation of a signal from near-infrared light is very small, optical noise has to be reduced to obtain a sufficient S/N ratio (signal to noise ratio). Therefore when the characteristics or a change thereof at a certain region inside of the target 10 are detected or measured using near-infrared light, it is especially important to use the method for reducing optical noise according to the present embodiment.

For the detection or measurement using near-infrared light, a technique of reducing optical noise is important for the imaging described in Section 2.3 and for the signal detection or the measurement of spectroscopic characteristics (e.g., light-absorbing characteristics or wavelength dependency of light-scattering characteristics) described in Section 2.4.

Note here that a method of reducing optical noise described in the present embodiment is not unsuitable for a detection signal obtained using light at the visible range or mid-wavelength/far-infrared region. A method of reducing optical noise described later in Chapter 3 or later may be used for a detection signal obtained using light at the visible range or mid-wavelength/far-infrared region. In that case, the amount of noise is reduced and the S/N ratio is improved more.

In addition to the method of the present embodiment for reducing optical noise described specifically in Chapter 3 or later, the following feature about the wavelength band may be used. As a result, a sufficient S/N ratio can be obtained, and the accuracy or reliability of signal detection or measurement can be enhanced.

Such a feature about the wavelength band additionally used can have a great effect when the composition or the structure inside of the living body, the active state or a change in the active state is detected or measured using near-infrared light. This is because the living body contains a lot of substances absorbing light in a specific wavelength range of near-infrared light specified in the range of 0.7 to 2.5 µm. This means that near-infrared light in the specific wavelength range that such substances absorb is absorbed a lot in the living body, and the amount of detection signal decreases greatly. Therefore, light of wavelengths other than this specific wavelength range can be used for the detection or measurement, whereby unnecessary decrease in the amount of detection signal can be avoided.

Examples of the substances absorbing the specific wavelength range in the near-infrared range include oxygen concentration indicators, such as hemoglobin, myoglobin, cytochrome oxidase, and pyridine nucleotide. JP 2-240545 A (hereinafter called Patent Literature 2) describes the light-absorbing characteristics of these substances in details. The absorbance of hemoglobin and myoglobin (especially in the deacidification state) rapidly increases in the wavelength range of 850 nm or less. Therefore a desirable wavelength range to be limitedly used in the present embodiment is from 875 nm to 2500 nm including some margin.

The absorbance of oxygenated cytochrome oxidase slightly increases when the wavelength is 940 nm or less. Therefore considering the absorbance characteristics of the above oxygenated cytochrome oxidase as well, a more desirable wavelength range is from 950 nm to 2500 nm including some margin.

One of the substances in the living body that absorbs near-infrared light well includes water molecules. According to JP 2013-122443 A (hereinafter called Patent Literature 3), the region in the specific wavelength range relating to the water molecules that the water molecules absorbs the light the most has the center wavelength of 1.91 µm, and the half-value range of the absorbance is 1.894 to 2.061 µm. Therefore light limited to the range of 875 nm or more and 1890 nm or less or the range of 950 nm or more and 1890 nm or less to avoid the absorption of oxygen concentration indicators in the living body and water molecules may be used to detect or measure the composition or the structure inside of the living body, the active state or a change in the active state.

Water molecules absorb light in the range having the center wavelength of 1.43 µm and having the half-value range of absorbance that is 1.394 to 1.523 µm as well. Therefore light in the range of 875 nm or more and 1390 nm or less (or 950 nm or more and 1390 nm or less) and in the range of 1530 nm or more and 1890 nm or less to avoid this region as well may be used to detect or measure the composition or the structure inside of the living body, the active state or a change in the active state.

Water molecules absorb light (the absorbance thereof is relatively low) in the range having the center wavelength of 0.97 µm and having the half-value range of absorbance that is 0.943 to 1.028 µm as well. Therefore light in the range of 1028 nm or more and 1890 nm or less or in the range of 1028 nm or more and 1390 nm or less to avoid the absorption region of water molecules may be used to detect or measure the composition or the structure inside of the living body, the active state or a change in the active state.

The value of coherence length $l_{CL}$ is estimated by substituting the above wavelength range in (B·6). As described in Section 2.2, the value of coherence length $l_{CL}$ can be set in relation to (so as to correspond to) the detection characteristics of the detection unit 6 of the present embodiment. Let that the wavelength resolution (half width) of the example of the spectroscope 22 of FIG. 14E is 5 nm for high performance and is 50 nm for relatively lower performance.

Therefore in the case of Δλ=5 nm, the coherence length $l_{CL}$ nearly equals 0.18 mm at $\lambda_0$=950 nm, the coherence length $l_{CL}$ nearly equals 0.21 mm at $\lambda_0$=1028 nm, and the coherence length $l_{CL}$ nearly equals 0.71 mm at $\lambda_0$=1890 nm.

In the case of Δλ=30 nm, the coherence length $l_{CL}$ nearly equals 30 µm at $\lambda_0$=950 nm, the coherence length $l_{CL}$ nearly equals 35 µm at $\lambda_0$=1028 nm, and the coherence length $l_{CL}$ nearly equals 0.12 mm at $\lambda_0$=1890 nm.

Among the coherence lengths estimated as above, the maximum value is 0.71 mm, and so optical noise may be reduced so that the coherence length $l_{CL}$ becomes about 1 mm or more including some margin.

Chapter 3 Method for Reducing Optical Noise of the Present Embodiment Relating to Partial Coherency Chapter 2 describes the situation where partial coherent light generated from a panchromatic light source, such as a tungsten halogen lamp or a xenon lamp, may include optical noise mixed therein due to the vessel surrounding the filament. Chapter 3 describes a method of the present embodiment to reduce such optical noise due to light interference.

Section 3.1 Basic Principle to Reduce Optical Noise

Figure 8A:
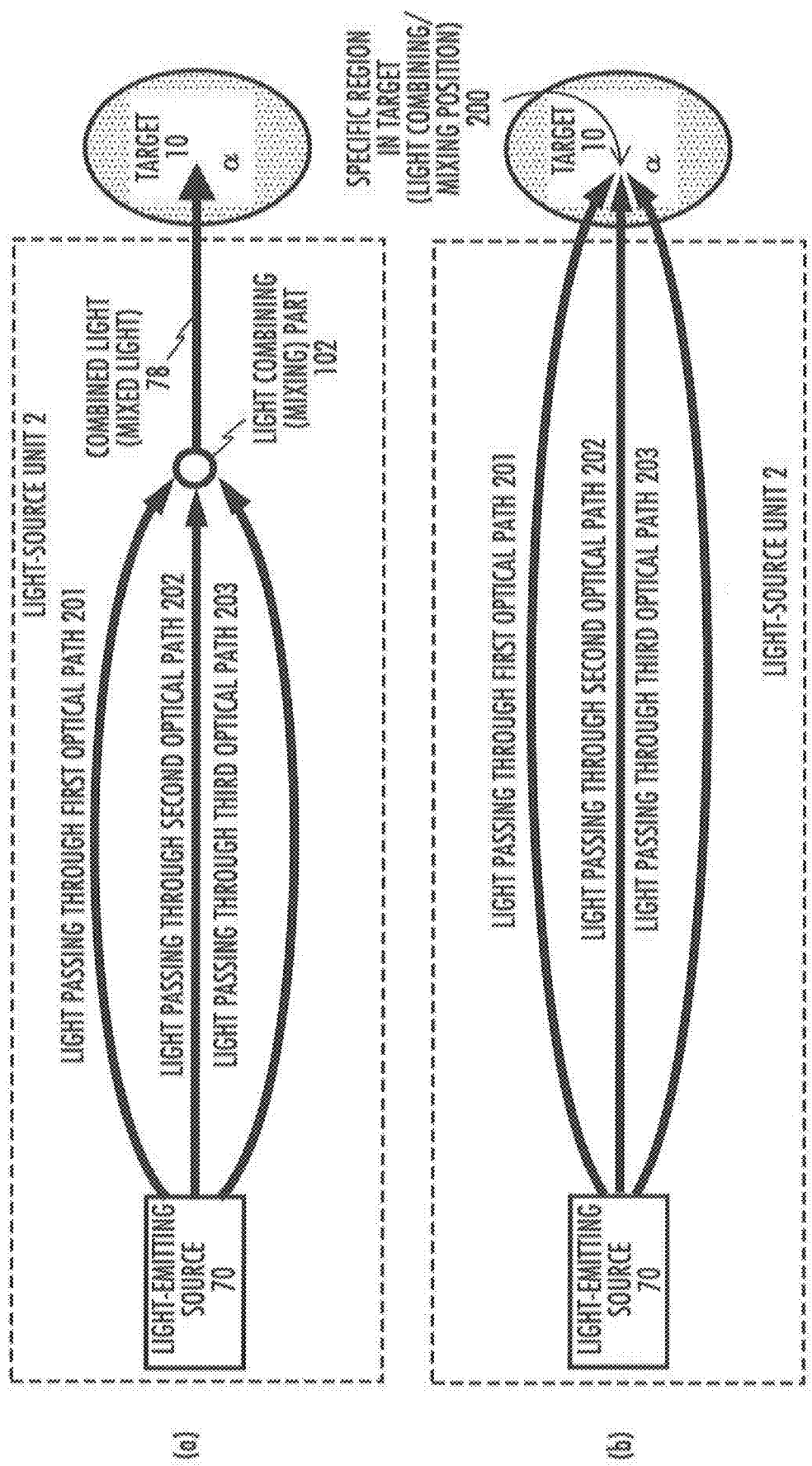
FIG. 8A describes the basic principle (A) of the method to reduce optical noise in the present embodiment.

Referring to FIGS. 8A and 8B, the following describes basic principle to reduce optical noise in the present embodiment.

The measurement apparatus having any one of the configurations of FIGS. 1A to 1C internally includes a plurality of optical paths from the light-emitting source 70 in the light-emitting unit 2 to the photodetector 80 in the detection unit 4, 6 via the target 10 (detection or measurement target) or a plurality of optical paths that are at least a part starting from the light-emitting source 70 or at least a part reaching the photodetector 80. These plurality of optical paths are combined or mixed at a predetermined position along the optical paths.

In accordance with the definition of the terms in Section 2.2, the mixed light generated immediately after "mixing" have partial incoherency and has greatly reduced partial coherency that the light has before the mixing. On the contrary, the combined light generated immediately after "combining" is allowed to have both of the states including "partial coherency" and "partial incoherency". The combined light may be in a middle state of them. For instance, a short-wavelength component of the combined light may have partial incoherency and a long-wavelength component thereof may have partial coherency.

As shown in FIG. 8A or FIG. 8B, the above-stated predetermined position where the plurality of optical paths are combined or mixed may be at least one of a light combining (mixing) part 102 along the optical path, a certain region (light combining/mixing position) 200 in the target 10 and the inside of the photodetector 80.

Especially when the predetermined position is present at some part along the optical path (light-combining (mixing) part 102 along the optical path), the predetermined position is present in a local region in the optical-axis direction of the combined light (mixed light) 78, that is, the predetermined position is localized at a certain position in the optical-axis direction.

Meanwhile, this predetermined position is not necessarily localized in the direction of a face (cross-sectional face of the light) perpendicular to the optical-axis direction. Therefore combination or mixing may be performed simultaneously at the cross-sectional face of the light as a whole of light beams 201, 202, and 203 passing through the optical paths. Alternatively the predetermined position (light-combining (mixing) part 102 along the optical path) may be disposed in a local region in the direction of the face (cross-sectional face of the light) perpendicular to the optical-axis direction.

At such a predetermined position for combining or mixing the plurality of optical paths, light beams passed through different optical paths may be substantially the same in the travelling direction or in the vibrating-plane direction of their electric field. They are not necessarily the same strictly.

Especially when the predetermined position is present at some part along the optical path (light-combining (mixing) part 102 along the optical path), the resultant combined light (mixed light) 78 passes through the optical path as in FIG. 8A(a) or FIG. 8B (a). If the travelling direction is not the same at the predetermined position (light-combining (mixing) part 102) among the light beams 201, 202 and 203 passed through different optical paths, these light beams 201, 202 and 203 will be separated again over a longer optical path of the combined light (mixed light) 78 and so their incoherency decreases.

When the optical path of the combined light (mixed light) 78 is short as well, the objective lens 25, the detecting lenses 28-1, 2 and the like of FIG. 7 act so as to separate these optical beams 201, 202 and 203 again in the target 10, at the spectroscope 22 or on the monitor camera 24. Therefore when the travelling direction is the same at the predetermined position (light combining (mixing) part 102 along the optical path) among the light beams 201, 202 and 203 passed through different optical paths, the accuracy of a detection signal or the sharpness of an image can be improved.

Similarly elements of an analyzer and a polarization beam splitter may be disposed in the detection unit 4, 6 to measure the polarization characteristics of the detection light 16. These elements are disposed so as to allow the light beams 201, 202 and 203 passed through different optical paths at the predetermined position (the light combining (mixing) part 102 along the optical paths) to have the same vibrating-plane direction of their electric field, whereby the detection signal characteristics can be improved.

These plurality of optical paths may have an optical arrangement such that their difference δ in optical length is larger than the coherence length $l_{CL}$. Then interference among the light beams passed through different optical paths can be avoided at the above-stated predetermined position, and so optical noise can be reduced. Such an optical arrangement can change the characteristics of the light passed through the plurality of optical paths at the predetermined position, i.e., their partial coherency decreases, and partial incoherency increases. As a result, the light beams passed through different optical paths are "mixed" at the above-stated predetermined position.

Such light beams passed through mutually different optical paths and having partial incoherency do not interfere, and so the optical noise can be reduced. Chapter 3.5 describes this effect in details mathematically, and this effect is based on the idea of calculating intensity sum of different oscillation periods and different phases of the optical noise components (corresponding to the second term on the right side of (B•28) or (B•18)) generated at different optical paths, so as to average (smooth) the optical noise characteristics. Therefore a larger number of operations of summing can improve the effect of averaging, that is, the effect of smoothing. That is, a larger number N of divisions to divide into a plurality of optical paths (corresponding to the number of operations of summing) can increase the effect of reducing optical noise.

Optical noise due to light interference can be reduced in this way, whereby adverse effects on the optical imaging described in Section 2.3 can be reduced. In addition, this can reduce adverse effects on the measurement of spectroscopic characteristics described in Section 2.4 and the optical detection using general detection light 16.

As described above, the present embodiment has an optical arrangement such that a difference δ in optical length among the plurality of optical paths is larger than the coherence length $l_{CL}$ so as to change the characteristics of the light at the predetermined position or in the optical path after the combination, i.e., their partial coherency decreases, and partial incoherency increases. Meanwhile if partial coherent light beams passed through different two optical paths are greatly different in their travelling directions or in their vibrating-plane directions of the electric field at the predetermined position, interference between the light beams hardly occurs when the light beams are combined at the predetermined position. In that case, the effect of reducing optical noise of the method of the present embodiment will be small. Therefore in order to obtain the effect of reducing optical noise from the present embodiment, the light beams are desirably similar to some extent in their travelling directions or in their vibrating-plane directions of the electric field at the predetermined position.

Figure 13A:
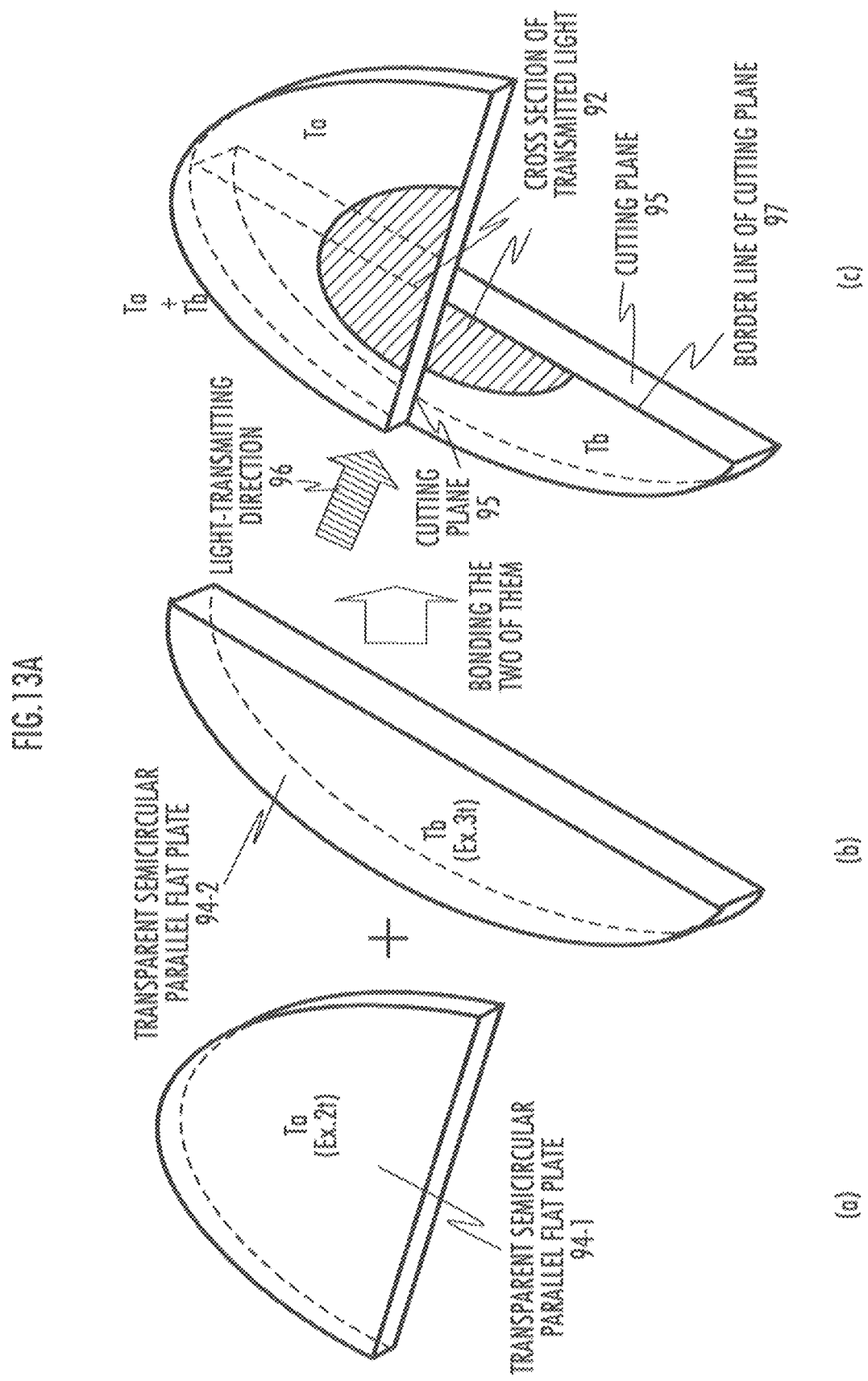
FIG. 13A describes another example of an optical characteristics changing member using wave-front divided light.

In the present embodiment, as shown in FIG. 8A or FIG. 8B, the number N of the plurality of optical paths (the number of dividing optical path) is "3" or more (desirably 4 or more as in Example of FIG. 13A, for example). The number of the optical paths may be 8 or more or 9 or more as in FIG. 13B(a) or FIG. 12C(c).

The photodetector 80 as described above includes every light-detection functional unit internally having a photoelectric conversion function. Specific examples of this light-detection functional unit include a semiconductor photodetector including a single light-detection unit and having a photoelectric conversion function as well as an avalanche (internal signal intensified) detector and a photomultiplier. Examples of a photodetector including a plurality of light-detection units (light-detection cells) include a line sensor including a plurality of detection cells arranged in one-dimensional direction, a plane sensor including a plurality of detection elements arranged two-dimensionally, and a position sensor (position detecting sensor) to detect a spot position of light applied in a predetermined plane region. The detector 80 includes the imaging device (monitor camera 24 in FIG. 14D) internally having these photoelectric conversion elements or the spectroscope 22 in FIG. 14E as well.

For the light-emitting source 70, a panchromatic light source, such as the tungsten halogen lamp or the xenon lamp described in Section 2.5 or an incandescent light bulb or a fluorescent lamp, is desirably used.

Section 2.5 describes, using (B•28), a transparent parallel flat plate disposed at some part along the optical path of diverging light emitted from the light-emitting source 70, the plate allowing the transmitted light to change in the intensity distribution periodically with a change in the measurement wavelength λ. Such a phenomenon occurs in any one of the cases including a panchromatic light source and including a monochromatic (single wavelength or narrow-wavelength range) light source.

As another method of applying this light to a spectroscope to obtain accurate spectroscopic characteristics (or light-absorbing characteristics), light beams in a narrow-wavelength range only are selected and applied to the target 10 at the same time, and the wavelength applied may be swept over time. For such a method, the intensity of narrow-wavelength range light beams applied at the same time may be monitored simultaneously, and a result of the monitoring may be fed back to the amount of detection light so as to remove a component of the variation in the amount of irradiated light for each measurement wavelength λ. This method, however, requires the time to sweep the wavelength to measure the spectroscopic characteristics (or light-absorbing characteristics), and so it is difficult to detect or measure a change at high speed in the target 10.

On the contrary, the method according to the present embodiment, which applies partial incoherent light beams to the target 10 from a panchromatic light source as the light-emitting source 70 and simultaneously detects/measures the intensities of detection light of a plurality of wavelengths with the spectroscope 22 of FIG. 14E, for example, enables high-speed detection/measurement. As a result, the method can have the advantageous effect of detecting or measuring a change at high speed in the target 10 accurately.

For the light-emitting source 70, a monochromatic light source, such as a LD (Laser Diode) or a LED (Light-emitting Diode) may be used.

FIG. 8A shows an example of the present embodiment including three optical paths in the light-source unit 2 from the light-emitting source 70 to a certain region α in the target 10. The present embodiment is not limited to three optical paths, and the optical path may be (set) divided more, e.g., into four or more optical paths, eight or more optical paths, or nine or more optical paths as stated above. The optical path may not be divided into a plurality of optical paths immediately after the light-emitting source 70, and may be divided into a plurality of optical paths at some part along the optical path after the light-emitting source 70.

The light-source unit 2 in FIG. 8A includes a plurality of optical paths having mutually different optical lengths (FIG. 8B). The light-source unit 2 may include the light combining (mixing) part 102 to combine (or mix) the light beams passed through these plurality of optical paths.

In the embodiment of FIG. 8A(a), the light combining (mixing) part 102 is disposed in the light-source unit 2. This light combining (mixing) part 102 corresponds to the predetermined position at some part along the optical path in the light-source unit 2 as stated above. The predetermined position (light combining (mixing) part 102) in this state corresponds to "some part along the optical path (of the irradiated light 12)" as the combining/mixing position in FIG. 9 as described later.

That is, in the embodiment of FIG. 8A(a), the optical path from the light-emitting source 70 to the light combining (mixing) part 102 includes first/second/third three optical paths, and light beams 201, 202 and 203 passed through these optical paths are combined (mixed) at the light combining (mixing) part 102. Then, these light beam 201, 202, and 203 are collected as the combined light (mixed light) 78, and are applied to the certain region α in the target 10.

In the embodiment of FIG. 8A(b), the optical path as a whole in the light-source unit 2 includes first/second/third three optical paths, and the light beams are combined (mixed) at the certain region (light combining (mixing) position) 200 in the target 10. In this case, therefore, the certain region (light combining (mixing) position) 200 in the target 10 corresponds to the predetermined position at some part along the optical path.

The predetermined position (certain region (light combining (mixing) position) 200 in the target 10) in this state corresponds to "certain region in the target 10 (including image-forming to the detector plane 86)" as the combining/mixing position in FIG. 9 as described later.

In the present embodiment, including both of FIG. 8A(a) and (b), the difference δ in optical length among the first/second/third optical paths satisfies δ>$l_{CL}$. Therefore the light beams 201, 202 and 203 passing through the first/second/third optical paths decrease in partial coherency to be mutually partial incoherent.

When partial coherency of the irradiated light (first light) 12 (FIGS. 1A to 1C) decreases in the light-source unit 2 as in FIG. 8A(a) or (b) in this way (to be partial incoherent light), the accuracy of imaging, signal detection (after photoelectric conversion), or spectroscopic measurement (e.g., measurement of wavelength dependency of the light-absorbing characteristics or light-scattering characteristics) at the certain range α (200) in the target 10 can be improved, and a reliable result can be obtained.

That is, as described later in Section 5.3 referring to FIG. 23A, multi-scattering occurs in the target 10. When partial coherent light is used for the target 10 as the irradiated light (first light) 12, interference of light occurs between multi-scattered light beams, which adversely affects the imaging, signal detection and spectroscopic measurement (the result contains a large optical-noise component). In addition, such partial coherent light leads to another adverse effect of interference of light resulting from the microscopic asperities at the surface of the target 10 or non-uniform distribution of the refractive index inside of the target 10 as described in Section 2.3.

When partial coherency of the irradiated light (first light) 12 decreases as in FIG. 8A(a) or (b) (to be partial incoherent light), such interference of light resulting from the inside or the surface of the target 10 as stated above can decrease.

FIG. 8B shows an example of the present embodiment including three optical paths in the detection unit 4, 6 from certain region β in the target 10 to the photodetector 80 in the detection unit 4, 6. The present embodiment is not limited to three optical paths, and the optical path may be (set) divided more, e.g., into four or more optical paths, eight or more optical paths, or nine or more optical paths as stated above. The optical path may not be divided into a plurality of optical paths immediately after region β in the target 10, and may be divided into a plurality of optical paths at some part along the optical path after the target 10.

In the embodiment of FIG. 8B(a), the light combining (mixing) part 102 is disposed in the detection unit 4, 6. This light combining (mixing) part 102 corresponds to the predetermined position at some part along the optical path in the detection unit 4, 6 as stated above. The predetermined position (light combining (mixing) part 102) in this state corresponds to "some part along the optical path (of the detection light 16)" as the combining/mixing position in FIG. 9 as described later.

That is, in the embodiment of FIG. 8B(a), the optical path from region β in the target 10 to the light combining (mixing) part 102 includes first/second/third three optical paths, and light beams 201, 202 and 203 passed through these optical paths are combined (mixed) at the light combining (mixing) part 102. Then, these light beams 201, 202, and 203 are collected as the combined light (mixed light) 78, and reach the photodetector 80.

In the embodiment of FIG. 8B(b), the optical path as a whole in the detection unit 4, 6 includes first/second/third three optical paths, and the light beams are combined (mixed) on the photodetector. Therefore the photodetector 80 corresponds to the predetermined position at some part along the optical path in this case.

The predetermined position (photodetector 80) in this state corresponds to "the detector plane 86 in the photodetector 80" as the combining/mixing position in FIG. 9 as described later.

In the present embodiment, including both of FIG. 8B(a) and (b), the difference δ in optical length among the first/second/third optical paths satisfies δ>$l_{CL}$. Therefore the light beams 201, 202 and 203 passing through the first/second/third optical paths decrease in partial coherency to be mutually partial incoherent.

FIG. 9 shows the list of various conditions relating to a method for implementing the basic idea (basic principle) of the present embodiment shown in FIGS. 8A and 8B.

FIGS. 8A and 8B show the configuration, in which the optical path (at least a part thereof) in the light-source unit 2 or in the detection unit 4, 6 includes a plurality of optical paths, and the light beams passed through these optical paths are combined/mixed. Alternatively, the present embodiment may be configured so that the optical path is divided into a plurality of optical paths, leading to the combination/mixing of light beams that is performed across the light-source unit 2 and the detection unit 4, 6 or so that the optical path is divided into a plurality of optical paths, leading to the combination/mixing of light beams that is performed in each of the light-source unit 2 and of the detection unit 4, 6.

Additionally as in a near-infrared microscopic apparatus of FIG. 7, an optical noise reduction device or a partial coherent reduction device 64 to implement "the optical path being divided into a plurality of optical paths, leading to the combination/mixing of light beams" is disposed to be common in the light-source unit 2 and the detection unit 6.

Such a common disposition enables a large decrease in the amount of optical noise resulting from light interference, and so an accurate and reliable detection signal can be obtained.

In FIG. 9, the fields of "optical path state before combining/mixing" correspond to the options for a method of configuring a plurality of optical paths immediately after the light-emitting source 70 of FIG. 8A. That is, the present embodiment may be implemented as any one of the two methods of configuring a plurality of optical paths using "diversity of the light-emitting state" of the irradiated light (first light) 12 emitted from the light-emitting source 70 and of configuring a plurality of optical paths by performing a division into a plurality of optical paths for the irradiated light (first light) 12 (described in the field of optical path state/operation) or as the combination of these methods.

When a plurality of optical paths are configured using "diversity of the light-emitting state" as stated above, any one of "different light-emitting regions" and "different light-emitting methods" as described in the field of the details or the combination of them may be used.

For instance, when light is not emitted from one point but the light-emitting region is expanded, light beams emitted from different light-emitting regions may be combined, and the combined light may be used as the irradiated light (first light) 12. On the contrary, when the emission direction of the light emitted from the light-emitting source 70 is expended, light beams emitted in the different directions (considering the different light-emitting direction as a plurality of optical paths) may be combined, and the combined light may be used as the irradiated light (first light) 12.

For the detection light (second light) obtained from region β of the target 10 to be detected or measured shown in FIG. 8B, options of the present embodiment include "different light-emitting regions" described in the field of "the details" included in "diversity of the light-emitting state" in the field of "optical path state/operations" and "optical path dividing operation" in the field of "optical path state/operations". That is, any one of the two ways or the combination of them may be performed in the present embodiment.

For instance, when the target 10 to be detected or measured is a microscopic light-scattering object 66 having a micro structure of FIG. 4, for example, the optical arrangement (FIG. 8B) (so as to have "different light-emitting regions") having a difference δ in optical length between the light obtained from point α and the light obtained from point β that is larger than $l_{CL}$ ($δ>l_{CL}$) can reduce partial coherency between the light and can reduce the amount of optical noise.

For both of the irradiated light (first light) 12 of FIG. 8A and the detection light (second light) 16 of FIG. 8B, any one of the method of wave front dividing and of the method of amplitude dividing or the combination thereof may be selected for the "details" in the "optical-path dividing operation" in the field of "optical path state/operations".

"Wave front dividing" refers to a method of spatially dividing a cross-sectional face of the light on a cutting plane perpendicular to the optical axis along the travelling direction of the light. After the wave-front dividing, each divided piece of the light is often deformed in the cross section as compared with the state before the wave-front dividing. When wave front dividing is performed using a transparent parallel flat plate, the divided pieces of the light are the same in the travelling direction. Even when the divided pieces of the light are the same in the travelling direction, each divided piece of the light after the wave-front dividing is considered to pass through a different optical path in the present embodiment.

Meanwhile, in the case of "amplitude dividing", each divided piece of light keeps their shape in the cross-section of light, and the optical path is divided into a plurality of different optical paths. Amplitude dividing is often performed using an optical element, such as a beam splitter or a polarization beam splitter.

For a specific method of combining or mixing a plurality of optical paths, the travelling direction of light is changed or controlled for each of the plurality of optical paths. Any method may be used for the "method of combining/mixing light".

Firstly the following describes the "method of combining/mixing light" that can be used for all states/operations in the field of "the details". In FIGS. 8A and 8B to describe the basic principle to reduce optical noise, light beams 201, 202 and 203 passing through the first/second/third optical paths having mutually different optical lengths are collected toward a predetermined position. This predetermined position corresponds to the light combining (mixing) part 102, the photodetector or a certain region (light combining (mixing) position) 200 (point α) in the target 10.

Therefore FIG. 9 describes the "method of combining/mixing method" for all of these optical paths. For supplemental explanation of the "method of combining/mixing method", "changing/controlling the course of each optical path" is added. In the description of the present embodiment, an optical element to change or control the course of each of the plurality of different optical paths is collectively called an "optical characteristics changing member". That is, all of the single optical elements or the combination of these optical elements described in the field of the "method of combining/mixing light" in FIG. 9 to change/control the course of each optical path corresponds to the "optical characteristics changing member".

These optical characteristics changing members may have the following functions:

(A) a function of changing/controlling the optical length for each of the plurality of optical paths (corresponding to the function of "changing optical path 76" in FIG. 10 described later); and (B) a function of combining (or mixing) a plurality of optical paths at a predetermined position.

In the description of the present embodiment, an optical member to exert at least one of these functions (may exert both of the functions at the same time) is called an optical characteristics changing member.

This optical characteristics changing member may have a physical structure that is a single unit disposed at one position along the optical path. Alternatively, the optical characteristics changing member may be the combination of a plurality of members that are disposed along the optical path in a distributed manner. In the case of such a distributed disposition, a part of the optical characteristics changing member may have the function of above (B) and the remaining part disposed at a different position may have the function of above (A) so that their functions are separated at different positions. One example of changing/controlling the travelling direction of light for a plurality of optical paths by any methods of "different light-emitting regions", "different light-emitting methods", "wave front dividing" and "amplitude dividing" may be to use a refraction element such as a lens. In the present embodiment, examples of the "refractive element" include a spherical lens, an aspherical lens, a Fresnel lens, a prism and a transparent parallel flat plate.

Other examples may include a diffraction element, a light-reflecting element, and an optical-phase conversion element. Examples of the diffraction element include a diffracting grating and a hologram element, and this element may be blazed to have an inclined microscopic plane.

The optical-phase conversion element refers to an optical element to change the phase of light (irradiated light 12 or detection light 16) locally or entirely after the light passes through the element or is reflected from the element. To implement this function, the optical-phase conversion element internally has a microscopic distribution of refractive index or has microscopic asperities at the surface. The optical-phase conversion element of the present embodiment may include a random phase shifter having a surface of a specific period or random microscopic asperities, a defuser, or a sand treatment plate.

To change/control the course of each of the plurality of optical paths, a waveguide element may be used. The waveguide element includes a light guiding path formed or integrated on an optical fiber or a predetermined plate to guide the travelling direction of light.

As another method, instead of changing/controlling the travelling direction of light to the "predetermined position", light beams collected at the "predetermined position" only may be extracted from light beams having a plurality of travelling directions. This method corresponds to "extraction of combined/mixed light at the detection unit 6" in FIG. 9. For instance, the photodetector 80 in the detection unit 4, 6 of FIG. 8B performs "photo-detection (photoelectric conversion) at a specific local position only". Then, an image-forming relationship (confocal relationship) is formed between the "certain local position" on the photodetector 80 in the detection unit 4, 6 and the "predetermined position β" in the target 10, whereby information can be detected/measured only on the "predetermined position β" substantially. The details are described later in Section 3.9 referring to FIG. 20.

A prism or a special lens may be additionally used at some part along the optical path of the light emitted from the "different light-emitting regions", so as to collect the light emitted from a wide light-emitting region. As described in Section 2.2 referring to FIG. 2A, the difference δ in optical length between the light reaching point γ from a and the light reaching point γ from point β is larger than the coherence length $l_{CL}$, then their mutual coherency decreases (partial incoherency increases) and so the amount of optical noise decreases. To this end, the distance between point α and β is desirably large. To this end a prism or a special lens may be used at some part along the optical path to collect the light emitted from a wide light-emitting region. The details are described later in Section 3.9 referring to FIG. 24A and FIG. 24B.

The special lens includes a lens in an aspherical state. Specifically the special lens includes a lenticular lens, a cylindrical lens, or a Fresnel lens.

For the "method of combining/mixing light" of the light beams divided into a plurality of optical paths by "amplitude dividing", a reflecting element of a polarized nature, a transmitting element (e.g., polarization beam splitter) of a polarized nature, or a beam splitter of a non-polarized nature may be used. As means to achieve the same vibrating-plane direction of the electric field among the light beams passed through mutually different optical paths, a phase plate, an analyzer or a polarization beam splitter may be additionally used.

As described above referring to FIGS. 8A and 8B and described later referring to FIG. 10, light beams in the "optical path state before combining/mixing" of FIG. 9 pass through a plurality of optical paths and are combined/mixed at the "combining/mixing position". During the process, a change in optical path 76 is generated so as to change the optical characteristics of the combined light (mixed light) 78 (to decrease partial coherency and increase partial incoherency).

The "combining/mixing position" or the "spatially identical region" in FIG. 9 and the "light combining (mixing) part 102) in FIGS. 8A and 8B correspond to the above-stated "predetermined position". In one specific example of the present embodiment, this predetermined position disposed at some part along the optical path of the irradiated light 12 and the detection light 16 may be a core region 142 inside of the optical fiber 100. The details are described later in Section 3.4 referring to FIG. 14A. Alternatively, the predetermined position may be a position after passing through the optical-phase conversion element in the present embodiment. The details are described later in Section 3.4 referring to FIG. 14B.

When the predetermined region to combine or mix light beams passed through a plurality of optical paths" as described at the beginning of Section 3.1 is the certain region 200 in the target 10, this includes image-forming on the detector plane 86 or the like for the above-stated reason. The details are described later in Section 3.9 referring to FIG. 20. In this case, therefore, the method of "extraction of combined/mixed light at the detection unit 6" is used in the field of "method of combining/mixing light".

When the predetermined region to combine or mix light beams passed through a plurality of optical paths as described at the beginning of Section 3.1 is the inside of the photodetector 80, this corresponds to the detector plane 86 in the photodetector 80 in the field of "combining/mixing position" of FIG. 9. As described above, the photodetector 80 in the present embodiment is not limited to a photodetector including a single light-detection cell only, and includes every light-detection functional unit internally having a photoelectric conversion function. Therefore, when the imaging apparatus is included, the imaging plane (detector plane) 86 of the monitor camera 24 in FIG. 14D corresponds to the "predetermined position".

As one type of the photodetector 80, the spectroscope 22 of FIG. 14E includes the pinhole or slit 130 corresponding to the "predetermined position". This example of the embodiment corresponds to the "pinhole or slit 130" in the field of "combining/mixing position" of FIG. 9.

Figure 10:
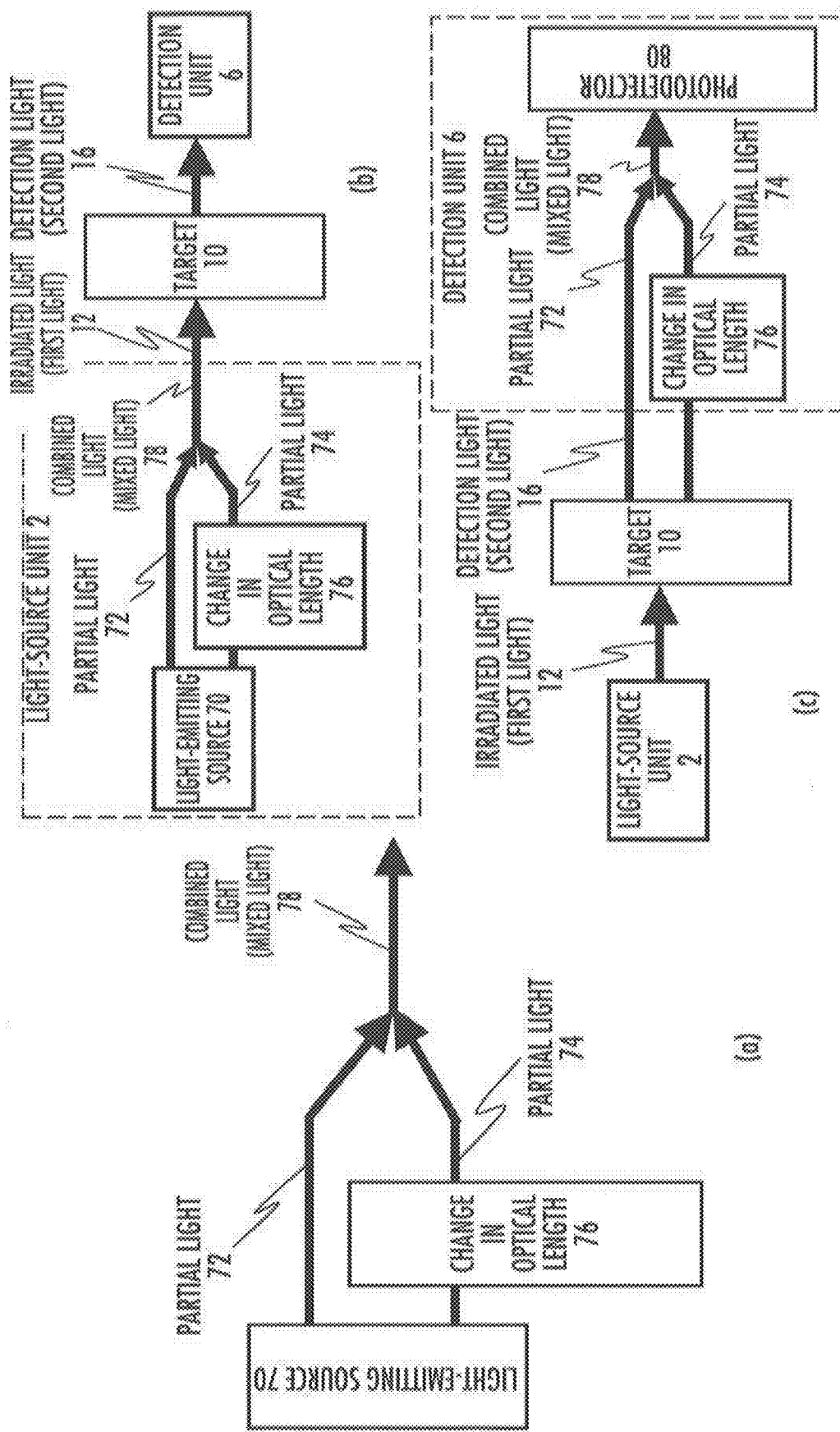
FIG. 10 describes another method to reduce optical noise in the present embodiment.

Referring to FIG. 10, the basic principle of the method to reduce optical noise in the present embodiment is described below from another viewpoint. As shown in FIG. 10(*a*), a change in optical length 76 is basically generated in another part 74 that is different from a part 72 of the light emitted from the light-emitting source 70 in the present embodiment. The amount of δ of the change in optical length 76 is desirably larger than coherence length $l_{CL}$ that is defined by (B•6) or (B•12). Thereafter these parts of light are mixed as mixed light 78 (this may be combined light). Therefore the optical characteristics of the mixed light 78 are changed by this method so as to decrease their partial coherency and increase their partial incoherency. Therefore according to the basic principle of the present embodiment shown in FIG. 10, when it is viewed along the optical path travelling from the light-emitting source 70, a change in optical length 76 is generated, and then the combined light (mixed light) 78 is generated.

Note here that the amount δ of the change in optical length 76 is not necessarily larger than coherence length $l_{CL}$ for all of the wavelengths. This is because, as described in the latter half of Section 2.7, the coherence length $l_{CL}$ that is defined by (B•6) or (B•12) varies greatly with the center wavelength $\lambda_0$ as a target. Therefore when panchromatic light is generated from the light-emitting source 70, the amount of the change in optical length may be larger than the coherence length $l_{CL}$ for the shortest wavelength to be used. In this case, partial coherence remains on the longer-wavelength side in the combined light 78.

FIG. 10(b) shows an example of the present embodiment, in which the optical operation of FIG. 10(a) is performed in the light-source unit 2. In this case, the combined light (mixed light) 78 is applied to the target 10 as the irradiated light (first light) 12.

FIG. 10(c) shows an example of the present embodiment, in which the optical operation of FIG. 10(a) is performed in the detection unit 4, 6. That is, a change in optical length 76 is generated in a part 74 of the detection light (second light) 16 obtained from the target 10, and then the part is combined (mixed) with the remaining part 72 of light. Then, the obtained combined light (mixed light) 78 reaches the photodetector 80.

FIG. 8A corresponds to FIG. 10(b) and FIG. 8B corresponds to FIG. 10(c). FIG. 10 clearly shows a change in optical length 76 generated in FIGS. 8A and 8B.

As described at the beginning of Section 3.1, the light originally belonging to the part 72 and the light belonging to the part 74 are desirably the same in their travelling direction (or the vibrating-plane directions of the electric field) at the inside of the optical path of the combined light (mixed light) 78 of FIG. 10 (at least at the starting position of the optical path of the combined light (mixed light) 78). This can suppress separation of the light again inside of the target 10 or on the photodetector 80, and so an excellent image or an accurate detection signal can be obtained.

The following describes a material for the optical characteristics changing member as described above or for a substrate of the optical characteristics changing member. Particularly the following describes points to note for selection of the material when near-infrared light described in Section 2.6 is used for the irradiated light 12 or the detection light 16. The optical characteristics changing member in this embodiment basically includes various types of optical members described in the fields (columns) of "method of combining/mixing light" (changing/controlling the course of each optical path) in FIG. 9. Alternatively, any material for optical devices may be used.

In the entire optical characteristics changing member or its entire substrate, a part to transmit the irradiated light 12 or the detection light 16 is desirably made of a material of transmitting light well. Known transparent plastic resins, which are available at relatively low cost, include acrylic resin PMMA (Poly-Methyl-Metacrylate) and PC (polycarbonate) resin. These plastic resins, however, contain a lot of atomic groups (methyl groups or methylene groups) including carbon atoms and hydrogen atoms only.

These atomic groups absorb near-infrared light described in Section 2.6. Particularly the light at the center wavelength of the absorption band belonging to the first overtone of the stretching generated in the atomic groups is greatly absorbed. This center wavelength of the absorption band is in the range of about 1710 nm to 1795 nm. For instance, when the light of the center wavelength passes through a transparent PMMA resin plate of 1 mm in thickness, the amount of transmitted light decreases to about half. In this way, such a material absorbs a great amount of light. Therefore when near-infrared light is used for the irradiated light 12 or the detection light 16, transparent plastic resins should be avoided as the material of the optical characteristics changing member or its substrate. Then, an inorganic material and not an organic material is desirably used for a material of transmitting near-infrared light well.

Known inorganic materials transmitting such light well include optical glass, $CaF_2$, $MgF_2$, LiF or KBr. Therefore these inorganic materials are suitable for the material of the optical characteristics changing member (or the substrate of the optical characteristics changing member).

For the reasons of manufacturing, typical optical glass includes a lot of hydroxyl groups (—OH groups). The center wavelength of the absorption band belonging to the first overtone of the stretching of such hydroxyl groups is in the range of 1395 nm to 1595 nm or in the vicinity of the range. This means that light passing through the optical glass including hydroxyl groups a lot is absorbed in such a wavelength range.

Therefore when near-infrared light in the wavelength range described in Section 2.6 is used for the irradiated light 12 or the detection light 16, a material with less hydroxyl groups is desirably selected for the optical characteristics changing member (or the substrate of the optical characteristics changing member). Specifically the experimental result shows that the specifically permitted amount of hydroxyl group has to be 100 ppm or less. Especially for accurate measurement of near-infrared spectra, the amount of 1 ppm or less is desirable. In this way, a material including the hydroxyl groups with the permitted amount or less is selected, whereby light absorption in the wavelength range of 1395 nm to 1595 nm can be avoided. This can lead to the effect of accurate measurement of spectroscopic characteristics in the entire wavelength range of near-infrared light.

Specifically such a light-transmitting material in the permitted range can be purchased by designating it as "a glass material that is controlled during manufacturing so as to include less hydroxyl groups", "anhydrous quartz glass" or "anhydrous quartz". All of these materials are manufactured while controlling the temperature and keeping the humidity low in the atmosphere with high-level of cleanliness (in the clean room) Since they are manufactured in the clean room with low humidity, moisture entering the materials in the air can be avoided, so that the amount of hydroxyl groups can be suppressed in the permitted range. Such a manufacturing method can prevent the incorporation of impurities, which causes the deterioration of materials, and so the manufactured materials can have high degree of purity. As a result, such a light-transmitting material can be stored stably for a long term, and so the characteristics (performance) of the optical characteristics changing member produced using such a material last long.

Section 3.2 Applications of Emitted Light into Different Directions

Section 3.1 is the summary about the method of reducing optical noise of the present embodiment using the list of options in FIG. 9. Section 3.2 or later describes the specific example of these options in details. The examples of the present embodiment described in Section 3.2 or later are just illustrative, and every combination in FIG. 9 is included in the present embodiment.

FIG. 11 shows an example of the method of combining/mixing different optical paths at some part along the optical path of the irradiated light 12 using "different light-emitting directions" in the field of "optical path state before combining/mixing" in FIG. 9 and using the light-reflecting element as the means to change the course of a specific optical path.

Light is emitted in all directions from a tungsten filament 50 as one type of the light-emitting source 70 in the light-source unit 2. In many cases, the forward emitted light 84 (corresponding to first optical path) only is used as in FIG. 11(*a*).

On the contrary, in the present embodiment, a back mirror 82 as the light-reflecting element is disposed on the rear side so as to return the backward emitted light 88 (corresponding to second optical path) to the inside of the tungsten filament 50. A distance of going from the tungsten filament 50 and returning from the back mirror 82 generates a change in optical length 76. As compared with the example of calculation at the latter half of Section 2.7, the difference δ in optical length generated here is much larger than the coherence length $l_{CL}$.

The backward emitted light 88 (second optical path) passing through the inside of the tungsten filament 50 follows the same optical path as the forward emitted light 84 (first optical path). Thereby, the forward emitted light 84 (first optical path) and the backward emitted light 88 (second optical path) are mixed.

In the example of the present embodiment in FIG. 11, partial coherency of the mixed light decreases greatly. Therefore, even when a transparent parallel flat plate is disposed at some part of the optical path of this scattered light, the amount of optical noise can be suppressed to be relatively small. In addition, in the example of the embodiment of FIG. 11, the light emitted from the tungsten filament 50 can be used Section 3.3 Optical Characteristics Changing Member Having the Function of Wave Front Dividing Section 3.3 describes a specific example of the present embodiment, in which "wave front dividing" is performed in the "optical-path dividing operation" of FIG. 9.

The following describes an example, in which a refractive element or a diffraction element is used as an optical element for the "wave front dividing". Alternatively, a light-reflecting element, an optical-phase conversion element, or a waveguide element may be used therefor. For instance, a light-reflecting face is configured to have a different step height for each region as shown in FIGS. 12C to 13C described later, whereby the optical length may be changed (after reflection) from one place to another for reflection in the cross-section of light 92.

In the example of the present embodiment described in Section 3.3, some part along the optical path of the irradiated light 12 or the detection light 16 is set for the field of "combining/mixing position" in FIG. 9.

FIG. 12A shows an example of the present embodiment including an "diffraction element" or a "refractive element" as the "method of combining/mixing light" of FIG. 9. A blazed diffraction grating or a prism 128 is disposed at a partial region (region through which transmitted light 110-1 passes) of the cross section of light at some part along the optical path of the irradiated light 12 or the detection light 16 so as to change the travelling direction of the transmitted light 110-1.

Thereafter the transmitted light 110-1 and transmitted light 110-2 are combined or mixed at a transmission diffraction grating 120. At this time, first-order diffracted light of the transmitted light 110-1 is allowed to be the same as zero-order light of the transmitted light 110-2 in their travelling direction.

The optical length between the blazed diffraction grating or prism 128 and the transmission diffraction grating 120 is different between the transmitted light 110-1 and the transmitted light 110-2. In this way, the example of the present embodiment of FIG. 12A changes the optical characteristics of the combined light (mixed light) 79 (to decrease partial coherency and increase partial incoherency) by using a change in optical length resulting from a difference in the travelling path of the light.

FIGS. 12B to 13C show the examples of the present embodiment including parallel flat plates having transmittivity as the refractive element to implement "wave front dividing" of FIG. 9. Let that n denotes the refractive index in the parallel flat plates having transmittivity and d denotes the thickness. Then, a difference δ in optical length represented by (B•13) is generated between the light beams travelling through a first optical path going straight in the parallel flat plates and through a second optical path going straight in vacuum (air) of d in length.

Then in the examples of the present embodiment shown in FIGS. 12B to 13C, the optical characteristics of the combined light (mixed light) 78 are changed (to decrease partial coherency and increase partial incoherency) by using a change δ in optical length of the transmitted light resulting from a difference in refractive index. Therefore the optical element including the combination of the transparent parallel flat plates 94, 114, and 116 shown in FIGS. 12B to 13C is one type of the optical characteristics changing member (or optical-length conversion element between separated waves 90).

As shown in FIG. 12B, a cutting plane 95 of the parallel flat plat is accurately parallel to the optical axis of the transmitted light. Therefore wave front dividing occurs in the light passing through the optical characteristics changing member (optical-length conversion element between separated waves 90) at the boundary 97 with the cutting plane (of the parallel flat plate) in the cross section 92 of the transmitted light. Since each beams of the transmitted light subjected to the wave front dividing has a different optical length, the beams will pass through different optical paths.

FIG. 12C shows another example of the embodiment for the optical characteristics changing member (optical-length conversion element between separated waves 90) shown in FIG. 12B. The longitudinal sides of the transparent parallel flat plate 114-2 of t in thickness are disposed in the X-axis direction. Then as shown in FIG. 12C(a), the longitudinal sides of the transparent parallel flat plate 114-1 of 5t in thickness are disposed in the X-axis direction, and are stacked (bonded) on the transparent parallel flat plate 114-2 of t in thickness. As a result, three regions are defined along the Y-axis direction, the regions having thickness of 0t, and 1t and 6t.

Next, the longitudinal sides of the transparent parallel flat plate 114-3 of 2t in thickness are disposed in the Y-axis direction. Then as shown in FIG. 12C(b), the longitudinal sides of the transparent parallel flat plate 114-4 of 2t in thickness are disposed in the Y-axis direction, and are stacked (bonded) under the transparent parallel flat plate 114-3 of 2t in thickness. As a result, three regions are defined along the X-axis direction, the regions having thickness of 4t, and 2t and 0t.

Next, as shown in FIG. 12C(c), FIG. 12C(b) and FIG. 12C(a) are stacked (bonded). Then the transmitting direction 96 of partial coherent light is aligned in the Z-axis direction from below to above. As a result, the optical path is divided into nine regions in the direction of a cross section of the light that is orthogonal to the light-passing direction 96. The thicknesses of the parallel flat plate 114 through which light passes along the optical paths are 10t, 8t, 6t, 5t, 3t, t, 4t, 2t, and 0t in the order from the upper left. The difference δ in optical length for each optical path at the corresponding region is given by (B•13).

As described in the first half of Section 3.1, the effect of reducing optical noise increases with the number N of dividing the optical path (corresponding to the number of operations of summing as stated above). Therefore when the optical path of the light is divided into different N pieces of optical paths by the optical characteristics changing member corresponding to at least any one of the options described in the field of "details" in the field of the "optical path state before combining/mixing" in FIG. 9 (i.e., this is not limited to wave front dividing corresponding to the example of the embodiment of FIG. 11C, and may be amplitude dividing and different light-emitting directions), all of the light beams passing through their corresponding optical paths are different in the difference δ in optical length. The example of FIG. 12C satisfies this condition. That is, all of the light beams passing through nine regions divided on the cross section of light (passing through different nine optical paths) are different in the difference δ in optical length.

The following is another description on this. That is, the optical characteristics changing member is the combination of refractive elements each having a different thickness (this is not limited to a parallel flat plate, and may be a prism or a lens) to divide the optical path into a plurality of optical paths. Let that mt (m is an integer) denotes a thickness of the refractive element of each optical path, all of the optical paths after dividing have different values of m. Such characteristics of the optical characteristics changing member are not limited to the structure of FIG. 12C, and they apply to the structure of FIGS. 13A to 13C as well. Such characteristics may apply not only to the "wave-front distribution" in the field of the "optical path state before combining/mixing" in FIG. 9 but also to the "amplitude distribution" and the "different light-emitting directions".

Further for at least any one of the options described in the field of "details" in the field of the "optical path state before combining/mixing" in FIG. 9 (e.g., this is not limited to wave front dividing corresponding to the example of the embodiment of FIG. 11C, and may be amplitude dividing and different light-emitting directions), the optical arrangement of the present embodiment is desirably such that a difference δ in optical length among the light beams passing through mutually different optical paths is larger than the coherence length $l_{CL}$ given by (B•6) or (B•12). In the example of the embodiment of FIG. 9(c), the minimum value of the differences in thickness between different regions is t. Therefore considering (B•13), the optical arrangement may be set so as to satisfy the following condition for the above reason, $$(n-1)t > l_{CL} = \lambda_0^2/\Delta\lambda \qquad (B•29).$$

For instance, when the refractive index of the refractive element is 1.5, the value of t may be set at 2 mm or more based on the calculation example including the margin described in the latter half of Section 2.7. Alternatively, the upper limit of the wavelength used may be smaller than 1.89μ,m, and the value of t may be set at 1 mm or more for a small size of the optical system as a whole. When the detection unit 4, 6 (or photodetector) having the value of Δλ larger than 5 nm, the value of t may be 0.5 mm or more, desirably may be 0.3 mm or more.

The following is another description on this. That is, the optical characteristics changing member is the combination of refractive elements each having a different thickness (this is not limited to a parallel flat plate, and may be a prism or a lens) to divide the optical path into a plurality of optical paths. Let that mt (m is an integer) denotes a thickness of the refractive element of each optical path, t satisfies the condition of (B•29). Such characteristics of the optical characteristics changing member are not limited to the structure of FIG. 12C, and they apply to the structure of FIGS. 13A to 13C as well. Such characteristics may apply not only to the "wave-front distribution" in the field of the "optical path state before combining/mixing" in FIG. 9 but also to the "amplitude distribution" and the "different light-emitting directions".

In an application example of the present embodiment, both of the above structures may be combined, and the characteristics of the optical characteristics changing member can be described as follows. That is, in the optical characteristics changing member that allows the division of the optical path into N pieces of optical paths, let that mt (m is an integer) denotes a thickness of the refractive element of each optical path (or mδ denotes the optical length when the light passes through each optical path), then all of the N pieces of optical paths have different values of m and satisfy the condition of (B •29) (or $δ > l_{CL}$).

The optical characteristics changing member of FIG. 12C divides the wave front into nine regions by combining three regions along the Y-axis direction and three regions along the X-axis direction. Such a method for division is called "XY division" in the description of the present embodiment. Such XY division it not limited to FIG. 12C, and the number of divisions may be any number as long as the number of divisions in one-axis direction is two or more (e.g., two regions in the Y-direction and two regions in the X-direction, and the total is four regions after division).

In FIG. 12C, the X-axis and the Y-axis are mutually orthogonal. Alternatively the X-axis and the Y-axis may be obliquely crossed, for example (the X-axis and the Y-axis are crossed at angles other than 90 degrees). In another method for wave front dividing, division may be performed along one-axis (X-axis) direction only, which is called "X-axis division". In another method, the optical characteristics changing member may have a part for X-axis division and another part for Y-axis division, and these parts may be distributed at different positions on the optical path.

Figure 13B:
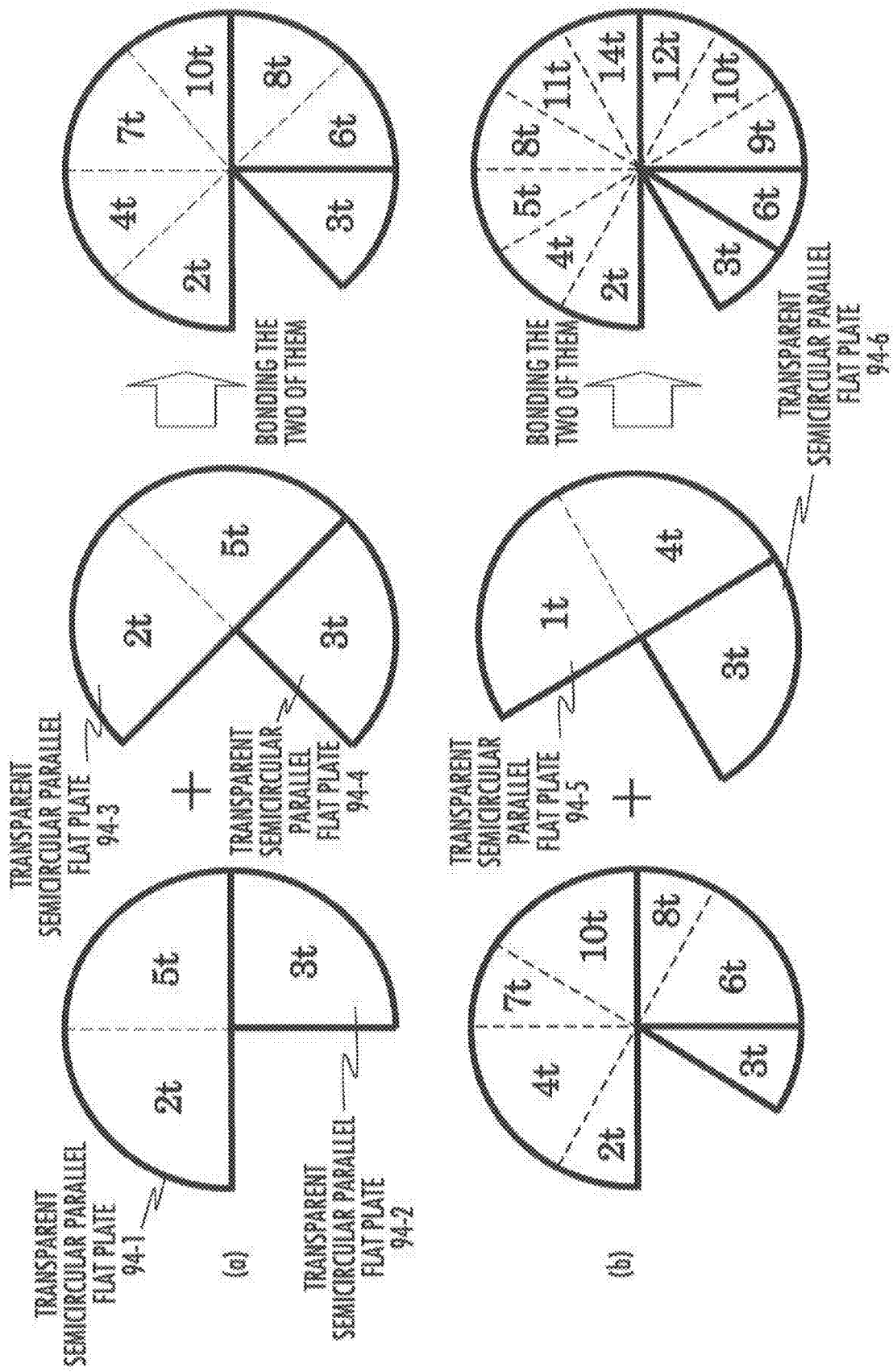
FIG. 13B describes an application example of an optical characteristics changing member using wave-front divided light.

The following describes "angle division" as another method of wave front dividing, referring to FIGS. 13A to 13B. In this method, a (circular) cross section of the transmitted light 92 is divided in angular directions along the dividing borders 97 among the optical paths each passing through the center of the circle. Such angular division may be performed at some part along the optical path because MTF (Modulation Transfer Function) characteristics at the image-forming part do not deteriorate and so good imaging characteristics can be obtained.

For instance, the cutting plane 95 of the transparent parallel flat plate 94-1 of 2t in thickness Ta is disposed laterally as in FIG. 13A(a). Next, a transparent parallel flat plate 94-2 (FIG. 13A(b)) of 3t in thickness Tb is disposed so that the cutting plane 95 is disposed longitudinally and is stacked (bonded) under the transparent parallel flat plate 94-1. Thus the optical characteristics changing member having the structure of FIG. 13A(c) is prepared. Then, the light transmitting direction 96 is set to be parallel to the cutting plane 95. As a result, the cross section 92 of transmitted light is angular-divided into four quadrants so that the borders 97 of the cutting planes are mutually orthogonal.

In the optical characteristics changing member of FIG. 13A(c), the positions through the optical paths pass through in the light-transmitting direction 96 have the thicknesses of Ta (e.g., 2T), Ta+Tb (e.g., 5t), Tb (e.g., 3t), and "0" in the order from the first quadrant. In this way, the positions (regions) through which the optical paths pass have different values of m for the thickness mt (the values of m are 2, 5, 3 and 0 in the order from the first quadrant), and t satisfies (B·29) (e.g., 0.3 mm or more).

The optical characteristics changing member of FIG. 13A(c) includes the transparent semicircular parallel flat plates 94-1 and 2 that are integrated by bonding. Alternatively, a plurality of members may be disposed along the optical path in a distributed manner. In this case, the divided regions may be disposed so as not to be overlapped, but to be shifted by a predetermined angle (e.g., when two members are disposed in a distributed manner, they are shifted by 45 degrees).

FIG. 13B shows an application example of FIG. 13A(c). The drawing of FIG. 13B(a) on the right shows the structure obtained by stacking two of the optical characteristics changing members each having the structure of FIG. 13A(c) while shifting them by 45 degrees. The optical paths (divided regions) of this optical characteristics changing member have the thicknesses of 10t, 7t, 4t, 2t, 0, 3t, 6t, and 8t.

The drawing of FIG. 13B(b) on the left shows the structure obtained by stacking two of the optical characteristics changing members each having the structure of FIG. 13A(c) while shifting them by 30 degrees and not 45 degrees. The drawing of FIG. 13B(b) in the middle shows the structure obtained by stacking a transparent semicircular parallel flat plate 94-5 of 1t in thickness and a transparent semicircular parallel flat plate 94-6 of 3t in thickness while shifting them by 90 degrees, and the drawing of FIG. 13B(b) on the right shows the optical characteristics changing member obtained by stacking (bonding) the structure on the left on the structure in the middle. This structure has the cross section 92 of the transmitted light that has equally twelve divided regions (the number of divided optical paths N=12).

The optical characteristics changing member of FIG. 13B on the right includes the transparent semicircular parallel flat plates 94-1 and 2 that are integrated by bonding. Alternatively, a plurality of members may be disposed along the optical path in a distributed manner. In this case, the divided regions may be disposed so as not to be overlapped, but to be shifted by a predetermined angle (e.g., when two of the structures of FIG. 13B on the right are disposed in a distributed manner, they are shifted by 22.5 degrees).

Figure 13C:
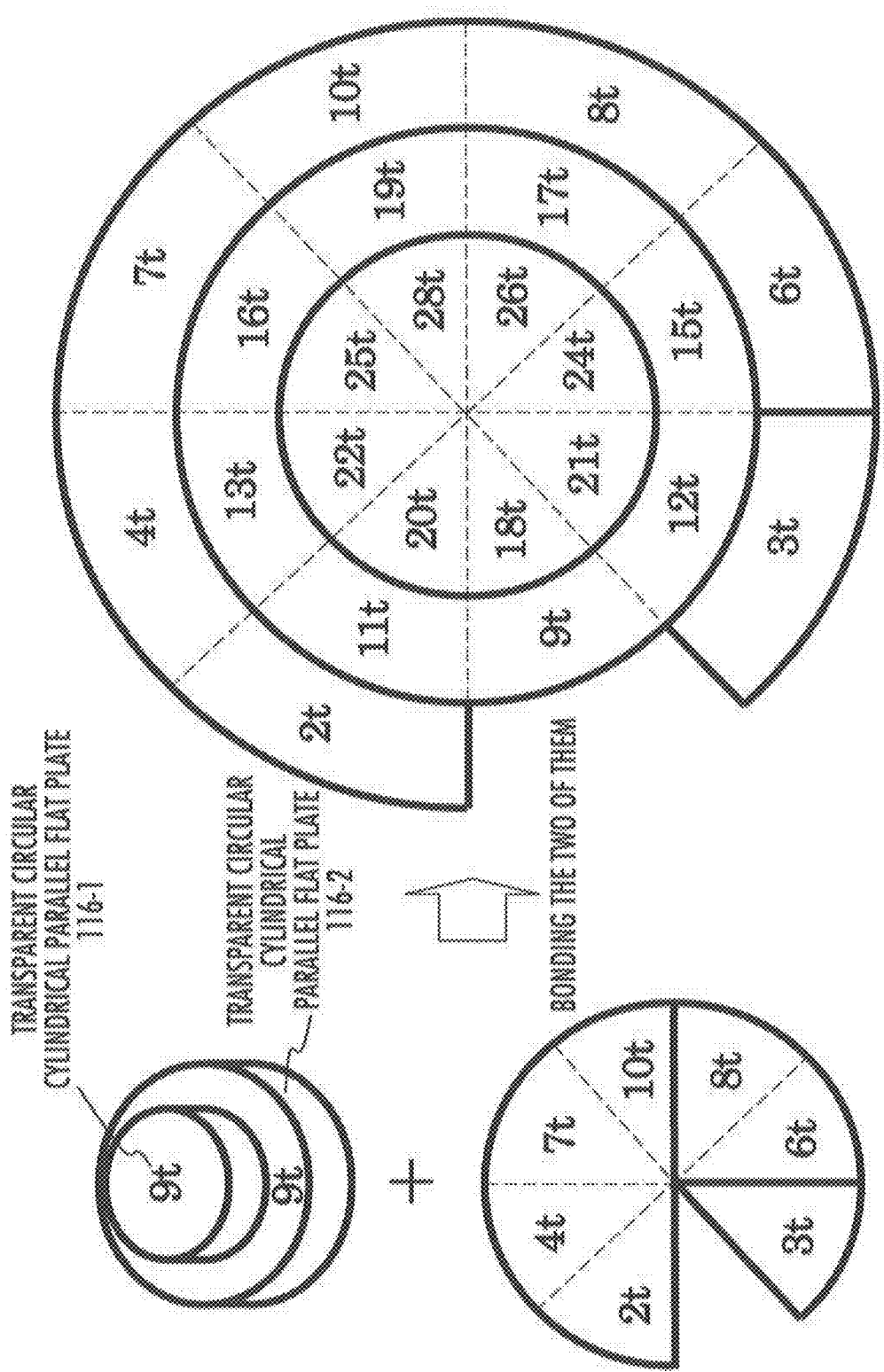
FIG. 13C describes another application example of an optical characteristics changing member using wave-front divided light.

A method of radially dividing (dividing optical path) a circular cross section 92 of the transmitted light into regions is called "radial division" in the present embodiment. FIG. 13C shows an example of the combination of the wave front dividing of the cross section 92 of the transmitted light by the radial division and the angular division.

The drawing of FIG. 13C on the right shows the optical characteristics changing member configured by stacking two transparent circular cylindrical parallel flat plates 116-1 and 116-2 each having a thickness of 9t, and by stacking (bonding) this on the structure of FIG. 13B(a) on the right.

The structure of FIG. 13C on the right has the cross section 92 of the transmitted light that is divided into 24 (3×8), and 24 different optical paths (the number N of optical paths=24) are defined at the same time. Let that mt denotes the thickness of each optical path (divided region), all of the positive integers from 0 to 28 other than 1, 5, 14, 23, and 27 are assigned to these optical paths (divided region) as the values of m.

The drawing of FIG. 13C on the right is obtained by angular division and radial division performed at the same time in the integrated optical characteristics changing member. Alternatively, a plurality of optical characteristics changing members each having the same function may be disposed along the optical path in a distributed manner. In one example, a part for angular division and another part for radial division may be separated in the optical characteristics changing member, and they may be distributed on the optical path.

In the examples of the embodiment in FIG. 12C through FIG. 13C, the regions are equally divided in X/Y direction, in angular directions and in radial directions. Alternatively, the optical path (region) in the present embodiment may be divided non-equally. The number N of optical paths (the number of divisions) generated in the optical characteristics changing member may be any value of two or more. The cross section 92 of the transmitted light of the present embodiment may be wavefront divided by any another method.

As roughly described in Section 3.1 and described in details in Section 3.5 mathematically, a larger number N of optical paths (the number of divisions) generated in the optical characteristics changing member can increase the effect of reducing optical noise. As shown with the drawing of FIG. 13C on the right having 24 divisions (N=24), according to the method of wavefront dividing by changing the thickness of the refractive element for the transmitted light or changing the step height for the reflected light, any larger number N of optical paths (or the number of divided regions) generated in the optical characteristics changing member can be set. Further, this can facilitate the optical arrangement such that the amount of light passing through each optical path after N-division can have substantially the same.

On the contrary, it is difficult for the amplitude dividing shown in FIG. 9 to divide the optical path into a lot of optical paths while keeping the same intensity of light. Even when a plane enabling amplitude dividing into a plurality of optical paths can be formed, only two of the divided optical paths among them can have intensity close to the largest one. The remaining divided optical paths tend to have greatly reduced intensity.

The optical characteristics changing member having the function of wave front dividing may be a prism having an input face and an output face of light that are inclined, or may be a prism having one non-planar face. In this case, however, displacement in optical axis often occurs for each of the optical paths after transmitting.

On the contrary, when a transparent parallel flat plate as an element making up the optical characteristics changing member is used as shown in FIGS. 12B to 13C and the light-transmitting direction 96 is set in the direction perpendicular to the plane of the element, such displacement in optical axis after transmitting does not occur, and all of the optical paths after transmitting (outgoing) can be kept parallel to each other. This facilitates the combining (mixing) operation of different optical paths. Further even when disposing the objective lens 25 and the detecting lenses 28-1, 2 after the combining (mixing) operation as in FIG. 7, for example, displacement hardly occurs close to the focusing point, and so a clear image and an accurate detection signal can be obtained.

When the optical characteristics of the irradiated light (first light) 12 or the detection light (second light) 16 are changed by a wave-front dividing function, a border line (border line of wave front dividing) appears in a cross section orthogonal to the travelling direction of the light, and the optical characteristics are changed across the border line. The border line 97 of the cutting plane as shown in FIG. 12B or 13A corresponds to a specific example of such a border line of wave front dividing.

The light-emitting source 70 including the tungsten filament 50, for example, (FIG. 11 or FIGS. 14A, B) generates heat during light emission. To cool this light-emitting source 70, a mechanical fan is often used. When this mechanical fan rotates, small mechanical vibrations occur. These mechanical vibrations may be transmitted to the optical characteristics changing member having the function of the wave front dividing. Then due to the influences from the mechanical vibrations, the border line of wave front dividing also may vibrate mechanically to a small extent.

As described in Section 3.1 at the last part about a material to be used for the optical characteristics changing member (or of its substrate), there is a material having a large absorption band in the near-infrared region. Therefore if an optical characteristics changing member having the function of wave front dividing is prepared using such a material having a large absorption band in the near-infrared region, a noise component may be incorporated into the detection signal of the light at the wavelength in such an absorption band obtained from the detection unit 4, 6 (FIGS. 1A, B, C). This noise component occurs in synchronization with the mechanical vibrations of the border line of wave front dividing as stated above. To remove such a noise component, the material of the optical characteristics changing member having the function of wave front dividing also is selected while considering the last part of Section 3.1.

That is, an inorganic material and not an organic material is desirably used for a material of the optical characteristics changing member having the function of wave front dividing (or its substrate). Known examples of the inorganic materials include optical glass, $CaF_2$, $MgF_2$, LiF or KBr.

Particularly a low-OH material is suitable, which satisfies the condition of the amount of hydroxyl group included in the material of the optical characteristics changing member having the function of wave front dividing (or of its substrate) that is 100 ppm or less (desirably 1 ppm or less). A specific example of such a material includes "a glass material that is managed during manufacturing so as to include less hydroxyl groups", "anhydrous quartz glass" or "anhydrous quartz".

The material of the optical characteristics changing member having the function of wave front dividing (or its substrate) is selected in this way, which can lead to the effect of obtaining accurate spectroscopic characteristics with less influences from mechanical vibrations.

Section 3.4 Combination (Mixing) of Divided Wavefronts

Section 3.4 describes a method of combining/mixing of light passed through the optical characteristics changing member described in Section 3.3. As described in Section 3.1 referring to FIG. 10. the optical path of light is divided into a plurality of optical paths using the optical characteristics changing member, and then the light passed through the different optical paths are combined or mixed. For the optical path state before combining/mixing described in the following, the light may have any state (option) including the wave front dividing as well as the other states described in the field of the "optical path state before combining/mixing" in FIG. 9. These options may be combined, and FIG. 14A and FIG. 14B show examples of the combination of "different light-emitting directions" and "wave front dividing".

That is, the example of the embodiment of FIG. 14A and FIG. 14B has the state (option) having different light-emitting directions including the emitting direction from the light-emitting source 70 (tungsten filament 50) directly to the collimator lens 26 and the emitting direction toward the back mirror 82. At the same time, an optical characteristics changing member including the combination of a transparent parallel flat plate 94-1 of Tb in thickness and a transparent parallel flat plate 94-2 of Ta in thickness is disposed at a part along the optical path for wave front dividing.

For the option corresponding to the field of "combining/mixing position" of FIG. 9, the first half of Section 3.4 gives a description corresponding to "some part along the optical path (of the irradiation light 12 or the detection light 16). The latter half of Section 3.4 gives a description corresponding to the "detector plane 86 in the detector 80" and the "pinhole or slit 130". The following firstly gives a description corresponding to "some part along the optical path (of the irradiation light 12 or the detection light 16).

In FIG. 14A, the optical system corresponding to the light combining (mixing) part of FIG. 8A(a) includes the combination of a collecting lens 98 and an optical fiber 100. After passing through the optical characteristics changing member having the function of wave front dividing, the beams of light in all of the optical paths have a parallel state. When these beams of light are collected at the collecting lens 98, the equiphase wave surface of all of the light beams is a plane perpendicular to the optical axis on the collecting surface. This state equals the state where "the light beams passed through different optical paths are the same in the light travelling direction" described at the first half of Section 3.1.

Then this collecting surface corresponds to the "predetermined position present in a local region in the optical axis direction" described at the first half of Section 3.1. Then, the input face of the optical fiber 100 is set to be coincident with this predetermined position. During the light passing through the optical fiber 100, the light beams passed through different optical paths wave-front divided by the optical characteristics changing member are mixed. As a result, the optical fiber 100 emits combined light (mixed light) 78 from the outgoing face (exit 108 of the combined light).

A portion from the back mirror 82 and the entrance of the optical fiber 100 on the left in FIG. 14A may be stored in the light-source unit 2 of FIGS. 1A to 1C, FIG. 7, FIG. 8A or FIG. 10(b). Then the exit 108 of the combined light of the optical fiber 100 on the right may be disposed close to the target 10.

The optical fiber 100 has a very high-degree of flexibility, and the length of the optical fiber 100 may be any length (e.g., 50 m or less). This leads to the effect of isolating the target 10 from influences from heat or vibrations generated close to the light-emitting source 70 (tungsten filament 50).

The field of "method of combining/mixing light" in FIG. 9 includes the "optical-phase conversion element" (e.g., a random phase shifter, a defuser, or a sand treatment plate) having microscopic asperities at the surface so as to change the phase of the transmitted light or the reflected light locally. FIG. 14B describes a specific example of the embodiment by this method.

Similarly to FIG. 14A, different light-emitting directions (forward and backward) are used as the different optical paths. The optical characteristics changing member including the combination of the transparent semicircular parallel flat plates 94-1, 2 is not limited to the structure shown in FIGS. 12C to 13C, and any structure may be used as long as it enable wave front dividing.

The "optical-phase conversion element" described in the field of "method of combining/mixing light" of FIG. 9 corresponds to a transparent flat plate having one face with random microscopic asperities (light combining part 102-2) 104. The light beams passed through all of the optical paths are diffused simultaneously at the face with these microscopic asperities, and travel in a wider range of direction. Based on these characteristics, a part of the light beams diffused from every position of the face with the microscopic asperities will travel in the same specific direction. As described in Section 3.3, in the "wave front dividing", the light beams passing through different positions on the cross section 92 of transmitted light (FIG. 12B or FIG. 13A) are in mutually different optical paths. Therefore, the light beams passed through (or reflected from) the "optical-phase conversion element" and extracted in the specific travelling direction are in the state of "the light beams passed through different optical paths are the same in the light travelling direction", which corresponds to the first half of Section 3.1.

As a specific method of extracting the light beams in the specific direction after passing through (reflected from) the optical-phase conversion element, the light beams passed through the pinhole or slit 130 on the light-collecting face of the detecting lens 28-2 may be used as shown in FIG. 14E, for example. Alternatively, as shown in FIG. 14D, the imaging plane (detector plane) 86 of the monitor camera 24 is disposed on the light-collecting face of the detecting lens 28-2, and the light beams applied to specific pixels in the imaging face only may be detected.

Instead of extracting the light beams travelling in the specific direction after passing through (reflected from) the optical-phase conversion element, the light beams passed through the transparent flat plate (light-combining part 102-2) 104 having one face with random microscopic asperities will be mixed (combined) in the wave front 106 at a predetermined distance from the transparent flat plate. In this way, light may be mixed (combined) by a diffraction phenomenon of the light.

When the light is mixed (combined) using the optical-phase conversion element in this way, the light will be mixed (combined) at certain distance or longer irrespective of the travelling direction of the light. Therefore the combined light (mixed light) 78 can be generated without precise optical arrangement or optical-axis alignment, and so not-expensive measurement apparatuses can be mass-produced.

Alternatively, as in FIG. 14B an optical-phase conversion element may be directly bonded to a part (the exit of light) of the optical characteristics changing member (including transparent semicircular parallel flat plates 94-1, 2) so as to ingrate the optical characteristics changing member and the optical-phase conversion element. With this configuration, such an integrated optical device can have both of the functions of separating (dividing) optical path and of combining/mixing the light, and so an existing measurement apparatus (or a microscopic apparatus) can be altered easily.

In FIG. 14B, the integrated device of the optical-phase conversion element (the transparent flat plates (light combining part 102-2) 104 having one face with random microscopic asperities) and the optical-phase conversion element is disposed in the light-source unit 2. Alternatively, such an integrated device may be disposed in the detection unit 6 or may be disposed in both of the light-source unit 2 and the detection unit 6 as in FIG. 7. In this case, the integrated device of the optical-phase conversion element and the optical characteristics changing member corresponds to the optical noise reduction device or a partial coherent reduction device 64.

FIG. 14C shows an example of the method using the "diffraction element" in the field of the "method of combining/mixing light" of FIG. 9. In FIG. 14C, a blazed diffraction grating 124 is used as the diffraction element, and any optical device may be used therefor as long as it has a function of combining (mixing) the light by diffraction.

A diffraction element typically is used to divide the transmitted light or the reflected light. Looking at the optical path to divide the light the opposite way, however, the light is combined (mixed). Based on this property, combined light (mixed light) 78 is generated.

An optical characteristics changing member based on wave front dividing is configured by combining the transparent parallel flat plates 114-1 and 2. Then, an optical device to change the travelling direction of light, such as a Fresnel prism (blazed hologram) 122, is disposed at the exit of at least a part of this optical characteristics changing member. This optical device to change the travelling direction of light and the optical characteristics changing member may be bonded for integration.

Then the light beam 110-1 passed therethrough and having the travelling direction changed is combined with the light beam 110-2 passed through the transparent parallel flat plate 114-1 only at the blazed diffraction grating 124. Therefore the combined part of the Fresnel prism (blazed hologram) 122 and the blazed diffraction grating 124 is the light combining (mixing) part 102-3, which corresponds to the light combining (mixing) part 102 of FIG. 8A(a) or FIG. 8B(a).

In the example of the embodiment of FIG. 14C, the transmitted light 110-1, 2 is used. Alternatively, combined light (mixed light) 78 may be generated from reflected light.

FIG. 14D shows an example of the embodiment corresponding to the "detector plane 86 in the detector 80" in the field of "combining/mixing position" of FIG. 9. This example of the embodiment enables clear imaging of an enlarged image of a minute light-scattering object 66.

Through the combination of the objective lens 25 and the detecting lens 28-2, the imaging plane (detector plane) 86 in the monitor camera 24 becomes the image-forming plane of the micro light-scattering object 66. A part of this image-forming optical system (or a confocal optical system) is used for combining/mixing the light. The image-forming optical system (or confocal optical system) collects the light starting from one point at one point on the image-forming plane irrespective of the optical path of the light. Then, the light beams passed through all optical paths are combined/mixed at the light-collecting position on the image-forming plane.

Therefore an optical characteristics changing member to divide (separate) an optical path into a plurality of optical paths having different optical lengths is disposed at some part along the optical path of the image-forming optical system, whereby the optical arrangement shown in FIG. 8B(b) and FIG. 10(c) can be obtained. From another perspective, the light combining (mixing) part 102-4 including the combination of the detecting lens 28-2 of FIG. 14D and the imaging plane (detector plane) 86 of the monitor camera 24 may correspond to the light combining (mixing) part 102 of FIG. 8B(a).

The spectroscope 22 in FIG. 14E has a structure to measure the spectroscopic characteristics of only the light passing through the pinhole or slit 130 disposed at the entrance. That is, the light passing through the pinhole or slit 130 is returned to parallel light by the condenser lens 134-1, and the wavelength of the light is separated by diffraction at the blazed diffraction grating 126. Then, these beams of light subjected to wavelength separation are collected by the condenser lens 134-2 to the one-dimensional line sensor 132. The distribution of intensity of the light applied to this one-dimensional line sensor 132 is detected so as to measure the spectroscopic characteristics.

In this example of the embodiment as another application in FIG. 14E as well, the beams of light passed through a plurality of optical paths having different optical lengths are combined (mixed) by the image-forming optical system (or confocal optical system). In this case, the beam of the light from the micro light-scattering object 66 along the optical axis of the objective lens 25 only passes through the pinhole or slit 130 disposed at the image-forming position (or confocal position).

In order to measure the spectroscopic characteristics only at the local area in the micro light-scattering object 66, the image-forming position (or confocal position) of this local area is set to be coincident with the pinhole or slit 130 at the entrance of the spectroscope 22. Alternatively, a pinhole or slit 130 as a single unit may be disposed at a predetermined position along the optical position (at the image-forming position (or confocal position) corresponding to the local area of the micro light-scattering object 66).

When parallel flat plates 94-1, 2 are disposed at some part along the optical path of scattered light or along the optical path of collected light in the image-forming optical system, unnecessary interference of light occurs as shown in (B•28) in Section 2.5. In addition, an image formed will deteriorate due to spherical aberration as described later in Chapter 6. Therefore in the examples of the embodiment of FIG. 14D or FIG. 14E, the optical characteristics changing member including the transparent semicircular parallel flat plates 94-1 and 2 is disposed at some part along the parallel optical paths. In a specific example of the embodiment for this, the irradiated light 12 is made parallel between the collimator lens 26 and the light-collecting lens 98 as shown in FIG. 22. Then the transparent semicircular parallel flat plates 94-1 and 2 as the optical characteristics changing member are disposed at some part along the parallel optical paths. Alternatively, an optical characteristics changing member in any mode described in the field of "method of combining/mixing light" in FIG. 9 may be disposed at some part along the parallel optical paths. As a result, unnecessary interference of light can be removed to remove optical noise, and so the image formed can be clear.

The optical characteristics changing member disposed at some part along the parallel optical paths is not limited to FIG. 14D or FIG. 14E, and any member having the function of "wave front dividing" or "amplitude dividing" in FIG. 9 may be used therefor.

In Section 3.4, the method of mixing or combining light passed through a plurality of optical paths obtained by dividing through "wave front dividing" is mainly described in the above. As shown in the field of "details" in FIG. 9, light passed through a plurality of optical paths obtained by dividing through "amplitude dividing" may be mixed or combined.

When the light passed through a plurality of optical paths obtained by dividing through "amplitude dividing" is mixed or combined, the mixed light in the present embodiment may have the same direction of the vibrating-plane (of the electric field). When the beams of light passed through two optical paths obtained by dividing through "amplitude dividing" have the vibrating planes that are mutually inclined (do not coincide with each other completely), their vibrating-plane directions may be made coincide during the processing of combining (or mixing). In one specific example for this method, an optical component having a predetermined vibrating plane only may be extracted (transmitted) using an analyzer 496 or a polarization beam splitter 492 shown in FIG. 33.

When the vibrating-plane direction of the mixed light is displaced using the analyzer 496 or the polarization beam splitter 492 as stated above, the mixed light becomes linearly polarized light. Alternatively, this may be circularly polarized light or elliptically polarized light in the present embodiment as long as the mixed light is uniform in polarization characteristics. Such an operation is not limited to the mixing or combining of light passed through a plurality of optical paths obtained by dividing through "amplitude dividing", and this operation may be used for any method described in the field of "details" in FIG. 9.

When signal detection/measurement (including detection of spectroscopic characteristics), imaging or detection/measurement of wavefront aberration characteristics is performed at the detection unit 6 (FIG. 1A to 1C) using the mixed light as stated above, the operation for a polarization plane may be involved, which is an optical operation for a specific vibrating plane of the electric field as shown in FIG. 33, for example. If the mixed light is not uniform in polarization characteristics (among different optical paths before mixing), partial coherency increases during the operation for a polarization plane inside of the detection unit 6 and so optical noise may increase. On the contrary, when the mixed light is uniform in polarization characteristics (in the direction of vibrating planes), optical noise can be suppressed during the operation for a polarization plane inside of the detection unit 6. Therefore signal detection/measurement (including detection of spectroscopic characteristics), imaging or detection/measurement of wavefront aberration characteristics can be performed stably.

Section 3.5 Light Intensity Formula of Partially Incoherent Light Indicating Optical Noise Reduction Effect Section 3.1 gives a quantitatively description on the reduction in optical noise by the method of the present embodiment. Section 3.5 gives a qualitative description on the effect of the method by way of formulas.

The following considers the case of equally dividing the cross section 92 of transmitted light (equal division into N regions) by the angular division shown in the examples in FIGS. 13A to 13B. As already described in Section 2.5, the thickness T of the vessel (quartz glass) 67 of the tungsten halogen lamp in FIG. 6, for example, is low in uniformity. Therefore the average thicknesses Tm of the N-divided regions are different in value for each region m.

Due to the function of the optical characteristics changing member of FIGS. 13A to 13B, the beams of light passed through different optical paths show mutually partial incoherency. As a result, their amplitude characteristics are not combined (summed) as shown in (B•19) at their mixing position. Instead, their intensity (amount of light) of the beams passed through different optical paths is simply added at the mixing position.

Based on such a situation, the light intensity characteristics obtained after mixing of the beams of partial incoherent light can be shown as follows by modifying (B•28).

[Math. 8]

$$I_C = |\Psi|^2 \approx \frac{1}{2} - \frac{1}{2N} \sum_{m=1}^{N} \cos\left\{\frac{\pi(n-1)Tm \cdot NA^2}{\lambda n^2}\right\} \quad (B \cdot 30)$$

The second term on the right side of (B•30) shows the amount of optical noise generated from interference of light. Since the average thickness Tm included in the numerator of this second term is different for each optical path, a period of a change varies with the measurement wavelength λ. Presumably cosine waves having these different periods are averaged, and so a maximum value of the variable amplitude of the second term on the right side decreases.

Comparison between (B•28) showing the distribution of detection intensity of partial coherent light and (B•30) showing the distribution of detection intensity of partial incoherent light shows that the amount of optical noise can be reduced considerably by the method of the present embodiment. That is the description by way of an example of the angular division of FIGS. 13A to 13B, and a similar result to the above can be obtained for all of the options for "optical path state before combining/mixing" in FIG. 9.

As described at the last part in Section 2.6, irradiated light 12 (or detection light 16) from a panchromatic (not monochromatic) light source often has an optical noise component of about 0.1 to 1.0% due to the vessel inside of the light source. In the example of the present embodiment, the amount of optical noise component decreases to be 0.5% or less in average (or 0.1% or less in average, desirably 0.05% or less or 0.02% or less in average) due to the effect of (B•30). The amount of optical noise component herein is defined as a ratio of the optical noise component (corresponding to the average amplitude value of the second term on the right side of (B•30)) when the DC component (the coefficient of the first term on the right side of (B•30)) is set at "1". The experimental data of FIG. 23A(c) referred to in Chapter 5, for example, shows that the optical noise component decreases significantly (satisfying the above numeral value).

When all of the average thicknesses Tm of the different optical paths are the same, (B•30) and (B•28) are completely identical. Therefore the effect of reducing a variation in optical amount (optical noise) with a change in the measurement wavelength λ, does not appear. (B•30) shows that the light beams passed through different optical paths decrease in their partial coherency and increase in their partial incoherency. The method of the present embodiment to reduce optical noise, however, is not always versatile, and its effect of reducing optical noise decreases when strong interference of light occurs in the optical system (e.g., when all of values of Tm are the same).

Even when all of the average thicknesses Tm of the different optical paths are not the same, if the number N of the divided optical paths is small, beat is generated for the second term on the right side of (B•30). For simplified explanation, the following describes the case of N=2. Even when T1≠T2, the values of the wavelength λ that makes the value of the second term on the right side of (B•30) ½ and −½ are present. Since the interval between these wavelengths (wavelength difference) is much larger than the period in (B•28), the range of wavelength to be detected/measured may be set in a range narrower than the interval, whereby the effect of reducing optical noise can be obtained. Note here that the structure of an optical system that hardly generates the beat is preferable.

To this end, the number N of the divide optical paths in the present embodiment is 3 or more, 4 or more, 8 or more, or desirably 9 or more. To increase this number N of the divided optical paths, a plurality of options described in the field of "details" in FIG. 9 may be combined for use in the example of the present embodiment.

Section 3.6 Devised Structure of Optical Characteristics Changing Member

Section 3.6 describes points to note during the use of the optical characteristics changing member having the function of wave front dividing described in Section 3.3, and the technically devised structure. In one example, an optical characteristics changing member is configured, including the combination (by bonding) of a transparent semicircular parallel flat plate 94-1 of T in thickness and a transparent semicircular parallel flat plate 94-2 of 2T in thickness.

As shown in FIG. 15(a), when reflection of light occurs at the interface between the adhesion layer 112 and the transparent semicircular parallel flat plate 94-1 or 2, interference occurs between the reflected light and light travelling straight, and optical noise increases. In addition, reflection of light occurs at the interface between the transparent semicircular parallel flat plate 94-1 or 2 and the air as shown in FIG. 15(a), and so unnecessary interference of light may occur.

If the cutting plane 95 of the transparent semicircular parallel flat plate 94-2 is inclined relative to the optical axis of the transmitted light 110-2 as shown in FIG. 15(c), or if the border line 97 of the cutting plane is expanded, such a part in a shadow generates an unnecessary loss in the amount of transmitted light. Further, the parallel faces of the transparent semicircular parallel flat plate 94-2 are not so parallel, the travelling angle (angle with the travelling direction of the transmitted light 110-2) of the transmitted light 110-1 after passing through the transparent semicircular parallel flat plate 94-2 increases. Therefore the beams of light after mixing are often not the same in their travelling direction (see the description at the first half in Section 3.1).

To avoid the reflection of light at the interface between the transparent parallel flat plate 114-1, 2 and the adhesive layer 112, the interfaces of them may be disposed substantially parallel to the optical axes of the transmitted light 110-1, 2 as shown in FIG. 16A(a). In another method, the refractive index of the adhesive layer 112 may be the same as the refractive index of a material of a member to be bonded (i.e., of the glass material making up the transparent parallel flat plate 114-1, 2) in the example of the present embodiment.

To avoid the reflection of light at the surface and the rear face of the transparent semicircular parallel flat plate 94-1, 2 in FIG. 15(b), antireflection coating layers 118-1 to 3 may be disposed at the surface and the rear face of the transparent semicircular parallel flat plate 94-1, 2. That is, not only for the "wave front dividing" but also for all options in the "details" of FIG. 9, the antireflection coating layers 118-1 to 3 may be formed at the interface of the optical characteristics changing member and air (vacuum) to avoid reflection of light. As a result, unnecessary interference of light can be avoided, and so an increase in optical noise can be avoided.

To avoid a loss in the amount of transmitted light at the border line 97 of the cutting plane or at the cutting plane 95 described referring to FIG. 15(c), the accuracy to manufacture the optical characteristics changing member is increased. Specifically, the width of the border line 97 of the cutting plane in the optical characteristics changing member is set at 1 mm or less (0.5 mm or less or desirably 0.2 mm or less). Let that T denotes the maximum thickness of the optical characteristics changing member and η denotes the inclination angle of the cutting plane 95 relative to the optical axis of the transmitted light 110-2, the accuracy of manufacturing is specified so that the value of T tan η is 1 mm or less (desirably 0.5 mm or less or 0.2 mm or less).

The beginning of Section 3.1 describes "beams of light passed through a plurality of optical paths being combined or mixed at a predetermined position". To implement this, the permissible range of the accuracy to manufacture the optical characteristics changing member (e.g., the accuracy of parallelism in the optical characteristics changing member) is specified.

For instance, in the example of FIG. 14E, the beams of light are combined or mixed at the pinhole or slit 130. Therefore the beam passed through the transparent semicircular parallel flat plate 94-1 only and the beam passed through the transparent semicircular parallel flat plate 94-2 as well have to pass through the pinhole or slit 130 at the same time.

θ denotes the inclination angle of both of the planes of the transparent semicircular parallel flat plate 94-2 having the refractive index n. Then let that denotes the inclination angle of the beam travelling after passage through the transparent parallel flat plate, the following relationship holds approximately, $$\zeta \approx (n-1)\theta \quad \text{(B·31)}.$$

F denotes the focal length of the detecting lens 28-2. Then a denotes the value of ½ of the pinhole radius/slit width W. D denotes the displacement of the position where the beam of light passed through the transparent semicircular parallel flat plate 94-2 as well is collected on the surface of the pinhole or slit 130 relative to the position where beam of light passed through the transparent semicircular parallel flat plate 94-1 only is collected on the surface of the pinhole or silt 130. Then the approximation can be obtained as in D≈Fζ. Then the condition of enabling the beams of light to pass through the pinhole or slit 130 is D<a. Then, based on them, the following relationship holds.

[Math. 9]

$$\theta < \frac{a}{F \cdot (n-1)} \quad \text{(B·32)}$$

Therefore the accuracy to manufacture the optical characteristics changing member (e.g., the accuracy of parallelism in the optical characteristics changing member) is specified so as to satisfy this relationship.

Section 3.7 Comparison with Conventional Technique Based on Wave Front Dividing

The following describes a difference between the conventional technique described in Patent Literature 1 mentioned in the above and the present embodiment.

In Patent Literature 1, the optical length of the beams is changed using the optical fiber 100-1 and the optical fiber 100-2 as shown in FIG. 17, and then the beams are mixed by the collimator lens 136. According to this technique, however, the beams of light after mixing are not in the same in the travelling direction. That is, the exits of the optical fibers 100-1, 2 are disposed at the front focal planes of the collimator lens 136, and therefore the parallel beams of light after the passage through the collimator lens 136 travel in different directions between α and β. As a result, the travelling directions a and β after passing through the collimator lens 136 are mutually inclined in the equiphase wave surface (wave front), so that combination or mixing of the light cannot be performed precisely. This means an insufficient effect of reducing partial coherency of light.

As shown in FIG. 8A or FIG. 10(b), according to the present embodiment, all of the beams of combined light (mixed light) 78 are allowed to have the same travelling direction (irrespective of the optical paths before combining/mixing) and then they are applied to the target 10. Accordingly when the collected light is applied to the target 10 as shown in FIG. 1C or FIG. 7, all of the beams of light can be effectively applied to the specific region α in the target. Then, this leads to the effect of yielding precise signal detection, precise imaging and precise spectroscopic characteristics for the measurement or observation of a local specific region in the micro light-scattering object 66 as in FIG. 14D or FIG. 14E, for example.

Section 3.8 Optical Characteristics Changing Member Having the Function of Optical Waveguide The following describes an example of the present embodiment including a "waveguide device" (optical fiber/optical waveguide) described as the optical devices to be used in the field of "method of combining/mixing light" of FIG. 9. In this example of the present embodiment, the length of the waveguide device is longer than a predetermined distance, whereby the optical length is changed for each optical path of the beam of light passing through the waveguide device so as to reduce partial coherency. The optical length for each optical path of the beam of light passing through the waveguide device may be longer the coherence length given by (B•6) or (B•12). That is, the predetermined distance may correspond to the coherence length.

The range of the maximum incident angle ε of the beam incident into the optical fiber 100-2 through the entrance is specified with NA (strictly, this is represented by NA=sin ε in the vacuum (in the air)). When the value of ε is small enough, NA≈ε holds. ξ denotes the incident angle in the core region 142 of the optical fiber 100-2. Let that n denotes the refractive index of the optical fiber 100-2 in the core region 142, then the approximation of ε≈n×ξ holds based on Snell's law.

The value of the optical path difference δ between the light passing through an optical path going straight through a center part of the core region 142 of the optical fiber 100-2 and the light passing through an optical path through a part close to the interface between the core region 142 and the clad layer 144 as well is roughly calculated.

As shown in FIG. 18(a), the optical path passing through a part of the interface between the core region 142 and the clad layer 144 as well travels along a curve. For simplified calculation, this curve is approximated as a straight line. That is, it is considered that the optical path in the core region 142 travels straight and total reflection occurs at a part close to the interface between the core region 142 and the clad layer 144.

The optical path difference δ between such an optical path and the optical path going straight through a center part of the core region 142 per unit length of the optical fiber 100-2 can be represented as follows, $$\delta^* \approx \{(1/\cos \xi)-1\}n \quad \text{(B·33)}.$$

Therefore, based on FIG. 18, the condition of making the total value δ=Lδ* of the optical path difference after passing through the optical fiber 100-2 longer than the coherence length $l_{CL}$ given by (B•6) or (B•12) will be given as follows.

[Math. 10]

$$L > \frac{l_{CL}}{n \cdot \left\{\frac{1}{\cos(NA/n)} - 1\right\}} \quad \text{(B·34)}$$

Where L denotes the overall length of the optical fiber 100-2. The overall length L of the optical fiber 100-2 may be longer than the length satisfying this (B•34), whereby partial coherency of the light passing through the optical fiber 100-2 can be reduced.

This (B•34) is not limitedly applied to the optical 100-2 only, but may be applied to every waveguide device (e.g., an optical waveguide formed (integrated) on a board).

Section 3.9 Method for Combining/Mixing Light Emitted from Different Regions

The following describes an example of the present embodiment for "different light-emitting regions" in FIG. 9. This example also is based on the basic principle described in Section 3.1. That is, in this example of the embodiment, beams of the light are generated from a plurality of light-emitting regions (e.g., region α and region β close to the tungsten filament 50 in FIG. 2A) such that the difference δ between mutual optical lengths to the specific region (or measurement point) γ in the target 10 is longer than the coherence length $l_{CL}$ given by (B•6) or (B•12), and then these beams of light are mixed and applied to the target 10. Alternatively the detection light 16 via the target 10 (light detected by the photodetector 80 in FIG. 8B or FIG. 10) may include combined light or mixed light of the beams of light generated from such region α and region β.

Referring to FIGS. 19A and 19B, Section 3.9 outlines the basic method of the embodiment that is applied to the "different light-emitting regions" (FIG. 9) described above referring to FIG. 8A. After that, referring to FIGS. 20 to 21C and FIGS. 24A and 24B, the specific example of the embodiment is described.

Section 3.9 describes the different light-emitting regions by way of an example of the light-emitting source 70 including the tungsten filament 50. The light-emitting source is not limited to this, and every light-emitting source 70 having the characteristics of emitting beams of light simultaneously from a relatively wide range can be applied to the following description. The following describes an example of "one light-emitting source 70" having different light-emitting regions. Alternatively, different light-emitting regions may be distributed over different light-emitting sources. That is, in this example of the embodiment, the beams of light emitted from a plurality of different light-emitting sources may be mixed, and the mixed light may be used as the irradiated light (first light) 12 (FIGS. 1A to 1C). In this case, the light-source unit 2 of FIGS. 1A to 1C internally includes such a plurality of different light-emitting sources. Also in this case, the beams of light emitted from the plurality of different light-emitting regions are substantially the same in the travelling direction (or in the vibrating-plane directions of the electric field) at the light combining (mixing) part 102 (FIG. 8A(a)) as described in Section 3.1.

FIG. 19A shows the basic method of the embodiment obtained by applying the description referring to FIG. 8A(b) to the "different light-emitting regions" (FIG. 9). In FIG. 19A(b), an optical-path changing device 210, which corresponds to a kind of the optical characteristics changing member, is disposed between the light-emitting source 70 (tungsten filament 50) and the target 10. The structure of FIG. 19A(a) does not include such an optical-path changing device, so that light emitted from the light-emitting source 70 (tungsten filament 50) is directly applied to the target 10.

In both of FIGS. 19A(a) and (b), region α corresponding to the specific region 200 in the target is the place to combine/mix the light. Note that all of the light beams emitted from the light-emitting source 70 (tungsten filament 50) do not pass through region α in the target 10. Only a part of the light beams emitted from the light-emitting source 70 (tungsten filament 50) pass through region α, and the beams passed through this region α only are selectively extracted by the detection unit 6. Then this region α corresponds to the "specific region 200 in the target 10" or "including image-forming on the detector plane 86" in the field of "combining/mixing position" in FIG. 9, and this is described later in details referring to FIG. 20.

When the difference δ1, δ2 between the optical length from a plurality of light-emitting regions in the same light-emitting source 70 to point α corresponding to the specific region 200 in the target is longer than the coherence length $l_{CL}$ given by (B•6) or (B•12), then the beams of light emitted from these light-emitting regions can have reduced partial coherency.

For the reason of geometric disposition in FIG. 19A(a), a larger distance between the light-emitting source 70 (tungsten filament) 50 and the target 10 means a smaller optical-length difference δ1, δ2. Conversely when a distance between the light-emitting source 70 (tungsten filament) 50 and the target 10 decreases, the values of the optical-length difference δ1, δ2 decreases to the distance between the light-emitting regions on the light-emitting source 70 (tungsten filament 50).

That is, when the distance between the light-emitting regions on the same light-emitting source 70 is longer than the coherence length $l_{CL}$ given by (B•6) or (B•12), then partial coherency of the light decreases irrespective of the distance between the light-emitting source 70 (tungsten filament 50) and the target 10. Therefore in this example of the embodiment, the width (length) of a wide light-emitting region in the light-emitting source 70 may be set longer than the coherence length $l_{CL}$ given by (B•6) or (B•12).

Particularly when the tungsten filament 50 is used as the light-emitting source 70, the width of a light-emitting region is different between vertically and horizontally. In this case (when the width (length) of the wide light-emitting region is different from one direction to another of the light-emitting source 70), the length of the largest part in width of the light-emitting region in the light-emitting source 70 may be set longer than the coherence length $l_{CL}$.

If the distance between the light-emitting source 70 and the target 10 is small enough and the largest width of the light-emitting region in the light-emitting source 70 is the same as the coherence length $l_{CL}$, then partial incoherency can be obtained only for between the beams of light emitted from the light-emitting regions at both ends of the light-emitting source 70. In this case, the beams of light emitted from the light-emitting region close to the center part of the light-emitting source 70 keep partial coherency.

As described in the first half part in Section 3.1 (or in Section 3.5), a larger number N of the optical paths having a mutual optical-length difference δ longer than the coherence length $l_{CL}$ is desirable. Therefore from the viewpoint of the effect of reducing optical noise, a larger width of the light-emitting region in the light-emitting source 70 is better. Therefore in order to always obtain a good effect of reducing optical noise irrespective of the distance between the light-emitting source 70 and the target 10, the length at a part having the largest width of the light-emitting region in the light-emitting source 70 is desirably larger than $N \times l_{CL}$. Note here that the value of N is 2 or more or, 3 or more, 4 more, or desirably 8 or more.

In other words, the optical system may be disposed so that the beams of light emitted from a wide light-emitting region wider than $N \times l_{CL}$ in the light-emitting source 70 can be applied to the target 10. Alternatively, the optical system may be disposed so that the beams of light emitted from a wide light-emitting region wider than $N \times l_{CL}$ in the light-emitting source 70 can reach the photodetector 80 (FIG. 8B or FIG. 10(c)) in the detection unit 4, 6 via the target 10.

Section 3.1 describes the two functions that the optical characteristics changing member can exert. The optical-path changing device (optical characteristics changing member) 210 used in FIG. 19A(b) is to change the optical path of the light emitted from the light-emitting source 70 (mainly the travelling direction) to (A) change/control the optical length of each optical path.

That is, the optical-path changing device (optical characteristics changing member) 210 changes the travelling direction (optical path) of the beams of light emitted from a plurality of different light-emitting regions on the light-emitting source 70 (tungsten filament 50).

For the optical-path changing device (optical characteristics changing member) 210, the optical-phase conversion element or the diffraction element described in the field of "method of combining/mixing light" in FIG. 9 may be used. Thereby the beams of light passing through the optical-path changing device (optical characteristics changing member) 210 are diffused. Then a part of the diffused beams of light reaches region α in the target 10 of the specific region in the target (light combining/mixing position) 200.

As described above, the difference δ1, δ2 between the optical lengths from a plurality of light-emitting regions in the same light-emitting source 70 to point α in the target 10 increases with a decrease in the distance between the light-emitting source 70 and the target 10. However, the light-emitting source 70 (tungsten filament 50) generates heat and vibrations (including rotating vibrations from a heat-dissipating fan) a lot, and so it is difficult to shorten the distance between the light-emitting source 70 and the target 10. To solve this, the optical-path changing device (optical characteristics changing member) 210 is disposed between the light-emitting source 70 (tungsten filament 50) and the target 10. This optical-path changing device is brought closer to the target 10, whereby the difference δ1, δ2 between the optical lengths from a plurality of light-emitting regions in the light-emitting source 70 can be increased, which leads to the effect of easily reducing partial coherency of the light.

Actually each light-emitting region in the light-emitting source 70 emits scattered light. As described below, however, the following considers the case where substantially parallel beams of light from the light-emitting regions in the light-emitting source 70 reach the optical-path changing device (optical characteristics changing member) 210 through the optical path including the specific region 200 in the target 10 that is coincident with the light combining/mixing position. In this case, similarly to the description on FIG. 19A(a), when the width (length) of the wide light-emitting region in the light-emitting source 70 is longer than the coherence length $l_{CL}$, the combined light easily decrease in partial coherency.

Similarly to FIG. 19A(a), in FIG. 19A(b) as well, the length at a part having the largest width of the light-emitting region in the light-emitting source 70 is desirably larger than $N \times l_{CL}$ (the value of N is 2 or more, 3 or more, and may be 8 or more). In the method for FIG. 19A(b) as well, the optical system may be disposed so that the beams of light emitted from a wide light-emitting region wider than $N \times l_{CL}$ in the light-emitting source 70 can be applied to the target 10. Alternatively, the optical system may be disposed so that the beams of light emitted from a wide light-emitting region wider than $N \times l_{CL}$ in the light-emitting source 70 can reach the photodetector 80 (FIG. 8B or FIG. 10(c)) in the detection unit 4, 6 via the target 10. These conditions may be applied not only to FIG. 19A but also to FIG. 19B(a) and FIG. 19B(b).

In the method shown in FIG. 19A(a) and (b), only the beams of light passed through region α in the target 10 are extracted selectively in the detection unit 4, 6, whereby the specific region 200 in the target is set at the light combining/mixing position. On the contrary, in the method shown in FIG. 19B(a) and (b), the light combining (mixing) part 102 is disposed in the light-source unit 2, whereby combined light (mixed light) 78 is generated. In this case, the difference δ1, δ2 between the optical lengths from a plurality of different light-emitting regions in the light-emitting source 70 to the light combining (mixing) part 102 is longer than the coherence length $l_{CL}$, so as to decrease mutual partial coherency.

FIG. 19B shows the basic method of the embodiment obtained by applying the above description referring to FIG. 8A(a) to the "different light-emitting regions" (FIG. 9).

In FIG. 19B(a), beams of light emitted from a plurality of different light-emitting regions in the light-emitting source 70 directly reach the light combining (mixing) part 102. On the contrary, in FIG. 19B(b), the optical-path changing device (optical characteristics changing member) 210 similar to FIG. 19A(b) is disposed between the light-emitting source 70 and the light combining (mixing) part 102.

FIG. 20 shows a specific example of the embodiment, in which region α in the specific region 200 in the target is set at the light combining/mixing position in FIGS. 19A(a) and (b). FIG. 20(a) corresponds to FIG. 19A(a) and FIG. 20(b) corresponds to FIG. 19A(b). In both of FIGS. 20(a) and (b), region α in the target 10 corresponds to the specific region 200 in the target 10 in the field of "combining/mixing position" in FIG. 9.

The spectroscope 22 and the monitor camera 24 are disposed in the detection unit 6, and these devices can detect the detection light (second light) 16 obtained from the target 10 to measure the interior of the target 10. The position of the imaging plane (detector plane) 86 (see FIG. 14D) in the monitor camera 24 and the position of the pinhole or slit 130 (see FIG. 14E) in the spectroscope 22 have the image-forming (confocal) relationship with region α (point α) in the target 10. Therefore the monitor camera 24 and the spectroscope 22 selectively extract a signal obtained from region α (point α) in the target 10. The detector plane is disposed in this way, which corresponds to "including image-forming on the detector plane 86" in the field of "combining/mixing position" in FIG. 9.

Meanwhile beams of light emitted from a plurality of different light-emitting regions in the light-emitting source 70 (FIG. 20(a)) or the beams of light passed through the optical-path changing device (optical characteristics changing member) 210 are expanded as diffused light. Then a part of the beams of light emitted from all of the plurality of different light-emitting regions in the light-emitting source 70 pass through region α in the target 10. Therefore the beams of light emitted from the plurality of different light-emitting regions in the light-emitting source 70 are combined/mixed by the image-forming optical system in the detection unit 6 substantially at region α (point α) in the target 10.

FIG. 20 includes the monitor camera 24 and the spectroscope 22 to detect a signal. Alternatively any signal detection means (photodetector 80 in a broad sense) may be disposed at the image-forming position (confocal position) in the present embodiment.

Figure 21A:
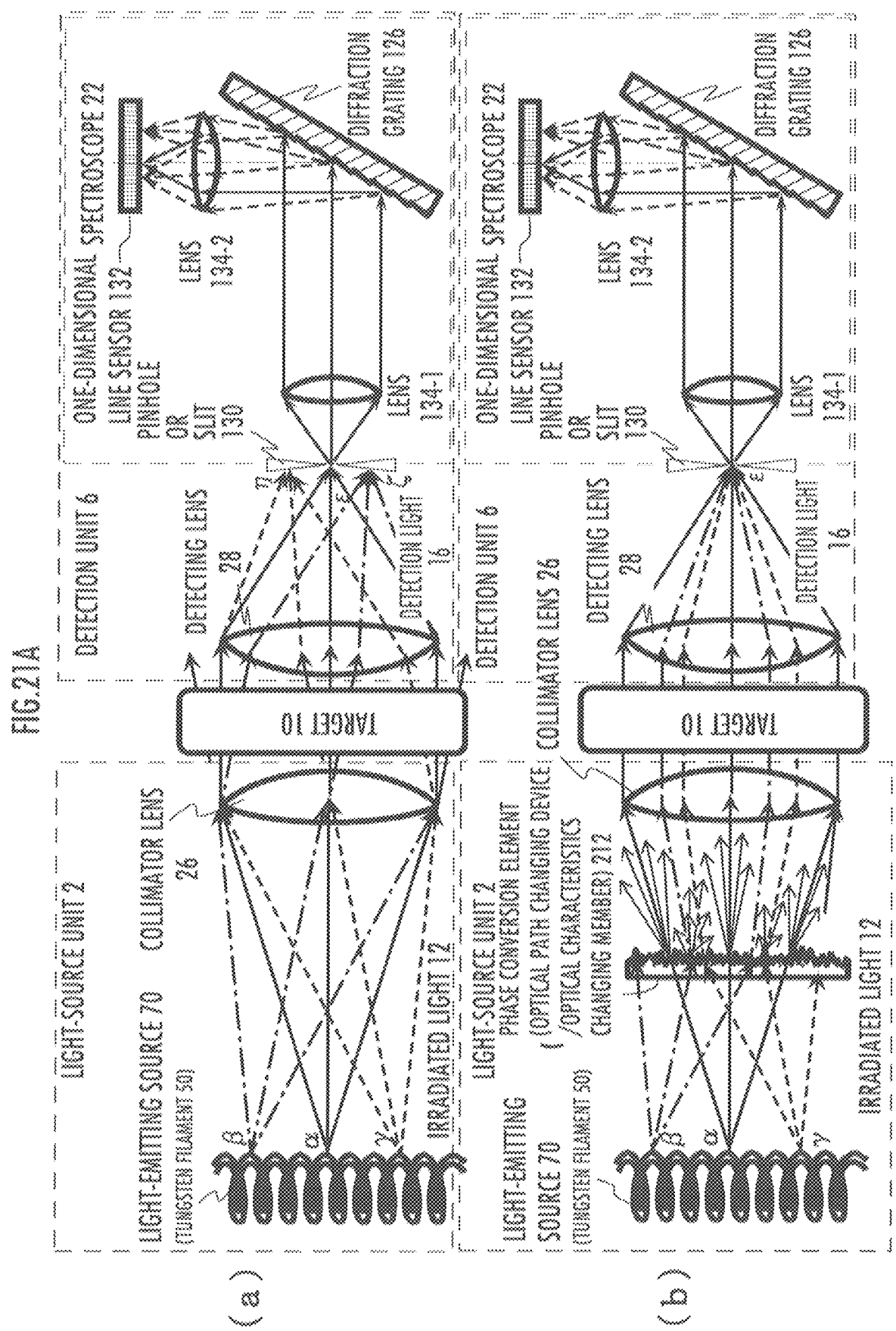
FIG. 21A describes an exemplary method (A) to combine/mix beams of light generated at different light-emitting areas with a phase conversion element.

FIG. 21A describes a specific example of FIGS. 19B(a) and (b). FIG. 21A(a) corresponds to FIG. 19B(a) and FIG. 21A(b) corresponds to FIG. 19B(b). FIG. 21A includes the spectroscope 22 as an example of the photodetector 80. Alternatively, a photodetector 80 having any function may be used as means to detect a signal obtained from the target 10.

In FIG. 21A(a), the collimator lens 26 plays a part of the role of the light combining (mixing) part 102 in FIG. 19B(a). That is, beams of the scattered light emitted from a plurality light-emitting region (regions α, β, and γ) in the light-emitting source 70 are partially combined (mixed) on the collimator lens 26.

The equiphase wave surfaces (wave fronts) after passage through the collimator lens 26, however, are mutually inclined among the light-emitting regions α, β, and γ (their travelling directions are not the same). Therefore this state is not the case where the beams are totally combined (mixed) similarly to FIG. 17.

Such beams of light passed through the collimator lens 26 generate multi-scattering in the target 10, and are diffused. The detection unit 6 as the combination of the detecting lens 28 and the pinhole or slit 130 extracts parallel beams only having the same travelling direction among beams of the detection light 16 via the target 10 for detection. Therefore in the example of the embodiment shown in FIG. 21A(a), the combination of the collimator lens 26 and the target 10 (multi-scattering therein) (strictly the combination including the detection unit 6) makes up the light combining (mixing) part 102.

In FIG. 21A(b), a phase conversion element 212 (specifically a defuser, a random phase shifter, a sand treatment plate or the like) is used as the optical-path changing device 210 as one type of the optical characteristics changing member in FIG. 19B(b) so as to further diffuse the travelling direction of the beams of light emitted from the light-emitting regions α, β and γ in the light-emitting source 70 (to change the travelling direction of the light in a wider direction). As a result, parallel beams of the light after passing through the collimator lens 26 include the beams of light emitted from the light-emitting regions α, β and γ (in the parallel beams of light, beams of light emitted from the light-emitting regions α, β, and γ and passed through different optical paths are the same in travelling direction).

Then in FIG. 21A(b) also, similarly to FIG. 21A(a), the combination of the detecting lens 28 and the pinhole or slit 130 in the detection unit 6 selectively detects parallel beam components only via the target 10.

Therefore in FIG. 21A(b), the collimator lens (strictly the combination including the detection unit 6) corresponds to the light combining (mixing) part 102 in FIG. 19B(b).

In FIG. 21A(b), the irradiated light 12 after passing through the collimator lens 26 include a lot of non-parallel components as well. Specifically to make the beams of combined light (mixed light) 78 applied to the target 10 have the same travelling direction so as to improve their partial incoherency, a beam expander may be disposed between the collimator lens 26 and the target 10, and a pinhole may be disposed at a light-collecting part at some part therebetween.

FIG. 21B shows another example of the embodiment including the phase conversion element 212 to implement the optical-path changing device 210 that realizes the function of (A) controlling/changing the optical length for each of a plurality of optical paths of the functions of the optical characteristics changing member. A panchromatic light source, such as a tungsten halogen lamp or a xenon lamp, encloses halogen gas (iodine or bromine compound) or xenon gas in the vessel. This vessel 214 has microscopic asperities formed at the inner wall or the outer wall to have phase-conversion characteristics. As a result, this can change the optical paths of the beams of light emitted from a plurality of different light-emitting regions on the light-emitting source 70 (tungsten filament 50), and so can change/control the optical length for each of the plurality of optical paths.

Then the beams of light passed through the different optical paths are combined (mixed) by the back mirror 82. As shown in FIG. 21B, a vessel (and a back mirror 82) having the phase-conversion characteristics may be used for the inner wall or the outer wall, which can lead to the effect of generating light with less partial coherency at very low cost. Alternatively, the optical-phase conversion element or the diffraction element described in the field of "method of combining/mixing light" in FIG. 9 may be disposed close to the vessel 214.

The beams of light reflected from the back mirror 82 turn parallel beams of light, and so an optical characteristics changing member having the function of wave front dividing, although not shown, as shown in FIGS. 12A to 13C may be disposed at some part along the optical paths of the parallel beams. Alternatively, the light combining (mixing) part 102-1 including the collecting lens 98 and the optical fiber 100 of FIG. 14A may be disposed after this optical characteristics changing member. For the optical fiber 100 used for this, a bundle-type optical fiber 300 of FIG. 21C may be used.

Referring to FIG. 21C, another example of the embodiment for the optical-path changing device (optical characteristics changing member) 210 of FIG. 19B(b) is described below. The combination of the imaging lens 215, the collimator lens 26, and the bundle-type optical fiber group 300 (optical fiber 100) corresponds to this optical-path changing device (optical characteristics changing member) 210.

Particularly the bundle-type optical fiber group 300 (optical fiber 100) has the function of collecting the beams of light emitted from the light-emitting regions (regions (points) α, β and γ) in a very wide range on the light-emitting source 70 and applying these beams of light to the target 10. The bundle-type optical fiber group 300 (optical fiber 100) has another effect of shielding heat generated from the tungsten filament 50 of the light-emitting source 70 and vibrations from the cooling fan at between the entrance and the exit of the fiber.

Beams of the diffused light emitted from the different light-emitting regions (regions (points) α, β and γ) on the light-emitting source 70 pass through the imaging lens 216 to form an image on the incident plane of the bundle-type optical fiber group 300 (optical fiber 100). Let that D denotes the width of the light incident region of the bundle-type optical fiber group 300 (optical fiber 100) and M denotes the magnification of imaging by the imaging lens 216, then the beams of light emitted in the range of D/M as the width of the wide light-emitting region on the light-emitting source 70 can pass through the bundle-type optical fiber group 300 (optical fiber 100). Herein, the following relationship is satisfied desirably, $$D/M > N \cdot l_{CL} \qquad (B\cdot35).$$

Where $l_{CL}$ is given by (B•6) or (B•12), and N is a positive number of 1 or more (desirably N is 2 or more, 4 or more or 8 or more). Particularly since the bundle-type optical fiber group 300 (optical 100) can have a large value of D, it can have a larger number N. As a result, the beams of light passed through the bundle-type optical fiber group 300

(optical 100) can have greatly reduced partial coherency (their partial incoherency increases significantly).

Beams of the light emitted from the regions (points) (α, β and γ) on the light-emitting source 70 form an image at the points ε, ζ, and η, respectively, in the light incoming region of the bundle-type optical fiber group 300 (optical fiber 100). Since the bundle-type optical fiber group 300 (optical fiber 100) can transmit the incident light as it is, the beams of the light are emitted from these points ε, ζ, and η in the light-outgoing region.

The beams of light emitted from these points ε, ζ, and η in the light-outgoing region of the bundle-type optical fiber group 300 (optical fiber 100) turn parallel beams via the collimator lens 26, and these parallel beams have mutually displaced travelling directions (the equiphase wave surfaces (wave fronts) of the parallel beams are inclined mutually).

To let the beams of light emitted from the points ε, ζ, and η in the light-outgoing region of the bundle-type optical fiber group 300 (optical fiber 100) have the same travelling direction, the phase conversion element 212 is used as the optical characteristics changing member. The optical characteristics changing member used here has the function corresponding to (B) combining (mixing) a plurality of optical paths described in Section 3.1. This phase conversion element (optical characteristics changing member) 212 corresponds to the light combining (mixing) part 102 in FIG. 19B(b).

Since this phase conversion element (optical characteristics changing member) 212 diffuses the transmitted light (converts the transmitted parallel light into diffused light), the irradiated light 12 applied to the target 10 includes non-parallel light components a lot. Therefore the combination of the detecting lens 28 and the pinhole or slit 130 are used to selectively extract parallel beam components only of the beams of light via the target 10 for signal detection. Strictly therefore the combination of the phase conversion element (optical characteristics changing member) 212, the detecting lens 28 and the pinhole or slit 130 makes up the light combining (mixing) part 102 in FIG. 21C.

FIG. 20 to FIG. 20C show a part of a specific example of the embodiment of FIGS. 19A and 19B. Not limited to these specific examples of the embodiment, any other specific method to implement FIG. 19A or FIG. 19B may be used. That is, as described in Section 3.1, the optical characteristics changing members may have the following functions:

(A) a function of changing/controlling the optical length for each of the plurality of optical paths (corresponding to the function of "changing optical length 76" in FIG. 10 described later); and (B) a function of combining (or mixing) a plurality of optical paths at a predetermined position.

The optical characteristics changing member in any mode to implement (B) combining (or mixing) a plurality of optical paths may be used as the light combining (mixing) part 102 of FIG. 19B. The optical characteristics changing member in any mode to implement (A) changing/controlling the optical length of each of a plurality of optical paths may be used as the optical-path changing device (optical characteristics changing member) 210 of FIG. 19A(b) or FIG. 19B(b). For this optical characteristics changing member, any optical device or the combination thereof described in the field of the "method of combining/mixing light" in FIG. 9 may be used.

In FIG. 20(b), FIG. 21A(b) or FIG. 21B/C, the phase conversion element 212, 214 is used to change the optical path of light (travelling direction). Note that an optical-phase conversion element 212, 214 having any characteristics cannot always decrease the partial coherency effectively. FIG. 22 shows the experimental system to be used for measurement of the characteristics of the optical-phase conversion element 212 and the effect of reducing partial coherency. The optical system of FIG. 22 corresponds to another application example of the present embodiment as well.

In the experiment, three options of "different light-emitting regions", "different light-emitting directions" and "wave front dividing" are combined for the "optical path state before combining/mixing" in FIG. 9.

The back mirror 82 has the radius of curvature of 19 mm, and the focal length for both of the collimator lens 26 and the collecting lens 98 is 25.4 mm (magnification of imaging M=1). The collimator lens 26, the collecting lens 98, the expand lens 218 and the detecting lens 28 all have the same diameter of parallel light flux at the aperture that is 25 mm.

The light-incoming region of the bundle-type optical fiber group 300 (optical fiber 100) has the width D of 5 mm. As a result, the value on the left side of (B•35) is 5 mm. The helical tungsten filament 50 used has the length of about 5 mm, and the beams of light emitted from substantially the entire wide light-emitting region of the light-emitting source 70 can be applied to the target 10. The bundle-type optical fiber group 300 (optical fiber 100) has the length of 2 m, which is capable of shielding heat generated from the tungsten filament 50 of the light-emitting source 70 and vibrations from the cooling fan at between the entrance and the exit of the fiber.

For the combination of the transparent semicircular parallel flat plates 94-1, 2 and the combination of the transparent semicircular parallel flat plates 94-3, 4, two pairs of the optical characteristics changing members to divide angles by 45 degrees as shown in FIG. 13B(a) are used. To increase the number of optical paths divided, these plates are set at angles while mutually rotating them by 22.5 degrees. The value of t shown in FIG. 13B(a) is 1 mm, and optical glass usually called BK-7 is used. The transparent semicircular parallel flat plates 94-1, 2 and the transparent semicircular parallel flat plates 94-3, 4 are bonded using adhesive having the same refractive index as that of BK-7.

The focal lengths of the expand lens 218 and the detecting lens 28 are set at 50 mm and 250 mm, respectively. After passing through the optical-phase conversion element (optical characteristics changing member) 212, the beams of light are diffused (turn diffused light). Then the combination of the detecting lens 28 and the pinhole or slit 130 is used to selectively extract parallel beam components only of the beams of light after passing through the target 10.

For the target 10, polyethylene film of 30 μm in thickness that is transparent in the visible range is used. The polyethylene film as the target 10 is not opaque for near-infrared light as well. Therefore it can be considered that the combination of the detecting lens 28 and the pinhole or slit 130 used substantially can selectively extract and detect parallel beam components only that are incident on the target 10 (emitted from region α, region β, and region γ, and are incident on the target while having the same travelling direction).

The phase conversion element (optical characteristics changing member) 212 has one face that is a sand treatment plate having different sizes of sand grains. The phase conversion element (optical characteristics changing member) 212 has a flat-plate part on the other side having antireflection coat.

FIG. 23A shows the measurement wavelength dependency of a ratio of the amount of detection light (transmittance) before inserting the target 10, in which the amount of detection light before inserting the target 10 is normalized uniformly at 100%. A variation in measurement result also is examined when the size of sand grains used to generate the sand treatment plate of the phase conversion element (optical characteristics changing member) 212 is changed. FIG. 23A(a) shows the result when the size of sand grains used is #1200 (Ra (average value of roughness) is 0.35 μm). FIG. 23A(b) shows the result when the size of sand grains used is #800 (Ra (average value of roughness) is 0.48 μm), and FIG. 23A(c) shows the result when the size of sand grains used is #400 (Ra (average value of roughness) is 1.2 μm).

A difference between the transmittance at the wavelength of 1.213 μm and the transmittance at the wavelength of 1.360 μm increases from FIG. 23A(a) to FIG. 23A(c). A variation between FIG. 23A(a) and FIG. 23A(b), however, is relatively small. A large effect appears in FIG. 23A(c).

On the contrary, a difference in light transmittance between the actually-measured minimum value at the wavelength of 1.213 μm and an interpolated value (at the same wavelength position) estimated from an envelope curve connecting the surroundings is similar at about "0.5%" among (a), (b) and (c) of FIG. 23A.

Figure 23B:
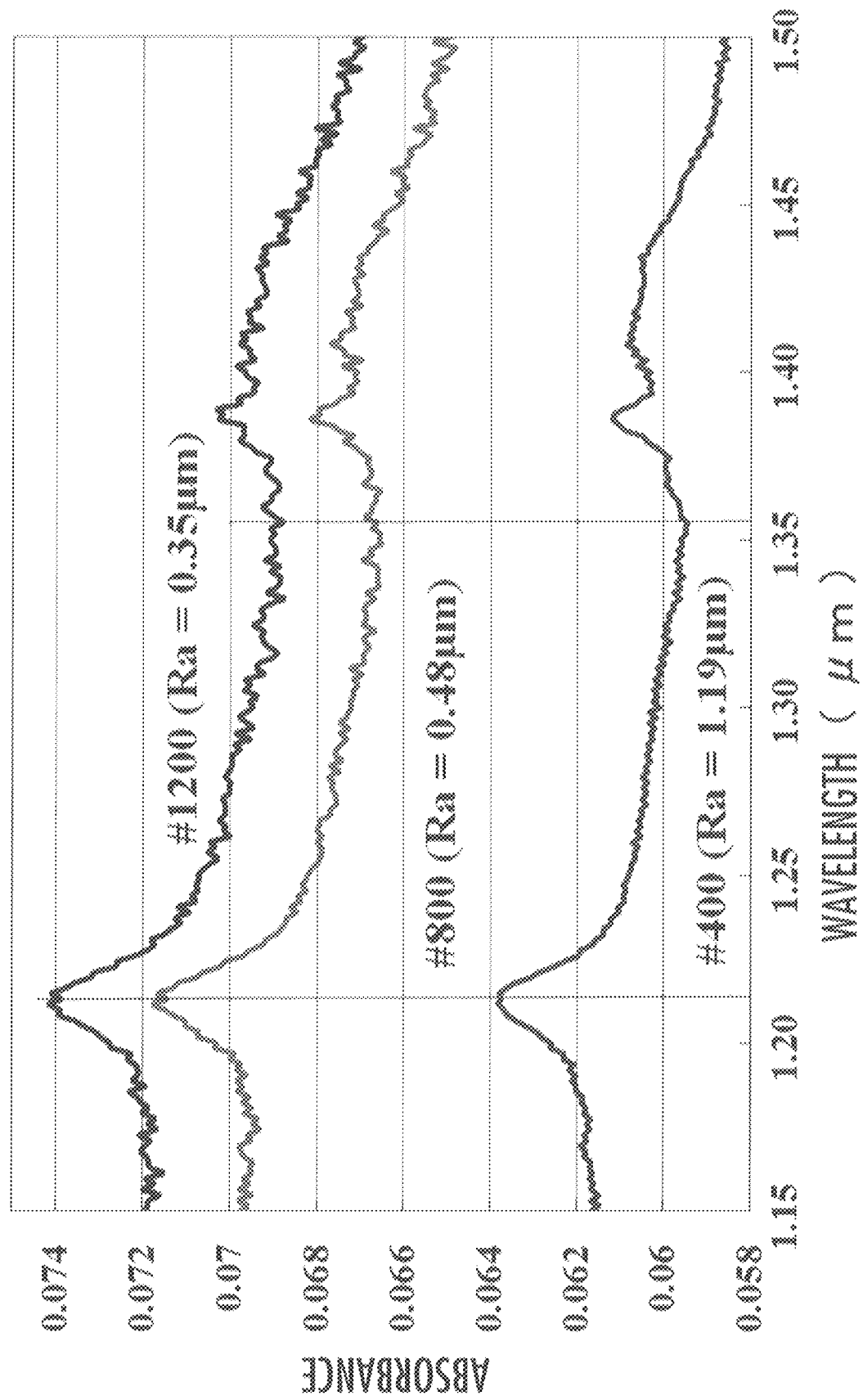
FIG. 23B describes the effect (B) of combining/mixing light with a phase conversion element.

While FIG. 23A shows a relative variation in transmittance, FIG. 23B shows a variation in absorbance. Absorbance here shows the value of common logarithm representing the reciprocal of the transmittance. FIG. 23B shows that a difference between the maximum absorbance at the wavelength of 1.213 μm and the surroundings is substantially similar irrespective of the size of sand grains. The height of the overall base line in FIG. 23B, however, changes among the sizes of sand grains. A factor to generate such maximum absorbance at the wavelength 1.213 μm and the overall base line is described later in details in Chapter 5.

In the characteristics of the absorbance in FIG. 23B, a lower base line leads to improved measurement accuracy of the spectroscopic characteristics (light absorption characteristics). That is, the measurement accuracy is the highest for #400 (average value of roughness Ra is 1.2 μm). The measurement accuracy changes to some extent between #800 (average value of roughness Ra is 0.48 μm) and #1200 (average value of roughness Ra is 0.35 μm).

Such an average value of roughness Ra shows the average amount of microscopic mechanical asperities on the sand treatment plate. Therefore the average amount δ of the phase difference generated after passing through the sand treatment plate can be obtained by substituting the value of "Ra" into "d" of (B•13). When the refractive index n of BK-7 at the wavelength of 1.213 μm is 1.5, δ=0.6 μm can be obtained for Ra=1.2 μm. This value is about half of the wavelength 1.213 μm. Similarly the average of the phase difference corresponding to Ra=0.48 μm is 1/5, and the average of the phase difference corresponding to Ra=0.35 μm is 1/7.

Therefore when the phase conversion element (optical characteristics changing member) 212 is used in the example of the present embodiment, this can lead to the effect of having the average of the phase difference generated due to the phase conversion element that is 1/6 or more of the used wavelength (desirably 1/5 or more or 1/4 or more).

Patent Literature 1 also describes an example of including a diffraction grating or a diffuser to reduce the optical noise. Patent Literature 1, however, does not disclose the performance of the optical-phase conversion element or the diffraction element required to have the actual effect. This Literature does not disclose the relationship with the optical characteristics/optical arrangement in the detection unit 6, either.

Figure 24A:
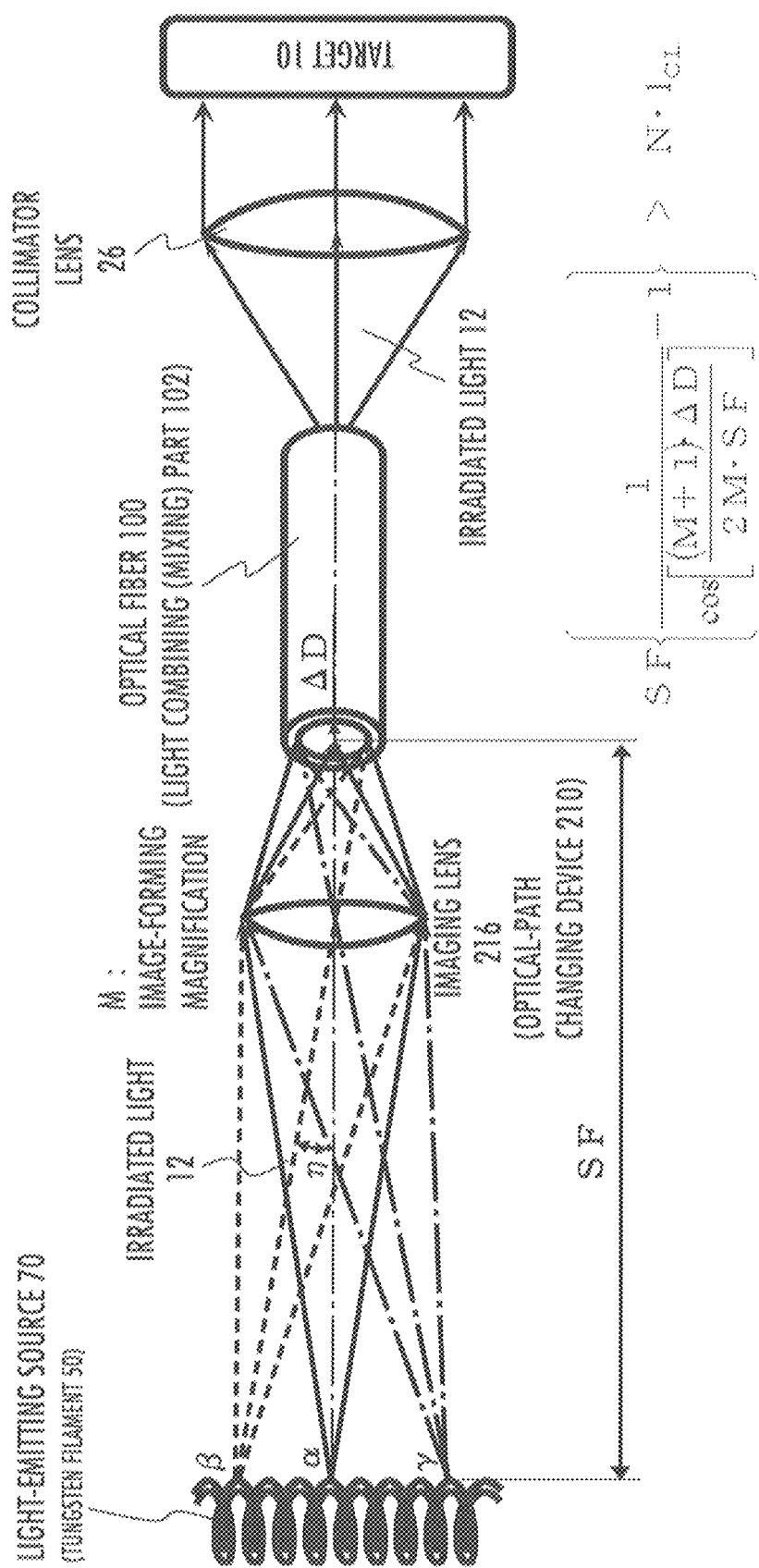
FIG. 24A describes an exemplary method (A) to combine/mix beams of light generated at different light-emitting areas with a waveguide device.

The first half of Section 3.9 explains that since the beams of light emitted from a distant and wide light-emitting region (light-emitting points) in the light-emitting source 70 have a large optical-length difference, such beams of the light emitted from a wide light-emitting region (light-emitting points) in the light-emitting source 70 are desirably applied to the target 10 or are detected at the photodetector 80. FIG. 24A and FIG. 24B show an application example of the embodiment to implement such a method.

In FIG. 24A, irradiated light 12 emitted from a wide light-emitting region (between light-emitting points β and γ) in the light-emitting source 70 is reduced in the light-emitting region with the imaging lens having the imaging magnification M so as to pass through the incoming region of the optical fiber 100. Then the irradiated light 12 passed through the outgoing region of the optical fiber 100 is converted into parallel beams of light at the collimator lens 26, and is applied to the target 10.

Alternatively, the beams of light may be collected at a local region in the target 10 by the collimator lens 26 (so as to form an image at the outgoing region of the optical fiber 100). FIG. 24A illustrates a single optical fiber 100 only, and the optical fiber may be a bundle-type optical fiber group.

The image-forming system of FIG. 24A includes a single imaging lens 216 only, and the image-forming system may include a plurality of lenses. In a specific example of this, as shown in FIG. 22, the image-forming system may include the collimator lens 26 and the light-collecting lens 98. Further as described in the last part in Section 3.4, an optical characteristics changing member having the function of wave front dividing (or other functions) may be disposed for the irradiated light in a parallel state (parallel light flux) generated by the collimator lens 26 and the collecting lens 98. FIG. 22 shows, as one example of this optical characteristics changing member, the combination of transparent semicircular parallel flat plates 94-1 and 2.

The imaging lens 216 in FIG. 24A plays a role of (A) changing/controlling the optical length of each of a plurality of optical paths as the optical characteristics changing member. Therefore this imaging lens 216 is included in the optical-path changing devices 210 described referring to FIG. 19B(b).

The optical fiber 100 in FIG. 24A plays a role of (B) combining (or mixing) a plurality of optical paths as the optical characteristics changing member. In FIG. 24B also, the optical fiber 100 plays the same role. Therefore this optical fiber 100 corresponds to the light combining (mixing) part 102 described referring to FIG. 19B(b).

As described referring to FIG. 24A, ΔD denotes the core diameter of the optical fiber 100 at the incoming region. M denotes the image-forming magnification (lateral magnification) of the imaging lens 216. In this case also, when the condition obtained by replacing D in (B•35) with ΔD is satisfied, then the combined light (mixed light) 78 (FIG. 10(b)) in the optical fiber 100 shows partial incoherency.

From a different viewpoint, the optical-length difference δ between beams of light entering the optical fiber 100 is examined below. Firstly, point α (a region) on the light-emitting source 70 is disposed on the optical axis of the imaging lens 216. Next, an optical path is considered, which is emitted from point β (β region) on the light-emitting source 70 and passes through the center point of the imaging lens 216, and then reaches the end in the incoming region of the optical fiber 100 (border position between the core region and the clad layer). η denotes the angle between this optical path and the optical axis of the imaging lens 216. SF denotes the distance from the light-emitting source 70 to the incoming region of the optical fiber 100.

Since the distance between point α (α region) and point β (region β) on the light-emitting source 70 is ΔD/(2M), when 11 is small enough, the following can be obtained by approximation.

[Math. 11]

$$\eta \approx \tan\eta = \frac{\frac{\Delta D}{2} + \frac{\Delta D}{2 \cdot M}}{SF} = \frac{(M+1) \cdot \Delta D}{2M \cdot SF} \quad (B\cdot 36)$$

The optical-length difference δ between from point α (region α) to the incoming region of the optical fiber 100 and from point β (region β) to the incoming region of the optical fiber 100 is given by,

[Math. 12]

$$\delta = SF\left\{\frac{1}{\cos\eta} - 1\right\} = SF\left\{\frac{1}{\cos\left[\frac{(M+1)\cdot\Delta D}{2M\cdot SF}\right]} - 1\right\} \quad (B\cdot 37)$$

Therefore the condition for mixing the beams of light in the optical fiber 100 so as to decrease partial coherency (increase partial incoherency) is as follows.

[Math. 13]

$$SF\left\{\frac{1}{\cos\left[\frac{(M+1)\cdot\Delta D}{2M\cdot SF}\right]} - 1\right\} > N \cdot 1_{CL} \quad (B\cdot 38)$$

Where N is a positive number of 1 or more. The coherence length $1_{CL}$ as stated above is given by (B•6) or (B•12). Then, when a similar approximation to (B•24) is applied to the left side of (B•38), this can be deformed as follows,

[Math. 14]

$$SF\left\{\frac{1}{\cos\left[\frac{(M+1)\cdot\Delta D}{2M\cdot SF}\right]} - 1\right\} \approx \frac{(M+1)^2 \cdot \Delta D^2}{8M^2 \cdot SF} > N \cdot 1_{CL} \quad (B\cdot 39)$$

The approximation of (B•39) shows that a ratio of the core diameter ΔD at the incoming region of the optical fiber 100 to the image-forming magnification (lateral magnification) M of the imaging lens 216 is an important factor. That is, it is desirable that the image-forming magnification (lateral magnification) M of the imaging lens 216 be as small as possible and the core diameter ΔD at the incoming region of the optical fiber 100 be as large as possible. Then, the distance SF from the light-emitting source 70 to the incoming region of the optical fiber 100 is preferably shorter.

That is, the optical arrangement of FIG. 24A may be set so as to satisfy (B•38) or (B•39), whereby optical noise (generated by the influence from the vessel inside of the light-emitting source 70, for example) can be reduced. The above image-forming magnification M is not limited to the configuration including a single imaging lens 216, and the image-forming magnification (lateral magnification) to form any image-forming optical system (confocal optical system) may be used for the above expression.

In FIG. 21A(b), FIG. 21C or FIG. 22, the phase conversion element 212 is used as means to implement the function of the optical characteristics changing member to (B) combine (or mix) a plurality of optical paths. This method, however, has low efficiency of light that is used for signal detection in the detection unit 4, 6. As compared with this, the combination of the image-forming optical system (confocal optical system) and the optical fiber 100 in FIG. 24A (or FIG. 24B) leads to the effect of applying partial incoherent light to the target 10 effectively as well as to the effect of introducing the light to the photodetector 80 in the detection unit 4, 6 effectively (for signal detection at the photodetector 80).

The range of incident angle of light that can be incident on the optical fiber 100 from the incoming region of the optical fiber 100 as stated above is represented with the value of NA. Many commercially available optical fibers 100 have the value of NA that is relatively small, such as 0.22. Therefore when (B•38) or (B•39) is satisfied, only a part of the irradiated light 12 emitted from the light-emitting source 70 passes through the imaging lens 216. FIG. 24B shows a method to modify this to increase the use efficiency of the irradiated light 12 and make the value of SF in (B•38) or (B•39) smaller.

In an application example of the present embodiment of FIG. 24B, the optical-path changing device 210 is disposed at the incoming region (or in a vicinity thereof) of the optical fiber 100 so as to increase the substantial value of NA of light that can be incident on the optical fiber 100. For one specific example of such an optical-path changing device 210, a micro concave lens 230 may be used. Alternatively, any optical device having the function of widening the range of incident angle of light that can be incident on the optical fiber 100 may be used for the optical-path changing device 210.

A concave lens or a cylindrical concave lens 240 may be disposed at a position close to the light-emitting source 70. This implements the function of decreasing the image-forming magnification M of the image-forming system from the light-emitting source 70 to the micro concave lens 230 (optical-path changing device 210) and of making the value of mechanical distance SF between them smaller at the same time.

In FIG. 24B, the collimator lens 26 and the collecting lens 98 are disposed between the light-emitting source 70 and the optical fiber 100 so as to make the irradiated light 12 parallel between the lenses. Alternatively, only one imaging lens 216 may be disposed between the light-emitting source 70 and the optical fiber 100, and a concave lens or a cylindrical concave lens 240 may be disposed at some part along the optical path.

When a light-emitting source, such as a tungsten filament 50, which is greatly different in width of the light-emitting region between the long-side direction and the short-side direction, is used for the light-emitting source 70, a cylindrical concave lens 240 may be disposed, for example, so as to change the image-forming magnification M in the long-side direction and the short-side direction of the light-emitting region.

In the optical arrangement of FIG. 24B, astigmatism occurs in the vicinity of the incoming region of the optical fiber 100. Astigmatism called here is a phenomenon in which the collecting position of light emitted from point α on the light-emitting source 70 is displaced between the long-side direction and the short-side direction of the light-emitting region on the optical axis in the vicinity of the incoming region of the optical fiber 100. This displacement can be made smaller by setting the image-forming magnification M at less than 1. As a result, light can be guided into the core region 142 of the optical fiber 100 in the vicinity of the incoming region of the optical fiber 100 in many cases, irrespective of astigmatism.

In another method of changing the image-forming magnification M in the long-side direction and the short-side direction of the light-emitting region, two cylindrical concave lenses may be disposed at a position where the irradiated light 12 is parallel between the collimator lens 26 and the collecting lens 98 so as to configure a beam expander, instead of disposing the cylindrical concave lens 240 between the light-emitting source 70 and the collimator lens 26.

In FIG. 24B, transparent semicircular parallel flat plates 94-1, 2 as the optical characteristics changing member having the function of wave front dividing are disposed at some part along the optical path of the irradiated light 12 in a parallel state, which decreases partial coherency (increases partial incoherency) of the irradiated light 12. Alternatively, any optical characteristics changing member described in the field of "method of combining/mixing light" in FIG. 9 (the combination thereof) may be disposed at some part along the optical path.

The interior of the light-source unit 2 of FIG. 1A (or FIG. 1B or FIG. 1C) may be configured as in FIG. 24B (or FIG. 24A or FIG. 24C). The light-emitting source 70 generates heat, and a fan is used for cooling the heat. This fan may be a source of vibrations. The optical fiber 100 disposed between the target 10 and the light-emitting source 70 as stated above can have the effect of protecting the target 10 from the influences of heat and vibrations.

In another method of changing the image-forming magnification M in the long-side direction and the short-side direction of the tungsten filament 50 in the image-forming (confocal) optical system of FIG. 24B, an aspherical lens may be used instead of a spherical lens of FIG. 24A. Alternatively, a prism 220 or a lenticular lens 222 may be disposed at some part along the optical path.

Specifically in FIG. 24C, for both (a) and (b), the optical fiber 100 is used for the light combining (mixing) part 102. Then the combination of the imaging lens 216 and the prism 220 is used as the optical-path changing device 210 in FIG. 24C(a). In another application example of the embodiment, the combination of the imaging lens 216 and the lenticular lens 222 is used as the optical-path changing device 210 in FIG. 24C(b).

Section 3.10 Application Examples of Combining (Mixing) of Beams of Light Emitted from Different Areas Section 3.9 describes a method for changing the optical length between different optical paths when the beams of light emitted from different regions in the same light-emitting source 70 are mixed (or combined). Thereby the mixed (combined) light can have reduced partial coherency (increased partial incoherency). This section describes a technique of increasing the optical-length difference between different optical paths and a method for more efficient mixing (combining), which are developed techniques from the technique described above.

In both of FIG. 21C and FIG. 22, the entrance of the bundle-type optical fiber group 300 (optical fiber 100) corresponds to the image-forming position for the light-emitting source 70 (tungsten filament 50). In FIG. 21C, such an image-forming optical system includes only one optical-path changing device 210 (imaging lens 216). Meanwhile in FIG. 22, the image-forming optical system includes the combination of a plurality of optical-path changing devices (the collimator lens 26 and the collecting lens 98) that are disposed at spatially different positions. Compared with the image-forming optical system including a single optical-path changing device 210 (imaging lens 216 in FIG. 21C), the optical system including the combination of a plurality of optical-path changing devices (the collimator lens 26 and the collecting lens 98 in FIG. 22) that are disposed at spatially different positions can increase the optical-length difference between the different optical paths. Such an image-forming optical system including the combination of a plurality of optical-path changing devices that are disposed at spatially different positions leads to the advantageous effect of further decreasing the partial coherency of the light. The following describes its basic principle.

Figure 51:
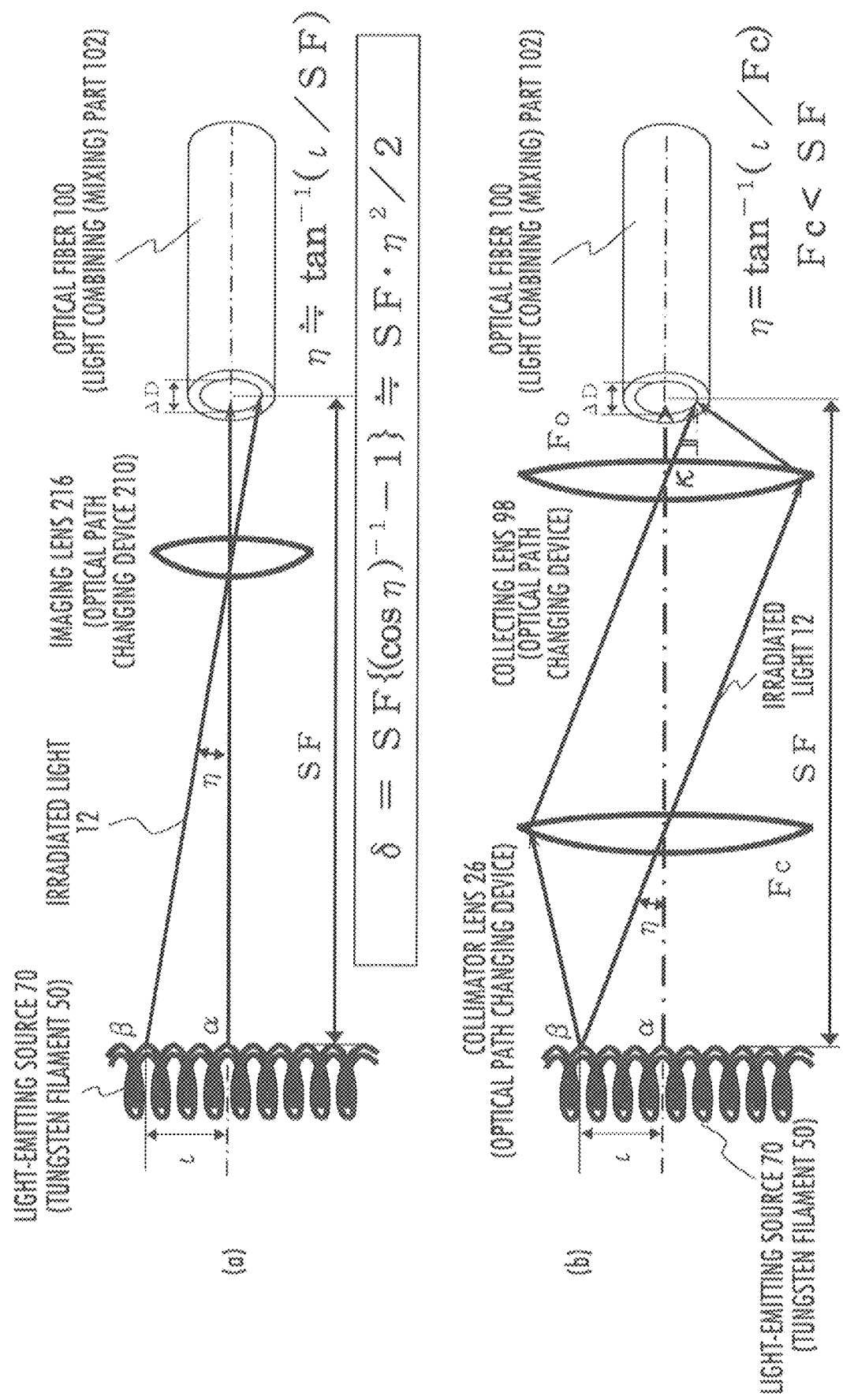
FIG. 51 describes a comparison of optical-length differences between imaging optical systems relative to light-emitting source.

FIG. 51 shows an image-forming optical system configured to form an image of light emitted from the light-emitting source 70 (tungsten filament 50) at the entrance of the optical fiber 100 (light combining (mixing) part 102). In FIG. 51(a), the image-forming optical system includes only one imaging lens 216 (optical-path changing device 210). Meanwhile in FIG. 51(b), the image-forming optical system includes the combination of a plurality of optical-path changing devices (the collimator lens 26 and the collecting lens 98) that are disposed at spatially different positions.

Basically the irradiated light 12 passing through the plurality of optical-path changing devices (the collimator lens 26 and the collecting lens 98) may be scattered light or converging light. For instance, as shown in FIG. 22 and FIG. 24B, an optical system is assumed, which includes an optical characteristics changing member configured to change the optical length for each of the optical paths obtained by dividing the irradiated light 12 (of the optical cross section) by wave front dividing, and the optical characteristics changing member is inserted between the plurality of optical-path changing devices (collimator lens 26 and collecting lens 98). The following considers an example of FIG. 22 or FIG. 24B, which includes the optical characteristics changing member that is the combination of transparent parallel flat plates 94-1 to 4. It is generally known that when the parallel flat plates 94-1 to 4 are disposed at some part along the optical path of scattered light or along the optical path of collected light in the image-forming optical system, aberration occurs in the image-forming optical system. Therefore the irradiated light 12 passing through the plurality of optical-path changing devices (the collimator lens 26 and the collecting lens 98) is desirably parallel light. Such parallel light leads to the advantageous effect of forming a correct imaging pattern of the light-emitting source 70 (tungsten filament 50) with less aberration at the entrance of the optical fiber 100 (light combining (mixing) part 102).

A typically available optical fiber 100 made of an inorganic material (e.g., anhydrous quartz glass) has the core diameter $\Delta D$ of 1.0 mm or less in most cases. Meanwhile, a tungsten filament 50 included in a tungsten halogen lamp has a typical length in the longitudinal direction (twice the distance t between point $\alpha$ and point $\beta$) of 4 cm, which is 40 times or more of the core diameter $\Delta D$. Therefore the image of light emitted from the tungsten filament 50 has to be reduced in size to be 1/40 or less so as to form an image at the entrance of the optical fiber 100. In order to form an image that is reduced in size to be 1/40 or less using only one imaging lens 216 as in FIG. 51(a), the imaging lens 216 has to be disposed close to the entrance of the optical fiber 100.

In the drawing, SF denotes the distance from the tungsten filament 50 to the entrance of the optical fiber 100. Then the light-emitting point on the light-emitting source 70 (tungsten filament 50) along the extended line of the optical axis of the imaging lens 216 is defined as point α. The optical system is then configured so that this point α coincides with the midpoint of the tungsten filament 50 in the longitudinal direction. Consider the case where the irradiated light 12 emitted from point β located at the end face of the tungsten filament 50 in the longitudinal direction passes through the center of the optical axis of the imaging lens 216. η denotes the angle between this irradiated light 12 and the optical axis of the imaging lens 216. ι denotes the distance between point α and β.

When the imaging lens 216 is disposed close to the entrance of the optical fiber 100, the following approximation holds.

$$\eta \approx \tan^{-1}(\iota/SF) \qquad (B\cdot 42)$$

Then a difference δ between the optical length of the irradiated light 12 that is emitted from point β, passes through the imaging lens 216 and reaches the entrance of the optical fiber 100 and the optical length of the light that is emitted from point α and reaches the entrance of the optical fiber 100 can be approximated as follows, when the value of η is small enough, $$\delta = SF\{(\cos\eta)^{-1}-1\} \approx SF\cdot\eta^2/2 \qquad (B\cdot 43)$$

As indicated in (B•43), the optical-length difference δ changes as a function of the square of the angle η. When the image-forming optical system includes only one imaging lens 216 (optical-path changing device 210), however, the angle η cannot have a large value.

When the coherence length $l_{CL}$ given by (B•6) or (B•12), natural number N (this must be 1 or more, and a larger value is desirable, such as 2 or more or 4 or more), and the above optical-length difference δ have the following relationship, $$\delta \geq N\cdot l_{CL} \qquad (B\cdot 44)$$

the light passed through the light combining (mixing) part 102 (optical fiber 100) can have decreased partial coherency (increased partial incoherency).

When the image-forming optical system includes only one imaging lens 216 (optical-path changing device 210), however, (B•44) cannot be satisfied for a sufficient large N because the value of the angle η is small. As a result, such an optical system has difficulty to achieve a sufficient effect of decreasing partial coherency (increasing partial incoherency).

Next, the characteristics of the image-forming optical system (FIG. 51(b)) including the combination of a plurality of optical-path changing devices (the collimator lens 26 and that collecting lens 98) that are disposed at spatially different positions are as follows. In this case, the focal length Fc of the optical-path changing device (collimator lens 26) disposed front can be set at a value that is much smaller than SF (Fc<<SF). Then the relational expression for the angle η will be as follows, $$\eta \approx \tan^{-1}(\iota/Fc) \qquad (B\cdot 45)$$

Since Fc can be set small enough (Fc<<SF) in (B•45), the angle η can be large. Therefore a large value of angle η can be substituted in (B•43), and so a large optical-length difference δ can be obtained. In this way, the combination of a plurality of optical-path changing devices that are disposed at spatially different positions allows (B•44) to hold for a sufficient large N, and so the effect of greatly decreasing the partial coherency (increasing the partial incoherency) can be obtained.

In FIG. 51(b), the optical axis of the image-forming optical system including the combination of a plurality of optical-path changing devices (the collimator lens 26 and the collecting lens 98) is indicated with the alternate long and short dash line. Then point α indicates the intersection between the extended line of the optical axis and the light-emitting source 70 (e.g., tungsten filament 50). Point β indicates the light-emitting point in the light-emitting source 70 that is farthest away from this point α. ι denotes the distance between point α and β.

The optical-length difference δc between the beams of the irradiated light 12 emitted from these point β and point α and then passing along the optical axis of the optical-path changing device (collimator lens 26) disposed front will be as follows, $$\delta c = Fc\{(\cos\eta)^{-1}-1\} \approx Fc\cdot\eta^2/2 \qquad (B\cdot 46)$$

Herein the angle η satisfies (B•45).

Next the irradiated light 12 emitted from the point β and passing along the optical axis of the optical-path changing device (collecting lens 98) that is disposed at the rear is considered as follows. Fo denotes the focal length of this optical-path changing device (collecting lens 98) that is disposed at the rear. Then as shown in FIG. 51(b), denotes the inclination angle of the travelling direction of this light relative to the optical axis. The optical-length difference δo between the optical path after passing through the optical-path changing device (collecting lens 98) along the optical axis and reaching the entrance of the optical fiber 100 and the optical path passing along the optical axis will be as follows, $$\delta o = Fo\{(\cos\kappa)^{-1}-1\} \approx Fo\cdot\kappa^2/2 \qquad (B\cdot 47)$$

Therefore optical designing may be performed so that the total of the optical-length differences of the light emitted from point α and point β and reaching the entrance of the optical fiber 100 satisfies the following relationship.

$$\delta c + \delta o \geq N\cdot l_{CL} \qquad (B\cdot 48)$$

This can lead to the effect of decreasing partial coherency (increasing partial incoherency). In (B•48), the coherence length $l_{CL}$ is given by (B•6) or (B•12). The value of the natural number N must be 1 or more, and a larger value is desirable, such as 2 or more or 4 or more.

The example of FIG. 51 includes the optical fiber 100 as the light combining (mixing) part 102. As stated above, however, a typically available optical fiber 100 made of an inorganic material (e.g., anhydrous quartz glass) has the core diameter ΔD of 1.0 mm or less in most cases, and so the light-emitted pattern from the light-emitting source 70 has to be reduced in size for image-forming.

When the image-forming magnification is small, an optical path generated has a large incident angle η of the irradiated light 12 to the entrance of the optical fiber 100. The maximum incident angle η that can enter the core area 142 of the optical fiber 100 is defined as NA value (NA=sin η). Then a typical optical fiber 100 has the value of NA that is relatively small, such as 0.22. Then if the image-forming magnification to the entrance of the optical fiber 100 is small, a part of the irradiated light 12 passed through the optical path having a large incident angle η cannot enter the core area 142, which leads to the problem of a greatly decrease in the light use efficiency.

Figure 52:
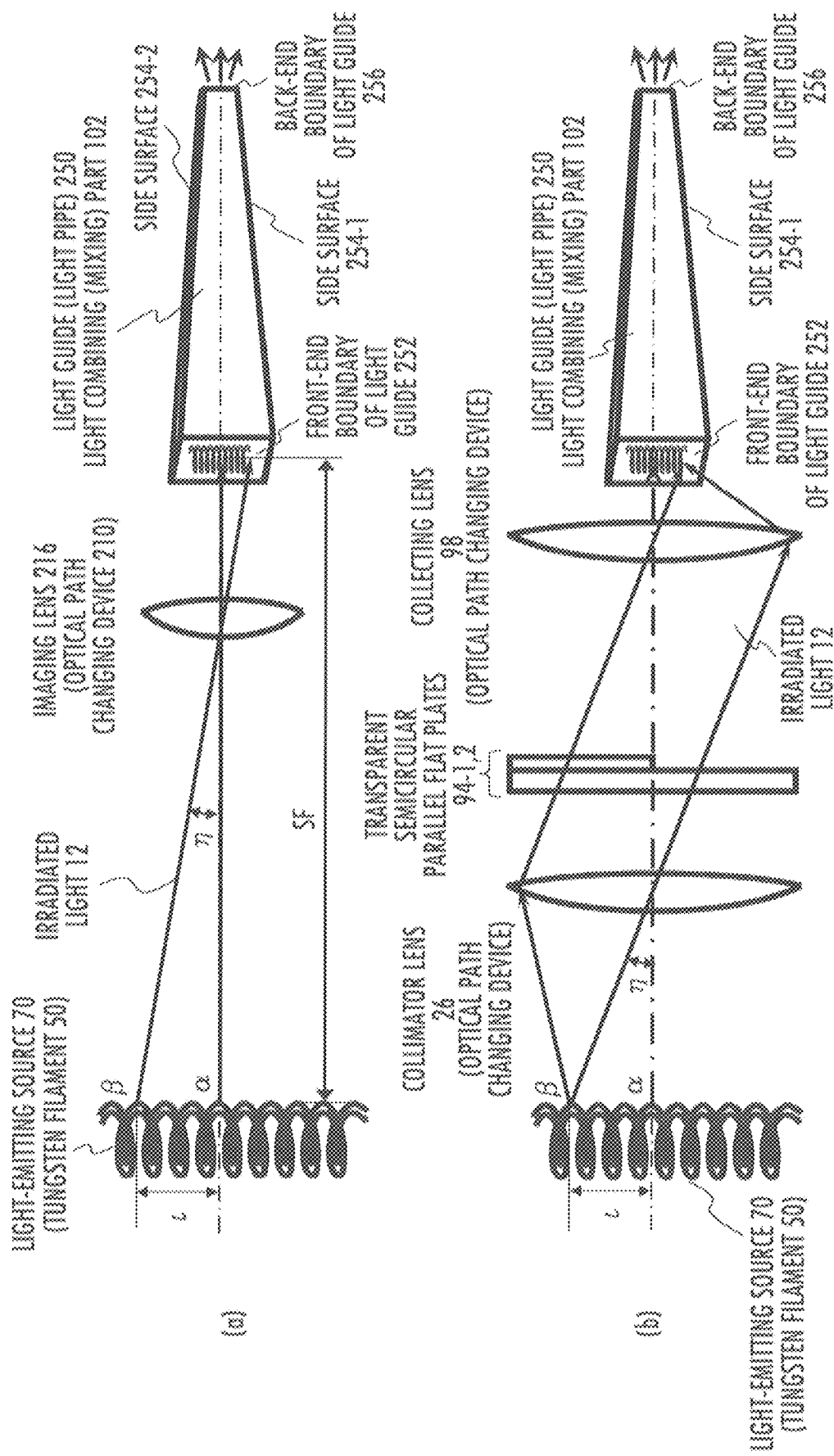
FIG. 52 describes another example of light combining (mixing) part.
Figure 53:
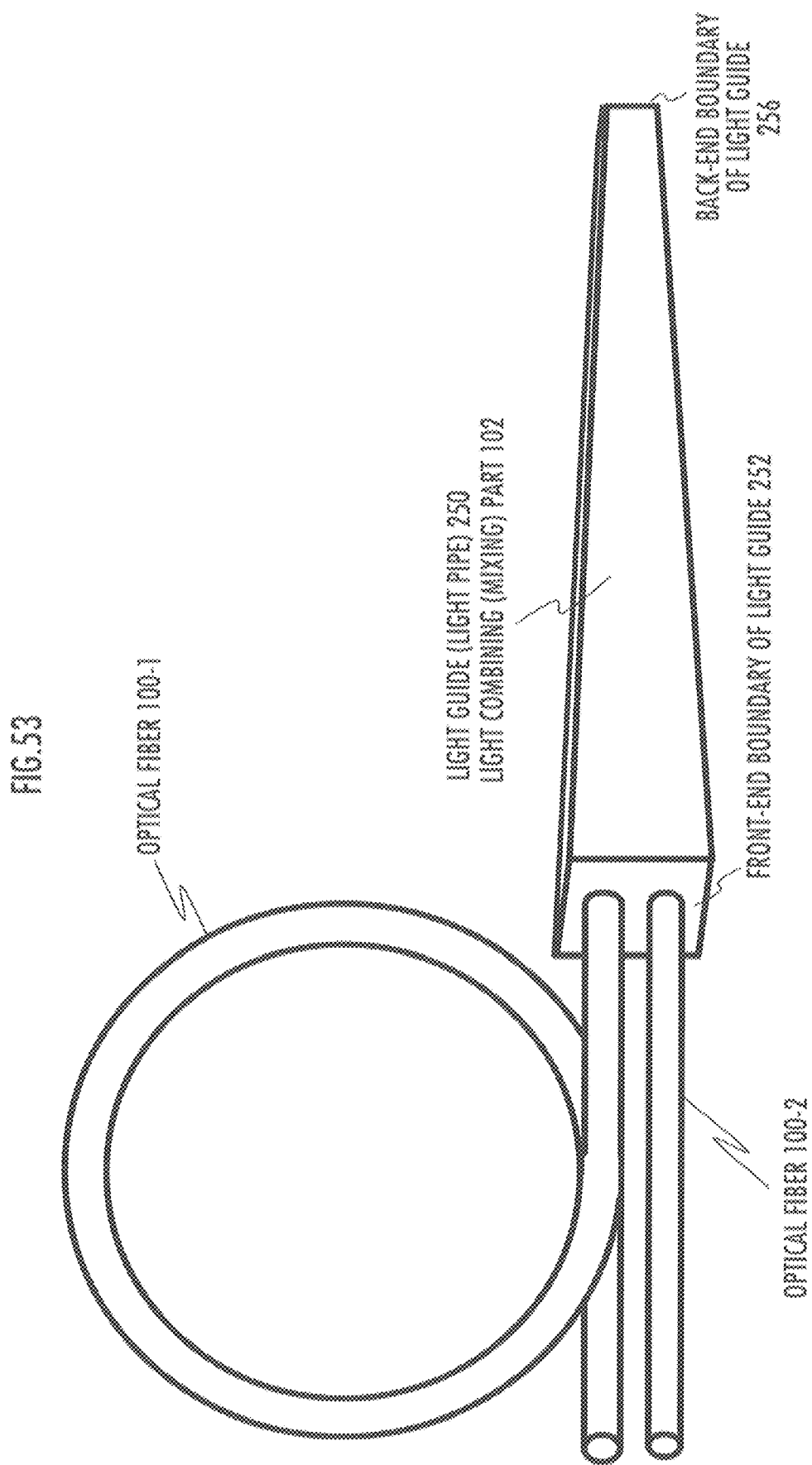
FIG. 53 describes another application example including a light guide (light pipe).
Figure 54:
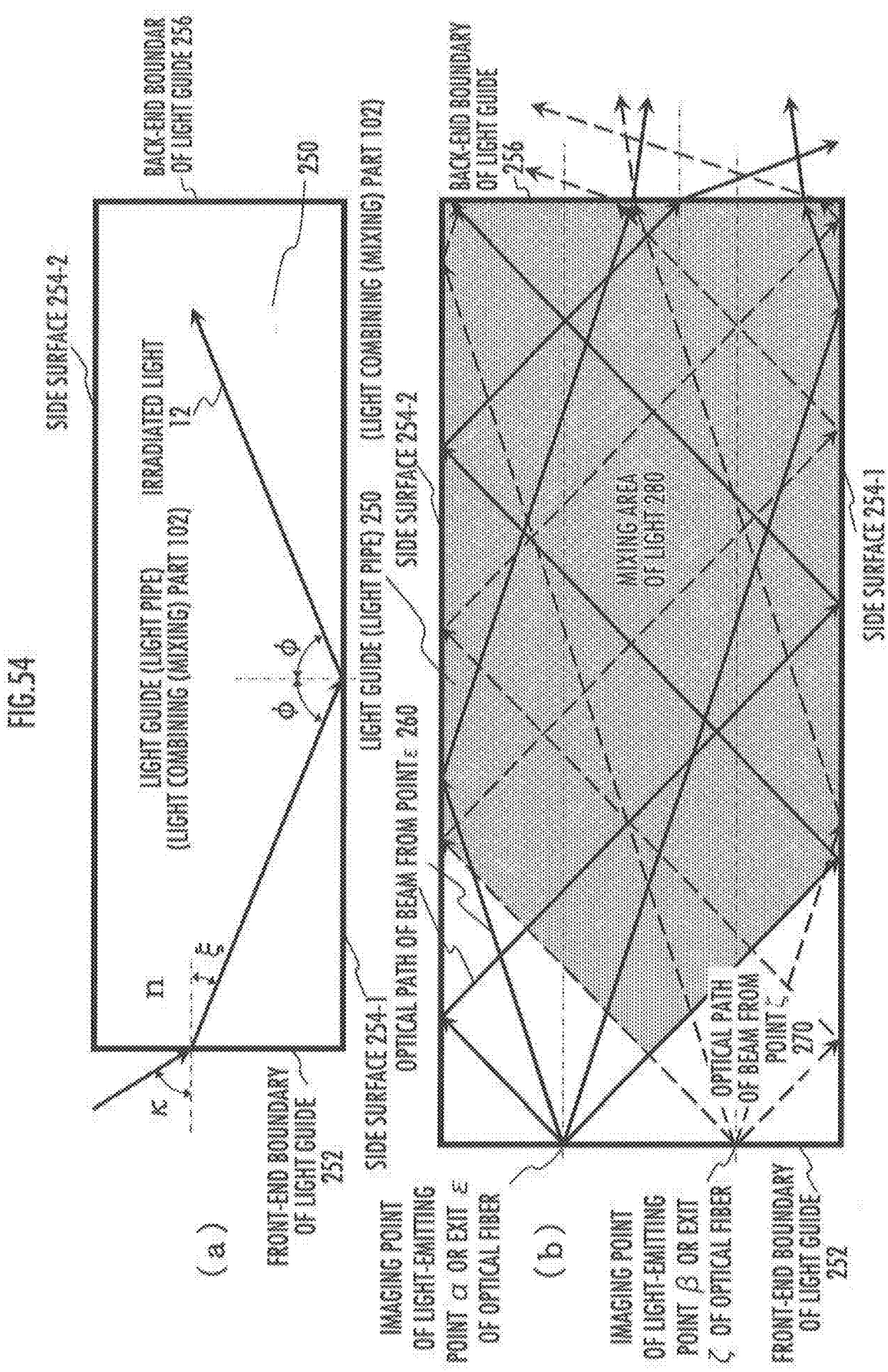
FIG. 54 describes the principle to combine (mix) light in a light guide (light pipe).

To solve this problem, a light guide or light pipe 250 may be used for the light combining (mixing) part 102 as shown in FIGS. 52 to 54. The light guide (light pipe) 250 is a sort of a waveguide device shown in FIG. 9, which is a transparent optical device through which light can pass. That is, light (e.g., irradiated light 12) is incident from the front-end boundary 252 of the light guide (pipe), and passes through the light guide (pipe) while total-internally reflecting at the side surface 254, and then leaves the optical guide (pipe) through the back-end boundary 256.

Beams of the light passed through different paths before the entrance to the light guide (light pipe) 250 (e.g., beams of light emitted from different light-emitting points α and β in the light-emitting source 70) pass through the interior of the light guide (light pipe) 250 to be mixed (mixed or combined). This light guide (light pipe) 250 may have any shape as long as the light (irradiated light 12) passing through the light guide (light pipe) 250 does not leak (total reflection is not inhibited) from the side surface 254. A specific example of the shape of this light guide (light pipe) 250 includes a prismatic column or a circular cylindrical column (or a shape close to a pyramid or circular cone).

The refractive index n inside of the light guide (light pipe) 250 is always larger than the refractive index of air (vacuum). Therefore the incident angle κ (η) of the irradiated light 12 at the front-end boundary 252 of the light guide (light pipe) is allowed to have any value in the range of 0-degree≤κ≤90 degrees (see FIG. 54(*a*)). This leads to the effect that light loss through the incident face (the front-end boundary 252 of the light guide (light pipe)) to the light guide (light pipe) 250 is small.

For instance, when light is incident perpendicularly to a flat glass having the refractive index n of 1.5, reflection at about 4% occurs at the incident surface. Then, AR coating (Antireflection coating) may be applied to both of the front-end boundary 252 and the back-end boundary 256 of the light guide (light pipe) (to control the reflectance of 1% or less, desirably 0.5% or less) so as to reduce the light loss through the front-end boundary 252 and the back-end boundary 256.

The light guide (light pipe) 250 used to combine or mix light can reduce the constraint on the image-forming magnification (between the light-emitting source 70 and the front-end boundary 252 of the light guide (light pipe)). This is because, when a cuboid light guide (light pipe) 250 made of a transparent inorganic material (e.g., anhydrous quartz glass) is used, such a light guide (light pipe) 250 of any dimensions can be easily manufactured (such a light guide (light pipe) 250 can have a high degree of freedom in dimension). This can lead to the effect of improving the degree of freedom for designing the image-forming optical system as well (including the optical-path changing device 210) along the optical path.

FIG. 54 shows a quadrangular prism-shaped light guide (light pipe) 250 as one specific example. FIGS. 52 and 53 show an intermediate-shaped light guide between a quadrangular prism and a quadrangular pyramid whose tip end has been removed. Alternatively, a shape of the light guide may be (a part of) a hexagonal prism or hexagonal pyramid or (a part of) a triangular prism or triangular pyramid.

For the reason described at the last part of Section 3.1, this light guide (light pipe) 250 is desirably made of an inorganic material and not an organic material. Examples of the inorganic material include optical glass, $CaF_2$, $MgF_2$, LiF or KBr.

Particularly a low-OH material is suitable, which satisfies the condition of the amount of hydroxyl group included in the material of the light guide (light pipe) 250 that is 100 ppm or less (desirably 1 ppm or less). A specific example of such a material includes "a glass material that is managed during manufacturing so as to include less hydroxyl groups", "anhydrous quartz glass" or "anhydrous quartz".

As shown in FIG. 52, the optical-path changing device 210 (imaging lens 216 or the combination of the collimator lens 26 and the collecting lens 98) functions to configure an image-forming optical system. When the plurality of optical-path changing devices (the collimator lens 26 and that collecting lens 98) are disposed at different positions as in FIG. 52(*b*), an optical characteristics changing member (FIG. 9) may be disposed between these devices. Such an optical characteristics changing member may have the function of generating an optical-length difference by wave front dividing. In a specific example, any method described above in Section 3.3 can be used. In FIG. 52(*b*) as one example, transparent semicircular parallel flat plates 94-1, 2 are disposed at a parallel-light flux part between the collimator lens 26 and the collecting lens 98.

Due to the function of the image-forming optical system, an imaging pattern for the light-emitting pattern on the light-emitting source 70 (e.g., tungsten filament 50) is projected on the front-end boundary 252 of the light guide (pipe). The entire light forming this projected image (imaging pattern) enters the light guide (light pipe) 250 (light combining (mixing) part 102), and then goes out from the back-end boundary 256 of the light guide (pipe).

FIG. 52 shows an example where the imaging pattern reduced in size is projected (the image-forming magnification is less than 1). Alternatively, a pattern of any image-forming magnification may be projected on the front-end boundary 252 of the light guide (pipe). In this case, the front-end boundary 252 of the light guide (pipe) is desirably have a size larger than that of the projected imaging pattern. Thereby, the light use efficiency of the irradiated light 12 entering the front-end boundary 252 of the light guide (pipe) can be improved.

In the example of FIG. 52, the side surfaces 254-1, 2 of the light guide (light pipe) 250 (light combining (mixing) part 102) are slightly inclined (tapered) relative to the optical axis. As a result, the back-end boundary 256 of the light guide (pipe) is smaller than the front-end boundary 252. Then, the density of the light (irradiated light 12) passing through the light guide (light pipe) 250 (light combining (mixing) part 102) is higher at the back-end boundary 256 than at the front-end boundary 252.

As described above, the core area 142 of a typical optical fiber 100 has the diameter ΔD of about 0.6 mm. The light guide (pipe) may have the inclined side surfaces 254-1, 2 as stated above so that the back-end boundary 256 of the light guide (pipe) is smaller than such a diameter. For instance assume the case where the light emitted from the back-end boundary 256 of the light guide (pipe) passes through the optical fiber 100. By changing the size of the back-end boundary 256 using the inclined side surfaces 254-1, 2, the light use efficiency can be improved during optical coupling between the light guide (light pipe) 250 and the optical fiber 100 (to prevent a large light loss at the optical joining part).

In the example of the light guide (light pipe) 250 of FIG. 52, the side surfaces 254-1, 254-2 are flat faces that are slightly inclined (tapered). Alternatively, any one of the four side surfaces 254 of the light guide (light pipe) 250 only may be inclined. Alternatively, a part of the side surfaces 254-1, 2 may be curved to be inclined partially. Note here that, in this case, the light guide (light pipe) has to have a shape such that light passing through the light guide (light pipe) 250 is reflected (totally reflected) at the side surfaces 254-1, 2 or has to have a structure such that light is reflected at the side surfaces 254-1, 2 (for example, the side surfaces 254-1, 2 have a light-reflecting layer for inwardly reflecting of the light).

In the example of FIG. 52, the light guide (light pipe) 250 (light combining (mixing) part 102) are quadrangular in cross section. Alternatively, the light guide (light pipe) may be circular or elliptical in cross section with consideration given to the efficiency of optical joining with the optical fiber 100, for example.

Such inclined side surfaces 254-1, 2 are used to change the size of the front-end boundary 252 and the back-end boundary 256 appropriately, which can lead to the effect of easy matching with the size of the back-end boundary 256 that is required from the size of the light-emitting part of the light-emitting source 70 and the optical system to be disposed after light combining (mixing).

Alternatively, the side surfaces 254-1, 2 may be parallel to the optical axis (i.e., the front-end boundary 252 and the back-end boundary 256 have the same size).

FIGS. 52 to 54 omit the optical path after passing through the back-end boundary 256 of the light guide (light pipe). As described above, when the size of the back-end boundary 256 of the light guide (light pipe) is small, the light after passing through the back-end boundary 256 of the light guide (pipe) can be dealt with as the scattered light from a pseudo point light source. Then, the light emitted from the back-end boundary 256 of the light guide (pipe) can be dealt with as the irradiated light (first light) 12 emitted from the light-source unit 2 of FIG. 1A.

As shown in FIG. 24A, a collimator lens 26 may be disposed immediately after the back-end boundary 256 of the light guide (pipe) to have a substantially parallel light state, so as to irradiate the target 10 with parallel light as in FIG. 1B (or FIG. 21A).

As shown in FIG. 1C, an objective lens 25 may be disposed at some part along the optical path of the substantially parallel light, so as to irradiate the target 10 with substantially converging light. For the irradiation with substantially converging light, a part of the optical system in FIG. 7, FIG. 14E or FIG. 20 may be used.

That is, the light guide (light pipe) 250 may be disposed as the light combining (mixing) part 102 in the light-source unit 2 shown in FIGS. 1A to 1C. An optical-path changing device 210 as a kind of the optical characteristics changing member may be disposed in the light-source unit 2 (before the light combining (mixing) part 102) so as to generate a change in optical length 76 (FIG. 10) for a part of the optical path. Alternatively any optical characteristics changing member of FIG. 9 may be disposed in the light-source unit 2 of FIGS. 1A to 1C so as to have the function described in Section 3.1 referring to FIG. 8A or FIG. 10(a)(b).

The back-end boundary 256 of the light guide (pipe) may be optically joined with the optical fiber 100 so as to dispose an optical system as in FIG. 24 at the exit of the optical fiber 100. The back-end boundary 256 of the light guide (pipe) may be optically joined with the bundle-type optical fiber 300 so as to dispose an optical system as in FIG. 21C or 22 at the exit of the bundle-type optical fiber 300.

In the system of the present embodiment, the optical fiber 100 or the pinhole or slit 130 may be disposed at some part along the optical path as shown in the examples of FIG. 14A, FIG. 14E, FIG. 16B, FIG. 18, FIG. 21A, FIG. 21C, FIG. 22, FIG. 24A, FIG. 24B and FIG. 24C. The size of the back-end boundary 256 may be narrowed with the optical guide (optical pipe) 250 (light combining (mixing) part 102). This can bring the optical effect substantially equal to the pinhole or slit 130. It is said that these optical devices disposed at some part along the optical path of "partially coherent light" can increase the spatial coherency. As a result, the irradiated light (first light) 12 or the detection light (second light) 16 can have increased partial coherency, so that optical noise tends to increase.

On the contrary, the irradiated light 12 is allowed to pass through the light guide (light pipe) 250 at a position close to the light-emitting source 70 (inside of the light-source unit 2 or in the vicinity of the outgoing position from the light-source unit 2) as in the system of the present embodiment, whereby beams of the light emitted from different light-emitting points of the light-emitting source 70 are combined or mixed inside of the light guide (light pipe) 250. In this way, the partial coherency of the irradiated light 12 is decreased (the partial incoherency is increased) beforehand at a position close to the light-emitting source 70 (inside of the light-source unit 2 or in the vicinity of the outgoing position from the light-source unit 2). Then, the optical fiber 100 or the pinhole or slit 130 disposed at some part along the following optical path does not cause an increase in partial coherency of the irradiated light 12 (a decrease in partial incoherency). In this way, the light guide (light pipe) 250 disposed inside of the light-source unit 2 or in the vicinity of the outgoing position from the light-source unit 2 can lead to the effect of reducing optical noise.

The front-end boundary 252 of the light guide is disposed at the imaging position of the light-emitting source 70 as in FIG. 52, from which excellent light use efficiency can be obtained for the light emitted from the light-emitting source 70. Instead, the front-end boundary 252 of the light guide may be disposed at a non-imaging position of the light-emitting source 70. In a specific example thereof, another optical device other than the imaging lens 216 (such as another optical characteristics changing member of FIG. 9) may be disposed between the light-emitting source 70 and the light guide (light pipe) 250 in FIG. 52(a), or no optical device may be disposed between the light-emitting source 70 and the light guide (light pipe) 250. Alternatively, a non image-forming optical system may be configured.

FIG. 53 shows another application example of the system of the present embodiment. Section 3.7 describes differences from the conventional technique shown in FIG. 17. Since the travelling direction of the beams of light after passing through the collimator lens 136 are different between α and β in FIG. 17, their partial coherency does not decrease (partial incoherency does not increase) in this configuration.

On the contrary, both of the beams outgoing from the optical fibers 100-1 and 100-2 pass through the light guide (light pipe) 250 in the application example of the present embodiment. Both of these beams of light are combined or mixed in the light guide (light pipe) 250, so that their travelling direction becomes the same. The interior of the light guide (light pipe) 250 functions as the light combining (mixing) part 102 in the application example of FIG. 53 as well.

In the above description, the function of the light guide (light pipe) 250 as the light combining (mixing) part 102 is utilized. Referring now to FIG. 54, the basic principle of the function of the light combining (mixing) part 102 is described. As described above, incident light with large incident angle η cannot enter the core area 142 of the optical fiber 100. Therefore when the optical fiber 100 is disposed at some part along the optical path (of the irradiated light 12, for example), a large loss of the light amount occurs at the entrance. On the contrary, FIG. 54(a) shows the reason why the light amount does not decrease at the front-end boundary 252 of the light guide (light pipe).

Light entering the air (or vacuum) with the incident angle κ is refracted with the angle of refraction in a transparent medium of n in refractive index. The approximate expression representing the relationship between the incident angle κ and the angle of refraction ξ is described above with (B•14). Instead of the approximation, these angles can be represented precisely as follows by Snell's law.

$$\sin \kappa = n \sin \xi \quad \quad (B•49)$$

In (B•49), "sin κ≤1" always has to hold. The maximum value of the angle of refraction satisfying "sin κ=1" is called the angle of total internal reflection. For instance, when n=1.5, the angle of total internal reflection will be 41.8 degrees from (B•49).

In FIG. 54(a), the irradiated light 12 travelling in the air (or in the vacuum) passes through the front-end boundary 252 of the light guide (pipe) and enters the interior of the light guide (light pipe) 250. This optical path is seen in the opposite direction. When the light passing through the light guide (light pipe) 250 arrives at the front-end boundary 252 with angle the light is refracted to have angle κ and travels in the air (or in the vacuum). When the angle at the front-end boundary 252 of the light guide (pipe) is larger than 41.8 degrees, the light will be totally reflected at the front-end boundary 252 of the light guide (pipe) and so cannot exit through the light guide (pipe) to the air (or the vacuum).

In this way, although there is a constraint on the arrival angle at the interface in the refractile body, there is no constraint on the arrival angle (incident angle κ) of the incident light (irradiated light 12) in the air (or in the vacuum). This means that, as long as the incident angle is in the range of 0-degree≤κ≤90-degree, the irradiated light 12 of any incident angle κ can pass through the front-end boundary 252 of the light guide (light pipe). The strict optical calculation shows that a loss of the light amount occurs slightly during the passage through the front-end boundary 252 of the light guide (pipe) due to minor light reflection. Such a loss of the light amount can be greatly reduced by applying an AR (antireflection) coating at the front-end boundary 252 of the light guide (light pipe). Therefore such a light guide (light pipe) 250 used as the light combining (mixing) part 102 (see FIG. 8A or 8B) can lead to the effect of obtaining excellent light use efficiency of the light (irradiated light 12) passing through the light guide (light pipe) 250.

Then the irradiated light 12 passing through the light guide (light pipe) 250 is reflected (totally reflected) from the side surface 254-1 in the light guide (light pipe) 250. φ denotes the angle of reflection (angle of total internal reflection) at this time. As shown in FIG. 54(a), when the side surface 254-1 of the light guide (light pipe) 250 and the front-end boundary 252 of the light guide (pipe) are orthogonal, the angle of refraction ξ and the angle of reflection (angle of total internal reflection) φ have the following relationship.

$$\xi + \phi = 90\text{-degree} \quad \quad (B•50)$$

When the irradiated light 12 enters the front-end boundary 252 of the light guide (light pipe) 250 with any incident angle κ, the angle of refraction ξ of the irradiated light will be always 41.8-degree or less as stated above. Therefore the angle φ will be always "48.2-degree or more" from (B•50). Then such φ≥48.2 means that the irradiated light 12 passing through the light guide (light pipe) 250 is reflected (totally reflected) from the side surface 254-1, 2 in the light guide (light pipe) 250, and no optical loss occurs during the reflection due to the reason as stated above. That is, the light guide (light pipe) 250 used to generate combined light (mixed light) 78 (see FIG. 10) can lead to the effect of greatly reducing the optical loss during light combining (mixing).

As the examples of the optical characteristics changing member used to generate the combined light (mixed light) 78, the above describes the diffraction grating 120, 124 (FIG. 12A, 14C), the optical fiber 100 (FIG. 14A, FIG. 24A, FIG. 24B, or FIG. 24C) or the phase conversion element 102-2, 212 (FIG. 14B, FIG. 21A(b), FIG. 21C, or FIG. 22), for example. When light passes through such an optical characteristics changing member, a loss of the amount of transmitted light occurs to some extent for any optical characteristics changing member. As compared with these optical characteristics changing members, the amount of optical loss of the light guide (light pipe) 250 (which similarly belongs to the optical characteristics changing member) is very small.

The light guide (light pipe) 250 illustrated in FIG. 54 has a cuboid shape. On the contrary, the light guide (light pipe) 250 illustrated in FIG. 52 or 53 has at least partially inclined side surfaces 254-1, 2. A part of the side surfaces 254-1, 2 may be curved so that the amount of inclination is partially changed. In this case, the angle between the front-end boundary 252 or the back-end boundary 256 of the light guide (pipe) and the side surfaces 254-1, 2 is not 90-degree (having such a part at least locally).

Then the following relationship holds based on (B•50), where μ☐ denotes the (at least local) slope angle of the side surfaces 254-1, 2.

$$\xi + \phi + \mu = 90\text{-degree} \quad \quad (B•51)$$

Substitution of the maximum value of the angle of refraction (41.8-degree when the refractive index n is 1.5) and the critical angle for total reflection at the side surfaces 254-1, 2 (φ=41.8-degree) into (B•50) results in μ=6.4-degree. That is, in order to generate total reflection at the side surfaces 254-1, 2, the slope angle μ at the side surfaces 254-1, 2 has to be 6.4-degree or less.

Considering errors of the angles of the front-end boundary 252 or the back-end boundary 256 during the manufacturing of the light guide (light pipe) 250 or a variation in refractive index n due to a change of the wavelength of the irradiated light 12, the slope angle μ at the side surfaces 254-1, 2 is desirably set at 6-degree or less (more desirably 5-degree or less).

The above calculation is based on the assumption that the surfaces of the side surfaces 254-1, 2 of the light guide (pipe) are exposed to the air (the vacuum). The present embodiment is not limited to such a condition, and the slope angle μ at the side surfaces 254-1, 2 of the light guide (pipe) may be set at 5-degree or more, for example. In this case, the condition for total reflection at the side surfaces 254-1, 2 does not hold, and so a light-reflecting layer may be applied to the side surfaces 254-1, 2 of the light guide (pipe).

FIG. 54(b) shows the situation where beams of the irradiated light 12 travelling through the light guide (light pipe) 250 are combined (mixed) while repeating total reflection. Point ε of the front-end boundary 252 of the light guide corresponds to the imaging point of the light-emitting point α of the light-emitting source 70 (tungsten filament 50) in FIG. 52 or the exit of the optical fiber 100-2 in FIG. 53. Similarly point corresponds to the imaging point of the light-emitting point β of the light-emitting source 70 (tungsten filament 50) or the exit of the optical fiber 100-1. As shown in FIG. 54(b), both of the beams of light pass through different optical paths in the vicinity of points and When the light travels a bit away from these points through the light guide (light pipe) 250, then the optical path 260 of the beam from point ε and the optical path 270 of the beam from point are mutually overlapped. Then, the overlapped area of the optical paths 260 and 270 is the mixing area 280 of the light, so that the beams of the light are combined (mixed). Then the beams of the light are further combined (mixed) while repeating total reflection at the side surfaces 254-1, 2 in the light guide (light pipe) 250. When the beams pass through the back-end boundary 256 of the light guide (pipe), they turn the combined light (mixed light) 78 as shown in FIG. 8A, 8B or 10.

When the combined light (mixed light) 78 is generated using the diffraction grating 120, 124 in FIG. 12A, 14C or the phase conversion element 102-2, 212 in FIG. 14B, FIG. 21A(b), FIG. 21C, or FIG. 22, which are examples of the optical characteristics changing member, the operation of combing (mixing) light is performed only once.

On the contrary, in the light guide (light pipe) 250, the optical paths are overlapped (i.e., light combining/mixing) a plurality of times corresponding to the repeated total reflections at the side surfaces 254-1, 2. Therefore such a configuration can improve the degree of combining (mixing) of the beams emitted from the light-emitting source 70 and passed through different optical paths, and so can improve the efficiency of decreasing partial coherency (increasing partial incoherency).

Section 3.11 Method for Reducing Partial Coherency of Electromagnetic Waves Having Wavelength Longer than Near-Infrared Light and Application Examples In the system of the present embodiment shown in FIGS. 1A to 1C, the irradiated light (first light) 12 is applied to the target 10, and the internal characteristics or state of the target 10 are measured using the detection light (second light) 16 obtained from the target 10. The irradiated light (first light) 12 or the detection light (second light) 16 repeats multiscattering in this target 10. When the irradiated light 12 or the detection light 16 is partial coherent light, optical noise occurs in the detection light 16 and the penetration length of the irradiated light 12 into the target 10 decreases as described later in Chapter 5.

Such a phenomenon is not limited to near-infrared light or infrared light, and occurs for electromagnetic waves having longer wavelengths as well. Meanwhile in order to increase the directionality of electromagnetic waves by Radar (Radio Detection and Ranging), wave front of the electromagnetic waves are flattened typically. Such a way, however, increases the coherency of electromagnetic waves, and so the penetration length of the light into the target 10 decreases. When electromagnetic waves of a single frequency are used for a radar, the light has coherency and not partial coherency. Experimental data using near-infrared light of Chapter 5 shows that a similar phenomenon happens for electromagnetic waves having a longer wavelength. When wave front of electromagnetic waves is disturbed so as to decrease the partial coherency (or coherency) of electromagnetic waves, their directionality decreases significantly.

The following describes a method of generating electromagnetic waves having low (partial) coherency while keeping sufficient directionality as an application example of the present embodiment. Each of electromagnetic wave source/receiving parts 292 of FIG. 55(a) includes an antenna common to transmission and reception of electromagnetic waves, a transmission circuit to generate electromagnetic waves and a reception circuit of electromagnetic waves (detection circuit), which are not illustrated in the drawing. These mutually different electromagnetic wave source/receiving parts 292-1 to -n (antennas therein) emit electromagnetic waves 290-1 to -n having directionality, respectively, i.e., the electromagnetic waves passing through different travelling paths. These electromagnetic waves are then mutually overlapped spatially to mix the electromagnetic waves. To this end, a plurality of these independent electromagnetic wave source/receiving parts 292 each emitting electromagnetic waves 290 having directionality are disposed close to each other to have the same radiation direction. Then, mixed electromagnetic waves 294 having directionality can be formed at a position sufficiently distant from these electromagnetic wave source/receiving part 292-1 to -n.

The following describes a mechanism to generate such mixed electromagnetic waves 294 having directionality in details. Electromagnetic waves 290-1 to -n emitted from the electromagnetic wave source/receiving part 292-1 to -n each have directionality. At a position sufficiently distant from the electromagnetic wave source/receiving part 292-1 to -n, however, these electromagnetic waves 290-1 to -n each are expanded spatially (in the plane perpendicular to the travelling directions). Therefore when these plurality of electromagnetic wave source/receiving part 292-1 to -n are disposed densely one-dimensionally or two-dimensionally, the electromagnetic waves 290-1 to -n are extended at a sufficiently distant position (on the right of FIG. 55(a)) and are spatially overlapped. These electromagnetic waves 290-1 to -n are mixed at this overlapped part, and so the mixed electromagnetic waves 294 having directionality can be formed. Since each of the electromagnetic waves 290-1 to -n has directionality, their directional characteristics do not change even after the mixing.

As described in Section 3.1 with reference to FIG. 10, a change in optical length 76 of a part 74 of the light emitted from the light-emitting source 70 so as to satisfy (B•44) does not generate interference of the light with another part 72 of the light. Section 2.2 describes the cause of the interference of light based on uncertainty principle.

In view of the cause of interference of light (between electromagnetic waves) as described above, the electromagnetic waves 290-1 to -n emitted from different electromagnetic wave source/receiving part 292-1 to -n do not interfere with each other. Accordingly the mixed electromagnetic waves 294 having directionality generated by the method as stated above have low (partial) coherency (high (partial) incoherency) while keeping high directionality. Such mixed electromagnetic waves 294 having directionality can increase the penetration length into the target 10 as described later in Chapter 5. This means that the internal characteristics or state of the target 10 can be measured at a deeper area. Further, noise due to interference of multi-scattered light 370 in the target 10 can be reduced, and so the characteristics can be detected accurately.

The method described in Section 3.1 to Section 3.10 (combining (mixing) electromagnetic waves passed through different travelling paths (optical paths) or changing the optical length of a part of the electromagnetic waves, followed by combining (mixing)) is not limited to this application example, and may be used for electromagnetic waves in a frequency range described in this Section 3.11 as well.

Each of the electromagnetic wave source/receiving part 292-1 to -n internally includes at least one radar antenna. Such a radar antenna has a structure of a Yagi antenna or any structure including a hemispherical, elliptic or parabolic-shaped reflective mirror configured to make electromagnetic waves spherically emitted from one point parallel to each other (parabola antenna). Frequency band of radio waves suitable for the antenna structure used in the present embodiment ranges from a low-frequency band to a middle-frequency band. Specifically radio waves as a target include LF waves (low frequency waves: long waves) in the range of 30 kHz to 300 kHz as well as MF waves (middle frequency waves: middle waves) in the range of 300 kHz to 3 MHz, HF waves (high frequency waves: short waves) in the range of 3 MHz to 30 MHz and VHF waves (very high frequency waves: long waves) in the range of 30 MHz to 300 MHz.

AC current flowing through one conducive wire causes emission of electromagnetic waves around the wire. As these electromagnetic waves pass through this conductive wire, induced current flows through the wire, and so the electromagnetic waves can be detected. Therefore a transmission circuit to generate electromagnetic waves is connected to a reception circuit of electromagnetic waves (detection circuit), whereby one radar antenna can function as the source to generate electromagnetic waves and as the receiving part of electromagnetic waves.

FIG. 55(b) shows an application example of the present embodiment, which include an electromagnetic wave (standing wave) generating source 292 capable of radiating microwaves that can be used for microwave ovens or radars. The international standard specifies the frequency used for microwave ovens as 2.45 GHz (the wavelength is 12.2 cm). The use of 915 MHz (the wavelength is 32.8 cm) is permitted limitedly in the United States.

To increase the directionality of microwaves emitted from magnetron electromagnetic wave generating sources 296-1 to -n, waveguide antennas 298-1 to -n are disposed at the exit of the microwaves. These waveguide antennas 298-1 to -n specifically have a cuboid or circular cylindrical (or a pyramid or circular conical) hollow tube so as to allow microwaves to be reflected repeatedly at the inner wall of this hollow tube while increasing their directionality for radiation to the outside.

These waveguide antennas 298-1 to -n can be used as the exit to radiate microwaves as well as a part of a receiver (microwave detector) of microwaves coming in from the outside. When these waveguide antennas 298-1 to -n are used as the receiver of microwaves in this way, each of the waveguide antennas 298-1 to -n may include a pre-amplifier circuit and a signal-processing circuit (not illustrated) connected at one end.

Each of the magnetron electromagnetic wave generating sources 296 may internally have a thermionic tube structure that is disposed in a strong DC magnetic field. The cathode disposed at the center of the hollow of the vessel is heated by a heater. Then thermoelectrons emitted from this cathode move toward the anode due to the action of the applied electrical field. At this time, the thermoelectrons emit microwaves while drawing a cycloid curve due to the influences from the outside DC magnetic field.

This magnetron electromagnetic wave generating source 296 has the practical frequency range from 100 MHz to 200 GHz. Therefore "microwaves" used in the example of the present embodiment have a wider sense indicating a high-frequency band in the category of radio waves. That is, the microwaves in the present embodiment are not limited to SHF (super high frequency) waves (microwaves in a narrow sense) in the range of 3 GHz to 30 GHz defined as microwaves in a narrow sense, and may include a wider frequency range. That is, the microwave frequency region includes VHF waves in the range of 30 MHz to 300 MHz, UHF waves (ultra high frequency waves) in the range of 300 MHz to 3 GHz, EHF waves (extremely high frequency waves: millimeter waves) in the range of 30 GHz to 300 GHz.

Microwaves radiated to the outside of the waveguide antennas 298-1 to -n turn electromagnetic waves 290-1 to -n, respectively, having directionality. As shown in FIG. 55(b), the electromagnetic waves 290-1 to -n having high directionality also are expanded in the perpendicular plane at a position away from the waveguide antennas 298-1 to -n. As shown in FIG. 55(b), a plurality of sets each including the magnetron electromagnetic wave generating source 296 and the waveguide antenna 298 are densely disposed in one direction or in the plane direction. Then, at a position away from the waveguide antennas 298-1 to -n, the electromagnetic waves 290-1 to -n having directionality are spatially overlapped and so are mutually combined (mixed). In this way, the mixed electromagnetic waves 294 having directionality are generated by combining (mixing), which are electromagnetic waves with low (partial) coherency.

A phased array antenna is known, which includes the two-dimensionally arranged waveguide antennas 298-1 to -n each having the hollow part that is rectangular (or square) in cross section. This structure can optimize wave fronts of the microwaves emitted from all of the waveguide antennas 298-1 to -n because this can increase the directionality of the microwaves. In the structure of these antennas, only one magnetron electromagnetic wave generating part 296 is used. Therefore microwaves emitted from these antennas have very high degree of coherency.

Although the way of arranging the waveguide antennas 298-1 to -n are similar between them, the phased array antenna and the application example shown in FIG. 55(b) are basically different in the effect of reducing coherency. Specifically the conventional phased array antenna configured to generate microwaves having high degree of coherency using the only one magnetron electromagnetic wave generating part 296 has a short penetration length into the target 10 and the electromagnetic waves have large noise mixed into the detection signal. As compared with this, the application example of the present embodiment including a plurality of mutually independent magnetron electromagnetic wave generating sources 296-1 to -n can have a large penetration length into the target 10 and the noise mixed into the detection signal can be greatly reduced.

Hereinafter the generating source of the mixed electromagnetic waves 294 having high directionality and having low degree of (partial) coherency (high degree of (partial) incoherency) as in the method of FIG. 55(a) or (b) is called a directional electromagnetic wave generating/receiving part 362. This directional electromagnetic wave generating/receiving part 362 internally includes a plurality of sets of the electromagnetic waves source/receiving parts 292-1 to -n or the magnetron electromagnetic wave generating parts 296-1 to -n and the waveguide antennas 298-1 to -n. This directional electromagnetic wave generating/receiving part 362 internally includes a function of receiving (detecting) electromagnetic waves (or microwaves) from the outside as well.

Microwave ovens can heat food based on the principle to let water in the food absorb energy of microwaves for generation of the heat. The mechanism to absorb energy of electromagnetic waves depends on the wavelength band of the electromagnetic waves used. As described later in Section 5.2 referring to FIG. 27, biased electronic orbital of molecules absorbs the energy during irradiation with visible light. When irradiated with near-infrared light, group vibration in an atomic group including hydrogen atoms absorbs the energy. When irradiated with infrared light of a longer wavelength, atoms composing the molecules vibrate.

When irradiated with electromagnetic waves of a longer wavelength, the vibration of atoms composing the molecules cannot absorb the electromagnetic waves, but the rotation of the molecules as a whole or their translation motion absorbs the energy. Note here that such rotation of the molecules as a whole or their translation motion occurs often in liquid and not in a solid. That is, water molecules in the liquid state (and not in a solid state) absorb the electromagnetic waves having the frequency ranging from 30 kHz to 300 GHz or from 30 MHz to 300 GHz the best. In other words, water molecules and not a solid absorb the energy of electromagnetic waves having such frequencies more.

It is said that, due to dielectric loss of water itself, the frequency maximizing the absorption of electromagnetic wave energy is in the range of 20 GHz to 80 GHz (this maximum frequency varies with temperatures). The efficiency of absorbing electromagnetic wave energy by water, however, does not differ much with a change in the frequency of electromagnetic waves. As a result, water molecules can absorb the energy sufficiently by setting the frequency of electromagnetic waves for microwave ovens at 2.45 GHz (or 915 MHz), and so food can be heated. For the same reason, water molecules can absorb energy well and generate heat with electromagnetic waves having the frequencies in the range from 30 MHz (or 3 MHz) to 300 GHz as well.

In another application example of the present embodiment, such a phenomenon may be used to search for a water source or a metalliferous deposit 386. Specifically a target for searching is irradiated with mixed electromagnetic waves 294 having directionality. Then, interaction with the mixed electromagnetic waves 294 is compared among the measurement areas.

If a searching target has a water source 386, the water source 386 will absorb the energy of the mixed electromagnetic waves 294. Since a water source 386 absorbs electromagnetic waves (microwaves) well, the amount of electromagnetic waves reflected in the water source 386 (the amount of backward scattering) decreases relatively. A change in the amount of electromagnetic waves reflected (the amount of backward scattering) is examined by the directional electromagnetic wave generating/receiving part 362, whereby the amount of electromagnetic waves reflected (the amount of backward scattering) in the water source 386 can be found. When absorbing the energy of the electromagnetic waves (microwaves), the temperature of the water source 386 rises. The water source 386 can be found also by examining such a temperature rise.

The amount of electromagnetic waves reflected (scattered) increases at a metalliferous deposit 386 compared with other areas. Therefore an area showing more electromagnetic waves reflected (scattered) than other areas may include a metalliferous deposit 386.

Recent researches have revealed that there is water on the surface on the moon. Water on the moon surface is electrolyzed by electricity obtained from sunlight with a solar panel 384 to obtain oxygen molecules and hydrogen molecules. Then rocket fuel can be produced using the oxygen molecules and hydrogen molecules. Organisms can live on the moon using the oxygen molecules. Various types of metals may be extracted from metalliferous deposits embedded in the moon, and these metals can be used for materials of a construction on the moon, a mobile object or a rocket toward other planets.

The following describes one example of such applications to search for resources in the moon's surface. The following method may be used to search for a resource in the earth or for a resource of extraterrestrial areas (e.g., asteroids, planets, or satellites).

Figure 56:
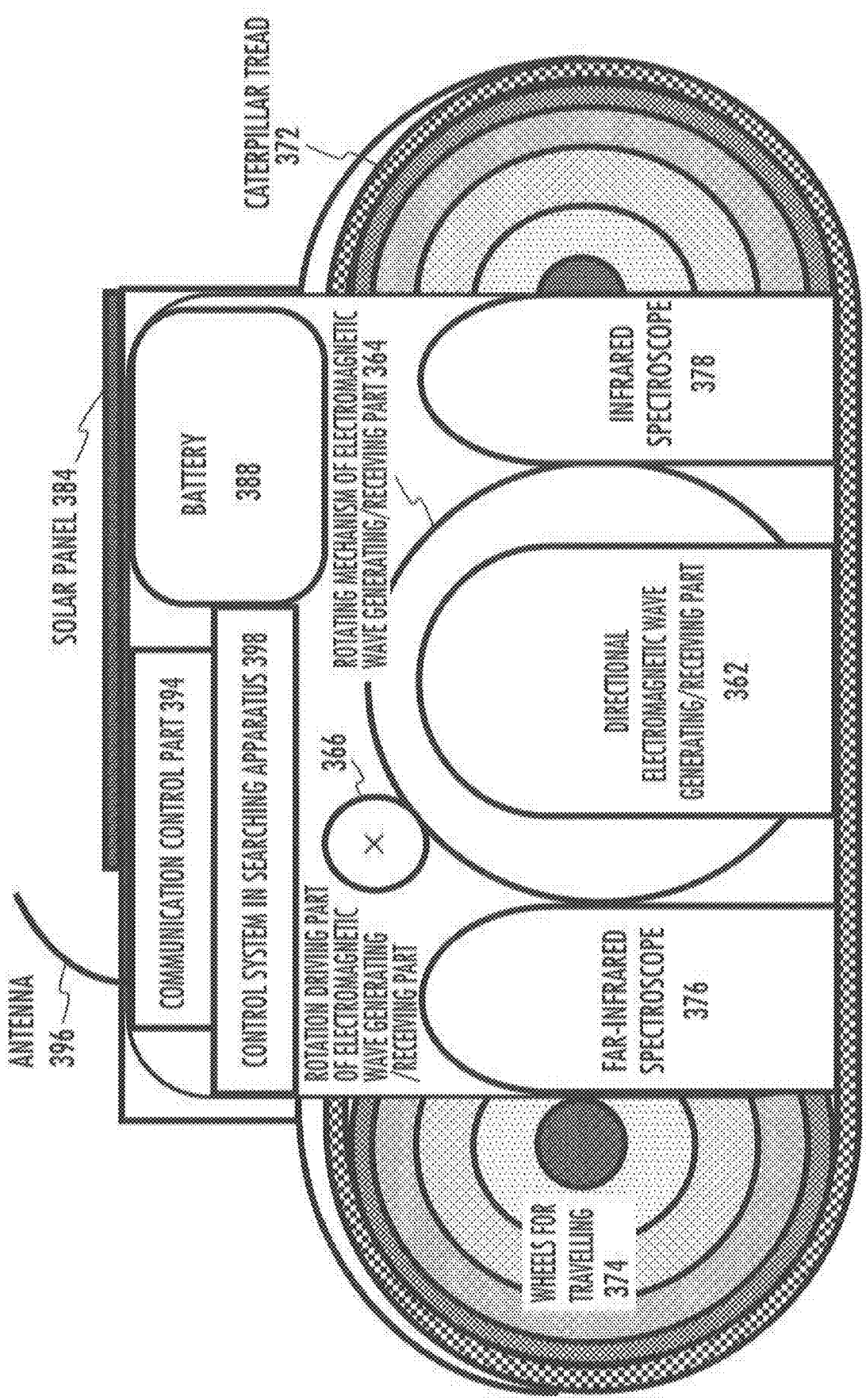
FIG. 56 describes the structure of a water source/metalliferous deposit searching apparatus in the present embodiment.

FIG. 56 shows an exemplary structure of a water source/metalliferous deposit searching apparatus that can be used to search for the position of a water source or a metalliferous deposit 386 on the moon's surface (or to search for a resource of an extraterrestrial area other than the moon). A caterpillar tread 372 similar to a combat vehicle comes directly in contact with the moon's surface. Then wheels for travelling 374 rotate to move the caterpillar tread so as to allow the water source/metalliferous deposit searching apparatus to run on the moon's surface.

Figure 55:
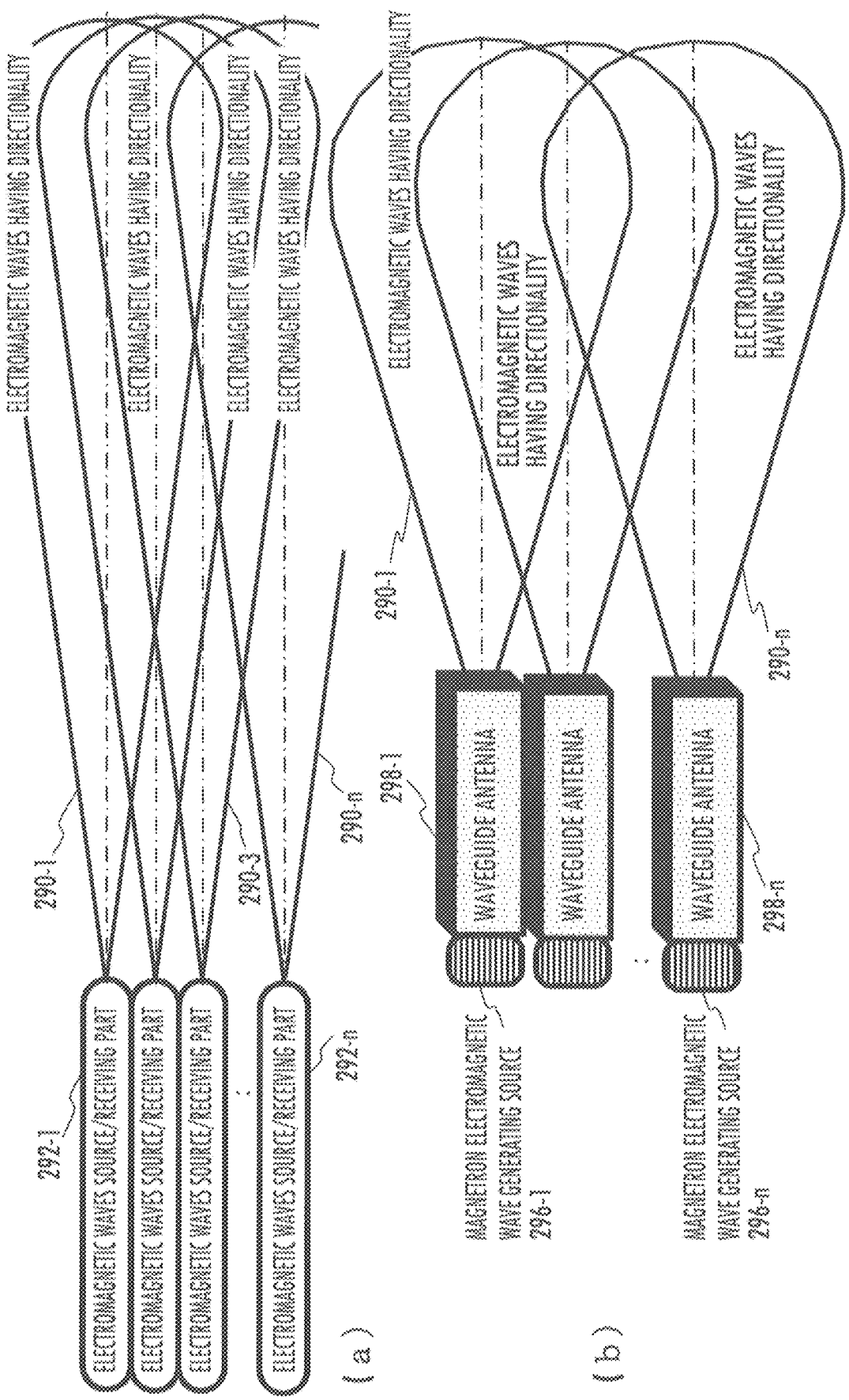
FIG. 55 explains how to generate electromagnetic waves having high directionality and low partial coherency.

A center part of FIG. 56 shows the internal structure of the water source/metalliferous deposit searching apparatus. The directional electromagnetic wave generating/receiving part 362 having the internal structure of FIG. 55 is disposed to radiate mixed electromagnetic waves 294 having downward directionality (i.e., toward the underground of the moon or a center part of the extraterrestrial area other than the moon) and receive (detect) the mixed electromagnetic waves reflected (backward scattered) and returning from the below (i.e., the underground of the moon or a center part of the extraterrestrial area other than the moon).

This directional electromagnetic wave generating/receiving part 362 may be stored in the rotating mechanism 364 of the electromagnetic wave generating/receiving part so as to be inclined in any direction. In response to the rotation of the rotation driving part 366 of this electromagnetic wave generating/receiving part, the rotating mechanism 364 of the electromagnetic wave generating/receiving part as a whole rotates slightly in any direction. Using this mechanism, the mixed electromagnetic waves 294 having directionality can be radiated in any direction under the moon's surface. Similarly, the mixed electromagnetic waves 294 scattered or reflected from any direction under the moon's surface also can be received (detected).

As shown in FIG. 56, the water source/metalliferous deposit searching apparatus internally includes a far-infrared spectroscope 376 and an infrared spectroscope 378. The far-infrared spectroscope 376 does not have a light source, and has a structure capable of measuring spectroscopic characteristics (spectroscopic spectra) of far-infrared light radiated from the underground of the moon. The infrared spectroscope 378 internally includes its own light source of infrared rays. Infrared light emitted from this light-emitting source is applied to the moon' surface or to the space close to the moon's surface. Then, the spectroscopic characteristics (spectroscopic spectra) of the reflected light or scattered light from the moon's surface or the space close to the moon's surface are examined.

Electric power generated by the solar panel 384 at the top face of the water source/metalliferous deposit searching apparatus is stored in a battery 388, which enables the activity at night. A communication control part 394 controls wireless communication with external devices via the antenna 396. A searching device control system 398 integrally controls/manages the operation of these parts.

Figure 57:
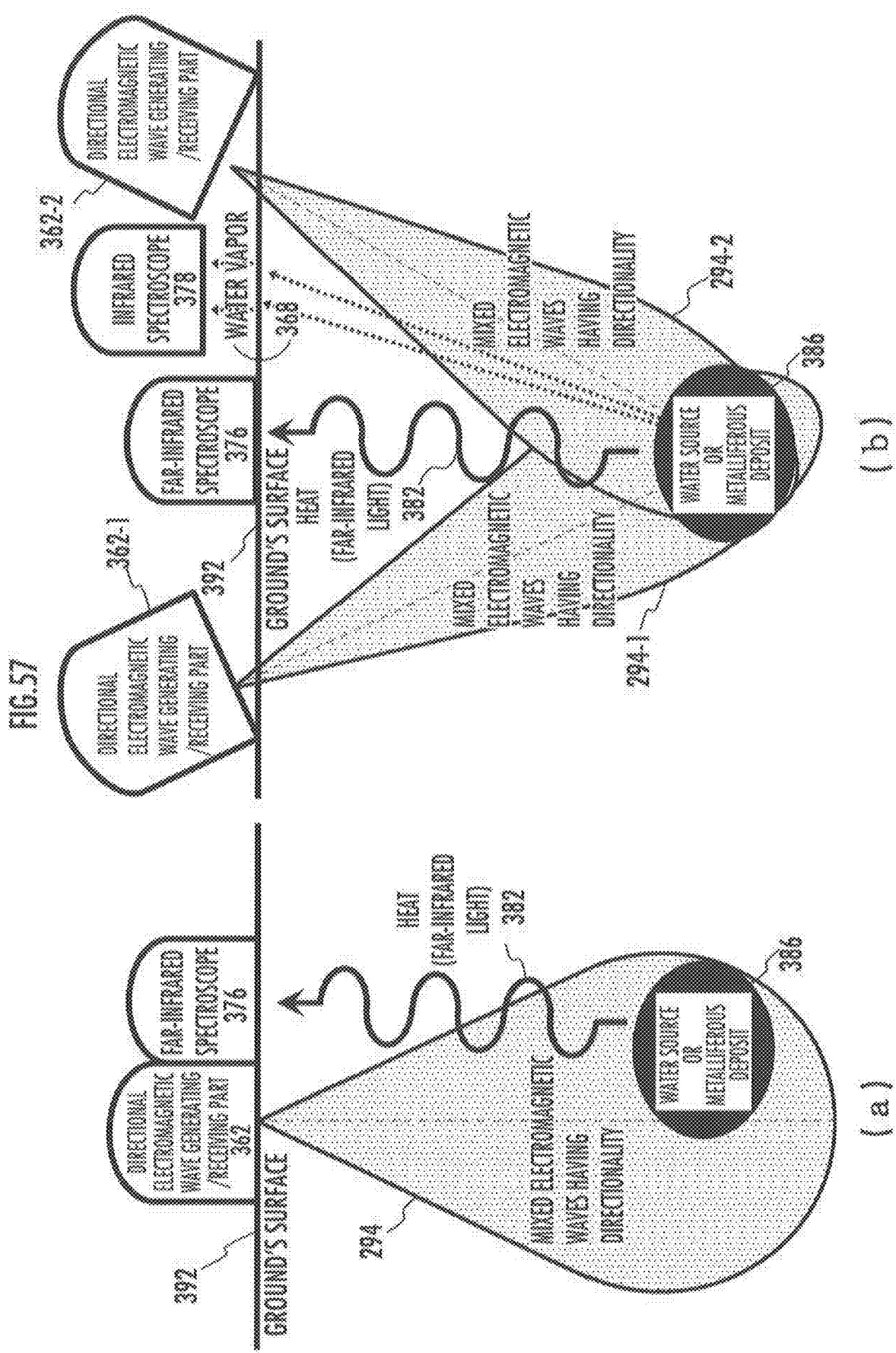
FIG. 57 describes an exemplary method of searching for the position of a water source or a metalliferous deposit at an extraterrestrial area.

FIG. 57 shows an exemplary method of searching for the position of a water source or a metalliferous deposit under the moon's surface using this water source/metalliferous deposit searching apparatus (or searching for a resource of an extraterrestrial area other than the moon). FIG. 57(a) shows an exemplary method of searching for the position of a water source using only one water source/metalliferous deposit searching apparatus. FIG. 57(b) shows an exemplary method of searching for the position of a water source using a plurality of water source/metalliferous deposit searching apparatuses. In an application example of the present embodiment, the possibility of embedded water source or metalliferous deposit 386 may be investigated firstly using a simple method of FIG. 57(a), followed by the detailed investigation of a possible area by the method of FIG. 57(b).

In the simple searching of FIG. 57(a), the directional electromagnetic wave generating/receiving part 362 emits the mixed electromagnetic waves 294 having directionality toward the immediately below the water source/metalliferous deposit searching apparatus. The emitted mixed electromagnetic waves 294 having directionality are reflected (backward scattered) at every place inside of the ground's surface 392 and are returned to the directional electromagnetic wave generating/receiving part 362. The time immediately after the emission of the mixed electromagnetic waves 294 till returning to the directional electromagnetic wave generating/receiving part 362 varies with the reflected (backward scattered) position of the mixed electromagnetic waves 294. Thus the mixed electromagnetic waves 294 having directionality and in a pulse form are emitted for a short period of time, and a change in detected intensity of the mixed electromagnetic waves 294 returning to the directional electromagnetic wave generating/receiving part 362 relative to the intensity immediately after the emission is detected. In this way a change over time immediately after the emission is measured, whereby information on the depth direction from the ground's surface 392 can be expected to some extent.

As described in Section 5.1 referring to FIG. 26(b), the detection accuracy in the depth direction greatly deteriorates actually due to the influences from the multi-scattered electromagnetic waves 294. Interference between this multi-scattered light 380 (electromagnetic waves) and the backward scattered light 390 (electromagnetic waves) to be measured, if occurred, further degrades the detection accuracy. In the application example of the present embodiment, the mixed electromagnetic waves 294 having directionality have greatly lowered coherency (incoherency is remarkably improved), and so interference between the multi-scattered light 380 (electromagnetic waves) and the backward scattered light 390 (electromagnetic waves) does not occur. This can lead to the effect of improving the detection accuracy.

When a metalliferous deposit is searched for in this way, the amount of the mixed electromagnetic waves 294 reflected (backward scattered) from an area including the metalliferous deposit 386 is large. Therefore a metalliferous deposit 386 may be present at an area having increased detection intensity immediately after the emission of the mixed electromagnetic waves 294.

On the contrary, at an area where a water source 386 is present, the mixed electromagnetic waves 294 are absorbed a lot. This results in a large decrease in the amount of the mixed electromagnetic waves 294 reflected (backward scattered) from such an area.

The amount of the mixed electromagnetic waves 294 reflected (backward scattered) may decrease greatly not only at the water source 386 but also at an area including a hollow. In this way, the water source 386 and the hollow area can be distinguished by comparing the amount of reflection (the amount of backward scattering) from a deeper position. That is, when a lot of energy of the mixed electromagnetic waves 294 is absorbed at the water source 386, the amount of reflection (the amount of backward scattering) of the mixed electromagnetic waves 294 will be smaller from a deeper position. On the other hand, since no energy of the mixed electromagnetic waves 294 is absorbed at the hollow area, the amount of reflection (the amount of backward scattering) of the mixed electromagnetic waves 294 will be larger from a deeper position.

Other physical parameters may be used in addition to the detection of a change in the amount of reflection (the amount of backward scattering) of the mixed electromagnetic waves 294 for improved searching accuracy. When the interior of a water source or a metalliferous deposit 386 is irradiated with the mixed electromagnetic waves 294, the energy is absorbed at a surface part of the water source or the metalliferous deposit 386, and a temperature locally rises there. This temperature rise may be detected to improve the detection accuracy of the position of the water source or metalliferous deposit 386.

Every substance radiates light of a wavelength corresponding to the temperature of the substance. In one example of the relationship between wavelengths and temperatures at the maximum intensity position of light radiated from a black body, the wavelengths are 10.3 μm at 0° C., 8.05 μm at 50° C., and 7.75 μm at 100° C. Therefore spectroscopic characteristics of the light radiated from a black body at the water source or the metalliferous deposit 386 or at the vicinity thereof may be measured with the far-infrared spectroscope 376.

Instead of observing far-infrared light 382 directly, a temperature change in the vicinity of the ground's surface 392 may be measured using transferring of heat 382 generated at the water source or the metalliferous deposit 386.

Temperatures are 100° C. or higher in daytime and are 150° C. below zero or lower at night on the surface of the moon 392. Therefore when a temperature change may be measured at night (150° C. below zero or lower), high measurement accuracy can be obtained.

As described above referring to FIG. 55(b), thermoelectrons are emitted from the cathode in the magnetron electromagnetic wave generating source 296 when the cathode is heated by a heater. Heat generated during the operation of the directional electromagnetic wave generating/receiving part 362 adversely affects the temperature change as stated above. To avoid such adverse effect, a plurality of water source/metalliferous deposit searching apparatuses may be combined as in FIG. 57(b).

Specifically a water source or a metalliferous deposit 386 is irradiated with mixed electromagnetic waves 294 having directionality from the directional electromagnetic wave generating/receiving part of one of the water source/metalliferous deposit searching apparatuses 362 and a temperature change as stated above may be measured by another water source/metalliferous deposit searching apparatus that does not generate heat.

Alternatively as shown in FIG. 57(b), composite electromagnetic waves 294-1, 2 having directionality may be applied from a plurality of directional electromagnetic wave generating/receiving parts 362-1, 2 simultaneously. Then, the composite electromagnetic waves 294 are detected (received) by the plurality of directional electromagnetic wave generating/receiving parts 362-1, -2. This can lead to the effect of reducing the influences from the electromagnetic waves 294 that are internally multi-scattered.

When irradiating with composite electromagnetic waves 294-1, 2 having directionality simultaneously from a plurality of directional electromagnetic wave generating/receiving parts 362-1, -2 disposed at different positions, the energy of the composite electromagnetic waves 294-1, 2 is concentrated on a predetermined part only. Using this concentrated energy, the temperature of a part of the water source 386 may be increased at 100° C. or higher. A part of the water source 386 with the temperature increased at 100° C. or higher boils and starts diffusion. A part of the water vapor 368 diffused from the moon's surface (100° C. or higher) in daytime is emitted to the outside of the ground's surface 392. This emitted water vapor 368 may be observed by the infrared spectroscope 378 (FIG. 56), whereby the presence of a water source 386 can be confirmed at the energy-concentrated area.

Water molecules absorb infrared-light intensively in the vicinity of 2.73 μm, 2.66 μm and 6.27 μm as the center wavelength. Therefore when the light-absorbing characteristics obtained by the infrared spectroscope 378 show light-absorption common to these wavelength bands, it can be estimated that water vapor 368 is emitted above the ground's surface 392.

Figure 58:
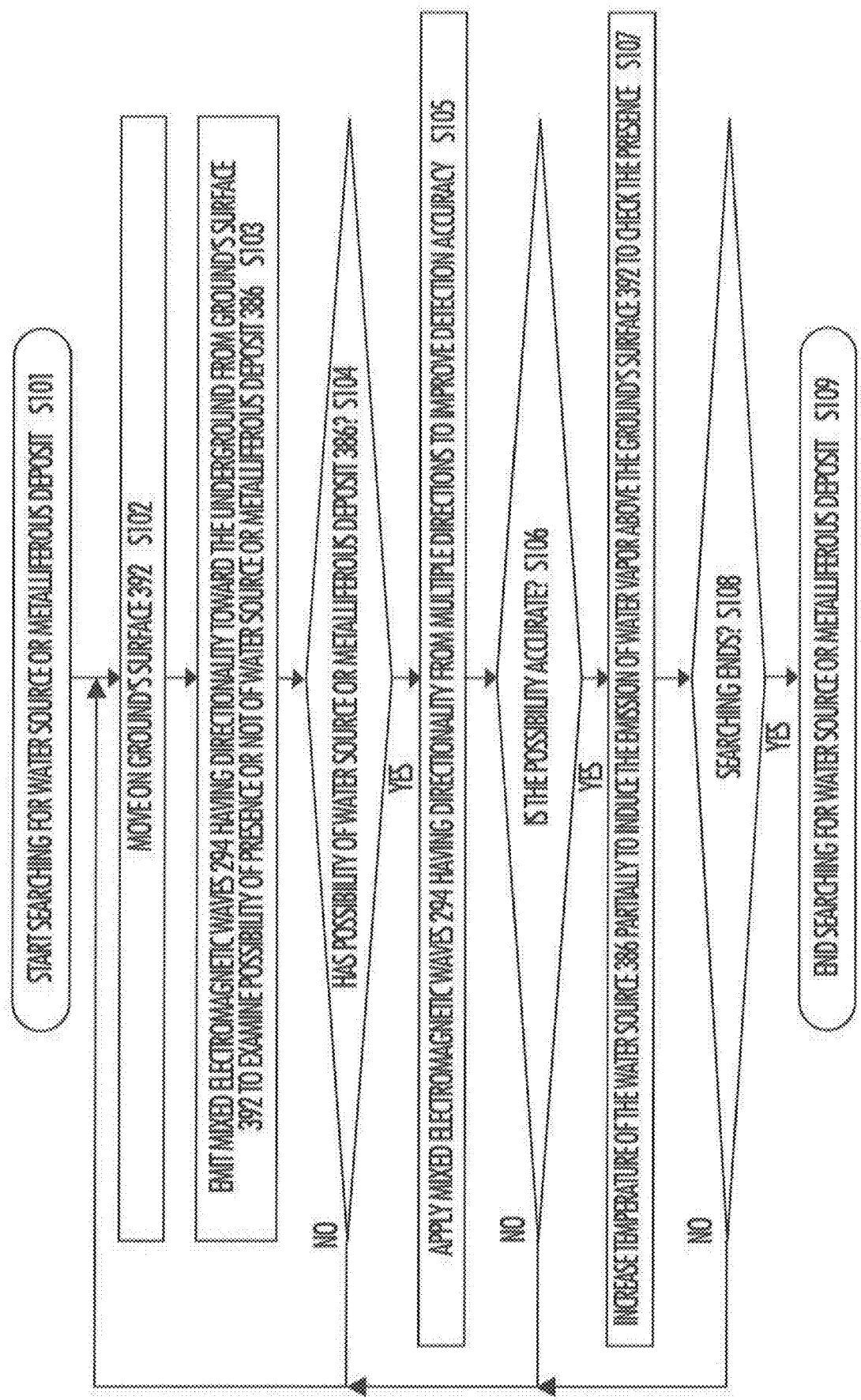
FIG. 58 describes an exemplary procedure for searching for the position of a water source or a metalliferous deposit at an extraterrestrial area.

FIG. 58 shows a series of the searching procedure as described above. When searching for the place of a water source or metalliferous deposit 386 starts (S101), a water source/metalliferous deposit searching apparatus starts to move in a searching target area (e.g., the ground's surface 392 of the moon or an extraterrestrial area (such as satellites, asteroids, or planets)) as shown at S102. At a first searching place, as shown in FIG. 57(*a*), the water source/metalliferous deposit searching apparatus emits mixed electromagnetic waves 294 having directionality toward the underground (toward a center part under the moon's surface, and of a satellite, an asteroid, or a planet) from the ground's surface 392. To search for a water source or metalliferous deposit 386 using the emitted mixed electromagnetic waves 294 having directionality, the mixed electromagnetic waves 294 reflected (backward scattered) from the inside and returning may be detected. At the same time, the far-infrared spectroscope 376 may be used to detect a change in characteristics of heat (far-infrared light) 382 generated at the inside (or the vicinity of the surface) of the water source or metalliferous deposit 386.

As a result, a determination can be made whether there is a possibility of the presence of a water source or metalliferous deposit 386 at the first searching place (S104). If there is no such a possibility (No at S104), the water source/metalliferous deposit searching apparatus moves to another searching place (S102).

In this way, at the first step, mapping of areas having the possibility of the presence of a water source or metalliferous deposit 386 is performed. At the following step, searching accuracy is improved for the possible areas (Yes at S104).

At the next step, examination from multiple perspectives starts using a plurality of water source/metalliferous deposit searching apparatuses as shown in FIG. 57(*b*). In one example, as shown at S105, mixed electromagnetic waves 294 having directionality are applied simultaneously to the candidate places of the water source or metalliferous deposit 386 from multiple directions. Then, the mixed electromagnetic waves 294 obtained from the places are detected (received). In parallel, heat (or far-infrared light) 382 generated from a target area may be measured using the far-infrared spectroscope 376.

If a result of such accurate investigation shows that a candidate place of the water source or metalliferous deposit 386 is not correct (No at S106), the water source/metalliferous deposit searching apparatus moves to another mapping place (S105).

On the contrary, for an area having an increased possibility for the water source or metalliferous deposit 386 (Yes at S106), further investigation for verification may be performed at S107. At this step, mixed electromagnetic waves 294-1, 2 having directionality are concentrated to one place from multiple directions so as to increase the temperature of the water source or metalliferous deposit 386. Then water vapor 368 diffused close to the ground's surface 392 and emitted above the ground's surface 392 may be detected using the infrared spectroscope 378.

In this way, the water source/metalliferous deposit searching apparatus continues to move on the ground's surface 392 till the end of searching (Yes at S108).

FIG. 55 describes a method to generate electromagnetic waves (mixed electromagnetic waves 294 having directionality) with reduced partial coherency. Referring to FIGS. 56 to 58, a method for searching for resources is described above as an example of the application field of these electromagnetic waves 294. The water source/metalliferous deposit searching apparatus of FIG. 56 has a form of running on the ground's surface 392.

Alternatively, mixed electromagnetic waves 294 having directionality may be emitted from the above of the ground's surface 392. To emit the mixed electromagnetic waves from the above of the ground's surface 392, a directional electromagnetic wave generating/receiving part 362 may be mounted on a helicopter, an airplane or a satellite, for example. Alternatively, a directional electromagnetic wave generating/receiving part 362 may be disposed under the ground below the ground's surface 392 to measure a regular change.

The method (a part thereof) shown in FIGS. 57 and 58 may be used to search for resources in the earth. Especially, when an application example of the present embodiment is used to search for resources in the earth, this may be dedicated to searching for metalliferous deposit.

Section 3.12 Simple Description on Method for Controlling Partial Coherency of Light The above description till Section 3.11 (the previous section) explains a method for controlling partial coherency of light mainly quantitatively using a lot of mathematical expressions. This gives theoretical strictness to some extent to the method, but the description tends to be difficult to understand. To solve such difficulty, Section 3.12 gives a simply and intuitive explanation about the method of controlling partial coherency of light in the present embodiment. That is, theoretical strictness decreases a bit in this section 3.12.

Figure 59:
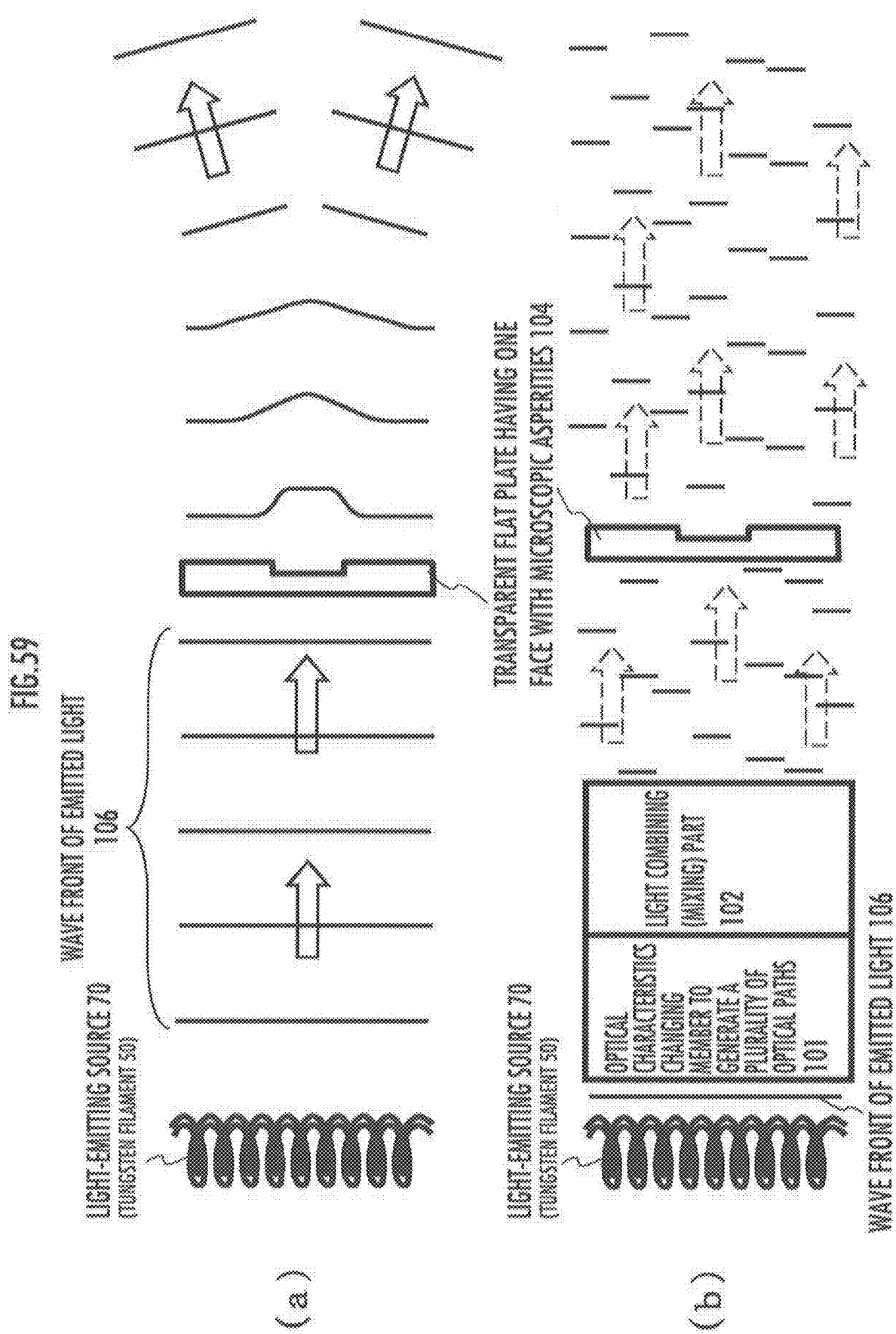
FIG. 59 simply explains a difference in partial coherency of light in the present embodiment.

Referring to FIG. 59(*a*), this drawing shows interference of conventional light having partial coherency qualitatively. Light emitted from a light-emitting source 70 (e.g., a tungsten filament 50) travels straight while having a relatively flat wave front (equiphase wave surface) 106. When this light passes through a transparent flat plate 104 having one face with microscopic asperities, distortion occurs in the continually extended wave front 106.

Since the light travels in the direction perpendicular to the wave front 106, the travelling direction of the light is deflected so as to correspond to the distortion of the wave front 106. This results in a decrease in the amount of light travelling straight. The open arrows in FIG. 59(*a*) show the travelling directions of the emitted light. As a result of interference of the light due to the influences from the transparent flat plate 104 having one face with random microscopic asperities, 1) as shown on the right of FIG. 59(*a*), the intensity of light travelling in the direction of the open arrows increases, and 2) the amount of light travelling straight decreases.

FIG. 59(b) shows non-coherent light with reduced partial coherency, which can be obtained due to the technical feature of the present embodiment. Similarly to FIG. 59(a), light immediately after emitted from a light-emitting source 70 (e.g., a tungsten filament 50) travels straight while having a relatively flat and continually extended wave front 106.

Similarly to FIG. 8A and FIG. 8B, this light passes through the optical characteristics changing member 101 to generate a plurality of optical paths and the light combining (mixing) part 102. Then, the continually extended wave front 106 is divided into small parts. The wavelength of the light, however, does not change after passing through the optical characteristics changing member 101 to generate a plurality of optical paths and the light combining (mixing) part 102. Therefore the interval between equiphase wave surfaces (wave front interval) along the travelling direction of the light can be kept unchanged.

Since the wave front 106 of the light is divided into small parts, no distortion specific to the continually extended wave front 106 occurs after passing through a transparent flat plate 104 having one face with microscopic asperities. Therefore no inclination occurs for each of the divided small parts of the wave front 106, and so the light does not interfere and travels straight.

A method to divide the continually extended wave front 106 into small parts has the important technical novelty and inventiveness of the present embodiment. This is because the dividing a part of the continually extended wave front 106 simply spatially does not decrease partial coherency of the light.

That is, as described in Section 2.5 to introduce (B•22), light is combined based on the separated wave front at a backward position that is a short distance away from the position of separating a part of the wave front 106 spatially. The combined light takes over the original partial coherent property of the light.

Figure 60:
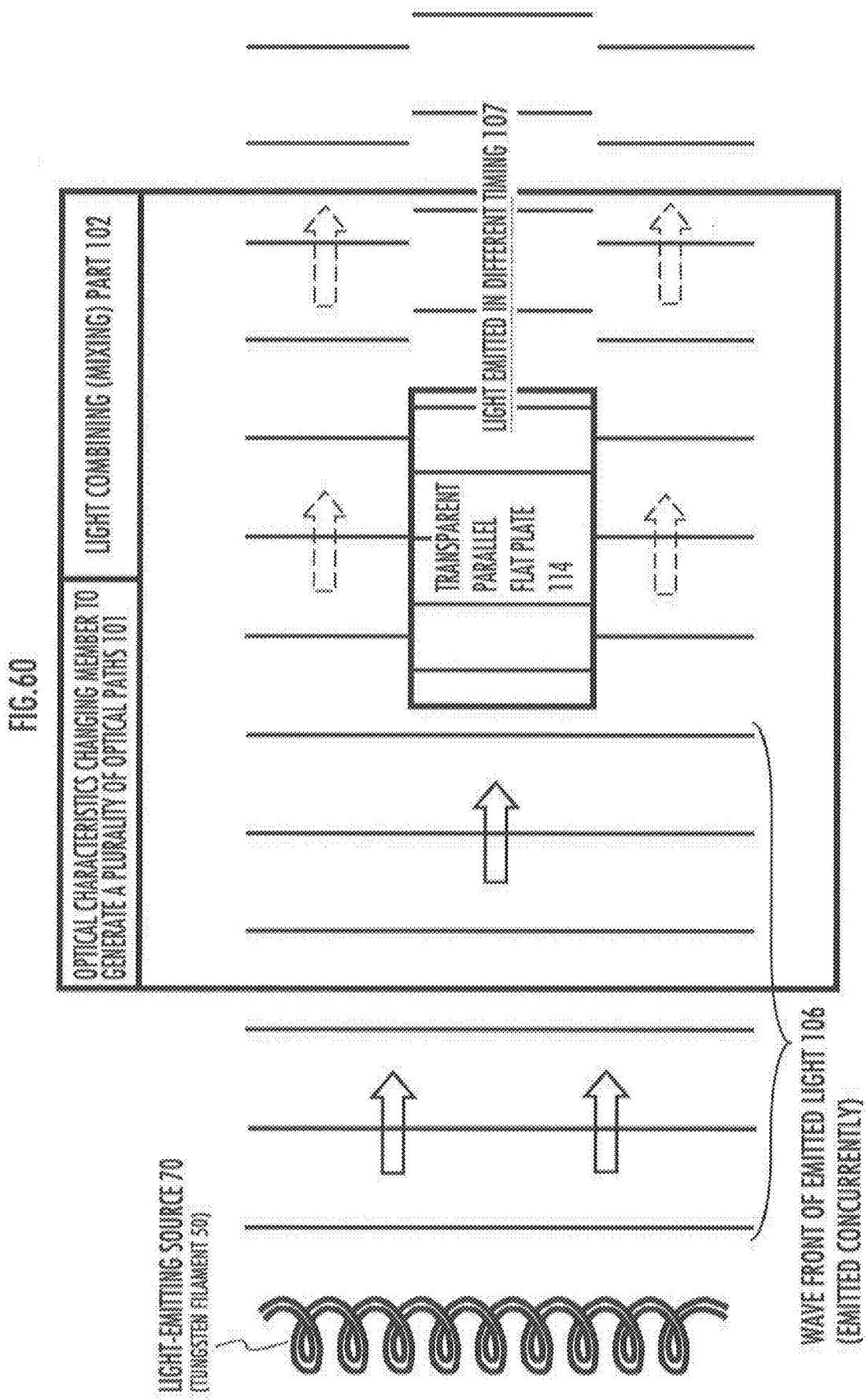
FIG. 60 simply explains a method for controlling partial coherency of light in the present embodiment.

Referring to FIG. 60, the following simply describes a method to control partial coherency of light in the present embodiment. Light immediately after emitted from a light-emitting source 70 (e.g., a tungsten filament 50) travels straight while having a relatively flat and continually extended wave front 106. Such a continually extended wave front 106 is the assembly of the beams of light that are emitted from the light-emitting source 70 at the same time.

FIG. 60 shows an image for easy understanding about the internal functions of the optical characteristics changing member 101 to generate a plurality of optical paths and the light combining (mixing) part 102. FIG. 60 just shows an image for easy understanding. The specific technical descriptions are given already at the parts before Section 3.11.

A transparent parallel flat plate 114 is placed at a part of the optical path through which the continually extended wave front 106 passes. Let that n denotes the refractive index in the transparent parallel flat plate 114, the velocity of the light passing through the plate decreases by 1/n. As a result, light 107 that is emitted in different timing from the surroundings passes through the transparent parallel flat plate 114. After that, this light 107 that is emitted in different timing is mixed with the remaining part of the continually extended wave front 106.

The correspondence between the image in FIG. 60 and the state of FIG. 8A or 8B is as follows. A transparent parallel flat plate 114 placed at a part of the optical path causes a difference in the optical paths 201 to 208 among the beams of light passing through inside and outside of the transparent parallel flat plate 114. Since these beams of the light passing through the transparent parallel flat plate 114 keep their travelling direction, mixed light 78 is generated behind the transparent parallel flat plate 114.

Considering the correspondence with FIG. 10, a change in optical length 76 occurs between the beams of light passing through the transparent parallel flat plate 114 (a part 74 of the light) and the beams of light passing through the outside (a part 72 of the light).

FIG. 60 shows the image by way of an example of the wave front dividing method to divide a part of the continually extended wave front 106. The method is not limited to wave front dividing, and different optical paths 201 to 208 or a change in optical length 76 may be generated by any method.

To divide the continually extended wave front 106 into small parts, a difference in emitting time between the time to emit the light from the light-emitting source 70 at the same time and the time 107 to emit the light that is emitted in different timing is an important factor. In other words, when the time difference Δt between them satisfies the condition different from (B•2) (Section 2.2), such dividing can be successively performed. Conditional expression ((B•6) or (B•12)) is given about the coherence length, which is associated with (B•2).

According to (B•2), a shorter frequency width Δν means extremely long Δt. For instance, the amount of irradiated light 12 is decreased extremely and one photon is applied to the target 10 sequentially. This is an experimental method called photon counting. Although each photon is emitted in different time, an interference pattern will be observed in the pattern obtained by integrating the arrival positions of all of the photons.

Each photon used in this experiment has a very narrow energy width (frequency width Δν), the shifting Δt between times to emit these photons one by one satisfies (B•2). Therefore this case does not correspond to the "dividing of the wave front 106".

OCT (Optical Computerized Tomography) is known as a technique to observe a three-dimensional pattern inside of a body. This technique is dividing the optical path of coherent light into halves by amplitude and applying only one of the divided optical path to the target 10. The remaining part of the light is used for reference light. The detection light 16 obtained from the target 10 and the reference light interfere with each other inside of the detection unit 6. Using non-coherency property when the optical-length difference between the detection light 16 from the target 10 and the reference light exceeds the coherence length, a noise component from a position other than the measurement target is removed from the signal.

A difference between such OCT technique and the present embodiment and the advantageous effects of the present embodiment are as follows.

A) in OCT, coherent light is applied to the inside of the target 10.

As described later in Section 5.1 referring to FIG. 26(b), backscattered light 390 as coherent light and multi-scattered light 380 interfere inside of the target 10. A detected image has a lot of optical noise due to the influences from this interference. On the contrary, mixed light 78 with low partial coherency is applied to the target 10 in the present embodiment. As a result, accurate detection signals can be obtained as described later in Chapter 5 referring to FIGS. 61 and 63.

B) in OCT, the detection light 16 and the reference light having optical-length difference are combined at the detection unit 6.

Figure 61:
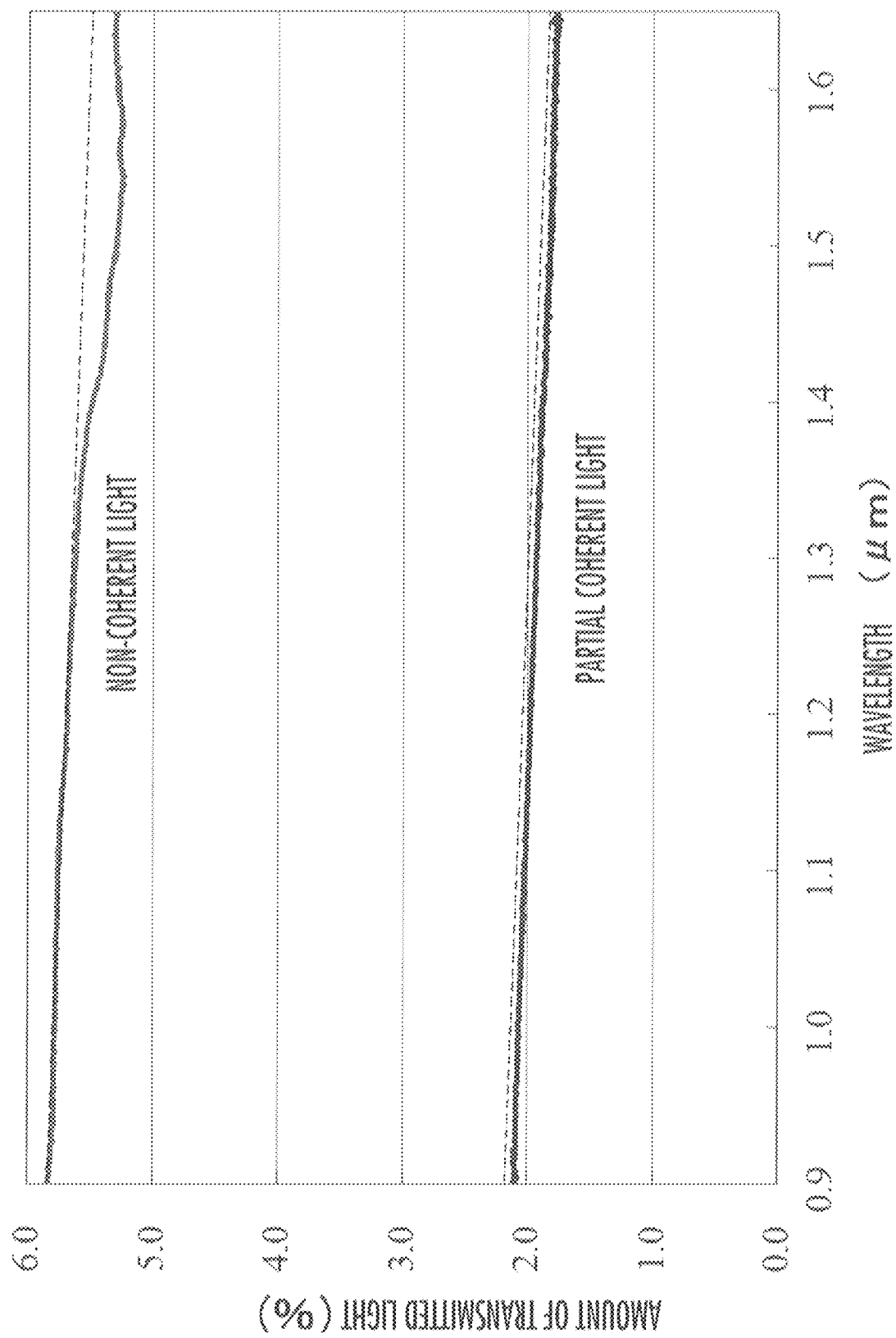
FIG. 61 shows a comparison of measurement result of characteristics of light passing through a silk sheet due to a difference in partial coherency of measured light.

As described later in Chapter 5 referring to FIG. 26(a) and FIG. 61, straight-travelling light 360 as coherent light and multi-scattered light 370 generated inside of the target 10 interfere. This makes the penetration length of coherent light penetrating into the target 10 shorter. On the contrary, mixed light 78 with low partial coherency is applied to the target 10 in the present embodiment. Therefore as shown in FIG. 61, the penetration length increases.

C) No compensation is performed for asperities on the surface of the target 10 in OCT.

Additionally, reference light in this technique has a flat wave front. Therefore a detected image is shifted in the depth direction, which corresponds to the asperities on the surface of the target 10. On the contrary, as described later in Chapter 6, the present embodiment has a function of compensating the asperities on the surface of the target 10 and a change in refractive index. This enables accurate depth-direction setting inside of the target 10.

Chapter 4 Method for Mixing/Separating Coherent Light and Partial Incoherent Light Chapter 3 describes a method of decreasing partial coherency and increasing partial incoherency of the irradiated light 12 or the detection light 16 used for detection and measurement of characteristics of the target 10. Meanwhile the measurement of OCT (optical computerized tomography) requires coherent light. Also for the measurement of wave front aberration described later in Chapter 6, the detection accuracy can be increased by coherent light. Chapter 4 describes a measurement apparatus based on both of coherent light and partial incoherent light.

Figure 25:
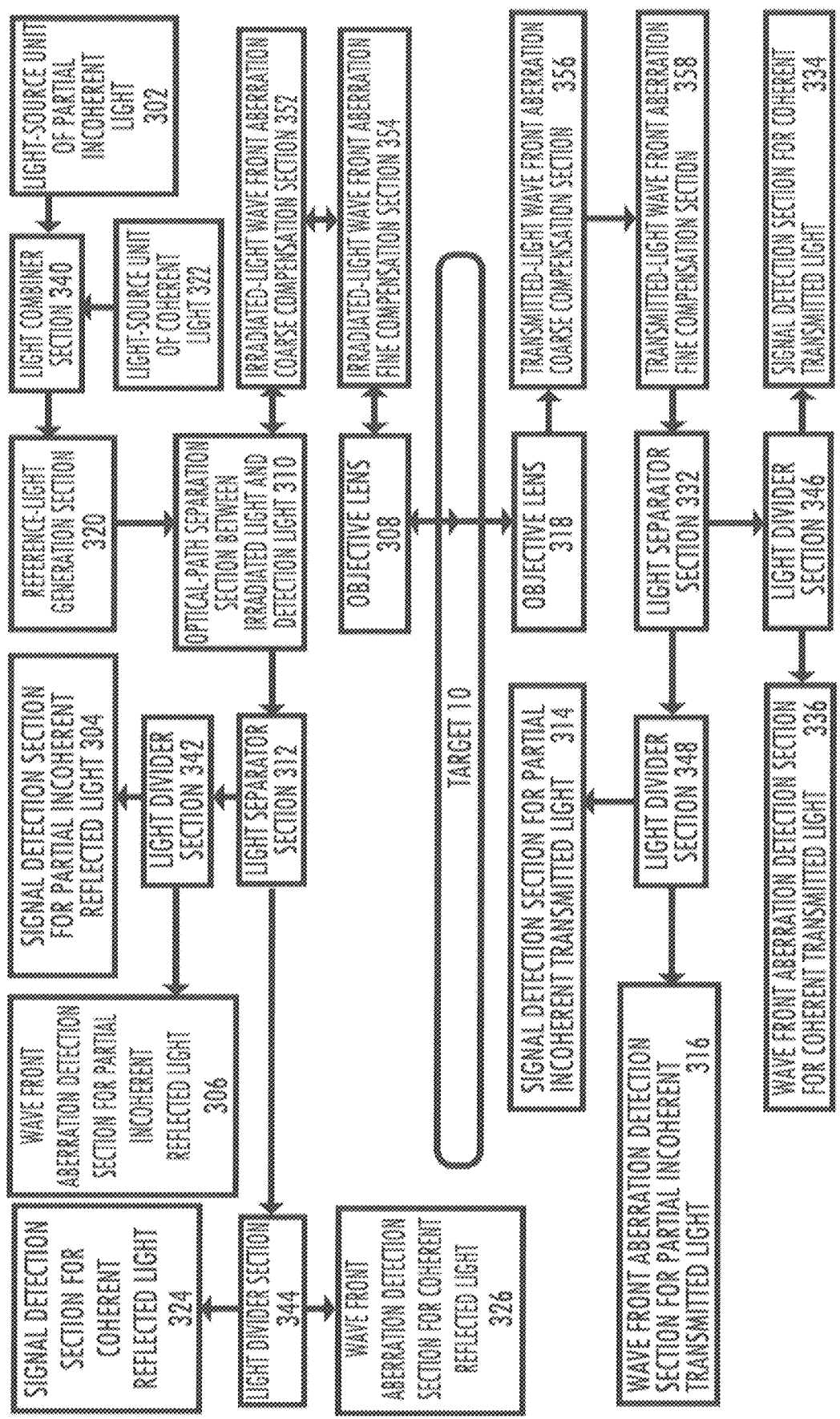
FIG. 25 describes a measurement apparatus based on both of coherent light and partial incoherent light.

Section 4.1 Exemplary Structure in Measurement Apparatus Based on Both of Coherent Light and Partial Incoherent Light FIG. 25 shows an exemplary structure of a measurement apparatus of the embodiment including both of a light-source unit 322 for coherent light, such as laser light source, and a light-source unit 302 for partial incoherent light. The arrows in FIG. 25 indicate the optical paths of light and the travelling directions.

The optical arrangement above the object 10 is similar to the optical arrangement of FIG. 1C(c). The light-source unit 2 in FIG. 1C(c) corresponds to the region made up of the light-source unit 302 for partial incoherent light, the light-source unit 322 for coherent light and the light combiner section 340 on the uppermost right part of FIG. 25. The light-source unit 302 for partial incoherent light has a specific configuration corresponding to the configuration in the light-source unit 2 described in Chapter 1 and Chapter 3. Beams of the light emitted from the light-source unit 302 for partial incoherent light and from the light-source unit 322 for coherent light are mixed at the light combiner section 340. A specific method for mixing is described later in Section 4.2.

Coherent light and partial incoherent light are mixed at the light combiner section 340, and reference light therefor is extracted in a reference-light generation section 320. This reference light includes a part for coherent light and a part for partial incoherent light. They are separately used for the detection of wave front aberration at a wave front aberration detection section 306 for reflected light having partial incoherency, at a wave front aberration detection section 316 for transmitted light having partial incoherency, at a wave front aberration detection section 326 for reflected light having coherency and at a wave front aberration detection section 336 for transmitted light having coherency. The remaining part of the light as a non-reference light at the reference-light generation section 320 is sent to an optical-path separation section between irradiated light and detection light 310.

The entire optical path on the upper left of the target 10 that is the light separation section 312 or later corresponds to the detection unit 6 in FIG. 1C(c). The entire optical system below the target 10 in FIG. 25 corresponds to the detection unit 4 in FIG. 1C(a).

The optical-path separation section between irradiated light and detection light 310 separates the optical path between the irradiated light 12 and the detection light 16 obtained by reflection from the target 10. In one example for the method for separating the optical path, a beam splitter 20 in FIG. 1C(c) may be used. The part below the target 10 corresponds to the detection unit 4 in FIG. 1C(a).

In FIG. 25, the irradiated light 12 may be collected into the target 10 by the objective lens 308, and the light passed through this collecting point may be collected by the objective lens 318. Therefore as in FIG. 1C(a) or (c), the following considers the case where the irradiated light 12 is collected at point α (α region) or point γ (γ region) in the target 10. As described later in Section 6.1, wave front aberration occurs during the course of the irradiated light 12 passing through the optical path toward point α (α region) or point γ (γ region) in the target 10. As a result, the detection light 16 is not collected at point α (region α) or point γ (region γ) and the collecting point becomes blurred. The amount of wave front aberration before reaching such point α (α region) or point γ (γ region) is expected in advance, and the inverse wave front aberration is added to the irradiated light 12 before entering the target 10. Thereby, wave front aberration generated inside of the target 10 can be cancelled, and the irradiated light 12 can be collected at point α (α region) or point γ (γ region) in the target 10.

To the wave front aberration generated in the detection light 16 leaving region α in the target 10 and going out of the target 10 also, the inverse wave front aberration is added to the detection light 16 at some part along the optical path of the detection unit 6. Thereby a favorable imaging pattern can be obtained on the detector plane of the photodetector 80 (FIG. 8B).

Such processing to give the wave front aberration to be corrected to the irradiated light 12 inside of the light-source unit 2 and to correct the wave front aberration in the detection light 16 obtained from the target 10 is called compensation of wave front aberration.

In the example of the embodiment of FIG. 25, wave front aberration is measured for the reflected light and the transmitted light of the target 10 separately, and the wave front aberration is compensated for each of the irradiated light 12 and the detection light 16. To increase the accuracy of compensation of wave front aberration, the compensation is performed by dividing the processing into two stages of course and fine. Herein, coarse compensation of wave front aberration is performed at an irradiated-light wave front aberration coarse compensation section 352 and a transmitted-light wave front aberration coarse compensation section 358. Fine compensation of wave front aberration is performed at an irradiated-light wave front aberration fine compensation section 354 and a transmitted-light wave front aberration fine compensation section 356.

That is, the irradiated light is roughly compensated for wave front aberration by the irradiated-light wave front aberration coarse compensation section 352. Then fine wave front compensation is performed for the remaining amount of wave front aberration by the irradiated-light wave front aberration fine compensation section 354.

For the detection light 16 obtained after passing through the target 10, the detection light is roughly compensated for wave front aberration by the detection-light wave front aberration coarse compensation section 356. Then fine wave front compensation is performed for the remaining amount of wave front aberration by the detection-light wave front aberration fine compensation section 358.

Wave front aberration of the transmitted light from the target 10 (optical path below the target 10) is compensated independently. To this end, the transmitted-light wave front aberration coarse compensation section 358 and the transmitted-light wave front aberration fine compensation section 356 are disposed in this order for the detection light 16 after passing through the objective lens 318.

For the reflected light from the target 10 (optical path above the target 10), the optical path is common between the irradiated light 12 and the detection light 16.

Therefore the wave front aberration generated in the irradiated light 12 when the irradiated light passes through the target 10 and the wave front aberration generated in the detection light 16 when the detection light is reflected from point γ (region γ) in the target 10 and returns are the same.

Therefore compensation of wave front aberration for the light-source unit 2 and for the detection unit 4, 6 can be common in the optical path above the target 10 based on the reflected light. In the example of the embodiment of FIG. 25, the irradiated-light wave front aberration coarse compensation section 352 and the irradiated-light wave front aberration fine compensation section 354 are disposed in this order between the optical-path separation section between irradiated light and detection light 310 and the objective lens 308.

To implement the compensation of wave front aberration as stated above, the wave front aberration actually generated in the target 10 has to be detected. These wave front aberration detection sections 306, 316, 326 and 336 detect/measure such wave front aberration.

These detection sections compare the characteristics of light between the light in an ideal state before the wave front aberration occurs and the light containing the wave front aberration, and detect a difference as the wave front aberration. That is, the detection sections generate, from the mixed light obtained at the light combiner section 340, the characteristics of the wave front in an ideal state before the wave front aberration occurs in the reference-light generation section 320. Then these wave front aberration detection sections 306, 316, 326 and 336 compare the detection light containing wave front aberration as input and the reference light obtained at the reference-light generation section 320 and set a difference therebetween as the wave front aberration to be detected.

Particularly in the example of the present embodiment, the compensation of wave front aberration is performed at the coarse compensation sections 352, 356 as stated above based on the wave front aberration obtained from partial incoherent light. Then the compensation of wave front aberration is performed at the fine compensation sections 354, 358 as stated above based on the wave front aberration obtained from coherent light.

That is, the result of detection/measurement of the partial-incoherent reflected light by the wave front aberration detection section 306 is fed back to the irradiated-light wave front aberration coarse compensation section 352. Further, the result of detection/measurement of the partial-incoherent transmitted light by the wave front aberration detection section 316 is fed back to the transmitted-light wave front aberration coarse compensation section 356.

In parallel to this, the result of detection/measurement of the coherent reflected light by the wave front aberration detection section 326 is fed back to the irradiated-light wave front aberration fine compensation section 354. Then, the result of detection/measurement of the coherent transmitted light by the wave front aberration detection section 326 is fed back to the transmitted-light wave front aberration fine compensation section 358.

As described in Chapter 6, when wave front aberration is detected using partial-incoherent light, the detection accuracy is low but the detection range (dynamic range) is very wide. On the contrary, when wave front aberration is detected using coherent light, the detection accuracy is high but the detection range (dynamic range) is very narrow. The example of the measurement apparatus of FIG. 25 are based on both of the light so as to have the advantageous effects of them effectively.

Coherent light and partial incoherent light mixed at the light combiner section 340 as stated above are mutually separated at light separator sections 312, 332. The light separated here is then divided by their corresponding light divider sections 342, 344, 346, and 368.

The divided parts of light are used separately for signal detection and detection of wave front aberration. That is, signal detection is performed by the signal detection section 304 for reflected light having partial incoherency, the signal detection section 314 for transmitted light having partial incoherency, the signal detection section 324 for reflected light having coherency, and the signal detection section 334 for transmitted light having coherency.

Then wave front aberration is detected by the wave front aberration detection section 306 for reflected light having partial incoherency, the wave front aberration detection section 316 for transmitted light having partial incoherency, the wave front aberration detection section 326 for reflected light having coherency and the wave front aberration detection section 336 for transmitted light having coherency.

Section 4.2 Method for Mixing and Separating Coherent Light and Partial Incoherent Light Section 4.2 describes a method of mixing and separating coherent light emitted from the light-source unit 322 for coherent light and partial incoherent light emitted from the light-source unit 302 for partial incoherent light in FIG. 25.

In the example of the present embodiment, at least any one of the following is used, and both of them may be used:

A] Using orthogonality of the vibration plane of (the electric field) (using a polarization beam splitter); and B] Using separation of the range of used wavelength (using an optical device having wavelength dependency for reflection/transmission).

Firstly, the method of A] using orthogonality of the vibration plane is described below. Although not illustrated, an analyzer (optical device having the property of transmitting/reflecting light having a specific vibration plane only) is disposed at each of the outlet of the light-source unit 322 for coherent light and at the outlet of the light-source unit 302 for partial incoherent light in FIG. 25. Then these analyzers are configured so that the vibration planes (of the electric field) are orthogonal between coherent light and partial coherent light.

In this case, a polarization beam splitter may be disposed in the light combiner section 340 to mix the coherent light and the partial incoherent light. Similarly a polarization beam splitter may be disposed in the light separator sections 312, 332 so as to separate the coherent light and the partial incoherent light based on the orthogonality of their vibration planes.

Next, the method of B] separating based on a difference in wavelength characteristics is described below. In this case, an optical device (bandpass filter) having the property of transmitting (or reflecting) light in a specific wavelength range only and of reflecting (or transmitting) light in other wavelengths is disposed in the light combiner section 340 and in the light separator sections 312, 332. Then the wavelength used is differentiated between coherent light and partial incoherent light to mix and separate them.

When detecting a change in absorption wavelength of an atomic group having a carbon atom or a nitrogen atom at the center described in Patent Literature 3, a change in absorption wavelength (a change in center wavelength of the absorption band) belonging to the stretching at a first overtone, a second overtone or a third overtone is desirably detected by partial incoherent light. In this case, coherent light having a wavelength other than in the above wavelength region may be used.

The wavelength range of near-infrared light described in Section 2.6 includes the absorption band belonging to the n-th overtone of the stretching as well as the absorption band belonging to a combination. For identification of belonging of these absorption bands, the absorption band belonging to the n-th overtone of the stretching can be identified relatively easily. On the contrary, a combination includes the combination of complicated factors. Therefore it is difficult to evaluate the belonging of a combination about such factors as well. Therefore the method of optical detection or the imaging method of the present embodiment mainly selects the wavelength of the absorption band belonging to the n-th overtone of the stretching as the detection/measurement target.

In this case, the lower limit wavelength of the absorption band corresponding to the first overtone is 1440 nm, and the upper limit wavelength and the lower limit wavelength corresponding to the second overtone is 1210 nm and 970 nm, respectively. The upper limit wavelength corresponding to the third overtone is 920 nm. Therefore, the wavelength of coherent light is desirably in the range of 930 nm to 960 nm or in the range of 1260 nm to 1390 nm.

FIG. 23B shows the experimental evidence on these numerical values. Presumably the absorption band around the wavelength 1.213 μm belongs to the second overtone of the asymmetric stretching of a methylene group having a carbon atom at the center. In the case of an atomic group having a nitrogen atom at the center, its wavelength of the absorption band of the second overtone has a bit smaller value.

Presumably the absorption band in the wavelength range of 1.35 μm and 1.50 μm in FIG. 23B belongs to the combination of a methylene group. A part of the wavelength region of 1260 nm to 1390 nm in which coherent light can be used includes the absorption band belonging to such a combination. This means that the method of optical detection or the imaging method of the present embodiment can exclude a change in wavelength of the absorption band belonging to the combination from the target.

Chapter 5 Interaction with Light Inside of Measurement Target

The following describes interaction with light generated inside of a target 10 (FIG. 1A to FIG. 1C).

Section 5.1 Light Scattering and Light Absorption Generated Inside of Target and Influences from Multi-Scattering When a target 10 includes an inorganic compound or a high-molecular compound including a living body, light scattering and light absorption are generated inside of the target 10.

The following explains the cause of the light scattering and light absorption inside of the target 10 based on the quantum mechanics. When light (electromagnetic waves) passes through a part of local electric dipole moment inside of the target 10, the vibration mode of the electric dipole moment transits from the ground state to the excited state because the light is absorbed.

Following the principle of induced emission described in quantum mechanics, a part of the light in the exited state returns to the ground state. The light generated at this time turns scattered light. Meanwhile when the energy in the exited state is converted into the internal lattice vibration (atomic vibration), this turns light absorption.

When light is scattered in the direction toward the incident direction, this is called forward scattering. When the light is scattered in the direction opposed to the incident direction, this is called back scattering. When the light is scattered laterally, this is called side scattering. When light is scattered inside of the target 10 a plurality of times, this is called multi-scattered light.

Figure 26:
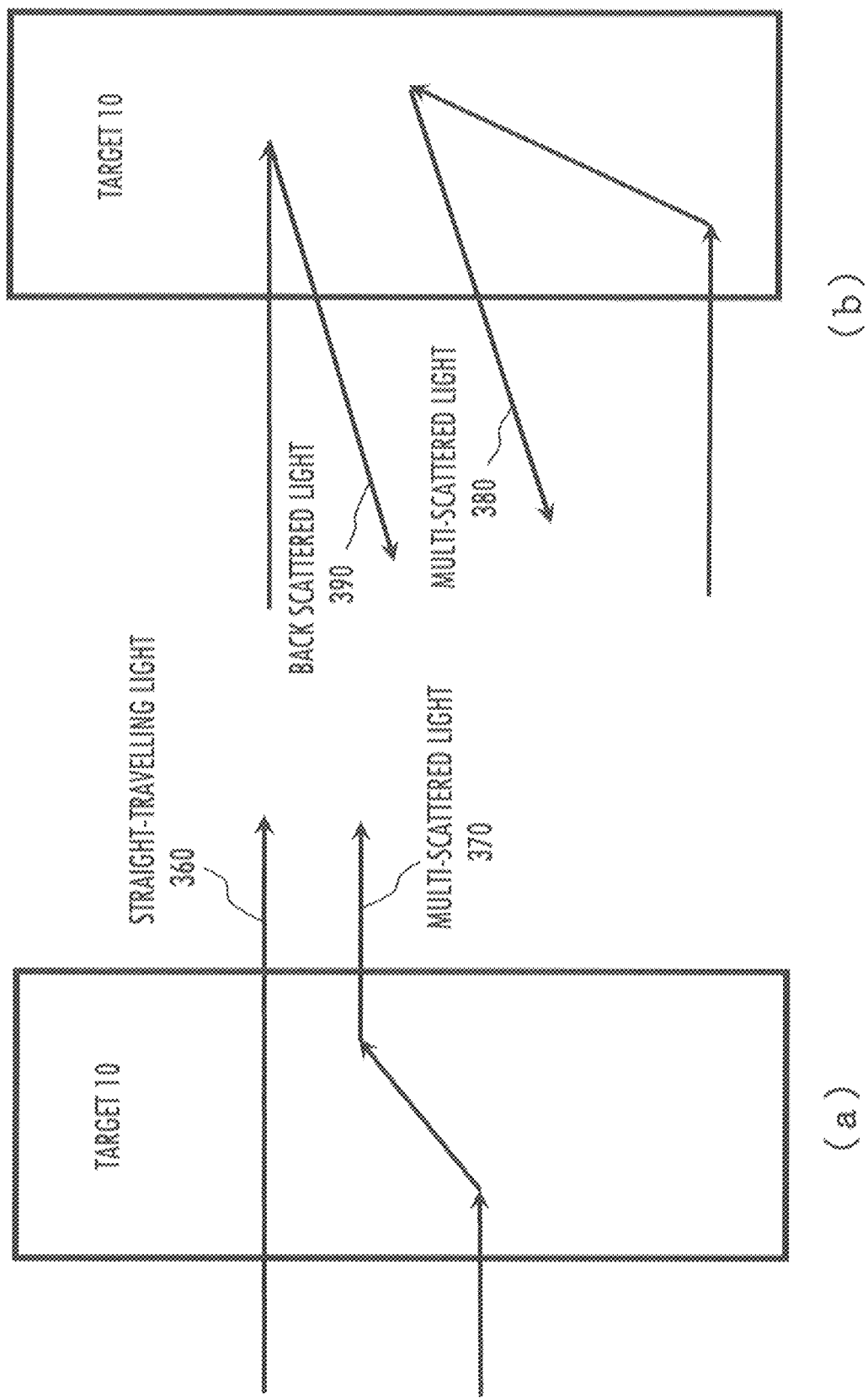
FIG. 26 describes influences from multi-scattered light inside of a target.

Such multi-scattered light generated inside of the target 10 adversely affects the signal-detection characteristics (including spectroscopic characteristics) and imaging characteristics. Referring to FIG. 26(*a*), this situation is described below. The following description considers the case of using partial coherent light as the irradiated light 12.

The transmitted light of the target 10 shown in FIG. 26(*a*) includes straight-travelling light 360. The transmitted light also includes multi-scattered light 370 subjected to scattering in the target 10 a plurality of times. Among such multi-scattered light 370, beams travelling in the same direction as the straight-travelling light 360 interfere with the straight-travelling light 360. As a result of such interference, the total amount of the light travelling straight may decrease.

Presumably FIG. 23B represents this phenomenon. In this drawing, #1200 has the highest partial coherency (low in partial incoherency), and #400 has the lowest partial coherency (high in partial incoherency). In a comparison of the absorbance of the baseline represented with the wavelength range from 1.25 μm to 1.35 μm, #1200 has the highest absorbance (the total amount of the transmitted light travelling straight is small). Presumably the factor of such a decrease in the total amount of transmitted light travelling straight may include the influences from partial coherent multi-scattered light.

FIG. 26(*b*) shows the situation where such influences from multi-scattered light are present also in the reflecting direction. There is back scattered light 390 subjected to back scattering once in the target 10 and returning to the reflecting direction. There is also multi-scattered light 389 subjected to scattering a plurality of times in the target 10 and returning to the reflecting direction. When this multi-scattered light 389 returns in the same direction as that of the back scattered light 390, interference occurs between them. Therefore in order to increase the accuracy of signal detection (including spectroscopic characteristics) and the accuracy of imaging using the back scattered light 390, partial incoherent light of the example of the present embodiment is desirably used.

Section 5.2 Relationship Between Factors of Scattering/Absorption and Scattering Cross-Section Section 5.1 describes light absorption and light scattering that are generated at a local part of electric dipole moment. Specific modes of the electric dipole moment having sensitivity to near-infrared light described in Section 2.7 mainly include the following two types:

1] electron orbit in a high-molecular compound (biased distribution of electron cloud); and 2] atomic group including hydrogen atoms (group vibration of atoms making up the function group).

A living organism or an organic chemical material internally includes a lot of high-molecular compounds. Such a high-molecular compound internally includes a skeleton formed with various types of the arrangement of nuclei. This skeleton is surrounded with an electron cloud (electronic orbital) 404 of FIG. 27 so as to bond these nuclei.

When irradiated light 12 enters the target 10, the distribution of this electron cloud is biased because it is induced by the electric field. Such biased distribution of the electron cloud corresponds to the electric dipole moment. As shown in FIG. 27, since the molecular size of a high-molecular compound 402 is relatively huge, the scattering cross-section thereof also is relatively large.

In such a distribution of the electron cloud around each nucleus making up the atomic group, the actual charge for each atom has a positive/negative value. Then when the irradiated light 12 passes through this atomic group 406, vibration occurs among the atoms (group vibration) depending on the polarity that is positive or negative of the actual charge for each atom. In this way, a difference in the actual charge for each atom making up this atomic group 406 makes up the electric dipole moment.

This atomic group 406 includes a center nucleus and 1 to 3 hydrogen nuclei around the center nucleus only, and so the size of the atomic group 406 itself is much smaller than the high-molecular compound 402. This means the atomic group 406 has a scattering cross-section that is much smaller than that of the high-molecular compound 402.

Section 5.3 Features of Scattering Cross-Section and Light Scattering

According to the textbook of Emil Wolf et al. (Max Born and Emil Wolf: Principles of Optics (1975, PERGAMON PRESS LTD) Chapter 13)), a light-scattering object having a small scattering cross-section like the atomic group 406 often generates Rayleigh scattering.

According to this textbook, a high-molecular compound 402 having a large scattering cross-section generates Mie scattering of a different type. In the light scattering of this type, Rayleigh scattered light is generated at various points of one high-molecular compound 402, and interfere occurs between such scattered light.

In other words, since the two types of electric dipole moment (light-scattering object) having sensitivity to near infrared light described in Section 2.7 have different scattering cross-sections, their light scattering states are different from each other.

Referring to FIG. 23B showing experimental data on the absorbance, a relationship with the two types of light-scattering objects (electric dipole moments) is considered as follows. As described above in Section 4.2, the absorption band around the wavelength 1.213 µm can belong to the second overtone of the asymmetric stretching of a methylene group having a carbon atom at the center.

Since a methylene group belonging to the atomic group 406 has a very small scattering cross-section, beams of the scattered light from the methylene group hardly interfere. Therefore a difference value of the absorbance from the baseline at the absorption band around the wavelength 1.213 µm in FIG. 23B (or FIG. 23A) will be substantially constant irrespective of the partial coherency of the irradiated light 12.

It is expected that the absorbance of the baseline represented with the wavelength range from 1.25 µm to 1.35 µm is greatly influenced from scattered light from the high-molecular compound 402 (FIG. 27). The characteristics of Mie scattering are similar to the characteristics of the beams of Rayleigh scattered light at various points in the high-molecular compound 402 that mutually interfere, and so the absorbance of the baseline may vary due to a difference in partial coherency of the irradiated light 12.

Section 5.4 Detection Characteristics Using Back Scattered Light (Reflected Light)

According to the description in the textbook as stated above, forward scattered light and back scattered light have a substantially same intensity in Rayleigh scattering. On the contrary, in Mie scattering, the intensity of back scattered light is order-of-magnitude smaller than that of the forward scattered light (in some cases, their orders decrease ¹⁄₁₀₀ to ¹⁄₁₀₀₀).

FIG. 27 schematically shows this difference. That is, the intensity of back scattered light obtained from the high-molecular compound 402 is very small. On the contrary, the intensity of back scattered light relative to the intensity of the total scattered light scattered from the atomic group 406 (although the scattering cross-section thereof is small) is large.

As described in Chapter 3, while decreasing partial coherency (increasing partial incoherency) of the irradiated light 12, optical detection (including spectroscopic characteristics) and imaging may be performed using the reflected light (back scattered light) as shown in (b) and (c) of FIGS. 1A to 1C. Thereby, the influences from the scattered light from the high-molecular compound 402 can be decreased, and a signal of the atomic group 406 or an image thereof can be detected/measured effectively.

Especially when the internal structure or state of the target 10 or a change thereof is to be measured using the reflected light (back scattered light) from the target 10, the penetration depth of the irradiated light 12 that can enter into the target 10 deeply is important.

When the Lanbert-Beer Law holds, the intensity of irradiated light 12 entering into the target 10 decreases exponentially as a function of the penetration depth. The reduction factor in this case is proportional to the absorbance in FIG. 23B. In FIG. 23B, when the phase conversion element of #400 is used (partial incoherency increases), the absorbance decreases to about ⁶⁄₇ from the case of #1200 (the partial coherency is relatively high).

Therefore the experimental data of FIG. 23B means that a decrease in partial coherency (increase in partial incoherency) of the irradiated light 12 leads to an increase in the penetration distance that the light can enter into the target 10 internally.

Note here that as shown in FIG. 22, when the back mirror 82 is used and the transparent parallel flat plates 94-1 to 4 are disposed at some part along the optical path as well as #1200, the partial coherency thereof can be decreased. Therefore as compared with the conventional technique without decreasing the partial coherency at all, this structure can have the absorbance that is much smaller than ⁶⁄₇.

Such a difference in the penetration depth of the irradiated light 12 into the target 10 can be explained as the influences of interference from multi-scattered light 370 on the straight-travelling light 360 shown in FIG. 26(a). That is, it can be expected that the relationship between the penetration intensity of the straight-travelling light 360 during the passage through the target (polyethylene sheet in the experimental data of FIG. 23B) 10 shown in FIG. 26(a) and the penetration depth have characteristics close to #400 in FIG. 23B. However, the beam 370 that travels straight after multi-scattering in the target 10 may interfere with the straight-travelling light 360. As a result, the absorbance is larger than that in the case of #1200, and so the penetration distance into the target 10 decreases presumably.

A cell membrane (lipid bilayer), an internal membrane or fat in a living body has a molecular structure that is similar to that of polyethylene as stated above. Therefore such a part has the characteristics of absorbance that are similar to FIG. 23B. Therefore considering this phenomenon as well, light having reduced partial coherency (increased partial incoherency) can have the advantageous effect of entering into a deeper region in the living body, i.e., the structure in a deeper area in the living body, the active state or a change thereof can be observed.

That is the description of the influences from the multi-scattered light 370 only inside of the target 10. In addition, the influences from wave front aberration mixed into the irradiated light 12 also have to be considered. Wave front aberration mixed into the irradiated light 12 includes the following two types:

1. wave front aberration generated inside of the target 10; and
2. wave front aberration generated at the interface (boundary plane between the air and the target 10) of the entrance of the target 10.

In any case, the phase of the light influenced from wave front aberration is shifted relative to the straight-travelling light 360 in the target 10 shown in FIG. 26(*a*).

As a result, interference occurs between the light, and so the penetration distance of the irradiated light 12 into the target 10 decreases.

They can be summarized as follows:

(1) when partial coherency is decreased (partial incoherency is increased) (example in Chapter 3); or (2) when wave front aberration due to the target 10 is improved (example in Chapter 6).

Then, the penetration distance of the irradiated light 12 into the target 10 can be increased, i.e., measurement can be performed in a deeper region.

In relation to this, the following describes the relationship between the penetration depth of the irradiated light 12 into the target 10 and the wavelength used. The Lambert-Beer law as stated above indicates the relationship between the penetration depth of the irradiated light 12 travelling straight in the target 10 and the intensity of the irradiated light 12 in the straight-travelling state. The factors to attenuate the intensity of straight-travelling light may include light absorption and light scattering inside of the target 10. Herein light reflection is considered as a part of light scattering (back scattered light). That is, when light scattering occurs often inside of the target 10, then the straight-travelling light attenuates greatly (the penetration depth is shortened).

As described in Section 5.3 referring to FIG. 27, the mode of the light scattering from a visible range to a near-infrared range can be divided into two types, including scattering having relatively small scattering cross-section (Rayleigh scattering) and scattering having relatively large scattering cross-section (Mie scattering, for example).

In any case, the possibility of light scattering (substantial scattering cross-section) rises sharply with a decrease in the wavelength used. Specifically the intensity of light scattering (possibility of scattering/scattering cross-section) in Rayleigh scattering is inversely proportional to the fourth power of the wavelength. Mie scattering also has a similar tendency.

The interior of every living body including animals, plants and microorganisms has a complicated structure, and so light scattering is generated in the individual structures. Therefore when the interior of a living body is irradiated with light from a visible range to a near-infrared range, the penetration depth of the light decreases sharply with a decrease in the wavelength used.

Conversely when near-infrared light having long wavelength is used, the possibility of light scattering (scattering cross-section) inside of the living body decreases greatly. As a result, near-infrared light as the irradiated light 12 can enter a deeper area inside of the living body. Therefore near-infrared light is suitable for analysis of the structure in a relatively deep area inside of the living body, analysis of compositions there, the active state or a change in the state.

Then the method of using light in a wavelength range (near-infrared light) as the irradiated light 12 described in Section 2.6 and the method of reducing partial coherency (increasing partial incoherency) described in Chapter 3 are combined, whereby the effect of increasing the penetration distance of the irradiated light 12 more inside of the living body can be obtained.

Alternatively the method of using light in a wavelength range (near-infrared light) as the irradiated light 12 described in Section 2.6 and the method of improving wave front aberration generated in the target 10 described in Chapter 6 may be combined, whereby the effect of increasing the penetration distance of the irradiated light 12 more inside of the living body can be obtained.

Alternatively all of the method of using light in a wavelength range described in Section 2.6, the method of reducing partial coherency (increasing partial incoherency) described in Chapter 3, and the method of improving wave front aberration described in Chapter 6 may be combined.

Section 5.5 Formulation on Interaction with Electromagnetic Waves Inside of Measurement Target Section 5.1 to Section 5.4 explains interaction with visible light or near-infrared light inside of the target 10 qualitatively. For further considerations of such interaction, Section 5.5 formulates this interaction. The following relational expressions are applicable not only to visible light or near-infrared light but also to general electromagnetic waves in the wide range from ultraviolet light to LF (low frequency) waves of 30 kHz.

Maxwell equation partially includes the following.

[Math. 58]

$$\nabla \times H = J + \varepsilon \frac{\partial E}{\partial t} \qquad (B \cdot 52)$$

The above (B•52) represents the electromagnetic field generated close to the flow of current J. Such induced current Ja that is generated by absorbing external electromagnetic waves is rewritten as follows.

[Math. 59]

$$\nabla \times H = -Ja + \varepsilon \frac{\partial E}{\partial t} \qquad (B \cdot 53)$$

$$\nabla \times H = -Ja + \varepsilon \frac{\partial E}{\partial t} \qquad (B \cdot 53)$$

ε denotes the permittivity in the dielectric body.

Maxwell equation can be represented also in other forms as follows, which show the state without charge.

[Math. 60]

$$\nabla \times E + \mu_0 \frac{\partial H}{\partial t} = 0 \quad (B \cdot 54)$$

[Math. 61]

$$\nabla \cdot E = 0 \quad (B \cdot 55)$$

Based on these relationships from (B•53) to (B•55), the following relational expression can be derived.

[Math. 62]

$$0 = \nabla \cdot (\nabla \cdot E) = \nabla^2 E + \nabla \times (\nabla \times E) \quad (B \cdot 56)$$
$$= \nabla^2 E + \mu_0 \frac{\partial Ja}{\partial t} - \mu_0 \varepsilon \frac{\partial^2 E}{\partial t^2}$$

Pε(r,t,ω) denotes local electric dipole moment or dielectric polarization in the dielectric body. ω denotes the angular frequency of the electromagnetic waves. For the permittivity co in the vacuum, the following relationship holds.

$$\varepsilon E = \varepsilon_0 E + P\varepsilon(r,t,\omega) \quad (B \cdot 57)$$

As shown in Section 5.1 and Section 5.2, electromagnetic waves are absorbed due to the vibration of local electric dipole moment Pσ(r,t,ω). Then, this local electric dipole moment Pσ(r,t,ω) and the induced-current Ja have the following relationship.

[Math. 63]

$$Ja = \frac{\partial P\sigma}{\partial t} \quad (B \cdot 58)$$

Based on (B•57) and (B•58), the following relational expression can be derived from (B•56).

[Math. 64]

$$\nabla^2 E - \mu_0 \varepsilon_0 \frac{\partial^2 E}{\partial t^2} = \mu_0 \frac{\partial^2}{\partial t^2} \{P\varepsilon(r, t, \omega) - P\sigma(r, t, \omega)\} \quad (B \cdot 59)$$

The left side of (B•59) represents wave characteristics of electromagnetic waves in the vacuum (i.e., the outside of the target 10). That is, the behavior of the irradiated light (first light) 12 and the detection light (second light) 16 shown in FIGS. 1A to 1C is given by (B•59). Then let that $P_\varepsilon = P_\sigma = 0$, (B•59) represents the equation about electromagnetic waves passing through the vacuum.

As described in Section 5.1 and Section 5.2, light absorption and light scattering inside of the target 10 are associated with vibration of the local electric dipole moment. Then, Pε on the right side of (B•59) relates to the generation of scattered light and Pσ relates to light absorption.

As described in FIG. 27 and Section 5.2, interaction with near-infrared light occurs due to the following two factors:
 1) electron orbit in a high-molecular compound (biased distribution of electron cloud); and
 2) atomic group including hydrogen atoms (group vibration of atoms making up the atomic group).

Therefore these two factors for the interaction relate to each of the above electric dipole moments Pε and Pσ.

Note here that (excitation) energy of group vibration in an atomic group is often diffused as interatomic vibration energy in the high-molecular compound rather than being emitted as scattered light. This means that group vibration in an atomic group contributes to Pσ more than to Pε (light absorption easily occurs). Therefore a part (a kind) of the electric dipole moment Pσ includes electric dipole moment $\mu_x$ in an atomic group shown in (C•7) (described later in Section 7.2).

Let that electromagnetic waves E(r,t) of the irradiated light (first light) 12 and the detection light (second light) 16 passing through the outside of the target 10 are represented as follows.

[Math. 65]

$$E = \sum_\omega E_\omega \exp\{i(kr - \omega t)\} \quad (B \cdot 60)$$

Then, variable separation is enabled for the electric dipole moments Pε and Pσ as follows.

[Math. 66]

$$P\varepsilon(r,t,\omega) = p_\varepsilon(r,\omega)\exp(-i\omega t) \quad (B \cdot 61)$$

[Math. 67]

$$P\sigma(r,t,\omega) = p_\sigma(r,\omega)\exp(-i\omega t) \quad (B \cdot 62)$$

Substitution of (B•61) and (B•62) into (B•59), the following relationship can be obtained,

[Math. 68]

$$\nabla^2 E - \mu_0 \varepsilon_0 \frac{\partial^2 E}{\partial t^2} = -\omega^2 \mu_0 \{p_\varepsilon(r, \omega) - p_\sigma(r, \omega)\}\exp(-i\omega t) \quad (B \cdot 63)$$

(B•63) shows that the intensity of scattered light and the amount of light absorption are proportional to the square of the angular frequency (frequency of vibrations) of the irradiated electromagnetic waves. When pε and pσ are uniformly distributed in a light-scattering object or a light-absorbing object, the intensity of scattered light and the amount of light absorption are proportional to the volume of the object (when no optical interference occurs). These characteristics correspond to Rayleigh scattering described in Section 5.3.

Then, it is known that the solution of the equation in the form of (B•63) is given as follows.

[Math. 69]

$$E(r_d, t) = \frac{\omega^2 \mu_0}{4\pi} \int_V \{p_\varepsilon(r_s, \omega) - p_\sigma(r_s, \omega)\} \frac{\exp i\{k(r_d - r_s) - \omega t\}}{|r_d - r_s|} dr_s \quad (B \cdot 64)$$

"$r_s$" in (B•64) denotes a local position vector of scattering source inside of the target 10. "$r_d$" denotes a position vector of detecting destination of the measurement point (detection unit 6 in FIGS. 1A to 1C) disposed at the outside of the target 10.

When the distribution of $\rho_\varepsilon$ and $\rho_\sigma$ is limited to a two-dimensional array, then (B•64) corresponds to the Fresnel-Kirchhoff formula, which is described in a general textbook for optics. Herein "$p_\varepsilon(r_s,t)-p_o(r_s,t)$" in (B•64) corresponds to the two-dimensional pupil function of the Fresnel-Kirchhoff formula. The "$p_\varepsilon(r_s,t)-p_o(r_s,t)$" in (B•64), however, has uniqueness because it has a three-dimensional distribution.

The remaining terms other than the pupil function in the integrand part in (B•64) represents spherical waves. The ride side of (B•64) represents the integral of the entire area inside of the target 10. Therefore (B•64) is affected by the interference between spherical waves. Therefore (B•64) represents interaction with electromagnetic waves having partial coherency (coherency) inside of the target 10.

The textbook by Emil Wolf et al. (Max Born and Emil Wolf: Principles of Optics (1975, PERGAMON PRESS LTD) Chapter 10) suggests how to formulate the interaction with electromagnetic waves with reduced partial coherency (or non-coherent) electromagnetic waves, which is a goal of the present embodiment. Referring to the description of this textbook, electromagnetic waves with reduced partial coherency (or non-coherency) are desirably formulated using the representation with "detected light intensity" and not the amplitude of electric field.

The integrated term in (B•64) represents the amplitude (electromagnetic field) of electromagnetic waves that are scattered/absorbed from a local area inside of the target 10. This means that combining of the amplitudes (electromagnetic field) of the electromagnetic waves leads to interference among the electromagnetic waves. On the contrary, for electromagnetic waves with reduced partial coherency (non-coherency), the intensity (amount of light) of electromagnetic waves that are scattered/absorbed from a local area inside of the target 10 is integrated (mixed). The intensity (amount of light) itself does not contain information on the phase. Therefore the result of integration does not have the interference effect, which is generated due to a different in phase.

Referring to (B•64), the above can be formulated as follows.

[Math. 70]

$$\left[ \langle r_d \rangle = \frac{\omega^4 \mu_0^2 \varepsilon_0}{16\pi^2} \int_V \frac{\{p_\varepsilon(r_s, \omega) - p_\sigma(r_s, \omega)\}^2}{(r_d - r_s)^2} dr_s \right] \quad (B \cdot 65)$$

Herein the energy $I(r_d,t)$ of electromagnetic waves conveyed in the vacuum can be represented as follows.

[Math. 71]

$$\left[ \langle r_d, t \rangle = \frac{\varepsilon_0 E^2 + \mu_0 H^2}{2} \right] \quad (B \cdot 66)$$

In (B•66), the following relationship holds.

[Math. 72]

$$\frac{\varepsilon_0 E^2}{2} = \frac{\mu_0 H^2}{2} \quad (B \cdot 67)$$

Considering (B•66) and (B•67), the coefficient in (B•65) is set.

Using (B•65), the detection intensity $I(r_d)$ obtained at the detection unit 6 (FIGS. 1A to 1C) can be theoretically expected from the intensity including local scattering and absorption inside of the target 10. Such a method of representing the light intensity matches well with (B•30) described in Section 3.5.

When a change in the intensity of the irradiated light 12 in the depth direction of the target 10 can be expected, the accuracy of theoretical calculation can be improved more. From the macroscopic perspective, the Lambert-Beer law may be approximately used, which formulates that a change in intensity of the irradiated light 12 in the depth direction of the target 10 decreases in an exponential manner.

In this way, the Lambert-Beer law and the theoretical calculation of (B•65) may be combined, by which the detected intensity I(rd) obtained at the detection unit 6 (FIGS. 1A to 1C) using electromagnetic waves with reduced coherency (or non-coherency) can be expected theoretically. As a result, the interior of the target 10 can be analyzed accurately about its local state or attributes.

Section 5.6 Effects on Measurement Result from Difference in Partial Coherency of Irradiated Light and the Considerations Referring to FIGS. 23A and 23B, Section 3.9 describes a difference in measurement result due to a difference in partial coherency of the irradiated light 12. Section 5.6 gives a further experimental result and the considerations on the result.

The experiment in Section 5.6 used the same system as in FIG. 22. Sand granules of #240 are used to prepare the sand treatment plate (average surface roughness Ra is 2.08 μm) of the phase conversion element (optical characteristics changing member) 212 so as to generate near-infrared light with substantially non-coherency.

In the experiment using conventional near-infrared light with partial coherency, the phase conversion element (optical characteristics changing member) 212 is not used. To have the same amount of detection light at the spectroscope 22, a ND (neutral-density) filter with OD (Optical Density) being 1.5 is disposed at the above-stated position.

For both of the experiments, the average of the measurements repeated 250 times is calculated.

FIG. 61 shows the spectroscopic characteristics of the light passing through a silk sheet of about 100 μm in thickness. In a comparison with light with wavelength of 0.9 μm, the transmittance of the conventional near-infrared light with partial coherency is 2% or more. On the contrary, the transmittance of the near-infrared light with substantially coherency is less than 6%, which is more than about three times. This experimental data also shows that near-infrared light with substantially coherency can increase the penetration length into the target 10 as compared with the conventional near-infrared light with partial coherency.

The amount of transmitted light in the wavelength direction of the conventional near-infrared light with partial coherency changes linearly (substantially the same as the broken straight line additionally shown for reference), and so any difference is not found on the absorbing characteristics.

On the contrary, the amount of transmitted light in the wavelength direction of the near-infrared light with substantially non-coherency shows characteristics that are very different from this. That is, when the wavelength is 1.35 μm or more, the amount of light greatly decreases from the broken straight line additionally shown for reference.

Figure 62:
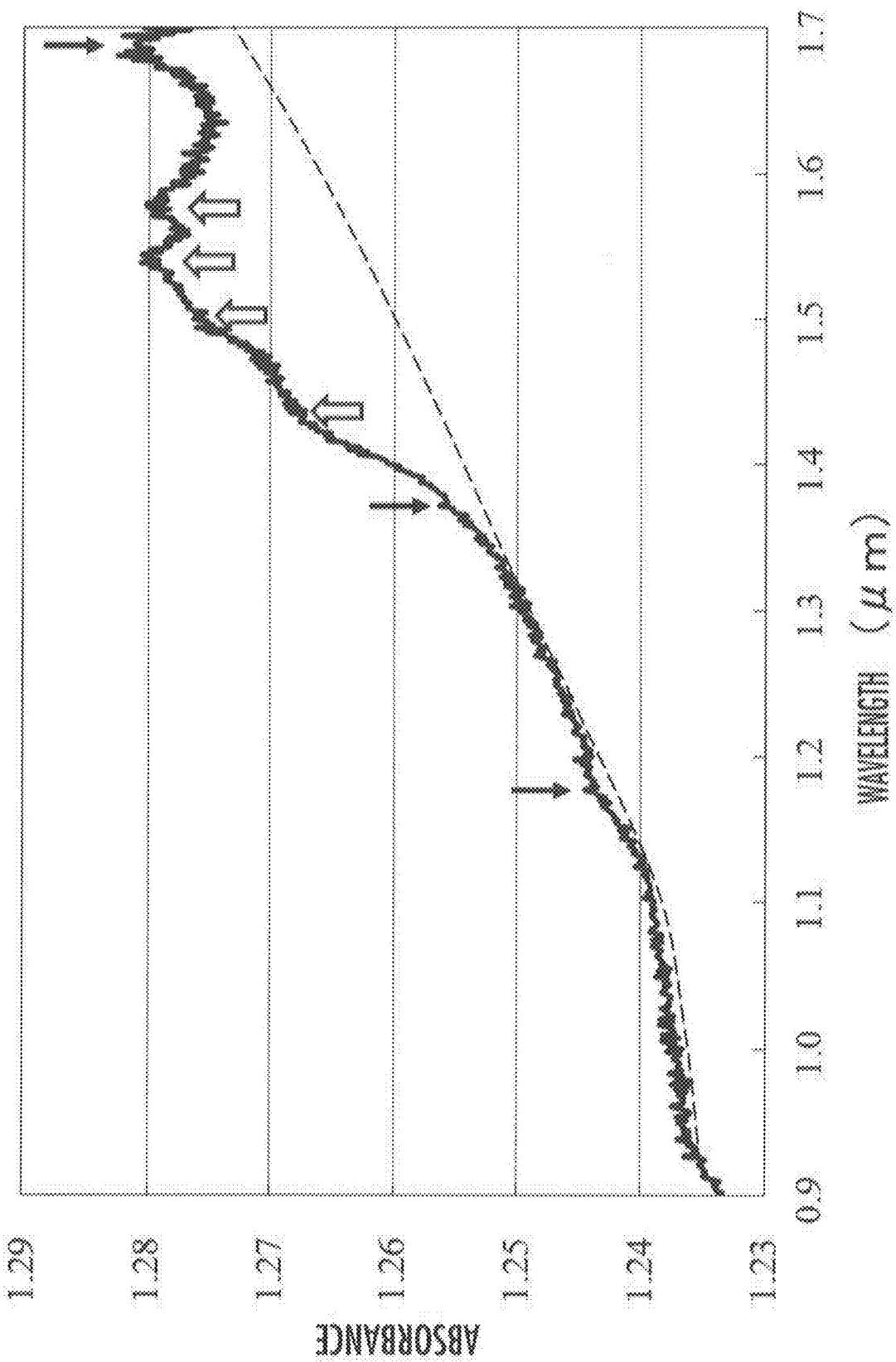
FIG. 62 shows a measurement result of characteristics of absorbance of a silk sheet.

FIG. 62 shows a result of the conversion of the characteristics of a change in transmitted light into a change in absorbance. The absorbance of the silk sheet of FIG. 62 has a plurality of peaks (local maximum). Herein $-\log_{10}(It/Ii)$ is specified as the absorbance. Ii denotes the incident intensity of the irradiated light (first light) 12. It denotes the transmitted intensity of the detection light (second light) 16 after the transmission of the silk sheet.

Figure 63:
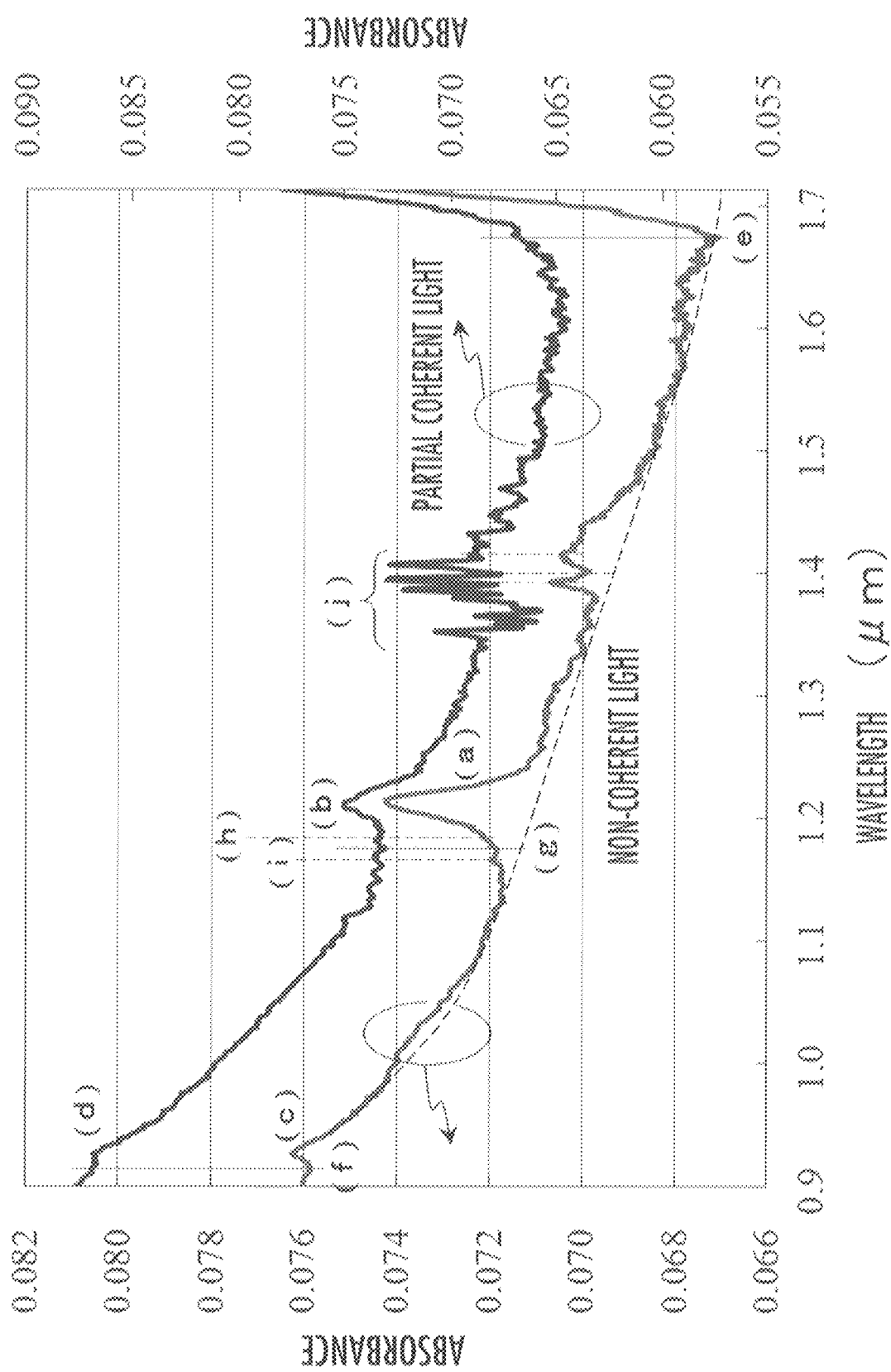
FIG. 63 shows a comparison of polyethylene sheet absorbance due to a difference in partial coherency of the measured light.

For comparison, FIG. 63 shows the absorbance characteristics of the transmitted light of polyethylene sheet of 30 μm in thickness. FIGS. 64(a) and (b) shows the molecular structure of polyethylene. Polyethylene has a simple structure having two hydrogen atoms bonded to each of the carbon atoms composing the principal chain. The center wavelength of the absorption band belonging to stretching of this polyethylene is at a position longer than 1.7 μm for the first-order overtone, at about 1.21 μm for the second overtone and at about 0.92 μm for the third overtone. The absorption band belonging to the combination is known to exist in the range from 1.39 μm to 1.42 μm.

Compared with such polyethylene, a silk sheet has a complicated molecular structure. A silk sheet is made of proteins called fibroin. As shown in FIG. 64(C), fibroin has a periodic structure for every 6-amino acid (hexapeptide). Then glycine G and alanine A mainly compose this periodic structure. Glycine has an amino residue including one hydrogen atom bonded with a carbon atom. Alanine has an amino residue including methyl group (—$CH_3$) bonded with a carbon atom.

It is known that the center wavelength of the absorption band belonging to stretching of this methyl group is a bit shorter than the center wavelength of a methylene group (—$CH_2$). It is also known that the center wavelength of the absorption band belonging to stretching of a glycine residue (—CH) is substantially similar to the center wavelength of a methylene group (—$CH_2$).

Therefore the peak (local maximum) positions indicated with downward arrows in the absorbance characteristics of FIG. 62 may result from group vibration of the methyl group (—$CH_3$) composing the amino residue of alanine. Considering a comparison with the absorption band of FIG. 63, these peaks may be the second overtone of stretching of methyl group (—$CH_3$), the combination, and the first overtone of the stretching in the ascending order of the wavelength.

Peak (local maximum) positions indicated with upward open arrows in FIG. 62 may be associated with a secondary amide (Amide II) in the peptide bond of protein.

As described later in Section 8.3 referring to FIG. 38, the fibroin has a β-sheet type crystalline part 602. In this β-sheet crystalline part 602, hydrogen-bond is formed between the secondary amides. Therefore any one of the peak (local maximum) positions indicated with the upward open arrows may be associated with this hydrogen bonding.

As shown in FIG. 61 at a lower part, the molecular structure of a silk sheet cannot be analyzed with the conventional near-infrared light with partial coherency. On the contrary, near-infrared light with substantial non-coherency of the present embodiment enables detailed analysis of the structure of an assembly having a complicated molecular structure as in the silk sheet.

Detailed considerations on the difference of partial coherency of the irradiated light 12 that affects the absorbance characteristics obtained from the transmitted light of a polyethylene sheet makes a difference between (B•64) and (B•65), which represent interaction, clear. The lower curve of FIG. 63 represents the case of the near-infrared light with substantial coherency, and the vertical axis on the left shows the absorbance in this case. The upper curve of FIG. 63 represents the case of the conventional near-infrared light with partial coherency, and the vertical axis on the right shows the absorbance in this case. Scales are greatly different between the left and right vertical axes.

Firstly in a comparison between (a) and (b) or (c) and (d), they are very different in the height of peaks relative to the gradient of the baseline indicated with the broken line. The apparent peak height greatly increases in the case of the near-infrared light with substantial non-coherency. A comparison between FIG. 23A and FIG. 23B shows that absolute peak height does not change very much between (a) and (b) or (c) and (d). The gradient of the baseline is higher for the measurement with the conventional near-infrared light with partial coherency. The C/N ratio (carrier to noise ratio) of a signal, however, is clearly better for the measurement with the near-infrared light with substantial non-coherency.

Next, the following considers the characteristics at the ends of the wavelengths near the absorption band shown in (e) and (f). In the measurement with the near-infrared light with substantial coherency, the absorbance greatly decreases at these positions. On the contrary, in the measurement with the near-infrared light with substantial coherency, the absorption band has a gentle curve at the ends. That is, they are greatly different in sharpness at the ends (edge parts of the absorption band) of the absorption band.

Such a change is not seen at the surroundings ((g) to (i)) of the absorption band belonging to the second overtone of the stretching. Such a change may not be seen there because of the presence of an absorption band due to another stretching. It is said that the absorption band having the center wavelength at 1.21 μm belongs to the second overtone of the symmetrical stretching of a methylene group (—$CH_2$). It is also said that the absorption band belonging to the second overtone of the asymmetrical stretching, whose height is small although, is present close to 1.19 μm as the center wavelength. Therefore the ends of the absorption band at the positions (g) to (i) are not gentle, and an absorption band belonging to the second overtone of the asymmetrical stretching may be detected there.

In the measurement with the near-infrared light with substantial coherency, large vibration is found at the position of (j) relating to the combination. Since the measurement result changes with the characteristics of the irradiated light 12, vibration at position (j) is different from Fermi resonance.

Changes at the wavelength regions of (e), (f) and (j) may result from a specific phenomenon generated at the edges of the absorption band. For instance, assume the case where the light of the wavelengths corresponding to the regions (e), (f) and (j) is applied to a methylene group (—$CH_2$) in polyethylene. Then the methylene group absorbs this light of the wavelengths, and then tries to transit to an exited state of the vibration. Due to the quantum effect shown by (A•60) in Section 7.2, however, the methylene group cannot transit to the exited state of the vibration. Instead, the electron cloud around the methylene group may absorb such light of the wavelengths for balancing (the value of $p_o(r_o,\omega)$ locally changes slightly).

When the value of $p_\varepsilon(r_\varepsilon,\omega)$ is small at a position close to the methylene group in polyethylene, a change in the value of $p_o(r_o,\omega)$ to some extent hardly affects the entire state in (B•65). In (B•64), however, interference occurs between the scattered light close to the methylene group and the scattered light at a place distant from the methylene group (i.e., the place having a large value of $p_\varepsilon(r_\varepsilon,\omega)$). As a result, a small change in value of $p_\varepsilon(r_\varepsilon,\omega)$ close to the methylene group is amplified greatly. The result of such amplifying may appear as the difference in the wavelength regions of (e), (f) and (j).

FIG. 63 shows the profile of the baseline with the broken line. Presumably this profile of the baseline relates to the biased electron orbital localized around a polymer. Then this broken line has a smaller value of the absorbance corresponding to a longer wavelength. On the contrary, the broken line (baseline) of the silk sheet shown in FIG. 62 has a larger value of the absorbance corresponding to a longer wavelength. Such a change in the baseline characteristics may relate to their structure of the polymer.

For instance, when the polymer has a fiber-like structure as in polyethylene polymer, it absorbs energy a lot from short-wavelength light as in FIG. 64(*a*) because electron orbital is biased a lot. On the contrary, the energy absorption efficiency of infrared light may deteriorate for long-wavelength light as shown in FIG. 64(*b*).

As shown in FIG. 64(C), fibroin composing a silk sheet has a periodic structure for every 6-amino acid. The electron orbital also has a periodic structure, which follows the periodic structure of this amino-acid sequence. This electron orbital suffers from the boundary condition at the edges of the block composing the periodic structure. Then energy necessary to transit from the ground state 393 of the electron orbital to the excited state 399 corresponds to the maximum absorption amount (wavelength having large absorbance) (see (A•60) in Section 7.2). This can explain the reason for the upward-sloping baseline (broken line) in FIG. 62.

In this way, the characteristics of the baseline of the absorbance characteristics can be explained based on the polymer structure using (B•65). Therefore based on the light-absorption characteristics of an unknown polymer or a polymer composing a living body using the near-infrared light with substantial coherency, A) the structure of the polymer can be estimated from the characteristics of the baseline; and B) the atomic group of the polymer can be estimated from the center wavelength of the absorption band.

Additionally,

C) the active state (or its change) of the living body can be estimated in real time based on the amount of wavelength shift from the standard value of the center wavelength of the absorption band.

Chapter 6 Method for Feed-Backing of Wave Front Aberration Generated Along Optical Path As a method of reducing optical noise mixed into the measurement apparatus 30, the example of the present embodiment describes performing at least one of the two ways in Section 2.1:

(1) lowering optical noise relating to partial coherency; and (2) performing feedback of the wave front aberration or the partial change in travelling direction due to the target 10.

The method of (1) is described mainly in Chapter 3. The method of (2) is described in this chapter 6.

Section 6.1 Principle of Generating Wave Front Aberration Inside of Target (Transparent Parallel Flat Plate)

Firstly referring to FIG. 28, the following describes basic principle of generating wave front aberration inside of the target 10.

As shown in FIG. 28(*a*), an objective lens 308 is used to collect the irradiated light 12 to point α in the vacuum (air). For simplified explanation, a transparent parallel flat plate having the refractive index n is considered as the target 10. When such a parallel flat plate (target 10) is disposed at some part along the optical path from the objective lens 308 to the collecting point, refraction occurs at the interface between the vacuum (air) and the parallel flat plate having the refractive index n. As a result, as shown in FIG. 28(*b*), the light is not collected at point β, and the light-collecting position is displaced along the optical path. This phenomenon is called wave front aberration.

For simplified explanation of FIG. 28(*b*), the surface of the target 10 has an optical flat plane (as stated above, wave front aberration occurs at a surface of a complete flat plane as well). Actually, however, the surface of the target 10 has asperities. Due to such asperities, more wave front aberration occurs.

Section 6.2 Method for Compensating Wave Front Aberration

Prior to the explanation of a method for compensating wave front aberration in Section 6.2, the following describes the reason why the light is not collected at point β in FIG. 28(*b*).

In FIG. 28(*a*), the optical length is the same among all optical paths from points divided on the pupil plane of the objective lens 308 to point α, and so the light is collected at point α. On the contrary, in FIG. 28(*b*), the target 10 having the refractive index n is inserted at some part along the optical path to point β. As a result, the optical-length difference δ is generated in accordance with (B•13). The value of this optical-length difference δ is different for each radial position on the pupil plane of the objective lens 308. Due to such a difference δ in optical-length difference, the collection of light at point β is blocked.

Based on the principle as stated above, an optical-length difference inverse of the optical-length difference δ is inserted before the pupil plane of the objective lens 308 for compensation. This compensation method corresponds to the method for compensating wave front aberration. This compensation of the optical-length difference δ is desirably performed with parallel light immediately before the incident (or immediately after the incident) on the objective lens 308.

As a specific method of compensation of wave front aberration as stated above, the cross section of the irradiated light 12 or the detection light 16 in a parallel-light state immediately before the incident (or after the incident) on the objective lens 308 is divided into mesh, and the optical length of each cell of the meshes may be changed in the present embodiment.

FIG. 29A shows a specific example of the structure in the irradiated-light wave front aberration coarse compensation section 352 and the transmitted-light wave front aberration coarse compensation section 356 of FIG. 25. The cross section of the irradiated light 12 or the detection light 16 is divided into cells that are two-dimensionally arranged vertically and horizontally.

Each cell has a light-reflecting plane 416-1 to 6 at the surface. Individual electrode parts 414-1 to 6 are disposed as lower layers of these light-reflecting planes 416-1 to 6. Between these individual electrode parts 414-1 to 6 and a common electrode part 410, piezoelectric devices 418-1 to 6 are disposed.

For instance, when predetermined voltage to the common electrode part 410 is applied to the individual electrode part 414-3, the thickness changes at the piezoelectric device 418-3. Then in accordance with such a change in thickness of the piezoelectric device 418-3, the optical length of the irradiated light 12 or the detection light 16 reflected from the surface of the light-reflecting plane 416-3 changes.

FIG. 29B shows a specific example of the structure in the irradiated-light wave front aberration fine compensation section 354 and the transmitted-light wave front aberration fine compensation section 358 of FIG. 25. In FIG. 29B as well, the cross section of the irradiated light 12 or the detection light 16 is divided into cells that are two-dimensionally arranged vertically and horizontally.

In the structure of FIG. 29B, a common electrode part 420 doubles as a light-reflecting plane. Then the irradiated light 12 or the detection light 16 is reflected from the common electrode part 420 that doubles as the light-reflecting plane. On the common electrode part 420 that doubles as the light-reflecting plane, liquid-crystal layers 428-1 to 3 are formed. Then the optical length changes with the orientation of liquid crystals in these liquid-crystal layers 428-1 to 3. These liquid-crystal layers 428-1 to 3 are separated by dividers 422. Then transparent electrode parts 424-1 to 3 are formed so as to change the orientation of liquid crystals.

In FIG. 29B, the optical length is changed by reflecting the irradiated light 12 or the detection light 16. Alternatively, the irradiated light 12 or the detection light 16 may pass therethrough to change the optical length.

Section 6.3 Common Part of Method of Detecting Wave Front Aberration

Section 6.3 firstly describes the interior of the reference-light generation section 320 of FIG. 25.

FIG. 1C describes the example of applying a convergent irradiated light 12 and then collecting the light at one point ($\alpha/\beta/\gamma$) only in the target 10. This is the description just for simplified explanation, and the light may be collected at a plurality of different points in the target 10. Alternatively, the irradiated light 12 in an example of the present embodiment may define a predetermined three-dimensional shape at a local region in the target 10.

When the irradiated light defines a three-dimensional shape or are collected at a plurality of points in the target 10, such control is performed in the reference-light generation section 320. As a basic principle for that, a plurality of image-forming patterns each having a confocal relationship is formed along the direction of optical axis in the example of the present embodiment.

A three-dimensional transmission pattern forming section 440 disposed in the reference-light generation section 320 has an internal structure including a plurality of two-dimensional transmission image forming layers 442, 444, and 446 that are stacked with a predetermined distance. These two-dimensional transmission image forming layers 442, 444 and 446 have a function of extracting light in a certain region only at the cross-sectional part of the detection light 16. These two-dimensional transmission image forming layers 442, 444 and 446 may be formed with a liquid-crystal shutter, for example.

Alternatively, any optical device may be used, which is disposed at some part along the optical path of the light and includes a predetermined pattern, inside of which only can transmit (or reflect) the light. For instance, a mechanical mask, a pinhole or a slit having a two-dimensional predetermined pattern shape may be used, and such a mechanical mask, a pinhole, or a slit may be removed or added for replacing to change the pattern shape. Alternatively, a two-dimensional switch array may be used, which is arranged two dimensionally and has light-transmission/reflection characteristics that locally change with an electric signal.

Each layer of the two-dimensional transmission image forming layers 442, 444 and 446 has an image-forming (confocal) relationship with a different depth position in the target 10. Then parallel light leaving the light combiner section 340 (FIG. 25) passes through these two-dimensional transmission image forming layers 442, 444 and 446, whereby an image-forming pattern to be formed in the target 10 is generated.

For instance, all of the beams of light passing through the two-dimensional transmission image forming layers 442 and 446 are allowed to pass through (i.e., the beams of light passing through the two-dimensional transmission image forming layers 442 and 446 are not blocked at all), and a pinhole structure is formed so as to let the light pass through region c only of the two-dimensional transmission image forming layer 444. In this case, light is collected only at point $\alpha$ in the target 10.

When a plurality of pinhole patterns are formed so as to allow beams of light to pass through a plurality of points only in the two-dimensional transmission image forming layer 444, then the light is correspondingly collected at a plurality of positions on the corresponding plane (image-forming plane) in the target 10.

A pinhole structure is formed, which lets the light pass through region c only of the two-dimensional transmission image forming layer 444, and then a pinhole structure is formed, which lets the light pass through region $\eta$ of the two-dimensional transmission image forming layer 442. Then an optical path for the light passed through region c and region $\eta$ is opened. Then, the light is collected at point $\alpha$ and point $\gamma$ having different depths in the target 10.

In this way, pinholes are formed at region $\varepsilon$, region $\zeta$ and region $\eta$, and the light is allowed to transmit the optical path of the light passed through these pinholes. Thereby light is collected at region $\alpha$, region $\beta$ and region $\gamma$ only.

Figure 30:
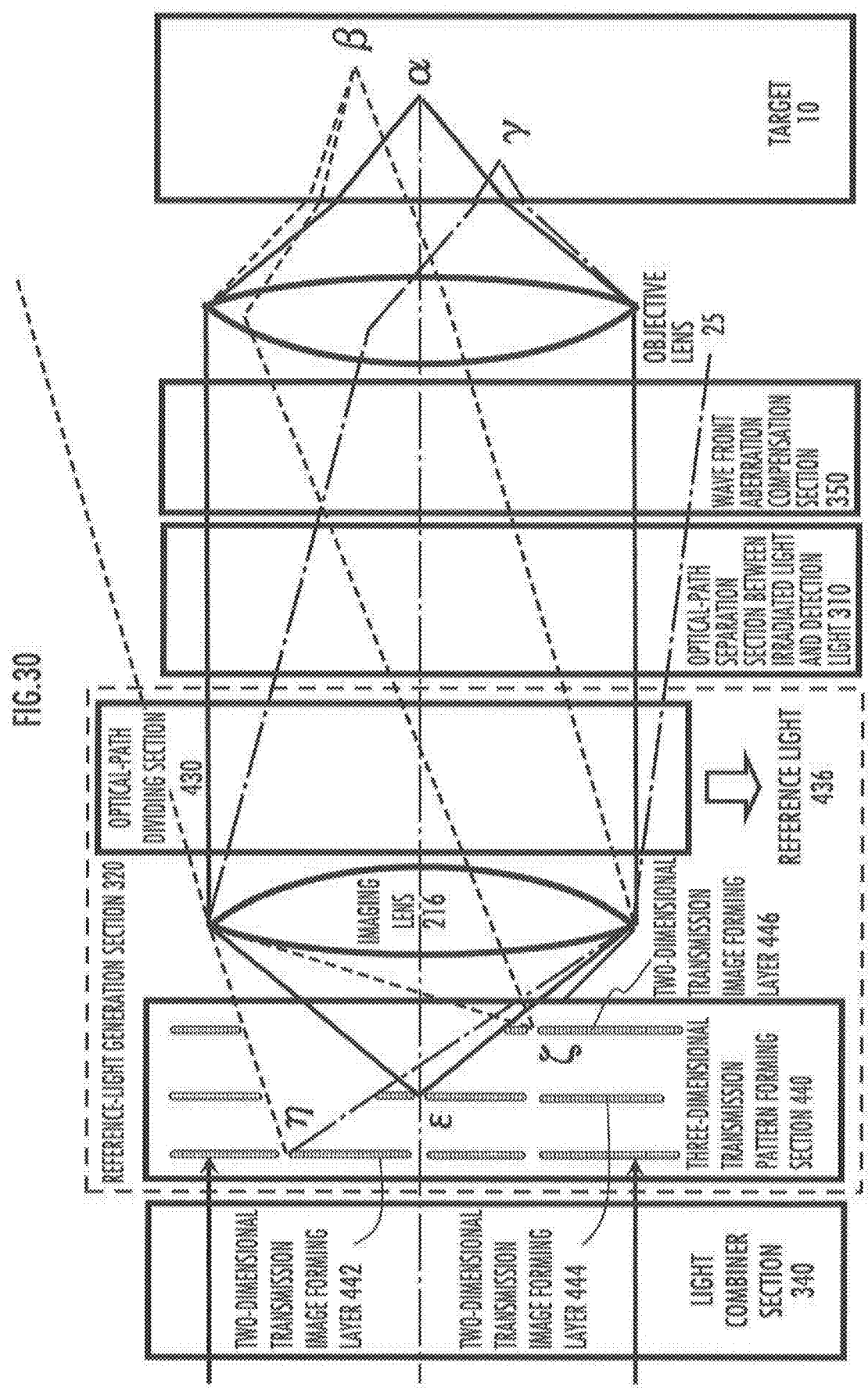
FIG. 30 describes the principle of generating reference light.

In FIG. 30, the plurality of two-dimensional transmission image forming layer 442, 444 and 446 are collectively stored in the three-dimensional transmission pattern forming section 440. Alternatively, beams of light passed through the two-dimensional transmission image forming layers 442, 444 and 446 disposed at mutually different positions may be combined at some part along the optical path before the target 10.

FIG. 30 shows the example of forming an image-forming pattern with a transmission pattern. Alternatively, an image-forming pattern may be formed with reflected light. A part of the light passed through this three-dimensional transmission pattern forming section 440 is amplitude-divided at an optical-path dividing section 430, which is then extracted as reference light 436. Although not illustrated in FIG. 30, the reference light 436 extracted here is divided into coherent light and partial incoherent light in the reference-light generation section 320.

Figure 32A:
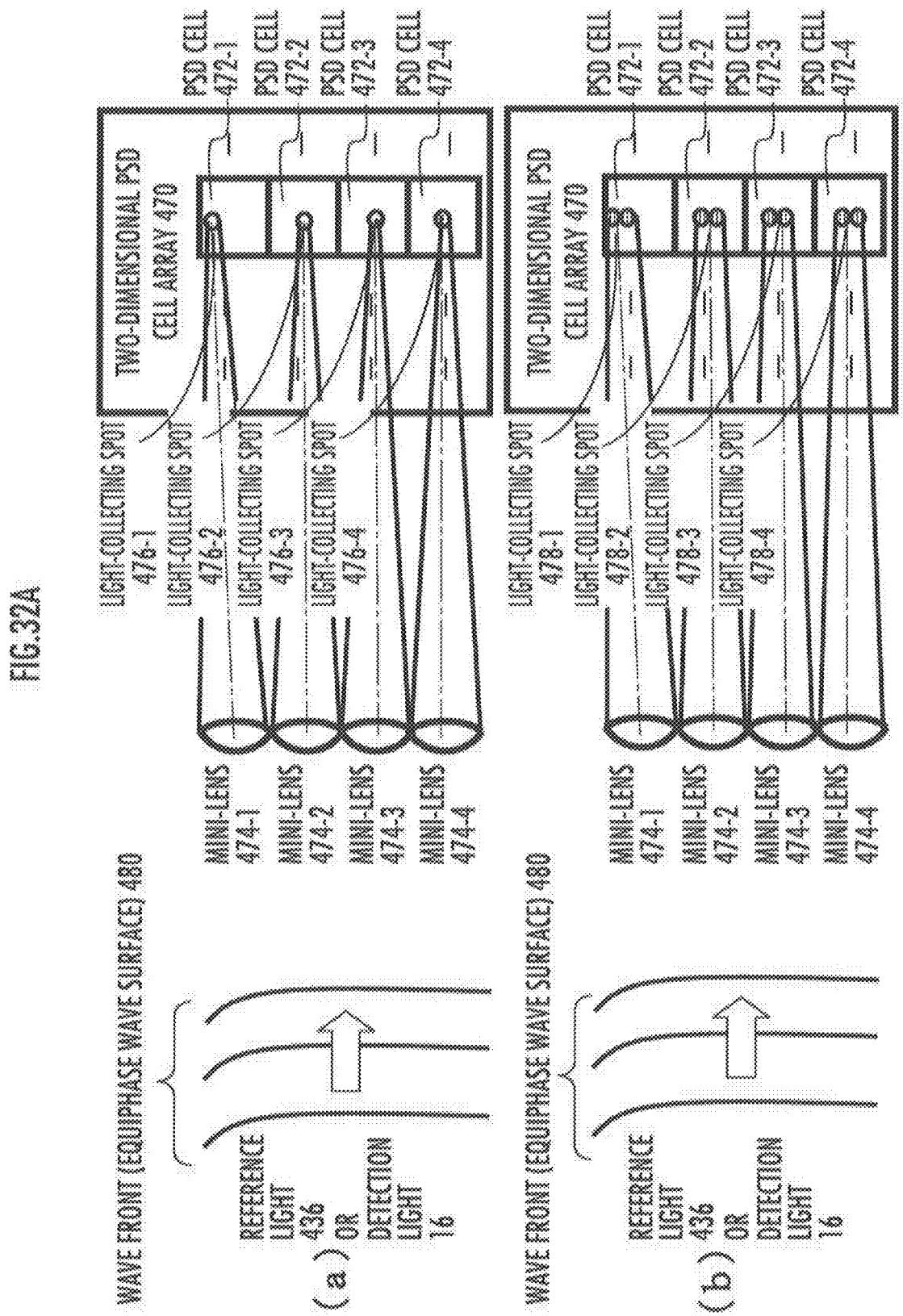
FIG. 32A describes the optical principle of a method for detecting wave front aberration using partial incoherent light.
Figure 32B:
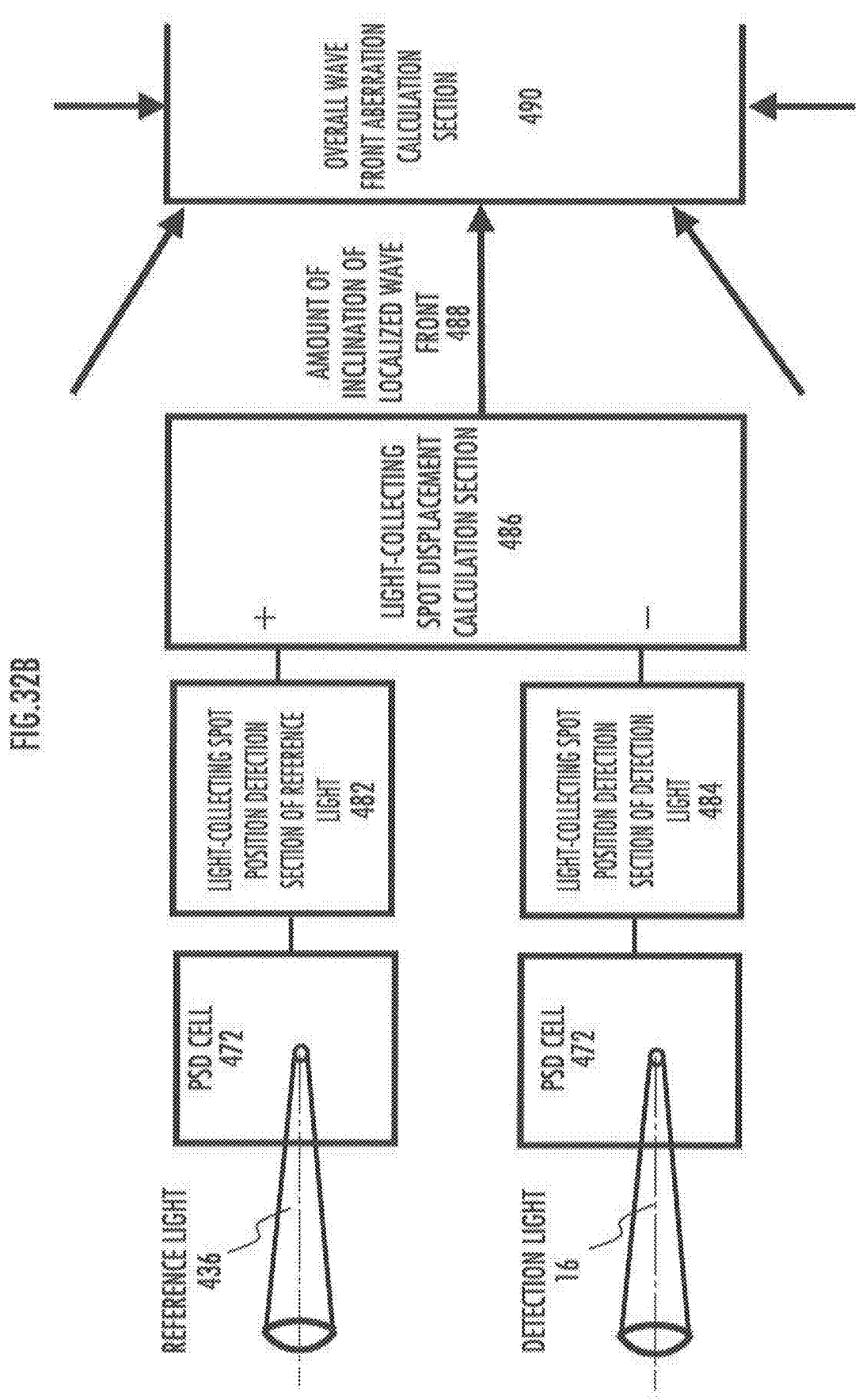
FIG. 32B shows a method of electric processing to detect wave front aberration using partial incoherent light.

Then the reference light 436 of the divided partial incoherent light is used as the reference light 436 in FIG. 32B. Similarly, the reference light 436 of the divided coherent light is used as the reference light 436 in FIG. 33.

In FIG. 30, the irradiated-light wave front aberration coarse compensation section 352 and the irradiated-light wave front aberration fine compensation section 354 in FIG. 25 are collectively described as the wave front aberration compensation section 350.

Referring to FIG. 26, Section 5.1 describes multi-scattered light that is generated inside of the target 10 to be measured/detected, which adversely affects the signal-detection characteristics and imaging characteristics. As described in Chapter 3, higher partial incoherency of light can reduce the influences of interference with the multi-scattered light 370. The method of Chapter 3, however, cannot reduce the generation of multi-scattering of light inside of the target 10.

For instance, as shown in FIG. 30, when the characteristics or an image are measured at a certain region (regions $\alpha$, β, and γ) only in the target 10, the influences of the multi-scattered light 370 can be reduced by using such a feature.

That is, as is clear from FIG. 26, most of the multi-scattered light 370 is scattered at a position other than region α/region β/region γ in the target 10. Therefore, an image-forming optical system (or a confocal optical system) may be disposed at some part of the detecting optical path so as to block the light scattered at positions other than region α/region β/region γ, whereby most of the multi-scattered light 370 can be removed from the detecting system.

In the example of the measurement apparatus of FIG. 25, such processing to reduce the influences from multi-scattered light is implemented in the light separator sections 312 and 332. Alternatively, any method to reduce the influences from multi-scattered light may be used at a stage before the optical path of the signal detection sections 304, 314, 324, and 334 and the wave front aberration detection sections 306, 316, 326, and 336.

As shown in FIG. 31 (a part of the structure is altered from the original optical arrangement for illustrative purpose), the light separator section 312, 332 in FIG. 25 internally includes an imaging lens 216, a three-dimensional transmission pattern image forming section 450, a collimator lens 26 and an optical-path separation section 430.

Similarly to the three-dimensional transmission pattern image forming section 440 of FIG. 30, this three-dimensional transmission pattern image forming section 450 has an internal structure including a plurality of two-dimensional transmission image forming layers 452, 454, and 456 that are stacked with a predetermined distance. These two-dimensional transmission image forming layers 452, 454 and 456 have a function of extracting light in a certain region only at the cross-sectional part of the detection light 16. To extract the light in a certain region only, transmission or reflection at the certain region only may be used. That is, although the example of FIG. 31 has the structure of extracting light passed through a locally opening part of a shutter (or light passed through a pinhole or a specific pattern region) only. Alternatively, light in a certain region only may be extracted by using reflected light obtained from an optical reflective film, for example. These two-dimensional transmission image forming layers 452, 454 and 456 may have a specific structure that is an optical device (light transmitting/reflecting device) or a mechanical structure (mask or pinhole) having a predetermined pattern, or an active shutter or switch, such as a liquid-crystal shutter.

For illustrative purposes, the imaging lens 216 is disposed outside of the light separator section 312, 332 in FIG. 31. Actually, however, the imaging lens 216 (before altering for illustrative purpose) is disposed inside of the light separator section 312, 332. In the optical arrangement of FIG. 25, the detection light 16 immediately after the passage of the objective lenses 308, 318 are parallel light. Then when this detection light 16 as parallel light enters the light separator section 312, 332, the light actually turns converging light because of the function of the imaging lens 216 that is disposed at the entrance of the light separator section 312, 332. Therefore originally the combination of the objective lenses 308 and 318 and the imaging lens 216 forms an image-forming relationship (confocal relationship) at the light-collecting region (regions α, β and γ) in the target 10 and in the three-dimensional transmission pattern image forming section 450. Just for illustrative purpose, FIG. 31 shows an altered structure. That is, this drawing shows that the imaging lens 216 alone, which is disposed outside of the light separator section 312, 332, can form an image-forming relationship (confocal relationship).

In FIG. 31, the following considers the case where region β (point β) and region ζ (point ζ) have a mutually image-forming relationship (confocal relationship). Then the detection light 16 obtained from region β (point β) in the target 10 is collected at region (point ζ) in the light separator section 312, 332.

The two-dimensional transmission image forming layer 452 has a shutter that is locally bored so as to allow the detection light 16 passed through region ζ (point ζ) only to be extracted (allowed to pass through). As a result, a component of the detection light 16 that passes through a bit distant part from region ζ (point ζ) is blocked. Through this operation, a component of light that is multi-scattered at a bit distant part from region β (point β) in the target 10 is not allowed to pass through the light separator section 312, 332. Meanwhile, the two-dimensional transmission image forming layers 454 and 456 have a shutter (allowing transmission of light) along the optical path of the detection light 16 passed through region ζ (point ζ). Then, the component of the detection light 16 passed through region ζ (point ζ) only is selectively extracted (allowed to pass through) at the three-dimensional transmission pattern forming section 450.

Similarly, the components of the detection light 16 that passes through region (point ε) and region η (point η) that are the image-forming positions (confocal positions) for region α (point α) and region γ (point γ) in the target 10 also are extracted (allowed to pass through). Then, the multi-scattered light scattered at distant positions from regions α, β, and γ (points α, β, and γ) in the target 10 is blocked in the three-dimensional transmission pattern forming section 450. As a result, adverse effects from the multi-scattered light scattered at positions other than the regions to be measured or detected in the target 10 can be removed, and so precise detection/measurement or imaging can be performed or wave front aberration can be detected.

The component of the detection light 16 that is extracted (passes through) at the three-dimensional transmission pattern forming section 450 turns substantially parallel light at the collimator lens 26. Then, the light in a substantially parallel state is separated into partial incoherent light and coherent light at the optical-path separation section 430. The separation at this optical-path separation section 430 is performed by the method described above in Section 4.2.

Section 6.4 Method for Detecting Wave Front Aberration Using Partial Incoherent Light The following describes the method for detecting wave front aberration using partial incoherent light in the wave front aberration detection section 306 for reflected light having partial incoherency and in the wave front aberration detection section 316 for transmitted light having partial incoherency in FIG. 25.

In this example of the embodiment, influences from light interference on the light-collecting spot 476 applied in a PSD (position sensitive detector) 472 is reduced using partial incoherent light. Then, the position of the light-collecting spot 476 applied to the PSD cell 472 is detected so as to detect a local state of the wave front aberration.

FIG. 32A shows the principle of such detection of wave front aberration. The reference light 436 or the detection light 16 is in an substantially parallel state via the light separator section 312, 332 described in Section 6.3 or the reference-light generation section 320 (FIG. 25). Then, mini-lenses 474-1 to 4 are two-dimensionally arranged on the cross-section of the light obtained by cutting such light in an substantially parallel with a plane (the plane perpendicular to the travelling direction of the reference light 436 or the detection light 16). A two-dimensional PSD cell array 470 is disposed on the back focal plane of these mini-lenses 474-1 to 4. On the surface of this two-dimensional PSD cell array 470, PSD cells 472-1 to 4 are arranged two-dimensionally, so that the beam of light as a part of the reference light 436 or the detection light 16 passing through one mini-lens 474 forms a light-collecting spot 476 in the corresponding PSD cell 472.

In the example of FIG. 32A(a), the reference light 436 or the detection light 16 passing through the mini-lenses 474-2 to 4 have a planar wave front (equiphase wave surface) 480 and travel straight in parallel to the optical axis. Therefore the beams of light passed through the mini-lenses 474-2 to 4 form light-collecting spots 476-2 to 4 at center parts of the PSD cells 472-2 to 4.

Meanwhile, the beam of the reference light 436 or the detection light 16 passing through the mini-lens 474-1 has a curved wave front (equiphase wave surface) 480 and has an upward travelling direction relative to the optical axis. Therefore when this beam of light passes through the mini-lens 474-1, then the beam forms a light-collecting spots 476-1 at an upper part in the PSD cell 472-1.

In this way, the position of the light-collecting spot 476 formed in the PSD cell 472 is detected, whereby the state of the wave front (equiphase wave surface) 480 of the light passed through the corresponding mini-lens 474 can be found. Then, the signals of position detection from these PSD cells 472 are connected, whereby the characteristics of the overall wave front (equiphase wave surface) 480 can be expected.

When coherent light is used for detecting this wave front aberration, the following problems occur. The wave front aberration included in the detection light 16 obtained only from regions $\alpha/\beta/\gamma$ (points) at the same time in FIG. 31 has to be detected. However, as described in Section 5.1 referring to FIG. 26, multi-scattered light 370, 380 is generated in the target 10, and such multi-scattered light is combined with the detection light 16. Then a light-interference pattern of the detection light 16 to be detected and the multi-scattered light 370, 380 appears in the PSD cell 472 as shown in FIG. 32A(b). As a result, the positions of the light-collecting spots 476-1 to 4 applied to the PSD cells 472-1 to 4 are erroneously detected.

In the example of the present embodiment, however, since partial incoherent light is used for detecting wave front aberration, the light-collecting spots 476-1 to 4 formed in the PSD cells 472-1 to 4 can have less influences from light interference. As a result, accuracy to detect the positions of the light-collecting spots 476-1 to 4 in the PSD cells 472-1 to 4 can be improved, and so wave front aberration can be detected accurately.

In the example of the present embodiment, wave front aberration is detected based on a comparison between the reference light 436 having an ideal state that is free from wave front aberration in the target 10 and the detection light 16 including wave front aberration generated in the target 10. This applies to both cases of using partial incoherent light and coherent light as the detection light 16.

The example of the present embodiment is not limited to the method for detecting wave front aberration in the detection light 16 obtained from one point (one region) only in the target 10. For instance, as shown in FIG. 31, the method enables the detection of wave front aberration included in the light obtained from a plurality of regions $\alpha/\beta/\gamma$ (a plurality of points) in the target 10 at the same time as well. Alternatively, wave front aberration may be detected while performing signal detection/measurement (including detection/measurement of spectroscopic characteristics) from the detection light 16 obtained from any three-dimensional pattern localized in the target 10.

In this case, such a localized any three-dimensional pattern is created artificially at the three-dimensional transmission pattern forming section 440 of FIG. 30. If no wave front aberration occurs in the target 10, such a three-dimensional pattern can be formed in the target 10 based on image-forming characteristics (confocal characteristics). Wave front aberration that can be a factor to inhibit the formation of a three-dimensional pattern in the target 10 may be detected/measured in the irradiation optical system beforehand, and then the inversed characteristics may be given to the wave-front aberration compensation section 350. Thereby such a three-dimensional pattern can be formed accurately in the target 10.

In parallel to this, ideal characteristics of the irradiated light 12 during the generation of a three-dimensional pattern localized at the three-dimensional transmission pattern forming section 440 are extracted as the reference light 436. The reference light 436 extracted in FIG. 30 is in a state of mixed light including the mixture of partial incoherent light and coherent light. Although not shown, the extracted reference light 436 is separated by the method described in Section 4.2. Therefore, the reference light 436 used in FIG. 32B includes a component of partial incoherent light only that is separated and extracted as stated above.

FIG. 32B shows a method of electric processing to detect wave front aberration using the reference light 436 and partial incoherent light. The reference light 436 and for the detection light 16 use separately the detection optical system shown in FIG. 32A(a).

A light-collecting spot position detection section 482 of the reference light detects the position of light-collecting spot of the reference light 436 on the PSD cell 472. In parallel to this, a light-collecting spot position detection section 484 of the detection light detects the position of light-collecting spot of the detection light 16 on the PSD cell 472.

Next, a light-collecting spot displacement calculation section 486 calculates a difference in position information between them, and calculates the displacement of the position of light-collecting spot of the detection light 16 relative to the position of light-collecting spot of the reference light 436. In the example of FIG. 32A(a), the light passing through the mini-lens 474-1 has a curved wave front (equiphase wave surface) that is inclined upward. In this case, the light-collecting spot 476-1 is located at an upper part of the PSD cell 472-1. In this way, based on the displacement of the position of the light-collecting spot 476-1, the amount of inclination of wave front of the light passing through the mini-lens 474-1 can be expected. This is the description of the principle, based on which the light-collecting spot displacement calculation section 486 outputs the information on the amount of inclination 488 of a localized wave front.

One light-collecting spot displacement calculation section 486 outputs the amount of inclination of wave front for the light passing through one mini-lens 474 only. Therefore, the amount of inclination of wave front for the light passing through all of the mini-lenses 474-1 to 4 in FIG. 32A have to be individually detected.

Specifically to this end, individual light-collecting spot displacement calculation sections 486 may be provided so as to correspond to all of the mini-lenses 474-1 to 4. In another method, when the rate of change of wave front aberration over time is very slow, the mini-lens 474 as a target of the amount of inclination 488 of the localized wave front may be switched in time series. That is, when the light-collecting spot position detection sections 482 and 484 are disposed close to the PSD cells 472-1 to 4, the mini-lenses 474-1 to 4 to output an input signal to the light-collecting spot displacement calculation section 486 may be switched in times series, which is not illustrated.

As a result, the amount of inclination 488 of wave front for the light passing through all of the mini-lenses 474-1 to 4 and their inclination directions can be input to an overall wave front aberration calculation section 490. This wave front aberration calculation section 490 integrates the information on the amount of inclination 488 of wave front for each of the mini-lenses 474-1 to 4 and their inclination directions, and so can expect the overall wave front aberration.

Section 6.5 Method for Detecting Wave Front Aberration Using Coherent Light

FIG. 33 shows a method for detecting wave front aberration using coherent light. Among the components of the reference light 436 extracted in FIG. 30, the component of coherent light only that is separated by the method described in Section 4.2 is used as the reference light 436 in FIG. 33. Assume here that prior to the detection of wave front aberration using coherent light as described in Section 4.1 referring to FIG. 25, the irradiated-light wave front aberration coarse compensation section 352 and the transmitted-light wave front aberration coarse compensation section 356 acts to correct large wave front aberration. Therefore the amount of wave front aberration to be detected in this Section 6.5 is in a small range that is the wavelength λ, or less to be used for the detection, for example. Although the detection range is very small, the detection accuracy is very high.

A signal of the amount of detection light for each of the pixels that are arranged two-dimensionally can be obtained from the imaging plane in the imaging cameras 500-1 to 4. The amplitude of the reference light 436 applied to a specific pixel is set as reference (the amplitude thereof is set at "1"), and A denotes the amplitude of the detection light 16. The amount of wave front aberration in this specific pixel corresponds to the phase shifting amount δ of the detection light 16 relative to the reference light 436. Therefore the amount of detection light obtained from this specific pixel can be given by the following expression, which is obtained by substituting (B•13) into (B•18).

[Math. 15]

$$I_C = |\Psi|^2 = \frac{1+A^2}{(1+A^2)^2} + \frac{2A}{(1+A^2)^2}\cos\{2\pi\delta/\lambda\} \quad (B\cdot 40)$$

(B•40) has a problem that the calculation result of (B•40) is the same between positive and negative values of □. This means that just combining the reference light 436 with the detection light 16 and detecting the amount of irradiated light for each pixel cannot yield an accurate wave front aberration on the detection light 16.

To solve this problem, in this example of the embodiment, a predetermined amount of phase shifting is added to the phase between the reference light 436 and the detection light 16, followed by combination, and then the amount of detection light for each pixel is measured. In a specific example, let that λ, denotes the wavelength of the reference light 436 and the detection light 16, then the wavelength λ, is divided into N. Then, phase shifting corresponding to m/N (m denotes a positive number) is added, and then the reference light 436 and the detection light 16 are combined. The amount of detection light for the specific pixel at this time is given by the following expression, instead of (B•40).

[Math. 16]

$$I_C = |\Psi|^2 = \frac{1+A^2}{(1+A^2)^2} + \frac{2A}{(1+A^2)^2}\cos\left\{2\pi\left(\delta+\frac{m}{N}\right)/\lambda\right\} \quad (B\cdot 41)$$

Variables in (B•41) are three types, including "A", "□" and "the polarity of □" (positive or negative). Therefore at least three simultaneous equations are necessary. Therefore N□3 is desirable in the example of the present embodiment.

A typically well-known birefringent optical device has different refractive indexes n between in the ordinary ray direction and in the extraordinary ray direction. Therefore based on the principle similar to (B•13), phase shifting occurs between the ordinary ray and the extraordinary ray after passing through a birefringent optical device. The amount of phase shifting m/N added in (B•41) is generated by means of such a birefringent optical device.

FIG. 33 shows a specific example of the arrangement of the optical system. The reference light 436 and the detection light 16 are mixed by a polarization beam splitter 492 (see Section 3.1 about the definition of the term "mixing"). This polarization beam splitter 492 reflects a S wave (Senkrecht Wave) component only in the reference light 436 and transmits a P wave (Parallel Wave) component only in the detection light 16. Then, the vibrating-plane direction (of the electric field) of the reference light 436 (S-wave direction) and the direction of the detection light 16 (P-wave direction) are mutually orthogonal in the light mixed by the polarization beam splitter 492. This means that interference does not occur between the reference light 436 and the detection light 16 in this mixed light.

At an unpolarized beam splitter 498-1, both of the S-wave component and the P-wave component are substantially the same in the optical reflectance and the optical transmittance. Therefore the reflected light at the unpolarized beam splitter 498-1 includes the reference light 436 and the detection light 16 of the same ratio.

An analyzer 496-1 is disposed at some part of the reflected optical path of the unpolarized beam splitter 498-1, and this analyzer extracts (transmits) only the component in the vibrating direction (of the electric field) inclined by 45 degrees relative to the S-wave direction and the P-wave direction of the polarization beam splitter 492. Then, since the reference light 436 and the detection light 16 included in the light extracted by the analyzer 496-1 are the same in the vibrating-plane direction (of the electric field), interference occurs between them. As a result, "m=0" in (B•41) is obtained as a signal of the amount of detection light obtained from one pixel in the imaging plane of the imaging camera 500-1.

FIG. 33 includes a standard λ/4 plate (quarter wave plate) 494 among the birefringent optical devices as stated above. Alternatively, any birefringent optical device may be used in this example of the embodiment. Then the direction of ordinary light or extraordinary light of the λ/4 plate 494 is the same as the S-wave direction or the P-wave direction of the polarization beam splitter 492

Then, after passing through one λ/4 plate 494-1, the phase shifting by ¼ wavelength is added to the phase between the reference light 436 and the detection light 16. Further after passing through a λ/4 plate 494-2, the phase shifting by ½ wavelength is added to the phase between the reference light 436 and the detection light 16. Further after passing through a λ/4 plate 494-3, the phase shifting by ¾ wavelength is added to the phase between the reference light 436 and the detection light 16.

Every time a predetermined value is added to the phase between the reference light 436 and the detection light 16, the light is extracted by the unpolarized beam splitters 498-2, 3, and is allowed to pass through the analyzers 496-2 to 4 for light interference between the reference light 436 component and the detection light 16 component.

As a result, the characteristics from "m=1" to "m=3" in (B•41) can be obtained as the signal of the amount of detection light obtained from one pixel in the imaging plane of the imaging cameras 500-2 to 4. By solving the thus obtained simultaneous equations, the relative amplitude A of the detection light 16 and the amount of wave front aberration δ can be calculated for each pixel.

Similarly to the overall wave front aberration calculation section 490 of FIG. 32B, the amount of wave front aberration δ for each pixel of the imaging camera 500 are combined, whereby the overall characteristics of wave front aberration can be calculated.

Chapter 7 Method for Calculating Characteristics of n-Th Overtone Limited to Specific Atomic Group in Polymer Section 7.1 Method for Reducing Optical Noise and Prediction of Wavelength of Absorption Band Belonging to Group Vibrations at Specific Atomic Group The system of the present embodiment mainly focuses on the provision of a method of understanding the composition, the structure or the active state in the target 10 to be detected/measured accurately. Therefore the present embodiment is not limited just to the improvement in accuracy of a detection signal and spectroscopic characteristics obtained from the target 10 and the improvement in clarity of the imaging, and can provide a technical means to improve the accuracy to understand the composition, the structure or the active state in the target 10 based on the obtained information.

As described in Section 2.1, the present embodiment shows the following two ways to reduce optical noise.

(1) Chapter 3 describes the method of lowering optical noise generated from partial coherency; and (2) Chapter 6 describes the method of lowering optical noise generated from wave front aberration inside of the target 10.

The methods in the embodiments described in Chapter 3 and Chapter 6 can improve the accuracy of a detection signal and spectroscopic characteristics obtained from the target 10 and can improve the clarity of imaging. To understand the composition, the structure or the active state in the target 10 based on information obtained from this, however, it is necessary to understand the principle of interaction between micro structures inside of the target 10 and light. To this end, Chapter 5 briefly describes the interaction between a light-absorbing object or a light-scattering object and light generated inside of the target 10.

That is, since group vibrations in a predetermined atomic group have a small scattering cross-section, beams of the scattering light from such an atomic group less likely interfere with each other. Therefore when partial incoherent light is used as the irradiated light 12, the absorption band belonging to group vibrations in the specific atomic group can be detected/measured relatively accurately.

When this is combined with the technique of reducing wave front aberration generated inside of the target 10 (Chapter 6), the absorption band belonging to group variations in the atomic group can be detected more accurately.

In this way, the characteristics of the absorption band that a specific region in the target 10 has can be detected accurately. However, it is still difficult to identify the vibration mode that the absorption band belongs to. If the vibration mode of each absorption band can be predicted accurately, this in combination with the result of detection/measurement can lead to the precise understanding of the composition, the structure or the active state inside of the target 10.

Currently the wavelength of the absorption band corresponding to fundamental vibration can be theoretically predicted using a quantum chemistry simulation program. On the contrary, there is no method enabling the easy prediction of a wavelength of the absorption band corresponding to a n-th overtone of group vibration.

As shown in the above, there is no method enabling the easy theoretical prediction of a wavelength of the absorption band of a n-th overtone of group vibration generated in a specific atomic group. Chapter 7 describes a method for solving this problem.

Section 7.2 Mathematical Presentation of Group Vibrations in Atomic Group

To introduce mathematical presentation to theoretically predict the wavelength value of the absorption band of a n-th overtone of group vibration generated in a specific atomic group, a part of the mathematical presentation described in Patent Literature 3 is used in the following. To clarify a difference between the mathematical presentations newly described in this specification and the above mathematical presentations already described in Patent Literature 3, the numbers (A•&&) of the mathematical presentations described in this literature are used as they are. For the mathematical presentations newly described in this specification, their numbers are (C•$$).

Figure 34:
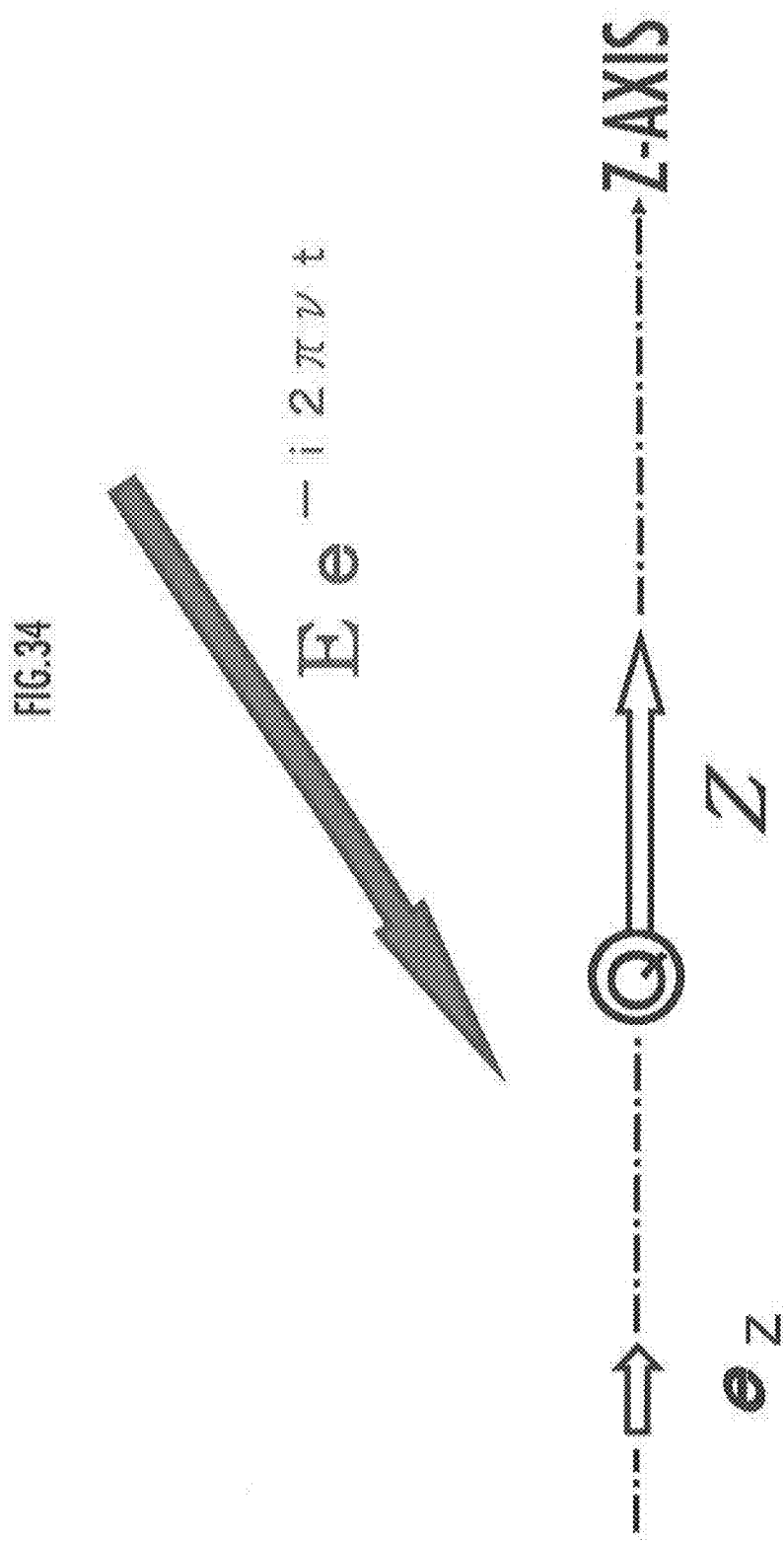
FIG. 34 describes a relationship between an external electric-field direction and the moving direction of charged particles moving in the electric field.

As shown in FIG. 34, the following considers the case where a charged particle having the charge amount of Q is disposed on Z-axis. Let that $e_Z$ denotes the unit vector on Z-axis. The work load corresponding to the movement of the charged particle by Z along the Z-axis against the external electric field $E e^{-i2\pi vt}$ will be given by (A•1).

[Math. 17]

$$U = -\int_0^Z Q(E \cdot e_Z) \exp(-i2\pi vt) dr = -Q(E \cdot Z) \exp(-i2\pi vt) \quad (A\cdot 1)$$

Herein (E•Z) denotes the inner product of vectors E and Z. Note here that (A•1) does not include the term for interaction with the magnetic field in the external electromagnetic waves, and such a term is sufficiently ignorable.

Based on (A•1), the following Schrodinger equations of (A•2) to (A•5) are given when a macromolecule including a specific atomic group interacts with the external electric field:

[Math. 18]

$$i\hbar \frac{\partial}{\partial t} \Psi(\ldots, rj, \ldots, \sigma j, \ldots, Ra, \ldots, t) = \quad (A\cdot 2)$$
$$\{H_{nucl} + H_{el}\} \Psi(\ldots, rj, \ldots, \sigma j, \ldots, Ra, \ldots, t)$$

-continued

[Math. 19]

$$H_{nucl} \equiv -\sum_{a=1}^{N} \frac{\hbar^2}{2Ma}\Delta a + \frac{e_0^2}{4\pi\varepsilon_0}\sum_{a>b}^{N} \frac{Za \cdot Zb}{|Ra-Rb|} - \sum_{a=1}^{N} Qa(E \cdot Ra)\exp(-i2\pi vt) \quad (A\cdot 3)$$

[Math. 20]

$$H_{el} \equiv -\sum_{j=1}^{n} \frac{\hbar^2}{2me}\Delta j - \frac{e_0^2}{4\pi\varepsilon_0}\sum_{i,=1}^{n}\sum_{a=1}^{N} \frac{Za}{|rj-Ra|} + H_{eladd} \quad (A\cdot 4)$$

[Math. 21]

$$H_{eladd} \equiv \frac{e_0^2}{4\pi\varepsilon_0}\sum_{i>j}^{n} \frac{1}{|ri-rj|} + \sum_{j=1}^{n} e_0(E \cdot rj)\exp(-i2\pi vt) \quad (A\cdot 5)$$

In above formulae, h denotes [Planck's constant]/$2\pi$ (Dirac constant), $e_0$ denotes the quantum of electricity, me is the mass of an electron, N denotes the number of atomic nucleuses composing the macromolecule, n denotes the number of electrons composing the macromolecule, t denotes time, Ma denotes the mass of an a-th atomic nucleus, Ra denotes a three-dimensional coordinate of the a-th atomic nucleus, Qa denotes a net atomic charge of the a-th atomic nucleus which is based on Mulliken's population analysis as well as a shielding effect by electrons surrounding the nucleus, rj denotes a three-dimensional coordinate of a j-th electron, and σj denotes a spin coordinate of the j-th electron.

Then using Born-Oppenheimer approximation, an atomic interaction part only is extracted from the equation. Firstly the Born-Oppenheimer approximation is used to assume that the wave function satisfying (A•2) can be approximated as in the following (A•6).

[Math. 22]

$$\Psi \approx \Psi_{nucl}(R_1, \cdots, Ra, \cdots, R_N, t) \cdot \Psi_{el}(\cdots, rj, \cdots, \sigma j, \cdots, Ra, \cdots, t) \quad (A\cdot 6)$$

Substituting (A•6) into (A•2), followed by transformation of the resultant can lead to the separation into the equation including Ψnucl only and the equation including Ψel only as in (A•7).

[Math. 23]

$$\frac{\left\{i\hbar\frac{\partial}{\partial t} - H_{nucl}\right\}\Psi_{nucl}}{\Psi_{nucl}} = -\frac{\left\{i\hbar\frac{\partial}{\partial t} - H_{el}\right\}\Psi_{el}}{\Psi_{el}} = W(R_1, \ldots, R_N, t) \quad (A\cdot 7)$$

(A•7) represents the values having equality as $W(R_1, \cdots, R_N, t)$. Based on (A•7), the following equation (A•8) can be obtained, which includes Ψnucl only, and this equation represents the atomic interaction.

[Math. 24]

$$i\hbar\frac{\partial}{\partial t}\Psi_{nucl}(R_1, \ldots, R_N, t) = \{H_{nucl} + W\}\Psi_{nucl}(R_1, \ldots, R_N, t) \quad (A\cdot 8)$$

In (A•8), $W(R_1, \cdots, R_N, t)$ includes all influences of optimized electron orbitals.

Next, a part of the equation corresponding to normal vibration of a specific atomic group that interacts with external electromagnetic waves is extracted from (A•8). Prior to this, a specific normal vibration part is extracted beforehand based on the analysis result of the vibration by a quantum chemistry simulation program. The result shows that stretching in the bonding direction of the center nucleus C and the surrounding hydrogen nucleus H in the specific atomic group corresponds to a sort of the normal vibration. Therefore the equation relating to group vibrations generated in this specific atomic group is extracted from (A•8). In the following calculation example of group vibrations, the relational expression to calculate the wavelength value of the absorption band of a n-th overtone for stretching is derived. The below-described or similar method can be extended to derive the relational expressions for deformations, combinations or the like.

In the following description, C denotes the center atom in a specific atomic group. That is, C represents the central atom. The center atom C in a specific atomic group is not limited to carbon atoms, which may be nitrogen atoms or oxygen atoms. The following assumes that this specific atomic group has a structure including such a center atom C and n pieces of hydrogen atoms surrounding the center atom, and these atoms are covalently bonded. In another example, one or more hydrogen atoms among these n pieces of hydrogen atoms may be hydrogen-bonded with a predetermined atom (or ion) other than in the target atomic group. In another example, a predetermined atom (or ion) other than in the target atomic group may not be hydrogen-bonded, but may be close to one or more hydrogen atoms.

Figure 35:
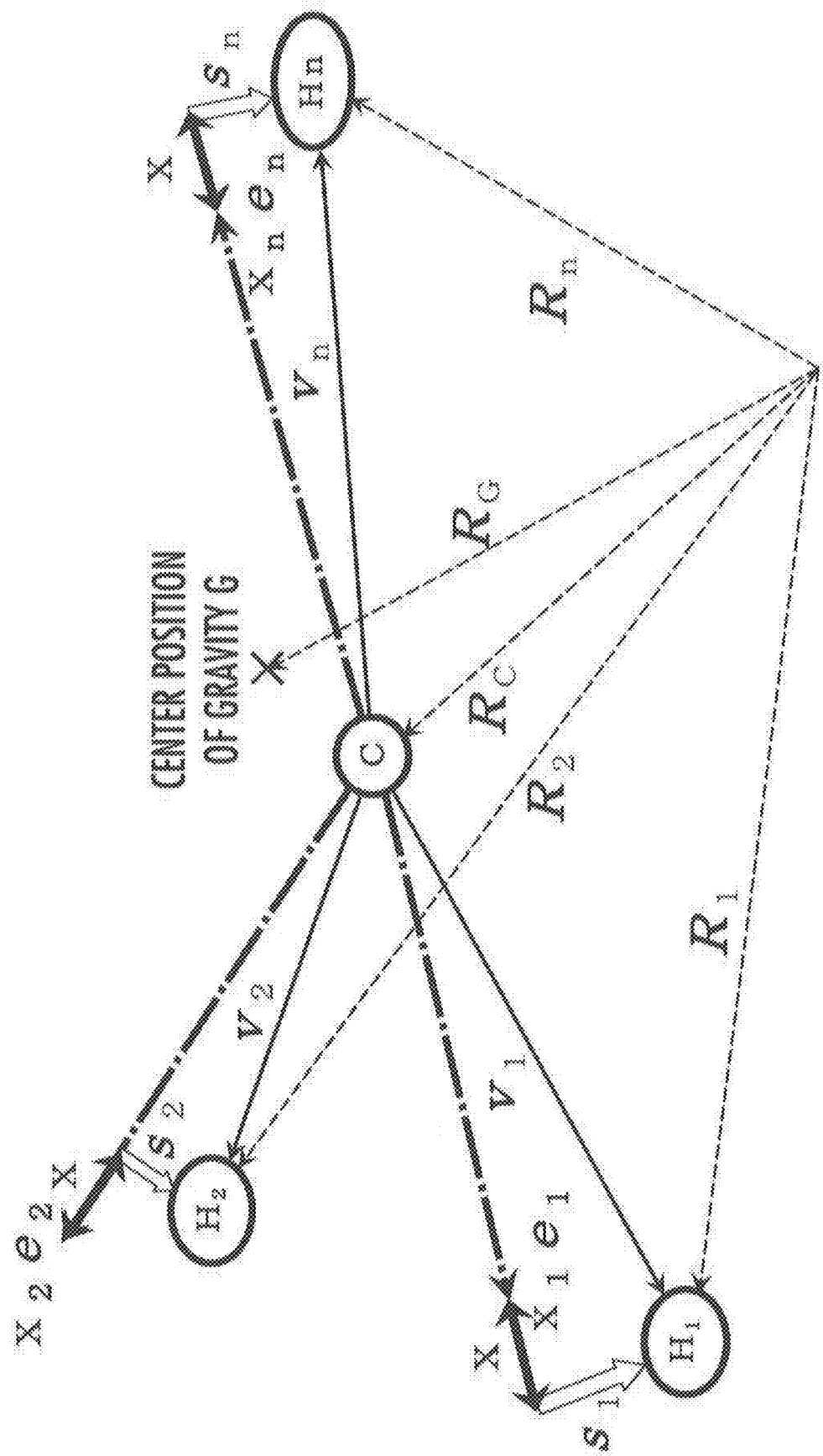
FIG. 35 shows position vectors of hydrogen atomic nucleus composing a specific atomic group.

FIG. 35 shows position vectors of the atoms composing the specific atomic group —CHn. In this drawing, $R_C$ denotes the position vector located at the position of the nucleus of the center atom C, and Ra denotes the position vector located at the position of the nucleus of the a-th hydrogen atom. $M_C$ denotes the mass of the center atom C and $M_H$ denotes the mass of one hydrogen atom. As shown in FIG. 35, the vector from the position of the nucleus of the center atom C to the position of the nucleus of the i-th hydrogen atom is shown as follows.

$$v_a = Ra - R_C \quad (C\cdot 1)$$

Then the following equation can be obtained from (C•1).

[Math. 25]

$$\sum_{a=1}^{N} Ra = \sum_{a=1}^{n} (R_C + v_a) = nR_C + \sum_{a=1}^{n} v_a \quad (C\cdot 2)$$

The position vector $R_G$ to show the center position of gravity of this specific atomic group is represented as follows.

[Math. 26]

$$R_G = \frac{M_C \cdot R_C + M_H\left(\sum_{a=1}^{n} Ra\right)}{M_C + nM_H} \quad (C\cdot 3)$$

Therefore substitution of (C•2) into (C•3) leads to the following relationship.

[Math. 27]

$$(M_C + nM_H)R_G = (M_C + nM_H)R_C + M_H\left(\sum_{a=1}^{n} v_a\right) \quad (C\cdot 4)$$

Next, the vector from the position of the nucleus of the center atom C to the position of the nucleus of the a-th hydrogen atom of the specific atomic group having a minimum total energy is defined as "$x_a e_a$", where $e_a$ denotes unit vector. Then the following relationships can be defined from FIG. 35:

$$v_1 \equiv (x_1 + x)e_1 + s_1 \quad (C\cdot 5); \text{ and}$$

$$v_a \equiv (x_a \pm x)e_a + s_a (2 \leq a \leq n) \quad (C\cdot 6).$$

In (C•5) and (C•6), x denotes deviation of the distance from the position of the nucleus of the center atom C to the position of the nucleus of the a-th hydrogen atom of the specific atomic group from such a distance when the specific atomic group as a whole has a minimum total energy.

In group vibrations in a specific atomic group, all of hydrogen atoms of this atomic group vibrate in conjunction with each other. In the example of the present embodiment, such a vibration state in conjunction with each other is approximated with the same parameter "x". According to classical mechanics, all of the hydrogen atoms are not always the same in the deviation during group vibration. A component of a difference from x for each hydrogen atom is internalized into "$s_i$" in (C•5) and (C•6).

The following description for the calculation example of group vibrations derives the expression to calculate the wavelength value of the absorption band of a n-th overtone for stretching. That is, when ± in (C•6) is +, this represents symmetrical stretching. When ± is −, this represents asymmetrical stretching or degenerate stretching.

Above Section 5.1 and Section 5.2 describe light absorption and light scattering that are generated when electric dipole moment localized in the target 10 vibrates (or transits to an exited state). When all of the hydrogen atoms move in conjunction by x from the state of all nuclei located at the positions where the specific atomic group as a whole has a minimum total energy (i.e., when $s_a=0$ holds for all of i), the electric dipole moment in the atomic group can be represented as follows relative to the center position of gravity $R_G$.

[Math. 28]

$$\mu_x \equiv Q_C(R_C - R_G) + \sum_{a=1}^{n} Qa(Ra - R_G)\Big|s_a = 0 \quad (C\cdot 7)$$

This (C•7) can be transformed as follows.

[Math. 29]

$$Q_C R_C + \sum_{a=1}^{n} QaRa = \mu_x + Q_C R_G + \left(\sum_{a=1}^{n} Qa\right) R_G \quad (C\cdot 8)$$

This (C•8) where "$s_a=0$" is substituted into the third term on the right side of (A•3). Then, the term on the interaction between the atomic group and the external electromagnetic field can be represented as follows.

[Math. 30]

$$\left\{Q_C(E\cdot R_C) + \sum_{a=1}^{n} Qa(E\cdot Ra)\right\}\exp(-i2\pi vt) = \\ \left\{(E\cdot \mu_x) + \left(Q_C + \sum_{a=1}^{n} Qa\right)(E\cdot R_G)\right\}\exp(-i2\pi vt) \quad (C\cdot 9)$$

(C•9) represents the approximation under the condition of "$s_a=0$". To improve the accuracy of approximation, the terms including vector "$s_a$" in (C•5) and (C•6) may be added to (C•9). However, since variable separation is performed described later, influences from such an operation are internalized into the potential function V(x). Therefore the relational expression derived finally will be the same in any case. Therefore for simplified explanation, the following describes the transformation of expressions based on the approximation of (C•9).

According to classical mechanics, the total kinetic energy in this specific atomic group can be represented as follows.

[Math. 31]

$$T = \frac{M_C}{2}\left(\frac{dR_C}{dt}\right)^2 + \frac{M_H}{2}\sum_{a=1}^{n}\left(\frac{dRa}{dt}\right)^2 \quad (C\cdot 10)$$

The substitution of (C•1) and (C•4) to (C•6) into (C•10), followed by deformation leads to the following.

[Math. 32]

$$T = \frac{M_C + nM_H}{2}\left(\frac{dR_G}{dt}\right)^2 - \\ \frac{M_H^2}{2(M_C + nM_H)}\left(\sum_{a=1}^{n}\frac{dv_a}{dt}\right)^2 + \frac{M_H}{2}\sum_{a=1}^{n}\left(\frac{dv_a}{dt}\right)^2 \quad (C\cdot 11)$$

The following relationship is used for the second term on the right side of (C•11).

[Math. 33]

$$\left(\sum_{a=1}^{n}\frac{dv_a}{dt}\right)^2 = \sum_{a=1}^{n}\left(\frac{dv_a}{dt}\right)^2 + 2\sum_{a=1}^{n}\sum_{b>a}\left(\frac{dv_a}{dt}\right)\left(\frac{dv_b}{dt}\right) \quad (C\cdot 12)$$

Then, this expression is approximated as follows.

[Math. 34]

$$\left(\frac{dR_G}{dt}\right)^2 \gg \frac{2M_H^2}{(M_C + nM_H)^2}\sum_{a=1}^{n}\sum_{b>a}\left(\frac{dv_a}{dt}\right)\left(\frac{dv_b}{dt}\right) \approx 0 \quad (C\cdot 13)$$

Then, (C•11) can be approximated as follows.

[Math. 35]

$$T \approx \frac{M_C + nM_H}{2}\left(\frac{dR_G}{dt}\right)^2 + \frac{M_H}{2}\left(1 - \frac{M_H}{M_C + nM_H}\right)\sum_{a=1}^{n}\left(\frac{dv_a}{dt}\right)^2 \quad (C\cdot 14)$$

The second term on the right side of (C•14) can be as follows based on (C•5) and (C•6).

[Math. 36]

$$\left(\frac{dv_a}{dt}\right)^2 = \left(\frac{dx}{dt}\right)^2 \pm 2\frac{dx}{dt}\left(e_a \cdot \frac{ds_a}{dt}\right) + \left(\frac{ds_a}{dt}\right)^2 \quad (C\cdot 15)$$

According to the analysis result for the vibration from a quantum chemistry simulation program, the group vibration corresponding to normal vibration often has the relationship of "$e_a \cdot d s_a/dt \approx 0$".

Therefore substitution of this approximation into (C•15) can change (C•14) as follows.

[Math. 37]

$$T \approx \frac{M_C + nM_H}{2}\left(\frac{dR_G}{dt}\right)^2 + \frac{Mx}{2n}\left(\frac{dx}{dt}\right)^2 + \frac{Mx}{2n}\sum_{a=1}^{n}\left(\frac{dv_a}{dt}\right)^2 \quad (C\cdot 16)$$

The condition to satisfy this approximation is examined in details in Section 7.3.

[Math. 38]

$$Mx \equiv nM_H\left(1 - \frac{M_H}{M_C + nM_H}\right) \quad (C\cdot 17)$$

This expression represents reduced mass relating to group vibration in the atomic group.

The first term on the right side of (C•16) represents kinetic energy of the center-of-mass system $R_G$. The second term represents the kinetic energy corresponding to the approximated group vibration. The third term represents the kinetic energy corresponding to movements other than them. That is, (C•16) shows that the total sum of the kinetic energy of the atomic nuclei of the specific atomic group can be divided into the kinetic energy for the center-of-mass system, the group vibration and the others.

Quantization of the kinetic energy corresponding to group vibration shown in (C•16) and a part of the first term on the right side of (A•3) can be rewritten as follows.

[Math. 39]

$$-\frac{\hbar^2}{2M_C}\Delta_C - \frac{\hbar^2}{2M_H}\sum_{a=1}^{n}\Delta a = \quad (C\cdot 18)$$

$$-\frac{\hbar^2}{2(M_C+nM_H)}\Delta_G - \frac{\hbar^2}{2Mx}\frac{\partial^2}{\partial x^2} - \frac{n\hbar^2}{2Mx}\sum_{a=1}^{n}\Delta s_a$$

The reason for such quantization is described in Patent Literature 3.

Next, approximation as $x_a \gg |s_a|^2 \approx 0$ in (C•5) and (C•6) leads to the following transformation/approximation of a part of the second term on the right side of (A•3).

[Math. 40]

$$\frac{e_0^2}{4\pi\varepsilon_0}\sum_{a=1}^{n}\frac{Z_a \cdot Z_C}{|R_a - R_C|} = \quad (C\cdot 19)$$

$$\frac{1}{4\pi\varepsilon_0}\sum_{a=1}^{n}\frac{Q_C Q_a}{|v_a|} \approx \frac{Q_C}{4\pi\varepsilon_0}\left(\frac{Q_1}{x_1 + x} + \sum_{a=2}^{n}\frac{Q_a}{x_a \pm x}\right)$$

Then, the rightmost side of (A•7) is approximated as follows.

$$W(R_1, \ldots, R_N, t) \approx W_{X(X)} + W_{OTHER}(R_1, \ldots, R_{N-n-1}, R_G,$$
$$s_1, \ldots, s_n, t) \quad (C\cdot 20)$$

The right side of (A•8) is transformed as follows.

$$H_{nucl} + W \approx H_X + H_{OTHER} \quad (C\cdot 21)$$

Then the following equation can be obtained from (C•9), (C•18) and (C•19).

[Math. 41]

$$Hx = -\frac{\hbar^2}{2Mx}\frac{\partial^2}{\partial x^2} + \quad (C\cdot 22)$$

$$\frac{Q_C}{4\pi\varepsilon_0}\left(\frac{Q_1}{x_1 + x} + \sum_{a=2}^{n}\frac{Q_a}{x_a \pm x}\right) + Wx - (E \cdot \mu_x)\exp(-i2\pi\nu t)$$

Similarly the details of $H_{OTHER}$ can be given by the following expression.

[Math. 42]

$$H_{OTHER} = -\sum_{a=1}^{N-n-1}\frac{\hbar^2}{2Ma}\Delta a - \frac{\hbar^2}{2(M_C + nM_H)}\Delta_G - \quad (C\cdot 23)$$

$$\frac{n\hbar^2}{2Mx}\sum_{a=1}^{n}\Delta s_a + W_{OTHER} + \frac{e_0^2}{4\pi\varepsilon_0}\sum_{Ra-Rb=v_t}\frac{Za \cdot Zb}{|Ra - Rb|} -$$

$$\left\{\left(Q_C + \sum_{a=1}^{n}Q_a\right)(E \cdot R_G) + \sum_{a=1}^{N-n-1}Qa(E \cdot Ra)\right\}\exp(-i2\pi\nu t)$$

The wave function described in (A•6) is assumed as follows.

[Math. 43]

$$\Psi_{nucl}(R_1, \cdots, Ra, \cdots, R_N, t) \approx \phi x \Psi x(x) \cdot \Psi_{OTHER}$$
$$(R_1, \cdots, R_{N-n-1}, R_G, s_1, \cdots, s_n, t) \quad (C\cdot 24)$$

Then, the variables can be separated as follows.

[Math. 44]

$$\frac{\{i\hbar\frac{\partial}{\partial t} - Hx\}\phi_X}{\phi_X} = -\frac{\{i\hbar\frac{\partial}{\partial t} - H_{OTHER}\}\phi_{OTHER}}{\phi_{OTHER}} = W^*(x) \quad (C\cdot 25)$$

Then (C•22) and (C•25) are approximated as follows.

[Math. 45]

$$\frac{Q_C}{4\pi\varepsilon_0}\left(\frac{Q_1}{x_1+x} + \sum_{a=2}^{n}\frac{Q_a}{x_a \pm x}\right) + Wx + W^*(x) \approx \kappa_2 x^2 + \kappa_3 x^3 + \kappa_4 x^4 \quad (C\cdot 26)$$

Then, the following Schrödinger equation can be derived from the expressions (C•22) and (C•24) through (C•26), which describes the group vibration.

[Math. 46]

$$i\hbar\frac{\partial}{\partial t}\phi_X = \qquad (A\cdot 27)$$
$$\left\{-\frac{\hbar^2}{2M_X}\frac{\partial^2}{\partial x^2} + \kappa_2 x^2 + \kappa_3 x^3 + \kappa_4 x^4 - (E\cdot\mu)\exp(-i2\pi\nu t)\right\}\phi_X$$

When the group vibration in a specific atomic group is given by (A•27), the equation solution can be derived as follows. The following also shows numerical presentation of the wavelength value of the absorption band corresponding to this.

Firstly, the wave function $\psi_X$ when "$\kappa_3=\kappa_4=E=0$" is defined as follows.

[Math. 47]

$$\varphi_X(x,t)=\exp(-i\underline{\varepsilon}_m t/\hbar)|\underline{m}\rangle \qquad (A\bullet 28)$$

Substitution of this (A•28) and "$\kappa_3=\kappa_4=E=0$" into (A27) can lead to the transformation into the equation of harmonic vibration.

[Math. 48]

$$\left\{-\frac{\hbar^2}{2M_X}\frac{\partial^2}{\partial x^2} + \kappa_2 x^2\right\}|\underline{m}\rangle = \underline{\varepsilon}_m|\underline{m}\rangle \qquad (A\cdot 29)$$

Then, the following equation is defined.

[Math. 49]

$$\beta \equiv \sqrt{2M_X\kappa_2}/\hbar \qquad (A\bullet 32)$$

Then, the solution of (A29) will be given by the following as described in Patent Literature 3.

[Math. 50]

$$|\underline{m}\rangle = \left(\frac{\beta}{\pi}\right)^{1/4}\sqrt{(2\beta)^m m!}\exp\left[-\frac{\beta}{2}x^2\right]\sum_{0\le 2J\le m}\left[-\frac{1}{4\beta}\right]^J \frac{x^{m-2J}}{J!(m-2J)!} \qquad (A\cdot 30)$$

[Math. 51]

$$\underline{\varepsilon}_m = \left(\frac{2\kappa_2}{\beta}\right)\left(m+\frac{1}{2}\right) \qquad (A\cdot 31)$$

Patent Literature 3 does not derive the equation for group vibration. Advantageously, the reduced mass Mx defined in Patent Literature 3 is simply changed into (C•17), whereby the expression (mathematical presentation) in Patent Literature 3 can be used as it is. Therefore for the solution of (A•27) as the Schrödinger equation to describe group vibration, the description in Patent Literature 3 is cited in the following.

Prior to the derivation of the final solution of (A27) that shows anharmonic vibration based on (A•30) and (A•31), the following finds the solution of the wave function in (A•27) when E=0. Specifically, the term "$\kappa_3 x^3+\kappa_4 x^4$" in (A27) is regarded as a sufficiently small perturbation term. Then, based on (A30) showing the solution of the harmonic-vibration equation, the perturbation solution is derived.

As described in Patent Literature 3, the eigen value of energy $\varepsilon_m$ for anharmonic vibration is given by the following (A38).

[Math. 52]

$$\varepsilon_m \cong \underline{\varepsilon}_m + \langle\underline{m}|\kappa_3 x^3 + \kappa_4 x^4|\underline{m}\rangle = \qquad (A\cdot 38)$$
$$\frac{2\kappa_2}{\beta}\left(m+\frac{1}{2}\right) + \frac{3\kappa_4}{4\beta^2}(2m^2 + 2m + 1)$$

(A38) shows that the eigen value of energy £m for anharmonic vibration depends on $\kappa_4 x^4$ term in (A27) only and is independent of $\kappa_3 x^3$ term. The wave function $|m\rangle$ can be given as follows.

[Math. 53]

$$|\underline{m}\rangle \cong \sum_u g_{mu}|\underline{u}\rangle \qquad (A\cdot 39)$$

Then, the following relationship holds.

[Math. 54]

$$g_{mu} = \frac{\langle\underline{u}|\kappa_3 x^3 + \kappa_4 x^4|\underline{m}\rangle}{\underline{\varepsilon}_m - \underline{\varepsilon}_u}, (u \ne m) \qquad (A\cdot 40)$$

See Patent Literature 3 for the details in (A•39).

A necessary amount of energy $h_{\nu_m}$ at the time when an energy level $\varepsilon_0$ is shifted to $\varepsilon_m$ is expressed by:

[Math. 55]

$$h\nu_m = \varepsilon_m - \varepsilon_0 = \frac{2\kappa_2}{\beta}m + \frac{3\kappa_4}{2\beta^2}(m^2+m) \qquad (A\cdot 60)$$

Accordingly, the following relationships hold from (A 60).

[Math. 56]

$$\frac{2\kappa_2}{\beta h} = 2\nu_2 - \nu_3 = 2\nu_1 - \frac{\nu_3}{3} \qquad (A\cdot 61)$$

[Math. 57]

$$\frac{3\kappa_4}{2\beta^2 h} = \frac{\nu_3}{3} - \frac{\nu_2}{2} = \frac{\nu_3}{6} - \frac{\nu_1}{2} \qquad (A\cdot 62)$$

where $\nu_1$, $\nu_2$ and $\nu_3$ denote frequencies of the fundamental vibration, the 1st overtone, and the 2nd overtone. With the use of (A•60) to (A•62) thus obtained, a value of a wavelength $\lambda_m$ (a frequency $v_m$) of a (m−1)th overtone can be estimated from the frequencies $v_1$, $v_2$, and $v_3$ of the fundamental vibration, the 1st overtone, and the 2nd overtone of the anharmonic vibration.

Comparison between the calculation based on the theoretical formula and the actual measurement shows that the result from the theoretical formula tends to be a bit smaller (in the range of 10 to 30% as the wavelength value). Accordingly when the theoretically predicted value and the experimental value are compared for the wavelength value of the absorption band of group vibration in the specific atomic group, the calculated theoretical value may be multiplied by a predetermined compensation coefficient, which then may be compared with the experimental value.

Section 7.3 Signification of Analyzing Group Vibration in Atomic Group

Conventionally a method for analyzing anharmonic vibration in a diatomic molecule (two-body system) has been known. In one specific example of the method, the motion in a diatomic molecule is separated into central motion of gravity or translation motion and relative motion. For this relative motion, an equation similar to (A•27) can be derived, where x denotes the deviation between the two atoms.

On the contrary, since group vibration is a many-body system having three or more targets (atomic nuclei) to be analyzed, its degree of freedom (the number of variables required for the analysis) increases considerably, and so the analysis is very complicated. Therefore no method of analyzing the characteristics of group vibration easily has been available.

As described in Section 5.2, biological molecules composing an organic polymer or a living body include many atomic groups including hydrogen atoms, i.e., a center atom, such as a carbon atom, an oxygen atom, or a nitrogen atom and hydrogen atoms surrounding the center atom are covalently bonded.

As described in Patent Literature 3, the activity in a living body, such as a biological reaction or a catalytic action, often occurs via hydrogen bond. It has been predicted theoretically that when a hydrogen-bonding reaction occurs temporarily between a hydrogen atom in the specific atomic group and another atom or another ion, the wavelength value of the corresponding absorption band also temporarily changes.

Accordingly a simplified method of theoretically analyzing group vibration in an atomic group can improve the accuracy of theoretic prediction for a change in wavelength of the absorption band and so improve the matching with experimental data.

The analysis result of normal vibration in an atomic group from a quantum chemistry simulation program shows that a plurality of hydrogen atoms composing the atomic group move in conjunction with each other. For instance, in all of the deformation, symmetrical stretching, asymmetrical stretching, and degenerate stretching, all of the hydrogen atoms composing the atomic group move in conjunction with each other.

As indicated with "±" in (C•6), each hydrogen atom in such stretching modes has a different moving direction. Note here that the (absolute value) of the deviation x from the position having minimum total energy is approximated as the same among all of the hydrogen atoms. Then, "$s_a$" denotes an error that actually occurs from the approximation for each hydrogen atom. In this way, individual motions of the hydrogen atoms also are considered to avoid easy approximation or assumption.

The relational expression is transformed (expanded) while adding some approximations. As a result, the present inventors found that, as shown in (C•16), the motion of all of the atoms composing an atomic group can be independently separated into "central motion of gravity", "the motion including common deviation x only" and "the motion of an error component $s_a$", i.e., the terms including corresponding variables can be mutually linearly-added. Such separation into the common deviation x and the error $s_a$ of the movement of each hydrogen atom in the relational expression enables separation of variables as in (C•25). As a result, a simple equation can be derived as in (A•27), which describes group vibration in an atomic group.

Additionally a calculation target (polyatomic molecule), which originally requires a motion analysis in a many-body system, can be analyzed with greatly reduced labor by an intensive analysis with one-dimensional equation of (A•27). To enable such an intensive one-dimensional analysis, the relational expression of (C•17) on reduced mass is very efficient. That is, these expressions intensively contain the information on the individual motions in a many-body system as follows:

1] the number n of hydrogen atoms in the specific atomic group in (C•17);

2] "±" in (C•6) that shows the corresponding type of stretching mode (polarity of positive or negative); and 3] values of the 2nd to 4th coefficients $\kappa_2$ to $\kappa_4$ of the potential part in (A•27).

The theoretical basis for such intensive analysis with one-dimensional equation needs that the approximation in (C•16) holds. This assumes that the condition of "$e_a \cdot d_{sa}/dt \approx 0$" holds. The following describes the range where such a condition holds. For such a condition, the following states are considered:

a] an atomic group has an instable state in water;

b] an atomic group has a stable structure and is in a static state that does not include any reaction (activity); and c] an atomic group has a dynamic state that may involve a temporal status change, such as a reaction and activity of the living body.

The situation [a] is examined as follows. The present inventors acknowledge that an atomic group having an oxygen atom as a center atom C is relatively instable in water. The experimental empiricism of the present inventors shows that a hydrogen atom in the "oxygen atom-hydrogen atom" bonding is highly likely substituted with a hydrogen atom in water. Although the method of Section 7.4 can give a theoretical predictive value, a simulation result of an atomic group having an oxygen atom at the center atom C may have a bit degraded reliability.

Similarly the experimental empiricism shows that one hydrogen atom H in an atomic group having the structure of —$NH_3^+$(N is a nitrogen atom) is highly likely liberated. This means that a simulation result for this structure also does not have high reliability.

Next, an atomic group having the structure of —$NH_n$ in $1 \leq n \leq 2$ is examined in the following. Many documents have reported the experiment to substitute a hydrogen atom in such a structure into deuterium. According to the documents, however, letting the structure stand one or two days is required to end the substitution. Therefore in the case of an experiment to end in a short time, its —$NH_n$ structure ($1 \leq n \leq 2$) is stable to some extent in water.

Meanwhile, an atomic group having a carbon atom as the center atom C is considered very stable.

In conclusion, for [a], the reliability of the simulation result depends on the types of center atom C in the atomic group.

Next, the following examines [b]. According to detailed examination on the analysis result for vibration from a quantum chemistry simulation program, in the group vibration corresponding to one type of normal vibration in a polymer, all hydrogen atoms of the specific atomic group vibrate in conjunction with each other. All of such hydrogen atoms of the atomic group often have a similar amplitude value of the vibration. This is the reason why the hydrogen atoms H that are placed in the atomic group having the structure of —CHn (center atom C is a carbon atom, a nitrogen atom, or an oxygen atom) have a relatively symmetrical structure.

In one very unique example, i.e., in one atomic group having a special sequence, a specific hydrogen atom only may have an amplitude value of the vibration that is different from other hydrogen atoms. In one example, the bonding direction between one hydrogen atom H and the center atom C may be the same as the vibrating-plane direction of the electric field E ((A•3)) of the external electronic field that induces the vibration. In general, however, the atomic groups —CHn in the target 10 are not oriented regularly, but are arranged in random directions. Therefore it is natural that, considering the average of all atomic groups, all of hydrogen atoms of a specific atomic group often have a similar amplitude value of the vibration.

Therefore when the atomic group having a stable structure in [a] is in the static state of [b], the simulation result attributed to the condition of "$e_a \cdot d_{sa}/dt \approx 0$" can be reliable to some extent.

Next, the following examines [c]. As described later in Section 7.3, when a living body is active internally (such as a biological reaction, a biochemical reaction or a catalytic reaction), hydrogen bonding may occur temporarily. In such a case, other atoms or other ions are close to one hydrogen atom in a specific atomic group.

In the atomic group having a relatively stable structure in water described in the above [a], the center atom C and surrounding hydrogen atoms H are covalently bonded, and so the interatomic distance (bond length) is relatively short. On the contrary, hydrogen-bonding distance with other atoms or other ions close to the hydrogen atom is relatively long. Therefore influences from the hydrogen-bonded hydrogen atoms H on the atomic vibration are limited to a perturbative effect.

Therefore when other atoms or other ions come close to the specific atomic group in the dynamic state of [c], the amplitude value of vibration for each hydrogen atom in the atomic group changes to some extent (due to the above perturbative effect) This case still satisfies the condition of "$e_a \cdot d_{sa}/dt \approx 0$".

The above results of examinations are summarized as follows. When a specific normal vibration (e.g., group vibration in a specific atomic group) generated at a specific region in a very complicated and huge polymer or living body is theoretically analyzed, the reliability of the analysis result depends on the type of atoms included in the structure causing the normal vibration, i.e., whether it includes "oxygen atom-hydrogen atom bonding" or "nitrogen atom-hydrogen atom bonding". This theoretical analysis result, however, is less influenced from whether the analysis target is in a static state or in a dynamic state. This result shows that the simplified theoretical analysis result obtained from the simulation described later in Section 7.4 can deal with the active state in the living body that changes overt time or a change thereof.

It is particularly important for the example of the present embodiment to enable the analysis of a huge molecule or composite body of a plurality of huge molecules having a complicated structure. That is, (Hamiltonian) $H_{nucl}$ described in (A•3) or (A•8) permits an enormous number of constituent atoms. Among such a huge molecule or composite body of a plurality of huge molecules, any atomic group to be analyzed can be selected. For the selected atomic group, the values of the 2nd coefficient $\kappa_2$ and the 4th coefficient $\kappa_4$ in (A•27) may be calculated by the method described in Section 7.4. Only this operation can predict the wavelength value of the relating absorption band by (A•32) and (A•38). (A•61) and (A•62) additionally may be used as needed.

The above describes the case of other atoms or other ions coming close to a specific atomic group during the activity of the living body (when a biological reaction or a catalytic action occurs, for example). When other atoms or other ions come close to a specific atomic group in this way, the wavelength value of the corresponding absorption band changes because the values of the 2nd coefficient $\kappa_2$ and the 4th coefficient $\kappa_4$ in (A•27) change due to the perturbative effect. Therefore a change of the wavelength of the corresponding to absorption band in this case also can be predicted theoretically by the method described in Section 7.4. That is, the active state of the living body can be predicted based on such a change of wavelength of the absorption band.

This method has another advantageous effect of enabling the identification of a structure in a functional bio-engineering product or the management of the manufacturing process described in Chapter 8.

The example of the present embodiment has been described above in Section 7.2 for expansion of numerical presentation (especially (C•5) and (C•6)) mainly by way of a change in internuclear bond length. Alternatively, the analysis in the present embodiment may be simplified about any structure or change in shape between the atoms composing the molecular. In this case, a relational expression similar to Section 7.2 may be expanded (transformed) instead of introducing (A•27), and a simplified equation may be introduced so as to correspond to another change (another variable). For instance, for deformation defining normal vibration in group vibration, a one-dimensional equation (having one variable) may be derived, considering a variation of a torsional angle between atoms composing a molecule to simplify the analysis.

Section 7.2 finally derives the equation (A•27) including only one variable x other than the time variable t to simplify the analysis. Alternatively a method for separating variables shown in (C•25) may be efficiently used to derive a plurality of independent equations at the same time, each equation including only one variable other than the time variable t.

When the plurality of independent equations each including a different variable holds at the same time, transition occurs at the same time among a plurality of different vibration modes. This state corresponds to the combination. The energy eigenvalue of the equation (A•27) including only one variable x is given by (A•38). For this combination, its energy level depends on the linear combination of the energy eigen values corresponding to their vibration modes. Then similarly to (A•60), the center wavelength value of the absorption band corresponding to the combination can be theoretically predicted.

Section 7.2 describes one example of the present embodiment about the simplified method for analysis of stretching. Additionally the method of expanding (transforming) the expression described in Section 7.2 may be modified, for example, by using torsional angle as the variable to be selected instead of internuclear bond length to derive the equation for analysis of deformation. Alternatively such expansion (transformation) of the expression may be extended so as to derive a plurality of independent equations each having a different independent variable by efficiently using variable separation. This enables the analysis of the combination.

Figure 36:
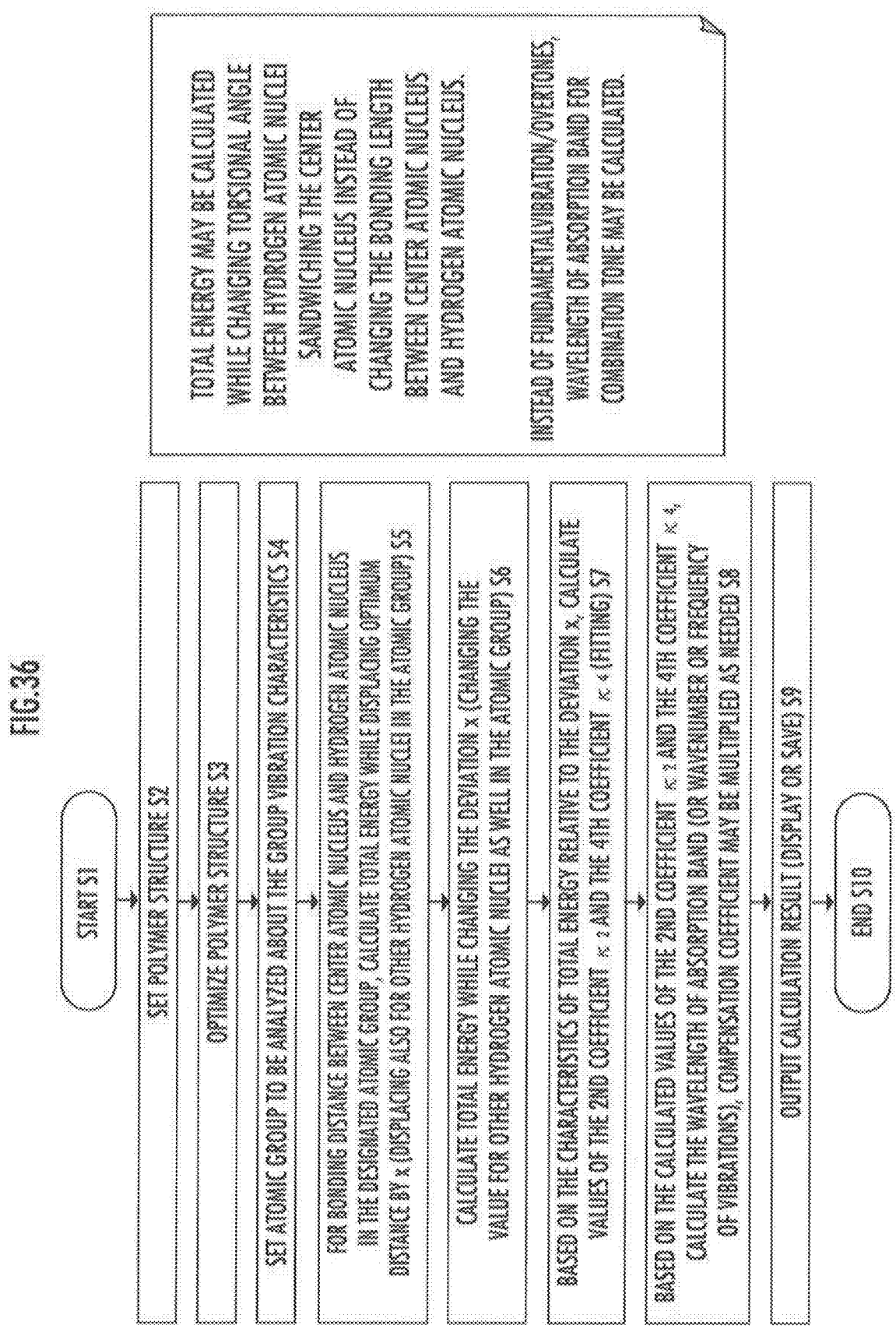
FIG. 36 describes a calculation method of group vibration in a specific atomic group by a quantum chemistry simulation program.

Section 7.4 Method for Simulating Absorption-Band Wavelength Belonging to Group Vibration Referring to FIG. 36, the following describes an example of the present embodiment enabling simplified analysis of the group vibration state using the combination of a quantum chemistry simulation program with (C•17), (A•27) or (A•60).

The analysis starts at S1, and at S2, the polymer structure (the arrangement of atoms composing the polymer) is set using a quantum chemistry simulation program. At S3, optimization routine is executed, which is included in a typical quantum chemistry simulation program.

As described in Section 7.3, the present embodiment enables the analysis of a huge polymer structure or a complicated composite body (structure) of these huge molecules about the structure or a reaction (active state or its change) at its local area (the area around a specific atomic group). Therefore, as shown in S4, the region to be analyzed about the local structure or a reaction (active state or its change) is designated. In one example, an atomic group to be analyzed about the group vibration characteristics may be designated.

To this end, a user may directly designate a target area. Alternatively, α region may be selected (configured) automatically. In this case, the user may designate the condition for setting an area beforehand, and the quantum chemistry simulation program may automatically find the area corresponding to the condition.

Specifically a user may designate the active area of a specific catalytic reaction or a biological reaction beforehand with the quantum chemistry simulation program. Then the quantum chemistry simulation program may automatically extract a specific hydrogen atom, and may select an atomic group including the hydrogen atom. This specific hydrogen atom may form hydrogen-bonding with other atoms or other ions during the catalytic reaction or the biological reaction.

At S4, a predetermined atomic group is set as the area to be analyzed about the vibration characteristics. Alternatively, a local area relating to any normal vibration in the polymer set at S2 may be set in the present embodiment. For instance, Patent Literature 3 designates two atoms involved in normal vibration in a polymer, and derives (A•27) as the equation to represent the normal vibration. This case, however, does not analyze the group vibration, and so the relationship expression showing the reduced mass is different from (C•17).

The structure in the atomic group set at S4 is optimized already at S3. That is, the distance (bond length) between the center nucleus in this atomic group and a surrounding hydrogen nucleus is optimized so that the total energy of the polymer can be minimum. Therefore the distance (bond length) between the center nucleus and the a-th hydrogen nucleus corresponds to "$x_a$" ($1 \leq a \leq n$) in (C•5) and (C•6).

In FIG. 36, after optimization of the polymer structure (S3), a local area (such as an atomic group) to be analyzed about the vibration characteristics is set (S4). Alternatively the order of these steps (the order of S3 and S4) may be reversed in the example of the present embodiment.

At the next step, the analysis of vibration characteristics in the atomic group (or a local area involved in any normal vibration) designated at S4 starts. The following describes a method of changing a bond length between two atoms (nuclei) in accordance with (A•27) in Section 7.2. Alternatively the torsional angle between two atoms (nuclei) sandwiching the center atom (nucleus) may be changed in the example of the present embodiment.

That is, in accordance with the calculation model of (C•5) and (C•6), the bond lengths of all hydrogen nuclei of the atomic group set at S4 and the center nucleus are changed (displaced) uniformly by x. Then at S5, the total energy of the polymer as a whole is calculated by the quantum chemistry simulation program. Whether to add or subtract x for the bond length of the a-th ($2 \leq a \leq n$) hydrogen atom, i.e., whether to use + or − of the sign "±" in (C•6) may change with the selected vibration mode to be analyzed, e.g., this includes symmetrical stretching, asymmetrical stretching, or degenerate stretching.

The absolute value of the deviation x is desirably smaller than "$x_a$" ($1 \leq a \leq n$) in (C•5) or (C•6). Therefore the deviation x set at S5 is preferably set in the range of ±0.1 Å to ±1.5 Å (desirably in the range of ±0.1 Å to ±1.0 Å).

Based on the characteristics of the change in total energy relative to the variation x of this bond length, the values of the 2nd coefficient $\kappa_2$ and the 4th coefficient $\kappa_4$ in (A•27) of Section 7.2 are estimated. To determine these two coefficients, a calculation result of total energy at only one point is insufficient for the deviation x. Therefore as shown in S6, the value of the deviation x has to be changed so as to calculate the total energy again in the present embodiment.

During this calculation, two points having the same absolute value |x| of the deviation and different polarities between positive and negative may be selected, and their total energy value may be calculated. Alternatively, additional two points having different absolute values |x| of the deviation and different polarities between positive and negative may be selected, and their total energy value may be calculated.

A larger number of the samples of the deviation x to calculate the total energy value (the frequency of calculation repeated to calculate the total energy while changing the deviation x) can improve the accuracy of fitting at S7.

At S7, based on the characteristics of the amount of change in total energy relative to the deviation x calculated at S5 and S6, the values of the 2nd coefficient $\kappa_2$ and the 4th coefficient $\kappa_4$ in (A•27) are calculated/fit. The fitting may be performed by the least-square approach, or may be performed by any other methods.

At S8, the values of the 2nd coefficient $\kappa_2$ and the 4th coefficient $\kappa_4$ obtained at S7 are used to theoretically calculate the wavelength of corresponding absorption band in accordance with (A•61) or (A•62). As described at the end of Section 7.2, the theoretically predicted result and the experimental value tend to have a difference of a certain ratio. To compensate this difference, a predetermined compensation coefficient may be multiplied as described at S8 as needed.

Finally the calculation result is displayed on the display or is output to store this in a recording medium, for example (S9), and then a series of theoretical vibration analysis ends (S10).

Section 8.4 in Chapter 8 briefly describes an example of the calculation of energy change when a hydrogen atom in an atomic group having specific hydrogen bonding is moved, and the involved change in absorption wavelength.

Chapter 8 Functional-Bio Material

Chapter 8 describes an application example of the target 10 in the present embodiment shown in FIGS. 1A to 1C.

Section 8.1 Functional-Bio Material

Section 2.4 describes an inorganic dielectric, an organic substance (highly-polymerized substance) or a living matter as an example of the target 10 of FIGS. 1A to 1C. The chapters before Chapter 8 mainly describe an "existing substance" as a specific example of the target 10. The present embodiment is not limited to the category of "existing substances" and may include a new substance as a specific example (application example) of the target 10. From such a viewpoint, Chapter 8 describes other application examples of the target 10.

As described in Chapter 5 and Chapter 7, the light (having less wave front aberration and less partial coherency/more partial incoherency) described in Chapters 3 and 6 is suitable to detect or measure the target 10 internally including an atomic group of —CHn. Therefore it is desirable that a new substance described as an application example of the target 10 includes such an atomic group of —CHn.

As described in Section 7.3, when other atoms or other ions temporarily come close to a hydrogen atom in a specific atomic group during the activity (such as biological reaction, biochemical reaction, or catalytic reaction) inside of a living body, then a wavelength of the corresponding absorption band may change. Therefore the structure of a living body or the biological activity can be suitably detected/measured with the light described in Chapter 3 and Chapter 6. Based on this, a functional bio-material is suggested as an application example of the target 10.

Such a functional bio-material in an application example of the present embodiment has affinity with nature as a typical attribute. Specific attributes are as follows:

1] each functional bio-material has a various unique function;

2] a functional bio-material unit does not exist alone in the existing natural world;

3] a functional bio-material is generated (manufactured) by using a part of the biological activity system or a mechanism of an existing living being in a similar manner.

4] a functional bio-material (including a material itself or its derivative or product) less influences the existing ecosystem or natural world;

5] both of the material itself or its derivative or product do not have independent proliferation potency under the existing natural environment, they do not have proliferation potency in the parasitic form to other living bodies) and;

6] when an existing living being eats such a material, it does not exert any conspicuous and unique function in the body other than nutritional support.

In addition to these attributes, the material may have at least one of the following attributes:

7] it has easy degradability after discarding (having a function of being degradable by microorganisms); and 8] during production (manufacturing), it does not generate waste that is difficult to be degraded, such as carbon dioxide.

Specific exemplary forms of the functional bio-material having these attributes may be used for a new industrial material (or raw material), unique food or a component having a unique function that does not exist in the existing natural world (corresponding to the attribute [2]).

Genetically-modified agricultural products are already available. Seeds obtained from these products, however, have independent proliferation potency under the existing natural environment, which do not satisfy the attribute [5]. Therefore even when a functional bio-material itself or its product (corresponding to seeds of genetically-modified agricultural products) in the present embodiment erroneously spills into the natural environment, there is no risk of disturbing the existing ecosystem (satisfying the attribute [4]).

Meanwhile, medical products have been developed using bio-techniques. Since these medical products are taken in the body for a unique function of therapeutic (healing) effect, medical products do not satisfy the attribute [6].

Many existing industrial plastic materials include carbon atoms or silicon atoms that are covalently bonded with a principal chain part, which are then repeatedly joined. Such a covalent-bonding part with carbon atoms or silicon atoms is strongly bonded, and so is hardly decomposed.

On the contrary, a peptide bonding part in protein is bonded more weakly than the covalently-bonding part, and so is easy decomposed due to the action of microorganisms. That is, a protein structure has easy degradability after discarding (satisfying the attribute [7]).

Chapter 9 describes the details of a method for generating (manufacturing) this functional bio-material. The following briefly describes the advantageous effects of the material in relation to the attribute [3].

To obtain a lot of sheep's wool, for example, a lot of labor and cost are necessary to raise sheep. On the contrary, a part of (similar) system or (similar) mechanism of the biological activity may be used, which includes the generation of amino acid by culturing a specific part only or using microorganisms, whereby a functional bio-material can be manufactured very efficiently.

Such a technique of developing or generating a functional bio-material using a part of (similar) system or (similar) mechanism of the biological activity is called "bio-engineering" in the system of the present embodiment.

Various kinds of proteins are known to have various unique functions corresponding to their conformations (satisfying the attribute [1]). Therefore the functional bio-material as an application example of the present embodiment may include amino acid. Therefore a functional bio-material as an application example of the present embodiment may be defined as a material (raw material, food or function component) containing amino acid at least partially and having a unique function.

Such a functional bio-material is not limited to the above definition and may be defined from another viewpoint. The above describes that a functional bio-material may contain amino acid at least partially. By considering the category of a functional bio-material based on such a viewpoint, a functional bio-material may include any artificial protein. In such a case, amino acid contained in artificial protein or its amino acid sequence or conformation may be controlled so as to have the unique function.

In the present embodiment, when a protein is different from various types of proteins existing naturally in amino acid sequence by 0.1% or more (desirably 1.0% or more), such a protein is called artificial protein. Many proteins have their unique conformations, and such a conformation greatly influences the unique function. Then when the amino acid sequence of the protein changes by even 0.1% (at least 1.0%), this conformation greatly changes. Therefore as described later in Section 8.2 or Section 8.3, in the present embodiment, a protein existing naturally may be changed in amino acid sequence by 0.1% or more (at least 1.0%) so as to change the conformation, so that artificial protein obtained may have the unique function.

The above described "functional bio-material containing amino acid at least partially" or "functional bio-material including artificial protein" necessarily does not have all of the attributes [1] to [6] as stated above. However, they desirably have affinity with nature.

Meanwhile, a functional bio-material of the present embodiment is not limited to just a final product, such as industrial materials/raw materials, food, or functional components, and may include the original material of such a product. A specific example of the original material included in a functional bio-material may include a cell having a nucleus that contains genome integrating generation information on the artificial protein. Then the genome of this cell is edited by known genome editing techniques, such as CRISPR (Clustered Regularity Interspaced Short Palindromic Repeats)/Cas9(CRISPR-Associated Protein 9), ZFN (Zinc Finger Nuclease) or TALEN (Transcription Activator-Like Effector Nuclease).

Gene information after such genome editing is once transferred to mRNA (Messenger Ribonucleic Acid), which is associated with the above [3], and then protein is synthesized with tRNA (Transfer Ribonucleic Acid). Therefore since such a genome in the cell has a storage function of information necessary to generate artificial protein having the unique function, such a genome may be included in the functional bio-material of the present embodiment. In addition to the function of storing information in genome, the cell has another function of generating (manufacturing) artificial protein in the cell.

The above described cell having a nucleus that contains a genome to record generation information on the artificial protein necessarily does not have all of the attributes [1] to [6] as stated above. Desirably such a cell does not have the form of seeds, fertilized eggs or viruses so as to satisfy the attribute [5], i.e., the material itself or its parasite form does not have independent proliferation potency under the existing natural environment.

Section 8.2 Classification of Functional-Bio Materials by their Ways to Exert Unique Functions FIG. 37 shows the classification of functional-bio materials of the present embodiment by their ways to exert the unique functions. Any functional-bio material or bio-engineering technique to generate the material has the unique interaction with the irradiated light 12 or the detection light 16 described in Chapter 3 or Chapter 6. Their specific parts for interaction or the details are written in the field of "optical detection targets" in FIG. 37. Using such irradiated light 12 or detection light 16, the structure of functional-bio materials can be analyzed and their manufacturing process can be managed using a change in the detection characteristics.

Following the description in Section 8.1, FIG. 37 shows examples of raw materials, components, food materials, enzymes or cells having their specific functions as the functional bio-materials. Alternatively functional-bio materials of the present embodiment may include any material that [2] does not exist already in the natural world, and that [3] can be generated (manufactured) by using a (similar) part of the biological activity system or a (similar) mechanism of an existing a living being.

For the purposes of illustration, FIG. 37 and Section 8.3 mainly describe the improvement of a fibroin structure having a fiber-like shape and included in hair as a specific example. Alternatively, the present embodiment may relate to the improvement of already existing any protein or polysaccharide.

As shown in FIG. 37, a functional-bio material of the present embodiment can exert their unique functions by the following ways:
  using a feature of conformation, including a change in amino acid sequence;
  substituting one type of monomer composing a polymer with another monomer;
  inserting or substituting a specific amino acid in a predetermined amino acid sequence;
  changing the structure of a predetermined active area in protein;
  giving a higher speed or higher performance to an enzyme or an existing enzyme to generate a new active area through hydrolysis or dehydrating condensation of a substrate;
  a cell having a nucleus that contains a genome to record amino acid sequence;
  a genome editing module or its carrier structure for performing a lot of genome editing operations efficiently; and
  producer cells of fibrous proteins.

Section 8.3 Examples of Functional-Bio Materials Having Functions Corresponding to their Amino Acid Sequence or Conformation The following describes a specific example corresponding to the list of FIG. 37. Section 8.3 describes how the functional-bio materials have their unique functions corresponding to "Different Conformations" and "Amino Acid Sequences" in the field of "Ways to have Functions" in FIG. 37. The descriptions in Section 8.3 are just one example, and any other methods to give functional-bio materials unique functions corresponding to "different conformations" and "amino acid sequences" may be used.

Firstly the following describes a functional-bio material that can have the unique function by changing the amino acid sequence of an existing protein so as to have a discriminative conformation.

A huge protein often has a part of the conformation that has a α-helix structure and a β-sheet structure. In this α-helix, a principal chain of amino acid defines a cylindrical structure while having a helical structure. Hydrogen bonding is formed along the longitudinal direction of this cylindrical structure and close to the surface of the lateral wall, and such hydrogen bonding keeps a certain degree of strength of the structure.

A β sheet has a structure like a many-layered pleated sheet like a folding screen, and hydrogen-bonding is generated in the sheet-layered direction to keep a certain degree of strength.

Then an absorption band occurs, which corresponds to the fundamental vibration, the first and the second overtones of stretching generated mainly from hydrogen atoms at these hydrogen-bonding areas. Based on the wavelength and the amount of light absorption at this absorption band, the conformation of the material can be expected to some extent. For a specific wavelength range of the absorption band generated at a hydrogen-bonding part, the first overtone has the range of 1.5 to 1.7 µm and the second overtone has the range of 1.0 to 1.2 µm. Note here that the distance (length) of hydrogen bonding in α-helix is a bit longer than in β-sheet, and so the wavelength at the corresponding absorption band is somewhat different between α-helix and β-sheet.

When a part of the hydrogen bonding in α-helix or β-sheet is cut due to a pressure applied externally or mechanical vibrations, the overall conformation changes. Using such a change, the material is used as a pressure sensor or a vibration sensor. This corresponds to "mechanical change in conformation" in the first line of FIG. 37. Based on the wavelength that changes in the amount of light absorption in the absorption band, the cutting part of the hydrogen bonding also can be expected.

A function-bio material that easily changes in conformation with temperatures can function as a thermosensitive sensor. This corresponds to "thermal change in conformation" in the second line of FIG. 37. The light-absorption characteristics change with such a temperature change as well for the same reason as above.

Fibroin is known as major components of silken threads of silkworms and cocoon filament of spiders. This is a special protein whose composition ratio of amino acids having small amino residues reaches 90%, glycine and alanine account for about 35% and about 27%, respectively, of the composition.

As shown in FIG. 38, fibroin existing naturally includes a β-sheet crystalline part 602 having a β-sheet structure and a non-crystalline part 604. Such a β-sheet crystalline part 602 accounts for about 40 to 50% (crystallinity) of the overall fibroin existing in the natural world. The curved line in the non-crystalline part 604 of FIG. 38 shows the principal chain of peptide-bonded amino acid.

Information on natural fibroin can be obtained from https://ja.wikipedia.org/w/index.php?title=フィブロイン&oldid=57333210.

When the hydrogen-bonding part of this β-sheet crystalline part 602 is irradiated with the irradiated light 12, the detection light 16 obtained from there has an absorption band with specific wavelengths corresponding to the hydrogen bonding of the β-sheet (the fundamental vibration, the first over tone, the second over tone and the combination of stretching). The wavelength of such an absorption band may be measured with the apparatus of FIG. 1A to FIG. 1C.

The amount of light absorption in the absorption band changes with the crystallinity. For instance, a decrease in crystallinity below 40% means a decrease in the amount of light absorption in the absorption band. An increase in crystallinity above 50% means an increase in the amount of light absorption. Therefore the crystallinity of fibroin can be quantitatively expected from the amount of light absorption at the corresponding absorption band that is measured from the detection light 16 from the fibroin.

Especially when near-infrared light described in Section 2.6 is used as the irradiated light 12, both of the absorption band belonging to the first overtone and the absorption band belonging to the second overtone of the stretching at the hydrogen-bonding part in the β-sheet can be detected at the same time. Then, the amount of light absorption at both of the absorption bands increases with an increase in the crystallinity (the amount of light absorption decreases with a decrease in crystallinity).

When an increase/decrease of the amount of light absorption is detected with only one wavelength region, the detection may include errors due to some disturbance noise. On the contrary, the present embodiment enables simultaneous measurement of the amount of light absorption at the absorption bands of a plurality of different wavelength regions (the wavelength value of the absorption band is smaller for the second overtone than for the first overtone), and the measurement accuracy of the crystallinity can be improved.

Figure 39B:
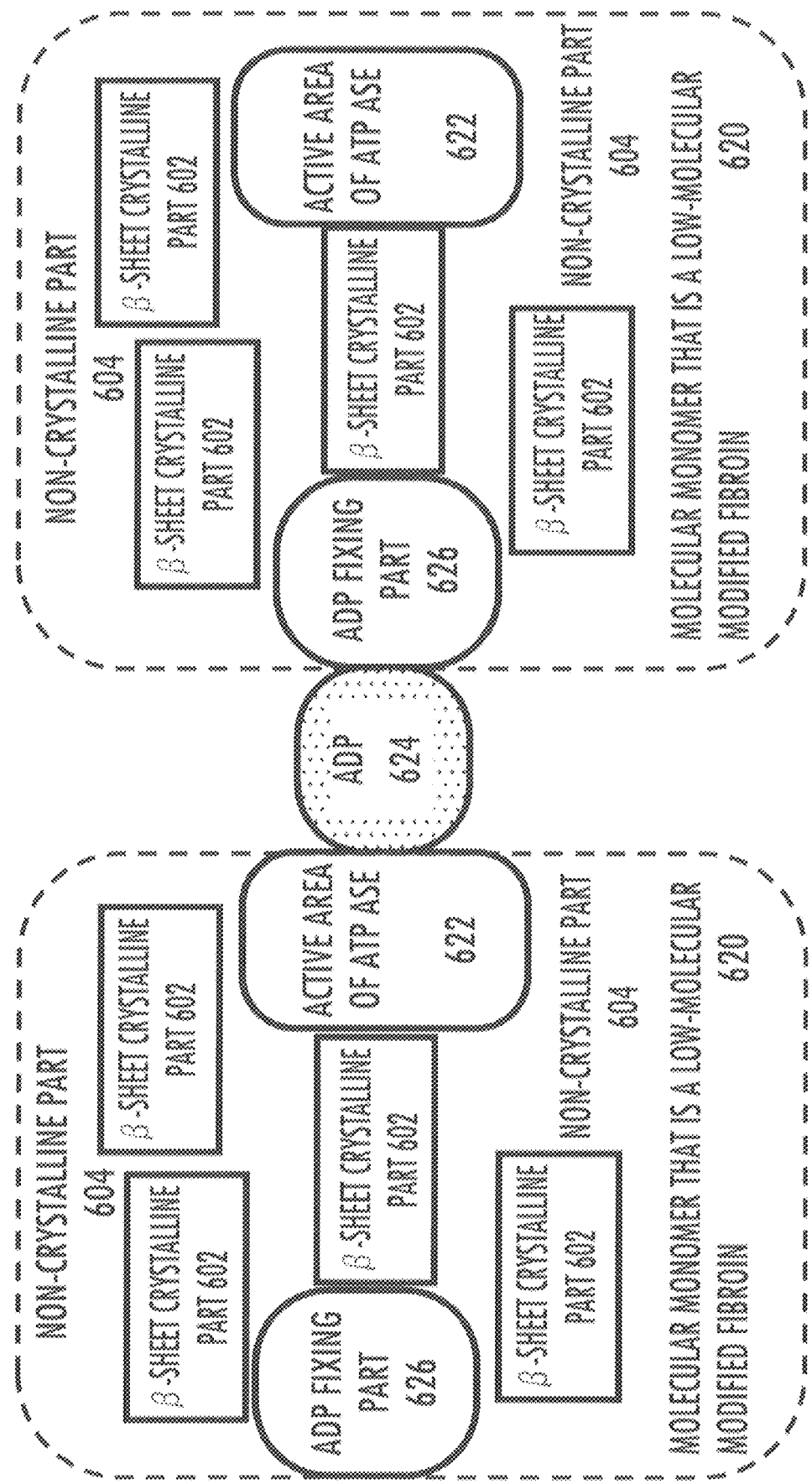
FIG. 39B shows an example (B) of a functional-bio material prepared by modifying fibroin.

FIG. 39A and FIG. 39B show examples of a functional-bio material prepared by modifying such natural fibroin. Both of them are based on the method briefly described at the end of Section 8.1. That is, amino acid sequence in an artificial protein is changed partially by genome editing. After transcribing this to mRNA, then protein is synthesized with tRNA (the details are described later in Section 8.5).

FIG. 39A(a) shows a structure having the crystallinity of modified fibroin that is 40% or less (desirably 35% or less), which corresponds to "Pleasant-touch soft material: reducing β-sheet crystallinity" in the third line of FIG. 37. This has lower ratio of hydrogen bonding of the β-sheet, and so the amount of light absorption at the corresponding absorption band is relatively low (for both of the first overtone and the second overtone).

The ratio of the β-sheet crystalline part 602 having a large strength (relatively hard) is low, and the ratio of non-crystalline part 604 is high. Therefore the material gives pleasant touch (texture) and is soft.

FIG. 39A(b) shows a structure having the crystallinity of modified fibroin that is 50% or more (desirably 55% or more), which corresponds to "rigid material, reinforcement material: increasing β-sheet crystallinity" in the fourth line of FIG. 37. This has higher ratio of hydrogen bonding of the β-sheet, and so the amount of light absorption at the corresponding absorption band is relatively high (for both of the first overtone and the second overtone).

The ratio of the β-sheet crystalline part 602 having a large strength (relatively hard) is high, and the ratio of non-crystalline part 604 is low. Therefore the material has high strength and rigidity, and is suitable for reinforcement purpose.

A method of using the absorption band obtained from the hydrogen-bonding part in α-helix or β-sheet is not limited to functional-bio materials having the structures of FIG. 39A (a) and (b), and may be used for checking of a structure in any functional-bio material internally having α-helix or β-sheet structure or for detection/measurement of a change in the structure.

FIG. 39A(c) shows the structure of adding amino acid having acid residue to the non-crystalline part 604 of modified fibroin, which corresponds to "containing acid residue" in the fifth line of FIG. 37. Such amino acid having acid residue typically has negative charge, and so easily reacts with other materials. Then, the charge amount is neutralized to reduce the reactivity with other materials for stabilized structure. To this end, as shown in FIG. 39A(c), a cation having positive charge is added to a carboxyl group 616 for esterification in the present embodiment. This cation is not limited to a sodium ion, which may be any cation.

The carboxyl group 616 contained in acidic residue amino acid has very high affinity with water. Therefore due to such acidic residue amino acid including cation added in the non-crystalline part 604, the resultant functional-bio material can have a very high water absorption rate.

Whether or the non-crystalline part 604 includes acidic residue amino acid with cation can be determined based on the presence or not of an absorption band at the wavelength value corresponding to the carboxyl group 616 (the second overtone or the first overtone of the stretching). The absorption band corresponding to the second overtone of the esterified carboxyl group exists in the wavelength region of 1.8 to 2.0 μm. Therefore detection light 16 from an artificial protein prepared to have the structure of FIG. 39A(c) may be checked whether any unique absorption band is observed or not in such a wavelength range. If no absorption band exists in such a wavelength range, it can be determined that no esterified acidic residue amino acid is included (the target artificial protein is not generated).

FIG. 39A(c) shows an example of integrating aspartic acid and cation 612 as the amino acid having acid residue. Alternatively, esterified (cation-added) glutamic acid may be integrated, for example.

Light in the above wavelength range may be used not only for the structure of FIG. 39A(c) but also for any functional-bio material including a carboxyl group for analysis about its structure and a change in the structure.

Since fibroin is a protein including more than ten types of amino acids, such fibroin has been developed to be used as nutraceutical foods. Fibroin, however, has a very large molecular weight of 350,000 to 370,000, and so has a problem for digestion absorption. Currently fibroin can be modified as oligopeptide that has a low molecular weight by enzymatic decomposition. However, the crunchy texture may be lost because it turns a powder form. In this way, this can lead to the problem of spoiling the texture.

FIG. 39B shows an example of the present embodiment to solve this problem. This corresponds to "oligopeptide bonding" in the sixth line of FIG. 37. That is, the texture like edible meat is provided by combining the powder forms, which often occurs in oligopeptide having a low molecular weight, so as to have the effect of improving the satisfaction of a user during eating.

Actin filament or myosin filament makes up a part of the major components of edible meat. The actin filament has a structure of bonding actin dimers with ADP and reinforcing the outside with tropomyosi. Note here that actin dimer is very small and an isolated actin dimer is in a powder form.

Referring to such an actin filament structure, a functional-bio material is prepared, which can give texture (during chewing) like edible meat to a low-molecular fibroin modified food. FIG. 39B shows an example of such a functional-bio material. Specifically at an end of the amino acid sequence in the molecular monomer 620 that is low-molecular modified fibroin, an ADP (Adenosine Diphosphate) fixing part 626 and an active area of ATP (Adenosine Triphosphate) Ase 622 are formed.

The molecular monomer 620 that is a low-molecular modified fibroin shown in FIG. 39B undergoes hydrolysis of ATP in salt solution such as KCl for polymerization. Firstly ATP fixed to the ADP fixing part 626 comes into contact with the active area of ATP Ase 622 together with magnesium ions. Then ATP is hydrolyzed because of the catalytic action of the active area of ATP Ase 622. At this time, γ-phosphate group is released, but the ADP 624 decomposed from APT is left and forms polymer (multimer).

When salt components such as KCl are removed from this aqueous solution containing the polymer (multimer) bonded by the ADP 624, the resultant has the property of easily changing into monomer. In this way, the multimer (polymer) structure shown in FIG. 39B shows non-toughness, which leads to the effect of promoting digestion and absorption in a human body.

Amino acid having basic residue, such as arginine or lysine, composing this active area APT Ase 622 is bonded with ATP or magnesium ions. At this time, hydrogen-bonding is generated between the basic residue and phosphate group. The absorption band belonging to the stretching of this hydrogen-bonding appears in the wavelength range of 1.4 to 1.6 μm for the first overtone and in the wavelength range of 0.95 to 1.1 μm for the second overtone. This absorption band is so special that it can distinguish the types of basic residue as a counterpart of the hydrogen-bonding from the wavelength of the absorption band (i.e., whether it is arginine, lysine or histidine).

When the polymer (multimer) state returns to the monomer state, the hydrogen bonding between the basic residue and phosphate group is disconnected. Therefore when the hydrogen-bonding between the basic residue and phosphate group is involved as in FIG. 39B, the detailed bonding stated can be monitored from the characteristics of light absorption of the detection light 16 from there.

Measurement of a structure, a bonding state or its change using near-infrared light is not limited to the example of FIG. 39B, which may be applied to any functional-bio material (and a change of the interior) involving hydrogen-bonding between basic residue and phosphate group.

An example of a voltage sensor function described in the seventh line of FIG. 37 is described below. According to Patent Literature 3, a voltage-gated ion channel includes a plurality of α-helix structures having a length penetrating a cell membrane. A part of at least one cell-membrane penetrating α-helix among them includes amino acid with charged-polar residue (basic residue or acid residue). When DC electric field (potential difference) is applied externally, electrostatic force acts on this charged-polar residue. As a result, conformation of the voltage-gated ion channel partially changes, and the gate opens.

In an example based on such a principle, which is described in "containing charge-polar residue" in the seventh line of FIG. 37, amino acid with charged-polar residue (basic residue or acid residue) is integrated into a part of an existing protein having a property of easily generating a change in conformation. Then, electrostatic force acts on this charged-polar residue, so that the conformation changes. This can realize the function as a voltage sensor.

To exert such a function as a voltage sensor, ions with reversed polarity have to be localized around amino acid having the charged-polar residue so that they are not neutralized about charge. Water (aqueous solution) in a living body includes a lot of sodium ions and chlorine ions. Amino acid with acid residue, such as aspartic acid or glutamic acid, is easily esterified and is bonded with cations, such as sodium ions, as shown in FIG. 39(c). As described above, the wavelength of the absorption band changes before and after esterification. Therefore it can be determined whether the voltage sensing part is esterified and is not neutralized about charge based on the wavelength of the absorption band in the light-absorption spectrum of the detection light 16 obtained from the functional-bio material as the voltage sensor.

Similarly, amino acid with basic residue, such as arginine, lysine or histidine, has the risk of neutralization in charge because anions such as chlorine ions are attached around the basic residue. Similarly to the hydrogen-bonding, when anions are attached around the basic residue as well, the wavelength of the absorption band changes (the wavelength increases by a predetermined amount). Especially in this case, the type of amino acid with basic residue and anions attached can be expected based on the wavelength value of the absorption band belonging to the first overtone or the second overtone of the stretching.

In this way, the factors of the instable function or problems of the functional-bio material having the function as a voltage sensor can be expected from the wavelength of the absorption band in the absorption spectrum of the detection light 16. Such a method is not limited to a voltage sensor, which may be applied to any functional-bio material having amino acid with basic residue. That is, a wavelength of the absorption band in the absorption spectrum of the detection light 16 can be obtained from any functional-bio material including amino acid with basic residue, and the factors of the instable function or malfunction relating to the attachment between the basic residue and the anions can be found based on the wavelength.

According to the first half of Section 8.3, the crystallinity of the modified fibroin that is 50% or more (desirably 55% or more) can improve the mechanical strength, and so the material is suitable for rigid material, reinforcement material (the fourth line of FIG. 37).

In this way, the crystallinity of modified fibroin is increased (to 50% or more), whereby a structure of a predetermined shape can be formed. The following describes a method of producing a structure having excellent formability as an application example of the present embodiment. In the following, a method of producing a structure by combining β-sheets including fibroin as a base is described as one example of the embodiment. Alternatively, a structure may be produced by combining α-helix structures, for example. Still alternatively, a structure may be produced by combining α-helix and β-sheet.

A basic unit (monomer block) includes a crystalline part having a β-sheet structure. Then a block is formed by assembling these basic units (polymers). Then these blocks are combined to form a structure. The structure is formed using a relatively large-sized (a size that a human can easily handle) as a unit, and so this has the effect of improving the user-friendliness during forming.

Further the basic units are joined inside of the assembly using a predetermined cohesion force, such as electrostatic force, and this can have the effect of preventing the breakage of the assembly. The following describes an example using electrostatic force as the force to join the basic units. That is, the basic unit has a structure of "charged area" at a part of (close to) the outer wall. In this charged area, a positively-charged area and a negatively-charged area may be mixed. Between at least two basic units, the positions of the positively charged area and the negatively charged area may coincide with each other.

Instead of electrostatic force, other forces, such as van der Waals' force, hydrogen-bonding force, ion-bonding force, or covalent-bonding force, may be used as the joining force between the basic units.

As described later in FIG. 49, some medium for cohesion may be used instead of letting the basic units (modified β-sheet crystalline parts (monomer blocks) 1602) only cohere with each other. Such a medium to help the cohesion may be the ADP 624 as in FIG. 39B, for example.

When a polymer is formed by assembling monomers, or when a structure is formed by assembling polymer blocks, the quality of aqueous solution containing the above mixture may be changed so as to induce the cohesion force, such as electrostatic force. In this example, the aqueous solution is substituted with pure water so as to reduce the concentration of anions (such as chlorine ions) and cations (such as sodium ions). Alternatively a pH value or a temperature of the aqueous solution may be changed in the present embodiment.

For illustrative purposes, the below-described exemplary structure includes proteins only. Alternatively, this may be a mixed material of protein and existing engineering plastic or may include another material.

Figure 49:
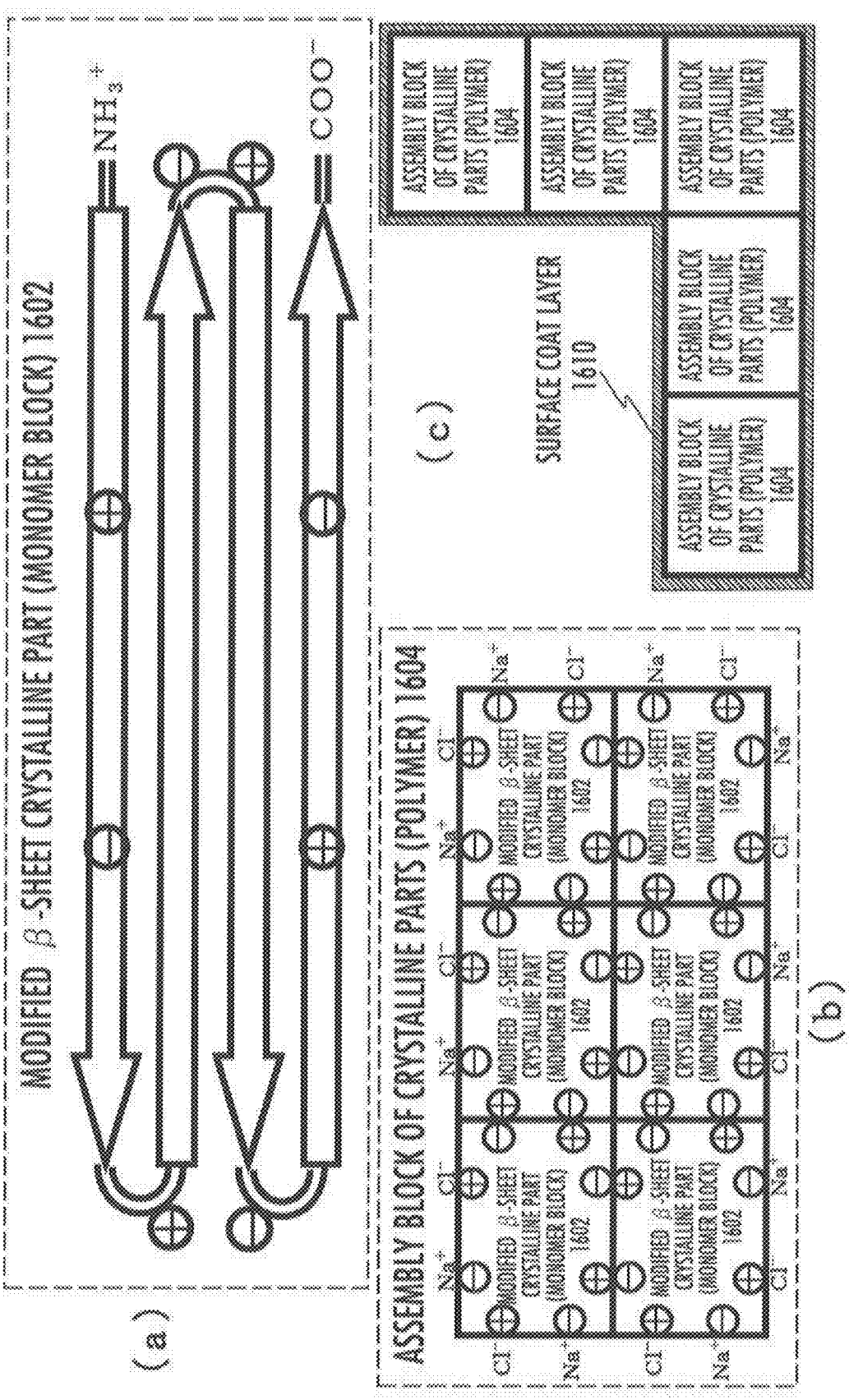
FIG. 49 describes an example of forming a structure by combining modified β-sheet crystalline parts.

As shown in FIG. 49(*a*), a β-sheet crystalline part in fibroin is a starting point as the basic unit (monomer block). This existing β-sheet crystalline part in fibroin is genome-edited as described later in Section 8.5 or Section 9.2, whereby a modified β-sheet crystalline part (monomer block) 1602 is created.

Among the twenty types of amino acids existing, alanine, valine, leucine, isoleucine, proline, phenylalanine, methionine, tryptophan, glycine and cysteine do not have charge or polarity, and they are called amino acids with non-polar residue. Proteins including such amino acid with non-polar residue only have a high hydrophobic property.

That is, when a structure that is less soluble in water is to be formed in an example of the present embodiment, 50% or more (desirably 70% or more or 80% or more) of the amino acid composing such a protein may be such amino acid with non-polar residue. This leads to the effect of water hardly entering the gap between the modified β-sheet crystalline parts (monomer blocks) 1602 in the crystalline-part assembled (polymer) block 1604 (FIG. 49(*b*)) and being less soluble in water due to the influences of the hydrophobic property. Such a condition of the composition can improve the structural (dimensional) stability of the structure as well because swelling due to water hardly occurs.

On the other hand, when a structure that is more soluble in water is to be formed, such as for a capsule of drug, the content of the amino acid with non-polar residue may be 50% or less (desirably 40% or less or 30% or less) in the protein composing the structure. Such a condition of the composition lets water enter the gap between the modified β-sheet crystalline parts (monomer blocks) 1602 (FIG. 49(*b*)) or between the crystalline-part assembled (polymer) blocks 1604 to reduce the cohesion force, and so the structure can be easily degraded in the water.

As described in the center part of Section 8.3, it is difficult to apply existing fibroin to foods because it has a large molecular weight, i.e., such fibroin is difficult for digestion/absorption. On the contrary, the basic unit (monomer block) of the present embodiment is only one crystalline part having a relatively small molecular weight (FIG. 49(*a*)). Further the content of the amino acid with non-polar residue may be 50% or less (desirably 40% or less or 30% or less) in the protein so as to increase the water solubility of the modified β-sheet crystalline part (monomer block) 1602 itself. Thereby the digestion/absorption in a living body can be more improved. This can lead to the effect of greatly improving the suitability for foods and cosmetics.

FIG. 49(*a*) shows the situation where linear protein is folded to form a β-sheet. Among the amino acids composing this protein, lysine, arginine and histidine are called amino acid with basic residue. Then the position in the protein where such amino acid with basic residue is placed is a positively-charged area in the crystalline part, which is indicated with the mark +.

That is, amino acid with basic residue is placed in the amino acid composing the modified β-sheet crystalline part (monomer block) 1602 shown in FIG. 49(*a*). As a result, a positively-charged area is formed at a part of (close to) the outer wall of the modified β-sheet crystalline part (monomer block) 1602 corresponding to the basic unit.

Meanwhile aspartic acid and glutamic acid in the twenty types of amino acid are called amino acid with acidic residue. Then the position in the protein where such amino acid with acidic residue is placed is a negatively-charged area in the crystalline part, which is indicated with the mark −.

That is, amino acid with acidic residue is placed in the amino acid composing the modified β-sheet crystalline part (monomer block) 1602 shown in FIG. 49(*a*). As a result, a negatively-charged area is formed at a part of (close to) the outer wall of the modified β-sheet crystalline part (monomer block) 1602 corresponding to the basic unit.

This example of the present embodiment is configured to have a charged area that is formed at a part of (close to) the outer wall of the modified β-sheet crystalline part (monomer block) 1602 corresponding to the basic unit, whereby a cohesion force can be increased using electrostatic force between the modified β-sheet crystalline parts (monomer blocks) 1602 of the structure. With this configuration, the bonding force between these monomers can increase, and so the mechanical strength of the structure as a whole increases.

As described later in details with reference to FIG. 50A, when aqueous solution contains living secretory microorganisms to synthesize proteins in a body, the aqueous solution contains a lot of chlorine ions and sodium ions. Since both of the ions have a high degree of ionization in the aqueous solution, they are less likely to form salt through ion-bonding with the charged areas as stated above. This means a lot of modified β-sheet crystalline parts (monomer blocks) 1602 dropped into this aqueous solution do not cohere.

On the contrary, the concentrations of chlorine ions and sodium ions in the aqueous solution containing a lot of modified β-sheet crystalline parts (monomer blocks) 1602 are lowered, which is then substituted with pure water, followed by drying. Then electrostatic force acts between the charged areas disposed at (close to) the outer wall of the modified β-sheet crystalline parts (monomer blocks) 1602, and the modified β-sheet crystalline parts cohere with each other.

As a result of the cohesion, an assembly block of crystalline parts (polymer) 1604 is generated as shown in FIG. 49(*b*). At this time, salt is generated between chlorine ions and sodium ions to neutralize the charge amount at the outer wall part of the assembly block of crystalline parts (polymer) 1604.

Then, this aqueous solution containing a lot of assembly block of crystalline parts (polymer) 1604 is substituted with pure water so as to remove chlorine ions and sodium ions, followed by drying. Then, the final structure is formed as shown in FIG. 49(*c*). As shown in FIG. 49(*c*), a surface coat layer 1610 is applied to the surface of the formed structure. This surface coat layer 1610 functions to remove the adverse effects of the charged area that is left close to the surface of the structure.

FIG. 50A shows an example of the forming procedure of the assembly block of crystalline parts (polymer) 1604 having the structure of FIG. 49(*b*). Firstly (S71), amino acid sequence (base sequence of DNA as a base of the transcription to amino acid) is designed, which is for genome editing described later in Section 8.5 or Section 9.2 (S72).

*Aspergillus oryzae* may be used as microorganisms to synthesize proteins in a body and secrete them to the outside of the body, or *Corynebacterium glutamicum* as a glutamic acid-producing bacterium may be used for this purpose. Alternatively *Escherichia coli*, which is crushed to be suitable for the extraction of proteins in a bacterial cell, may be used.

When the monomer block (modified β-sheet crystalline part) 1602 is generated using bacteria to secrete synthesized proteins (S74), the amount of secretion of the monomer block (modified β-sheet crystalline part) 1602 may be optically monitored (S75) using an optical management apparatus (measurement apparatus) 1020 shown in FIG. 46 (described later in details in Chapter 10).

At S78, thus secreted modified β-sheet crystalline parts (monomer blocks) 1602 are extracted and purified. The aqueous solution for this extraction and purification contains a lot of sodium ions and chlorine ions (having a state close to salt solution).

Next, this aqueous solution is substituted with pure water so as to lower the concentrations of chlorine ions and sodium ions, followed by drying. This allows the monomer blocks (modified β-sheet crystalline parts) 1602 to cohere (S78). As a result of the cohesion, an assembly block of crystalline parts (polymer) 1604 can be obtained.

Before forming the final structure, these assembly blocks of crystalline parts (polymers) 1604 desirably have a uniform size as shown in FIG. 49(*c*). Filtering may be used to extract such assembly block of crystalline parts (polymers) 1604 having sizes in a predetermined range (S79). Specifically these assembly blocks of crystalline parts (polymers) 1604 are temporarily dispersed in pure water, which is then allowed to pass through filter paper a plurality of times. The mesh size of the filter paper used can be changed to select the assembly block of crystalline parts (polymers) 1604 having sizes in a predetermined range only.

To keep the long-term stability of this assembly block of crystalline parts (polymers) 1604, the selected and extracted assembly block of crystalline parts (polymer) 1604 are stored in a dry atmosphere for a long time (S80).

The generation of the assembly block of crystalline parts (polymer) 1604 ends with the long-term storage in a dry atmosphere (S81). The thus generated assembly blocks of crystalline parts (polymer) 1604 have a powder form or granular form. They are managed in such a form temporarily, which can lead to the effect of improving the formability to the final structure.

Figure 50C:
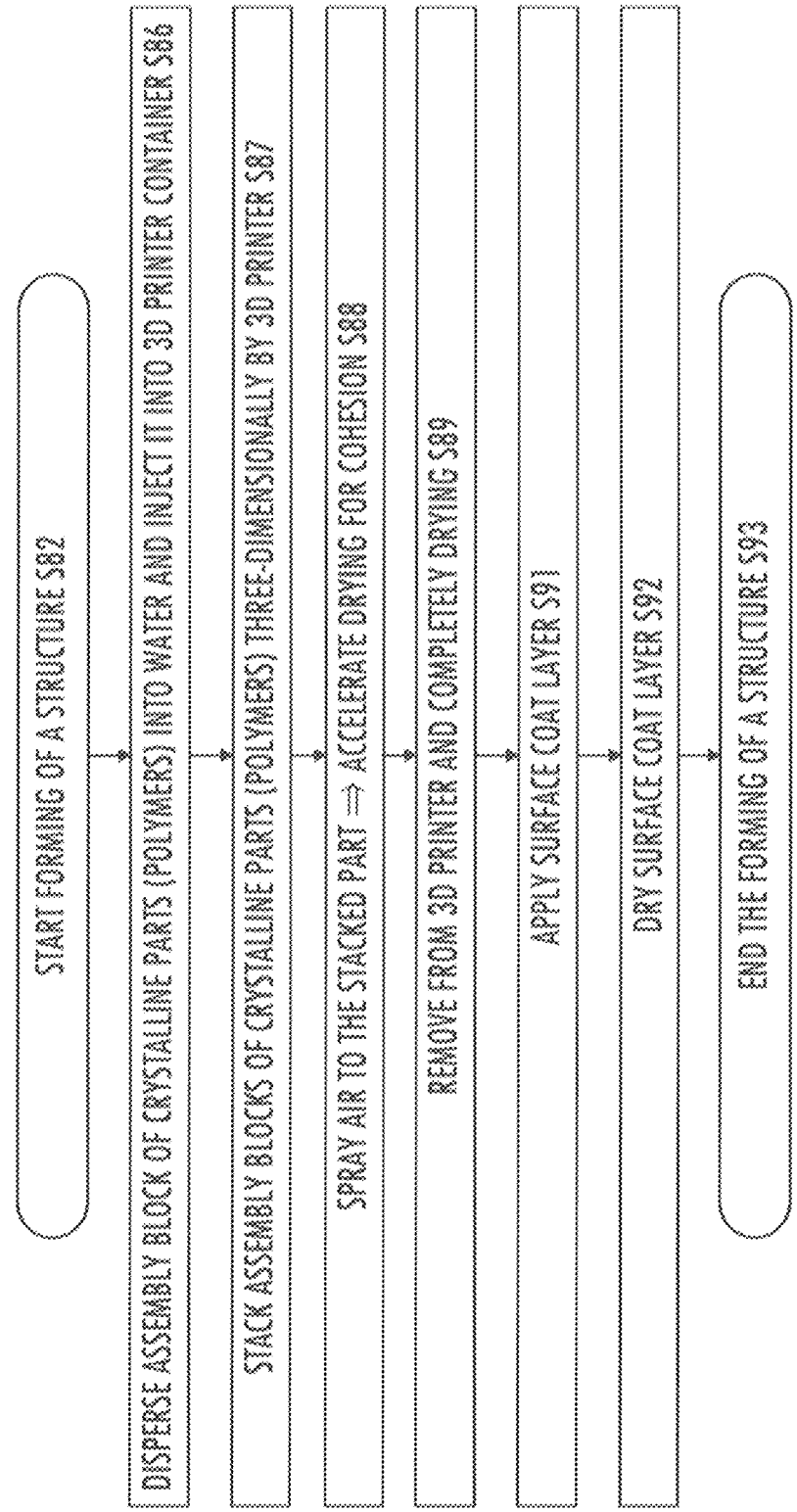
FIG. 50C describes an application example of the present embodiment, showing the procedure to form a structure of FIG. 49.

These powder-form or granular-form assembly block of crystalline parts (polymer) 1604 may be formed to a structure by a 3D printer or by casting. FIG. 50B shows one example of the procedure to form a structure by casting. FIG. 50C shows one example of the procedure to form a structure by a 3D printer.

As shown in FIG. 49(*b*), the assembly block of crystalline parts (polymer) 1604 have the outer wall that is in the state of salt including bonded sodium atoms or chlorine atoms. Desirably in any forming method, the powder-form or granular form assembly block of crystalline parts (polymers) 1604 are once dispersed into water (S83 and S86) to remove sodium atoms or chlorine atoms bonded at the outer wall, so as to increase the cohesion force between the assembly block of crystalline parts (polymers) 1604.

Specifically in FIG. 49(*b*), removal of sodium atoms or chlorine atoms surrounding the outer wall of the assembly block of crystalline parts (polymers) 1604 exposes the charged area of (close to) the outer wall. Electrostatic force acts between these exposed charged areas, which functions as a cohesion force between the assembly block of crystalline parts (polymer) 1604 in the structure.

Then, the assembly block of crystalline parts (polymer) 1604 are dispersed into water. This can improve the operability during forming greatly. That is, the assembly block of crystalline parts in this state can be used as ink to be used as a 3D printer/inkjet printer. When casting is performed for this dispersed state in water, a structure having a shape suitable for any fine shape of the mold can be created.

For instance, when an acrylic board is formed by casting, it takes all night to complete the cross-linking while controlling the temperature. On the contrary, the present embodiment can promote quick drying, whereby cohesion (S84) is enabled for a very short time.

When a structure is formed by a 3D printer, air may be blown (sprayed) to an upper part of the three-dimensionally stacked structure to speed up the drying (S88). As the drying is speeded up, a higher speed of the cohesion is enabled.

In any forming method, the finished structure is completely dried (S85, S89) so as to enhance the cohesion of the assembly blocks of crystalline parts (polymer) 1604.

After that, the surface coat layer is applied to the surface of the formed structure (S91), and is dried (S92) to end the forming of the structure (S93).

The above describes casing and a 3D printer as one example of the forming. The present embodiment is not limited to them, and any other forming methods may be used.

Section 8.4 Examples of Functional-Bio Materials Having Functions as Internal Structure of Active Area or Enzyme Section 8.4 describes an example of "internal structure of active area" and "new enzyme function" in the fields of "the ways to exert unique functions" of FIG. 37. The descriptions in Section 8.4 are just one example, and any other methods to give functional-bio materials unique functions as "internal structure of active area" or "enzyme" may be used.

Figure 40A:
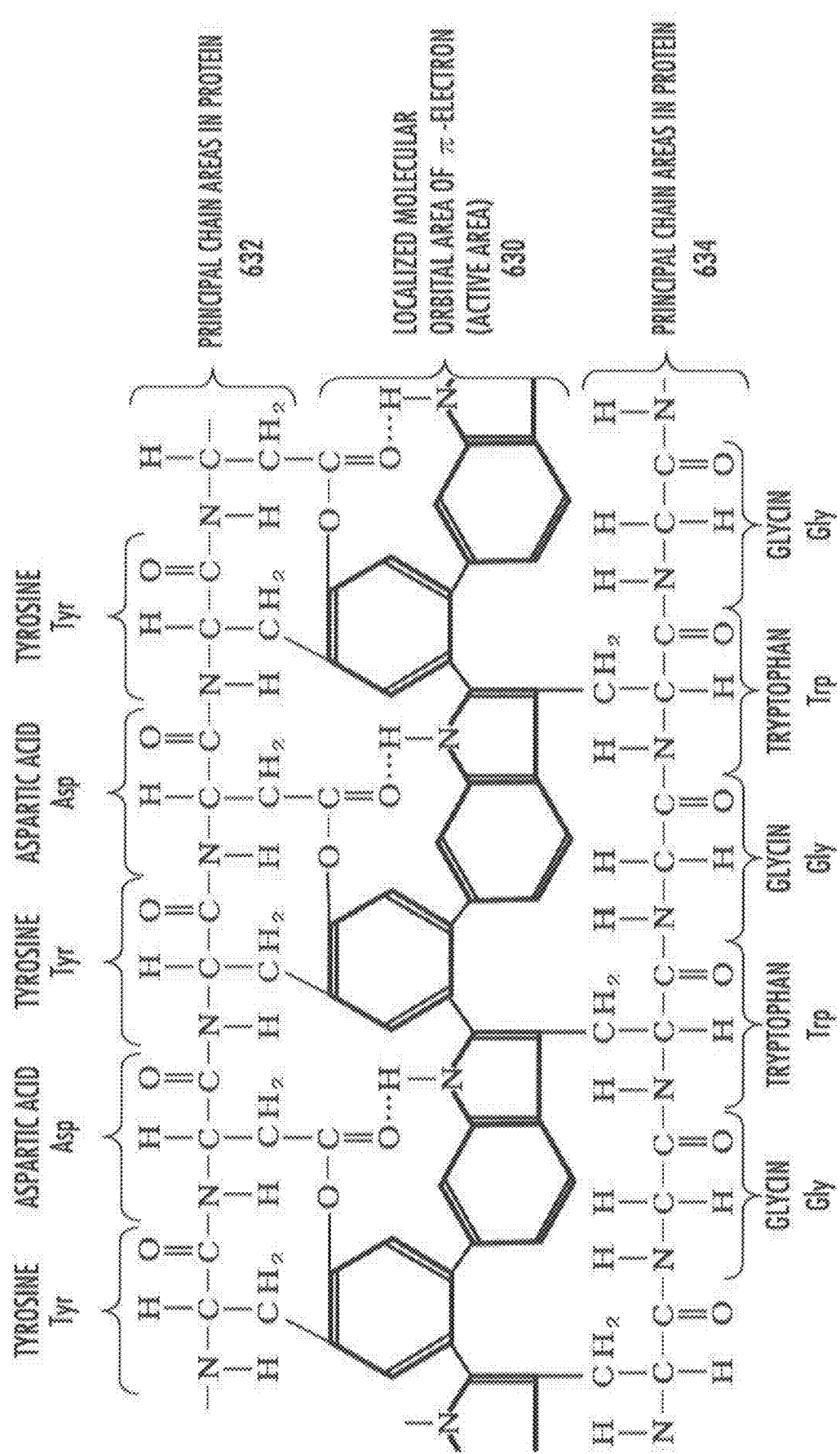
FIG. 40A shows an example of a functional-bio material internally having a conducting area.

FIG. 40A shows an example of the embodiment of exerting a conductive function using artificial protein. This example of the embodiment corresponds to "underwater conductive lines" in the ninth line of FIG. 37. In this example, a plurality of principal chain areas in protein 632, 634 are located on the outside and an active area is disposed between them. The internal active area 630 has a conducting structure.

For illustrative purposes, FIG. 40A describes a planar structure. The principal chain areas in protein 632, 634 may have a double-helical structure as in the double-helical structure of DNA (Deoxyribonucleic Acid). Accordingly, the active area 630 does not have a planar structure, and may have a helical structure.

When the active area 630 having a planar structure is exposed to water, this has a conductive property to some extent in pure water as well, and so electrical leakage occurs. Especially since aqueous solution in a living body includes a lot of sodium ions and chlorine ions, the amount of electrical leakage is large at the active area 630 having a planar structure.

When the principal chain areas in protein 632, 634 have a double-helical structure, they act as a coating to the outside and so have the insulating effect to prevent the electrical leakage from the active region 630 to the outside.

In the example of the present embodiment shown in FIG. 40A, the active area 630 having a helical structure is a localized molecular orbital area of π-electron. At a 6-atoms cyclic compound part and a 5-atoms cyclic compound part in the tryptophan Trp residue, electrons in a localized molecular orbital of π-electron are present. Then in the area where this localized molecular orbital of π-electron is continued, π-electrons can move in a local area. In the active area 630, localized molecular orbitals of π-electron are joined so as to let the active area 630 have a conducting function.

In FIG. 40A, localized molecular orbitals of π-electron in the 6-atoms cyclic compound part of the tyrosine Tyr residue are joined to join the localized molecular orbitals of π-electron in the localized molecular orbital area of π-electron (active area) 630. Additionally π-electrons in a carboxyl group of the aspartic acid Asp residue also may be joined to improve the conducting property.

Especially a carboxyl group in the aspartic acid Asp and the tryptophan Trp form a hydrogen bonding in the form of C—C═O . . . H—N<, where . . . shows the hydrogen-bonding part. With this configuration, the following advantageous effects can be obtained:

1. due to joined π-electrons in the carboxyl group, the conducting property in the active area 630 can be improved;
2. the strength of double-helical bonding between the principal chain areas in protein 632, 634 can be improved;
3. elasticity of the double-helix as a whole can be kept by the flexibility of the interatomic distance of the hydrogen bonding.

For a stable operation of the functional-bio material having a conductive function shown in FIG. 40A, the localized molecular orbital area of π-electron (active area) 630 has to be formed correctly. For one of the indexes indicating whether the localized molecular orbital area of π-electron (active area) 630 is correctly formed or not, a light-absorption spectrum may be observed using near-infrared light about the hydrogen-bonding state in the form of C—C═O . . . H—N<.

Simple hydrogen-bonding states in the form of C═O . . . H—N are often observed in a typical biological system. On the other hand, when it belongs to the hydrogen bonding in the localized molecular orbital area of π-electron (active area) 630 as in FIG. 40A, the wavelength value of the absorption band is somewhat different from the wavelength value of the absorption band obtained from a typical living body. Such a change in the wavelength value of absorption band may be measured so as to monitor whether the localized molecular orbital area of π-electron (active area) 630 is correctly formed or not. For this purpose, such a change in the wavelength value of the absorption band may be measured with the apparatus of FIG. 1A to FIG. 1C.

In a comparison of electronegativity of Pauling, hydrogen atoms have a smaller value than those of carbon atoms, nitrogen atoms and oxygen atoms. Therefore the actual charge of hydrogen atoms in a molecule is a positive value.

The localized molecular orbital area of π-electron (active area) 630 includes a lot of π-electrons are present, which can move relatively freely. This means that π-electrons tend to be unevenly distributed to be close to the nearest-neighboring nitrogen nuclei instead of hydrogen nuclei in the hydrogen-bonding part in the form of C—C═O . . . H—N<. As a result, the actual charge of nitrogen atoms decreases greatly (negative charge having a larger absolute value), and so the electrostatic attraction between hydrogen atoms and nitrogen atoms increases. Therefore as compared with the case where a lot of π-electrons are not present, the interatomic distance between hydrogen nuclei and nitrogen nuclei becomes shorter in the ground state (the state having the lowest energy of the entire molecule).

As described in Section 7.4, the total energy of the entire molecule is calculated when hydrogen nuclei is moved at S5 and S6 of FIG. 36. Since the interatomic distance between hydrogen nuclei and nitrogen nuclei is shorter in the ground state (the state having the lowest energy of the entire molecule) than the case where π-electrons are not present, the increased amount of the total energy increases when the interatomic distance between hydrogen nuclei and nitrogen nuclei is shortened.

Due to the influences from the above, the value of $\kappa_4$ in (A•27) or (A•38) increases at the calculation of S7 in FIG. 36. Then (A•60) shows that the wavelength values of the first overtone and the second overtone of the stretching belonging to hydrogen bonding are somewhat shorter in the environment including a lot of π-electrons than in the environment not including π-electrons. Patent Literature 3 describes a similar simulation method to the above. Patent Literature 3, however, does not disclose the calculation method of group vibration in a specific atomic group. Therefore the method described in Chapter 7 has uniqueness because it describes the calculation method of group vibration in a specific atomic group.

The following describes amino acid residue composing the localized molecular orbital area of π-electron (active area) 630 in the functional-bio material having a conducting function. The example of the embodiment shown in FIG. 40A includes the residues of tryptophan Trp, tyrosine Tyr, and aspartic acid Asp. The example of the present embodiment may include other residues of histidine, glutamic acid Glu, asparagine, glutamine and phenylalanine. The form of the localized molecular orbital area of π-electron (active area) 630 is not limited to FIG. 40A, and it may include any one type of the amino acid residues described above only. Alternatively any types may be extracted from the amino acid residues described above, and they may be combined to have any structure.

The following describes FET switching, underwater conductive lines, and NIRFP as the examples of unique functions with the "internal structure of active area" in FIG. 37. Any internal structure of active area may be generated based on catalysis with a specific enzyme. Note here that such an enzyme is not present in the existing natural world, and so this enzyme itself is included the functional-bio material (as described in "Ways to have Functions" in FIG. 37). Even when the function of a new enzyme is present in the existing natural world, such a new enzyme may be included in the functional-bio material of the present embodiment when speeding-up of the existing enzyme can be realized by the new enzyme.

The following describes an enzyme as well as the function of the enzyme by way of a method of generating the active area 630 of the functional-bio material having a conducting function shown in FIG. 40A.

As described at the end of Section 8.1, amino acid sequence is determined by genome editing, followed by transcription to mRNA, and then protein is synthesized with tRNA. Thereby principal chain areas in protein 632, 634 having the respective amino acid residues can be generated beforehand.

A first enzyme to catalyze dehydration condensation is used to bind tryptophan Trp residue and tyrosine residue to join two principal chain areas in protein 632 and 634. Next, a second enzyme having the function of dehydrogenase is used to join the residues in the direction of principal chain (the lateral direction in FIG. 40A).

For the order of catalysis, dehydrogenation condensation is promoted by the second enzyme, followed by the dehydration condensation with the first enzyme. Alternatively, the catalysis by the first enzyme and the second enzyme may be generated at the same time.

As described in Patent Literature 3, hydrogen bonding often is generated between a part of the substrate and a part of the enzyme during the catalysis with the above enzyme (during a contact between the substrate and the enzyme). The wavelength value of absorption band varies with types of atoms (or anions and cations) on the opposite sides to bond with hydrogen atoms during the hydrogen bonding. Such catalysis may be monitored in the example of the present embodiment based on a difference in wavelength value of absorption band appearing in the characteristics of light absorption. These characteristics of light absorption may be measured with the apparatus of FIG. 1A to FIG. 1C.

Figure 40B:
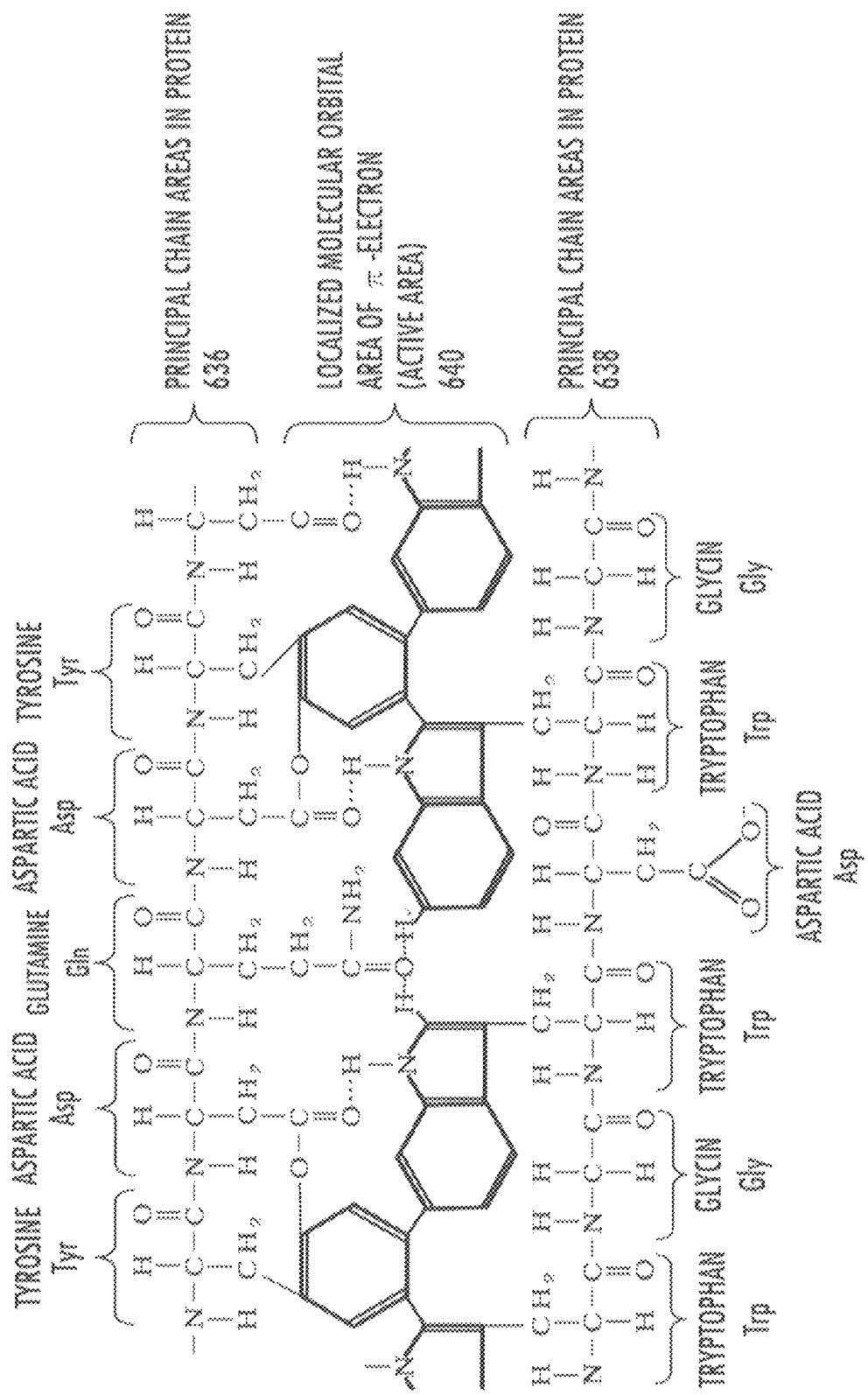
FIG. 40B shows an example of a functional-bio material having a function of power amplification or switching.

FIG. 40B shows another application example of the functional-bio material having a conducting function shown in FIG. 40A. This example corresponds to "FET switching" in the eighth line of FIG. 37. A FET (Field-Effect Transistor) as an electronic device has a function of power amplification or switching. This example shows such a function implemented with a functional-bio material. Basically this is the combination of "voltage sensor with charged-polar residue: changing conformation with charged-polar residue" in the eighth line of FIG. 37 and "underwater conductive lines" in the ninth line of FIG. 37.

This is configured so that the outside is coated with principal chain areas in protein 636, 638 so as to surround helically at the outside, which enables underwater use or use in aqueous solution basically, and a localized molecular orbital area of π-electron (active area) 640 is disposed internally. Although for illustrative purposes FIG. 40B shows a planar structure, it has a helical structure in the longitudinal direction similarly to FIG. 40A.

For this localized molecular orbital area of π-electron (active area) 640, the residues shown in FIG. 40B of tryptophan Trp residue, tyrosine residue Tyr, aspartic acid Asp and glutamine Gln are used. Other residues such as histidine, asparagin, glutamic acid and phenylalanine may be used. It may include only one of these residues, or may include any combination of these residues.

In FIG. 40B, a part common to FIG. 40A (including the method of generation) is the same as in the description referring to FIG. 40A. The following describes a different part only from FIG. 40A.

In the localized molecular orbital area of π-electron (active area) 630 of FIG. 40A, all of the tryptophan Trp residues and tyrosine Tyr residues are covalently bonded. Therefore the localized molecular orbital area of π-electron (active area) 630 has rigidness to some extent.

On the contrary, in FIG. 40B, one tyrosine Tyr is substituted with glutamine Gln. Since π-electrons are included at a bonding area between a carbon atom and an oxygen atom in the glutamine Gln residue, surroundings of the glutamine Gln can keep its conducting property.

Meanwhile, as shown in FIG. 40B, an oxygen atom in the glutamine Gln residue and a hydrogen atom in the tryptophan Trp residue forms hydrogen bonding (the area indicated with . . . in FIG. 40B). The force of this hydrogen bonding is weaker than the covalent bonding (between the tryptophan Trp residue and the tyrosine Tyr residue). Therefore deformation with elasticity is permitted at this part of the localized molecular orbital area of π-electron (active area) 640.

In the principal chain areas in protein 638 on the other side, aspartic acid Asp is bonded so that the charged-polar residue protrudes to the outside. Similarly to the description of the "with charged-polar residue" in the seventh line of FIG. 37 at the latter half of Section 8.3, when voltage (potential difference) is applied there externally, such a charged-polar residue of the aspartic acid Asp receives electrostatic force.

In response to the external electrostatic force applied on the aspartic acid Asp, deformation occurs at the weakest part (i.e., the hydrogen-bonding part of glutamine Gln residue) of the bonding force in the localized molecular orbital area of π-electron (active area) 640.

If this deformation is the largest, the hydrogen-bonding is disconnected, so that the conductivity in the localized molecular orbital area of π-electron (active are) 640 is lost. Even when the deformation is small, the electrical resistance in the localized molecular orbital area of π-electron (active area) 640 changes with a change in the bonding distance at the hydrogen-bonding area.

If a change in electrical resistance in the localized molecular orbital area of π-electron (active area) 640 corresponding to the external voltage (potential difference) applied to the aspartic acid (Asp) residue is sharp, the structure acts as a switching device (component). On the contrary, when such a change in electrical resistance corresponding to the external voltage (potential difference) is gentle, the structure acts as a power (current) amplifying device (component) like a FET device. This change in electrical resistance varies with the conformation of amino acid composing the functional-bio material or the conformation of the functional-bio material as a whole.

The above describes the aspartic acid Asp as an example of the voltage sensor part of FIG. 40B, and arginine, lysine, histidine or glutamic acid with charged-polar residue may be used for this purpose.

Figure 41:
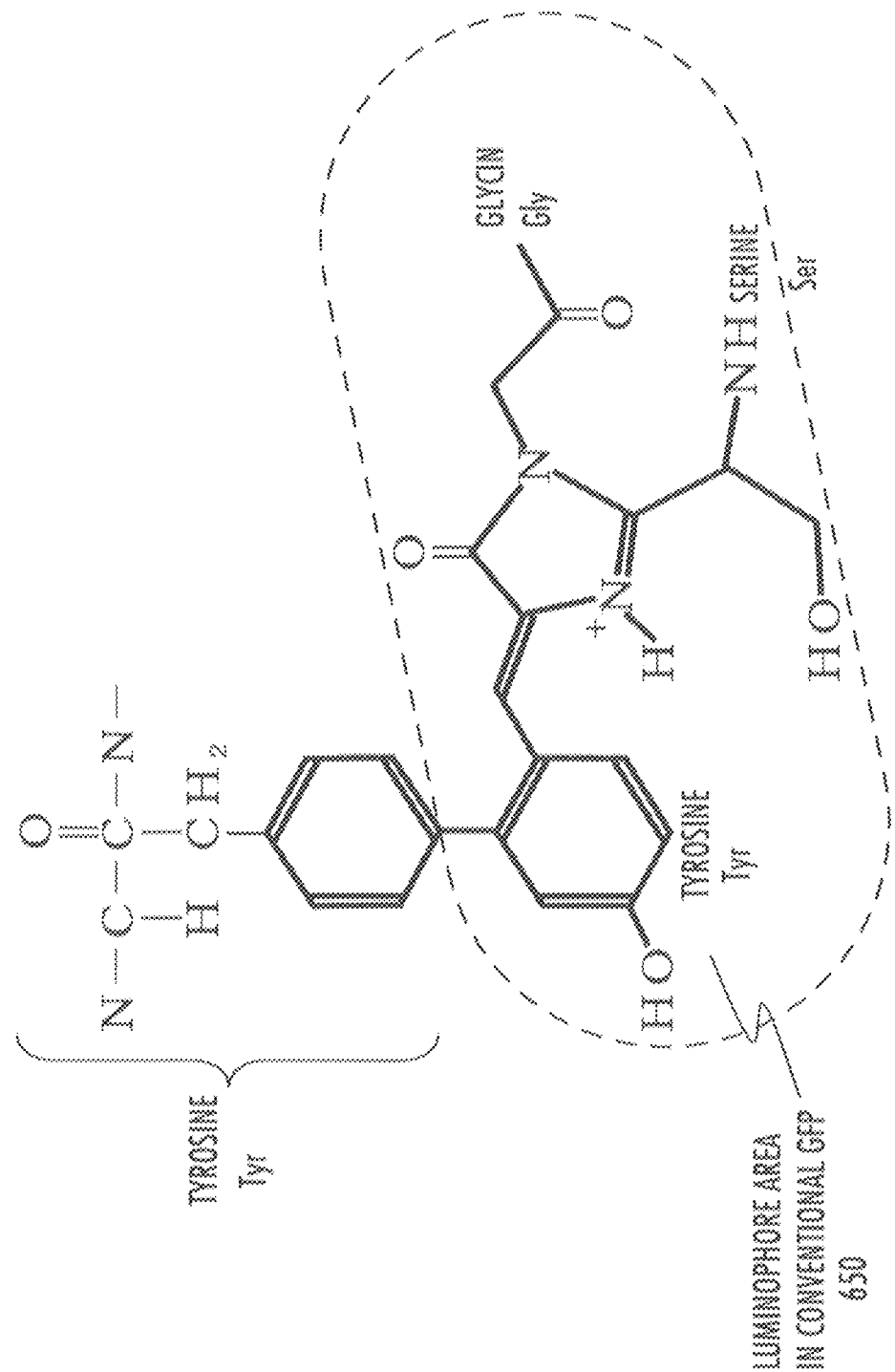
FIG. 41 describes an example of the internal structure of luminophore of fluorescent protein having a fluorescence wavelength in the near-infrared wavelength region.

Referring to FIG. 41, the following describes "NIRFP" in the tenth line of FIG. 37. A known fluorescent indicator substance used for the observation of the internal state of a living body includes GFP (Green Fluorescent Protein). This luminophore absorbs near-ultraviolet light with the wavelength of 397 nm and emits green visible light with the wavelength of 509 nm. Recently RFP (Red Fluorescent Protein) also has been commercially produced, which emits red visible light as fluorescent light.

As described at the latter half of Section 5.4, such red visible light still has a short penetration distance into a living body. Therefore RFP has a limit to observe a deep area of a living body.

To solve this problem, NIRFP ((Near Infra-Red Fluorescent Protein) having a fluorescence wavelength with the characteristics of wavelength range (near-infrared light) described in Section 2.6 has been demanded. This allows the observation of a deep area of a living body.

An existing luminophore (active area) of GFP is spontaneously formed through the cyclization/oxidization of three amino acid residues of serine Ser65, tyrosine Tyr66 and glycine Gly67. In FIG. 41, a luminophore area 650 in the conventional GFP shows a molecular structure of thus finally formed luminophore (active area).

As indicated with a double bond (double line of the bonding) in FIG. 41, presumably electrons in the localized molecular orbital of π-electrons in the luminophore area 650 in the conventional GFP affects the fluorescence characteristics. Then, the localized area of electrons in the localized molecular orbital of π-electron may be expanded so as to widen the fluorescence wavelength (or increase the value of fluorescence wavelength).

Although not illustrated in FIG. 41, the existing GFP includes a barrel structure (a tubular structure made up of β-sheet) that surrounds the luminophore area 650 of the conventional GFP. Then tyrosine Tyr may be inserted so as to extend inwardly of the barrel (or amino acid sequences before and after the tyrosine Tyr may be inserted as needed) at a part of the amino acid sequence defining this barrel structure.

Then dehydrating condensation may be generated using the enzyme that is developed for "generating new active area" in the eleventh line of FIG. 37, so as to allow the tyrosine Tyr inserted as in FIG. 41 to join with the luminophore area 650 in the conventional GFP. In this way, the localized area of electrons in the localized molecular orbital of π-electron may be expanded in the luminophore area so as to widen the fluorescence wavelength (or increase the value of fluorescence wavelength).

During the dehydrating condensation as stated above, hydrogen bonding may occur temporarily at the contact part between the substrate and the enzyme (to stabilize the structure) (see the description in Patent Literature 3). Therefore the absorption band at the corresponding wavelength in a change of the characteristics of light absorption during the dehydrating condensation may be observed, whereby it can be determined reliably whether the dehydrating condensation occurs or not. This enables the management as to whether the functional-bio material corresponding to NIRFP can be generated or not.

FIG. 41 describes the example of tyrosine Tyr residue added as an example of the NIRFP. Alternatively, any one of histidine, aspartic acid Asp, glutamic acid, asparagin, glutamine Gln, phenylalanine and tryptophan Trp having π electrons or the combination of them may be bonded additionally.

Some medical care of hereditary diseases (diseases resulting from genetic signatures) include genome editing to a patient or a fertilized ovum, such as CRISPR/Cas9, ZFN, or TALEN. This care requires the checking whether desired genome editing is performed correctly or not.

For this genome editing, the aforementioned NIRFP-making gene may be integrated adjacent to the part of the genome to be repaired corresponding to the hereditary disease. This can lead to the effect of enabling the prediction about the successfulness of genome repairing (whether the heredity disease can be cured or not) based on near-infrared light being emitted or not from the NIRFP. As described above, near-infrared light can penetrate into a living body deeply, and so this light enables noncontact and noninvasive observation of a body of a patient or an expectant mother from the outside. As a result, a patient or an expectant mother can be checked about whether their heredity disease can be cured out not without burden on them.

This can be combined with the technique of reducing partial coherency (increasing partial incoherency) of the near-infrared light in Chapter 3 and the technique of compensating wave front aberration in Chapter 6. Thereby the penetration distance in the living body can be more increased.

To irradiate with absorbed light before fluorescence, a patient may take a capsule containing a light-emitting device (e.g., light-emitting diode) of a predetermined wavelength or an endoscope or a catheter may be used.

For "enzyme function" in the fields of "Ways to have Functions" in FIG. 37, the above describes an example of enzyme relative to a new substrate. Additionally any new enzyme that can have a similar function to a conventional one with an existing substrate can be included in the functional-bio material as long as it can speed up the catalytic function of the conventional one.

For instance, "new speed-up degradative enzyme" in the twelfth line of FIG. 37 may be enzyme that can speed up the degradation of cellulose in plants by cellulase quickly to make starch.

In the active area of such cellulase, serine Ser, histidine and glutamic acid form a catalytic triad. For hydrogen atoms bonding with a nitrogen atom having π-electrons in this histidine residue, there is an absorption band having a unique wavelength (belonging to the first overtone and the second overtone of the stretching). Therefore the absorption band in the characteristics of light absorption may be observed in the present embodiment for monitoring the degradation rate of cellulose.

Section 8.5 Examples of Functional-bio Materials having Function relating to the Generation Procedure The following describes the generation procedure of an internal structure of polymer or functional-bio materials described in Sections 8.3 and 8.4.

The description in Section 8.3 referring to FIG. 39B briefly states actin filament. Actin filament as a major component of edible meat is similar to FIG. 39B, and includes actin dimers bonded via ADP. As described in Section 8.3, when salt component, such as KCl, is removed from the aqueous solution, disconnection easily occurs at the part of ADP624.

Meanwhile, tropomyosin helically tangling around the actin filament keeps a certain strength. Other molecules adhering also can increase the strength of the actin filament. Note here that excessive reinforcement by tropomyosin makes the edible meat harder.

For the embodiment of "artificial edible meat" in the thirteenth line of FIG. 37, a part of the components of the polymer may be substituted so that both of the appropriate strength (hardness) and texture (tenderness) suitable for food may be achieved at the same time.

Specifically tropomyosin tangling around the actin filament may be substituted with another protein having α-helix structure.

As described in Section 8.1, genome editing may be performed by CRISPR/Cas9, TALEN or ZFN to determine the unique amino acid sequence described from the center to the top of FIG. 37. For the functional-bio material having a function of storing the information on this amino acid sequence, "storage of amino acid sequence information on artificial protein in a cell" in the fourteenth line of FIG. 37 may be performed. Specifically this means a cell having a nucleus storing genome-edited DNA.

In the double-helix of a DNA, specific bases make a pair, and the pair forms hydrogen-bonding in the form of >N—H . . . N<. The hydrogen bonding of this type is unique that hardly appears in other cell areas. Therefore the absorption band appears in the characteristics of light absorption, which has a unique wavelength belonging to the second overtone, the first overtone and the fundamental vibration of the stretching that is generated in the hydrogen-bonding in the form of >N—H . . . N<.

The wavelength value of the absorption band corresponding to the stretching generated at the hydrogen-bonding area in the form of >N—H . . . N< in the DNA double-helix is theoretically predicted by simulation in accordance with the method described in Section 7.4. The value obtained by multiplying the compensation coefficient (Section 7.4) is 3408 nm for the fundamental vibration, 1698 nm for the first overtone and 1172 nm for the second overtone. Estimating the calculation error range of the simulation as ±20%, the actual wavelength value of the absorption band will be expected to be in the range of 4090 to 2726 nm for the fundamental vibration, 2038 to 1358 nm for the first overtone and 1406 to 938 nm for the second overtone.

It is difficult to observe the position of the nucleus in a living cell with a general optical microscope. In many cases, the nucleus is dyed for observation, and the cell will be damaged during this dyeing. On the contrary, by observing the absorption band at the unique wavelength position belonging to the second overtone, the first overtone, and the fundamental vibration of the stretching generated in the hydrogen-bonding in the form of >N—H . . . N<, the nucleus of a living cell can be located. Thereby, the storage position in the cell of amino acid sequence can be easily found.

For instance, the near-infrared microscopic apparatus of FIG. 7 may be modified so as to include another monitor camera at the position of the spectroscope 22, and a narrow-bandwidth bandpass filter (color filter) immediately before each monitor camera 24. Herein one of these bandpass filters (color filters) may have a transmission wavelength corresponding to the wavelength of the absorption band, and the other has a different transmission wavelength. Then a position having (slightly) different intensity distribution in the imaging pattern between them is extracted, whereby the position of the nucleus may be detected. Such a method can lead to the effect of locating the cell nucleus accurately without giving any damage to the nucleus.

In addition to the amino acid sequence information, the present embodiment includes another functional-bio material having a "genome editing function" to promote the editing of DNA base sequence in any genome. Chapter 9 gives detailed descriptions on an example having a devised vector carrier structure for genome editing of these sequences a lot and efficiently.

Alternatively a delivery carrier in cell nucleus shown in an example of the present embodiment may be used to deliver a gene regulator (or gene regulation factor) to the cell nucleus. This method can implement efficient gene regulation function.

The aforementioned near-infrared microscopic apparatus may be used as means to evaluate whether this carrier enables such delivery into the cell nucleus or not. In this case, a substance enabling optically position monitoring, such as GFP, is inserted in an internally packed area. Then, while checking the position of the cell nucleus by the above method, the internal position of the delivery carrier in cell nucleus is monitored in real time. As a result, this enables the checking as to whether the interior of the carrier has been delivered into the cell nucleus or not.

A cell storing the edited genome information in the nucleus has a specific function to store genome information including new amino acid sequence information. Meanwhile, a functional-bio material of the present embodiment may include a cell itself having a function of generating a functional-bio material based on such genome information. This corresponds to "generation/secretion in a cell" in the last line of FIG. 37.

Specifically the cell nucleus may have genome information relating to the generation of various types of functional-bio materials described from the top to the center of FIG. 37, generate a functional-bio material in the nucleus based on the information, and secrete the generated functional material to the outside of the cell.

A fermentation method with glutamic acid corresponds to an example of such process. A raw material, such as molasses from a sugar cane, is placed into a fermentation tank, and then glutamic acid-producing bacterium is cultivated under an appropriate condition. As a result, glutamic acid is ejected from the bacterial cell. In this way, various types of functional-bio materials described from the top to the center of FIG. 37 may be generated in microorganisms.

Instead of generating a functional-bio material by microorganisms, a hair follicle having edited genome information in the nucleus may be artificially cultivated. In this case, similarly to the process of growing hair from the hair follicle, a functional-bio material instead of hair is generated and is ejected from the hair follicle.

Such a hair follicle frequently synthesizes artificial proteins with tRNA. During this process of protein synthesis, hydrogen bonding occurs temporarily. By detecting the unique absorption band in the characteristics of light absorption belonging to the second overtone, the first overtone and the fundamental vibration of the stretching in the temporarily generated hydrogen-bonding, the process of protein synthesis can be managed. These characteristics of light absorption may be measured with the apparatus of FIG. 1A to FIG. 1C.

The following describes examples of generating (manufacturing) a functional-bio material using a part of the existing biological activity system or the mechanism in a similar manner. They include:

1. harvesting hair follicle from the epidermis of animals, such as sheep;

2. genome-editing a cell nucleus of the harvested hair follicle, the genome editing may be performed by CRISPR/Cas9, TALEN, or ZFN described in Section 8.1;

3. cultivating the genome-edited hair follicle, prior to this, the cell may be initialized by the method described in JP 2003-500255 A(hereinafter called Patent Literature 4) or JP-5098028-B (hereinafter called Patent Literature 5), and then the hair follicle may be grown under a specific environment; and 4. as in the hair generated in the hair follicle, the functional-bio material grown there is collected.

The thus generated and collected functional-bio material has a form having the hair follicle adhering to the end of the functional-bio material as in hair pulled from the scalp. When such hair follicle is left in the natural air instead of the culture environment, it will die because the nutritional support stops. That is, if such a hair follicle is left alone in the natural environment, it does not have self-propagating function and so does not adversely affect the natural environment.

The manufacturing process to generate (manufacture) a functional-bio material using a part of the biological activity system or a mechanism of an existing a living being in a similar manner has a very serious problem of the increase of unwanted bacteria (mixing of contamination). The hair follicle itself has resistance to disinfection to some extent as compared with microorganisms. Therefore sterilization and disinfection can be performed to the culture media to some extent, and so this can be countermeasure against the increase of unwanted bacteria and mixing of contamination.

Further, genome-editing (or initialization of cells) requires large-scale equipment, and so such an operation cannot be performed just anywhere. On the contrary, a cell to generate a functional-bio material (such as hair follicle) that is packaged in the culture medium can be easily conveyed and such a cell to generate a functional-bio material (such as hair follicle) can be grown relatively easily at any place.

Therefore such a cell to generate a functional-bio material (such as hair follicle) that is generated at a specific place may be delivered, whereby functional-bio materials can be easily generated (grown) at various places in the world. Therefore the functional-bio material shown in the example of the present embodiment has the effect of easily spreading this all over the world.

Not limited to the specific examples of the "artificial protein synthesis" in the fields of "Ways to Have Functions" in FIG. 37, that is, generation and secretion in the microorganisms, generation in a cell to generate a functional-bio material (such as hair follicle) and placing it outside of the cell, any other processes may be used. For instance, a cell to generate spider's threads in the body of a spider or a cell to generate silk in the body of a silkworm may be used. In such a case as well, by detecting the absorption band that is temporarily generated during protein synthesis in the cell, the manufacturing process can be managed.

Chapter 9 Genome-Editing Using Functional-Bio Materials

The following describes a specific example of the structure of a functional-bio material having the "genome-editing" described in the second last line of FIG. 37 and its actual operation example. Such a functional-bio material having the "genome-editing" function may be used as a starting point to generate the functional-bio material having every function shown in FIG. 37. Such a functional-bio material having the "genome-editing" function is required for a method of manufacturing a functional-bio material described in Chapter 10 as well.

When a functional-bio material having the "genome-editing" function is used for a human body or an animal, many secondary functions are required to ensure the safety and maintain the world ecosystem. To this end, Chapter 9 gives a description by way of an example of the cure for a genetic disease and cancer. The use of the functional-bio material having the "genome-editing" function is not limited to such an example, and may be used to generate the functional-bio material having every function shown in FIG. 37. When the functional-bio material is used for other purposes, the secondary functions described in Chapter 9 may be excluded appropriately.

Section 9.1 Example of Treatment for Affected Area Relating to DNA Damages and Current Problems To treat cancer having oncogene addiction, many molecular target medicines are available. Currently the mechanisms of effectiveness of these medicines involve damage of tumor cells (disruption of a cell membrane), phagocytosis, inhibition of a pathway of signal transduction in the tumor cell (such as inhibition of tyrosine kinase activity) and the like. In other words, all of these mechanisms of effectiveness act as a negative affection on the activity of tumor cells, which may lead to the risk of serious side reactions. That is, the action of the medicine to suppress the cell's activity may affect normal cells erroneously to inhibit their normal activities. Such a side reaction often occurs.

On the contrary, the example of the present embodiment is to transform the tumor cells into normal cells, and so have an advantageous effect of reducing the side reaction. A problem hardly occurs when normal cells experience normalization. Specifically for more than half of malignant tumors, abnormality of genes called p53 is found. If the action of this p53 gene can be transformed into normal, this may lead to the cure of many cancers.

A c-kit mutant gene relates to the occurrence of gastrointestinal stromal tumors. For such a tumor, inhibition of KIT tyrosine kinase activity brings the dramatic curative effect.

For another example, inversion of chromosome 2 causes a fusion gene EML4-ALK of an EML4 (Echinoderm Microtubule-Associated Protein-like 4) gene and an ALK (Anaplastic Lymphoma Kinase) gene. This fusion gene is said as the cause of a tumor. If this leads to gene expression, the occurrence of a tumor such as lung cancer has been reported. When an ALK blocking medicine (tyrosine kinase blocking medicine) is given to a patient of such a tumor, this medicine shows excellent effectiveness.

For another example of fusion genes, KIFSB-RET is reported, and lung cancer occurs due to the gene expression. To cure this cancer, vandetanib is considered efficient to block RET.

As described above, a tyrosine kinase blocking medicine often causes severe side reactions. Therefore genome-editing is directly performed using a vector carrier to the position of a c-kit mutant gene, the position of an ALK fusion gene or the position of a fusion gene KIF5B-RET as in the examples of the present embodiment so as to transform them to a normal gene sequence. Thereby it can be expected that these affected areas can be cured with less side reactions.

Figure 42:
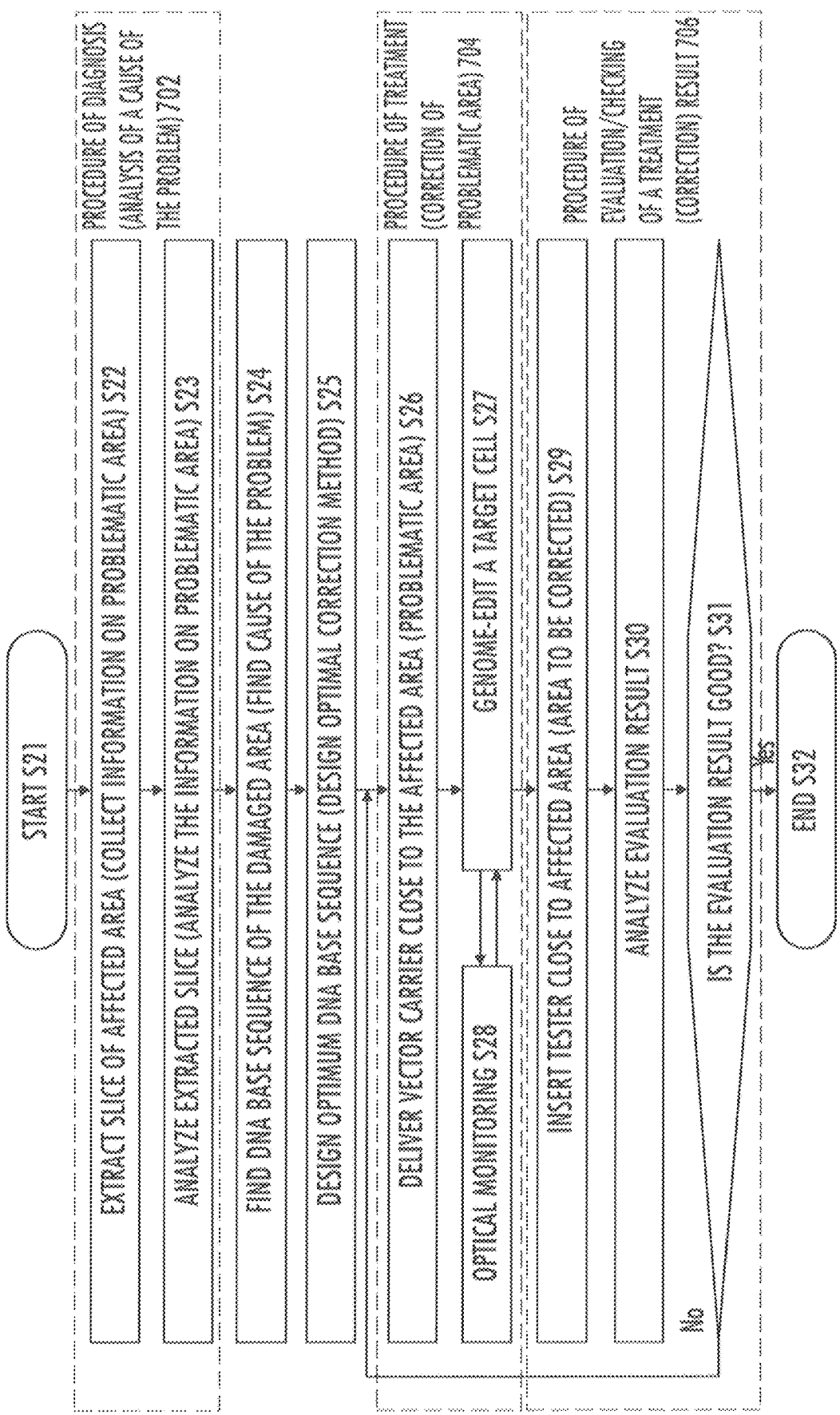
FIG. 42 describes an example of the treatment for an affected area (problematic area) relating to the damage of DNA.

FIG. 42 shows an example of the therapeutic procedure based on the present embodiment. This procedure is not necessarily limited to the field of medicine, but can be applied to more general fields as well. FIG. 42 describes the therapeutic procedure for a more general field in the parentheses. The procedure of FIG. 42 is not limited to correct problematic areas, and can be used to generate various types of functional-bio materials of FIG. 37 as well, for example.

The basic procedure for a problematic area (affected area) of the present embodiment includes "analysis of a cause", "correction" and "evaluation of the result (diagnosis, treatment and checking)".

In the procedure of diagnosis (analysis of a cause of the problem) 702, a slice of the affected area is extracted (collection of information on problematic area) at S22 and the slice is analyzed (analysis of the problematic information) at S23. For extraction of the slice (S22), the slice is surgically cut using a knife. When the affected area is inside of the body, an endoscope or a catheter may be used.

For analysis of the extracted slice (S23), the tumor is determined whether it is benign or malignant. When it is malignant, it is then checked about oncogene addiction.

If it has oncogene addiction, its DNA is analyzed so as to find the DNA base sequence of the damaged area corresponding to the cause of the problem (S24). Next based on the result, at S25, the optimum DNA base sequence is designed (optimal correction method is designed). Then based on the result of the optimization designing (S25), the "vector carrier" described in the second last line of FIG. 37 is manufactured (when a lot of standardized ones are available, the optimum vector carrier is selected). Vector refers to a DNA molecule to shift to a chromosome in the affected area (problematic area) for treatment (to correct the problematic area).

In the procedure of treatment (correction of problematic area) 704, firstly such a vector carrier has to be delivered close to the affected area (problematic area) (S26). When the affected area (problematic area) is exposed to the surface, this can be the application of a medicine containing the vector carrier. When the affected area (problematic area) is deeply inside of the body, the vector carrier may be delivered closer there using an endoscope or a catheter.

At the state of genome-editing (S27) in the target cell, which is described in details in Section 9.2, the progressive state of the editing has to be monitored in real time (S28). From a macro-perspective, the size of an affected area or the reachable depth greatly varies. In addition, the penetration rate into the affected area also varies with the place to deliver the vector carrier. Especially if the affected area (problematic area) is localized deeply inside of the body, the conventionally existing techniques have a great difficulty to understand the dispersed state of the vector carrier into the affected area.

Then, the effect of using near-infrared light with less optical noise, which is described in Chapter 3 and Chapter 6, for this optical monitoring (S28) is very large. As described in Section 2.6, near-infrared light with the wavelength range of 0.7 to 2.5 µm has excellent light transmission characteristics in a living body. Therefore the progressive state of the genome-editing can be monitored in real time by the measurement apparatus using such near-infrared light (FIGS. 1A to 1C).

As described later in Section 9.2, hydrogen bonding temporarily occurs, which has a unique form corresponding to each of the various events in the genome-editing in the target cell (S27) as follows:
- entrance of a genome-editing module into the cell nucleus;
- change in DNA base sequence; and
- gene expression.

Then as described in Patent Literature 3, the wavelength of the absorption band changes so as to correspond to each unique hydrogen-bonding.

Then, in the optical monitoring (S28), a change in light-absorbing spectrum of the near-infrared light obtained from the affected area (problematic area) being genome-edited is measured in real time, whereby the progressive state of the genome-editing can be observed precisely. When near-infrared light is used for the measurement of the range of the conventional techniques, sufficient detection accuracy cannot be obtained because of the influences from optical noise as described in Chapter 2. Accordingly at least one of the techniques described in Chapter 3 and Chapter 6 is used for the measurement apparatus (or microscopic apparatus) of FIGS. 1A to 1C for accurate observation.

In the procedure of evaluation/checking of a treatment (correction) result 706, the result of the "gene expression" is used. At this time, NIRFP described in the second last line of FIG. 37 may be used. Specifically a DNA base sequence to express NIRFP, which is described in the tenth line of FIG. 37 (and FIG. 41) and is described at the latter half of Section 8.4, also is placed in the vector carrier. Then, when a gene included in the vector carrier is expressed, whether the NIRFP also is generated or not in the cell is checked, whereby the effect of the genome-editing may be evaluated for confirmation.

At the step of inserting a tester close to the affected area (area to be corrected) at S29, visible light is guided using an endoscope or a catheter, so as to emit the visible light close to the affected area (area to be corrected) (in the patient's body). When the genome-editing is successfully performed, then NIRFP is generated in the cell. In that case, the NIRFP absorbs this visible light (excited by the energy of this visible light) and emits near-infrared light (emits fluorescence). Since near-infrared light passes through a living body well, a part of the light can pass through the living body to the outside.

For the analysis of the evaluation result (S30), analysis is performed as to whether the spectroscopic characteristics of the light emitted from the body includes or not the component of near-infrared light emitted from the NIRFP. When at least one of the techniques described in Chapter 3 and Chapter 6 is used for the optical path of the detection light 16 in this measurement apparatus (or microscopic apparatus), the detection accuracy can be improved.

To determine the evaluation result (S31), a determination is made whether the light includes or not a predetermined amount or more of the component of near-infrared light from the NIRFP. That is, when the spectroscopic characteristics emitted from the patient's body includes a predetermined threshold or more of the near-infrared light, the evaluation result is determined as good (Yes) (S31), and a series of the procedure ends (S32). On the contrary, when the amount of the near-infrared light is less than the predetermined threshold (No), then the effect of treatment (correction of the problematic area) is determined as insufficient. In this case, the procedure of treatment (correction of problematic area) 704 is repeated from the first step.

When the existing genome-editing techniques are used to mass-produce various types of functional-bio materials of FIG. 37, the following issues have to be considered mainly:

1. scalability of a replicated DNA and effective selectability of an editing target;
2. long-term safety in the cell after editing; and
3. management of base sequence before and after the editing and prevention of man-caused erroneous editing.

The first issue is described below. Molecules with low molecular weight and ions distributed outside of the nuclear membrane can pass through the nuclear pores and easily enter the cell nucleus. On the contrary, to deliver a molecule with high molecular weight into the cell nucleus, it needs support from the carrier protein. Therefore, an increase in the molecular weight of a replicated DNA molecule composing the vector means a difficulty to deliver such a replicated DNA molecule into the cell nucleus using the carrier protein. Further, due to the compatibility with such a carrier protein, the arbitrary property for the mode of a genome-editing module (the second light line of FIG. 37) is degraded greatly.

The next issue results from a nuclease that may be left in the cell nucleus after genome-editing. Such a nuclease is necessary to cut a part of the existing double-helix structure of DNA. This nuclease remains in the cell nucleus even after genome-editing, and this is like a state where a surgical knife is left in the body after the operation.

If the patient subjected to the series of treatment of FIG. 42 is infected with virus, a base sequence in the host cell or in the crRNA (CRISPR RNA) described later may change. Then, this leads to the risk of a disruption of a normal genome because of the action of the nuclease left in the cell.

This second issue is important when the genome-editing technique is used for treatment or a cell subjected to the genome-editing is cultured.

The last (third) issue is not so serious for the genome-editing in the laboratory. However, in the site where the genome-editing is performed frequently, countermeasure against the man-caused erroneous editing is important.

The example of the present embodiment described in the following Section 9.2 addresses these three issues.

Section 9.2 Structure of Nuclear Delivery Carrier and its Operation Principle

A nuclear delivery carrier as one example of the present embodiment can be used for efficient genome-editing function and such a gene regulating function. One of the application examples of the genome-editing function includes the correction of a problematic area as described in Section 9.1 referring to FIG. 42. The above describes the example of treatment of malignant tumors as one of the correction of a problematic area.

This Section 9.2 describes the structure of a nuclear delivery carrier and its operation principle. While describing them, the following shows a scheme to solve the three issues described in the latter half of Section 9.1 as well. Such a feature to solve these issues can be used not only for the treatment or the correction of a problematic area and mass-production of various types of functional-bio materials, but also for all uses.

When a genome-editing module enters the nuclear delivery carrier having a double packing structure of the present embodiment, this carrier is called a vector carrier. When a gene regulator enters there, the carrier is called a gene-regulating carrier. These carriers share the following properties:

having a double packing structure, including an inner pack inside of the carrier;

the inner pack being covered with a coating (membrane region in the carrier) separated from the interior;

this inner pack storing an object, such as a genome-editing module or a gene regulator; and delivering the object, such as a genome-editing module or a gene regulator, directly to the cell nucleus.

To this end, the inner packing membrane (outer membrane of the carrier inner pack) has a surface with a selective junction with the surface of the cell nucleus.

In response to the junction with the cell nucleus membrane of the selective junction, the object (genome-editing module or gene regulator) stored in the inner pack is delivered to the cell nucleus.

Additionally, the carrier inner pack may internally include a nuclear lamina.

Figure 43:
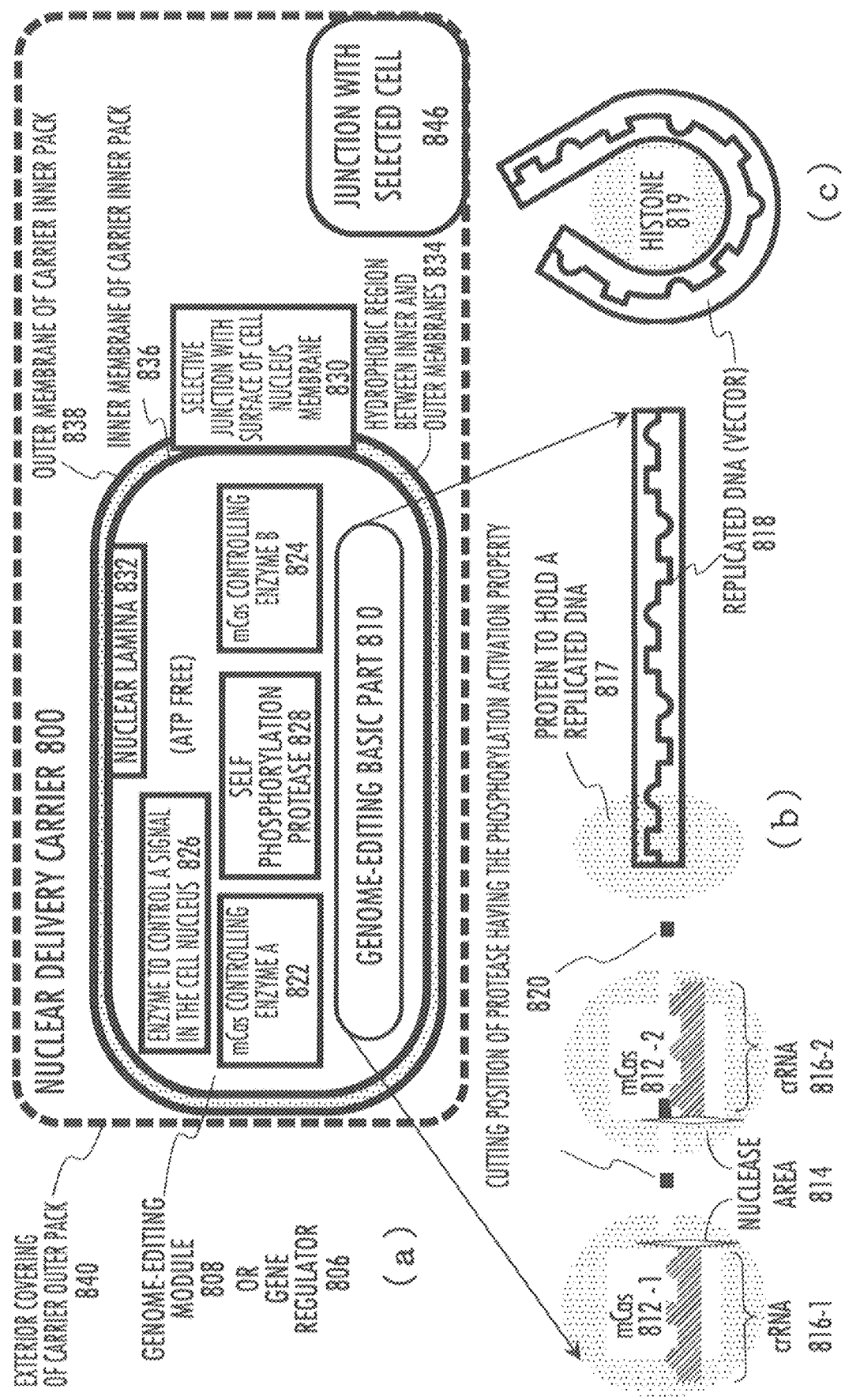
FIG. 43 describes an example of a nuclear delivery carrier having a double packing structure.

FIG. 43(*a*) shows an exemplary structure of the nuclear delivery carrier 800 in the present embodiment. The nuclear delivery carrier 800 is surrounded by an exterior covering of the carrier outer pack 840. This exterior covering of the carrier outer pack 840 may be made of proteins including the assembly of a lot of polypeptide chains or the envelope of a lipid bilayer.

When the nuclear delivery carrier 800 is selected as the vector carrier to be delivered into a malignant tumor cell (cancer cell), the exterior covering of the carrier outer pack 840 partially includes a junction 846 with the selected cell. For the junction 846 with the selected cell, a part of a ligand joining with a specific receptor on the cell membrane of the malignant tumor cell (cancer cell) surface may be used, or an antibody to specify a specific canner cell may be used.

For such a specific receptor, a VEGFR (Vascular Endothelial Growth Factor Receptor) or an EGFR (Epidermal Growth Factor Receptor) may be used for directly joining.

For the antibody to specify a cancer cell, a monoclonal antibody to specify this VEGFR may be used. Alternatively an antibody to recognize the ligand to be joined with the specific receptor and joining the ligand may be used. In this case, in response to the timing when the ligand joined with the vector carrier joins with the receptor, the object inside of the vector carrier is delivered into the malignant tumor cell (cancer cell).

The outer membrane 838 and the inner membrane 836 of the carrier inner pack in the nuclear delivery carrier 800 make up a lipid bilayer, and a hydrophobic region 834 is defined between these outer and inner membranes. This hydrophobic region is mainly made of lipid.

At a part of the outer membrane 838 of the carrier inner pack (and the inner membrane 836 of the carrier inner pack), a selective junction 830 (details are described later) is disposed to join with the surface of the cell nucleus membrane. With this configuration, the genome-editing module 808 and the gene regulator 806 stored in the inner pack can be stably delivered to the cell nucleus.

Such a selective junction 830 with the surface of the cell nucleus membrane can solve the first issue, i.e., "1. scalability of a replicated DNA and effective selectability of an editing target" described in Section 9.1. The outer membrane of the cell nucleus is directly connected with a part of an endoplasmic reticulum. Therefore if the genome-editing module 808 is released in the vicinity of the endoplasmic reticulum, genome-editing will fail. To avoid this, in the example of the present embodiment, the selective junction 830 with the surface of the cell nucleus joins with the cell nucleus membrane (including a nuclear lamina) only. This results in effective delivery of the genome-editing module 808 into the cell nucleus.

Then in response to the joining of the selective junction 830 with the surface of the cell nucleus membrane and the cell nucleus membrane (including a nuclear lamina), the cell nucleus membrane and the inner membrane 836/outer membrane 838 of the carrier inner pack fuse, so as to deliver the genome-editing module 808 into the cell nucleus. This allows the genome-editing module 808 of any size to be delivered to the cell nucleus, which means great improvement for the scalability of a replicated DNA.

The inner membrane 836 of the carrier inner pack internally includes the nuclear lamina 832. This nuclear lamina 832 may be made of a material similar to that of the nuclear lamina in the cell nucleus membrane. This can improve affinity of the carrier inner pack with the cell nucleus, and so allows the carrier inner pack and the cell nucleus to fuse well. Additionally, following the fusion, when the genome-editing module 808 or the gene regulator 806 enters the cell nucleus, damage on the cell nucleus membrane can be minimized.

As described later, due to the selective junction 830 with the surface of the cell nucleus membrane that inwardly protrudes from the inner membrane 836 of the carrier inner pack, the inner membrane 836 of the carrier inner pack and the nuclear lamina 832 join well. This can increase the relative strength of the inner membrane 836 and the outer membrane 838 of the carrier inner pack, and so can prevent the disruption of the membrane during conveyance.

When the carrier inner pack stores the gene regulator 806, the interior of the carrier inner pack may be filled with the same caryolymph as in the cell nucleus. Then, one or more types of the gene regulators 806, which will be described later, may be dispersed in this caryolymph. When the carrier inner pack storing the gene regulator 806 and the cell nucleus fuse so as to let the gene regulator 806 enter the cell nucleus, such caryolymph filling beforehand can minimize damage on the interior of the cell nucleus.

Meanwhile, when the carrier inner packs stores the genome-editing module 808, special caryolymph may be used, from which ATP (Adenosine Triphosphate) has been completely removed. Many biopolymers are phosphorylated through hydrolysis from ATP to ADP (adenosine diphosphate). This means that such phosphorylation does not occur under the ATP-free environment from which ATP has been completely removed.

Using this ATP-free state, genome-editing can be activated only for predetermined time duration immediately after the conveyance of the genome-editing module 808 into the cell nucleus. After such an effective duration, genome-editing is disabled. In this way, the genome-editing is disabled after the effective duration, which can avoid the state where a surgical knife is left in the body after the operation (corresponding to the automatic destruction of the knife in the body) as described in Section 9.1. As a result, the effect of 2. keeping the long-term safety in the cell after editing of the second issue in Section 9.1 can be obtained.

FIG. 43(*b*) shows an example of the detailed internal structure of a genome-editing basic part 810 included in the genome-editing module 808 of FIG. 43(*a*). While Section 8.1 describes CRISPR/Cas9, the present embodiment uses mCas (modified CRISPR-associated System) 812-1, 2 that is a partially modified Cas9. In this mCas812-1, 2, crRNA (CRISPR RNA) areas 816-1, 2 include components equivalent or similar to those in the existing Cas9.

The modified part of this mCas812-1, 2 is an "activity control mechanism" added to the conventional Cas9. For an example of this activity control, "activation by phosphorylation" is used. Any other method may be used for this activity control mechanism. For another example, they are separated before storing in the vector carrier for dispersion (to be a monomer state), and immediately after entering the cell nucleus, they may be polymerized to form a (polymerized) mCas.

That is, mCas812-1, 2 stored in the vector carrier is in an inactivated state under the ATP-free environment. Then, when this enters the cell nucleus, reaction occurs with ATP in the cell nucleus to activate a nuclease area 814. To implement phosphorylation causing the activation, the mCas812-1, 2 may have a self-phosphorylation function.

Alternatively, mCas-control enzyme A_822 having kinase (phosphorylation) property may be used. This mCas-control enzyme A_822 does not act in the ATP-free environment in the vector carrier. When this mCas-control enzyme A_822 enters the cell nucleus, this phosphorylates the mCas812-1, 2 using the ATP in the cell nucleus to activate the nuclease area 814. When the mCas812-1, 2 has a self-activation function in response to the self-phosphorylation, such mCas-control enzyme A_822 is not necessary.

Next, the following describes a method of exerting the function of the nuclease area 814 in the mCas812-1, 2 only for predetermined time duration (effective time duration). To this end, any means to inactivate the mCas812-1, 2 (or the nuclease area 814 therein) or an attribute for spontaneous inactivation is desirably given.

When the mCas812-1, 2 is phosphorylated through the hydrolysis of ATP, a part of the mCas812-1, 2 temporarily joins with a γ-phosphatic group in the ATP. Typically this joining does not last forever. When this mCas812-1, 2 does not have a self-phosphorylation function and the mCas control enzyme A_822 is scattered distantly, re-phosphorylation does not occur, and so the mCas812-1, 2 returns to an inactivated state. In this case, the activated duration corresponds to the duration that the γ-phosphatic group joins with a part of the mCas812-1, 2. Therefore, such an activity control mechanism (e.g., the phosphorylation area) given to the mCas812-1, 2 means that the mCas812-1, 2 has an attribute for spontaneous inactivation.

In another application example to inactivate the nuclease area 814, a mCas control enzyme B_824 may be used. This mCas control enzyme B_824 may include protease to degrade proteins, whereby the mCas812-1, 2 can be degraded in the activated state.

Instead of using this mCas control enzyme B_824, a marker to be easily distinguished from a contaminant may be given in the genome-editing basic part 810 by any method for destruction by phagocytosis.

For another application example, the mCas control enzyme B_824 may internally include phosphatase having a dephosphorylation function to remove the phosphatic group joined with a part of the mCas812-1, 2, and a substance (anions) to inhibit joining may be joined to avoid rejoining.

Then any means to set the time duration (effective duration of genome-editing) before inactivating the nuclease area 814 in the mCas812-1, 2 (activating the mCas control enzyme B_824) may be provided.

In the example of the present embodiment, a pathway of signal transduction in the cell nucleus may be used for the timer to indicate the effective duration of genome-editing. Known pathways of signal transduction in the cell nucleus include the pathway of phosphorylation that is Calmodulin CALM⇒CaM Kinase IV⇒CREB (cAMP Response Element Binding Protein) or the pathway for phosphorylation in the order of p38MAPK (the official name is described later)⇒MSK1⇒CREB.

The time required to transduce the signals in the pathway may be used as the timer (to set the effective duration).

Therefore, enzyme, such as calmodulin CALM or p38MAPK, serving as the starting point of the pathway of signal transduction in the cell nucleus may be set for enzyme to control a signal in the cell nucleus 826. Then, enzyme, such as CREB, is selected as mCas control enzyme B_824. This enzyme is induced by the phosphorylation of the enzyme close to the final point of the pathway of signal transduction in the cell nucleus and is activated. Then, the thus activated mCas control enzyme B_824 acts to inactivate the mCas812-1, 2 (the nuclease area 814 therein).

Genome-editing requires crRNA816-1 to detect the leading end of the DNA to be removed, crRNA816-2 to detect the terminal end of the DNA, and a DNA (vector) 818 to be replicated (to be replaced newly).

In the example of the present embodiment, as shown in FIG. 43(b), the genome-editing basic part 810 has a specific structure such that a replicated DNA holding protein 817 to hold replicated DNA (vector) 818, the mCas812-2 and the mCas812-1 are joined. They can be saved while having such a mutually joined form, whereby the third issue in Section 9.1 can be solved. This can facilitate the management of the base sequence relationship before and after the genome-editing, and can avoid man-caused erroneous editing.

FIG. 43(b) shows the example of the shape of the replicated DNA (vector) 818 that is like a straight line as a whole while having a double-helix structure. Alternatively, as shown in FIG. 43(c), a histone 819 including the tangled replicated DNA (vector) 818 may join with the mCas 812-2.

Since the interior of the genome-editing module 808 is free from ATP, the self-phosphorylation protease 828 is in an inactivated state. When this genome-editing module 808 enters the cell nucleus, its self-phosphorylation protease 828 is phosphorylated (activated) because of the ATP in the cell nucleus. As a result, the activated self-phosphorylation protease 828 cuts the cutting position 820 of the protease having the phosphorylation activation property.

The protein 817 to hold a replicated DNA may have a self-phosphorylation function. In the interior of the ATP-free inner pack, such protein 817 to hold a replicated DNA holds the replicated DNA (vector) 818. When the genome-editing module 808 as a whole enters a specific cell nucleus, ATP in the cell nucleus joins with the self-phosphorylation functional part. Then, the conformation of the protein 817 to hold a replicated DNA changes so as to release the replicated DNA (vector) 818. This enables the replicated DNA (vector) 818 to be integrated easily in the genome to be edited.

Alternatively, the protein 817 to hold a replicated DNA may change in the conformation, but may not have a self-phosphorylation function. In this case, the mCas-control enzyme A_822 is self-phosphorylated to activate the mCas812-1, 2 (the nuclease area 814 therein) and to phosphorylate the protein 817 of the replicated DNA so as to change the conformation.

Next, the following describes the gene regulator 806 to convey a gene regulator carrier. Such a gene regulator 806 includes substances involved in the selection of a gene to be expressed and in the control of gene transcription, for example. Therefore, the gene regulator 806 includes a repressor protein to suppress a gene and an activator protein to activate a gene. Additionally, the gene regulator 806 may include a substance relating to a pathway of signal transduction in the cell nucleus (the interior of the cell nucleus membrane).

In one ell, there is a very complicated pathway of signal transduction just to transmit the externally-given information to the interior of the cell nucleus. Therefore when a gene regulator 806 is inserted to the outside of the cell nucleus, this may lead to the risk of unexpected signal transduction. On the contrary, the example of the present embodiment directly delivers the gene regulator 806 into the cell nucleus, and so can regulate a gene efficiently and reliably.

Individual cells making up each part of a living body grow at their positions to be appropriate cells (to determine the fate of a cell) through information exchange (mainly chemical signals) with surroundings during the growth process. That is, individual cells experience gene expression corresponding to the part of the living body where the cells are placed.

For instance, the growth of a cell by culturing an initialized cell according to the method of Patent Literature 4 or Patent Literature 5 to be a cell functioning at a specific part of the living body requires a lot of time for the growth in a predetermined environment (long-term cultivation).

On the contrary, in the example of the present embodiment, such a cell can grow to a desired cell efficiently and for a short time simply by mixing a gene regulator carrier into the culture solution to culture the initialized cell. This gene regulator carrier internally includes a gene regulator 806 to promote the gene expression that is necessary for the growth of the initialized cell to a desired cell.

In this example of the present embodiment, a vector carrier and a gene regulator carrier may be given to one cell, and each of them may be given a plurality of times. Alternatively, vector carriers having different genome-editing modules 808 may be given a plurality of times, or gene regulator carriers having different gene regulators 806 may be given a plurality of times.

To grow a lot of genome-edited cells by giving a vector carrier, the vector carrier may be given, followed by giving of a gene regulator carrier. At this time, the gene regulator carrier may internally include MAPK (Mitogen-activated Protein Kinase) as the gene regulator 806.

Currently identified MARKs include three types of ERK (Extracellular Signal-regulated Kinase), JNK (c-Jun N-terminal Kinase), and p38MARK. The ERK has a function of extracellular signal regulation, and the operation in the cell nucleus has been confirmed.

The activated (phosphorylated) ERK phosphorylates (activates) CREB (cAMP Response Element Binding Protein), Ets, Jun, Fos, Elk, HIF1, STAT3 or the like in the cell nucleus to let them act on the gene. Such action on the gene contributes not only to proliferation but also differentiation and growth.

The activated (phosphorylated) JNK phosphorylates (activates) c-Jun, AFT-2, ELK-1, p53MAPK, NFAT, STAT3 or the like in the cell nucleus to let them act on the gene. Such action on the gene contributes not only to proliferation but also differentiation and apoptosis.

The activated (phosphorylated) p38MARK phosphorylates (activates) Ets-1, NFAT, Sap1, Stat1, Max, Myc, Elk1, p53MAPK, CHOP, MEF2, ATF-2, MSK1, MK2/3 or the like in the cell nucleus to let them act on the gene. Such action on the gene contributes not only to cytokine production and apoptosis.

The gene regulator 806 integrated into the gene regulator carrier is not limited to them, and CREB, Ets, c-Jun, Fos, Elk, HIF1, STAT1, 3, NFAT, Sap1, Max, Myc, CHOP, MEF2, ATF-2, MSK1, MK2/3, HMG-14, Smad, Co-Act, or TF relating to the pathway of signal transduction may be used. Alternatively, their combinations may be used.

For the gene regulator 806, Aurora AB that regulates the activity of a centrosome, a mitotic spindle or a kinetochore to progress the mitosis correctly may be used. Note here that excess intake of this may lead to the risk of canceration, and so the given dose should be taken into consideration.

FIG. 44(a) shows one example of the structure of a selective junction 830 with the surface of the cell nucleus membrane. The selective junction 830 with the surface of the cell nucleus membrane in this example of the embodiment includes a transmembrane part 870 and a cell nucleus detection part 850. Due to the action of this transmembrane part 870, the selective junction 830 with the surface of the cell nucleus membrane is localized at a membrane area that covers the interior 842 of the carrier inner pack in the nuclear delivery carrier 800. At at least a part of the transmembrane part 870, hydrophobic regions 852-1 to 6 are present. Then the cell nucleus detection part 850 detects or identifies the cell nucleus in the cell.

When this cell nucleus detection part 850 comes close to the cell nucleus, the transmembrane part 870 in the selective junction 830 with the surface of the cell nucleus membrane drags the membrane region that covers the interior 842 of the carrier inner pack so as to bring the carrier inner pack close to the cell membrane.

A specific example of this cell nucleus detection part 850 may be an antibody in the example of the present embodiment. Alternatively, any method may be used as long as it can detect or identify the position of the cell nucleus in this example of the embodiment.

The following describes antibody for the nuclear lamina 832 disposed inside of the cell nucleus as an example of the antibody to identify (detect) the cell nucleus. That is, the following describes the case using a nuclear lamina identifying antibody part 850 as an example of the cell nucleus detection part. Alternatively any antibody for every substance present at the surface of the cell nucleus or inside of the cell nucleus may be used.

Figure 44:
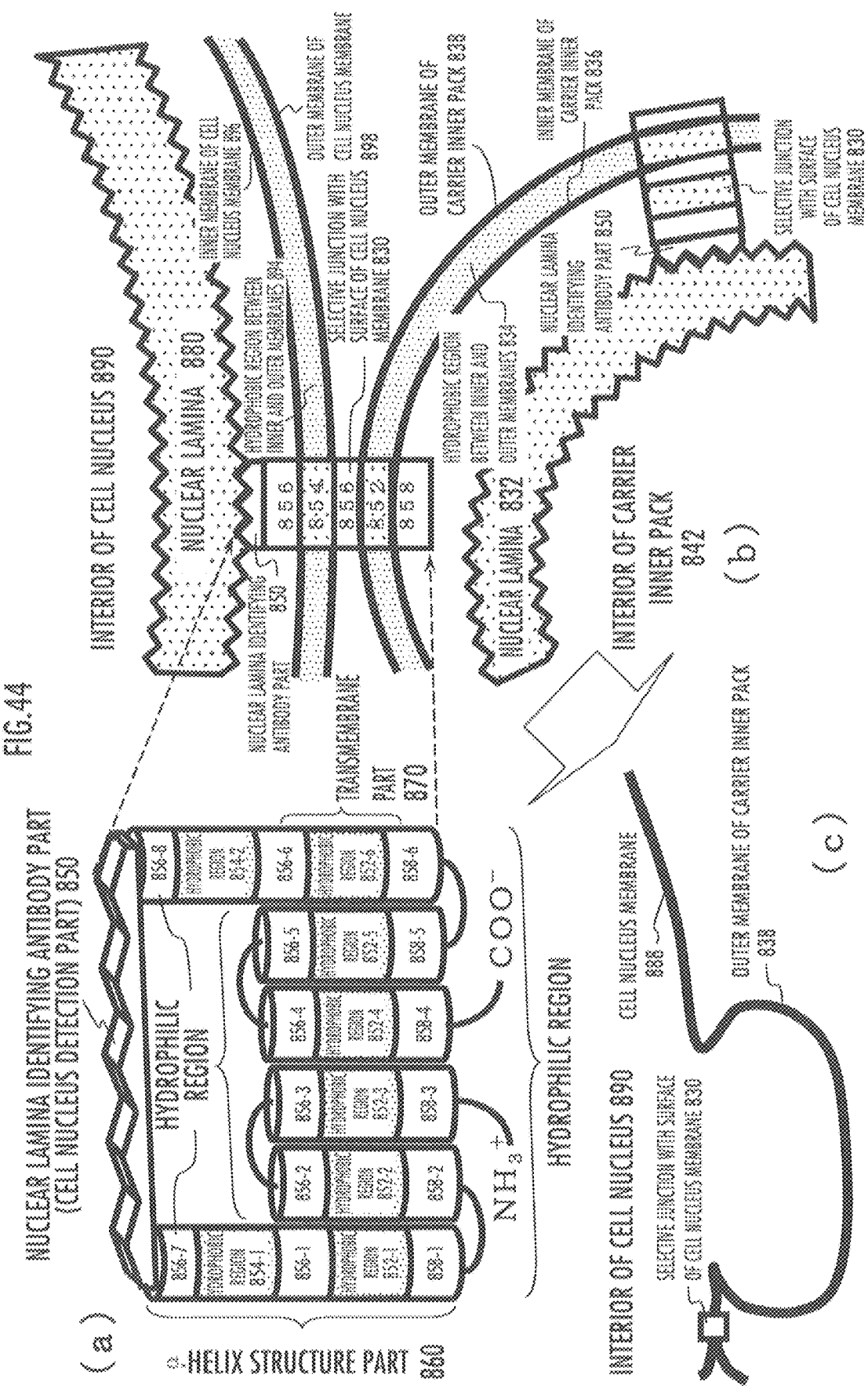
FIG. 44 describes a specific example of the structure of a selective junction with the surface of cell nucleus membrane and an example of the function.

For illustrative purposes, FIG. 44 shows a fitting/mating relationship between lateral faces of continuous triangular prisms to show the reaction (joining) between the antigen as the nuclear lamina 880 and the antibody. Such a shape of the joining part in FIG. 44 is not present actually.

The outer membrane 898 of the cell nucleus membrane joins with an endoplasmic reticulum, and so erroneous detection by the cell nucleus detection part 850 of the position of the endoplasmic reticulum has to be avoided. While an endoplasmic reticulum has a single-layered membrane structure, the cell nucleus membrane has a double-layered membrane structure including the inner membrane and the outer membrane. Then a lot of nuclear laminas 880 are localized around the inner membrane 896 of the cell nucleus membrane. That is, more nuclear laminas 880 are distributed at a relatively outer part of the cell nucleus. This property can be used for easy detection of the position of the cell nucleus from the outside.

The transmembrane part 870 penetrates once or more the membrane area (any one of the outer membrane 838 and the inner membrane 836) that externally covers the interior 842 of the carrier inner pack. In the example of FIG. 44(a), this penetrates repeatedly six times. The present embodiment is not limited to this, and penetration may be performed repeatedly any number of times, (e.g., twice, four times, seven times or twenty-four times).

The drawing shows that the transmembrane part 870 penetrates the membrane while holding a α-helix structure (defining a α-helix structure part 860). Alternatively, the transmembrane part may penetrate the membrane in any form. That is, it may have a membrane-penetrating form having a random structure or having a β-sheet structure.

The example of the embodiment of FIG. 44(a) shows six α-helix structure parts 860, and two of the α-helix structure parts 860 are longer than other four parts. Then, these two long α-helix structure parts 860 connect with the nuclear lamina identifying antibody part (cell nucleus detection part) 850 at their ends. Such a structure of the transmembrane part 870 connecting to the cell nucleus detection part (nuclear lamina identifying antibody part) 850 while being continuous as the α-helix structure 860 leads to the advantageous effect of strongly holding the cell nucleus detection part (nuclear lamina identifying antibody part) 850 inside of the selective junction 830 with the surface of the cell nucleus membrane.

Alternatively the transmembrane part 870 and the cell nucleus detection part (nuclear lamina identifying antibody part) 850 may be connected in any form. In one example, a β-sheet (crystalline) part may be disposed between the transmembrane part 870 and the cell nucleus detection part (nuclear lamina identifying antibody part) 850.

The α-helix structure part 860 having α-helix includes hydrophilic regions 856-1 to 8 and 858-1 to 6, and these hydrophilic regions include a lot of asparagin, glutamine, serine, threonine and tyrosine that are amino acids having polar residues. A part of these hydrophilic regions 856-1 to 8 and 858-1 to 6 may include lysine, arginine, histidine, aspartic acid, or glutamic acid that are amino acids having charged residues.

Meanwhile, the hydrophobic regions 852-1 to 6 and 854-1, 2 have a relatively small ratio of such amino acids, and include alanine, valine, leucine, isoleucine, proline, phenylalanine, methionine, tryptophan, glycine, cysteine or the like that are amino acids having non-polar residues.

FIG. 44(b) shows the position of the selective junction 830 with the surface of the cell nucleus membrane having the structure of FIG. 44(a) in the nuclear delivery carrier 800 (FIG. 43) and an example of the function thereof.

Similarly to the cell membrane of mammals, the membrane area that covers the inner pack of the nuclear delivery carrier 800 has a lipid bilayer structure including the outer membrane 838 of the carrier inner pack and the inner membrane 836 of the carrier outer pack. Between these outer membrane 838 of the carrier inner pack and inner membrane 836 of the carrier outer pack, a hydrophobic region 834 between the inner and outer membranes is present, and this hydrophobic region is mainly made of lipid.

Since lipid mainly includes carbon atoms and hydrogen atoms, it has a hydrophobic property. As in oil droplets that are separated in water and assemble together, the hydrophobic substance also has a property of assembling in aqueous solution (being pushed out of the water-molecule distributing area). Due to this property, the hydrophobic regions 852-1 to 6 in the transmembrane part 870 enter the hydrophobic region 834 between the inner and outer membranes.

As shown in FIG. 44(a), the selective junction 830 with the surface of the cell nucleus membrane includes hydrophobic regions 854-1, 2 as well as the hydrophobic regions 852-1 to 6. These hydrophobic regions 852-1 to 6 have a surface area that is larger than that of the hydrophobic regions 854-1, 2. Therefore, the hydrophobic regions 852-1 to 6 and not the hydrophobic regions 854-1, 2 enter the hydrophobic region 834 between the inner and outer membranes.

The cell nucleus membrane also includes a lipid bilayer membrane including the inner membrane 896 of the cell nucleus membrane and the outer membrane 898 of the cell nucleus membrane. Also between these inner membrane 896 of the cell nucleus membrane and outer membrane 898 of the cell nucleus membrane, a hydrophobic region 894 between the inner and outer membranes is present, and this hydrophobic region is mainly made of lipid. The nuclear lamina 880 is disposed inside of the inner membrane 896 of the cell nucleus membrane.

Therefore the nuclear lamina identifying antibody part (cell nucleus detection part) 850 in the selective junction 830 with the surface of the cell nucleus membrane has to enter the cell nucleus membrane to identify the nuclear lamina 880. To promote such action, the hydrophobic regions 854-1, 2 are disposed in the example of the embodiment.

That is, as shown in FIG. 44(b), these hydrophobic regions 854-1, 2 enter the hydrophobic region between the inner and outer membranes of the cell nucleus membrane. In this way, the nuclear lamina identifying antibody part (cell nucleus detection part) 850 is grounded firmly in the cell nucleus, whereby the joining of the nuclear lamina identifying antibody part (cell nucleus detection part) 850 with the nuclear lamina 880 can be promoted.

The nuclear delivery carrier 800 after injection into a cell and before absorption into the cell nucleus can move freely in the cell. During this movement, the above-mentioned hydrophobic regions 854-1, 2 may temporarily enter an endoplasmic reticulum, for example. The endoplasmic reticulum, however, has a single-layered structure, and has a different thickness from the cell nucleus membrane. Further, there is no nuclear lamina 880 inside of the endoplasmic reticulum, and so strong fixing by the nuclear lamina identifying antibody part (cell nucleus detection part) 850 does not happen. Therefore the nuclear delivery carrier 800 can leave from the endoplasmic reticulum soon and can restart the searching for the cell nucleus.

As described later about the method of manufacturing the nuclear delivery carrier 800 in Section 9.3, some nuclear delivery carriers 800 may be disposed so that their selective junctions 830 with the surface of the cell nucleus are directed toward the interior 842 of the carrier inner pack.

The nuclear lamina 832 in the interior 842 of the carrier inner pack also has a relatively strong structure. Therefore joining of the selective junction 830 with the surface of the cell nucleus membrane directed toward the interior 842 of the carrier inner pack with the nuclear lamina 832 can improve the strength of the inner membrane 836 and the outer membrane 838 of the carrier inner pack.

As shown in FIG. 44(c), at the position of the joining of the nuclear delivery carrier 800 with the cell nucleus membrane at the selective junction 830 with the surface of the cell nucleus membrane, the membrane area of the carrier inner pack is integrated into a part of the cell nucleus membrane. As a result, the contents (genome-editing module 808 or gene regulator 806) in the nuclear delivery carrier 800 are integrated into the cell nucleus 890.

Although not shown in details in FIG. 44(c), the inner membrane 836 of the carrier inner pack is integrated as a part of the inner membrane 896 of the cell nucleus membrane, and the outer membrane 838 of the carrier inner pack is integrated as a part of the outer membrane 898 of the cell nucleus membrane. In parallel with this, the nuclear lamina 832 in the interior 842 of the carrier inner pack also is integrated as a part of the nuclear lamina 880 of the cell nucleus.

Therefore at least one of the material, composition, structure and thickness of the nuclear lamina 832 in the interior 842 of the carrier inner pack may be the same as or similar to those of the nuclear lamina 880 in the cell nucleus, whereby the cell nucleus can receive minimum damage when the contents (genome-editing module 808 or gene regulator 806) of the nuclear delivery carrier 800 are delivered into the cell nucleus.

Similarly at least one of the material, composition, structure and thickness of the inner membrane 836 of the carrier inner pack may be the same as or similar to those of the inner membrane 896 of the cell nucleus membrane, whereby the cell nucleus can receive minimum damage.

Further, at least one of the material, composition, structure and thickness of the outer membrane 838 of the carrier inner pack may be the same as or similar to those of the outer membrane 898 of the cell nucleus membrane, whereby the cell nucleus can receive minimum damage.

Section 9.3 Method for Manufacturing Nuclear Delivery Carrier (for Mass Production)

G proteins and ion channels are known as membrane proteins, and they have a transmembrane part 870 having a α-helix structure 860. Then, referring to the amino-acid sequence information of them, the amino-acid sequence corresponding to the selective junction 830 with the surface of the cell nucleus membrane having the structure of FIG. 44(a) is firstly designed. Using this information, genome-editing is performed to *Aspergillus oryzae*, for example, and the selective junction 830 with the surface of the cell nucleus membrane is created by the method of FIG. 45 or FIG. 47, for example.

As described in details in Patent Literature 3, lipid molecules composing a cell nucleus membrane include a hydrophilic head and a hydrophobic tail including carbon hydride only. Therefore when an appropriate amount of such lipid molecules is injected into pure water in a petri dish, then a single-layered film of these lipid molecules aligned uniformly is formed on the entire surface of the pure water.

In this single-layered film, the hydrophilic heads face downward at the face in contact with the pure water. The hydrophobic tails face upward uniformly at the face in contact with the air.

In this state, a syringe needle is inserted into the pure water to inject the selective junction 830 with the surface of the cell nucleus membrane. As shown in FIG. 44(a), the selective junction 830 with the surface of the cell nucleus membrane has the hydrophobic regions 852-1 to 6, and so these regions are pushed by water molecules and move to the surface of the pure water. Then, the nuclear lamina identifying antibody part (cell nucleus detection part) 850 in the selective junction 830 with the surface of the cell nucleus membrane facing downward is localized at the surface where the single-layered film is formed. These hydrophobic regions 852-1 to 6 especially enter the region where a lot of hydrophobic tails are distributed in the single-layered film of the lipid molecules.

Next, a mesh or a plate having micro-pores, which is placed in the pure water in advance, is inclined, and is moved above from the pure water to the outside. Then, the layer of the lipid molecules enter into the gap of the mesh or the micro-pores of the plate, so that a lipid bilayer is formed.

This lipid bilayer internally includes the selective junction 830 with the surface of the cell nucleus membrane that are distributed. All of the nuclear lamina identifying antibody parts (cell nucleus detection parts) 850 in the dispersed selective junction 830 with the surface of the cell nucleus membrane do not have the same direction, and are directed in the mutually opposite directions in some of the selective junctions 830 with the surface of the cell nucleus membrane.

When the genome-editing module 808 is stored in the carrier inner pack, aqueous solution containing the mixture of the nuclear lamina 832 and the genome-editing basic part 810 in the ATP-free caryolymph is prepared in advance as shown in FIG. 43. This aqueous solution may include the mCas control enzyme A_822, the mCas control enzyme B_824, enzyme to control a signal in the cell nucleus 826, and self-phosphorylation protease 828 as needed.

When the gene regulator 806 is stored in the carrier inner pack, caryolymph containing the mixture of the nuclear lamina 832 and a predetermined gene regulator 806 is prepared in advance.

This caryolymph (aqueous solution) is sprayed toward a mesh or micro-pores of the plate blocked with a lipid bilayer. Then, based on the same principle as in making of soap bubbles, carrier inner packs can be created. Aqueous solution having the same constituent as that of the delivery carrier in cell membrane 800 is placed at the sprayed target position, whereby the carrier inner packs surrounded with the membrane region enter this aqueous solution.

As described above, the inner part of the inner membrane 386 of the carrier inner packs is lined with the nuclear lamina 832, and so keeps a predetermined strength. Such a structure of the inner membrane 386 of the carrier inner packs lined with the nuclear lamina 832 can lead to the effect of easily handling these carrier inner packs.

Next, by a similar method to the procedure to create the carrier inner packs, the nuclear delivery carriers 800 may be created.

Such a method enables relatively easy creation of the nuclear delivery carriers 800. The present embodiment is not limited to this method, and any method may be used.

Chapter 10 Method for Manufacturing Functional-Bio Materials and Process Management Chapter 10 describes a method for manufacturing functional-bio materials in the example of the present embodiment and a method for managing the process.

Section 10.1 Basic Procedure of Manufacturing Method and Process Management

During the production process of the functional-bio materials shown in FIG. 37, characteristics of light absorption change in the near-infrared region as described in Section 2.6. That is, these functional-bio materials are produced using a catalytic reaction of specific enzyme in some forms. According to Patent Literature 3, hydrogen-bonding occurs temporarily during this catalytic reaction, so that the wavelength of the absorption band changes in accordance with the form of this hydrogen-bonding. Therefore such a change in wavelength of the absorption band may be measured, whereby the state can be managed during the manufacturing of a functional-bio material. The methods described in Chapter 3 and Chapter 6 may be used for this, whereby the measurement accuracy of a wavelength change of the absorption band can be improved greatly.

Figure 45:
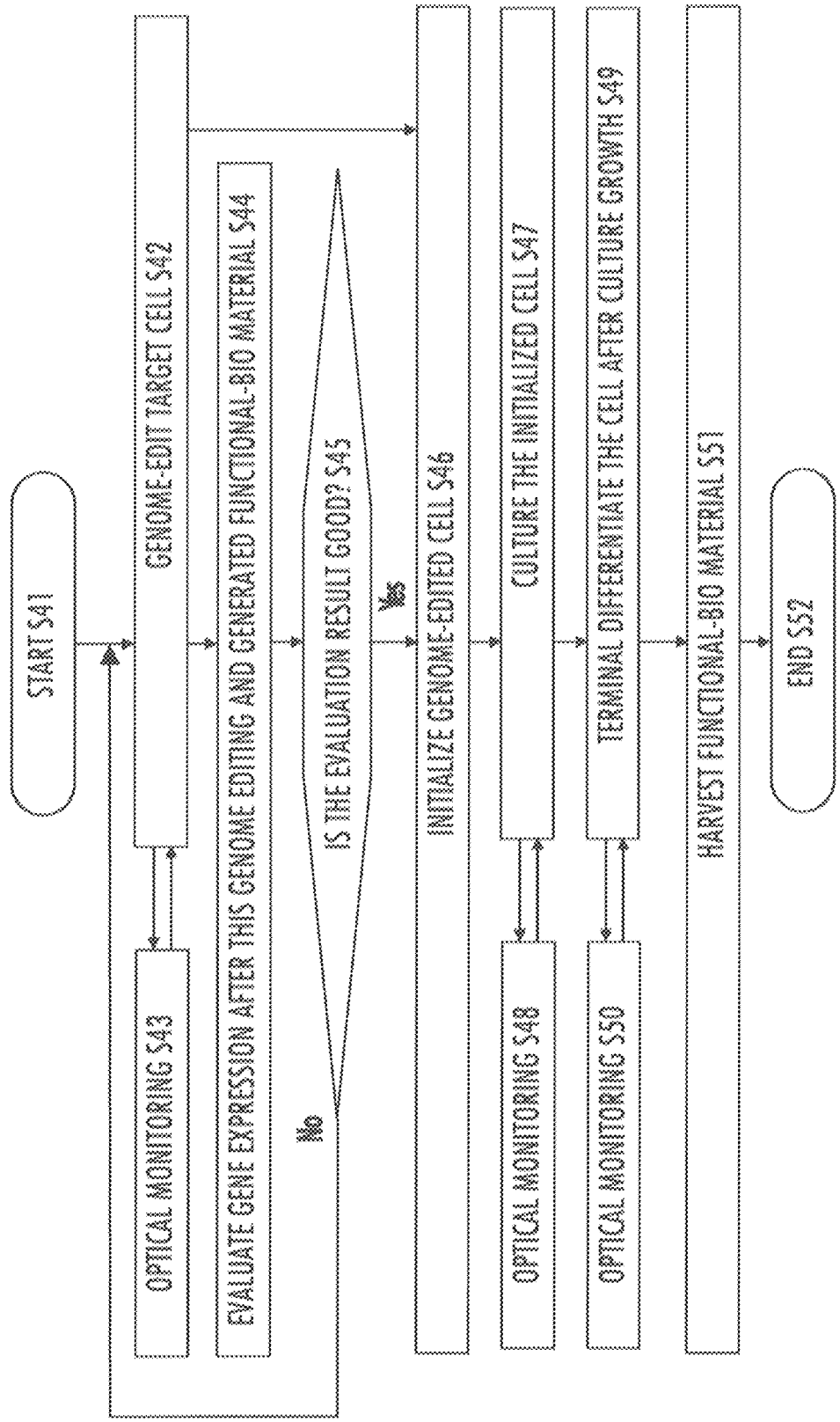
FIG. 45 describes one embodiment of a method for mass-producing functional-bio materials and a method for managing the process.
Figure 47:
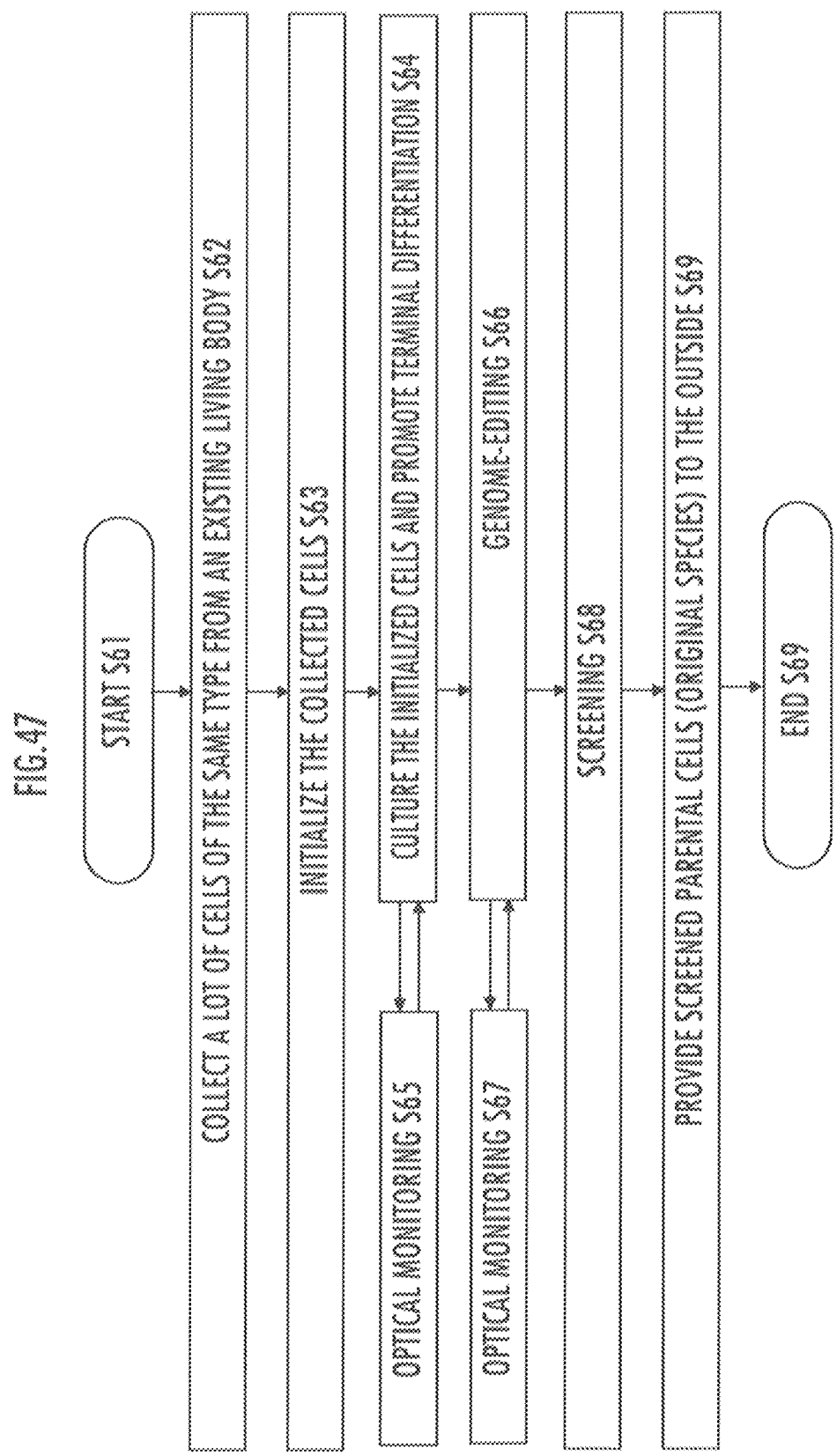
FIG. 47 describes an applied embodiment of a method for mass-producing functional-bio materials and a method for managing the process.

FIGS. 45 and 47 show a method of manufacturing a functional-bio material while managing the state of the process using near-infrared light. The method of FIG. 45 includes genome-editing (S42) using a vector carrier described in Chapter 9, followed by culture growth of a cell using a gene regulatory carrier (S47). The method of FIG. 47 includes cell culture using a gene regulatory carrier (S64), followed by genome-editing using a vector carrier (S66).

Alternatively genome-editing only or culture growth only may be performed, or both of them may be performed at the same time. They may be combined in random order.

The following describes one specific example of the mass-production method and the method for process management of FIG. 45 by way of an example to manufacture a functional-bio material using transgenic silkworm.

Referring to FIGS. 38 to 39A, Section 8.3 describes the "fibroin transformation" described in the third and fourth lines of FIG. 37 or the "fibroin containing acid residue" described in the fifth line of FIG. 37.

Cocoon from a silkworm includes a lot of fibroin, and so the "fibroin transformation" or the "fibroin containing acid residue" can be manufactured using transgenic silkworm.

At the first step to start the manufacturing (S41), genome-editing is performed in a target cell using a vector carrier described in 9.2 (S42). At this time, hydrogen-bonding temporarily occurs between bases in nucleotide. Therefore a change of the wavelength of the absorption band occurs at this time as described in Section 8.5.

When CRISPR/Cas9 is used for the genome-editing, DNA is cut at the nuclease area 814. At this time also, hydrogen-bonding occurs specific to this DNA cutting, and so a change in wavelength of the absorption band corresponding to this can be observed.

Optical monitoring at S43 means the management of process based on the observation of a wavelength change of the absorption band using near-infrared light (to manage the genome-editing state).

For transgenic silkworm, genome-editing at S42 is performed to a fertilized egg of the silkworm.

Evaluation is made whether such genome-editing is performed correctly or nor (S45). If the genome-editing is not correct (No), then the procedure returns to the genome-editing (S42). When evaluation of gene expression after this genome editing and of the generated functional-bio material is performed for the transgenic silkworm (S44), this corresponds to the analysis of the composition of cocoon from the grown silkworm or the analysis of the characteristics of the cocoon.

If the evaluation result (S45) is good (Yes), the procedure shifts to the next S46. When the genome-edited fertilized egg starts cell division, a part of the cells is separated and extracted, and is stored by freezing. If the evaluation (S44) on the growth of a larva from the remaining fertilized egg and on the pupa after metamorphosis is good, then the initialization is performed for the corresponding stored egg by freezing at S46. This initialization is performed by the method disclosed in Patent Literature 4 or 5.

A gene regulatory carrier is given to the initialized cell for culture growth (S47). For the gene regulator used here, MAPK family described at the latter half of Section 9.2 may be used.

When the gene regulator acts on a DNA, hydrogen-bonding temporarily occurs between a part of the gene regulator and a part of the DNA. Then the optical monitoring at S48 includes observation of a wavelength change of the absorption band specific to this hydrogen-bonding to manage the effect from the gene regulator on the DNA.

At the next S49, the cell after culture growth is terminal differentiated to harvest a functional-bio material (S51). To this end, the example of the present embodiment can have one of the two ways as follows. The first way is to let a larva of the silkworm grow from a fertilized egg and metamorphose to a pupa, and then to extract a cocoon only.

The second way is to give a gene regulatory carrier including a gene regulator to a cell in a culture solution so as to promote the terminal differentiation. This results in the growth of a silk cell in the culture solution, followed by disruption of the cell membrane. Then fibroin is extracted from the cell, which corresponds to harvesting of a functional-bio material at S51.

Also when the gene regulator acts on the DNA to promote terminal differentiation, hydrogen-bonding temporarily occurs. Therefore a wavelength change of the absorption band specific to this hydrogen-bonding may be observed and the effect from the gene regulator on the DNA may be managed. This step corresponds to the optical monitoring S50.

Optical monitoring is performed at S65 and S67 of FIG. 47 as well. The specific process is substantially the same as the above, and so the detailed descriptions are omitted.

In any one of the two ways, when extraction of fibroin (harvesting of a functional-bio material S51) ends, the manufacturing ends (S52). Instead, the cycle starting from the initialization of a cell at S46 or the culture growth at S47 may be repeated.

The above exemplifies a silk cell as a parental cell (original species) (FIG. 48) having the ability of producing a functional-bio material. A functional-bio material may be mass-produced in the example of the present embodiment as follows:

A] producing in a predetermined vessel without using a cell;

B] producing in a cell, and collecting a functional-bio material by disrupting the cell membrane;

C] letting a cell itself secrete a functional-bio material produced in the cell; and D] producing a functional-bio material in a cell, and expanding it to the outside of the cell while joining with the cell.

The present embodiment is not limited to these methods, and a functional-bio material may be manufactured by any method.

The method [B] is called an *E. Coli* method, in which protein is produced in an *Escherichia coli*. This method requires the step of disruption and purification, and so the manufacturing step is complicated and the manufacturing cost tends to increase relatively.

The method [C] to secrete protein produced in a fungus is suitable for *Aspergillus oryzae* or *Corynebacterium glutamicum*. Especially *Corynebacterium glutamicum* has a property of secreting a macromolecule while keeping the conformation using a channel called TatABC. Note here that there is an upper limit for the molecular size (molecular weight) of the macromolecule that can be secreted, and so it is difficult to directly secrete a large-sized functional-bio material.

On the contrary, the method [A] can easily produce and collect proteins of any size. Specifically simply by dropping DNAs into a specially-shaped test tube containing extraction liquid of *Escherichia coli*, proteins can be synthesized automatically. Such a specially-shaped test tube is divided by a special filter, whereby gene expression also is enabled using microdialysis.

Note here that unwanted bacteria easily increase in such an extraction liquid of *Escherichia coli*, and so the manufacturing is desirably performed in a specific environment free from contamination of bacteria (in a clean room). If sterilizing of the bacteria contaminated is performed for mass-production in a normal environment, a mRNA transcription system or a protein synthesis system may have serious damage.

The method [D] may be used for another application example of the present embodiment. A hair follicle allows sheep's wool or hair produced therein to extend to the outside while directly joining it with the hair follicle. As compared with [A], a hair follicle has resistance to sterilizing. Therefore this manufacturing method can be used easily in a normal environment by suitably selecting the sterilization.

Figure 46:
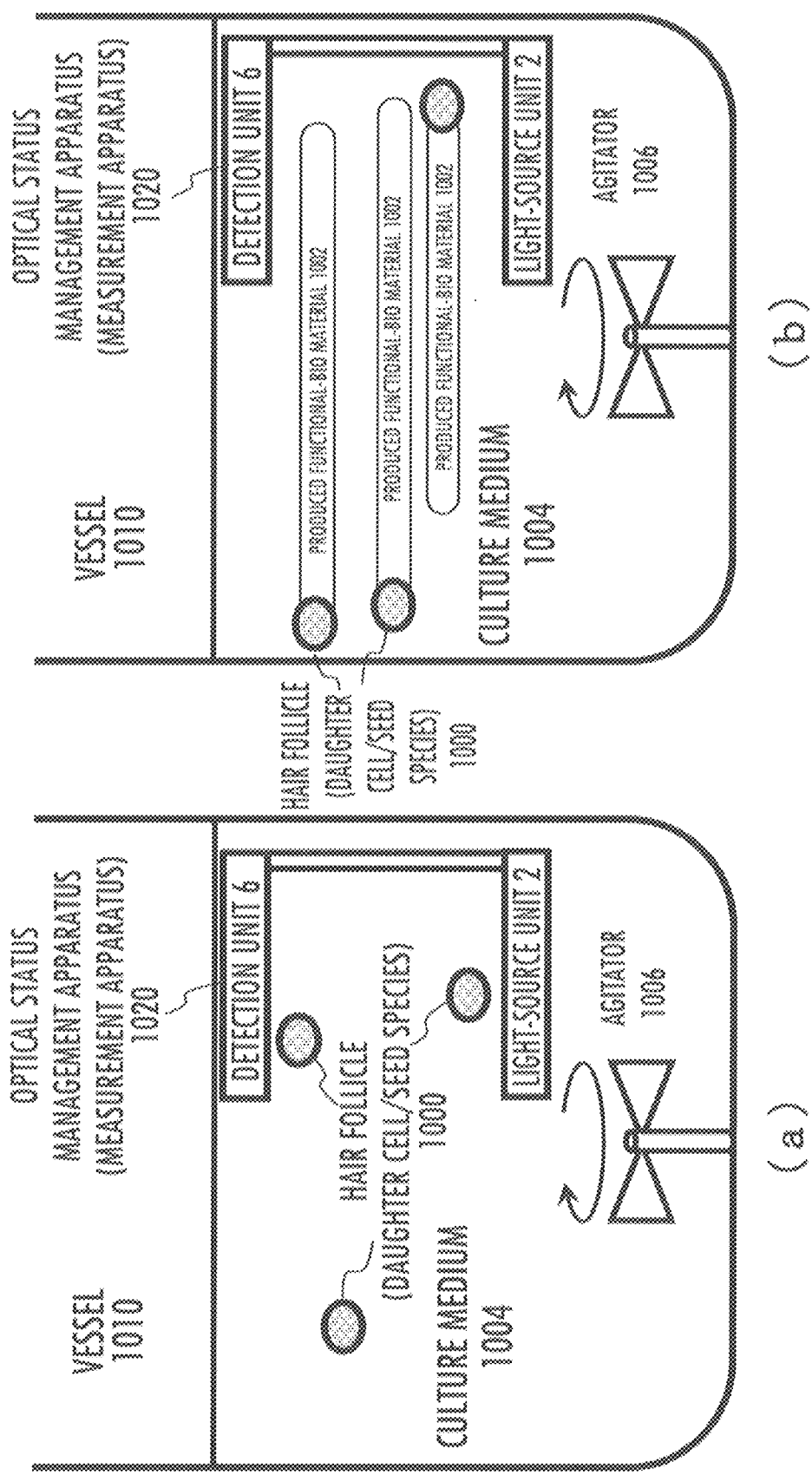
FIG. 46 describes an example of producing a functional-bio material using hair follicle.

FIG. 46 shows the state in which hair follicle 1000 is used a parental cell (original species) having the ability of producing a functional-bio material or a daughter cell (seed species) obtained from the parental cell by culture growth, and a functional-bio material 1002 is produced by the method [D].

As shown in FIG. 46, an agitator 1006 and an optical status management apparatus (measurement apparatus) 1020 are disposed beforehand in a predetermined vessel 1010. This optical status management apparatus (measurement apparatus) 1020 includes a light-source unit 2 and a detection unit 6 similarly to the structure of FIGS. 1A to 1C.

Although not shown in FIG. 46, the apparatus may include a pH adjuster to adjust a pH value in the culture medium 1004 and an oxygen supplier to supply oxygen gas to the culture medium 1004.

As shown in FIG. 46(*a*), a predetermined culture medium 1004 charged in the vessel 1010 is always agitated. In this state, a hair follicle (parental cell/original species or daughter cell/seed species) 1000 is placed. Under this environment, the hair follicle (parental cell/original species or daughter cell/seed species) 1000 is continuously cultured for predetermined time duration.

Then, as shown in FIG. 46(*b*), the hair follicle (parental cell/original species or daughter cell/seed species) 1000 coming with the produced functional-bio material 1002 can be obtained. This state is similar to hair coming with a hair follicle.

The produced functional-bio material 1002 can be collected by a very simple operation of taking out it from the culture medium 1004, which can be the effect of greatly shortening the mass-production steps.

FIG. 47 shows a mass-production method of the parental cell (original species) 1000 used here. At the first step S62 immediately after starting (S61), a lot of cells of the same type are collected from an existing living body. Specifically epidermis of animals, such as sheep, may be collected.

Immediately after that, the collected cells are initialized by the method described in Patent Literature 4 or Patent Literature 5 (S63). Then, a gene regulatory carrier including a gene regulator, such as MAPK family, is given to culture-grow the cells immediately after the initialization, and a gene regulatory carrier including a predetermined gene regulator is given to promote the terminal differentiation. Since the optical monitoring at S65 and S67 is the same as or similar to those in FIG. 45, the descriptions of them are omitted.

At Step S66, a vector carrier is given for predetermined genome-editing. Thereafter screening is performed (S68) to extract desirably genome-edited cells only, and these cells are provided to the outside as the parental cells (original species) 1000 (S69). Then the manufacturing procedure ends (S69).

The following is a supplemental description on the method for mass-producing the functional-bio materials described above from (A) to (D). In the methods from (B) to (D), a specific cell is used for mass-production of the functional-bio materials. The cell used here has to be selected correctly depending on the type of the mass-produced functional-bio material.

For example, protein obtained from a higher organism is generated in a cell by gene manipulation. For a cell belonging to a primitive organism, such protein obtained from a higher organism seems like invasion by a foreign substance. Every cell internally has proteinase to degrade protein. Therefore when protein obtained from a higher organism is generated in a cell belonging to a primitive organism, the cell detects it as the invasion of a foreign substance and degrades the synthesized protein by the proteinase.

In a specific example, when fibroin (obtained from an insect species) is generated in *Aspergillus oryzae* obtained from a microorganism, the secretion efficiency of the fibroin deteriorates significantly because of the action of the proteinase. When the activity of the proteinase is stopped to increase the secretion efficiency of the fibroin, the generation amount of another unnecessary foreign substance may increase.

For this reason, to mass-produce a functional-bio material obtained from a specific organism (including a partially modified substance of a bio material that the specific organism directly creates), a cell obtained from an organism in the same or a higher hierarchy than the specific organism is desirably used.

In a specific example, vegetables, rice, wheat or the like (a material composing them) as an artificial food is desirably mass-produced using a cell obtained from plants. An artificial edible meat (or actin filament composing the edible meat, for example) is desirably mass-produced using a cell obtained from mammals, birds or fish and not a cell from insects (such as a silk-thread cell of a silk worm).

In an example by the method (D), the above describes the case using the hair follicle cell 1000. For the above reason, the hair follicle cell 1000 obtained from a higher organism (e.g., obtained from mammals, such as sheep or a human) is desirably used.

In the method of (C) also, a cell obtained from a higher organism (e.g., mammals) is desirably used for mass production. The following describes an example using a pancreas β cell (or its modified cell) as a cell (obtained from a higher organism) to secrete an internally-produced functional-bio material to the outside.

Human insulin secreted from this pancreas β cell has a protein structure comprising two monomers. Specifically human insulin includes A chain made up of twenty-one amino acids and B chain made up of thirty amino acids, and these A and B chains are disulfide-bonded at two positions.

The pancreas β cell to secret insulin used in the example of the present embodiment is not necessarily obtained from human, but may be a pancreas β cell in other mammal's body. For a gene involved in the insulin generation in this pancreas β cell, genome-editing is performed as described in Chapter 9. Then, this is changed as a special cell to generate/secrete a functional protein suitable for a food or a function material, such as a part of a muscle cell.

In the example of FIG. 46, the hair follicle cell 1000 is used so as to correspond to the method (D). In the method (C), however, a functional protein is secreted from a cell as in the modified pancreas β cell, for example. In this case, the functional protein may be generated/secreted using the culture media 1004 and the apparatus to manage the manufacturing state (measurement apparatus) 1020 as shown in FIG. 46.

Section 10.2 Geographically Distributed Mass-Production Procedure

The methods shown in FIG. 45 or 47 mainly show the production of a functional-bio material 1002 at the same place. Alternatively, a functional-bio material of the example of the present embodiment may be produced over a widely distributed area including the place for each manufacturing step.

When a total volume of the produced functional-bio material 1002 increases, the cost to convey the material is very expensive. On the contrary, parental cells/original species, such as a hair follicles, as the base to produce a functional-bio material 1002 or daughter cells/seed species 1000 obtained by culture growth of the parental cells are very small, and so they can conveyed at relatively low cost.

Therefore they are conveyed to the area of consuming the functional-bio material 1002 in the form of parental cells/original species or daughter cells/seed species 1000, and at such a consuming area, the functional-bio material 1002 may be produced. Thereby the total cost can be greatly lowered.

Meanwhile, the vector carrier or the gene regulatory carrier described in Section 9.2 referring to FIGS. 43, 44 and 37 allows a genome-editing module or a gene regulator to directly enter the cell nucleus. Therefore due to the necessity of protecting natural environment or maintaining world ecosystem, the area of using a vector carrier or a gene regulatory carrier is desirably limited to a specific area.

Figure 48:
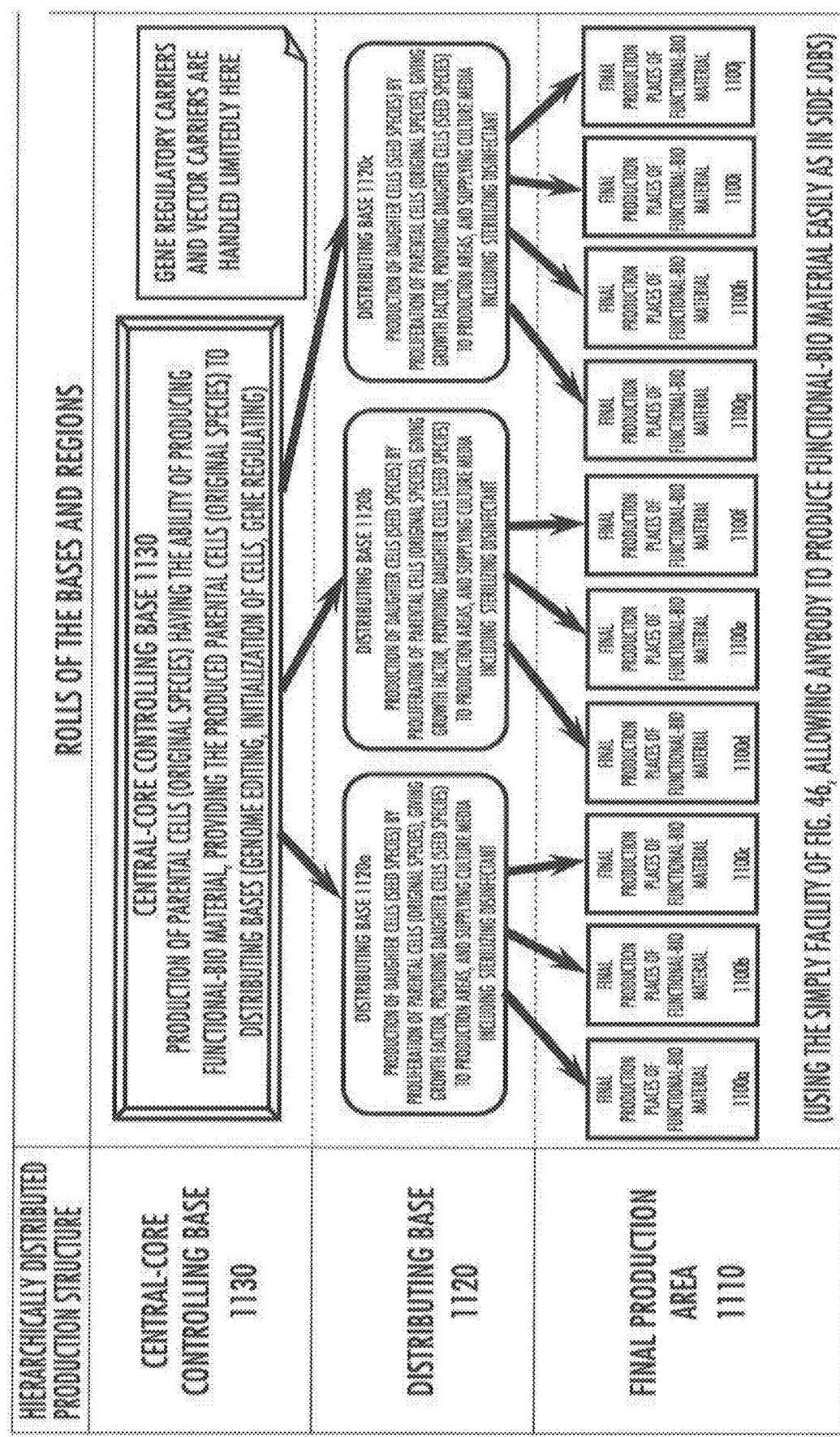
FIG. 48 describes an example of a geometrically-distributed method for producing a functional-bio material.

Therefore the example of the present embodiment shown in FIG. 48 has hierarchized production bases for the manufacturing steps. A central-core controlling base 1130 is collected at one place, in which gene regulatory carriers and vector carriers are limitedly handled. Management in this central-core controlling base 1130 is tightened, so as to thoroughly avoid the gene regulatory carriers and the vector carriers from going to the outside. Such a method can lead to the effect of avoiding and controlling adverse effects on the existing ecosystem or natural world.

That is, genome-editing, initialization of cells, and gene-regulating are performed only in the central-core controlling base 1130. Then parental cells (original species) 1000 having the ability of producing a functional-bio material are produced (mass-produced) there. The obtained parental cells (original species) 1000 are provided to distributing bases 1120.

At each of the distributing bases 1120*a* to 1120*c*, the provided parental cells (original species) 1000 are proliferated, and their daughter cells (seed species) are produced. To increase the proliferation effect, a growth factor is given to the cells.

Note here that such a growth factor given to promote the mitosis or growth of daughter cells (seed species) from the parental cells (original species) 1000 at the distributing bases 1120*a* to 1120*c* is only given from the outside of cells. That is, at these bases, a gene regulatory carrier is not used for direct delivery to the cell nucleus.

Culture media 1004 also are prepared, which include a sterilizing disinfectant (agent to prevent contamination) to prevent the contamination in the culture media 1004 under normal environment and with less damage on the daughter cells (seed species).

Then, those produced daughter cells (seed species) and culture media 1004 including a sterilizing disinfect are provided to the final production bases 1100*a* to 1100*j* of the functional-bio material.

These final production areas 1110 are located at the bottom of the hierarchically distributed production structure.

Then these final production places 1100a to 1100j of the functional-bio material are located close to the consuming places of the functional-bio material.

These final production places 1100a to 1100j of the functional-bio material include simplified facility described in FIG. 46 under normal environment, and purchase the daughter cells (seed species) and the culture media 1004 including a sterilizing disinfect from the distributing bases 1120. They may purchase the daughter cells and the culture media directly or via a network.

Then, the functional-bio material 1002 is produced by the method shown in FIG. 46, and so ordinary people can produce the functional-bio material under normal environment. Therefore according to the example of the present embodiment, anybody can produce a functional-bio material easily as in side jobs.

Section 10.3 Estimation of Functional-Bio Material Using Non-Coherent Near-Infrared Light Polyethylene having a molecular structure 408 in FIG. 64(*a*) or (*b*) has the light absorption characteristics shown in FIG. 63. A part of amino acid sequence 400 in a silk sheet (fibroin) has the characteristics shown in FIG. 64(*c*). This has the light absorption characteristics shown in FIG. 62.

Conventional straight-travelling light 360 having partial coherency optically interferes with multi-scattered light 370 during the passage through the silk sheet (see FIG. 26(*a*)). As a result, as shown in FIG. 61, light absorption characteristics of the silk sheet (fibroin) cannot be obtained with the conventional partial coherent light. On the contrary, accurate light absorption characteristics can be obtained with (non-coherent) near-infrared light with coherency reduced by the method described in Chapter 3.

Section 10.1 describes an exemplary method of managing the manufacturing process of a functional-bio material using the non-coherent light. Not limited to such management of the manufacturing process, the findings obtained from FIGS. 62 and 63 can be used to estimate (identify) the components or the molecular structure of a functional-bio material manufactured.

Food (excluding vitamins and minerals) can be roughly classified into a protein group, a glucide group and a lipid group. Not limited to a functional-bio material used for food, a functional-bio material used for materials also can be roughly classified into a protein group, a glucide group and a lipid group.

An atomic group (—NHn) including a nitrogen atom at the center is not included in a functional-bio material in the glucide group or the lipid group (FIG. 65). Instead, atomic groups (—CHn) each including a carbon atom at the center mostly make up a functional-bio material in the lipid group. Then the content of a hydroxyl group (—OH) in such a functional-bio material in the lipid group is very smaller than the content of such an atomic group. The content of methyl group (—CH$_3$) is low in a functional-bio material in the glucide group.

A functional-bio material in the protein group can contain any atomic group. Atomic groups other than —NH group exist in the amino acid residue. Therefore in the case of a functional-bio material containing artificial protein as a major component, types of the amino acids composing the major component of the artificial protein and their composition amounts can be estimated from the atomic groups detected in its light absorption characteristics.

A numeral in parenthesis at a lower part in each field of FIG. 65 indicates the value directly read from FIG. 62 or 63. A center part in the field is the citation from the document by Ozaki et al. (Yukihiro OZAKI, Satoshi KAWATA: Kin-sekigai Bunkou-hou (or near-infrared (NIR) spectroscopy) published by Gakkai Shuppan Center in Japan, 1996, pp 216 to 219).

In one example, in fibroin, glycine having a CH group accounts for 46% and alanine having a —CH$_3$ group accounts for 30%. Presumably peak (local maximum) positions indicated with downward arrows in FIG. 62 show the content of alanine that is 30%.

For thread of a spider, it is said that just alanine accounts for the most part of the β-sheet type crystalline part 602 (FIG. 38). Therefore measurement of the light absorption characteristics of the thread of a spider will show a great increase in the peak (local maximum) value at the positions of the downward arrows.

In a comparison between FIG. 62 and FIG. 63, the center wavelength of the absorption band belonging to the first overtone of the stretching exceeds 1.7 μm (in the range of 1.81 μm to 1.70 μm) for methyl group (—CH$_3$), and is 1.7 μm or less for methylene group (—CH$_2$) or for —CH group. The positions indicated with the downward arrows in FIG. 62 are 1.683 μm and 1.177 μm. Therefore when the center wavelength of the absorption band is observed close to 1.683 μm (in the range from 1.80 μm to 1.67 μm) or close to 1.177 μm (in the range from 1.23 μm to 1.12 μm), then the presence of methyl-group can be expected. In this way, the type of amino acid as the major component can be found based on whether the center wavelength of the absorption band of the light absorption characteristics from a functional-bio material exceeds 1.7 μm or not.

Although not illustrated, the center wavelength of the absorption band at the position of 1.7 μm is observed also for PMMA (Poly-Methyl-Metacrylate) or epoxy resin having methyl group.

Additionally, when the center wavelength of the absorption band is observed in the range from 1.23 μm to 1.15 μm or in the range from 0.94 μm to 0.86 μm, then the material highly likely includes methyl group, methylene group or —CH group.

Further, it can be easily expected from FIG. 65 whether a functional-bio material to be measured includes a material in a protein group or not. That is, when the functional-bio material includes a material in a protein group, the center wavelength of the absorption band exists in the range from 1.67 μm to 1.46 μm or from 1.11 μm to 0.97 μm.

The actual measurement result of FIG. 62 shows the centers of the absorption bands closer to 1.570 μm, 1.538 μm and 1.495 μm. Fibroin includes a β-sheet type crystalline part 602 (FIG. 38). Therefore when protein has a β-sheet structure, an absorption band having the center wavelength at (or in the vicinity of) any one of the values may be detected.

For instance, light absorption characteristics are obtained from a functional-bio material to be used (in the future) for food or materials (using the light with partial coherency reduced (or non-coherent light) as described in Chapter 3), and the composition (materials) of the functional-bio material can be estimated as follows.

Firstly for group vibration in an atomic group, the absorption band belonging to overtones of stretching is described below. FIG. 65 shows that 1.67 μm, 1.46 μm, 1.38 μm, 1.11 μm and 0.94 μm are border values of the measurement wavelengths.

That is, when the center wavelength of the absorption band observed in the light absorption characteristics is in the range from 1.67 μm to 1.46 μm or in the range from 1.11 μm to 0.97 µm, a functional-bio material as a target can be considered as a "protein group" (at least a part includes amino acid).

When the center wavelength of the absorption band observed is in the range from 1.46 µm to 1.38 µm or in the range from 0.99 µm to 0.94 µm, a functional-bio material as a target can be considered as a "glucide group" (at least a part includes polysaccharide, such as oligosaccharides or cellulose) or a "protein group" (at least a part includes amino acid).

When no center wavelength of the absorption band exists in the range from 1.67 µm to 1.46 µm or in the range from 1.11 µm to 0.97 µm, it can be estimated that a "glucide group" mainly composes the center composition of the functional-bio material.

When the center wavelength of the absorption band exists in the range from 1.67 µm to 1.46 µm or in the range from 1.11 µm to 0.97 µm, any one of the following highly likely occurs.

1) a "protein group" mainly composes the center composition of the functional-bio material, and 2) a "protein group" and a "glucide group" are mixed.

In FIG. 65, hydroxyl groups (—OH) are included in "lipid group" materials. A "lipid group", however, very highly likely includes methyl groups or methylene groups. Therefore the amount of hydroxyl group (—OH) (i.e., the intensity of the absorption band) observed in a "lipid group" often is hidden in a measurement error.

Similarly the possibility of the presence of a methyl group ((—CH$_3$) in a "glucide group" is very low. Therefore as stated above, when the center wavelength of the absorption band is present at the position of 1.7 µm or more, the material is categorized as any one of a "lipid group" or a "protein group". When no center wavelength of the absorption band exists in the range from 1.67 µm to 1.46 µm or in the range from 1.11 µm to 0.97 µm, it can be estimated that a "lipid group" makes up the center composition.

The following describes how to distinguish between an absorption band belonging to the overtones of stretching and an absorption band belonging to the combination in the light absorption characteristics. As shown with (a) and (c) of FIG. 63, the absorption band belonging to the overtones of stretching is relatively narrow and has large intensity (the height from the baseline to the center part). On the contrary, the absorption band belonging to the combination is relatively wide and has small intensity as in the surroundings of FIG. 63(j).

As described in Section 5.6 about the part of FIG. 63(j), partial coherent light is used for comparison, and it may be determined that a part generating large vibration belongs to the combination.

As described in Chapter 2 and indicated with the measurement result of FIG. 61, when conventional partial coherent near-infrared light is used, a detection signal will be embedded in optical noise. Conventionally, therefore, it is difficult to analyze the individual absorption bands belonging to group vibration in an atomic group. On the contrary, the present embodiment enables the generation of light with low partial coherency (non-coherency) by the method described in Chapter 3. Such light only can be used to analyze the characteristics of the individual absorption bands belonging to group vibration in an atomic group.

Section 10.4 Optical Characteristics of Functional-Bio Material in Present Embodiment This section describes optical characteristics of functional-bio materials manufactured in the present embodiment. Firstly the following describes optical characteristics of a functional-bio material using a "protein group" material. Next, optical characteristics of functional-bio materials having unique functions are described.

In this embodiment, for the structure of a functional-bio material using a protein-group material, the following two operations are performed:

A) a structure is formed using an α-helix, β-sheet or turned structure; and

B) the composition facilitating optical management of the manufacturing process is used.

(B) is described first. There are twenty types of amino acids in the natural world. Therefore, a functional-bio material may be made of the twenty-types of amino acids so that their composition ratios are the same. In this case, however, the light absorption characteristics of such a functional-bio material will be very complicated. Assume the case where a functional-bio material having very complicated absorption characteristics is manufactured. When a material originally has such a complicated characteristics, if the absorption characteristics are slightly changed during the process management, it is difficult to estimate what a kind of problem occurs.

A functional-bio material in the present embodiment may be manufactured so that the composition ratio of discriminative amino acid is high. This can lead to the effect of facilitating the analysis about the problem during the manufacturing. In the present embodiment, instead of specifying the numerical value of the composition ratio of a discriminative amino acid, the light absorption characteristics obtained from the manufactured functional-bio material are specified. The details are described later. As is understood from FIG. 66, the condition (A) can be satisfied by increasing the composition ratio of a discriminative amino acid.

Referring to FIG. 49, Section 8.3 describes an example of forming a structure by combining modified β-sheet crystalline parts 1602. In FIG. 49, a structure is formed from a plurality of assembly blocks of crystalline parts (polymer) 1604.

Not limited to such a combination of the blocks, fibriform protein may be twisted/braided, whereby a structure such as cloths may be formed. Silk thread including fibroin already having a β-sheet structure as a raw material corresponds to the fibriform protein. The secondary structure of collagen or tropomyosin categorized as fibriform protein has an α-helix structure.

Therefore a functional-bio material of the present embodiment forms a structure using an α-helix, β-sheet or turned structure. At least a part of a functional-bio material of the present embodiment internally has such a structure, which facilitates the forming of a macroscopic structure/shape of the functional-bio material and can achieve the stability of the shape of the molded article during the long storage.

To implement such a structure, a functional-bio material of the present embodiment is manufactured by increasing the composition ratio of amino acid that has easily an α-helix, β-sheet or turned structure.

FIG. 66 shows amino acids that easily have an α-helix structure and amino acids that easily have a β-sheet structure. In FIG. 66, amino acids are classified based on a difference of a center atom of the atomic group disposed at the forward end of the amino acid residue. The number of amino acids classified as a carbon group is the largest, and the number of amino acids classified as a nitrogen group is the smallest.

FIG. 66 shows that all of amino acids that easily have an α-helix or β-sheet structure include methyl group or methylene group. Therefore considering the description referring to FIG. 65 together, functional-bio materials of the present embodiment have absorbance characteristics such that their center wavelength of the absorption band exists in the range from 1.81 µm to 1.67 µm, in the range from 1.23 µm to 1.12 µm, or in the range from 0.94 µm to 0.84 µm.

Next the following describes the relationship between the composition ratio of amino acid and the detection characteristics. The silk sheet of about 100 µm in thickness has the absorbance characteristics as shown in FIG. 62, in which absorption bands associated with alanine having a methyl group appear at the positions indicated with downward arrows. Spider's thread has a higher composition ratio of alanine. Therefore for spider's thread, an absorption band having larger absorption intensity (higher in the absorbance characteristics) will appear near the same downward arrow positions.

In the present embodiment, instead of specifying the composition ratio of each amino acid, the height of the absorption band belonging to overtones of the stretching of a methyl group and a methylene group is specified (i.e., a difference between the value of the absorbance at the center-wavelength position of the absorption band and the baseline indicated with the broken line). Such specification using the height of the absorption band and not the composition ratio of each amino acid facilitates the quality control of the material during manufacturing or of the completed material.

Most of the noise components in the measurement result with non-coherent light in FIG. 62 and FIG. 63 results from electrical noise (dark current and shot noise) of the one-dimensional line sensor 132 (FIG. 22) in the spectroscope 22. Immediately before each measurement, dark current of the one-dimensional line sensor 132 is measured, and subtraction thereof is performed. However, it is difficult to remove the dark-current component that varies with time. By finding the average of measurements repeated 250 times, the influences from shot noise are reduced. However, such a reduction of the shot noise has a limit. Especially when the amount of the detection light 16 is low, the influences from the electrical noise is relatively larger.

The noise amplitude at the absorbance in the measurement result with non-coherent light in FIG. 63 can be estimated up to about 0.0003p-p. Since the silk sheet on the long-wavelength side has low transmittance of about 5.3%, the influences from electrical noise will be large. The noise amplitude can be estimated up to about 0.003p-p from FIG. 62.

Therefore the condition enabling stable signal detection of the example of the present embodiment is as follows for the absorbance of a functional-bio material of the present embodiment. That is, the height of the absorption band (a difference between the value of the absorbance at the center-wavelength position of the absorption band and the baseline indicated with the broken line) observed in the range from 1.81 µm to 1.67 µm, in the range from 1.23 µm to 1.12 µm, or in the range from 0.94 µm to 0.84 µm has to be 0.003 or more (desirably 0.0003 or more).

It is said that the composition ratio of alanine in fibroin is 30%. FIG. 62 shows that the height of the absorption band (a difference from the baseline) belonging to the first overtone of the stretching in this case is about 0.008. Similarly the height of the absorption band (a difference from the baseline) belonging to the second overtone is about 0.002.

When the composition ratio up to about 10% is detected, 0.008/3=0.0027 and 0.002/3=0.00067 can be obtained. Therefore based on the data of FIG. 62, the height of the absorption band observed in the range from 1.81 µm to 1.67 µm has to be 0.0027 or more (desirably 0.008 or more).

Similarly the height of the absorption band observed in the range from 1.23 µm to 1.12 µm has to be 0.00067 or more (desirably 0.002 or more).

In an application example of the present embodiment, the following considers the case of manufacturing a functional-bio material with spider's thread. It is expected that Spider's thread has a composition ratio of alanine that is 45% or more. Then, 0.008×45/30=0.012 and 0.002×45/30=0.003 can be obtained. Therefore when a functional-bio material is manufactured using spider's thread as a material, for example, the process may be controlled so that the height of the absorption band observed in the range from 1.81 µm to 1.67 µm is 0.012 or more, or the height of the absorption band observed in the range from 1.23 µm to 1.12 µm is 0.003 or more.

Next, the following considers an expected maximum value of the height of the absorption band (a difference from the baseline) belonging to a methyl group that may be observed. When synthetic protein having the composition ratio of alanine that is 100% is manufactured, 0.008×100/30=0.027 and 0.002×100/3=0.0067 can be obtained. Note here that the height of the absorption band will vary with measurement errors or the way of selecting the baseline, and therefore the height of the absorption band belonging to the first and the second overtones can be estimated as 0.054 and 0.0134, which includes the double margin.

These estimated values are based on the assumption of alanine 100%. As shown in FIG. 66, valine, isoleucine, leucine includes two methyl groups in one residue. Therefore when the composition ratio of these amino acids is 100%, the above values will be double. In this case, the heights of the absorption band belonging to the first and the second overtones (differences between the value of the absorbance at the center-wavelength position of the absorption band and the baseline indicated with the broken line) are 0.108 and 0.0268, respectively.

From the above (referring to FIG. 65 as well), the absorbance characteristics obtained from functional-bio materials of the present embodiment can be summarized as follows. A difference between the value of the absorbance at the center-wavelength position of the absorption band observed in the wavelength range from 1.80 µm to 1.67 µm and the baseline is in the range of 0.0027 to 0.108. A difference observed in the wavelength range from 1.23 µm to 1.12 µm is in the range of 0.00067 to 0.0268.

Next, the following considers the height of the absorption band belonging to a methylene group that may be observed. The ratio of a methylene group in polyethylene is relatively high. Therefore the value read at position (a) of FIG. 63 is 0.003, which is close to the value of the composition ratio 100%. Including double margin resulting from measurement errors or the way of selecting the baseline, the estimation will be 0.006 (=0.003×2). Assuming the composition ratio 10% or more, 0.003×10/100=0.0003 can be obtained. Including double margin with this, the minimum value can be estimated as 0.0003/2=0.00015.

Therefore considering the description in FIG. 65 as well, a difference between the value of the absorbance at the center-wavelength position of the absorption band observed in the wavelength range from 1.23 µm to 1.15 µm and the baseline is in the range of 0.00015 to 0.006.

Instead of forming a structure using a "protein group" as stated above, the following describes the optical characteristics of a functional-bio material having its unique function. For instance, as described in Section 8.3 referring to FIG. 39A(c), a carboxyl group 616 included in a functional-bio material can improve the water absorption rate. In FIG.

39A(c), before bonding cation 612 with the carboxyl group 616, a hydroxyl group (—OH group) in FIG. 65 exists. In this way, when a functional-bio material has a lot of hydroxyl groups (—OH group) or amino groups (—NHn), the hydrophilic characteristics of the functional-bio material is improved.

Therefore, as shown in FIG. 65, the manufacturing process of a functional-bio material having hydrophilic characteristics may be controlled so that the absorption band with the height (difference from the baseline) of 0.003 or more (desirably 0.0003 or more) is observed in the wavelength-range from 1.67 µm to 1.38 µm or from 1.11 µm to 0.94 µm.

Section 10.5 Method for Manufacturing Functional-Bio Materials Outside of Cell

The methods for manufacturing a functional-bio material in Section 10.1 and Section 10.2 mainly are to produce material at least in a predetermined cell. This section describes a method for manufacturing a functional-bio material outside of the cell as an application example of the present embodiment.

Figure 67A:
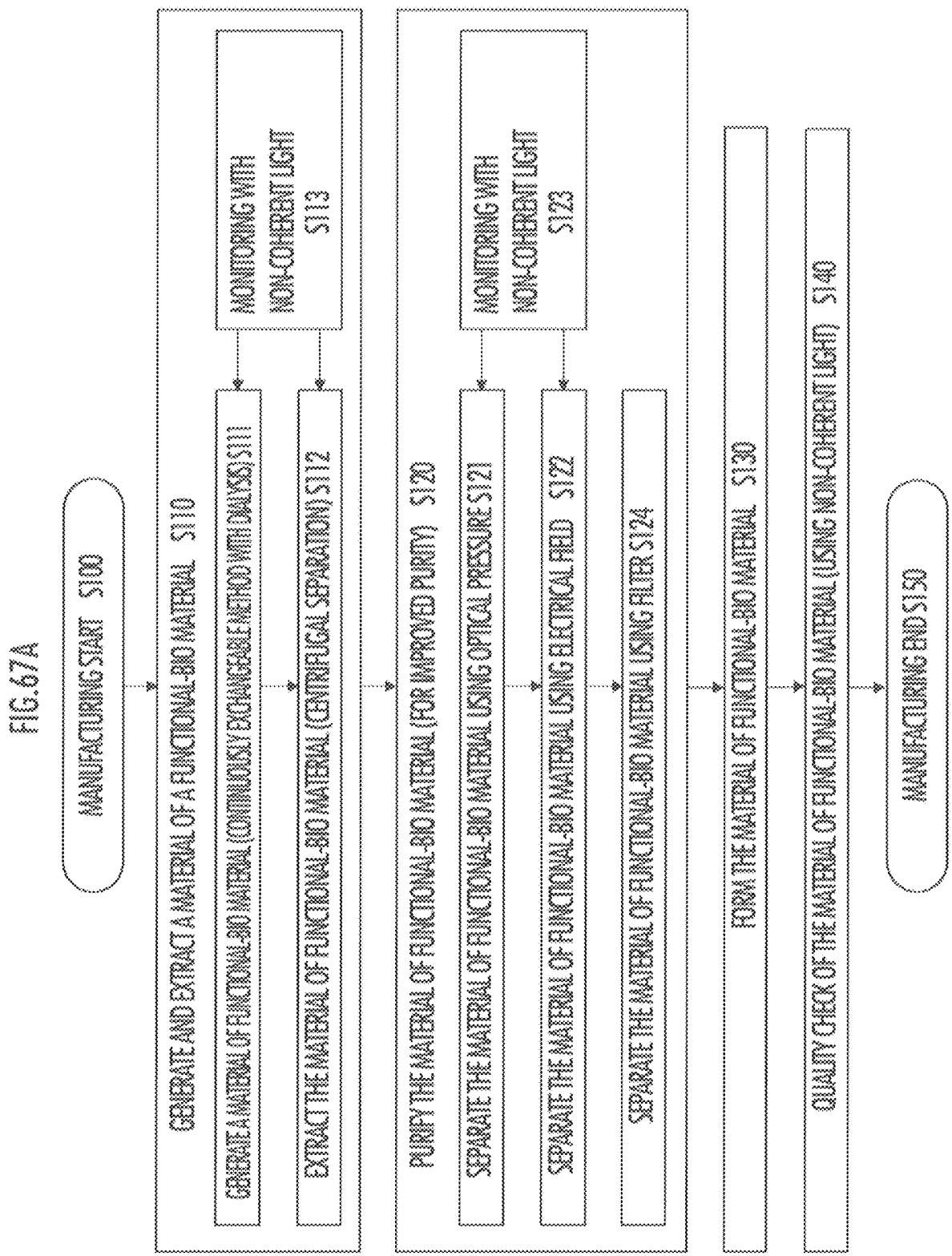
FIG. 67A describes another manufacturing process for a functional-bio material in the present embodiment.

FIG. 67A shows the basic manufacturing procedure. The procedure includes Step S110 to generate and extract a material of a functional-bio material, Step S120 to purify the material of the functional-bio material to improve the purity, Step S130 to form the functional-bio material, and final Step S140 to check the quality, and these steps are performed in this stated order.

Step S110 to generate and extract a material of a functional-bio material includes a continuously exchangeable method with dialysis at S111 and extraction of the material of the functional-bio material by a centrifugal separation method at S112. These steps are performed in parallel with monitoring (S113) using non-coherent near-infrared light shown in the present embodiment (Chapter 3). These steps are managed so that the optical characteristics described in Section 10.3 and Section 10.4 can be continuously obtained.

At S120 to purify the material of the functional-bio material, a material to be used for the functional-bio material only is separated by various methods, which is to improve the purity of the material. FIG. 67A shows the following specific examples of the purification:

1) A protein-group material only is separated for extraction based on the principle of optical tweezers (S121);

2) Electrical field is applied to aqueous solution to separate an electrically-charged material only for extraction (S122); and 3) A material in different size is separated using filter such as filter paper (S124).

Alternatively, other purification methods may be used. Any one of the methods may be selectively used.

Non-coherent near-infrared light shown in the present embodiment (Chapter 3) may be used to monitor the progress of the purification at Steps S121 and S122 (S123).

If the monitoring at S113 or S123 shows not-satisfactory characteristics different from the range described in Sections 10.3 and 10.4, the following method is performed to cope with such a situation. If the frequency of the failure to obtain the characteristics is low, a material beyond the target is selected and discarded. If the frequency is high, the manufacturing line is stopped once to find the cause of the problem.

At Step S110 to generate/extract a material of a functional-bio material and Step S120 to purify the material of the functional-bio material, the state of the generated polymer also has to be monitored at S113 and S123. Especially information on the bonding state in the polymer appears in the following characteristics as described in Section 5.6:

A) Profile characteristics of the baseline; and

B) Absorption band characteristics in the wavelength range of 1.67 µm to 1.46 µm (FIG. 65).

See the positions of peak (local maximum) indicated with upward open arrows in FIG. 62.

Therefore the process is desirably managed while evaluating these characteristics at the same time.

Figure 67B:
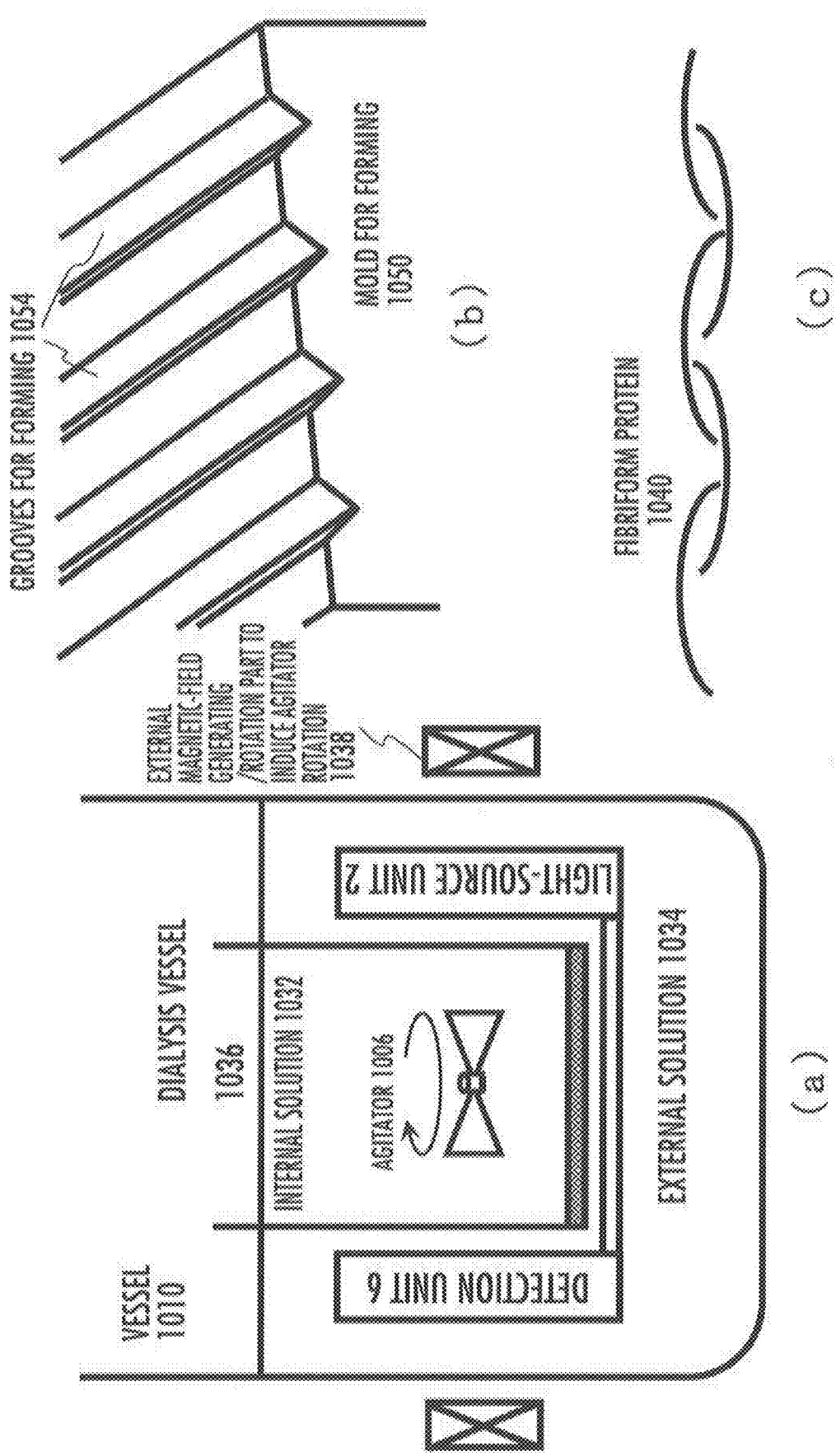
FIG. 67B describes generation and forming steps in the manufacturing process for a functional-bio material in the present embodiment.

FIG. 67B(a) shows one example of the method to generate and extract a material of the functional-bio material by a continuously exchangeable method with dialysis at S111. External solution 1034 to be poured into a transparent vessel 1010 includes a mixed aqueous solution made up of:

various types of amino acids to generate a material;

polysaccharide as source of energy for activity, such as glucose;

nucleoside triphosphates;

tRNA (Transfer Ribonucleic Acid);

various types of substrates relating to transcription and translation; and growth factors to promote the transcription and translation.

Internal solution 1032 to be poured into a dialysis vessel 1036 includes:

cell-free protein synthesis system (CF) reaction solution; and single chaining deoxyribonucleic acid (DNA) fragment to form a template to produce protein.

For such CF reaction solution, solution extracted from *Escherichia coli*, rabbit or wheat cell with embryo buds have been conventionally used. Recently solution extraction from eucaryote cell has been used in addition to the conventional solution.

As described in Section 10.1, proteins obtained from higher organism are desirably produced using cells obtained from organisms in the same or a higher hierarchy. Therefore, to produce a protein-group functional-bio material, solution extracted from cells obtained from organisms that are equal to or higher than an organism made up of the target protein may be used for the CF reaction solution. This can improve the productivity to manufacture the functional-bio material. Further, solution extracted from cells of an organism made up of proteins as a target may be used, whereby the affinity of the artificial protein to be produced with the CF reaction solution can be increased more. In that case, the productivity to manufacture the functional-bio material can be more improved.

For instance, when chicken meat is artificially produced as food, solution extracted from cells of chickens or solution extracted from cells of other types of bird species is desirably used for the CF solution. Similarly when beef or pork is artificially produced, solution extracted from cells of cows or pigs or of other mammals may be used for the CF reaction solution.

In another application example, the following considers the case of transplanting a normal muscle to the patient to treat the muscular atrophy. When such a muscle is artificially produced, solution extracted from human cells may be used for the CF reaction solution.

When a functional-bio material is artificially produced using silk or spider's thread, the CF solution may be extracted from cells of silk worms or spiders or of other types of insect species to produce the material. Alternatively solution extracted from human or mammal cells may be used for the CF reaction solution, whereby a relatively versatile material of artificial protein can be produced.

The single chaining DNA to form a template to produce protein may be artificially synthesized in accordance with the nucleotide sequence designed beforehand. Alternatively existing genome sequence may be edited by genome editing techniques, such as CRISPR/Cas9, ZFN or TALEN, described in Section 8.1 or 8.5, and then the single chaining DNA may be produced by opening the double helical structure.

The dialysis vessel 1036 containing this internal solution 1032 is placed in the vessel 1010 containing the external solution 1034 (FIG. 67B(a)) to start incubation. During the incubation, the system is kept at 28° C. to 40° C. for 1 hour or longer and 32 hours or shorter.

The dialysis vessel 1036 comes with an agitator 1006. When an external magnetic-field generating/rotation part 1038 to induce the rotation of the agitator rotates to rotate the agitator 1006, the agitator agitates the internal solution 1036.

The light-source unit 2 and the detection unit 6 to detect the detection light 16 obtained after transmission as shown in FIG. 1B(a) are disposed in the vessel 1010 to successively monitor (S113 of FIG. 67A) the state of producing the material of a functional-bio material (S111 of FIG. 67A)). Not limited to the incubation time of 1 to 32 hours as described above, the incubation may end at any timing when the monitoring at S113 shows the end of the production of the material.

Then the dialysis vessel 1036 is removed from the vessel 1010, and the internal solution 1032 is collected into another vessel. Then, this internal solution 1032 is allowed to stand at a low temperature to end the incubation. The temperature of the internal solution 1032 at this time is desirably in the range of 0° C. to 10° C. (desirably about 4° C.).

At the next step of extraction of the material of the functional-bio material at S112 of FIG. 67A, the solution is rotated at about 4° C. for 5 minutes with 12000 rpm for centrifugal separation. The top clear layer of the separated solution includes the produced material of the functional-bio material.

Monitoring using non-coherent light at S133 can show the range of the separated solution from the upper end that includes the produced material of the functional-bio material.

FIG. 67B(b) shows an example of the method for forming the functional-bio material at S130 of FIG. 67A. FIG. 67B(b) shows a forming method of a fibriform functional-bio material such as silk thread. A mold for forming 1050 has a surface with grooves 1054 for forming. When the purified internal solution 1032 is dropped there, the solution is collected into the grooves 1054.

When this is allowed to stand in the dry atmosphere, the water evaporates, and so a fibriform functional-bio material can be obtained. For instance, fibroin having a β-sheet crystalline part 602 (FIG. 38) and a single body of collagen or tropomyosin having an α-helix structure have a relatively short fiber structure. Then when the water in the purified internal solution 1032 evaporates, these fibers are mutually tangled, so that a unified and large fiber structure can be formed as in FIG. 67B(c). This thread may be woven to be fabric by a conventional method, and clothes or food may be produced using this fibriform functional-bio material.

The forming step (S130) of FIG. 67A is not limited to the above, and the forming may be performed by the method described in Section 8.3 referring to FIG. 49. Any other methods may be used for forming.

Figure 67C:
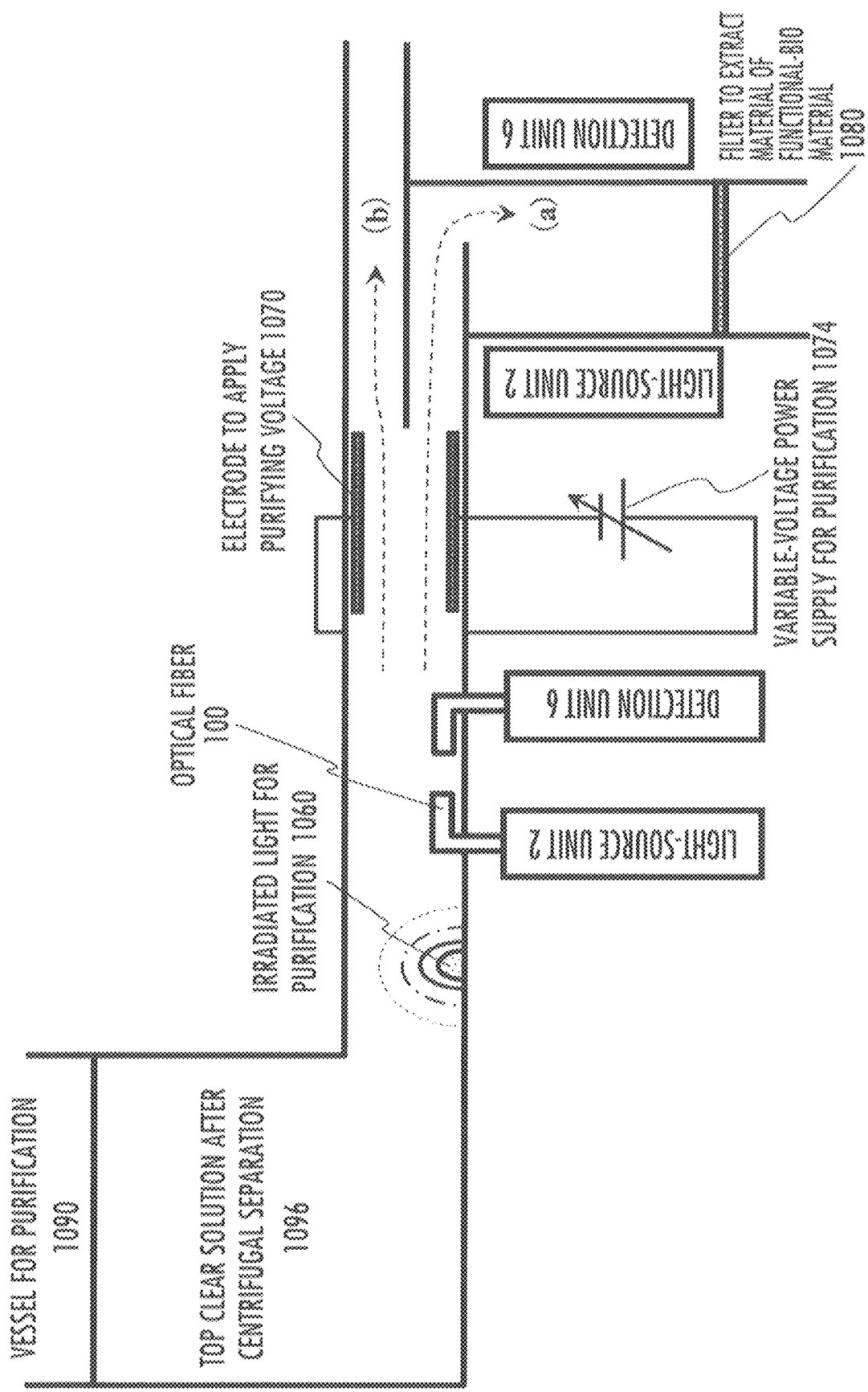
FIG. 67C describes purification step in the manufacturing process for a functional-bio material in the present embodiment.

FIG. 67C shows an example of the apparatus used at the purification step (S120) of FIG. 67A. The top clear solution 1096 obtained at the centrifugal separation (S112) of FIG. 67A is placed in a vessel for purification 1090. Then such top clear solution 1096 is allowed to move to the right by gravity.

A material of the functional-bio material may be separated based on the principle of optical tweezers (optical pressure) as shown in S121 of FIG. 67A. As shown in FIG. 65, a functional-bio material in a protein group selectively absorbs near-infrared light in the wavelength range from 1.67 μm to 1.46 μm and from 1.11 μm to 0.99 μm. Therefore near-infrared light in this wavelength range is used for the irradiated light for purification 1060 of FIG. 67C.

Force is generated from the place having a small intensity of this irradiated light 1060 (above in the sheet of FIG. 67C) to the place having a large intensity (below in the sheet). Using this force, the functional-bio material in a protein group only is allowed to move downward.

As shown in FIG. 67C, irradiated light 12 emitted from the light-source unit 2 is applied to the passage position of the top clear solution 1096 after centrifugal separation via an optical fiber 100. Then the detection light 16 obtained after the passage through the top clear solution 1096 travels through the optical fiber 100 to the detection unit 6. This optical system monitors the absorbance characteristics of the top clear solution 1096 in real time (S123). Then, the process to separate the functional-bio material from the top clear solution 1096 is managed based on this result.

Next, the following describes a method for purification using electrical field to be applied to the aqueous solution in S122 of FIG. 67A. Arginine, histidine and lysine among amino acids are positively charged. Nucleotide sequence in the template DNA is designed so that the amino acid sequence produced includes these positively-charged amino acids slightly more. As a result, polymer as the material of the functional-bio material is positively charged in the aqueous solution.

Voltage is applied to an electrode 1070 to apply purifying voltage from a variable-voltage power supply for purification 1074 to separate a material of the functional-bio material in a protein group (S122 of FIG. 67A). This step also is monitored using the combination of the power-supply unit 2 and the detection unit 6 (S123).

In this embodiment, polymer as the material of the functional-bio material is positively charged in the aqueous solution. When anions such as chlorine ions are mixed into the purified aqueous solution, then salt will be produced during the forming to be electrically neutral.

The thus purified aqueous solution moves in direction (a) of FIG. 67C, and is collected below. The aqueous solution containing other components moves in direction (b) for discarding.

A filter to extract a material of the functional-bio material 1080, such as filter paper, may be used to purify the material of the functional-bio material based on a difference in molecular size.

That is the description of the manufacturing method mainly about a functional-bio material in a protein group. Alternatively, a functional-bio material in a glucide group or a lipid group may be manufactured by the method of FIG. 67A.

For instance, glucose may be polymerized to produce starch as a food material. During the process to produce starch, a part of FIG. 67A may be used.

While certain embodiments have been described, these embodiments have been shown for illustrative purposes only and are not intended to limit the scope of the inventions. Indeed, these novel embodiments described above may be embodied in a variety of other forms, and various omissions, substitutions and changes may be made without departing from the spirit of the inventions. These embodiments and their modifications are included in the invention recited in the claims and their equivalents as well as in the scope and the spirit of the invention.

2 Light-source unit
4, 6 Detection unit
8 Feedback unit
9 Wall
10 Target
12 Irradiated light (first light)
16 Detection light (second light)
18 Beam splitter
20 Beam splitter
22 Spectroscope
24 Monitor camera
25 Objective lens
26 Collimator lens
28-1, 2 Detecting lens
30 Measurement apparatus
32 Column for reference sample
34 Column for measurement sample
36 Transparent glass vessel
38 Moving direction of glass vessel
42 Inlet
44 Outlet
46 Lid
48 Mirror face
50 Tungsten filament
52 Optical narrow-bandwidth bandpass filter (wavelength selective filter)
54 Electric-field amplitude of light having selected wavelength
56, 58 Light-transmitting object having one face with microscopic asperities
60 Incident light having partial coherency
62 Short-wavelength light having partial coherency
64 Optical noise reduction element or partial coherency reduction element
66 Micro light-scattering object
67 Vessel (quartz glass) of tungsten halogen lamp
68 Long-wavelength light having partial coherency
70 Light-emitting source
72, 74 A part of light
76 Change in optical length
78, 79 Combined light (mixed light)
80 Photodetector
82 Back mirror
84 Forward emitted light
86 Imaging plane (detector plane)
88 Backward emitted light
90 Optical characteristics changing member
92 Cross section of transmitted light
94-1 to 6 Transparent semicircular parallel flat plate
95 Cutting plane
96 Light-transmitting direction
97 Border line of cutting plane
98 Collecting lens
100, 100-1, 2 Optical fiber
101 Optical characteristics changing member to generate a plurality of optical paths
102, 102-1 to 5 Light combining (mixing) part
104 Transparent flat plate having one face with random microscopic asperities
106 Wave front of transmitted light
107 Light emitted in different timing
108 Exit of combined light
110-1, 2 Transmitted light
112 Adhesive layer
114-1 to 4 Transparent parallel flat plate
116-1 to 2 Transparent semicircular parallel flat plate
118-1 to 3 Antireflection coating layer
120 Transmission diffraction grating
122 Fresnel Prism/blazed Hologram
124, 126 Blazed Grating
128 Blazed Grating or prism
130 Pinhole or slit
132 One-dimensional line sensor
134-1, 2 Condenser lens
136 Collimator lens
142 Core area
144 Clad layer
200 Specific region in target (light combining/mixing position)
201, 206 Light passing through first optical path
202, 207 Light passing through second optical path
203, 208 Light passing through third optical path
210 Optical path changing device (optical characteristics changing member)
212 Phase conversion element (optical path changing device/optical characteristics changing member)
214 Vessel having phase conversion characteristics (microscopic asperities) at the inner wall or the outer wall
216 Imaging lens
218 Expand lens
220 Prism
222 Lenticular lens
230 Micro concave lens
240 Concave lens or cylindrical concave lens
250 Light guide/light pipe
252 Front-end boundary of light guide/light pipe
254-1, -2 Side Surface
256 Back-end boundary of light Guide/light pipe
260 Optical path of beam from point $\zeta$
270 Optical path of beam from point
280 Mixing area of light
290-1 to -n Electromagnetic waves having directionality
292-1 to -n Electromagnetic waves source/receiving part
294-1, 2 Mixed electromagnetic waves having directionality
296-1 to -n Magnetron electromagnetic wave generating source/receiving part
298-1 to -n Waveguide antenna
300 Bundle-type optical fiber group
302 Light-source unit of partial incoherent light
304 Signal detection section for partial incoherent reflected light
306 Wave front aberration detection section for partial incoherent reflected light
308 Objective lens
310 Optical-path separation section between irradiated light and detection light
312 Light separator section
314 Signal detection section for partial incoherent transmitted light
316 Wave front aberration detection section for partial incoherent transmitted light
318 Objective lens
320 Reference-light generation section
322 Light-source unit of coherent light
324 Signal detection section for coherent reflected light
326 Wave front aberration detection section for coherent reflected light
332 Light separator section 334 Signal detection section for coherent transmitted light
336 Wave front aberration detection section for coherent transmitted light
340 Light combiner section
342, 344, 346, 348 Light divider section
350 Wave front aberration compensation section
352 Irradiated-light wave front aberration coarse compensation section
354 Irradiated-light wave front aberration fine compensation section
356 Transmitted-light wave front aberration coarse compensation section
358 Transmitted-light wave front aberration fine compensation section
360 Straight-travelling light
362-1,-2 Directional electromagnetic wave generating/receiving part
364 Rotating mechanism of electromagnetic wave generating/receiving part
366 Rotation driving part of electromagnetic wave generating/receiving part
368 Water vapor
370, 380 Multi-scattered light
372 Caterpillar tread
374 Wheels for travelling
376 Far-infrared spectroscope
378 Infrared spectroscope
382 Heat (far-infrared light)
384 Solar panel
386 Water source or metalliferous deposit
388 Battery
390 Back scattered light
392 Ground's surface
393 Ground-state electron orbital in 6-amino acid period
394 Communication control part
396 Antenna
398 Control system in searching apparatus
399 Exited-state electron orbital in 6-amino acid period
400 Amino acid sequence of fibroin
402-1, 2 High-molecular compound
404-1, 2 Electron cloud
406-1, 2 Atomic group
408 Molecular structure of polyethylene
410 Common electrode part
414-1 to 6 Individual electrode part
416-1 to 6 Light reflecting plane
418-1 to 6 Piezoelectric device
420 Common electrode part that doubles as light-reflecting plane
422 Divider
424-1 to 3 Transparent electrode part
428-1 to 3 Liquid-crystal layer
430 Optical-path dividing section
436 Reference light
440, 450 Three-dimensional transmission pattern forming section
442, 444, 446 Two-dimensional transmission image forming layer
452, 454, 456 Two-dimensional transmission image forming layer
460 Optical-path separation section
470 Two-dimensional PSD (Position Sensitive Detector) cell array
472-1 to 4 PSD(Position Sensitive Detector) cell
474-1 to 4 Mini-lens
476-1 to 4 Light-collecting spot (without interference)
478-1 to 4 Light-collecting spot (with interference)
480 Wave front (equiphase wave surface)
482 Light-collecting spot position detection section of reference light
484 Light-collecting spot position detection section of detection light
486 Light-collecting spot displacement calculation section
488 Amount of inclination of localized wave front.
490 Overall wave front aberration calculation section
492 Polarization beam splitter
494-1 to 3 $\lambda/4$ plate (¼ phase plate)
496-1 to 4 Analyzer
498-1 to 3 Unpolarized beam splitter
500-1 to 4 Imaging camera
602 β-sheet crystalline part
604 Non-crystalline part
612 Aspartic acid+cation
616 Carboxyl group
620 Molecular monomer that is a low-molecular modified fibroin
622 Active area of ATP Ase
624 ADP
626 ADP fixing part
630, 640 Localized molecular orbital area of it-electron (active area)
632, 634, 636, 638 Principal chain areas in protein
650 Luminophore area in conventional GFP
702 Procedure of treatment (correction of problematic area)
704 Procedure of treatment (correction of problematic area)
706 Procedure of evaluation/checking of a treatment (correction) result
800 Nuclear delivery carrier
806 Gene regulator
808 Genome-editing module
810 Genome-editing basic part
812-1, 2 (Phosphorylated (activated))mCas(modified CRISPR-Associated System)
814 Nuclease area
816-1, 2 crRNA(CRISPR RNA)
817 Protein to hold a replicated DNA
818 Replicated DNA (vector)
819 Histone
820 Cutting position of protease having the phosphorylation activation property
822 mCas controlling enzyme A (kinase)
824 mCas controlling enzyme B (inhibitor/phosphatase)
826 Enzyme to control a signal in the cell nucleus
828 Self phosphorylation protease (self activation action internally having kinase and added ATP)
830 Selective junction with surface of cell nucleus membrane
832 Nuclear lamina
834 Hydrophobic region between inner and outer membranes
836 Inner membrane of carrier inner pack
838 Outer membrane of carrier inner pack
840 Exterior covering of carrier outer pack
842 Interior of carrier inner pack
846 Junction with selected cell
850 Nuclear lamina identifying antibody part (cell nucleus detection part)
852-1 to 6 Hydrophobic region
854-1, 2 Hydrophobic region
856-1 to 8 Hydrophilic region
858-1 to 6 Hydrophilic region
860 α-helix structure part
870 Transmembrane part
880 Nuclear lamina 888 Cell nucleus membrane
890 Interior of cell nucleus
894 Hydrophobic region between inner and outer membranes
896 Inner membrane of cell nucleus membrane
898 Outer membrane of cell nucleus membrane
1000 Hair follicle (parental cell/original species or daughter cell/seed species)
1002 Produced functional-bio material
1004 Culture medium
1006 Agitator
1010 Vessel
1020 Optical status management apparatus (measurement apparatus)
1032 Internal solution
1034 External solution
1036 Dialysis vessel
1038 External magnetic-field generating/rotation part
1040 Fibriform protein
1050 Mold for forming
1054 Grooves for forming
1060 Irradiated light for purification
1070 Electrode to apply purifying voltage
1074 Variable-voltage power supply for purification
1080 Filter to extract a material of the functional-bio material
1090 Vessel for purification
1096 Top clear solution after centrifugal separation
1100a to j Final production places of functional-bio material
1130 Central-core controlling base
1120a to 1120c Distributing base
1602 Modified β-sheet crystalline part (monomer block)
1604 Assembly block of crystalline parts (polymer)
1608 Finally formed structure
1610 Surface coat layer
A Amplitude of partially coherent light on one side
a ½ of the core radius of optical fiber or the pinhole radius/slit width
Asp Aspartic acid
C Light speed
Cl⁻ Chlorine ion
d Physical step height
D Width of light incoming region in bundle-type optical fiber group (single optical fiber) or displacement of light passed through optical characteristics changing member on the light-collecting face
F Focal length of collimator lens 26/detecting lens 28-2
G Center position of gravity of a specific atomic group
Gln Glutamine
Gly Glycine
k Wave number
L Overall length of optical fiber
$l_{CL}$ Coherence Length
M Image-forming magnification (lateral magnification) or light-separation number for partial coherency
m Suffixes of different optical paths/indexes (number of optical path)
N Number of different optical paths in measurement apparatus (number of a plurality of divided optical paths)
n Refractive index of light in transparent medium
NA Numerical Aperture
Na⁺ Sodium ion
R Distance from light-emitting point/scattering point to measurement point
Ra Average surface roughness in phase conversion element
r Radium of pupil surface of collimator lens 26
Ser Serine
SF Distance from light-emitting source to incoming region of optical fiber
SL Distance between condenser lens and line sensor
T Thickness of tungsten halogen lamp
Trp Tryptophan
Tyr Tyrosine
t time or thickness of parallel flat plate
ν r²
W Diameter of slit width or pinhole
z Distance in light-travelling direction
α, β Luminous point on tungsten filament, scattering point in specific area of target, or pseudo luminous point in target
γ Measurement point, luminous point on tungsten filament, or pseudo luminous point in target
ΔD Core diameter in optical fiber
Δt Time width
ΔY Displacement on line sensor
Δλ Selected wavelength width (wavelength range)
Δν Frequency width
δ Optical-length difference
$δ_{max}$ Maximum value of optical-length difference
ε Incident angle of incident light to optical fiber or imaging point
ζ Inclination angle of light beam travelling passed through transparent parallel flat plate or imaging point
η Travelling angle of light beam, inclination angle of cutting plane, or imaging point
θ Inclination angle of both of the planes of transparent parallel flat plate or diffraction angle
$λ_0$ Center wavelength
ν Frequency of vibrations
ξ Inclination angle of beam travelling through optical fiber or light guide (light pipe)
ρ Output angle in quartz glass
σ Phase amount of phase amount of combined light
τ Mechanical distance of intra-vessel optical path of tungsten halogen lamp
X Diffraction-angle coefficient relative to incident wavelength of diffraction grating.
ψ Combined wave of partially coherent light beams
Ψ Combined wave of the entire partially coherent light beams passing through collimator lens
+ Positively-charged area in crystalline part
+ Negatively-charged area in crystalline part
ι Distance between points α and β along the longitudinal direction of tungsten halogen lamp
κ Incident angle to front-end boundary of light guide (light pipe)
μ Slope angle of side surface of light guide (light pipe)
φ Angle of reflection in light guide (light pipe)

What is claimed is:

1. A light source, comprising:
a light-emitting source configured to provide emitted light;
a first optical characteristics changing member configured to divide an original optical path of the emitted light into first and second divided optical paths, wherein a first light beam and a second light beam of the emitted light pass through the first and second divided optical paths respectively, and the first light beam and the second light beam have a same prescribed wavelength; and
a second optical characteristics changing member configured to combine the first light beam and the second light beam to form combined light, the combined light being configured to be applied, wherein an optical length based on the prescribed wavelength of the first divided optical path is controlled to be different from another optical length based on the prescribed wavelength of the second divided optical path.

2. The light source according to claim 1, wherein a difference in optical length between the first divided optical path and the second divided optical path is controlled based on at least one of a difference in thickness of a refractive element, a difference in refractive index, a difference in step height, a difference in propagation direction, and a difference in propagation paths.

3. The light source according to claim 2, wherein the first and second light beams are condensed to be combined at a predetermined local region in a plane perpendicular to an optical-axis, and the first and second light beams have the same propagation direction after combination.

4. The light source according to claim 2, wherein the difference in optical length between the first divided optical path and the second divided optical path is larger than a coherence length.

5. The light source according to claim 4, wherein the combined light passes through an optical-phase conversion element before being applied.

6. The light source according to claim 1, wherein the first light beam and the second light beam are simultaneously collected as the combined light.

7. The light source according to claim 6, wherein the first and the second light beams are simultaneously combined at cross-sectional faces of the first and the second light beams.

8. A light generating method comprising:
emitting first and second light beams from a light-emitting source, the first light beam passing through a first optical path and having a prescribed wavelength, the second light beam passing through a second optical path and having the prescribed wavelength;
combining the first light beam and the second light beam to form the light, the light being configured to be applied,
wherein an optical length based on the prescribed wavelength of the first optical path is controlled to be different from another optical length based on the prescribed wavelength of the second optical path.

9. The light generating method according to claim 8, wherein a difference in optical length between the first optical path and the second optical path is based on at least one of a difference in thickness of a refractive element, a difference in refractive index, a difference in step height, a difference in propagation direction, and a difference in propagation paths.

10. The light generating method according to claim 9, wherein the first and second light beams are condensed to be combined at a predetermined local region in a plane perpendicular to an optical-axis, and the first and second light beams have the same propagation direction after combination.

11. The light generating method according to claim 9, wherein the difference in optical length between the first optical path and the second optical path is larger than a coherence length.

12. The light generating method according to claim 11, wherein the light passes through an optical-phase conversion element before being applied.

13. The light generating method according to claim 11, wherein the combination of the first and second light beams is performed using at least one of an image-forming optical system and a confocal optical system.

14. The light generating method to claim 8, wherein the first and the second light beams are simultaneously collected as the light.

15. The light generating method to claim 14, wherein the first and the second light beams are simultaneously combined at cross-sectional faces of the first and the second light beams.

16. A method of manufacturing functional biomaterial which has a predetermined function and a light absorption characteristic for a prescribed wavelength, wherein
at least one of a state of the functional biomaterial and a change in the state of the functional biomaterial are detected by applying light to the functional biomaterial,
the light is formed by a combination of a first light beam and a second light beam emitted from a light-emitting source,
the first light beam having the prescribed wavelength passes through a first optical path,
the second light beam having the prescribed wavelength passes through a second optical path, and
an optical length based on the prescribed wavelength of the first optical path is controlled to be different from another optical length based on the prescribed wavelength of the second optical path.

17. The method of manufacturing functional biomaterial according to claim 16, wherein the predetermined function relates to at least one of a different conformation, an amino acid sequence, an internal structure of active area, an enzyme function, a change of polymer, genome information, genome editing, gene regulating, and synthesizing artificial protein.

18. The method of manufacturing functional biomaterial according to claim 17, wherein the functional biomaterial comprises at least one of a base sequence in a DNA molecule and an amino acid sequence.

19. The method of manufacturing functional biomaterial according to claim 18, wherein the prescribed wavelength is in a wavelength range of 0.7 to 2.5 μm.

20. The functional biomaterial according to claim 17, wherein the first and the second light beams are simultaneously collected as the light.

* * * * *